United States Patent
Kim et al.

(10) Patent No.: US 11,812,623 B2
(45) Date of Patent: Nov. 7, 2023

(54) HETERO-CYCLIC COMPOUND AND ORGANIC LIGHT EMITTING DEVICE USING THE SAME

(71) Applicant: LT MATERIALS CO., LTD., Yongin-Si (KR)

(72) Inventors: Ji-Un Kim, Yongin (KR); Yu-Jun Jung, Yongin (KR); Nam-Jin Lee, Yongin (KR); Won-Jang Jeong, Yongin (KR); Jun-Tae Mo, Yongin (KR)

(73) Assignee: LT MATERIALS CO., LTD., Yongin-si (KR)

( * ) Notice: Subject to any disclaimer, the term of this patent is extended or adjusted under 35 U.S.C. 154(b) by 555 days.

(21) Appl. No.: 16/909,618

(22) Filed: Jun. 23, 2020

(65) Prior Publication Data

US 2020/0403157 A1    Dec. 24, 2020

(30) Foreign Application Priority Data

Jun. 24, 2019  (KR) .................. 10-2019-0075259

(51) Int. Cl.
*H10K 85/60* (2023.01)
*C07D 307/77* (2006.01)
*C07D 307/91* (2006.01)
*H10K 50/15* (2023.01)

(52) U.S. Cl.
CPC ......... *H10K 85/633* (2023.02); *C07D 307/77* (2013.01); *C07D 307/91* (2013.01); *H10K 85/636* (2023.02); *H10K 50/15* (2023.02); *H10K 85/615* (2023.02); *H10K 85/6574* (2023.02)

(58) Field of Classification Search
None
See application file for complete search history.

(56) References Cited

U.S. PATENT DOCUMENTS

| 4,356,429 | A | 10/1982 | Tang |
| 10,270,040 | B2 | 4/2019 | Ikeda et al. |
| 10,424,741 | B2 | 9/2019 | Lee et al. |
| 2016/0351816 | A1* | 12/2016 | Kim ............ H10K 85/626 |
| 2018/0186768 | A1 | 7/2018 | Jung et al. |
| 2018/0208836 | A1* | 7/2018 | Kuma ............ H10K 50/131 |
| 2018/0261774 | A1* | 9/2018 | Park ............ C07D 409/14 |
| 2019/0241548 | A1 | 8/2019 | Park et al. |
| 2019/0296248 | A1 | 9/2019 | Mun et al. |
| 2020/0231581 | A1 | 7/2020 | Chae et al. |
| 2020/0321530 | A1 | 10/2020 | Lee et al. |

FOREIGN PATENT DOCUMENTS

| CN | 104650029 A | 5/2015 |
| JP | 2018-156721 A | 10/2018 |
| KR | 10-2015-0098631 A | 8/2015 |
| KR | 10-2015-0146033 A | 12/2015 |
| KR | 10-2016-0147673 A | 12/2016 |
| KR | 10-2017-0096770 A | 8/2017 |
| KR | 10-1789998 B1 | 10/2017 |
| KR | 10-2019-0013353 A | 2/2019 |
| KR | 10-2019-0033911 A | 4/2019 |
| WO | WO 2017/090919 A1 | 6/2017 |
| WO | WO 2019/066242 A1 | 4/2019 |
| WO | WO 2019/124903 A1 | 6/2019 |

OTHER PUBLICATIONS

Extended European Search Report, dated Feb. 4, 2021, for European Application No. 20179205.8.
Kuwabara et al., "Thermally Stable Multilayered Organic Electroluminescent Devices Using Novel Starburst Molecules, 4.4',4"-Tri(N-carbazoly)triphenylamine (TCTA) and 4.4',4"-Tris(3-methylphenylphenyl-amino)triphenylamine (m-MTDATA), as Hole-Transport Materials." Advanced Materials, vol. 6. No. 9. 1994, pp. 677-679.

* cited by examiner

*Primary Examiner* — Christopher M Rodd
(74) *Attorney, Agent, or Firm* — Birch, Stewart, Kolasch & Birch, LLP

(57) ABSTRACT

The present application provides a hetero-cyclic compound capable of significantly enhancing lifetime, efficiency, electrochemical stability and thermal stability of an organic light emitting device, and an organic light emitting device comprising the hetero-cyclic compound in an organic material layer.

8 Claims, 3 Drawing Sheets

[FIG. 1]
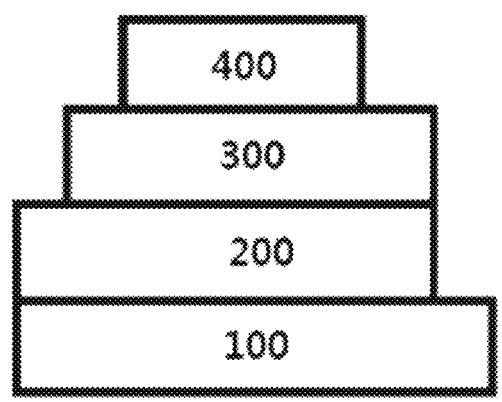
[FIG. 2]
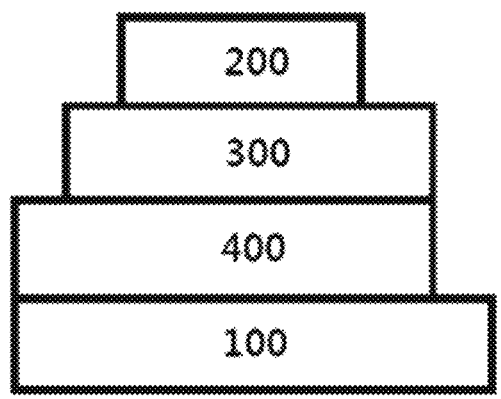

[FIG. 3]
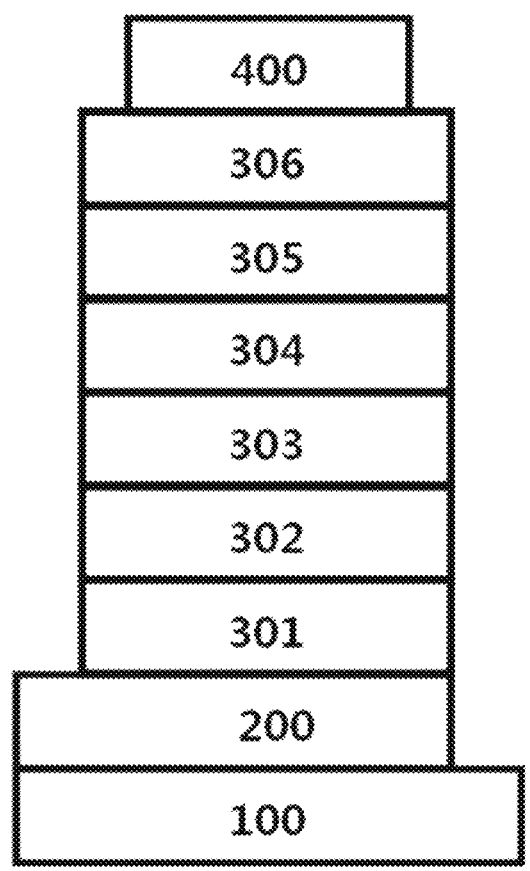

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETERO-CYCLIC COMPOUND AND ORGANIC LIGHT EMITTING DEVICE USING THE SAME

TECHNICAL FIELD

This application claims priority to and the benefits of Korean Patent Application No. 10-2019-0075259, filed with the Korean Intellectual Property Office on Jun. 24, 2019, the entire contents of which are incorporated herein by reference.

The present application relates to a hetero-cyclic compound, and an organic light emitting device using the same.

Background Art

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

Disclosure

Technical Problem

The present disclosure is directed to providing a hetero-cyclic compound, and an organic light emitting device comprising the same.

Technical Solution

One embodiment of the present application provides a hetero-cyclic compound represented by the following Chemical Formula 1.

[Chemical Formula 1]

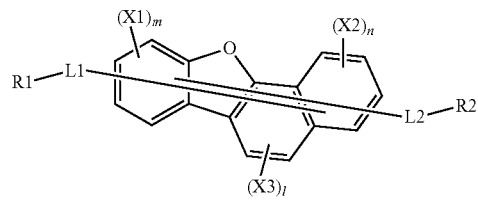

In Chemical Formula 1,

L1 is a direct bond; a substituted or unsubstituted arylene group having 6 to 60 carbon atoms; or a substituted or unsubstituted heteroarylene group having 2 to 60 carbon atoms, L2 is a direct bond; or a substituted or unsubstituted arylene group having 6 to 60 carbon atoms, R1 is a substituted or unsubstituted aryl group having 6 to 60 carbon atoms; a substituted or unsubstituted heteroaryl group having 2 to 60 carbon atoms; or a substituted or unsubstituted amine group, R2 is a substituted or unsubstituted aryl group having 6 to 60 carbon atoms; or a substituted or unsubstituted amine group, X1 to X3 are each independently hydrogen; deuterium; a halogen group; a substituted or unsubstituted alkyl group having 61 to 60 carbon atoms; a substituted or unsubstituted cycloalkyl group having 3 to 60 carbon atoms; a substituted or unsubstituted aryl group having 6 to 60 carbon atoms; or a substituted or unsubstituted hetero-cyclic group having 2 to 60 carbon atoms, m and n are each an integer of 1 to 4, and when m and n are 2 or greater, substituents in the parentheses are the same as or different from each other, l is 1 or 2, and when l is 2, substituents in the parentheses are the same as or different from each other, and m, n and l are m+n+l≤8.

Another embodiment of the present application provides an organic light emitting device comprising an anode, a cathode, and one or more organic material layers provided between the anode and the cathode, wherein one or more layers of the organic material layers comprise the hetero-cyclic compound represented by Chemical Formula 1.

Advantageous Effects

A hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer and the like in an organic light emitting device. Particularly, the hetero-cyclic compound represented by Chemical Formula 1 can be used as a material of a hole transfer layer or an electron blocking layer in an organic light emitting device. In addition, using the hetero-cyclic compound represented by Chemical Formula 1 in an organic light emitting device is capable of lowering a driving voltage of the device, enhancing light efficiency, and enhancing lifetime properties of the device by thermal stability of the compound.

DESCRIPTION OF DRAWINGS

FIG. 1 to FIG. 4 each schematically illustrate a lamination structure of an organic light emitting device according to one embodiment of the present application.

MODE FOR DISCLOSURE

Hereinafter, the present application will be described in detail.

One embodiment of the present application provides a hetero-cyclic compound represented by the following Chemical Formula 1.

[Chemical Formula 1]

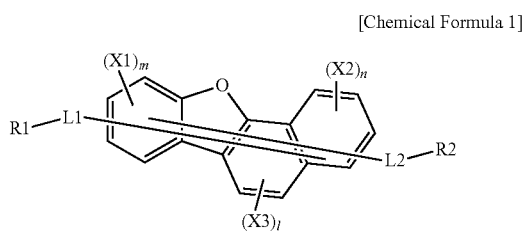

In Chemical Formula 1,

L1 is a direct bond; a substituted or unsubstituted arylene group having 6 to 60 carbon atoms; or a substituted or unsubstituted heteroarylene group having 2 to 60 carbon atoms, L2 is a direct bond; or a substituted or unsubstituted arylene group having 6 to 60 carbon atoms, R1 is a substituted or unsubstituted aryl group having 6 to 60 carbon atoms; a substituted or unsubstituted heteroaryl group having 2 to 60 carbon atoms; or a substituted or unsubstituted amine group, R2 is a substituted or unsubstituted aryl group having 6 to 60 carbon atoms; or a substituted or unsubstituted amine group, X1 to X3 are each independently hydrogen; deuterium; a halogen group; a substituted or unsubstituted alkyl group having 61 to 60 carbon atoms; a substituted or unsubstituted cycloalkyl group having 3 to 60 carbon atoms; a substituted or unsubstituted aryl group having 6 to 60 carbon atoms; or a substituted or unsubstituted hetero-cyclic group having 2 to 60 carbon atoms, m and n are each an integer of 1 to 4, and when m and n are 2 or greater, substituents in the parentheses are the same as or different from each other, l is 1 or 2, and when l is 2, substituents in the parentheses are the same as or different from each other, and m, n and l are m+n+l≤8.

By having a structure in which naphthobenzofuran is disubstituted with specific substituents such as an amine group, Chemical Formula 1 is capable of increasing a hole transfer ability by delocalizing a highest occupied molecular orbital (HOMO) energy level, and stabilizing HOMO energy. This allows formation of proper energy level and band gap when using the material of Chemical Formula 1 as a material of a hole transfer layer, an electron blocking layer, a prime layer or a light emitting layer in an organic light emitting device, which increases excitons in the light emitting region. Increasing excitons in the light emitting region means having an effect of increasing driving voltage and efficiency of a device.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a terphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a hetero-cyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a hetero-cyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

In the present specification, the spiro group is a group comprising a spiro structure, and may have 15 to 60 carbon atoms. For example, the Spiro group may comprise a structure in which a 2,3-dihydro-1H-indene group or a cyclohexane group spiro-bonds to a fluorenyl group. Specifically, the following spiro group may comprise any one of groups of the following structural formulae.

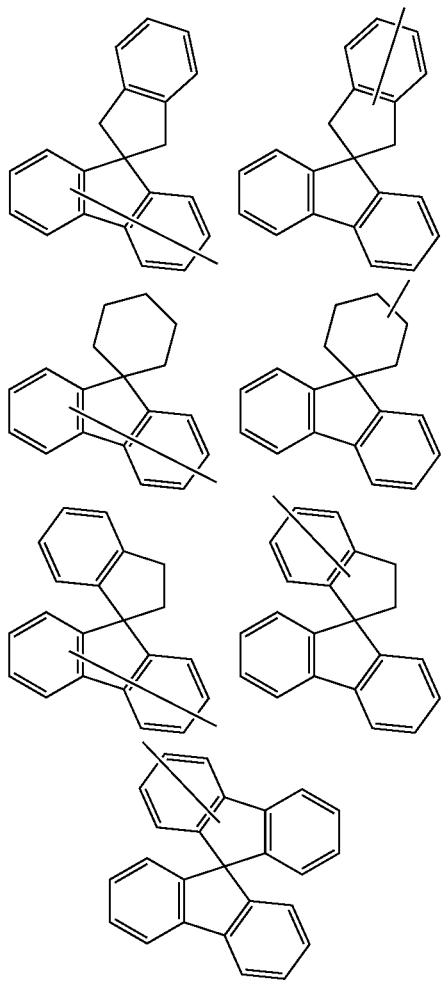

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

The hetero-cyclic compound according to one embodiment of the present application is represented by Chemical Formula 1. More specifically, the hetero-cyclic compound represented by Chemical Formula 1 may be used as a material of an organic material layer of an organic light emitting device by having structural properties of the core structure and the substituents as described above.

In one embodiment of the present application, L1 of Chemical Formula 1 may be a direct bond; a substituted or unsubstituted arylene group; or a substituted or unsubstituted heteroarylene group.

In one embodiment of the present application, L1 is a direct bond; a substituted or unsubstituted arylene group having 6 to 60 carbon atoms; or a substituted or unsubstituted heteroarylene group having 2 to 60 carbon atoms.

In one embodiment of the present application, L1 is a direct bond; a substituted or unsubstituted arylene group having 6 to 40 carbon atoms; or a substituted or unsubstituted heteroarylene group having 2 to 40 carbon atoms.

In one embodiment of the present application, L1 is a direct bond; a substituted or unsubstituted arylene group having 6 to 20 carbon atoms; or a substituted or unsubstituted heteroarylene group having 2 to 20 carbon atoms.

In another embodiment, L1 is a direct bond.

In another embodiment, L1 is a substituted or unsubstituted arylene group; or a substituted or unsubstituted heteroarylene group.

In another embodiment, L1 is a substituted or unsubstituted arylene group.

In another embodiment, L1 is a phenylene group.

In one embodiment of the present application, L2 of Chemical Formula 1 may be a direct bond; or a substituted or unsubstituted arylene group.

In one embodiment of the present application, L2 is a direct bond; or a substituted or unsubstituted arylene group having 6 to 60 carbon atoms.

In one embodiment of the present application, L2 is a direct bond; or a substituted or unsubstituted arylene group having 6 to 40 carbon atoms.

In one embodiment of the present application, L2 is a direct bond; or a substituted or unsubstituted arylene group having 6 to 20 carbon atoms.

In another embodiment, L2 is a direct bond.

In another embodiment, L2 is a substituted or unsubstituted arylene group.

In another embodiment, L2 is a phenylene group.

In one embodiment of the present application, R1 of Chemical Formula 1 may be a substituted or unsubstituted aryl group; a substituted or unsubstituted heteroaryl group; or a substituted or unsubstituted amine group.

In one embodiment of the present application, R1 is a substituted or unsubstituted aryl group having 6 to 60 carbon atoms; a substituted or unsubstituted heteroaryl group having 2 to 60 carbon atoms; or a substituted or unsubstituted amine group having 6 to 60 carbon atoms.

In one embodiment of the present application, R1 is a substituted or unsubstituted aryl group having 6 to 40 carbon atoms; a substituted or unsubstituted heteroaryl group having 2 to 40 carbon atoms; or a substituted or unsubstituted amine group having 6 to 60 carbon atoms.

In one embodiment of the present application, R1 is a substituted or unsubstituted aryl group having 6 to 20 carbon atoms; a substituted or unsubstituted heteroaryl group having 2 to 20 carbon atoms; or a substituted or unsubstituted amine group having 12 to 60 carbon atoms.

In another embodiment, R1 is a substituted or unsubstituted aryl group; or a substituted or unsubstituted amine group.

In another embodiment, R1 is a substituted or unsubstituted phenyl group; a substituted or unsubstituted biphenyl group; a substituted or unsubstituted naphthyl group; or a substituted or unsubstituted amine group.

In another embodiment, R1 is a phenyl group; a biphenyl group; a naphthyl group; or a substituted or unsubstituted amine group.

In another embodiment, R1 is a substituted or unsubstituted heteroaryl group; or a substituted or unsubstituted amine group.

In another embodiment, R1 is a substituted or unsubstituted amine group.

In one embodiment of the present application, R2 of Chemical Formula 1 may be a substituted or unsubstituted aryl group; or a substituted or unsubstituted amine group.

In one embodiment of the present application, R2 is a substituted or unsubstituted aryl group having 6 to 60 carbon atoms; or a substituted or unsubstituted amine group having 6 to 60 carbon atoms.

In one embodiment of the present application, R2 is a substituted or unsubstituted aryl group having 6 to 40 carbon atoms; or a substituted or unsubstituted amine group having 6 to 60 carbon atoms.

In one embodiment of the present application, R2 is a substituted or unsubstituted aryl group having 6 to 20 carbon atoms; or a substituted or unsubstituted amine group having 12 to 60 carbon atoms.

In another embodiment, R2 is a substituted or unsubstituted phenyl group; a substituted or unsubstituted biphenyl group; a substituted or unsubstituted naphthyl group; or a substituted or unsubstituted amine group.

In another embodiment, R2 is a phenyl group; a biphenyl group; a naphthyl group; or a substituted or unsubstituted amine group.

In another embodiment, R2 is a substituted or unsubstituted amine group.

In one embodiment of the present application, at least one of R1 and R2 of Chemical Formula 1 is a substituted or unsubstituted amine group.

When having a disubstituted structure in which at least one of R1 and R2 of Chemical Formula 1 has an amine group, a hole transfer ability may increase by delocalizing a highest occupied molecular orbital (HOMO) energy level, and HOMO energy may be stabilized. This allows formation of proper energy level and band gap as a host material, and as a result, effects of increasing driving voltage and efficiency of a device are obtained by increasing excitons in the light emitting region.

In one embodiment of the present application, R1 may be a substituted or unsubstituted aryl group; or a substituted or unsubstituted heteroaryl group, and R2 may be a substituted or unsubstituted amine group.

In one embodiment of the present application, R1 is a substituted or unsubstituted aryl group having 6 to 60 carbon atoms; or a substituted or unsubstituted heteroaryl group having 2 to 60 carbon atoms, and R2 is a substituted or unsubstituted amine group having 6 to 60 carbon atoms.

In one embodiment of the present application, R1 is a substituted or unsubstituted aryl group having 6 to 40 carbon atoms; or a substituted or unsubstituted heteroaryl group having 2 to 60 carbon atoms, and R2 is a substituted or unsubstituted amine group having 12 to 60 carbon atoms.

In another embodiment, R1 is a substituted or unsubstituted aryl group, and R2 is a substituted or unsubstituted amine group.

In one embodiment of the present application, R1 is a substituted or unsubstituted aryl group having 6 to 60 carbon atoms, and R2 is a substituted or unsubstituted amine group having 6 to 60 carbon atoms.

In one embodiment of the present application, R1 is a substituted or unsubstituted aryl group having 6 to 40 carbon atoms, and R2 is a substituted or unsubstituted amine group having 12 to 60 carbon atoms.

In another embodiment, R1 is a substituted or unsubstituted phenyl group; a substituted or unsubstituted biphenyl group; or a substituted or unsubstituted naphthyl group, and R2 is a substituted or unsubstituted amine group.

In another embodiment, R1 is a phenyl group; a biphenyl group; or a naphthyl group, and R2 is a substituted or unsubstituted amine group.

In another embodiment, R1 is a phenyl group; a biphenyl group; or a naphthyl group, and R2 is an amine group unsubstituted or substituted with one or more substituents selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted spirobifluorenyl group and a substituted or unsubstituted dibenzofuran group.

In another embodiment, R1 is a phenyl group; a biphenyl group; or a naphthyl group, and R2 is amine group unsubstituted or substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group.

In another embodiment, R1 is a phenyl group; a biphenyl group; or a naphthyl group, and R2 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group.

In another embodiment, R1 is a phenyl group, and R2 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group.

In another embodiment, R1 is a biphenyl group, and R2 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group.

In another embodiment, R1 is a naphthyl group, and R2 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group.

In another embodiment, R1 is a substituted or unsubstituted heteroaryl group, and R2 is a substituted or unsubstituted amine group.

In one embodiment of the present application, R1 is a substituted or unsubstituted heteroaryl group having 2 to 60 carbon atoms, and R2 is a substituted or unsubstituted amine group having 6 to 60 carbon atoms.

In one embodiment of the present application, R1 is a substituted or unsubstituted aryl group having 2 to 40 carbon atoms, and R2 is a substituted or unsubstituted amine group having 12 to 60 carbon atoms.

In one embodiment of the present application, R1 may be a substituted or unsubstituted amine group, and R2 may be a substituted or unsubstituted aryl group.

In one embodiment of the present application, R1 is a substituted or unsubstituted amine group having 6 to 60 carbon atoms, and R2 is a substituted or unsubstituted aryl group having 6 to 60 carbon atoms.

In one embodiment of the present application, R1 is a substituted or unsubstituted amine group having 12 to 60 carbon atoms, and R2 is a substituted or unsubstituted aryl group having 6 to 40 carbon atoms.

In another embodiment, R1 is a substituted or unsubstituted amine group, and R2 is a substituted or unsubstituted phenyl group; a substituted or unsubstituted biphenyl group; or a substituted or unsubstituted naphthyl group.

In another embodiment, R1 is a substituted or unsubstituted amine group, and R2 is a phenyl group; a biphenyl group; or a substituted or unsubstituted naphthyl group.

In another embodiment, R1 is an amine group unsubstituted or substituted with one or more substituents selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted spirobifluorenyl group and a substituted or unsubstituted dibenzofuran group, and R2 is a phenyl group; a biphenyl group; or a naphthyl group.

In another embodiment, R1 is an amine group unsubstituted or substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group, and R2 is a phenyl group; a biphenyl group; or a naphthyl group.

In another embodiment, R1 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group, and R2 is a phenyl group; a biphenyl group; or a naphthyl group.

In another embodiment, R1 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group, and R2 is a phenyl group.

In another embodiment, R1 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group, and R2 is a biphenyl group.

In another embodiment, R1 is an amine group substituted with one or more substituents selected from the group consisting of a phenyl group, a biphenyl group, a terphenyl group, a naphthyl group, a fluorenyl group unsubstituted or substituted with an alkyl group, a spirobifluorenyl group and a dibenzofuran group, and R2 is a naphthyl group.

When R1 and R2 positions are each substituted with one of an amine group and an aryl group, a proper homo energy level for hole injection and transfer may be formed while lowering the molecular weight. For example, when one of R1 and R2 is bisbiphenylamine and the other one is an aryl group, a homo energy level to readily conduct hole injection and transfer may be formed. In addition, by allowing a spatial structure of a material due to the bulky bisbiphenylamine, thermal stability, a major factor of a hole transfer layer, is secured, and a long lifetime device may be obtained.

In addition, when the aryl group is phenyl or biphenyl, conjugation expansion is suppressed and molecular thin film and interfacial arrangements are superior compared to a naphthyl group, and accordingly, a device having low voltage properties and high efficiency properties may be obtained through fast hole mobility.

In one embodiment of the present application, R1 and R2 of Chemical Formula 1 are each independently a substituted or unsubstituted amine group.

In one embodiment of the present application, R1 and R2 are each independently a substituted or unsubstituted amine group having 6 to 60 carbon atoms.

In one embodiment of the present application, R1 and R2 are each independently a substituted or unsubstituted amine group having 12 to 60 carbon atoms.

In another embodiment, R1 and R2 are each independently an amine group unsubstituted or substituted with one or more substituents selected form the group consisting of a phenyl group, a biphenyl group, a terphenyl group, a naphthyl group, a fluorenyl group unsubstituted or substituted with an alkyl group, a spirobifluorenyl group and a dibenzofuran group.

In one embodiment of the present application, X1 to X3 may be each independently hydrogen; deuterium; a halogen group; a substituted or unsubstituted alkyl group; a substituted or unsubstituted cycloalkyl group; a substituted or unsubstituted aryl group; or a substituted or unsubstituted hetero-cyclic group.

In another embodiment, X1 to X3 are each independently hydrogen; deuterium; a halogen group; a substituted or unsubstituted alkyl group; or a substituted or unsubstituted cycloalkyl group.

In another embodiment, X1 to X3 are each independently hydrogen; deuterium; or a halogen group.

In another embodiment, X1 to X3 are each independently hydrogen; or deuterium.

In another embodiment, X1 to X3 are each independently a substituted or unsubstituted aryl group; or a substituted or unsubstituted hetero-cyclic group.

In one embodiment of the present application, X1 to X3 are different.

In one embodiment of the present application, at least two of X1 to X3 are the same.

In one embodiment of the present application, X1 to X3 are the same.

In another embodiment, X1 to X3 are hydrogen.

In one embodiment of the present application, m and n of Chemical Formula 1 may be an integer of 1 to 4.

In one embodiment of the present application, when m and n of Chemical Formula 1 are 2 or greater, substituents in the parentheses may be the same as or different from each other.

In one embodiment of the present application, m and n of Chemical Formula 1 are 2.

In one embodiment of the present application, m and n of Chemical Formula 1 may be an integer of 1 to 4.

In one embodiment of the present application, when m and n of Chemical Formula 1 are 2 or greater, substituents in the parentheses may be the same as or different from each other.

In one embodiment of the present application, m and n of Chemical Formula 1 are 2.

In another embodiment, m and n of Chemical Formula 1 are 1.

In one embodiment of the present application, 1 of Chemical Formula 1 may be 1 or 2.

In one embodiment of the present application, when 1 of Chemical Formula 1 is 2, substituents in the parentheses may be the same as or different from each other.

In one embodiment of the present application, 1 of Chemical Formula 1 is 2.

In another embodiment, 1 of Chemical Formula 1 is 1.

In one embodiment of the present application, m, n and 1 of Chemical Formula 1 may be m+n+l≤8.

In another embodiment, m, n and 1 of Chemical Formula 1 are m+n+l≤6.

In another embodiment, m, n and 1 of Chemical Formula 1 are m+n+l≥3.

In one embodiment of the present application, Chemical Formula 1 may be represented by the following Chemical Formula 2.

[Chemical Formula 2]

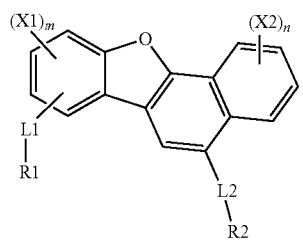

In Chemical Formula 2,
substituents have the same definitions as in Chemical Formula 1.

In one embodiment of the present application, Chemical Formula 1 may be represented by the following Chemical Formula 3 or 4.

[Chemical Formula 3]

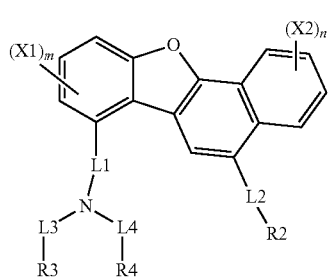

[Chemical Formula 4]

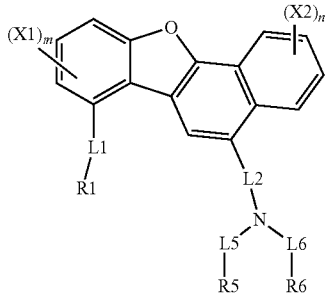

In Chemical Formulae 3 and 4,

L1, L2, R1, R2, X1, X2, m and n have the same definitions as in Chemical Formula 1, L3 to L6 are each independently a direct bond; or a substituted or unsubstituted arylene group having 6 to 60 carbon atoms, R3 and R4 are each independently a substituted or unsubstituted aryl group having 6 to 60 carbon atoms; or a substituted or unsubstituted heteroaryl group having 2 to 60 carbon atoms, and R5 and R6 are each independently a substituted or unsubstituted aryl group having 6 to 60 carbon atoms.

When the substituent positions correspond to the positions of Chemical Formulae 2 to 4, an energy level favorable to use in a highest occupied molecular orbital (HOMO) energy level and an organic material layer of a lowest unoccupied molecular orbital (LUMO) device, and by having a high T1 value, a long lifetime device with superior hole transfer ability and thermal stability may be obtained. Herein, the T1 value means an energy level value in a triplet state.

In one embodiment of the present application, Chemical Formula 1 may be represented by any one of the following Chemical Formulae 3-1 to 3-3.

[Chemical Formula 3-1]

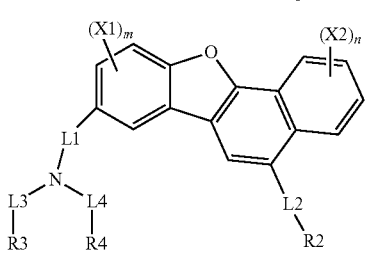

[Chemical Formula 3-2]

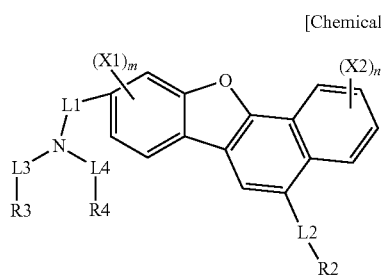

[Chemical Formula 3-3]

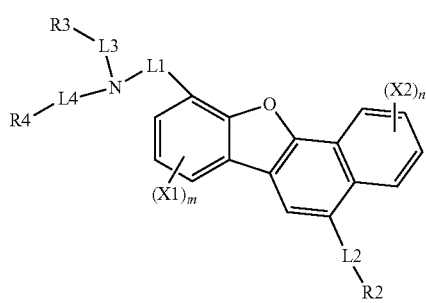

In Chemical Formulae 3-1 to 3-3,

L1, L2, R2, X1, X2, m and n have the same definitions as in Chemical Formula 1,

L3 and L4 are each independently a direct bond; or a substituted or unsubstituted arylene group having 6 to 60 carbon atoms, R3 and R4 are each independently a substituted or unsubstituted aryl group having 6 to 60 carbon atoms; or a substituted or unsubstituted heteroaryl group having 2 to 60 carbon atoms.

In one embodiment of the present application, Chemical Formula 1 may be represented by any one of the following Chemical Formulae 4-1 to 4-3.

[Chemical Formula 4-1]

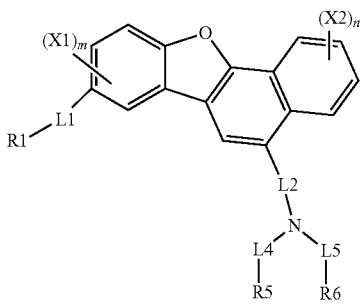

[Chemical Formula 4-2]

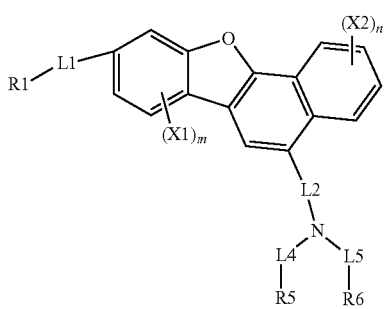

[Chemical Formula 4-3]

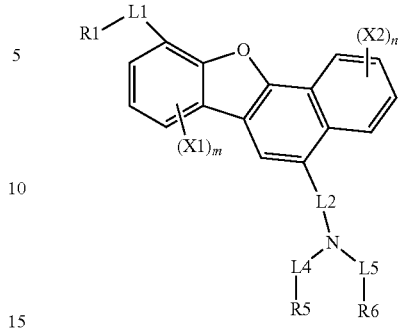

In Chemical Formulae 4-1 to 4-3,

L1, L2, R1, X1, X2, m and n have the same definitions as in Chemical Formula 1,

L4 and L5 are each independently a direct bond; or a substituted or unsubstituted arylene group having 6 to 60 carbon atoms, R5 and R6 are each independently a substituted or unsubstituted aryl group having 6 to 60 carbon atoms.

In one embodiment of the present application, L3 to L6 may be each independently a direct bond; or a substituted or unsubstituted arylene group.

In one embodiment of the present application, L3 is a direct bond.

In one embodiment of the present application, L4 is a direct bond.

In one embodiment of the present application, L5 is a direct bond.

In one embodiment of the present application, L6 is a direct bond.

In one embodiment of the present application, L3 to L6 may be each independently a substituted or unsubstituted arylene group.

In one embodiment of the present application, L3 is a phenylene group.

In one embodiment of the present application, L4 is a phenylene group.

In one embodiment of the present application, L5 is a phenylene group.

In one embodiment of the present application, L6 is a phenylene group.

In one embodiment of the present application, R3 and R4 are each independently a substituted or unsubstituted aryl group; or a substituted or unsubstituted heteroaryl group, and R5 and R6 may be a substituted or unsubstituted aryl group.

In one embodiment of the present application, R3 and R4 are each independently a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted spirobifluorenyl group; or a substituted or unsubstituted dibenzofuran group.

In one embodiment of the present application, R3 and R4 are each independently a phenyl group, a biphenyl group, a terphenyl group, a naphthyl group, a fluorenyl group unsubstituted or substituted with an alkyl group, a spirobifluorenyl group, a dibenzofuran group unsubstituted or substituted with an alkyl group.

In one embodiment of the present application, R3 and R4 are the same.

In one embodiment of the present application, R3 and R4 are different.

In one embodiment of the present application, R5 and R6 are each independently a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; or a substituted or unsubstituted spirobifluorenyl group.

In one embodiment of the present application, R5 and R6 are each independently a phenyl group, a biphenyl group, a terphenyl group, a naphthyl group, a fluorenyl group unsubstituted or substituted with an alkyl group, or a spirobifluorenyl group.

In one embodiment of the present application, R5 and R6 are the same.

In one embodiment of the present application, R5 and R6 are different.

According to one embodiment of the present application, Chemical Formula 1 may be represented by any one of the following compounds, but is not limited thereto.

HT-1

HT-2

HT-3

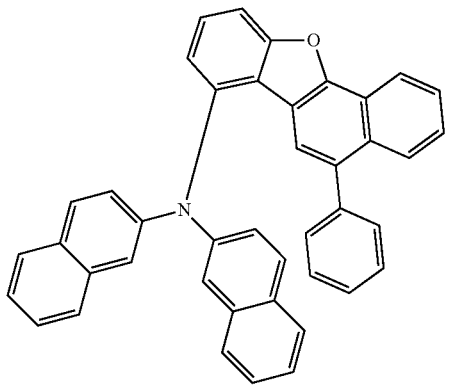

HT-4

HT-5

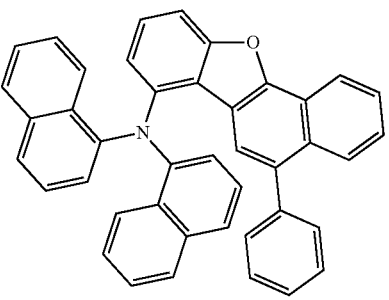

HT-6

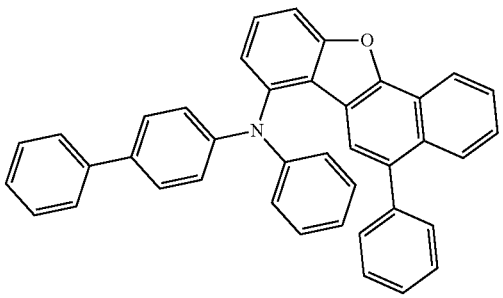

HT-7

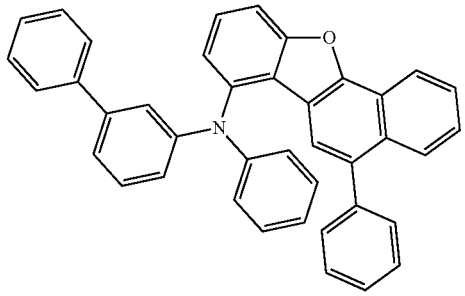

HT-8

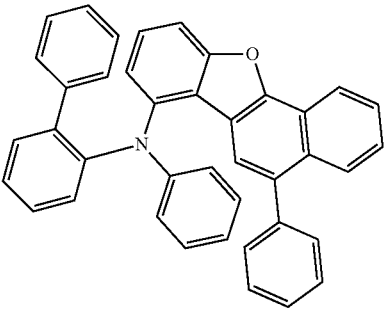

-continued
HT-9
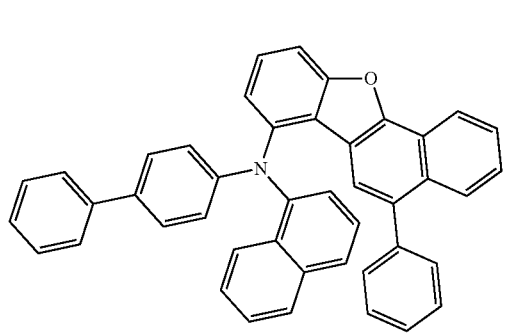
HT-10
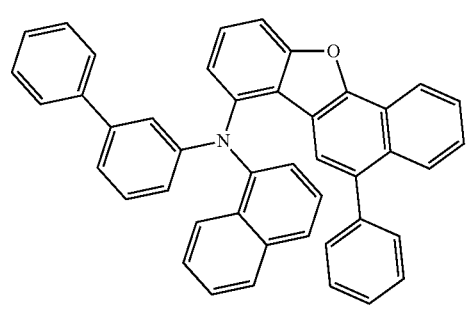
HT-11
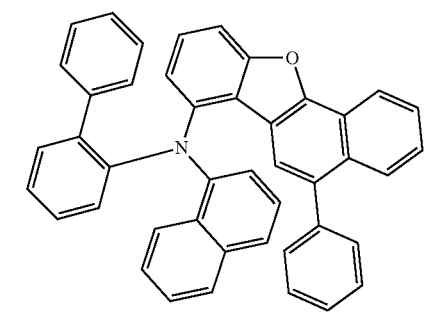
HT-12
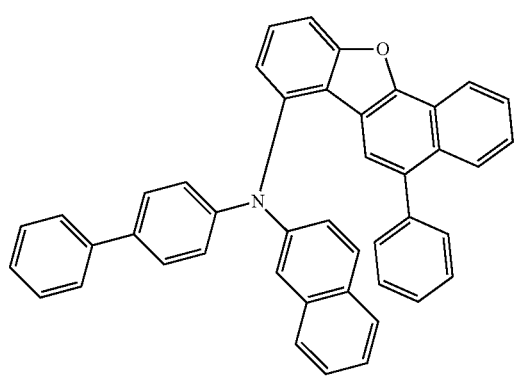
HT-13
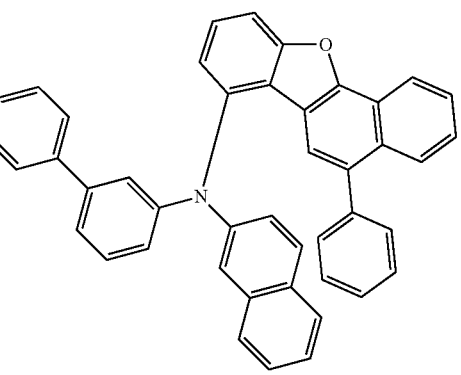
HT-14
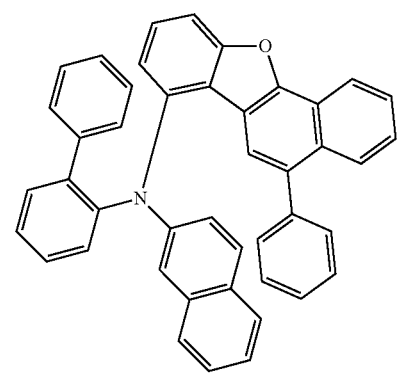
HT-15
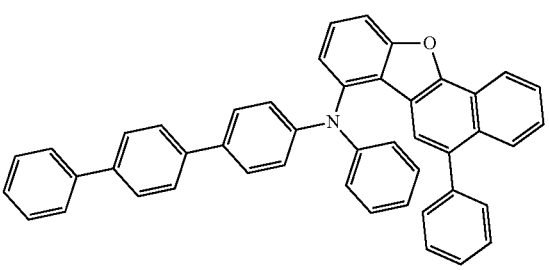
HT-16
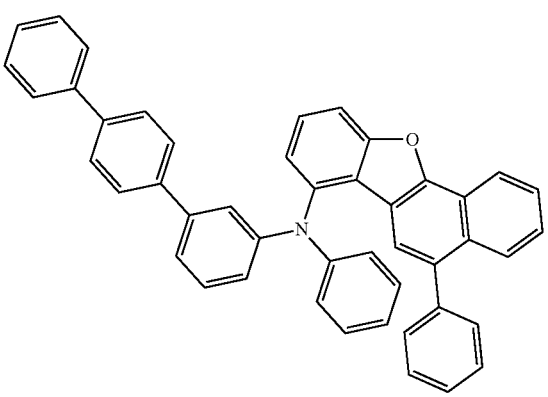

HT-17
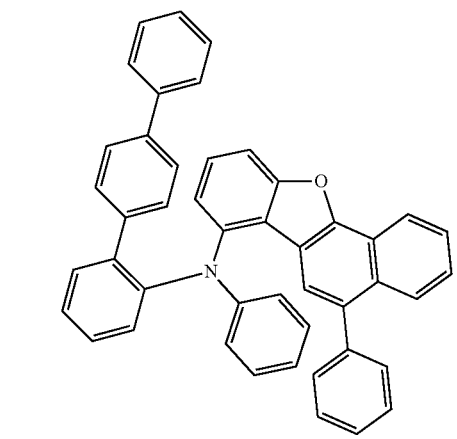
HT-18
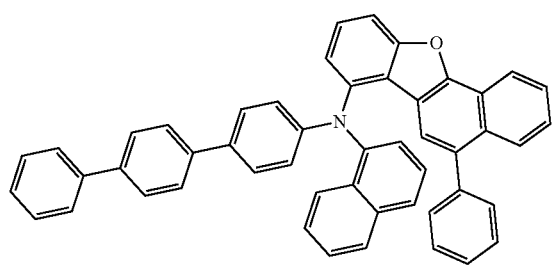
HT-19
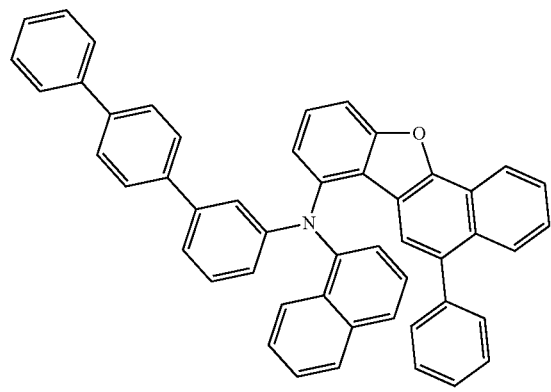
HT-20
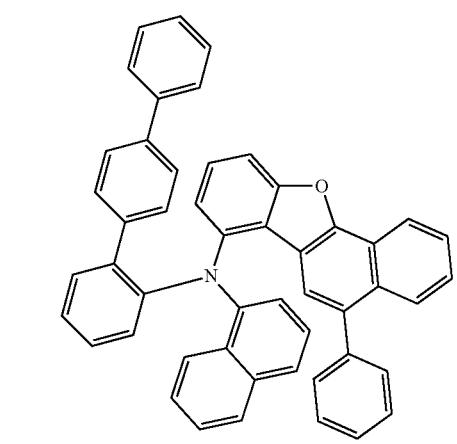
HT-21
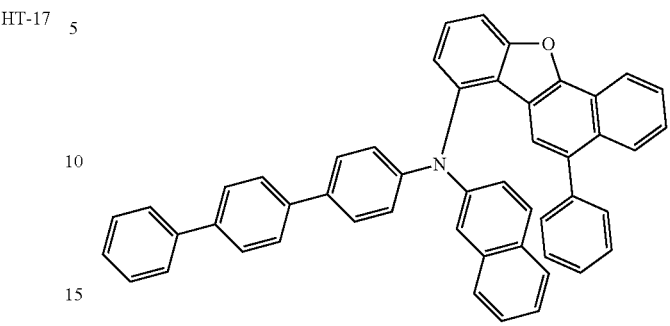
HT-22
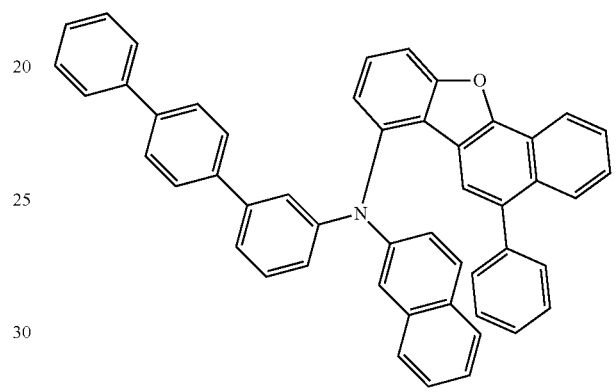
HT-23
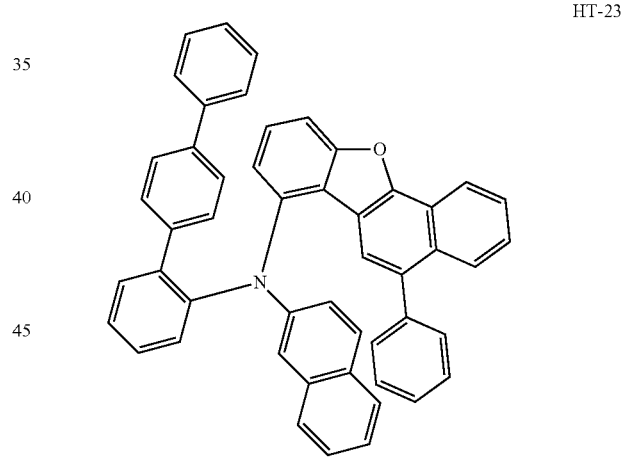
HT-24
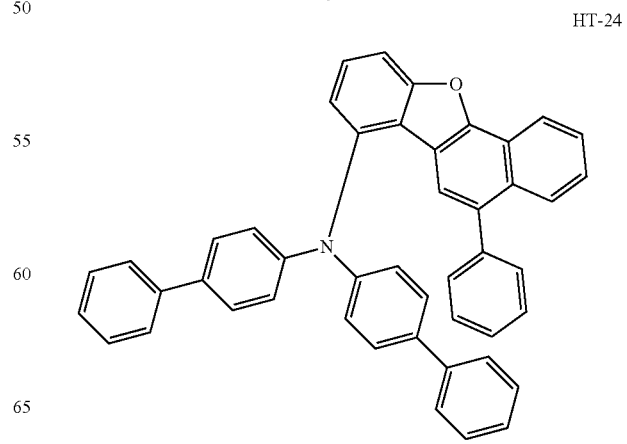

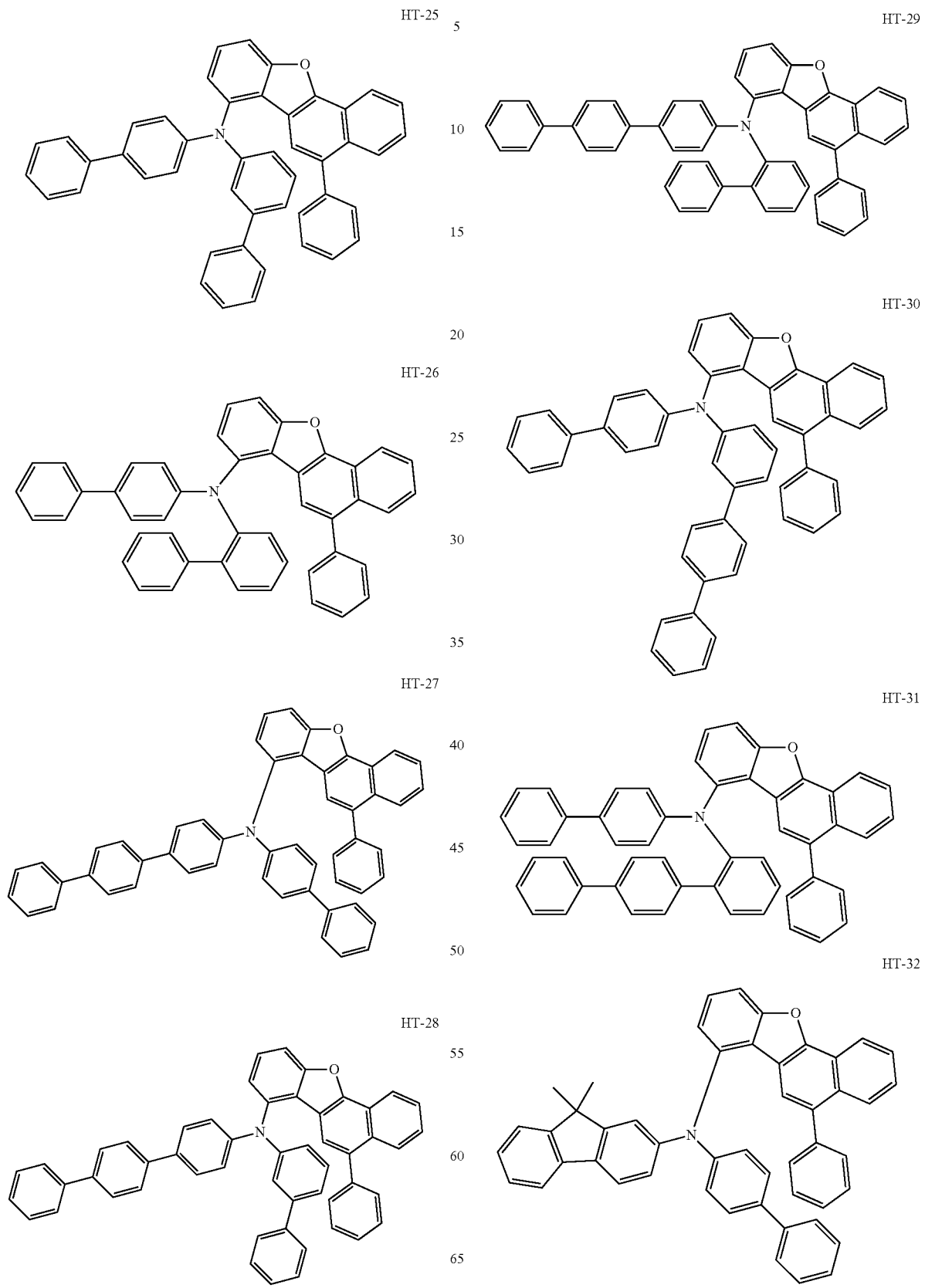

HT-33
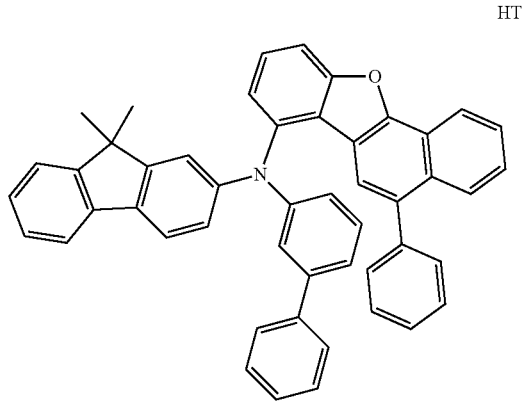
HT-34
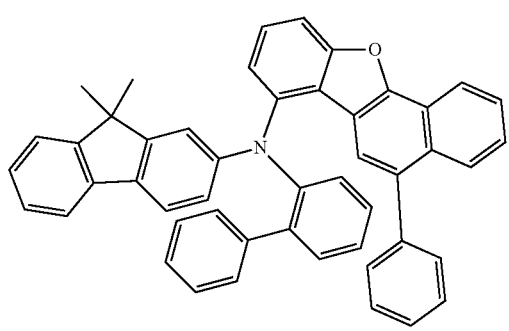
HT-35
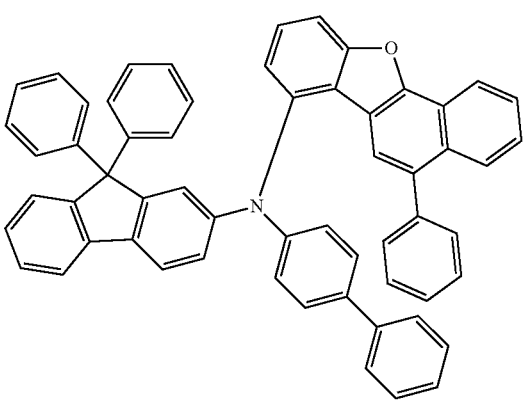
HT-36
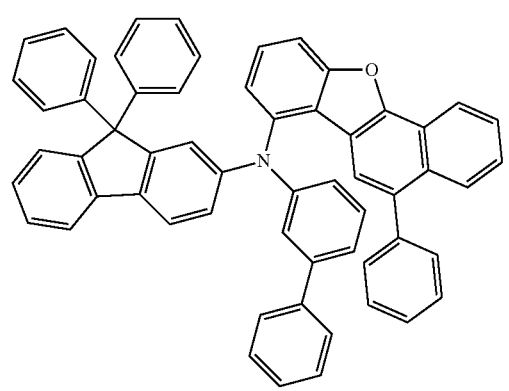
HT-37
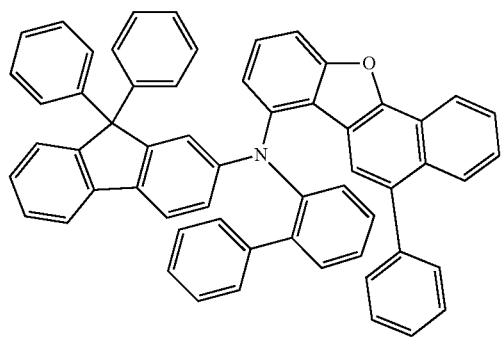
HT-38
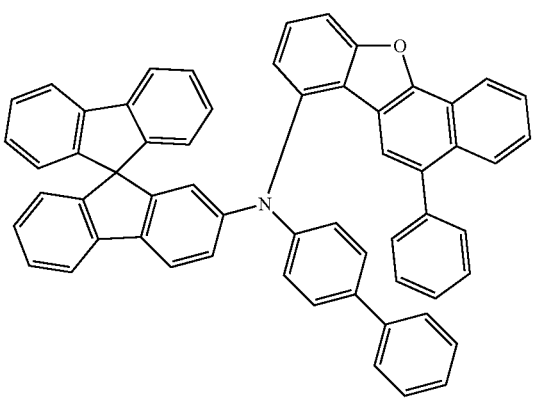
HT-39
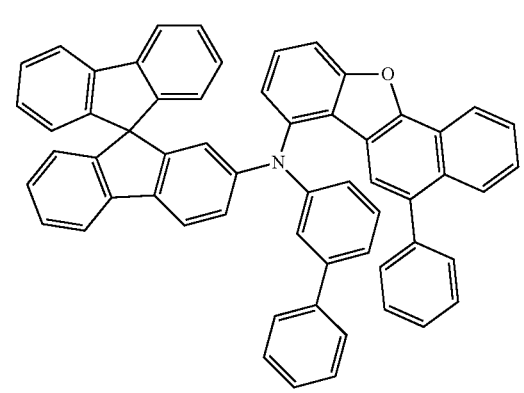
HT-40
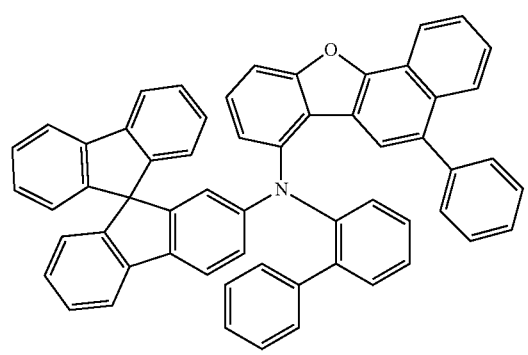

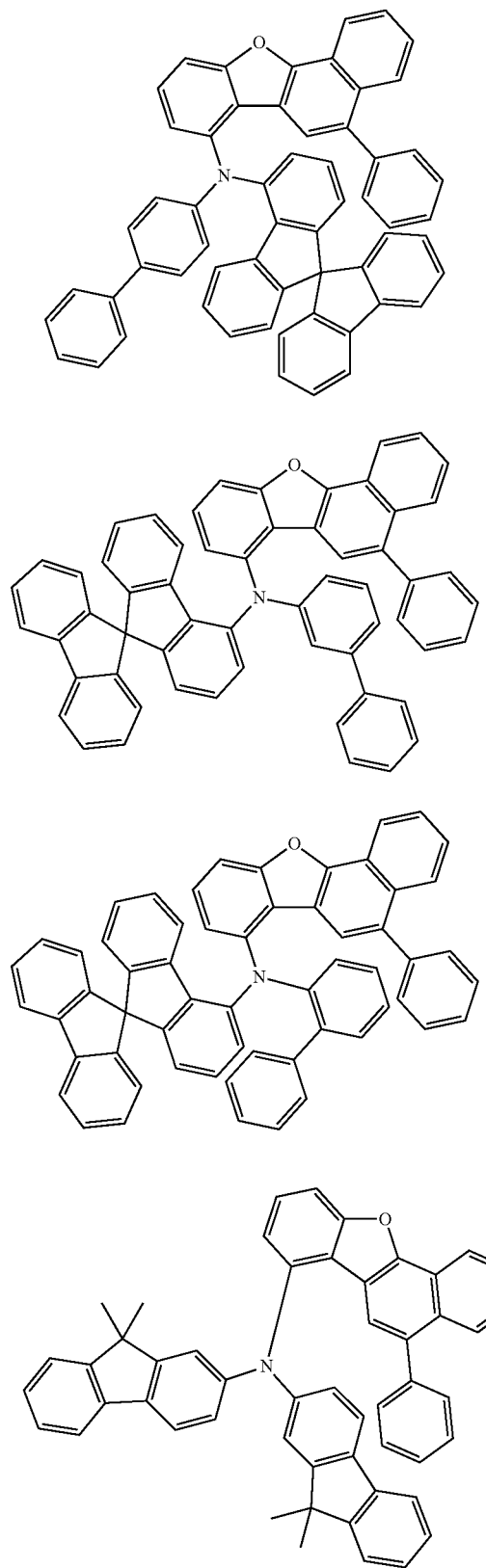
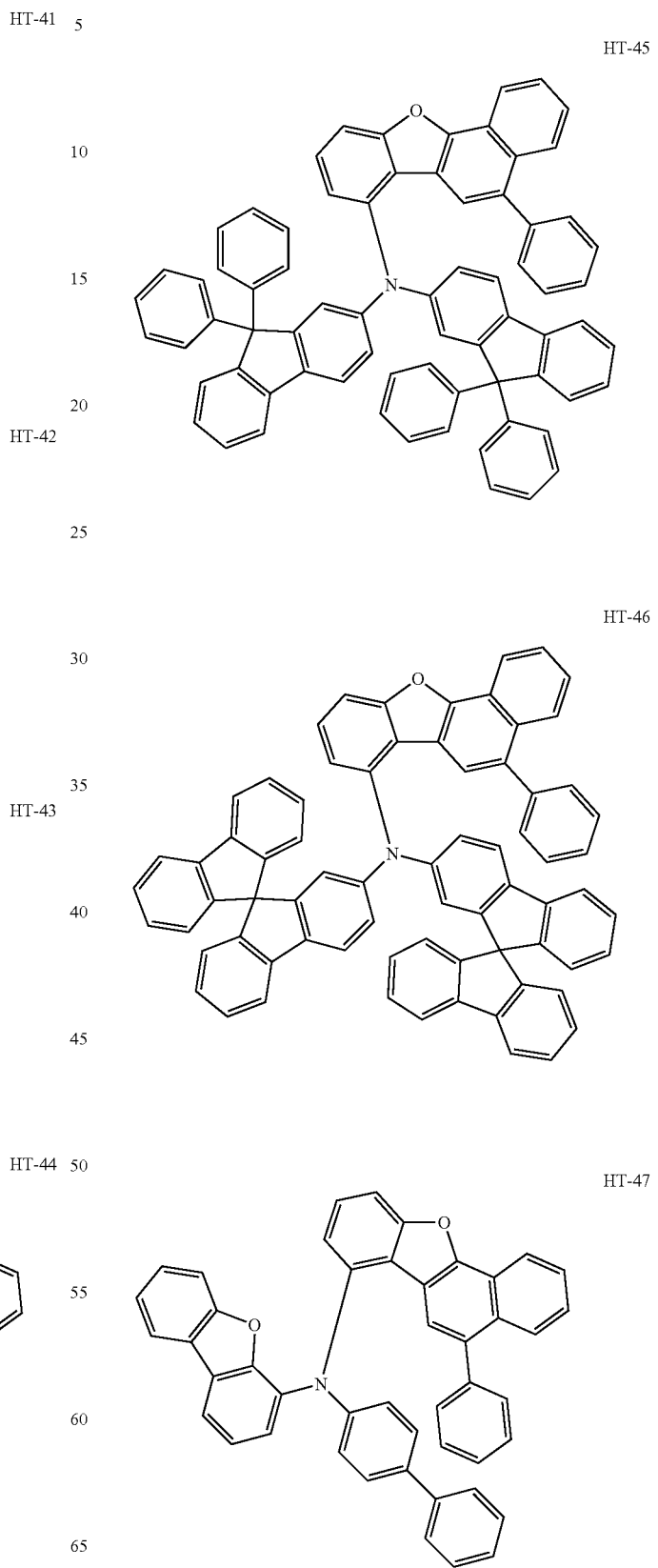

-continued
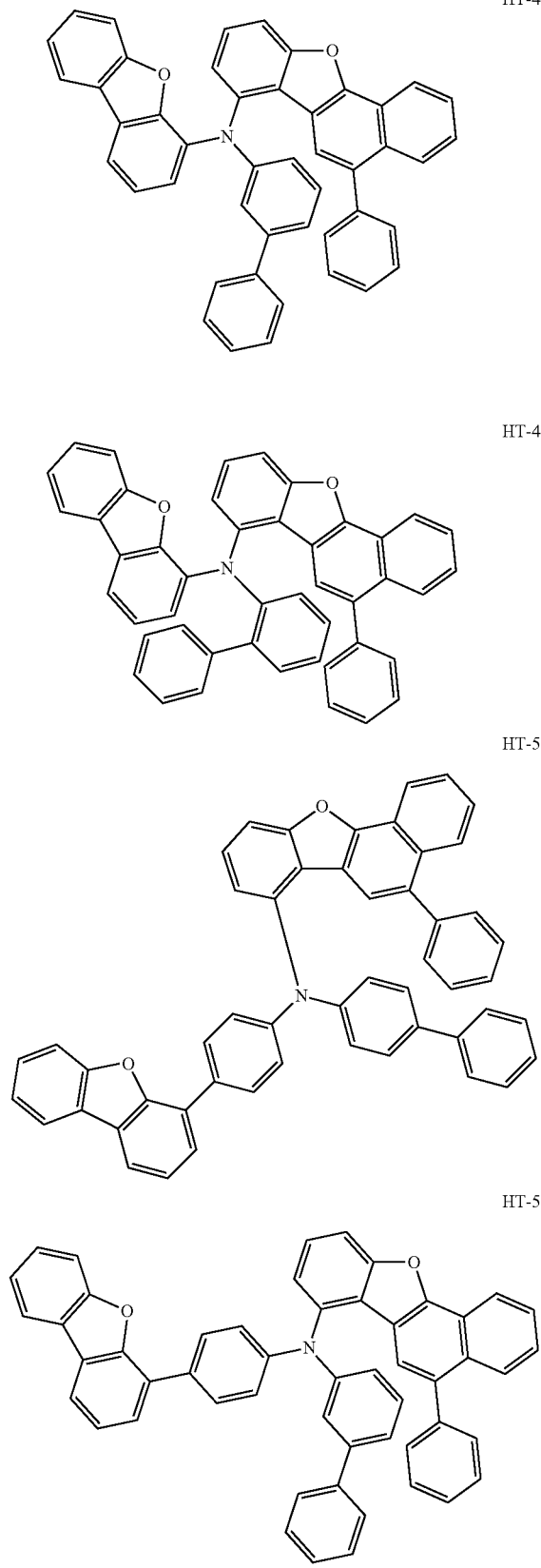
HT-48
HT-49
HT-50
HT-51
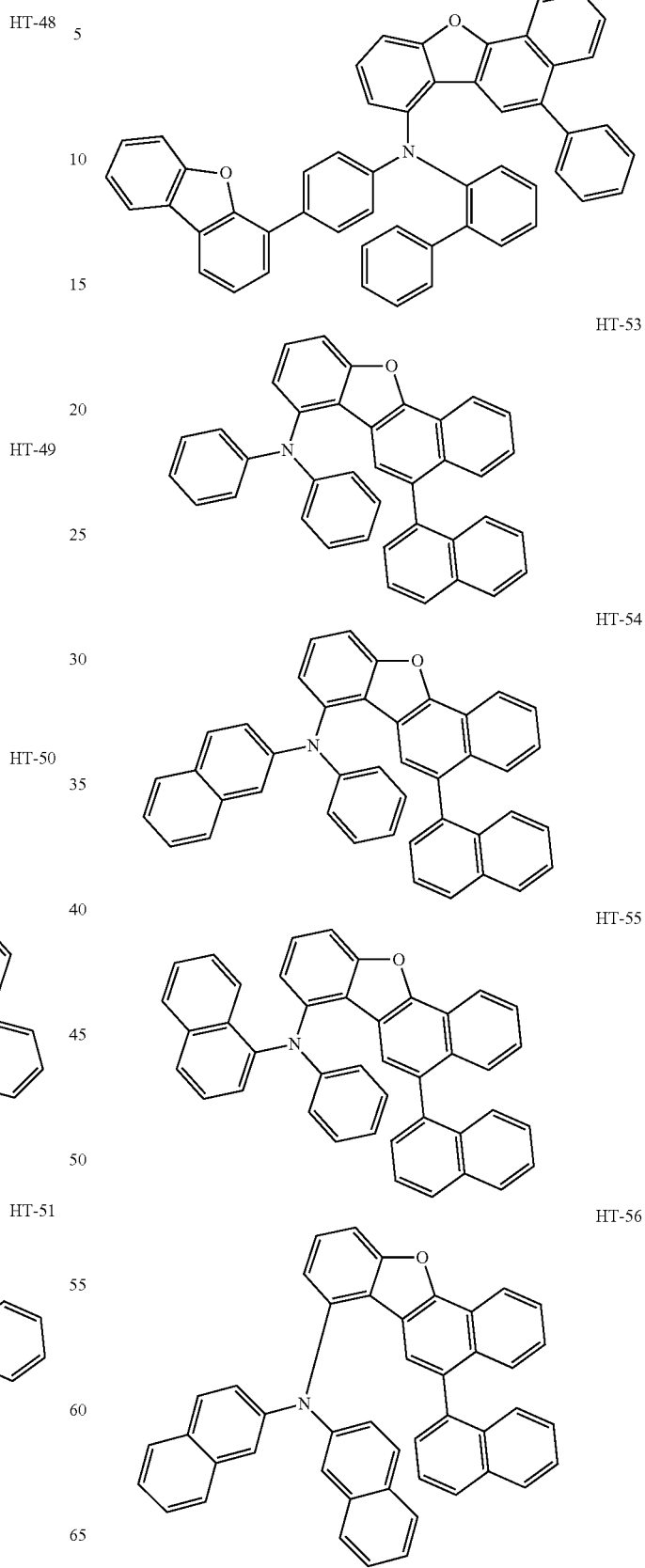
HT-52
HT-53
HT-54
HT-55
HT-56

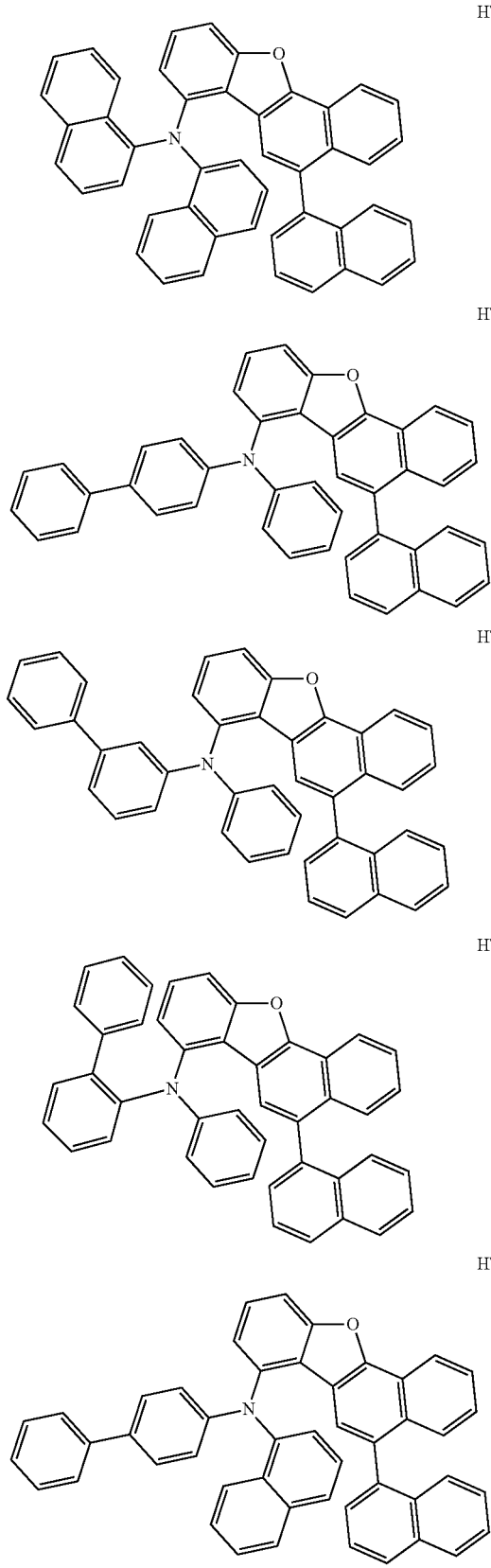
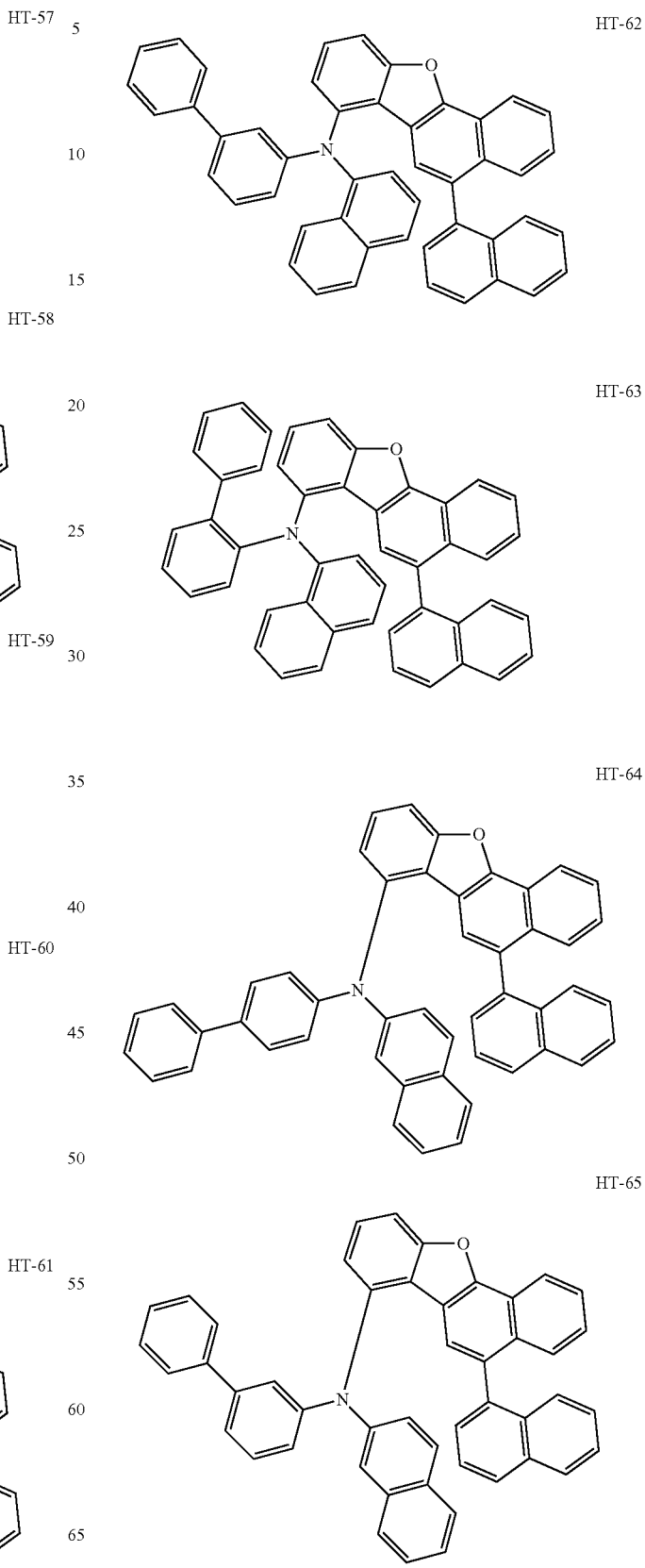

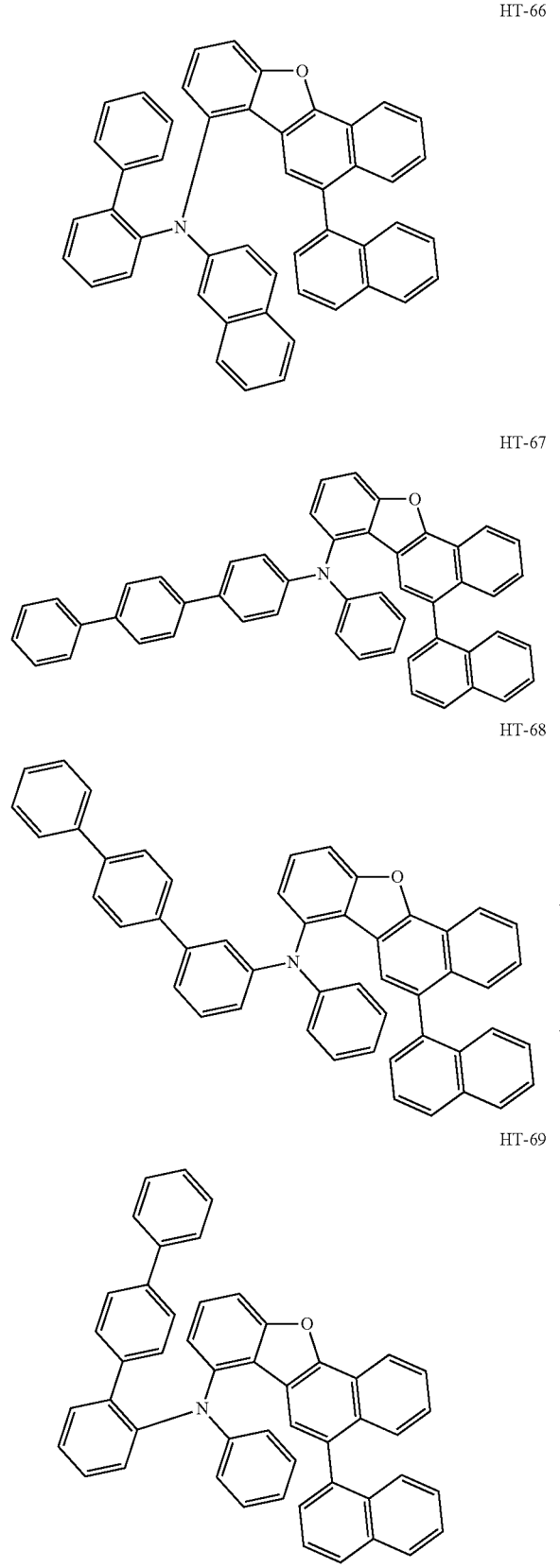

-continued
HT-74
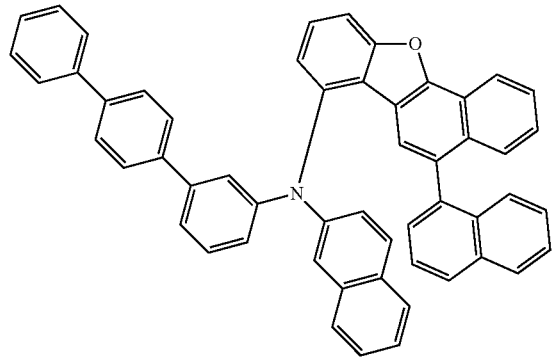
HT-75
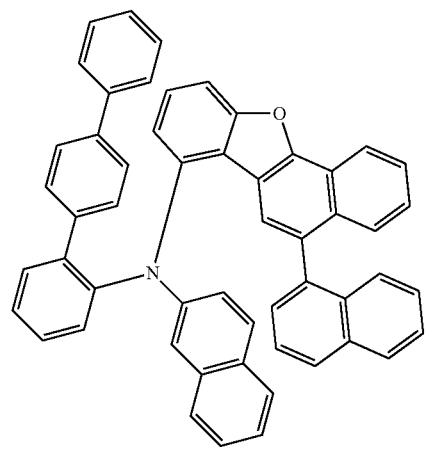
HT-76
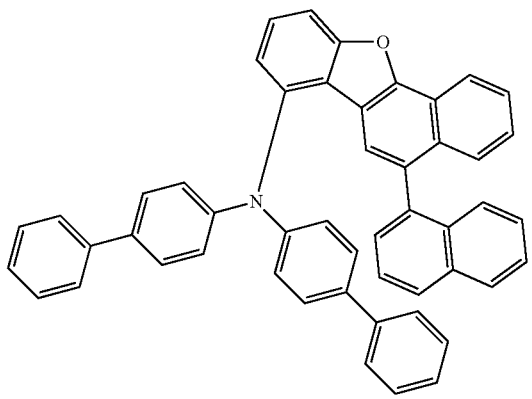
HT-77
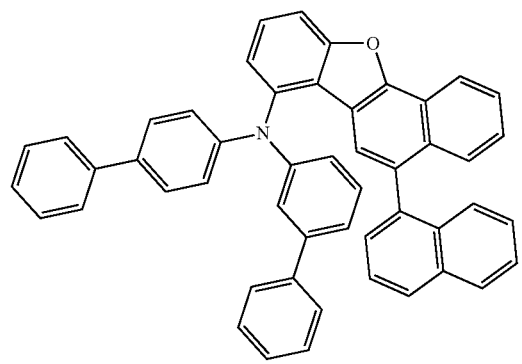
HT-78
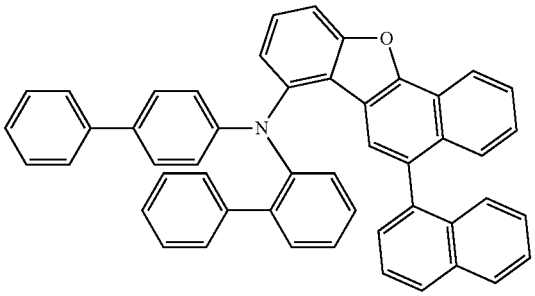
HT-79
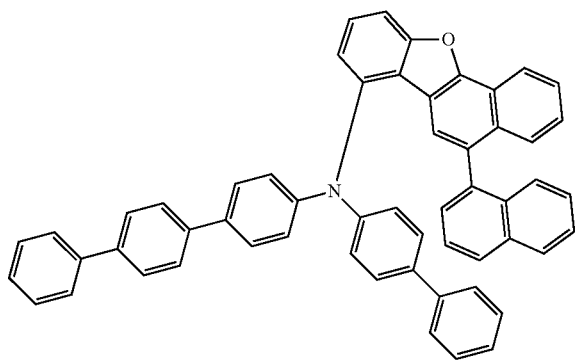
HT-80
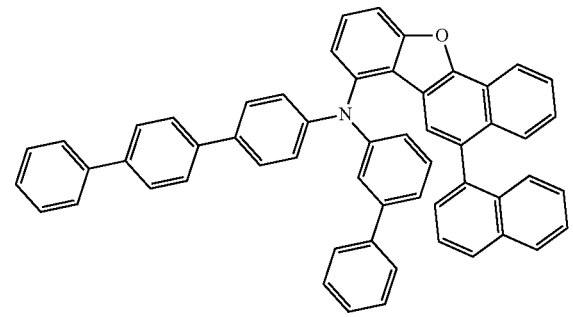
HT-81
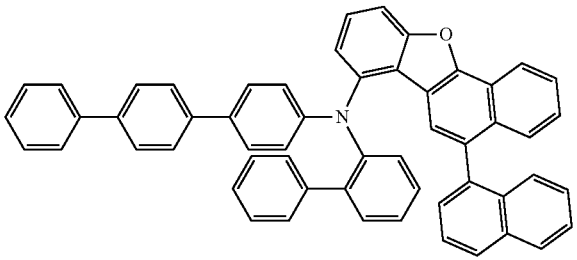

HT-82
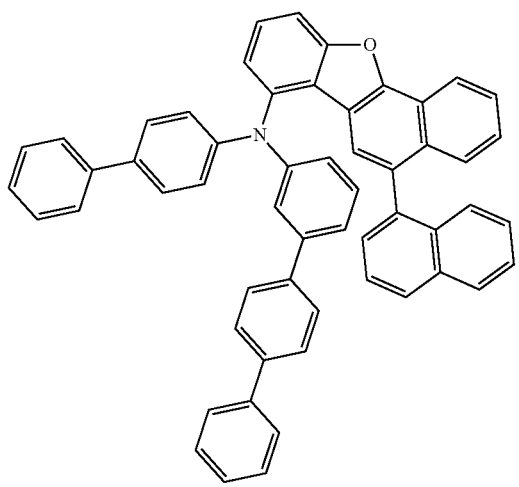
HT-83
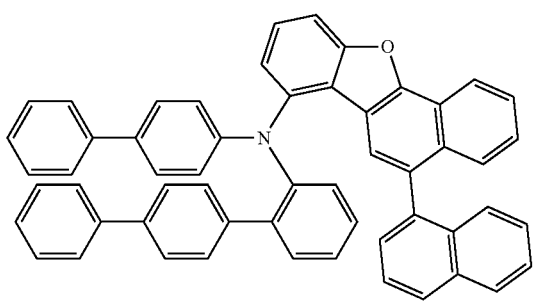
HT-84
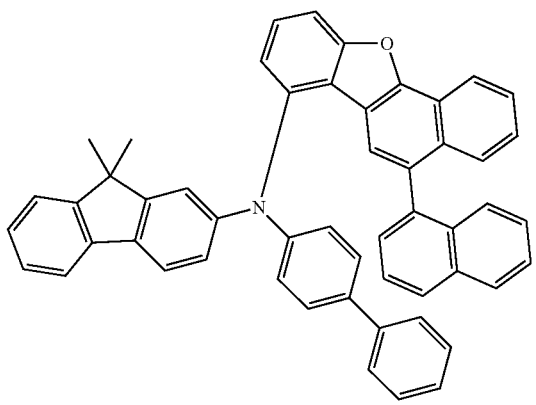
HT-85
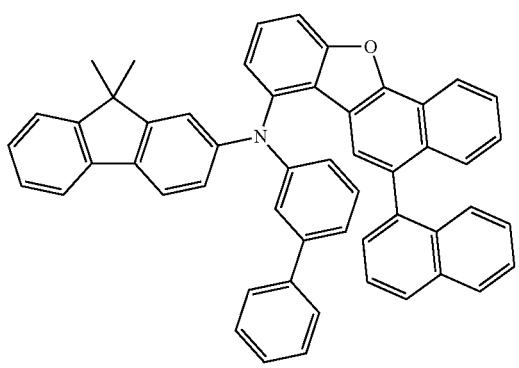
HT-86
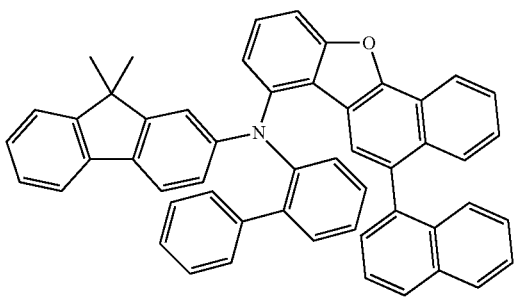
HT-87
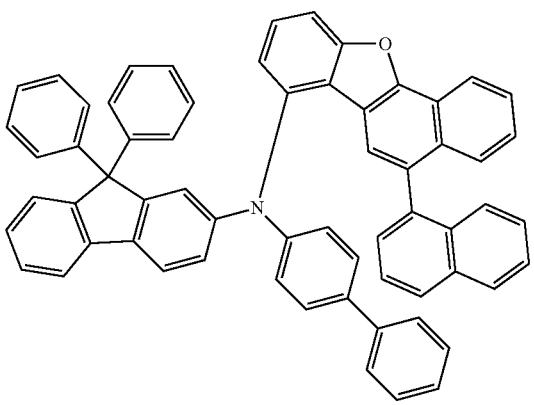
HT-88
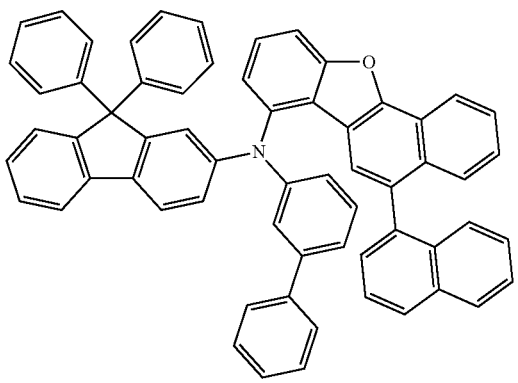
HT-89
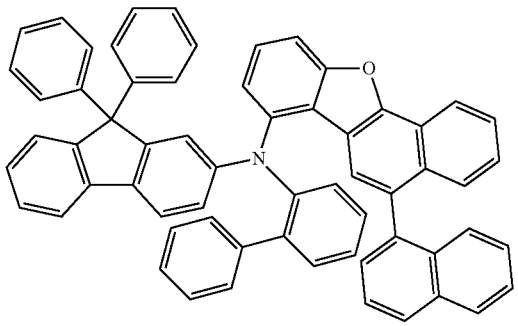

HT-90
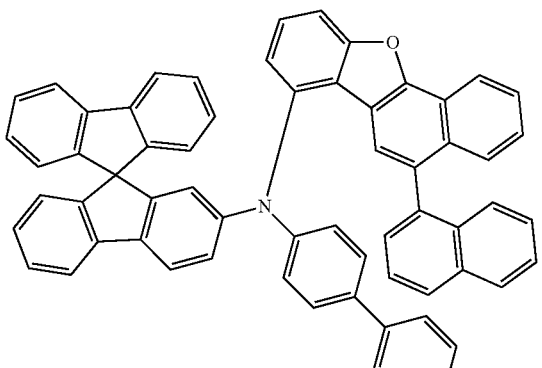
HT-91
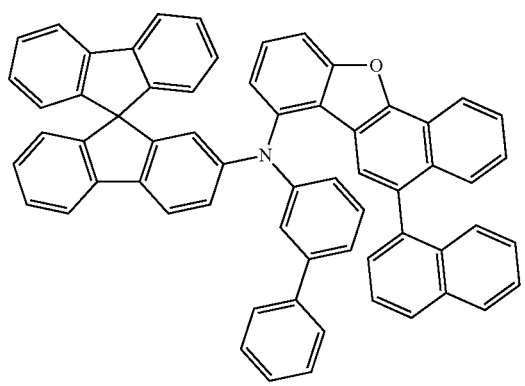
HT-92
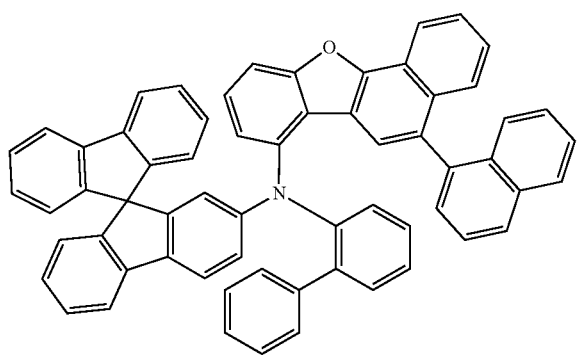
HT-93
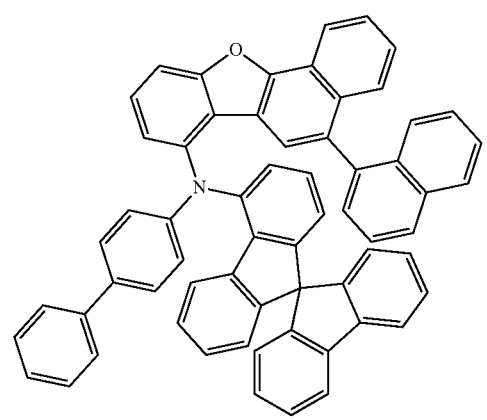
HT-94
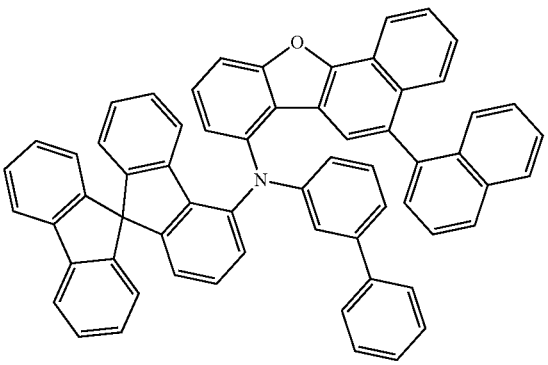
HT-95
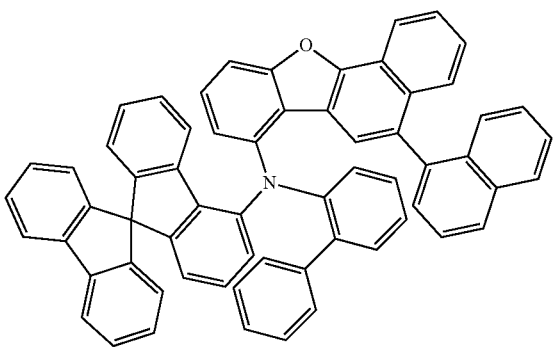
HT-96
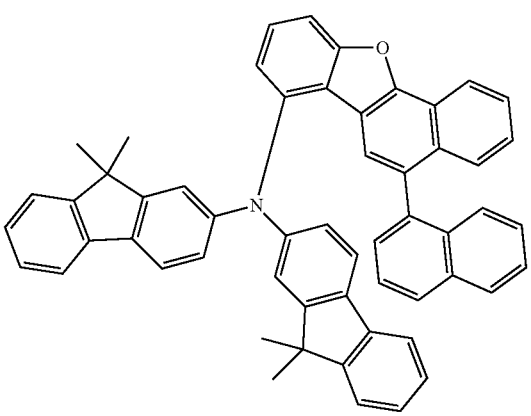

HT-97
HT-98
HT-99
HT-100
HT-101
HT-102
HT-103
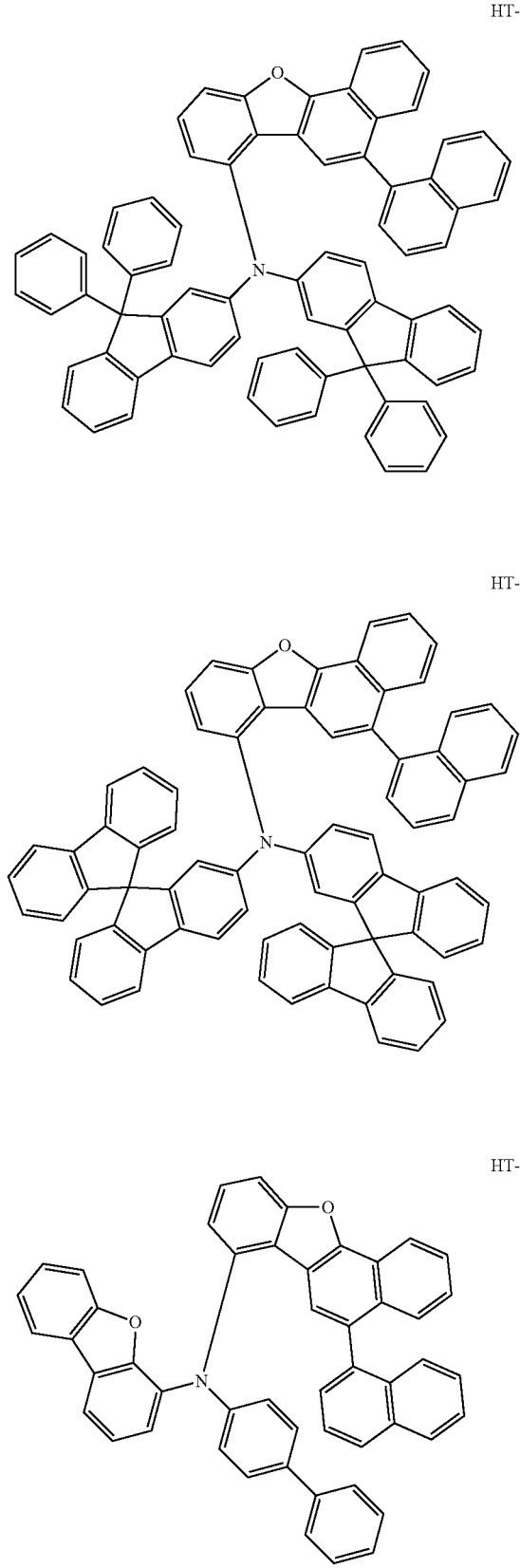
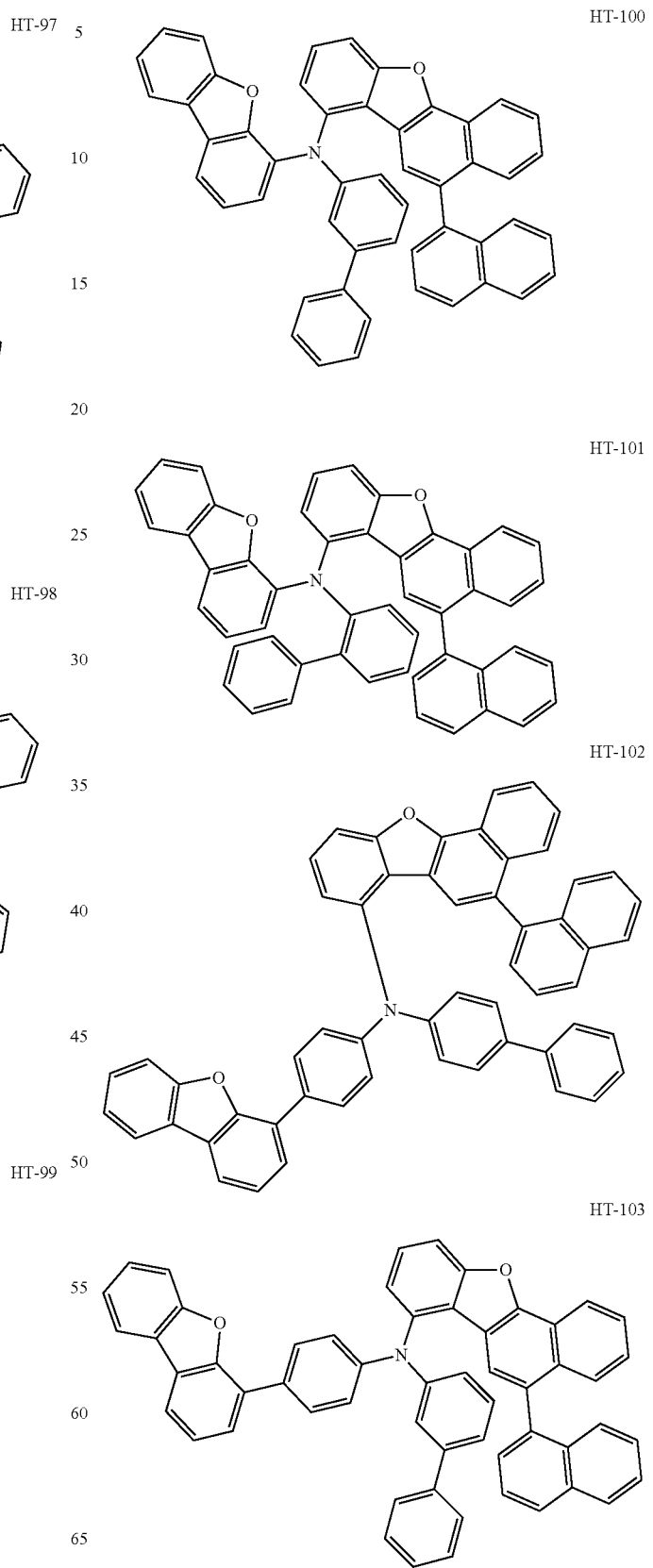

HT-104
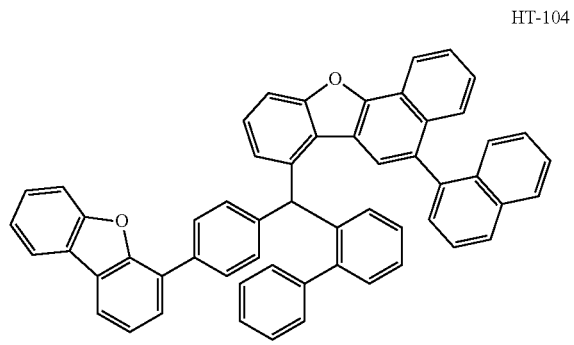
HT-105
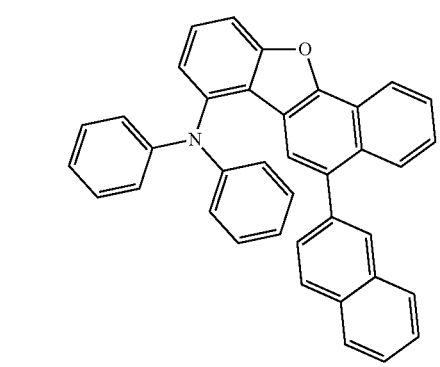
HT-106
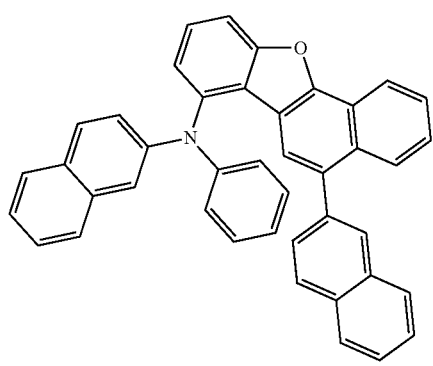
HT-107
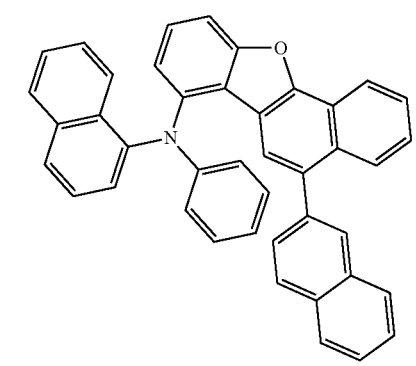
HT-108
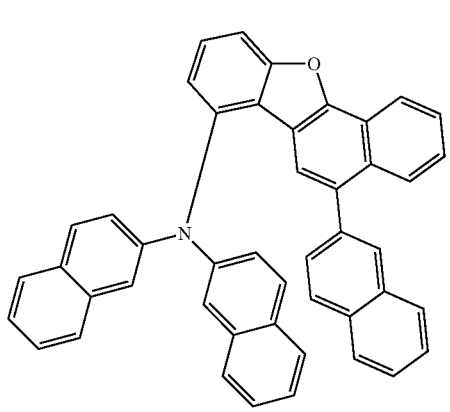
HT-109
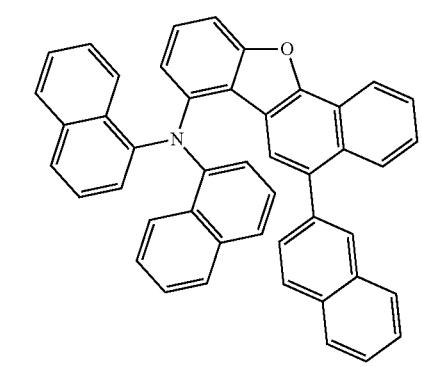
HT-110
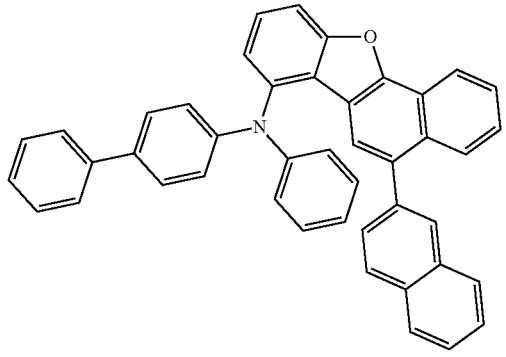
HT-111
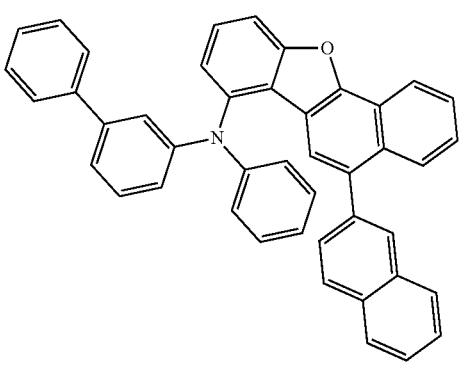

-continued
HT-112
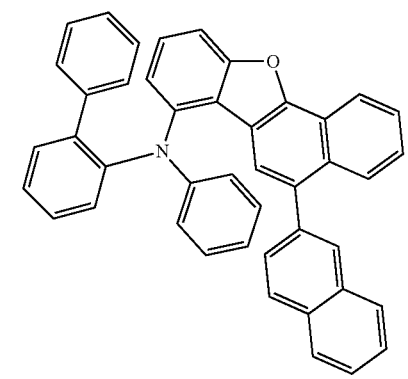
HT-116
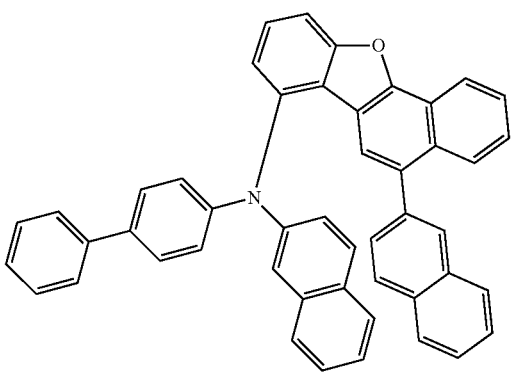
HT-113
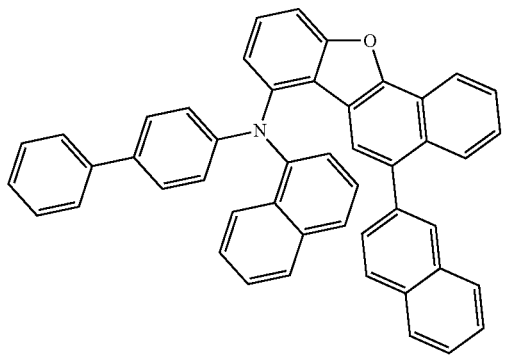
HT-117
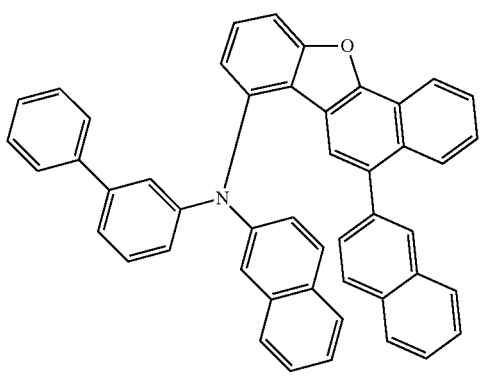
HT-114
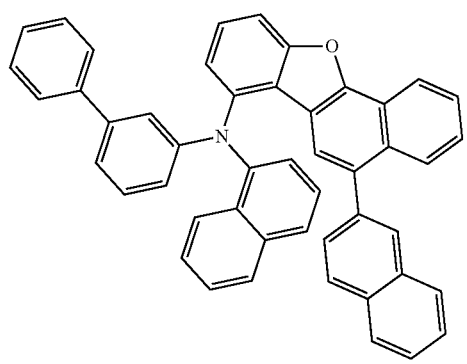
HT-118
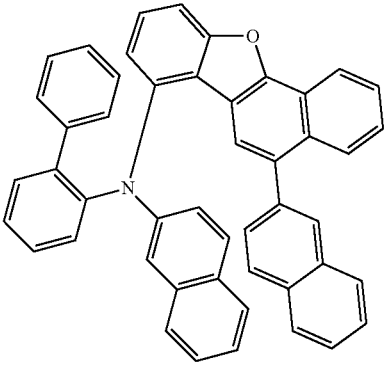
HT-115
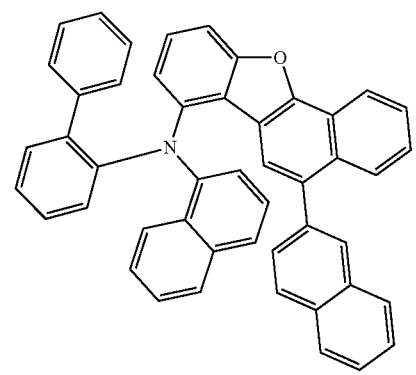
HT-119
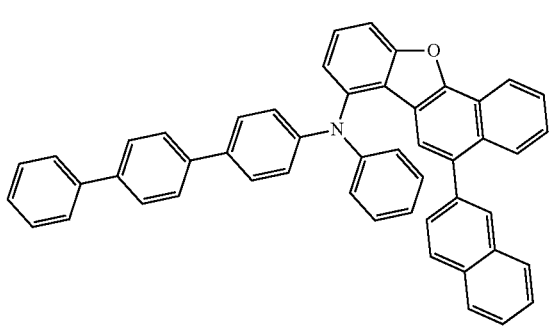

-continued
HT-120
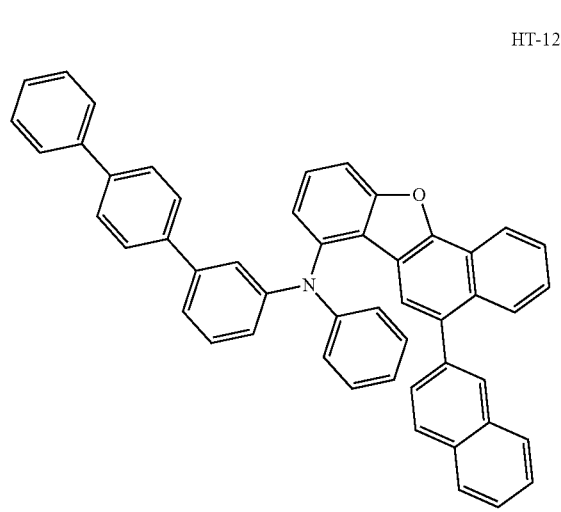
HT-123
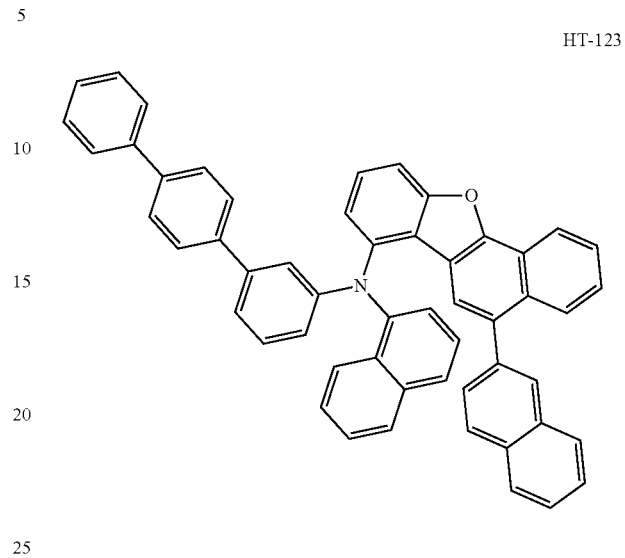
HT-121
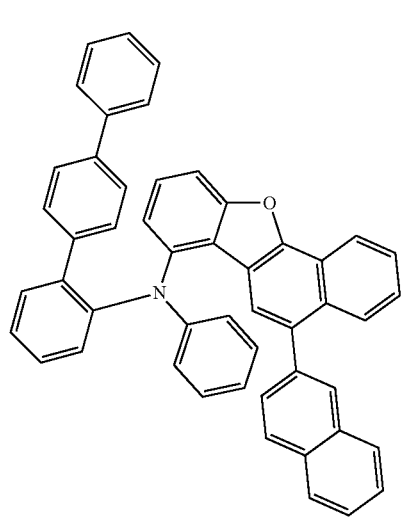
HT-124
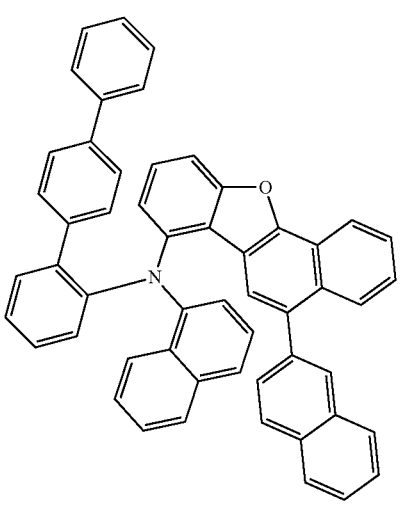
HT-122
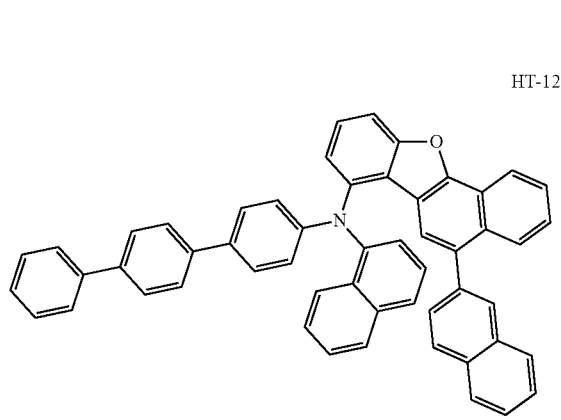
HT-125
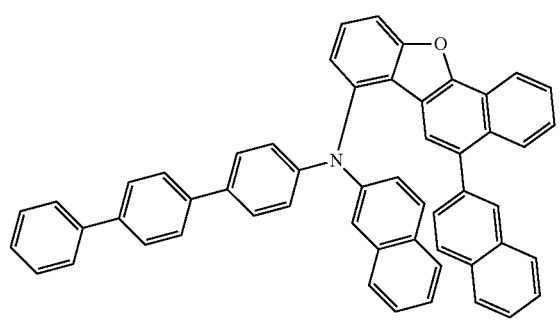

-continued
HT-126
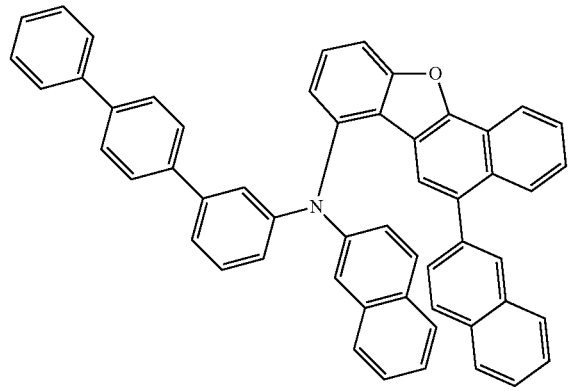
HT-127
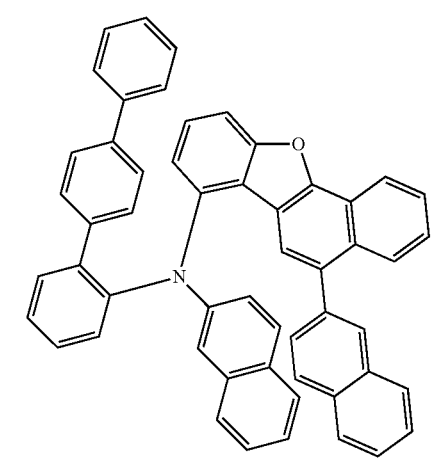
HT-128
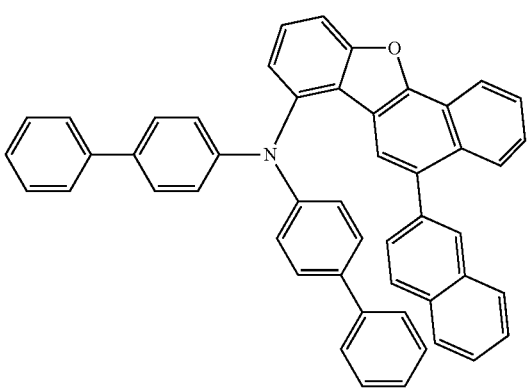
HT-129
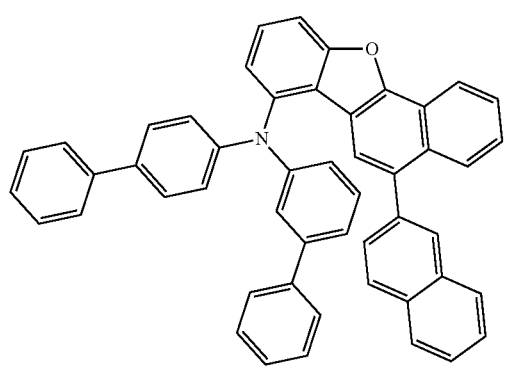
-continued
HT-130
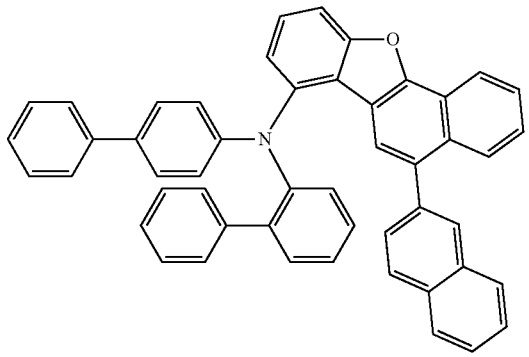
HT-131
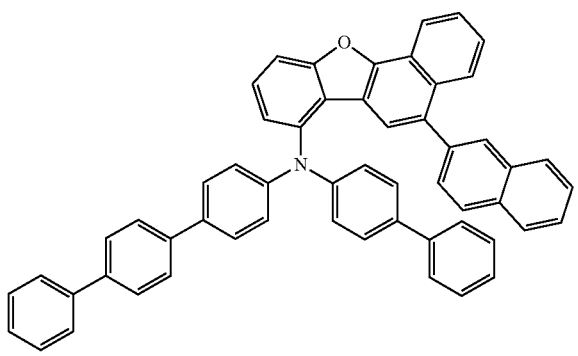
HT-132
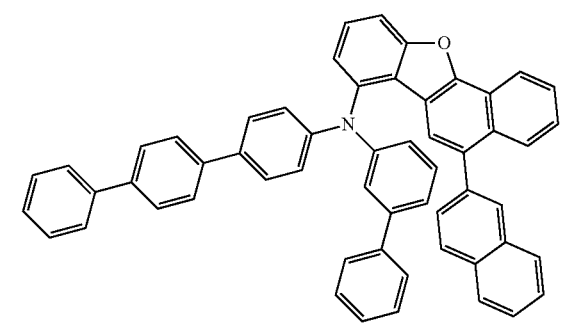
HT-133
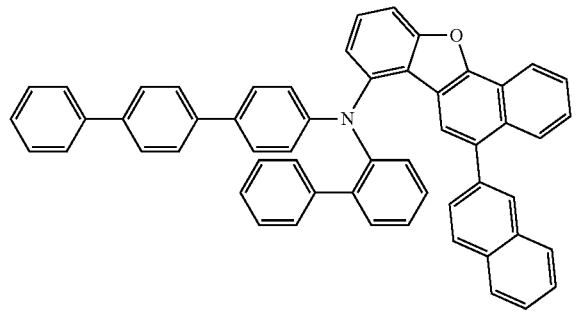

HT-134
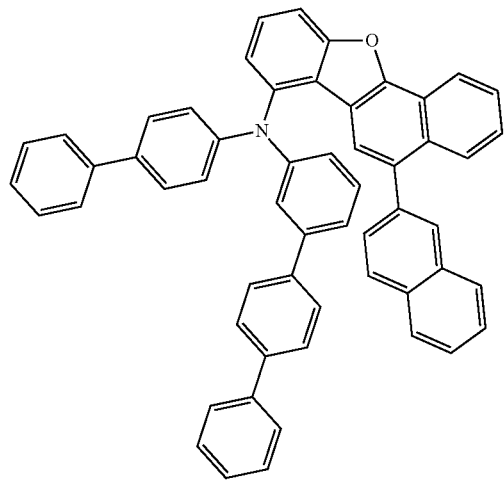
HT-135
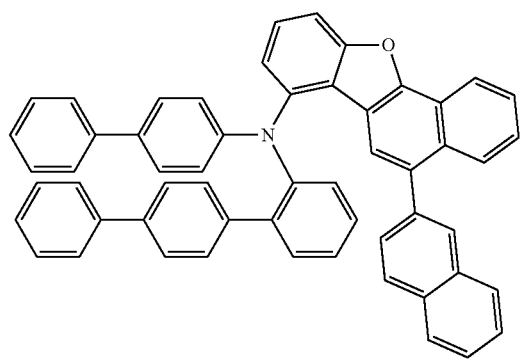
HT-136
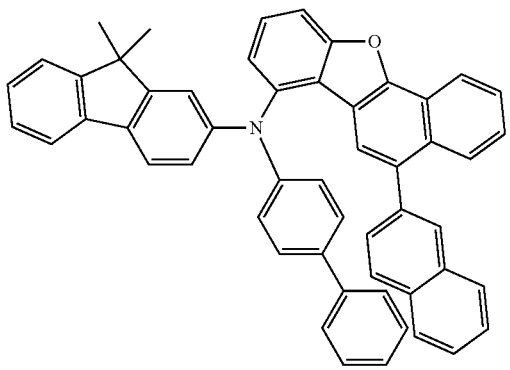
HT-137
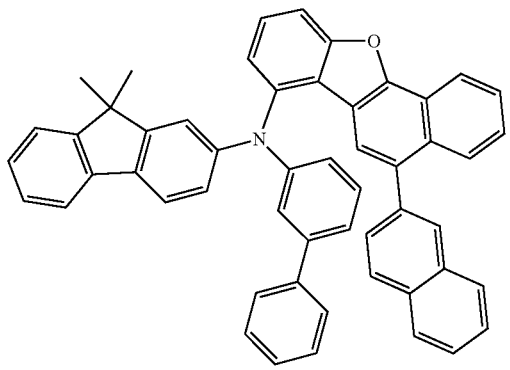
HT-138
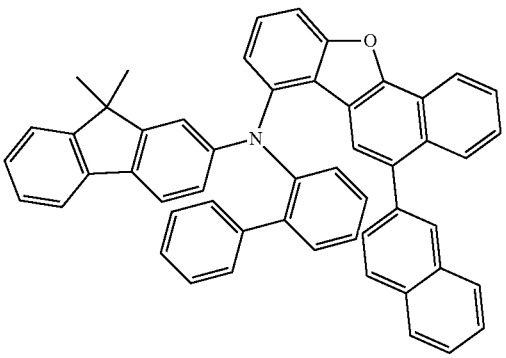
HT-139
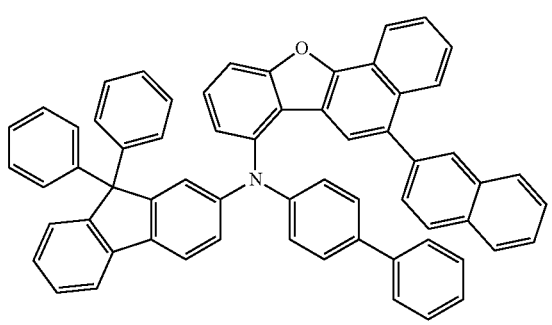 [SMILES: c1ccc(-c2ccc(N(c3ccc4c(c3)C(c3ccccc3)(c3ccccc3)c3ccccc3-4)c3cccc4oc5c6ccccc6c(-c6ccc7ccccc7c6)cc5c34)cc2)cc1]
HT-140
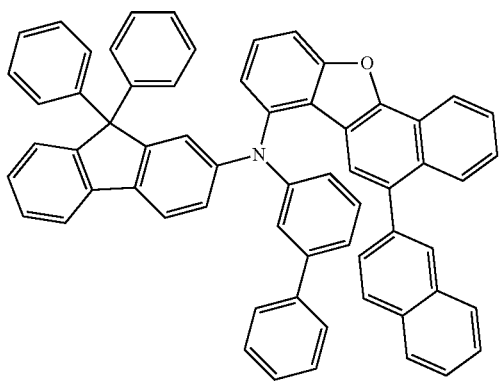
HT-141
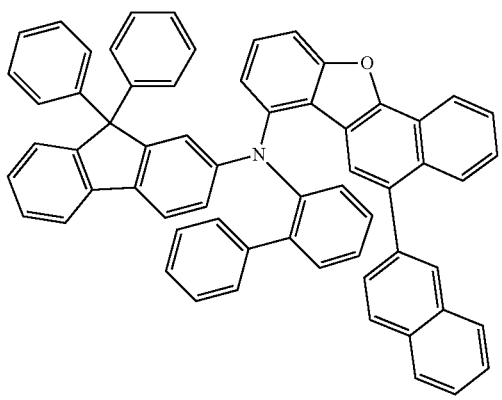

HT-142
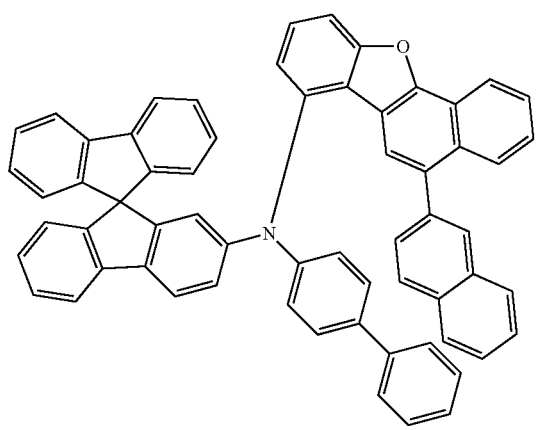
HT-143
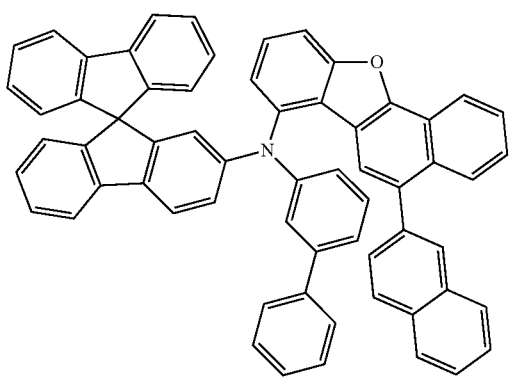
HT-144
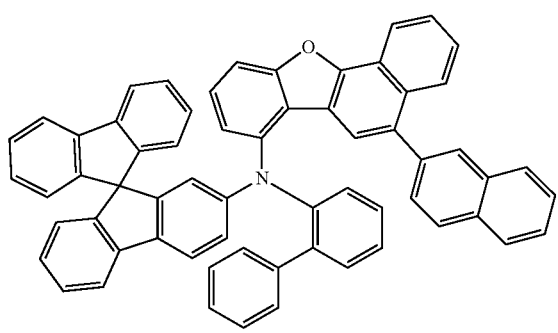
HT-145
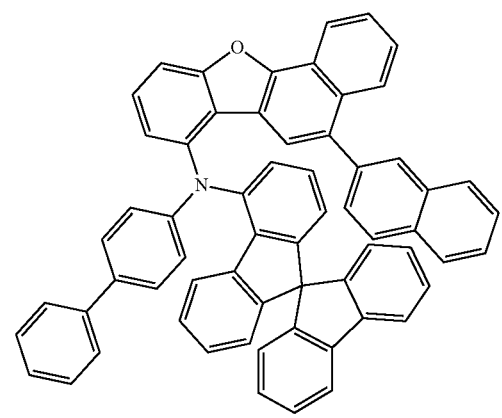
HT-146
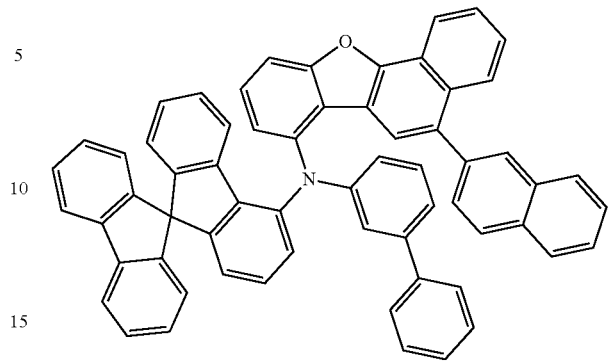
HT-147
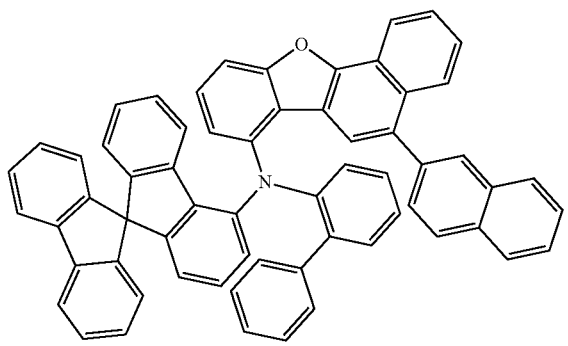
HT-148
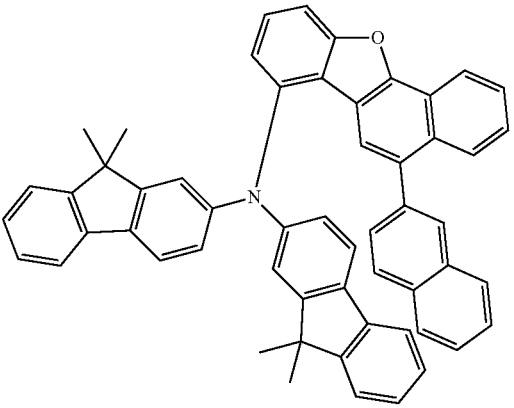
HT-149
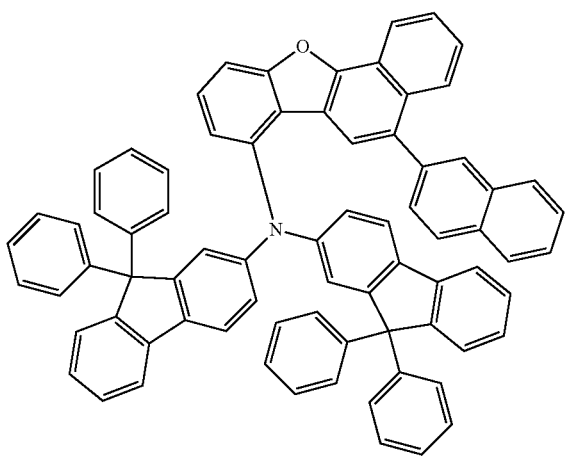

HT-150
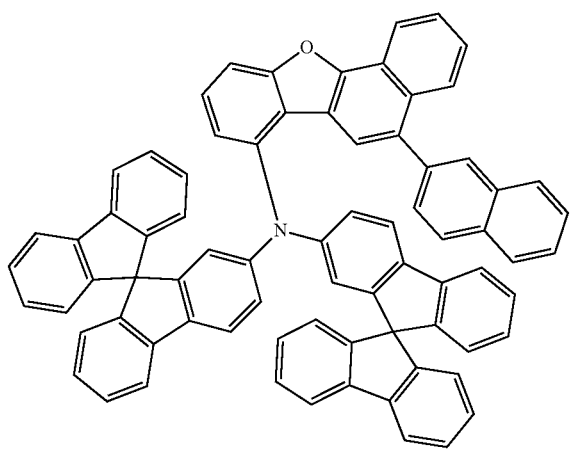
HT-151
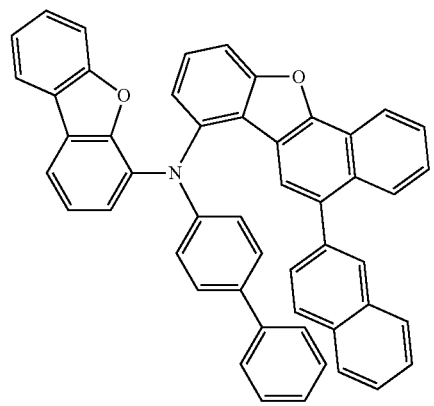
HT-152
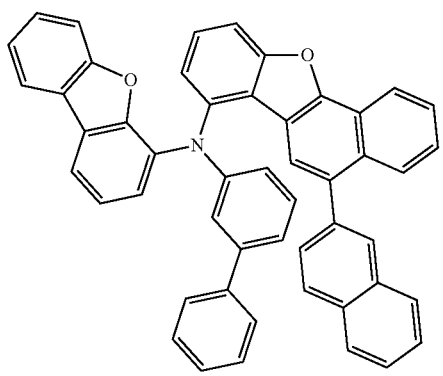
HT-153
HT-154
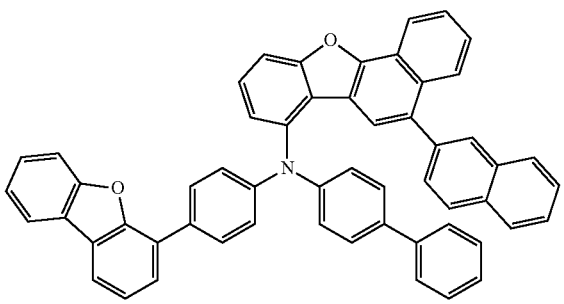
HT-155
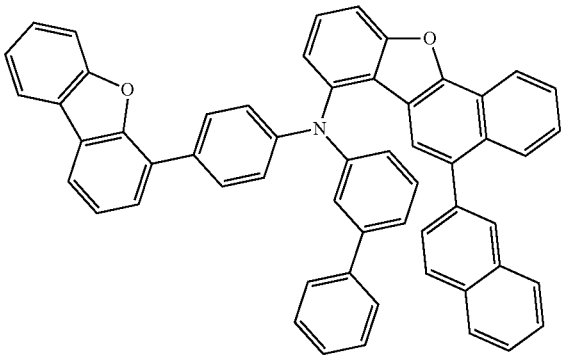
HT-156
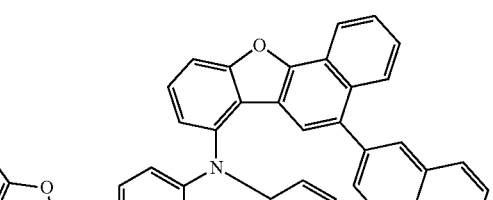
HT-157
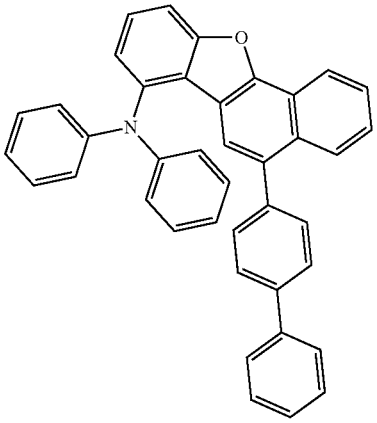

HT-158
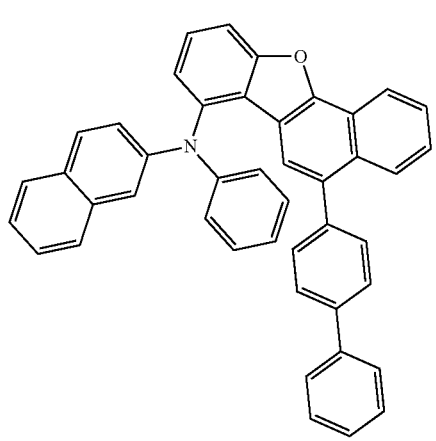
HT-161
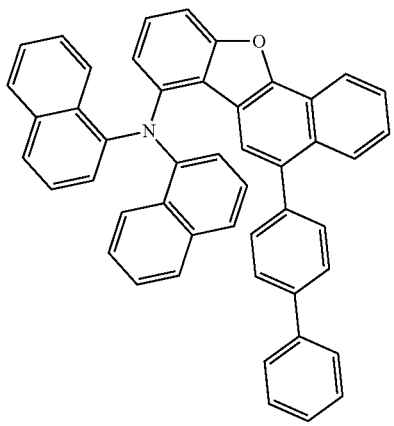
HT-159
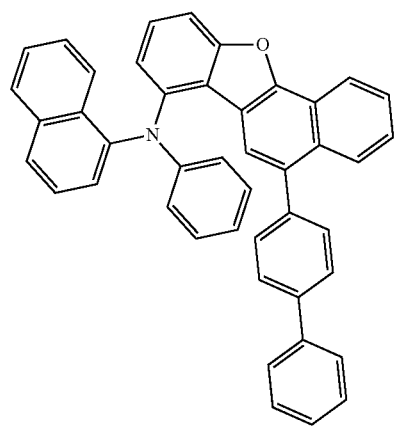
HT-162
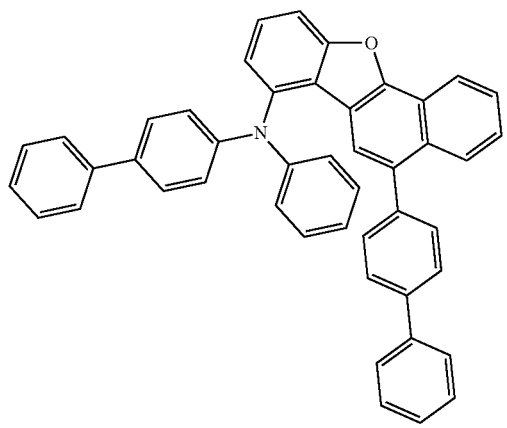
HT-160
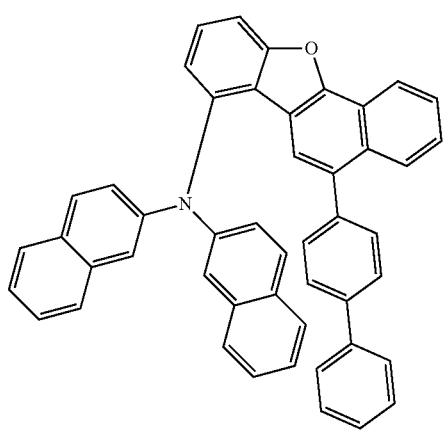
HT-163
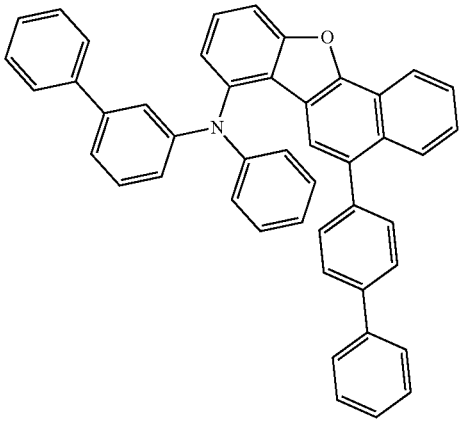

HT-164
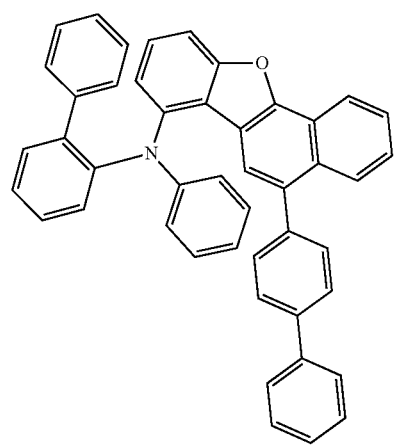
HT-167
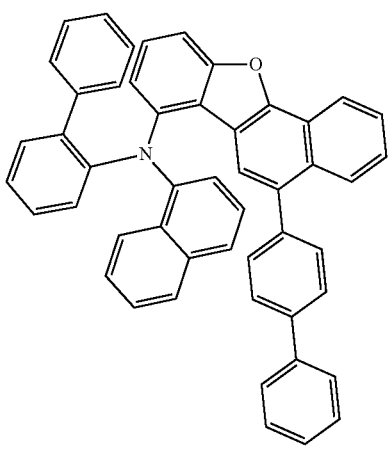
HT-165
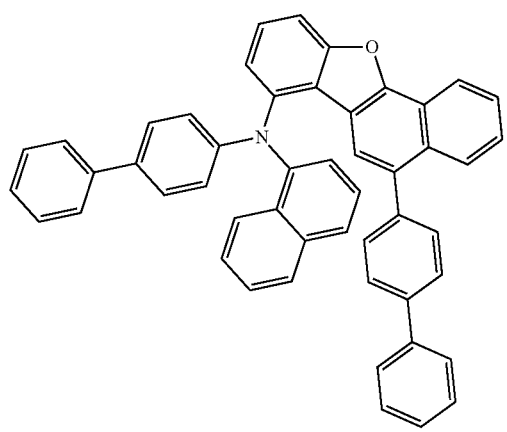
HT-168
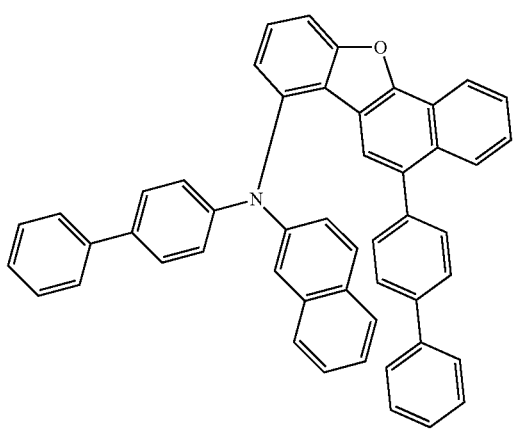
HT-166
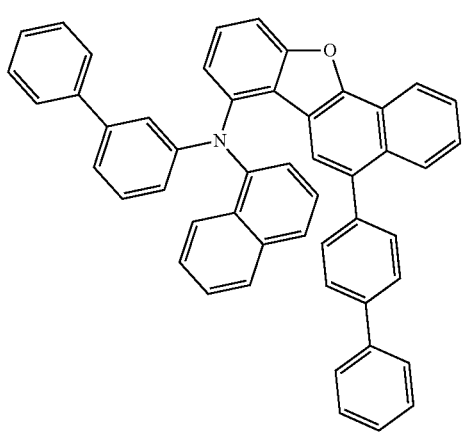
HT-169
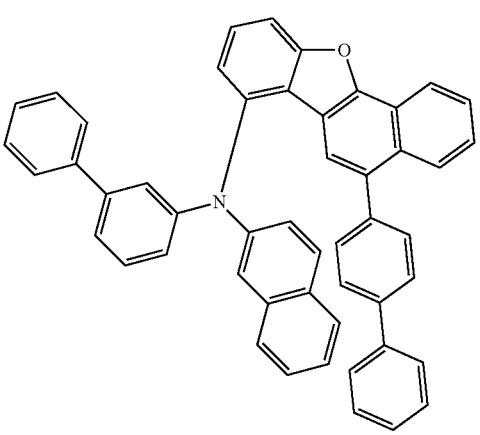

HT-170
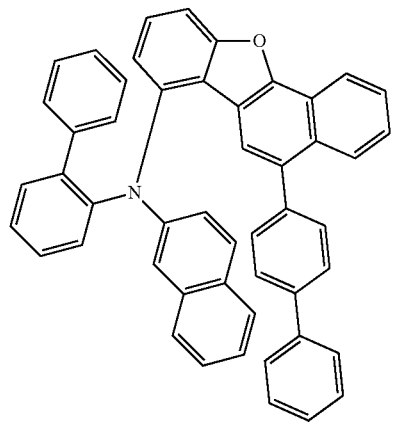
HT-171
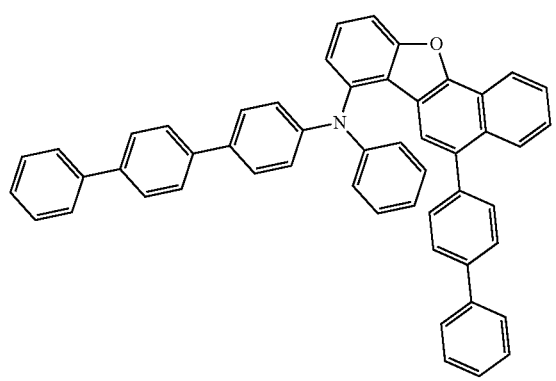
HT-172
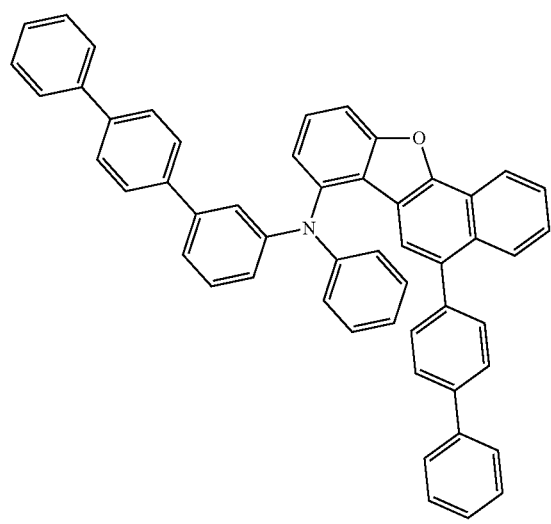
HT-173
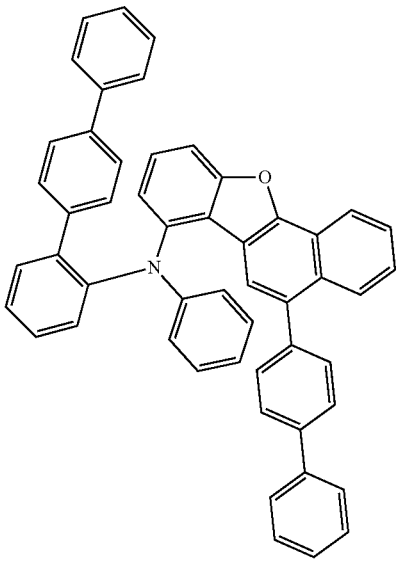
HT-174
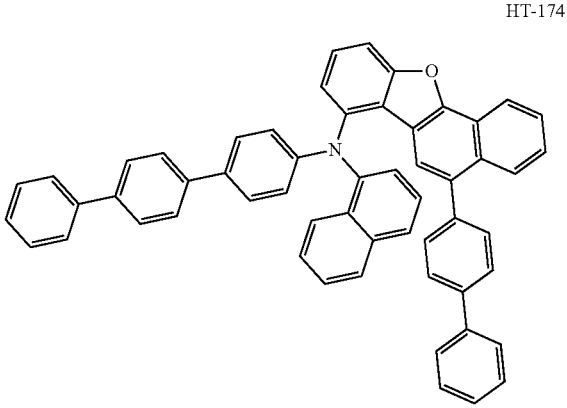
HT-175
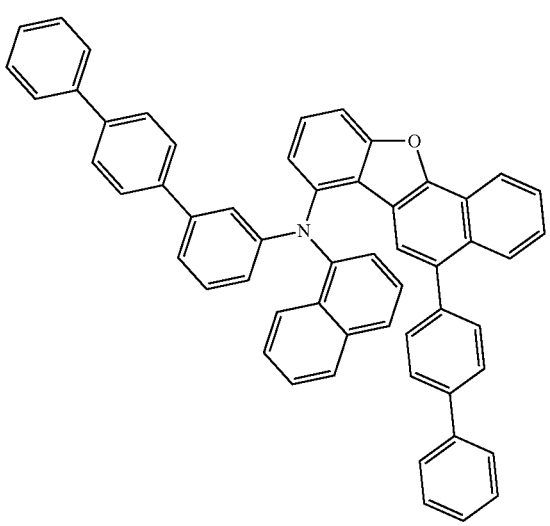

HT-176
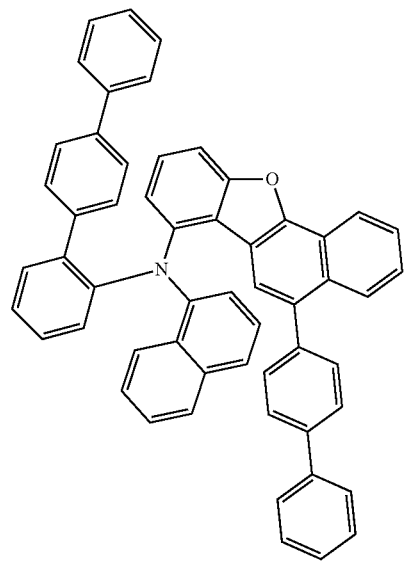
HT-179
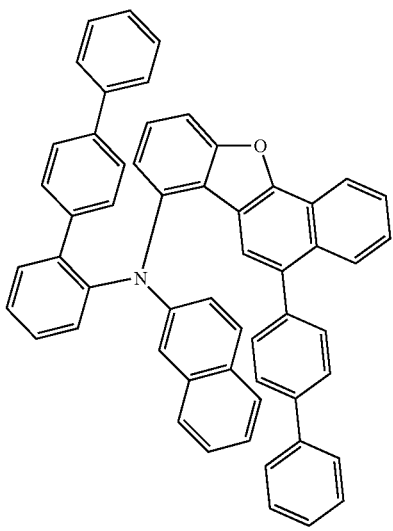
HT-177
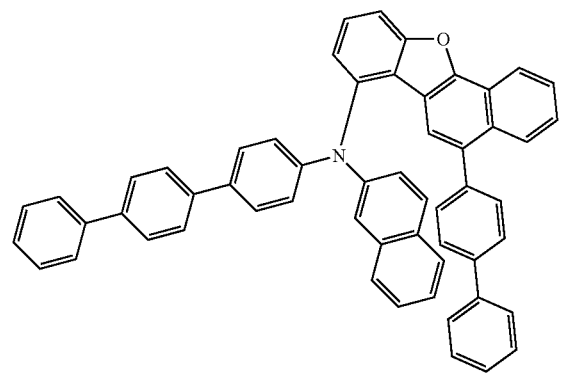
HT-180
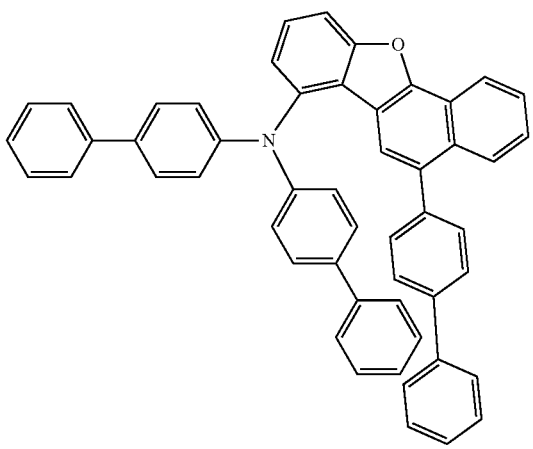
HT-178
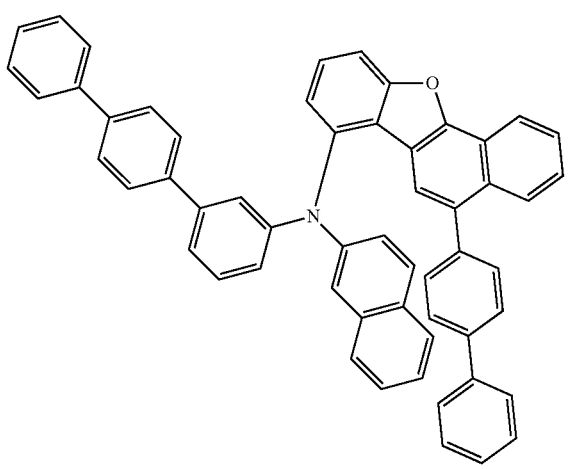
HT-181
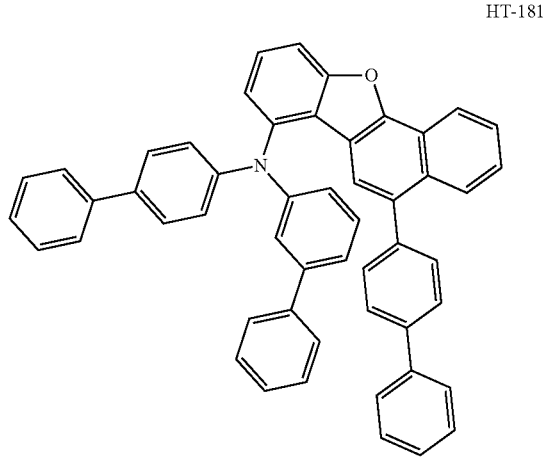

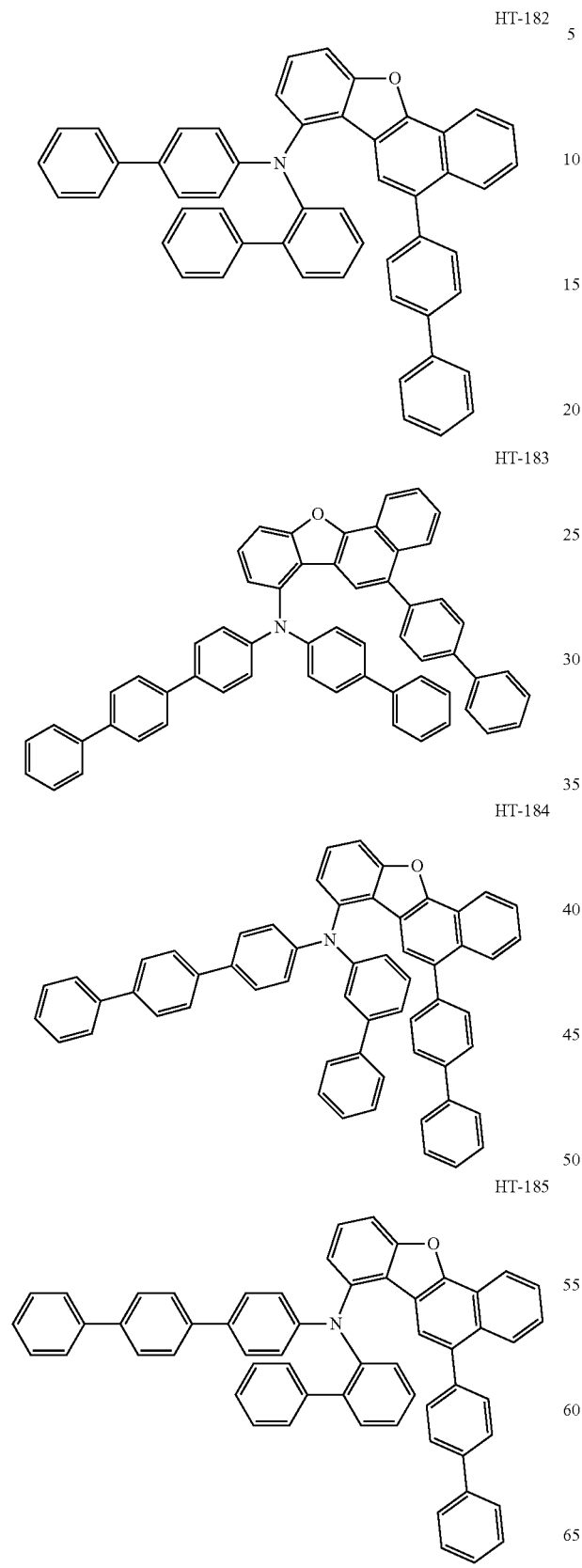
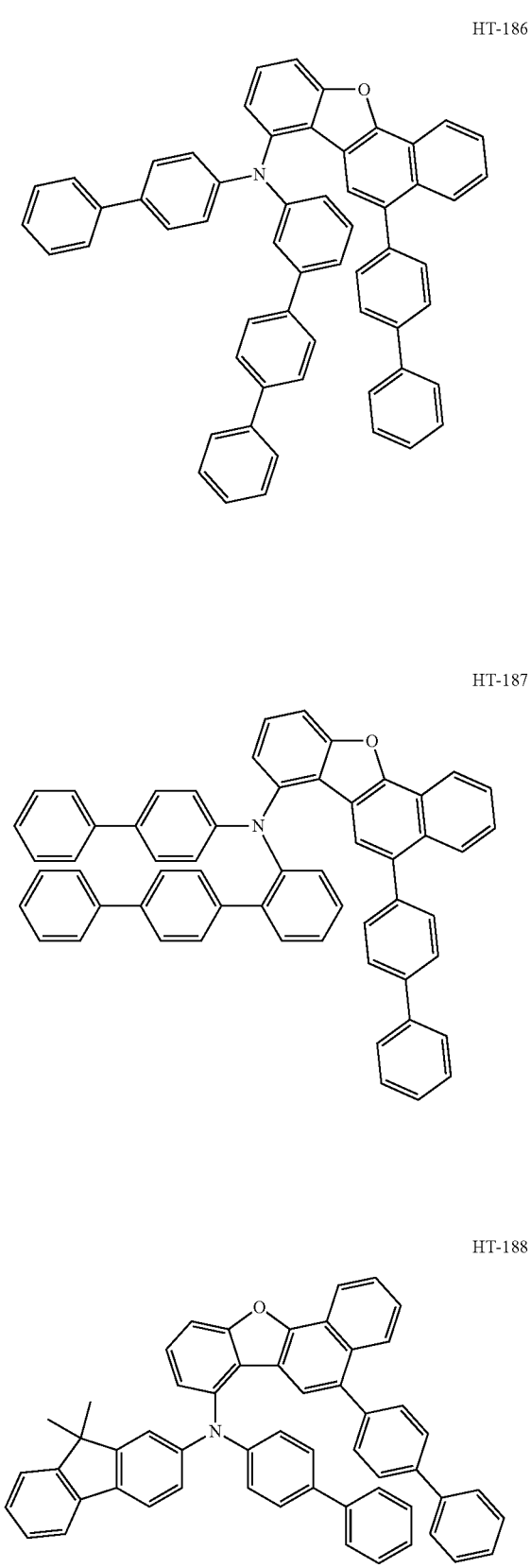

HT-189
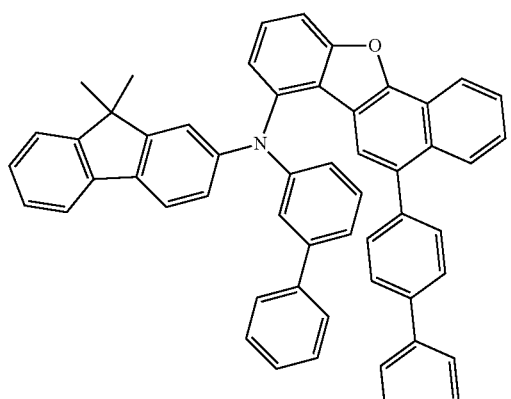
HT-190
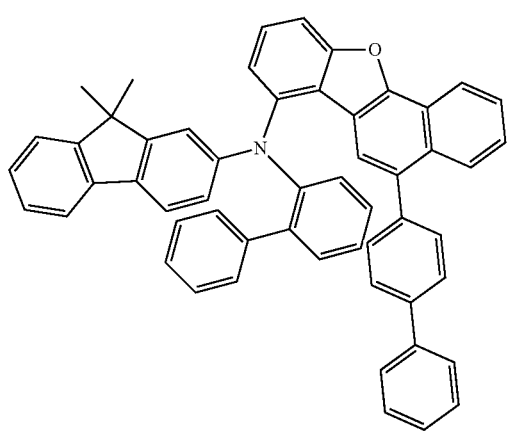
HT-191
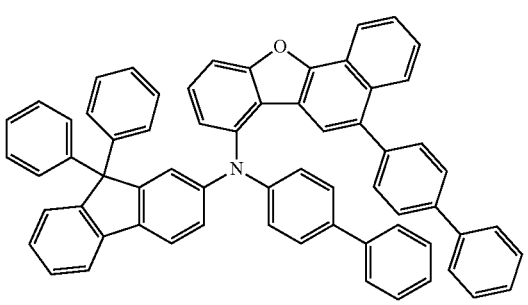 [SMILES: c1ccc(-c2ccc(-c3cc4c(oc5cccc(N(c6ccc(-c7ccccc7)cc6)c6ccc7c(c6)C(c6ccccc6)(c6ccccc6)c6ccccc6-7)c54)c4ccccc34)cc2)cc1]
HT-192
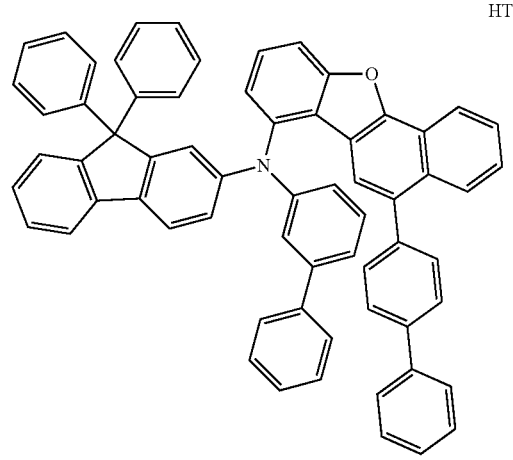
HT-193
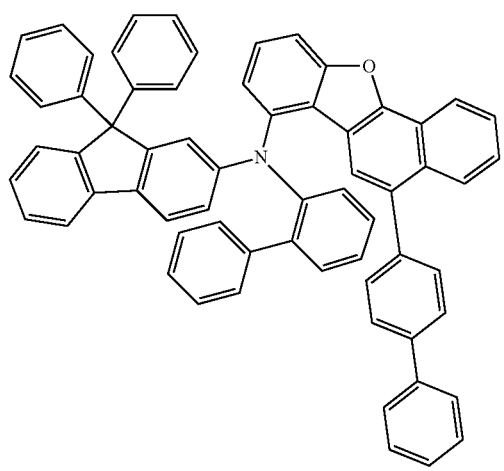
HT-194
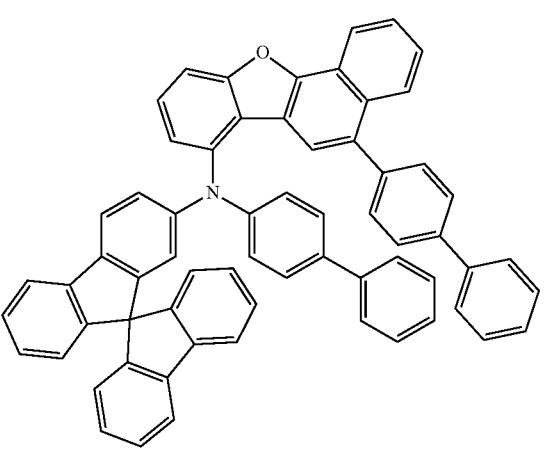
HT-195
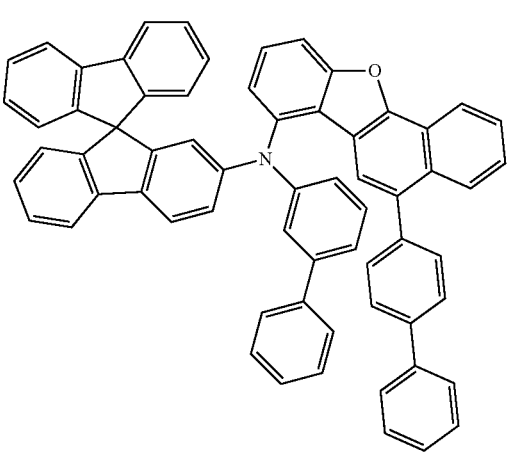

HT-196
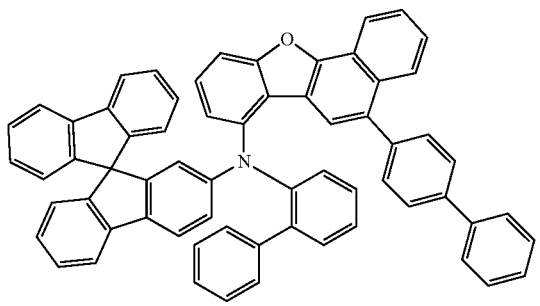
HT-197
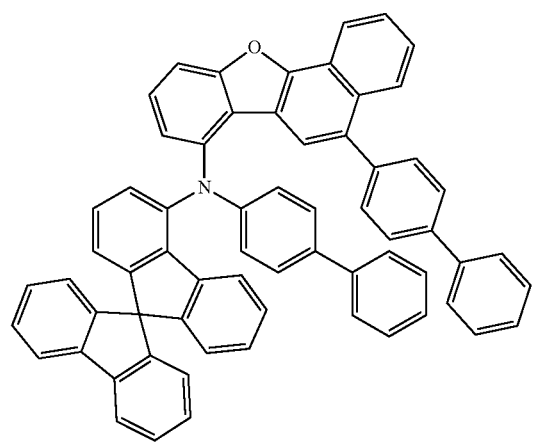
HT-198
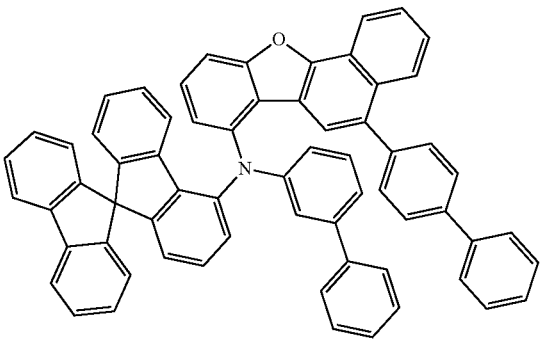
HT-199
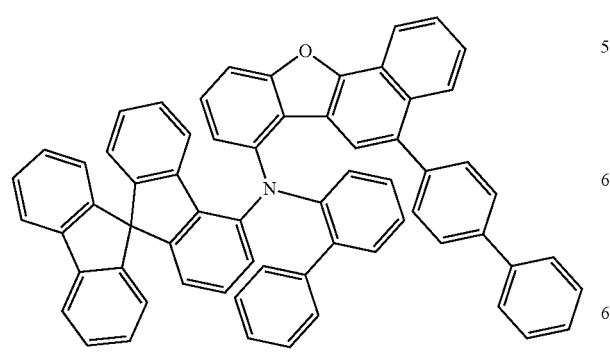
HT-200
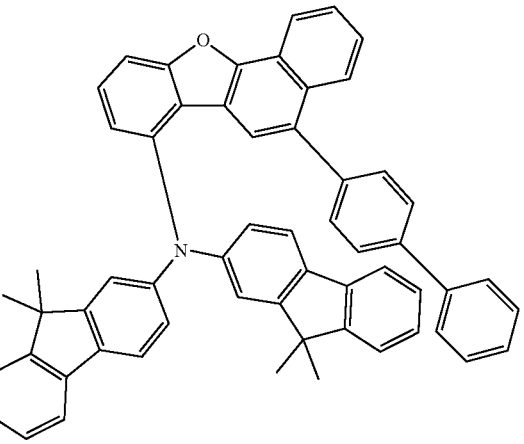
HT-201
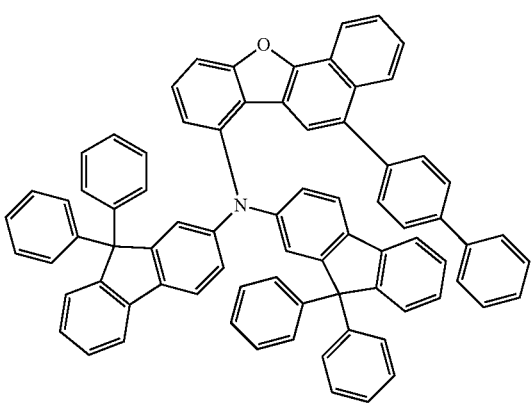
HT-202
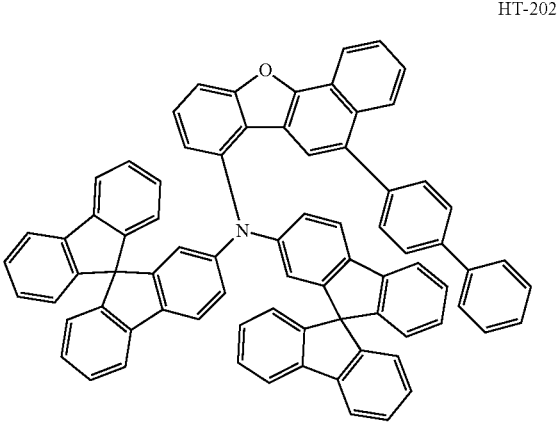
HT-203
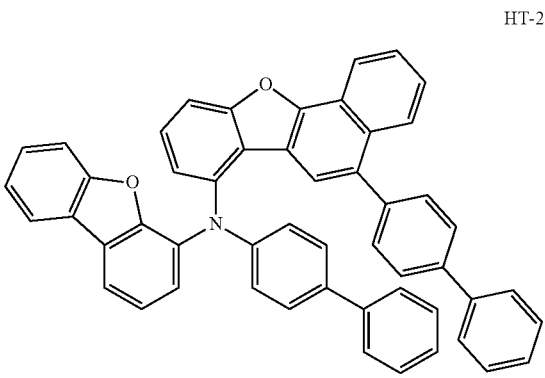

HT-204
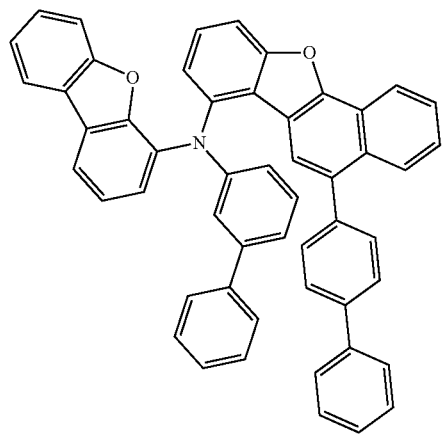
HT-205
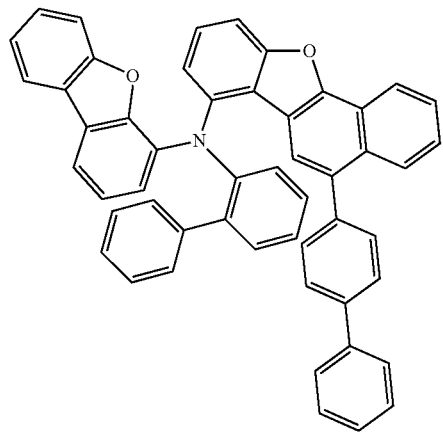
HT-206
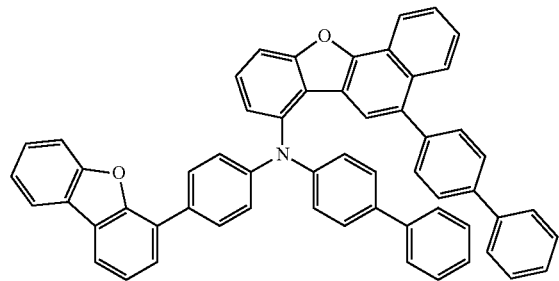
HT-207
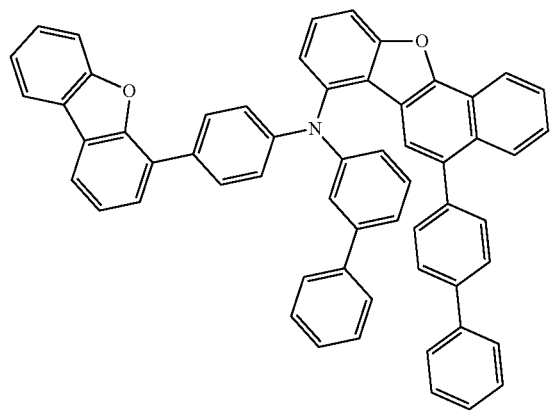
HT-208
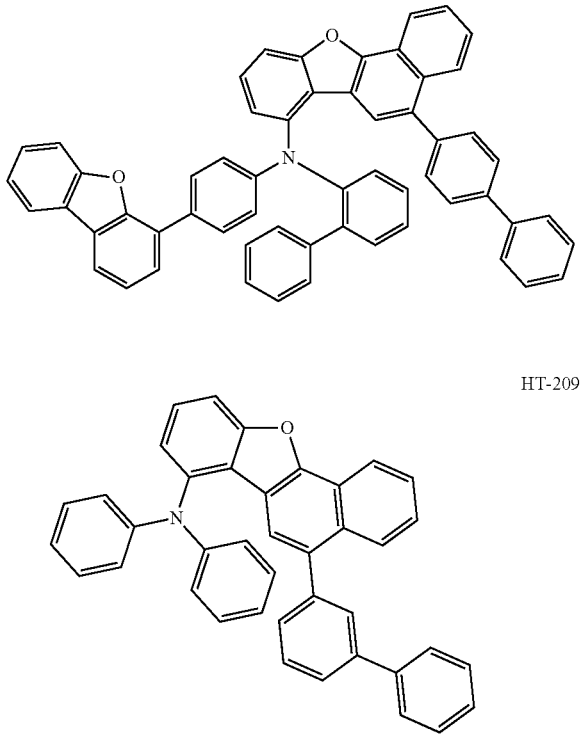
HT-209
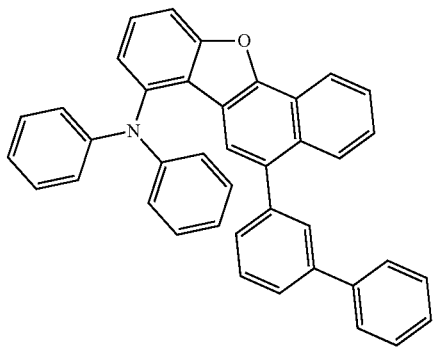
HT-210
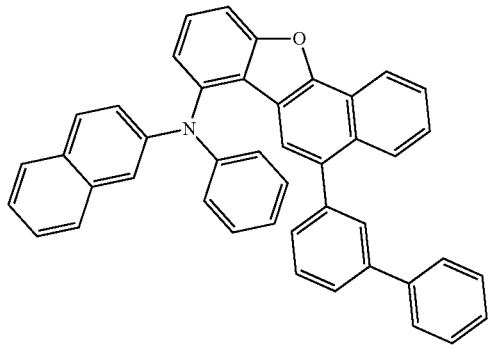
HT-211
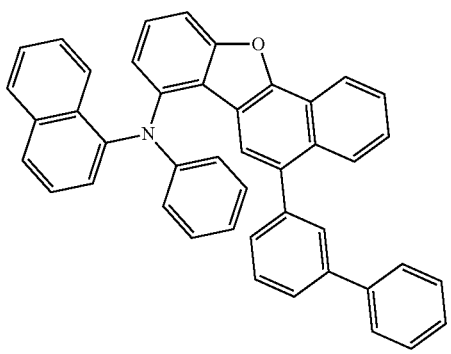

HT-212
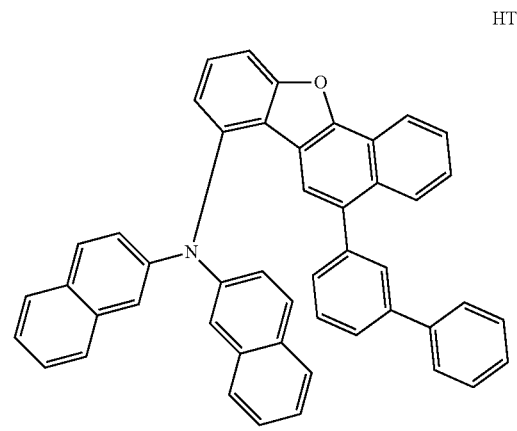
HT-213
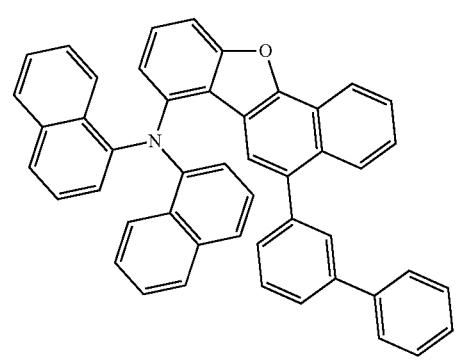
HT-214
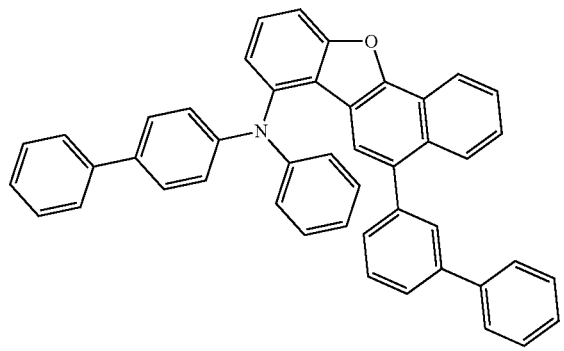
HT-215
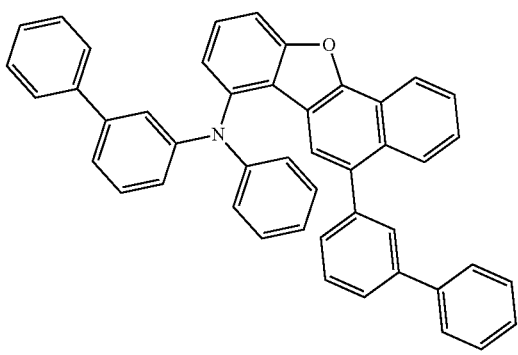
HT-216
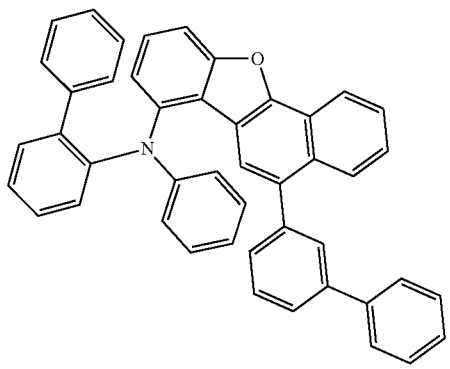
HT-217
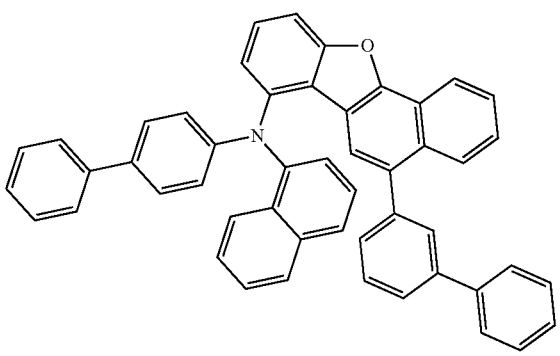
HT-218
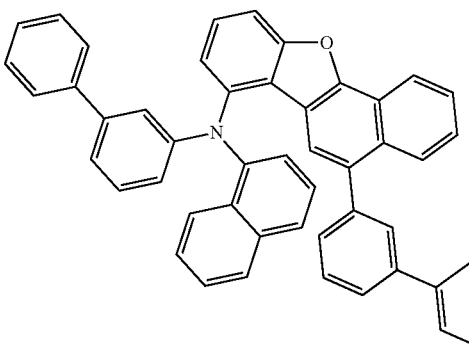
HT-219
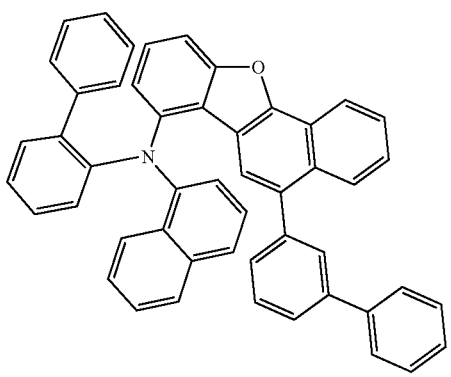

HT-220
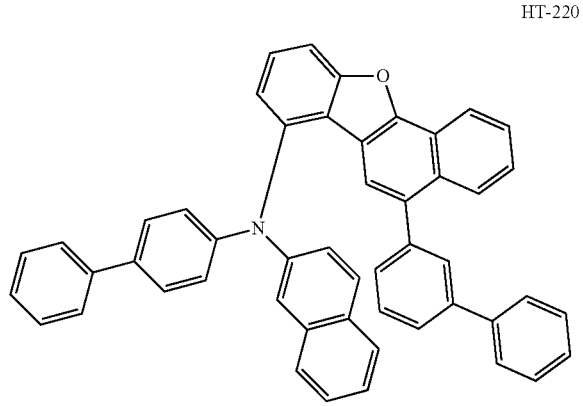
HT-221
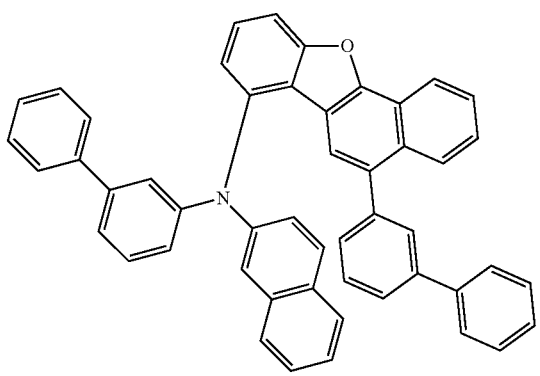
HT-223
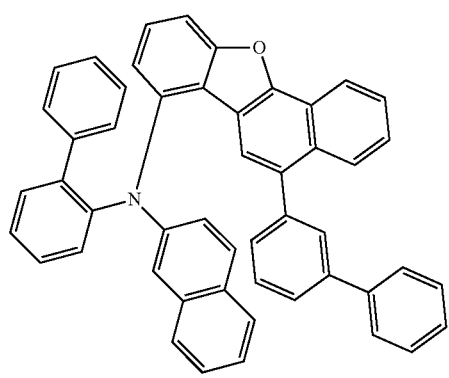
HT-223
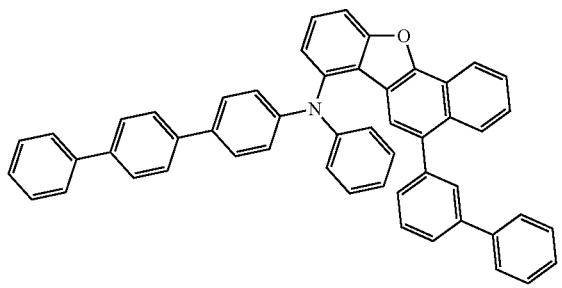
HT-224
HT-225
HT-226
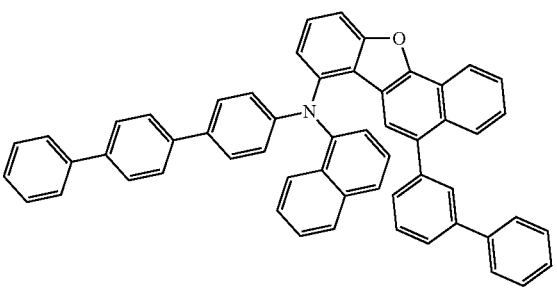

-continued
HT-227
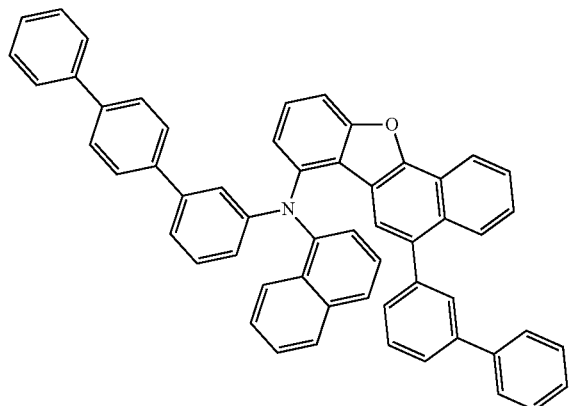
HT-228
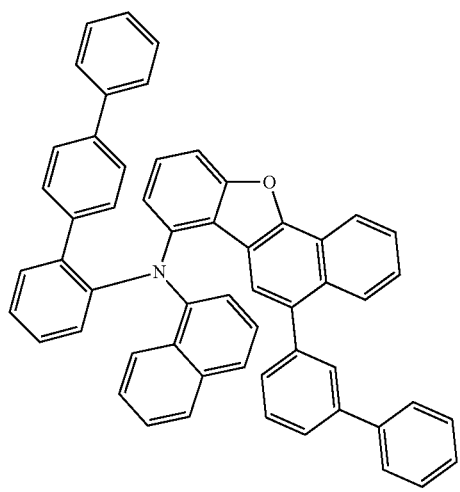
HT-229
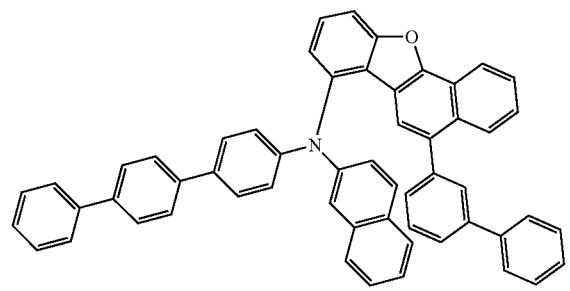
HT-230
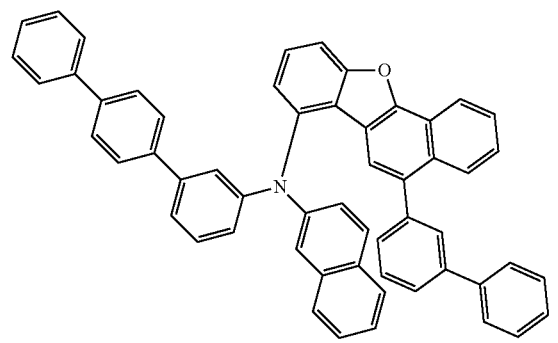
-continued
HT-231
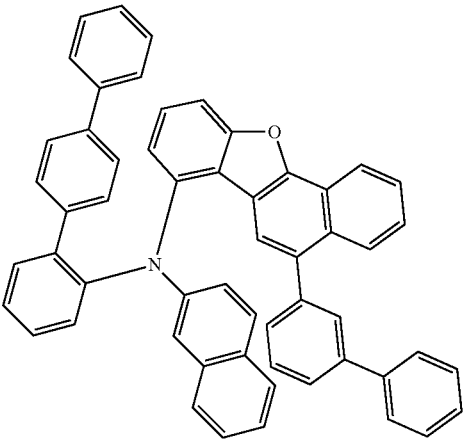
HT-232
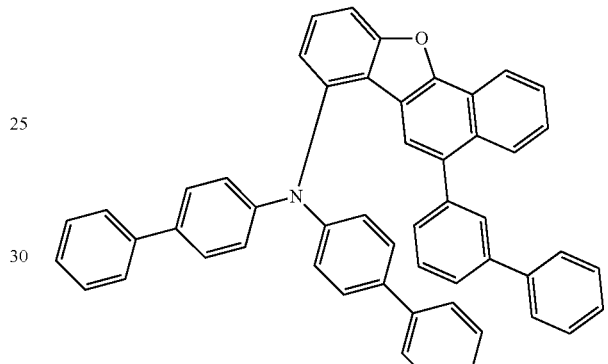
HT-233
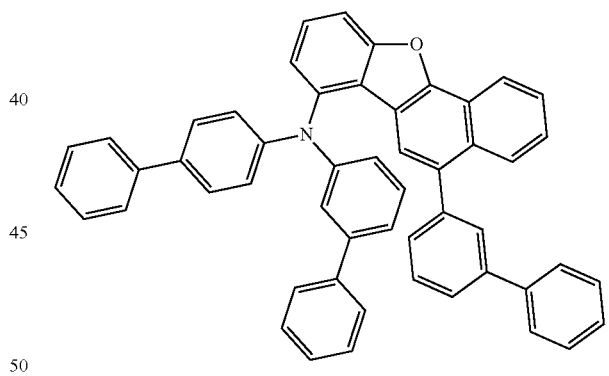
HT-234
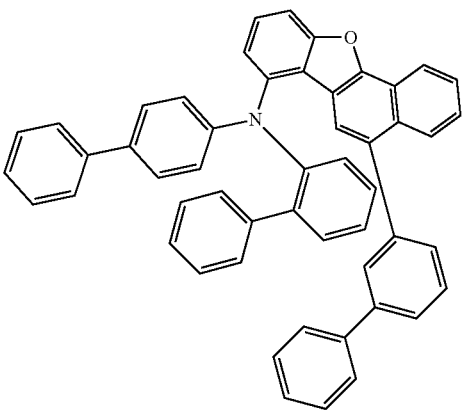

HT-235
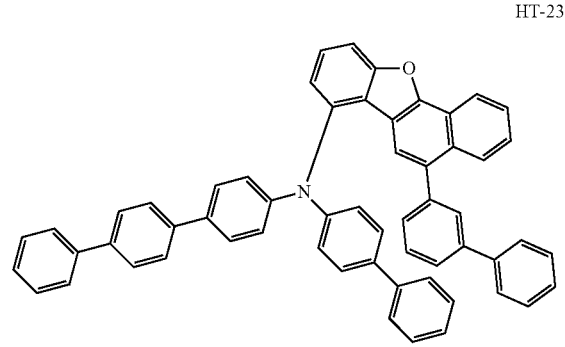
HT-236
HT-237
HT-238
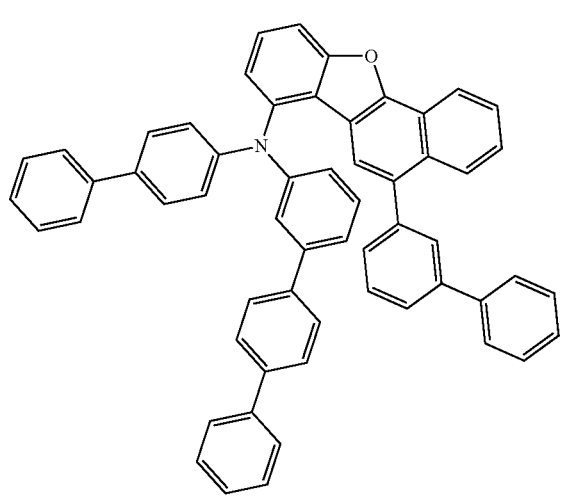
HT-239
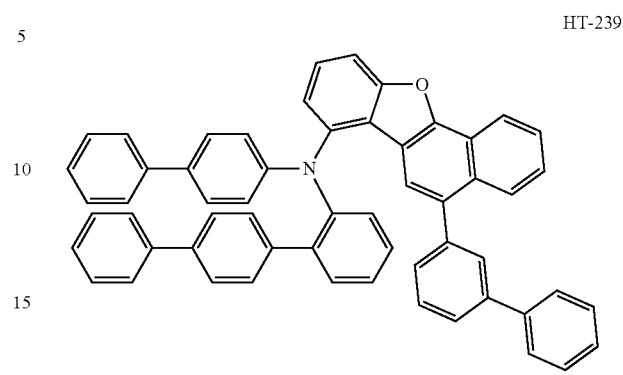
HT-240
HT-241
HT-242
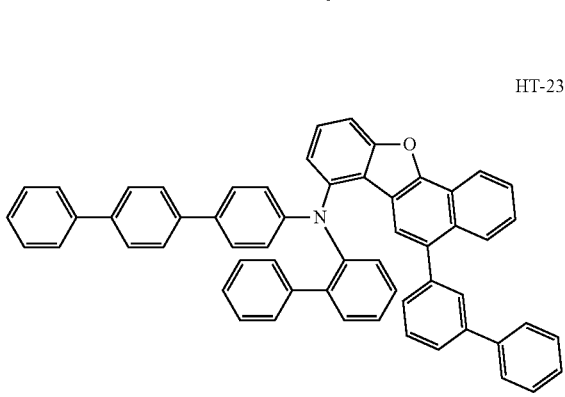

HT-243
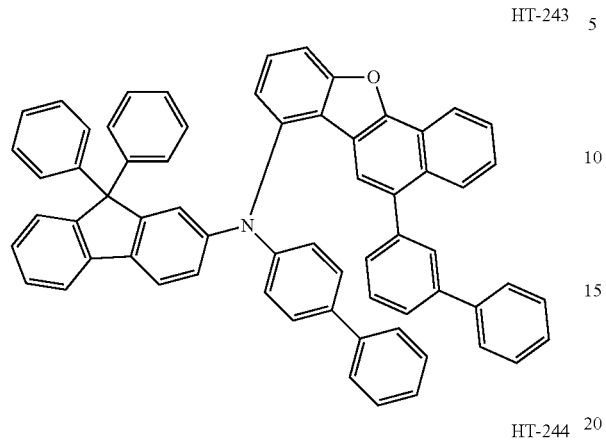
HT-244
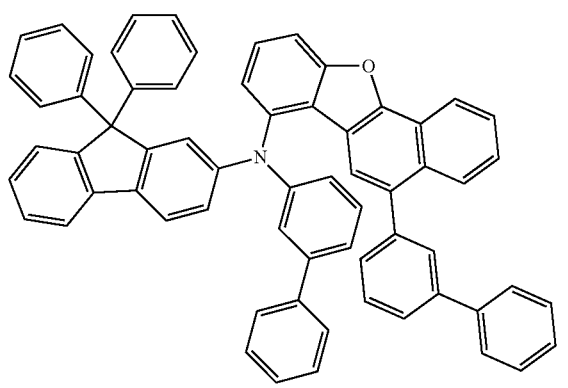
HT-245
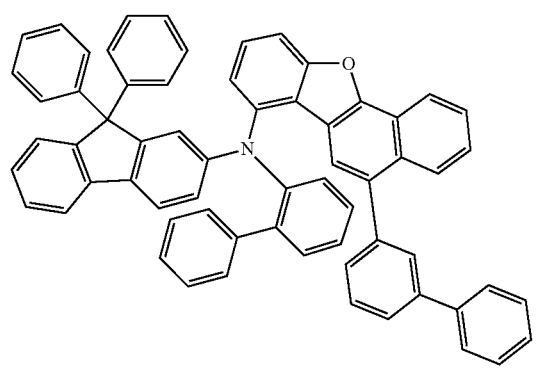
HT-246
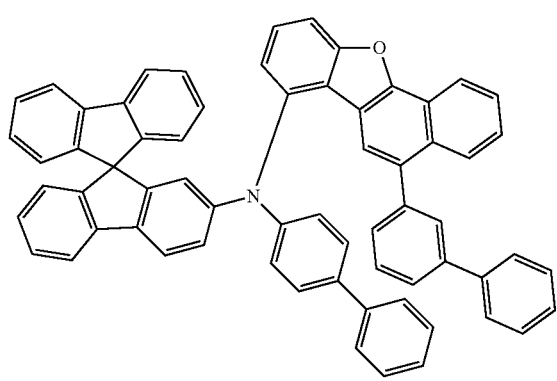
HT-247
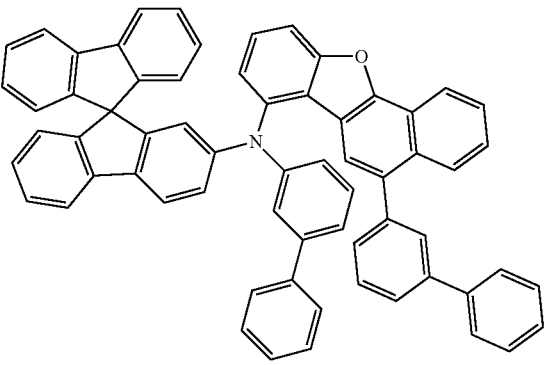
HT-248
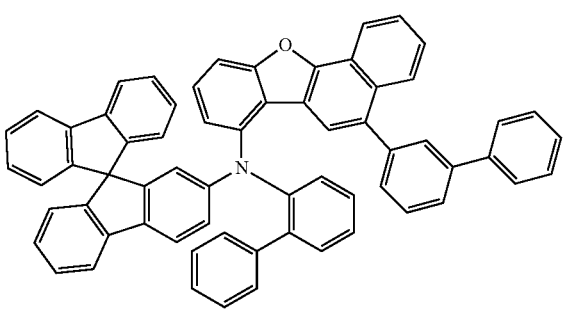
HT-249
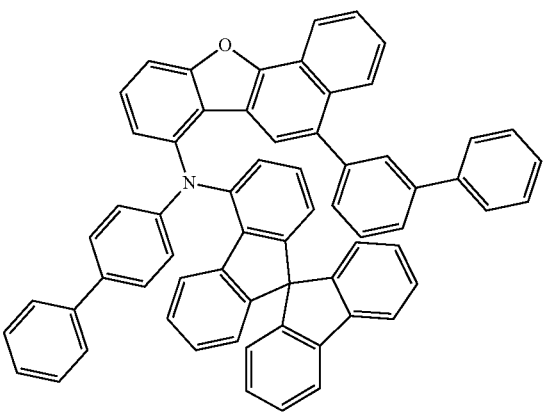
HT-250
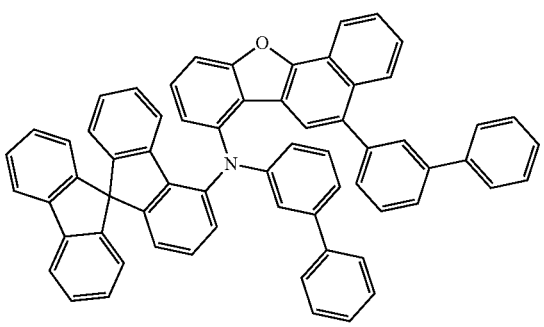

HT-251
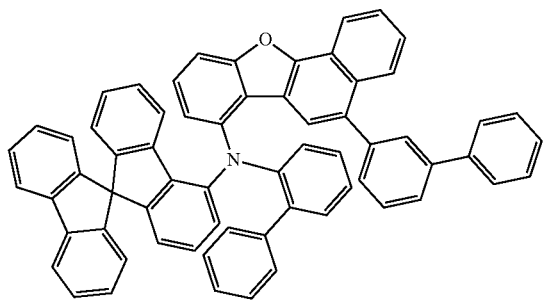
HT-252
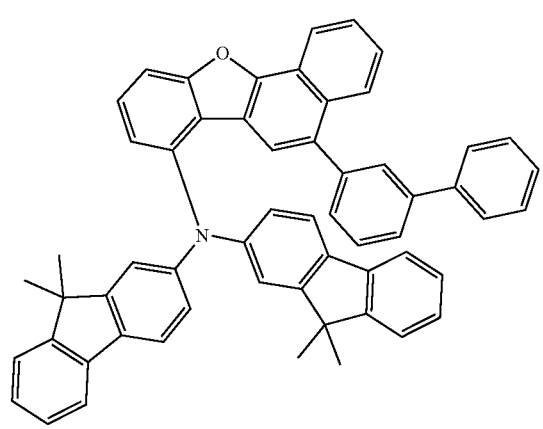
HT-253

HT-254
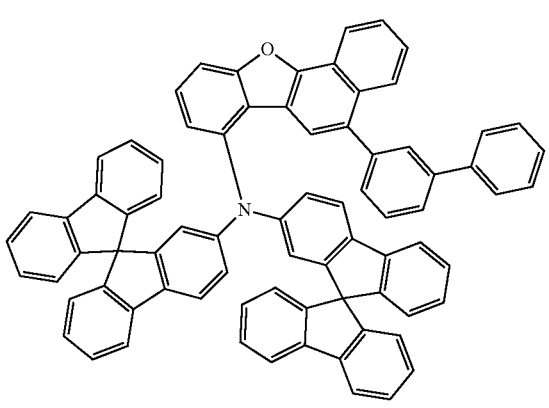
HT-255
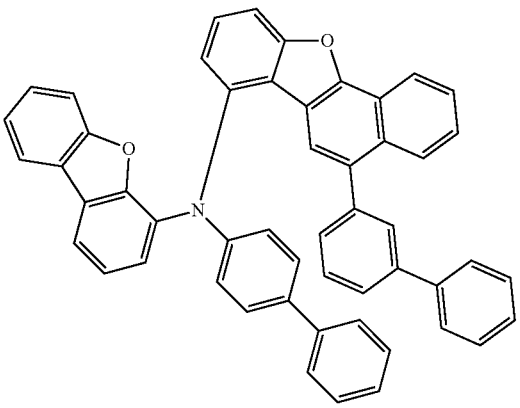
HT-256
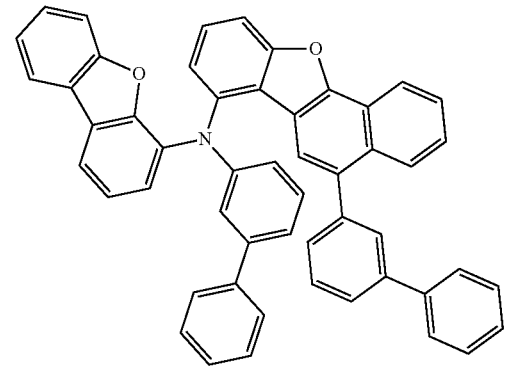
HT-257
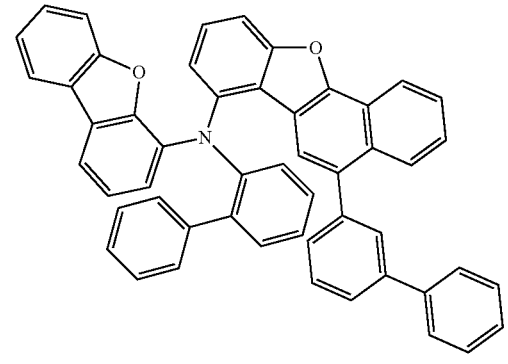
HT-258
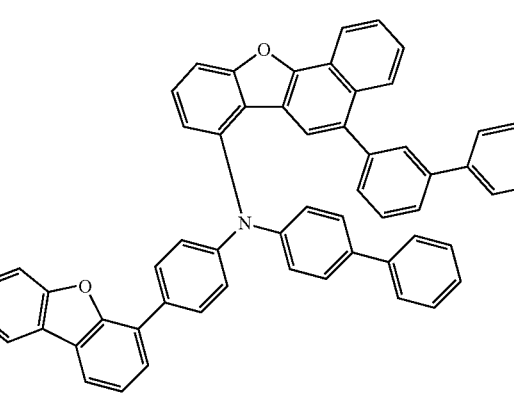

HT-259
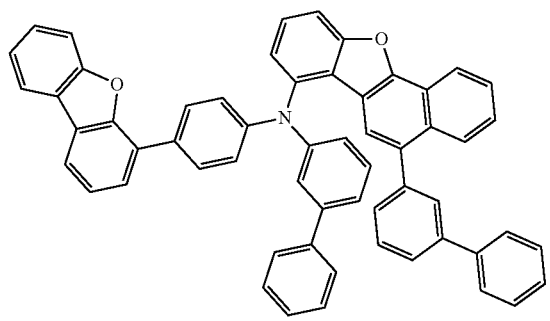
HT-264
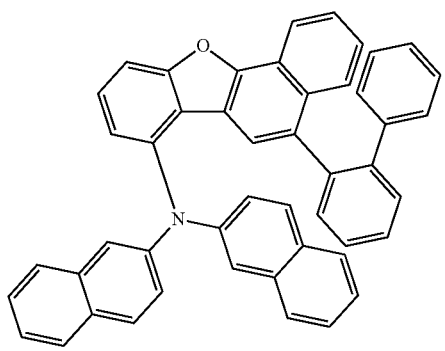
HT-260
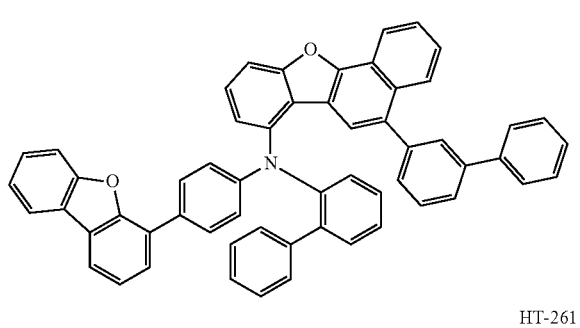
HT-265
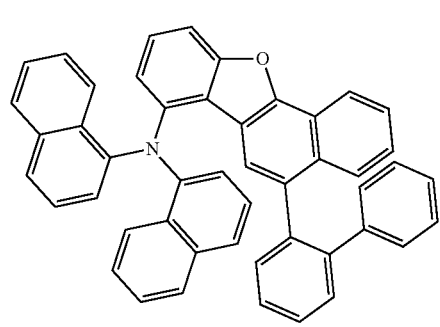
HT-261
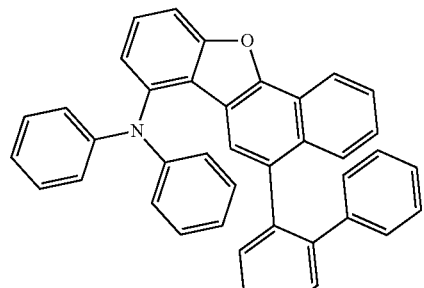
HT-262
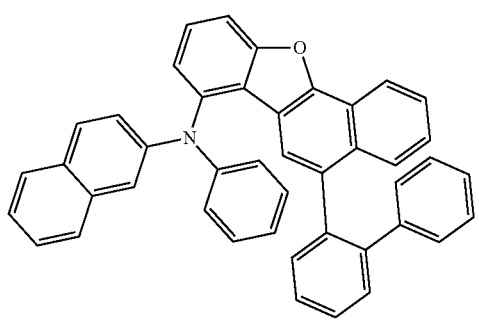
HT-266
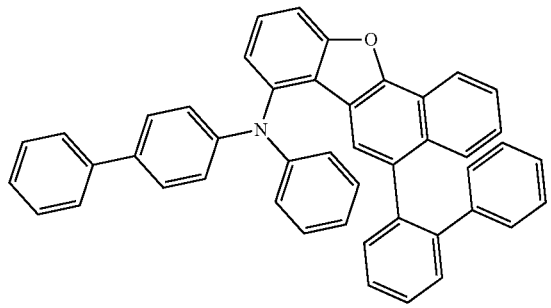
HT-263
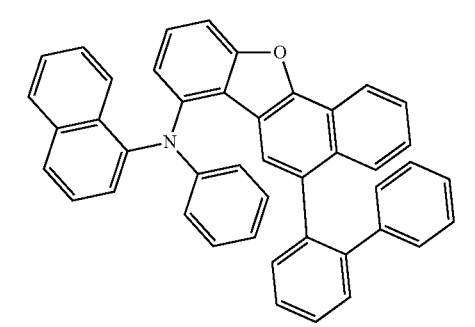
HT-267
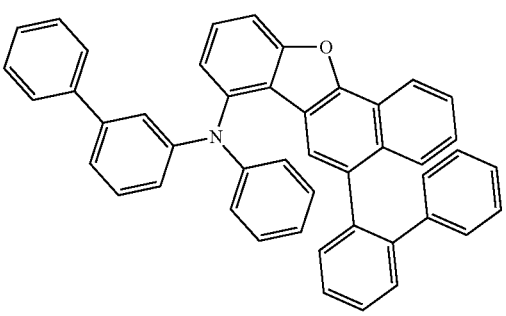

HT-268
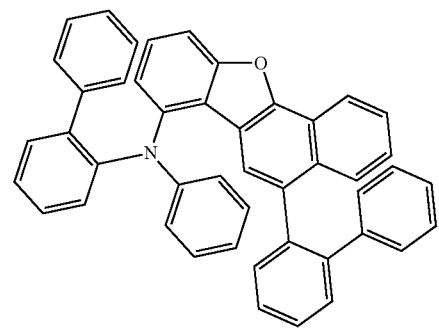
HT-269
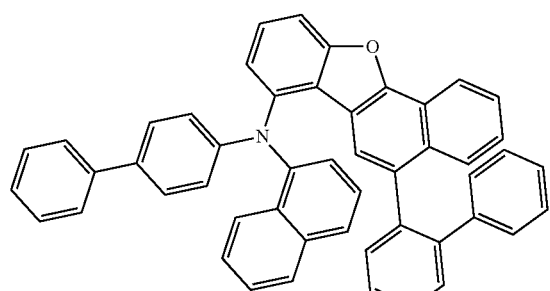
HT-270
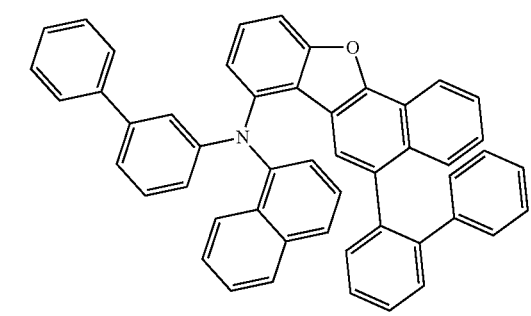
HT-271
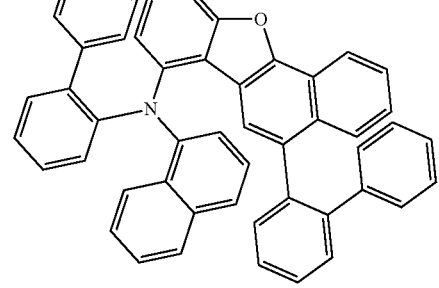
HT-272
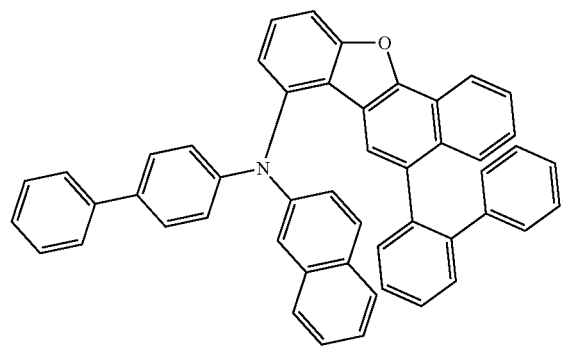
HT-273
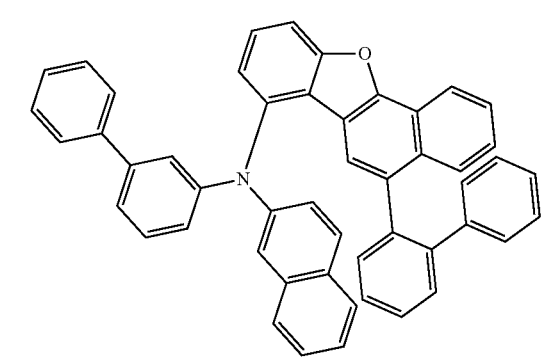
HT-274
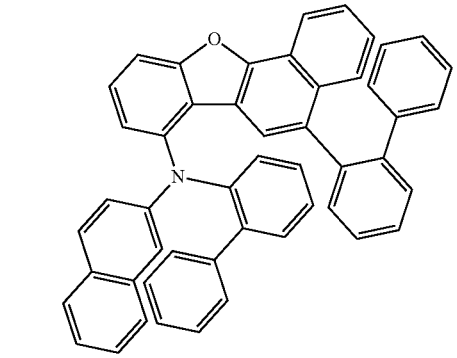
HT-275
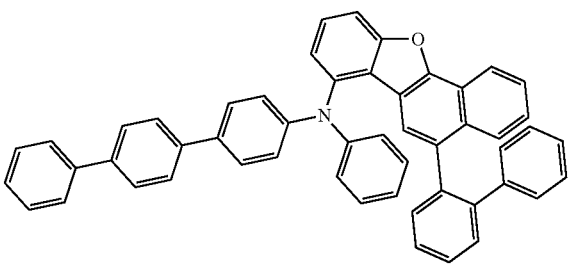

-continued
HT-276
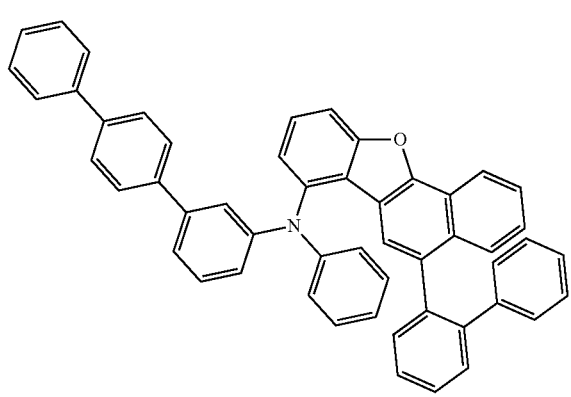
HT-277
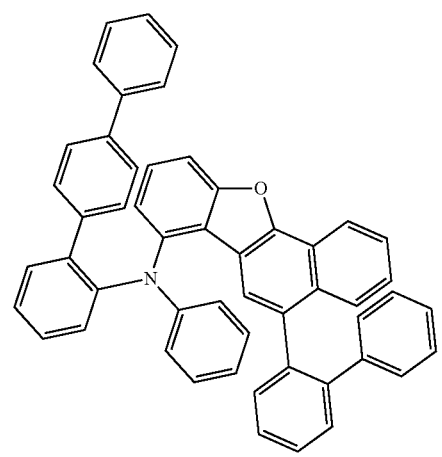
HT-278
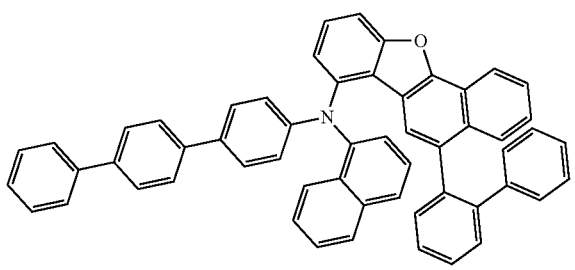
HT-279
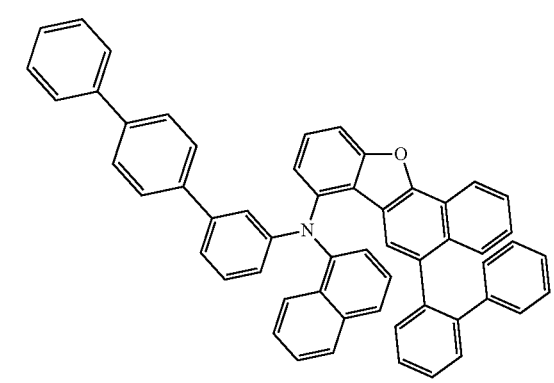
-continued
HT-280
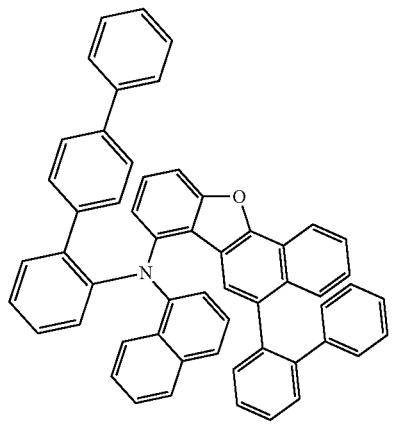
HT-281
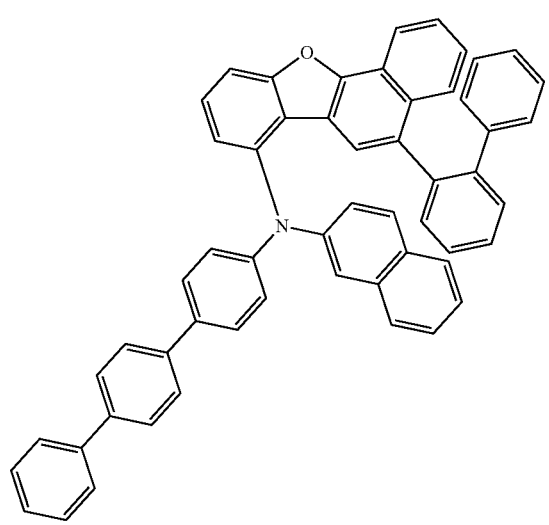
HT-282
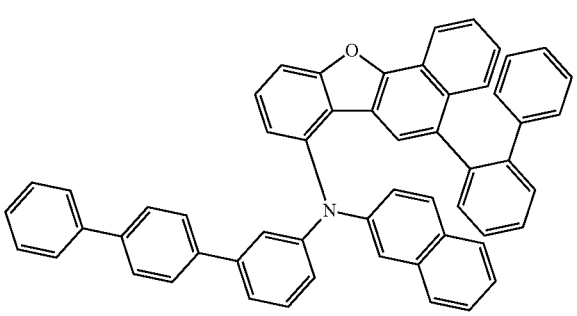
HT-283
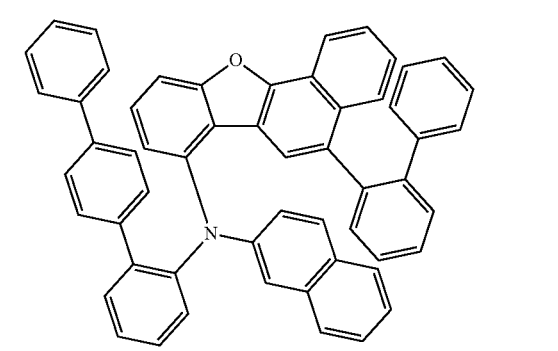

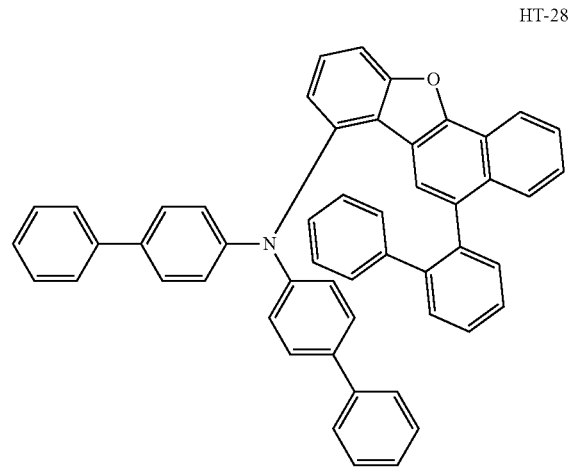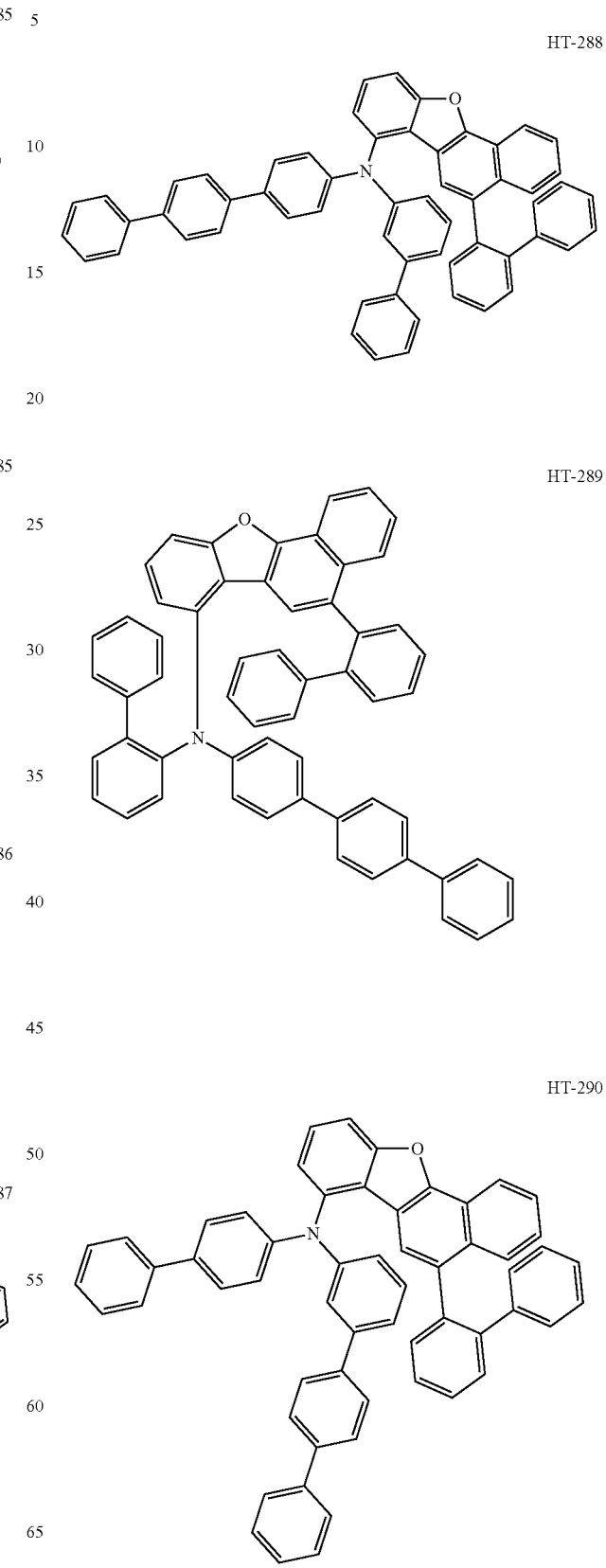

HT-291
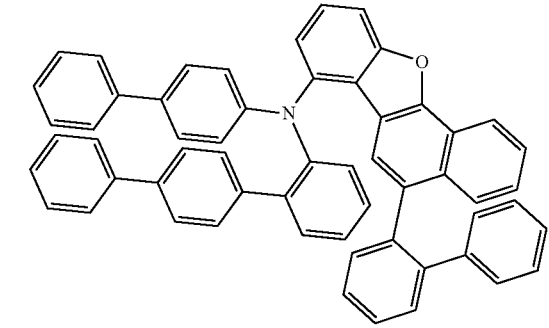
HT-294
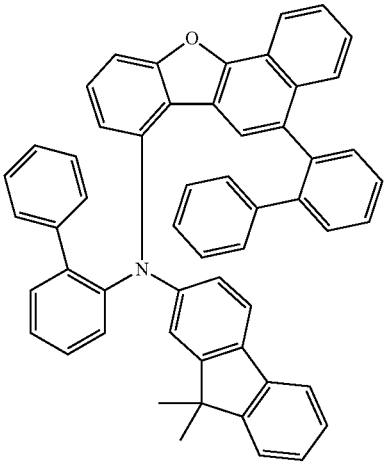
HT-292
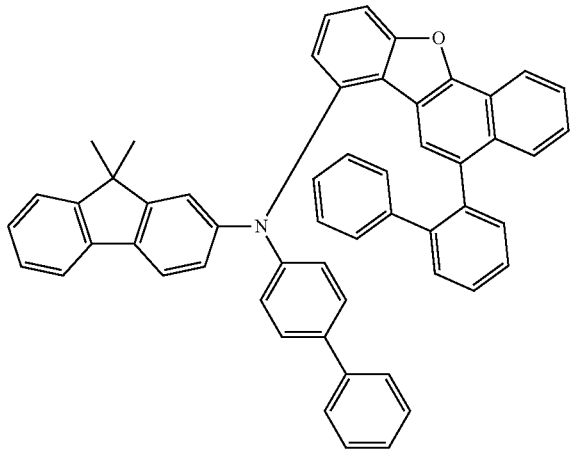
HT-295
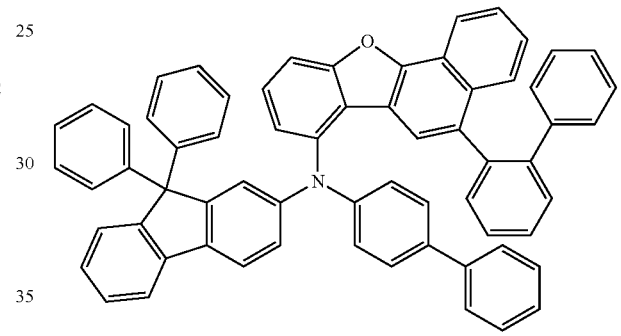
HT-296
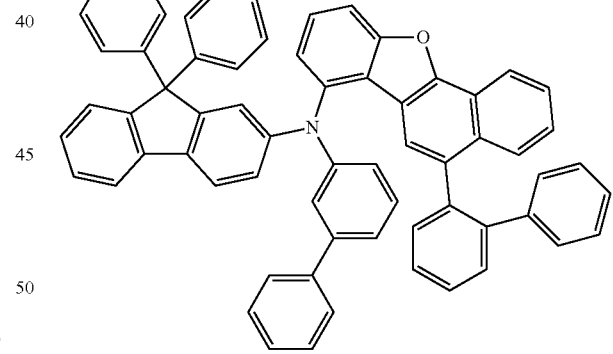
HT-293
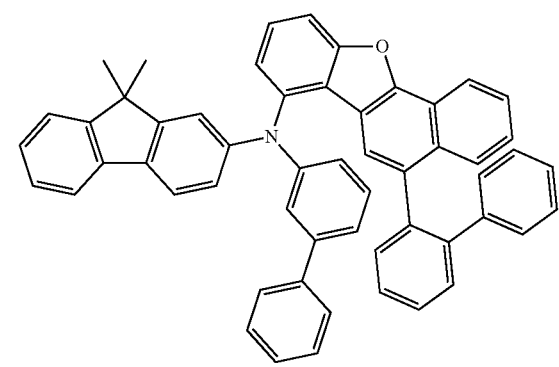
HT-297
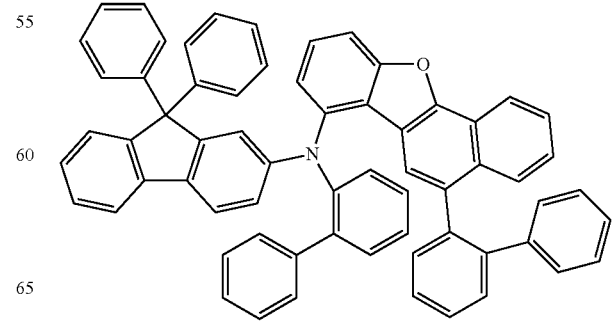

HT-298
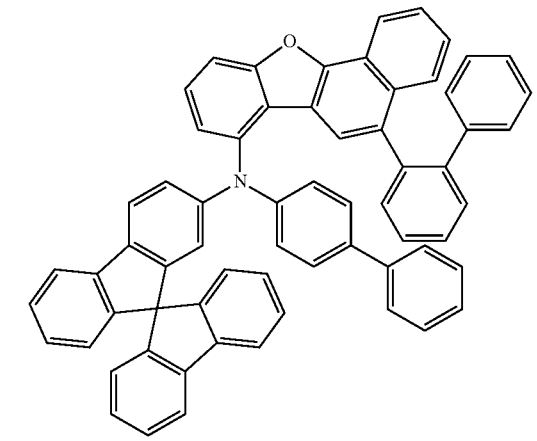
HT-299
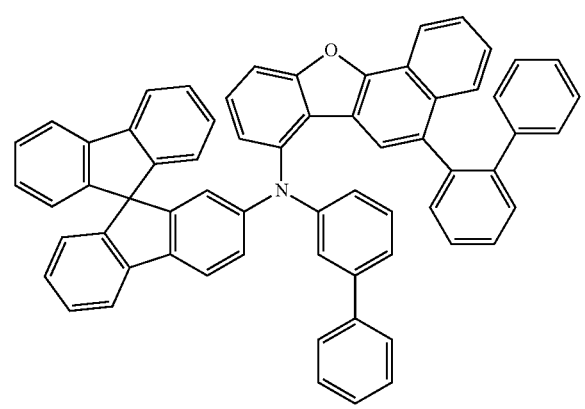
HT-300
HT-301
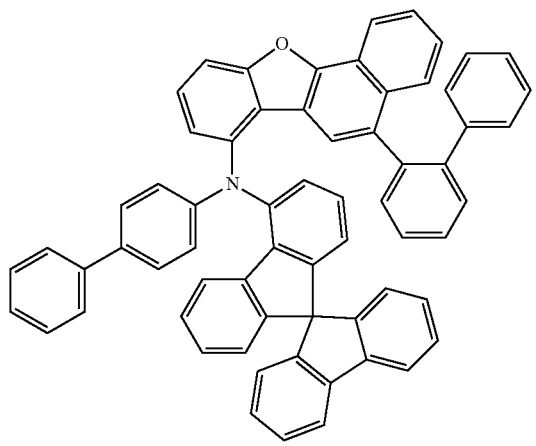
HT-302
HT-303
HT-304
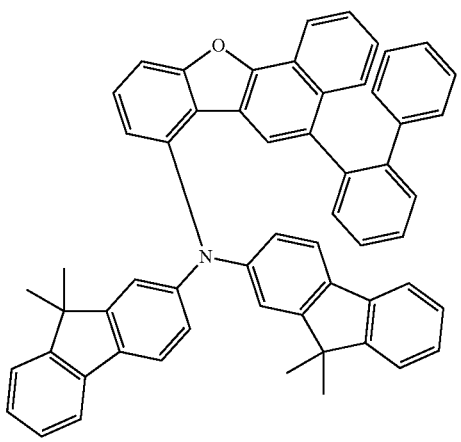

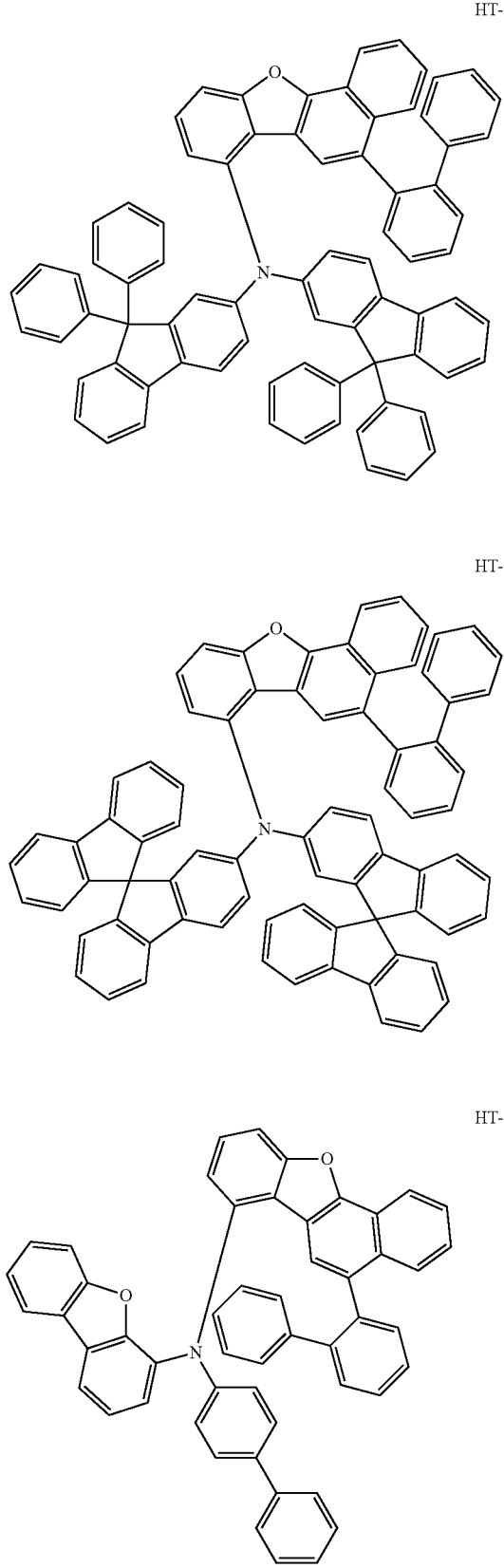
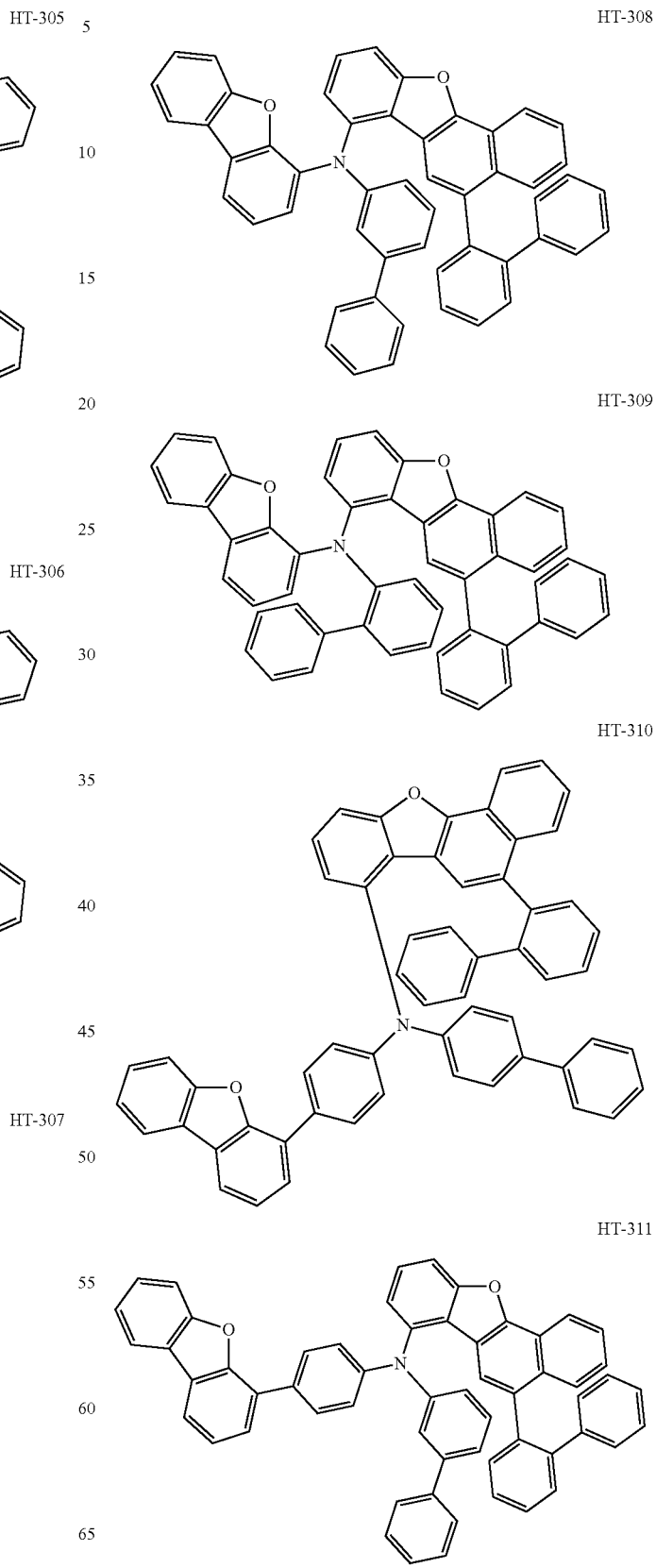

HT-312
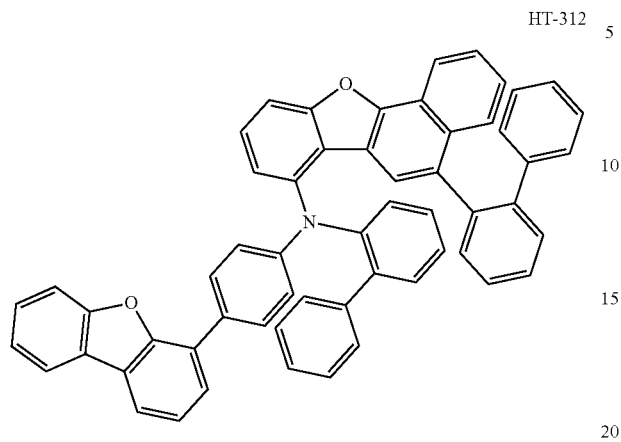
HT-316
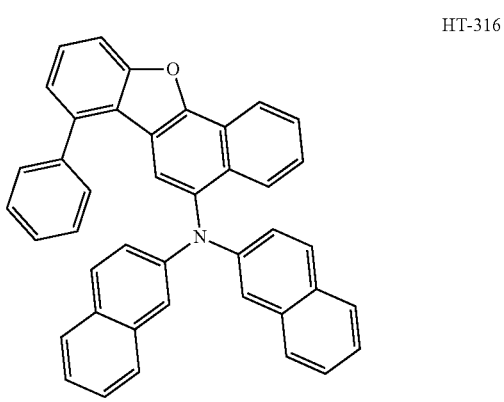
HT-313
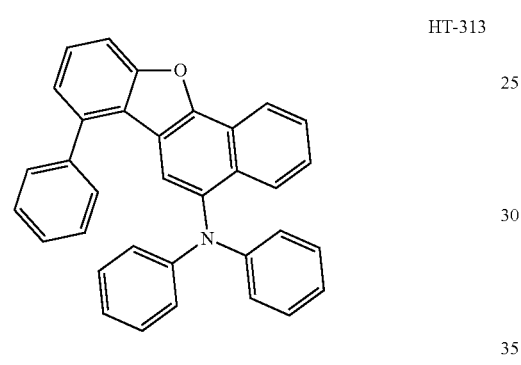
HT-317
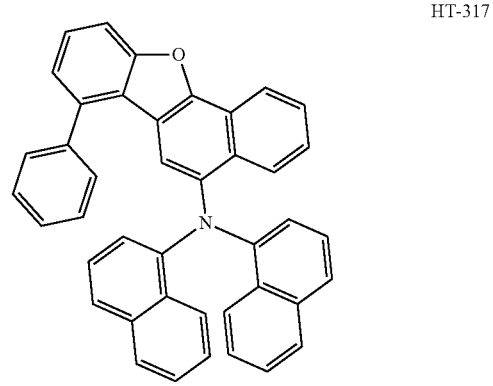
HT-314
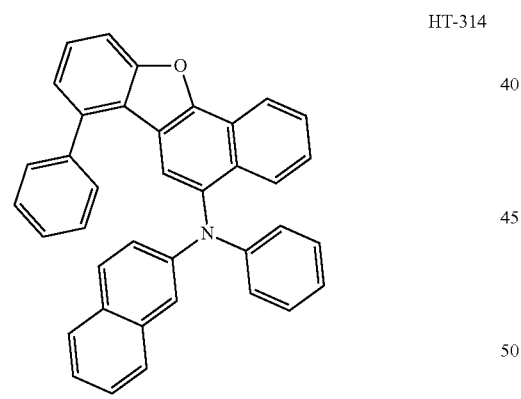
HT-318
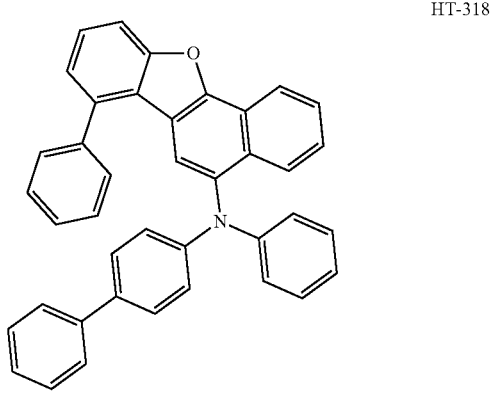
HT-315
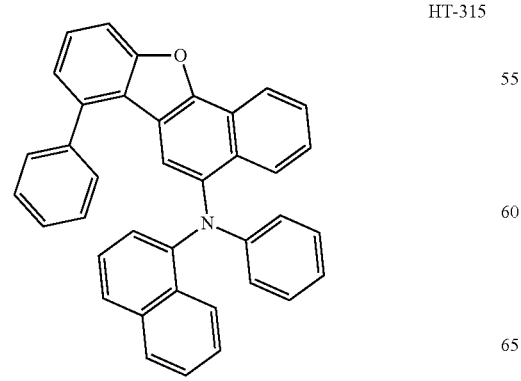
HT-319
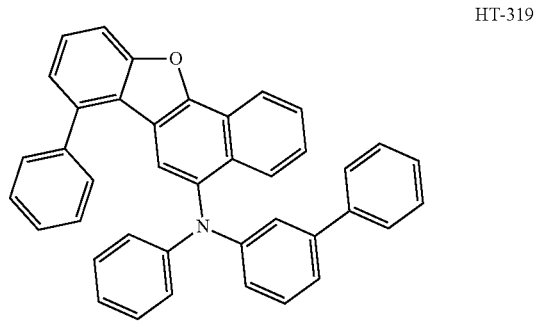

101
-continued
102
-continued
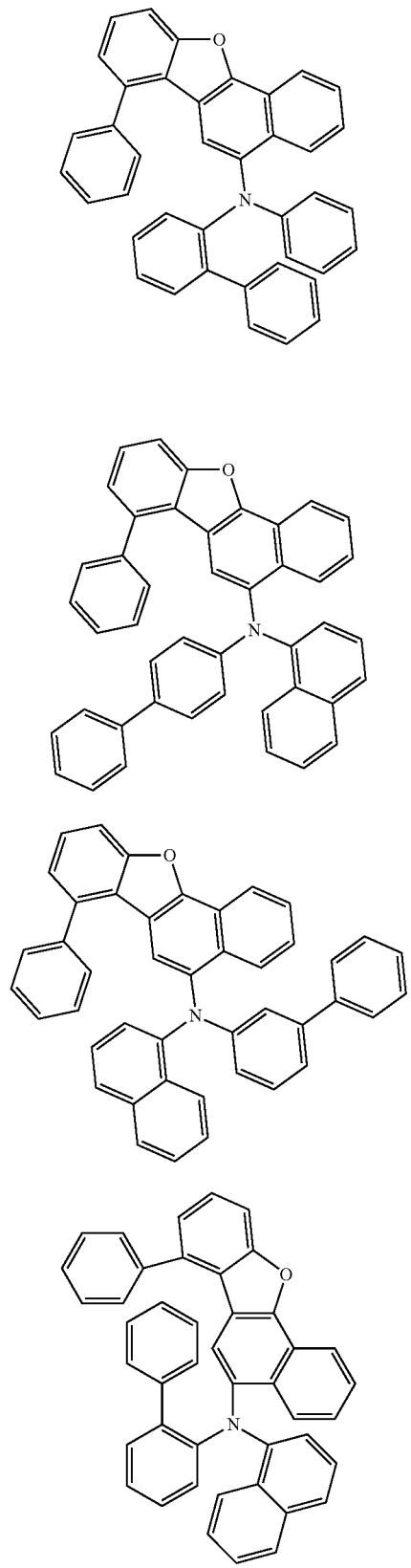
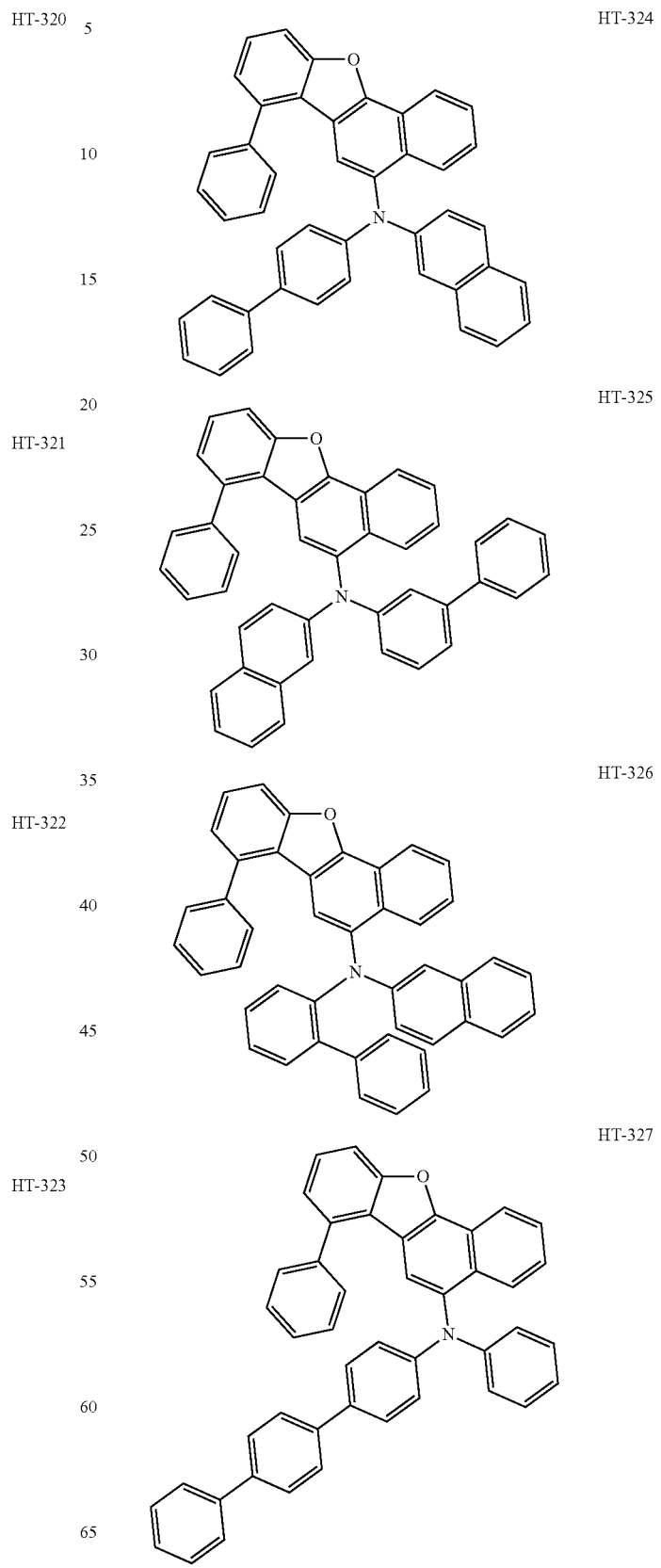

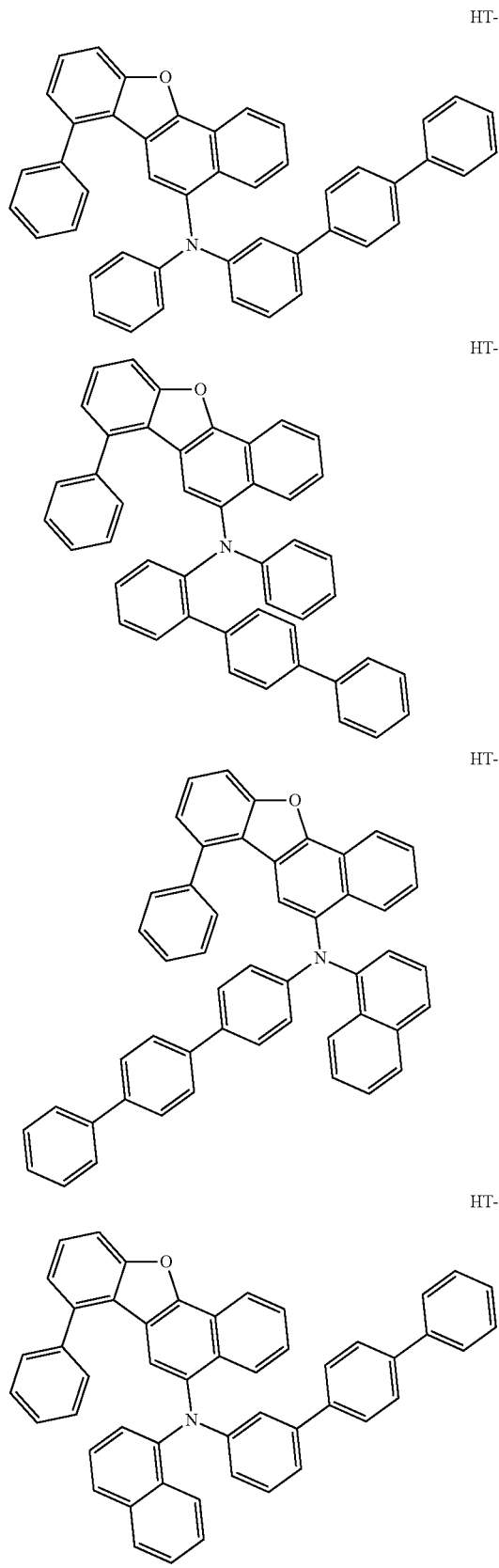
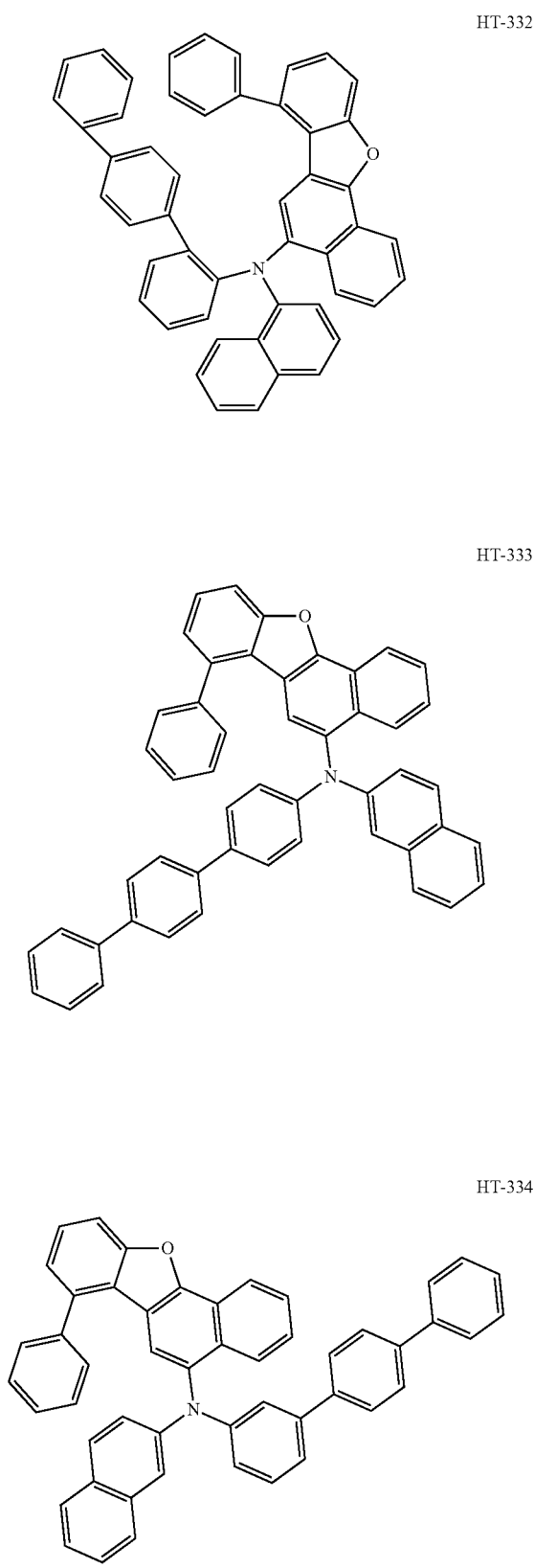

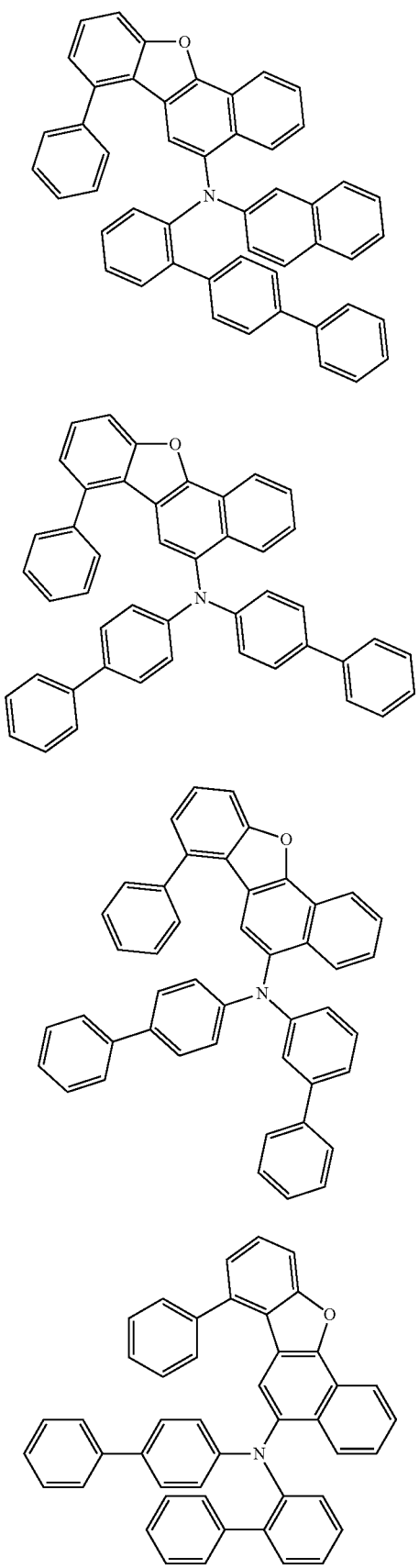

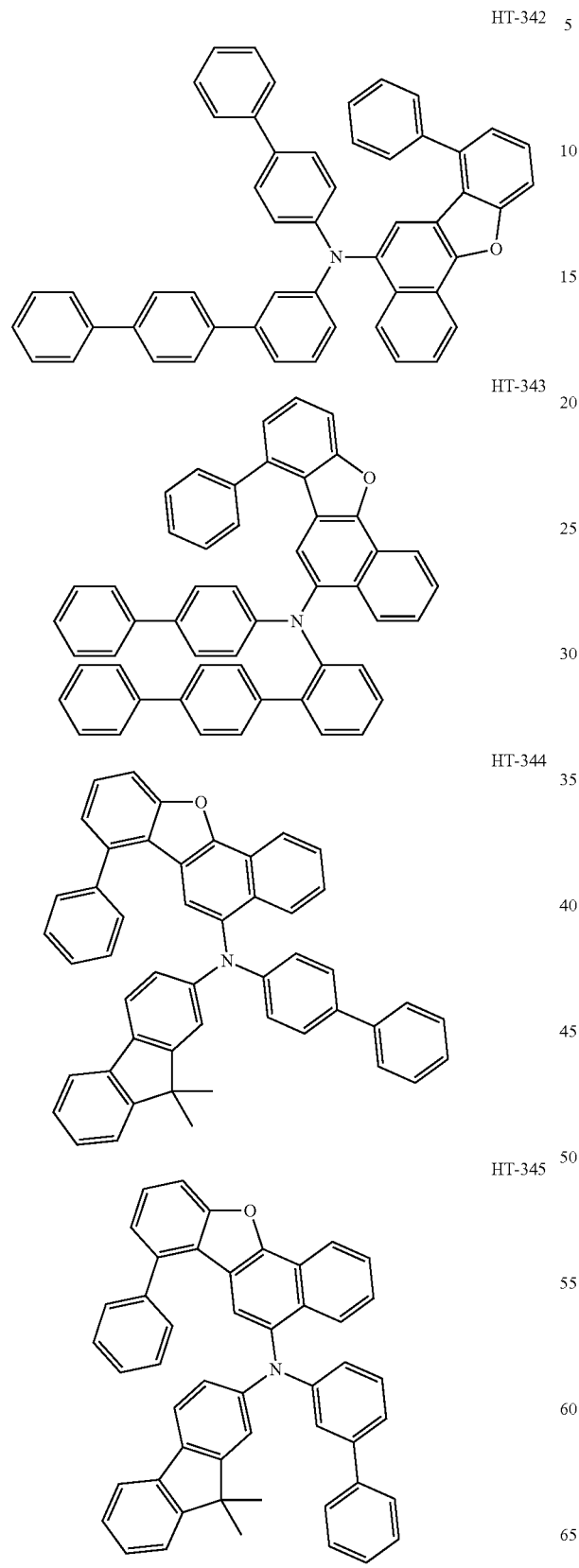
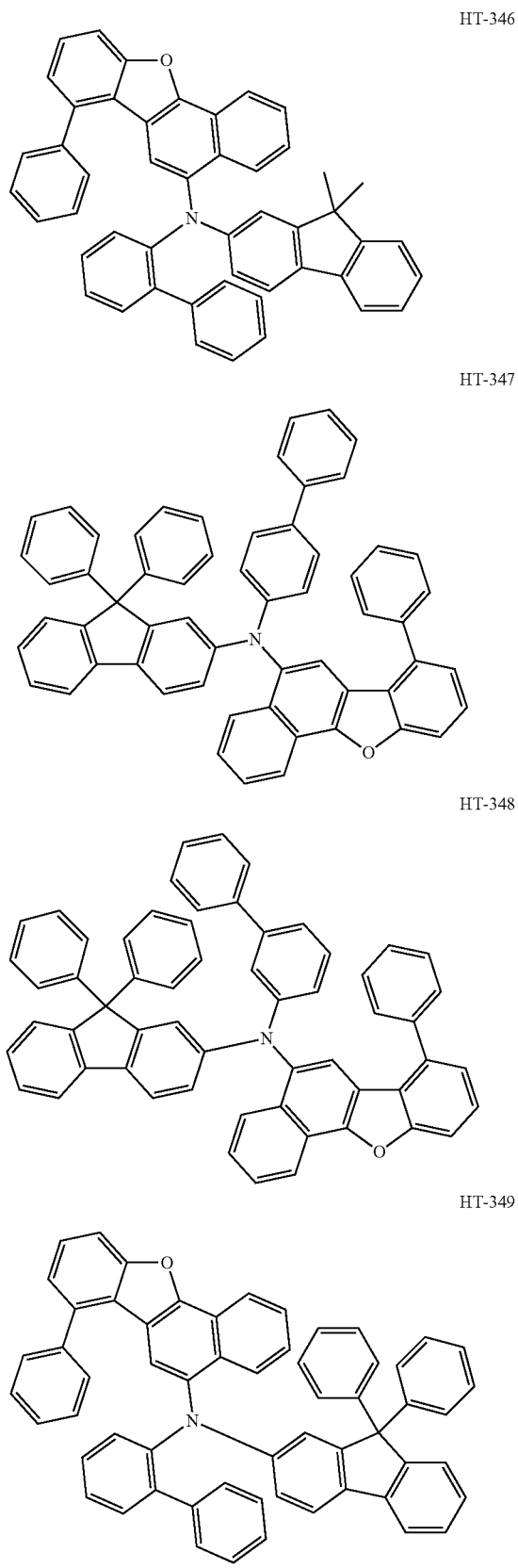

HT-350
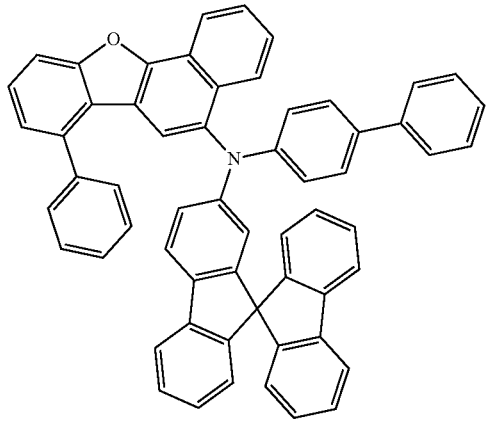
HT-351
HT-352
HT-353
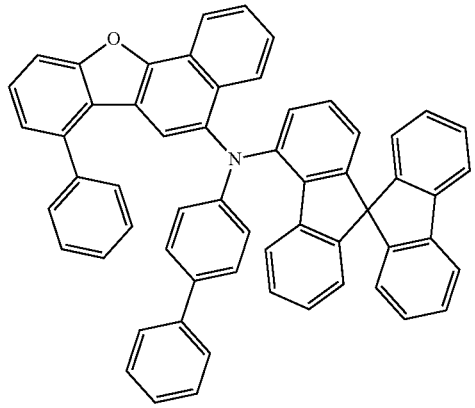
HT-354
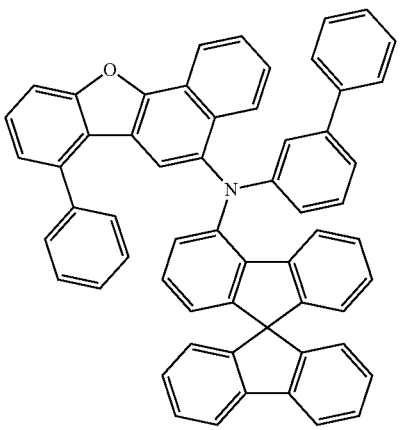
HT-355
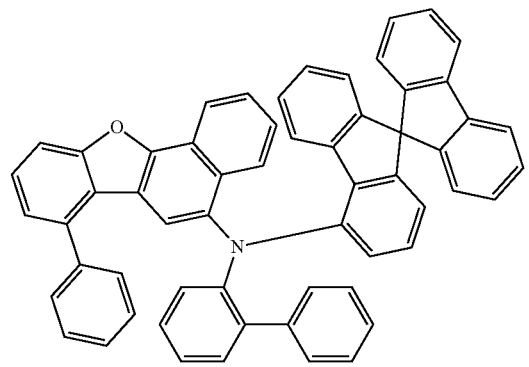
HT-356
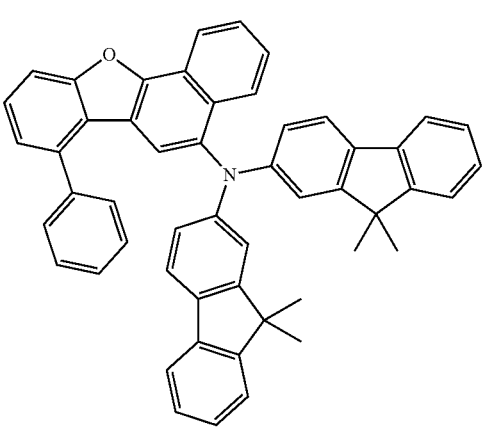

HT-357
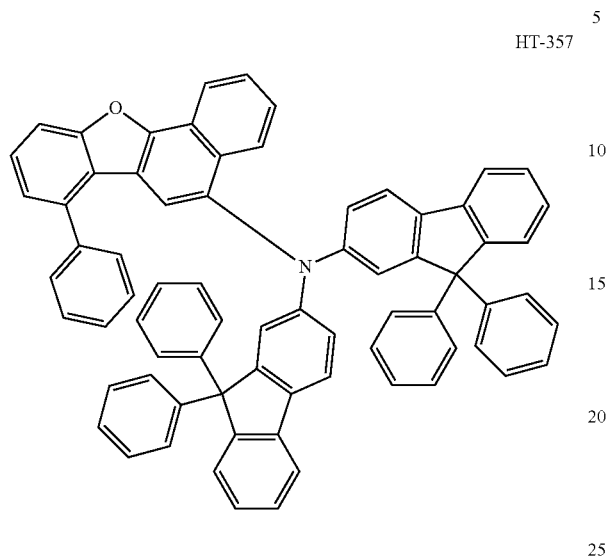
HT-358
HT-359
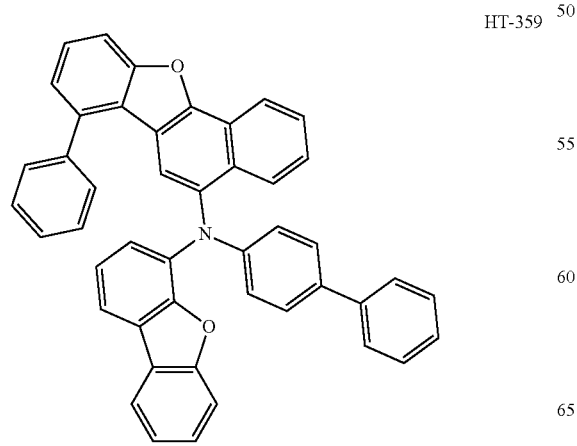
HT-360
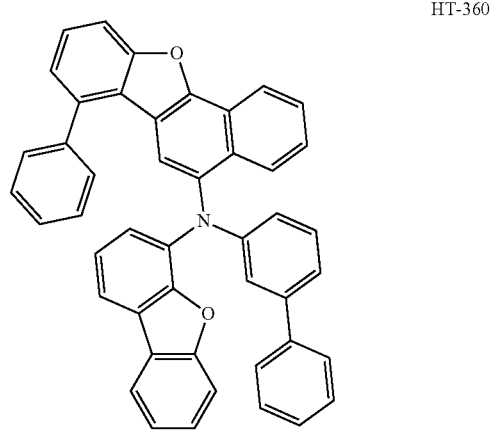
HT-361
HT-362
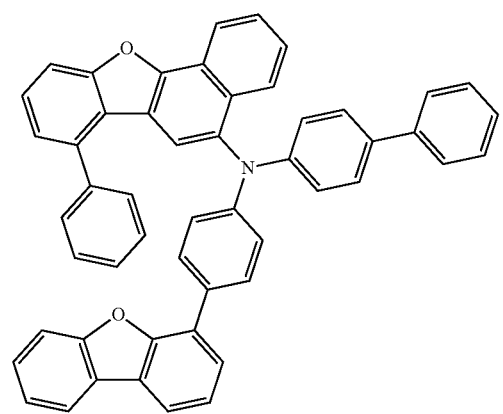

HT-363
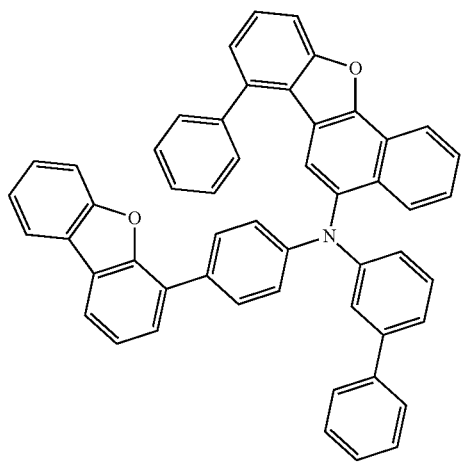
HT-364
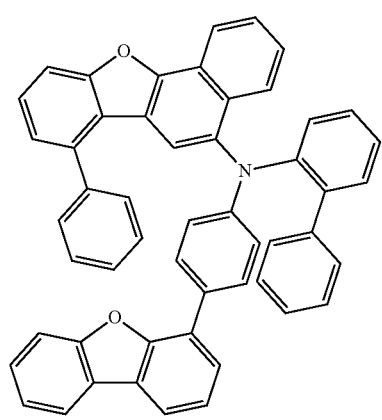
HT-365
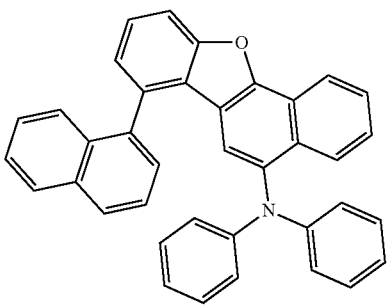
HT-366
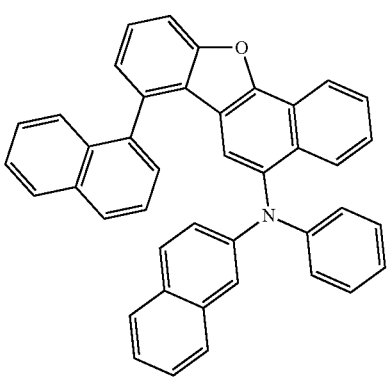
HT-367
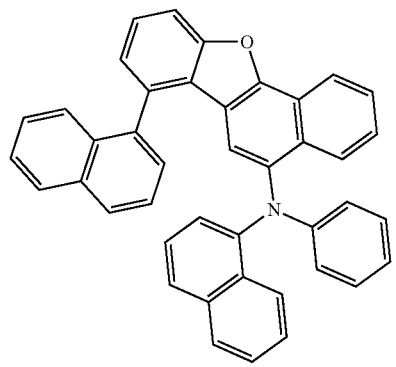
HT-368
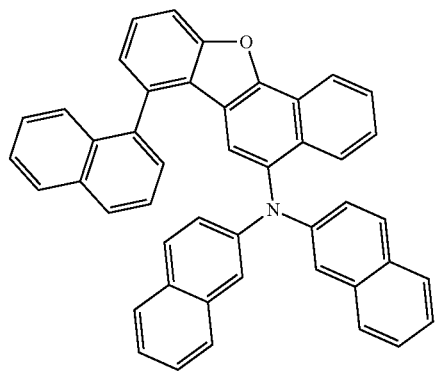
HT-369
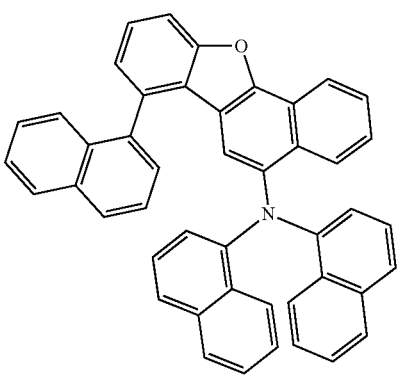
HT-370
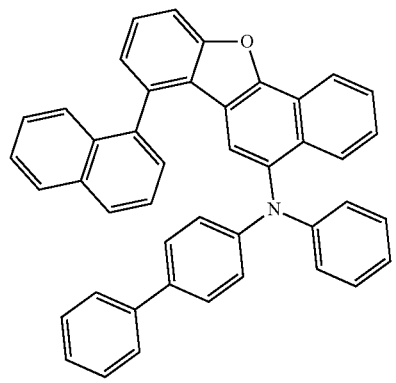

HT-371
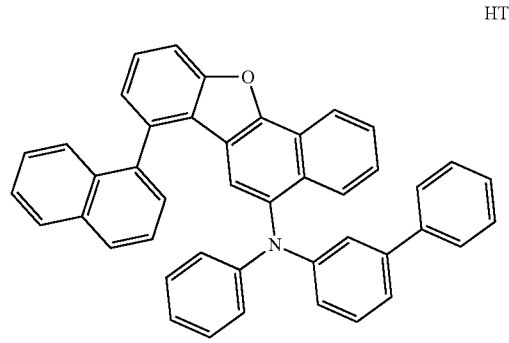
HT-372
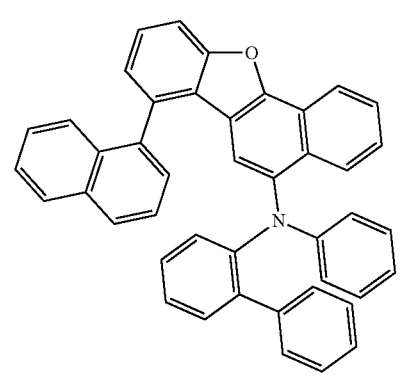
HT-373
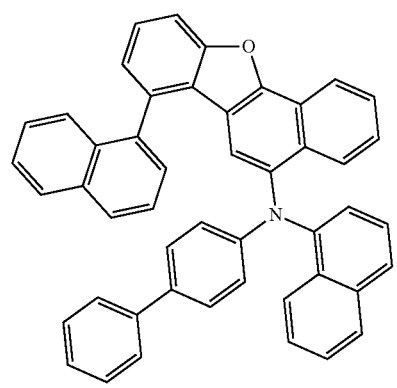
HT-374
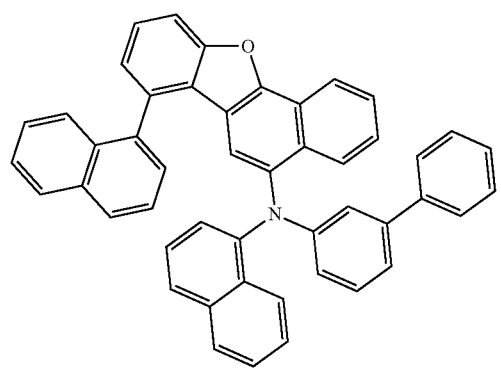
HT-375
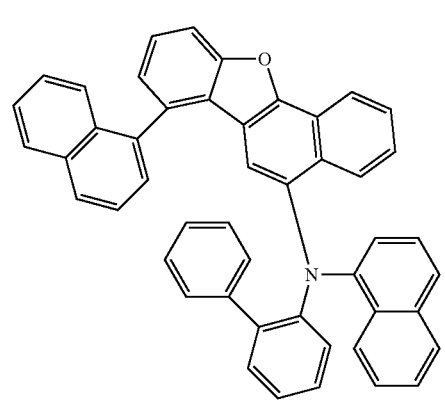
HT-376
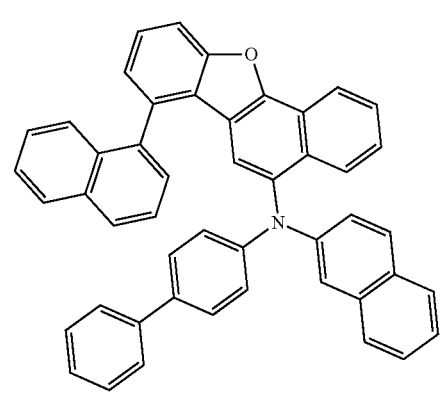
HT-377
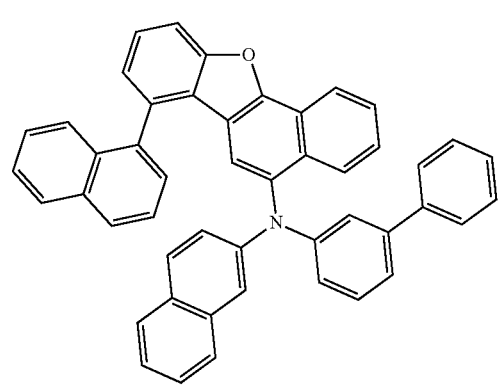
HT-378
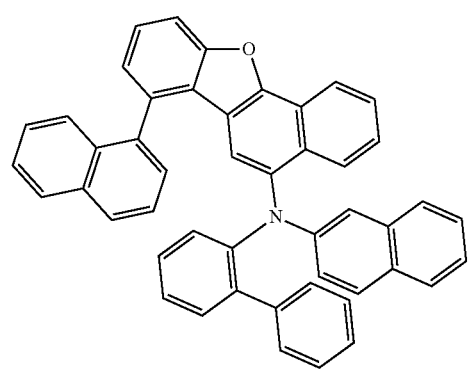

HT-379
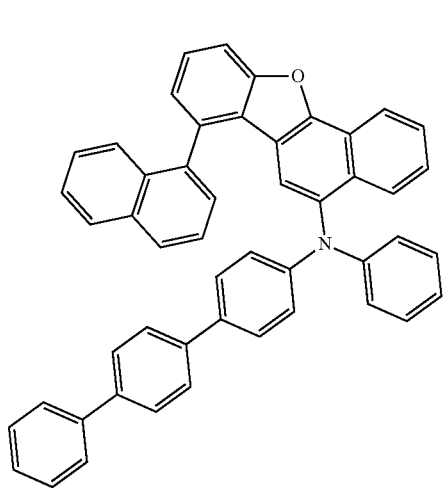
HT-382
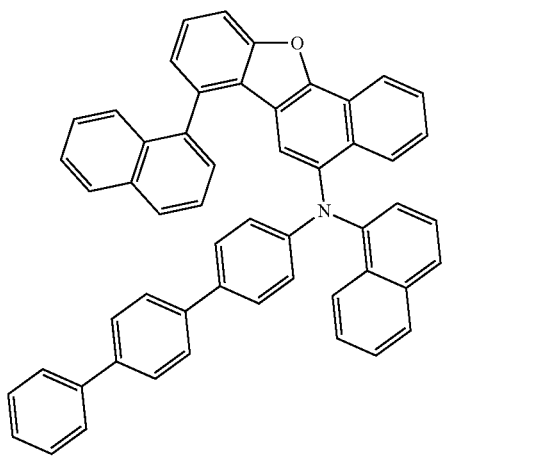
HT-380
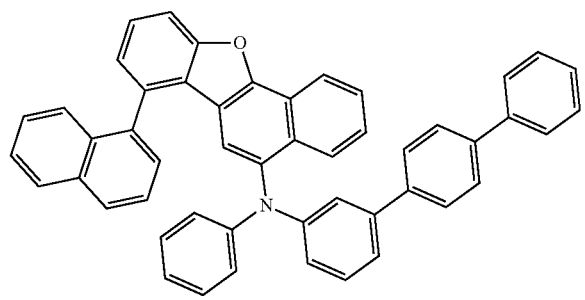
HT-383
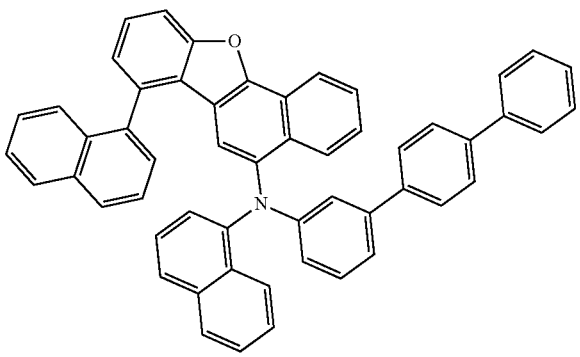
HT-381
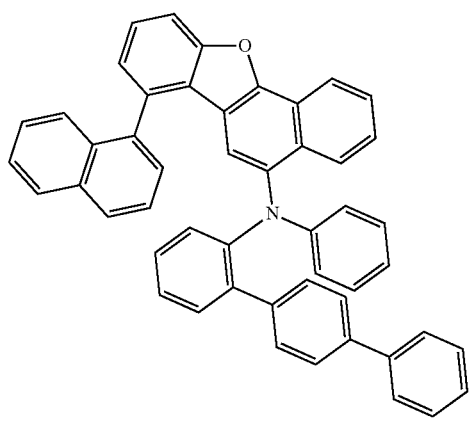
HT-384
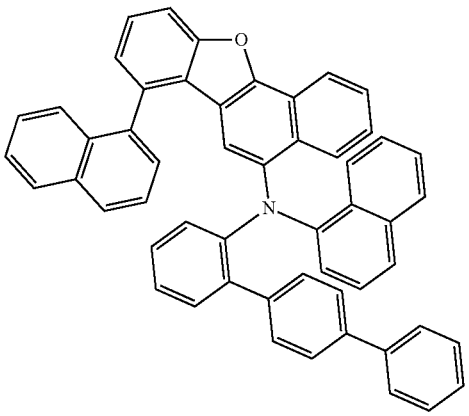

HT-385
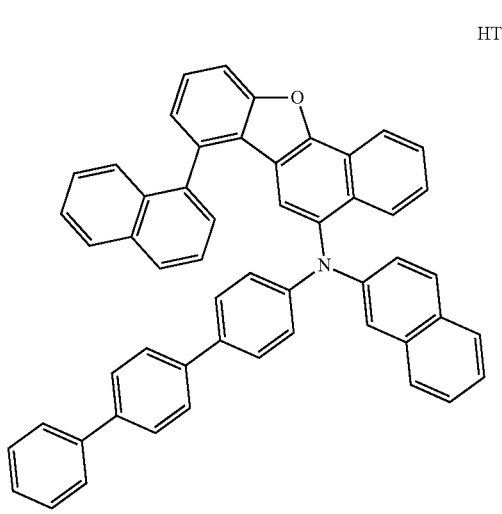
HT-388
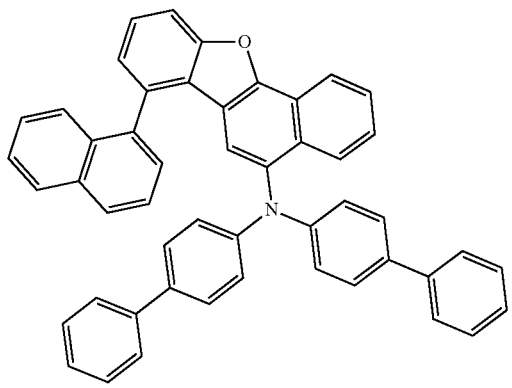
HT-386
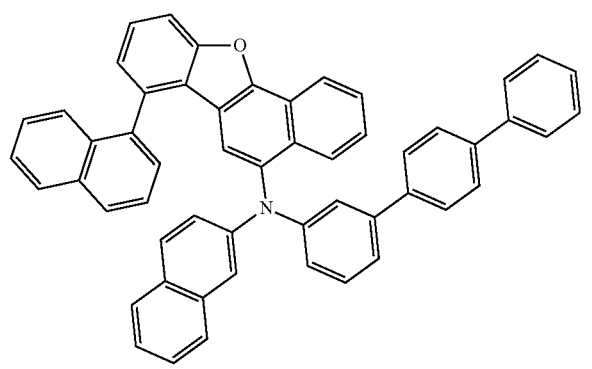
HT-389
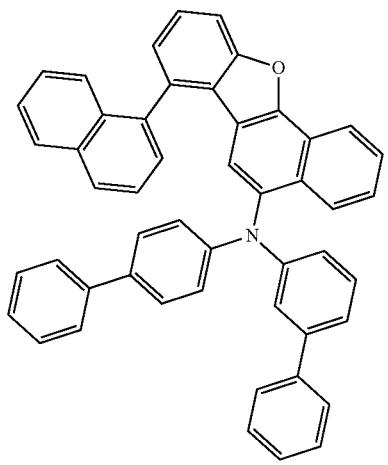
HT-387
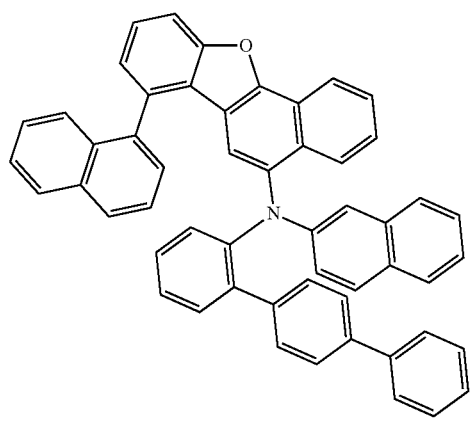
HT-390
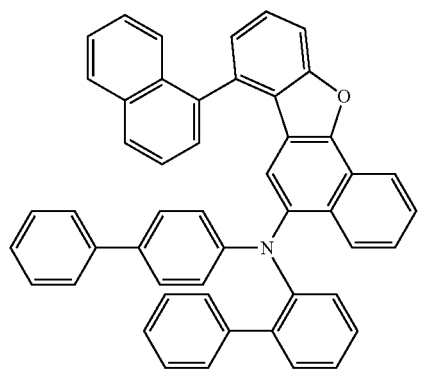

HT-391
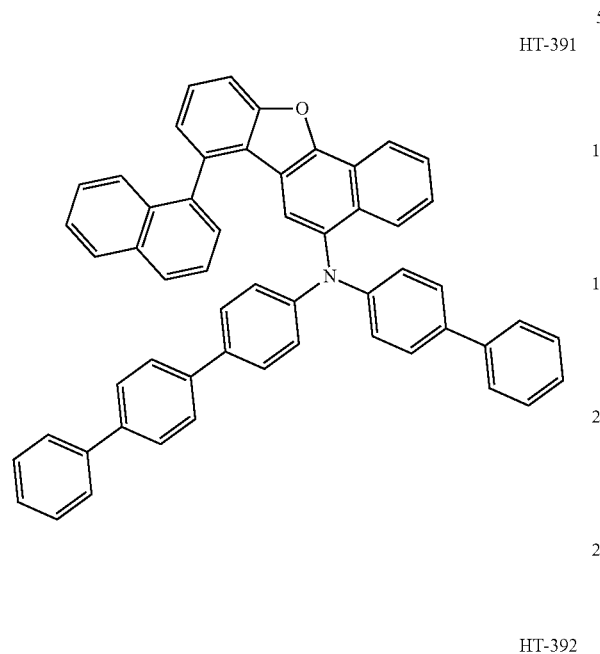
HT-394
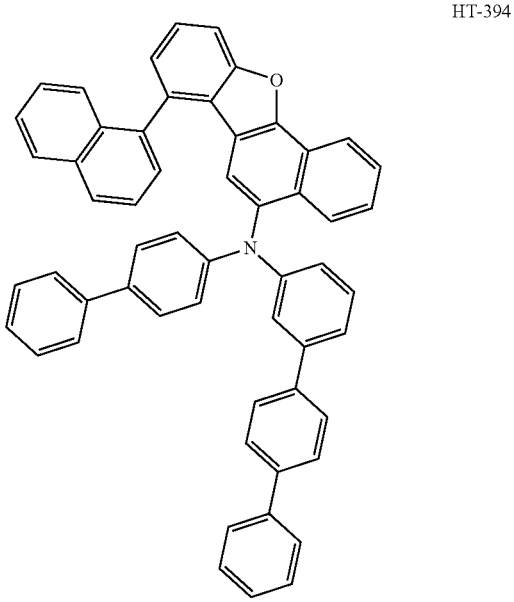
HT-392
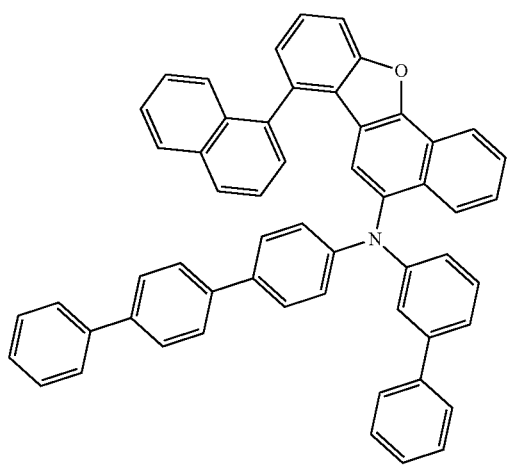
HT-395
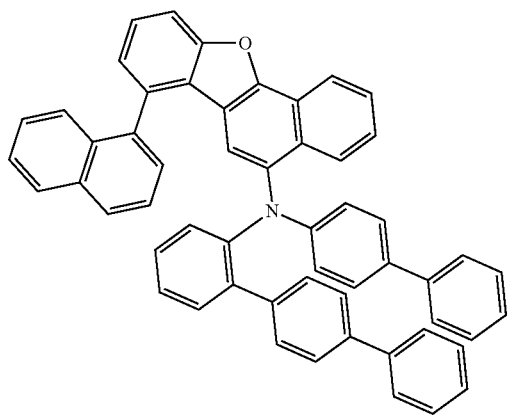
HT-393
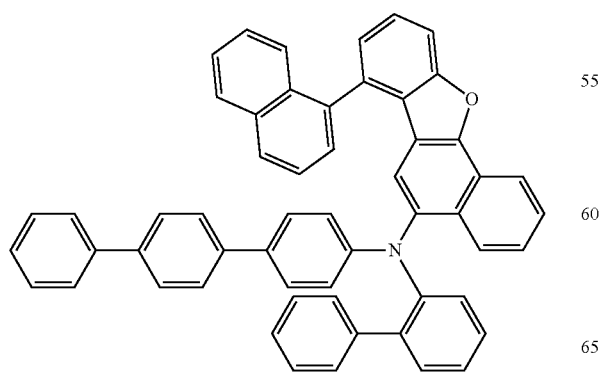
HT-396
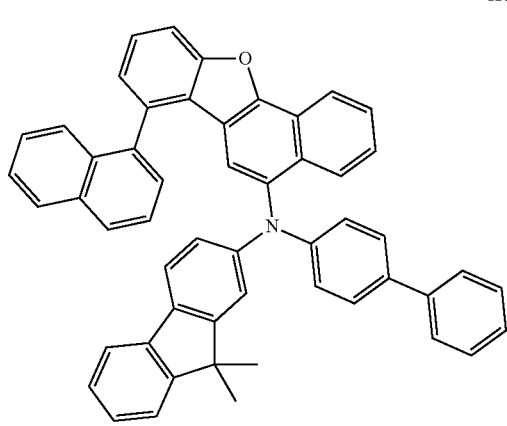

HT-397
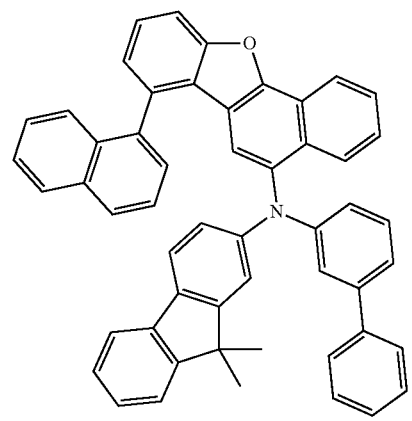
HT-398
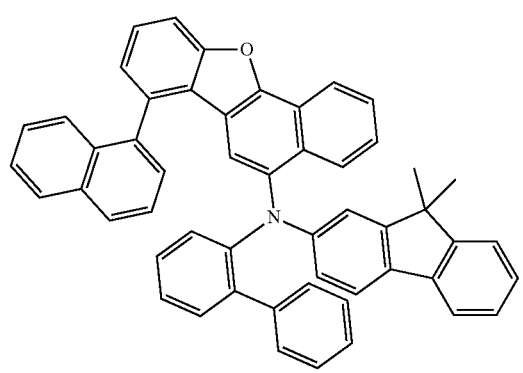
HT-399
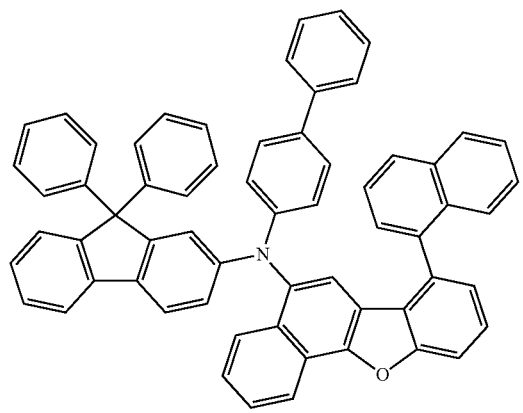
HT-400
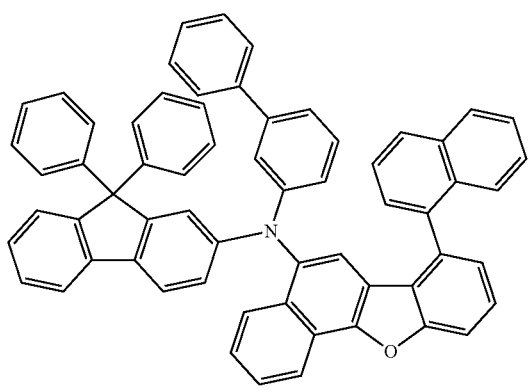
HT-401
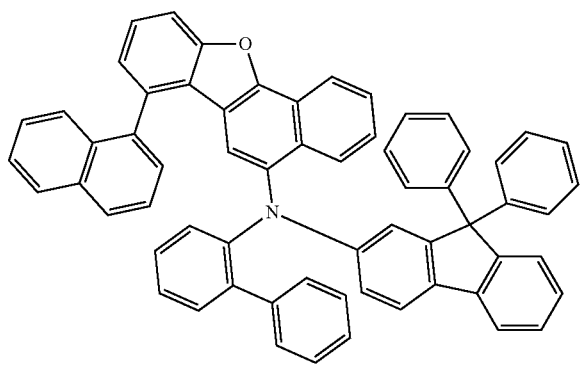
HT-402
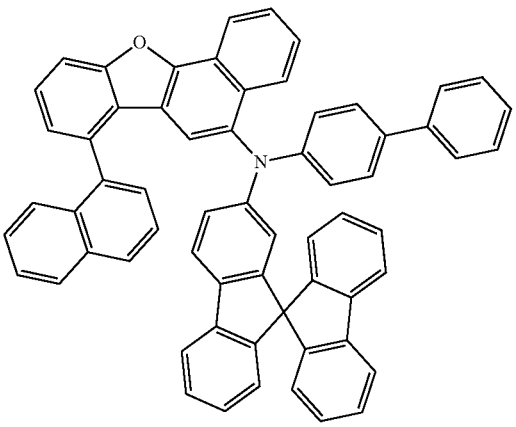
HT-403
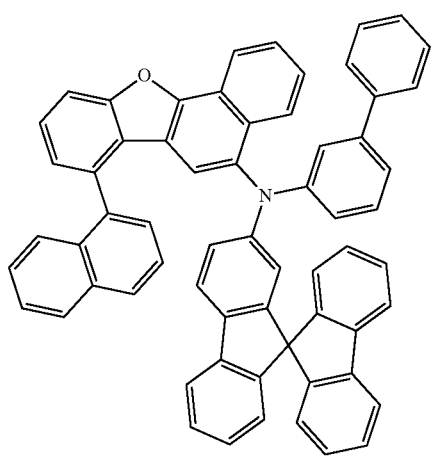

HT-404
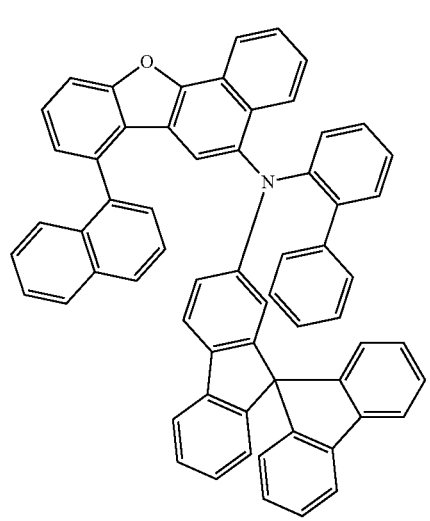
HT-407
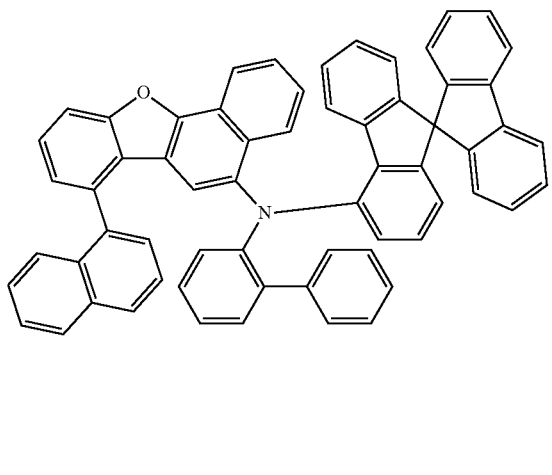
HT-405
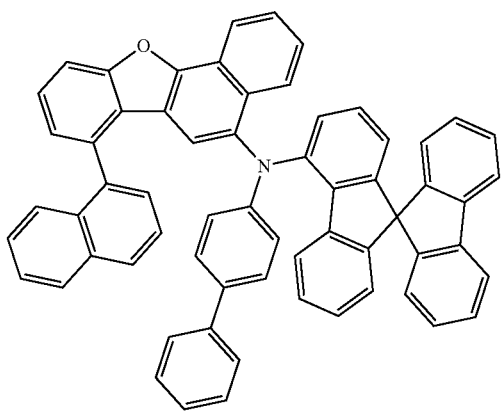
HT-408
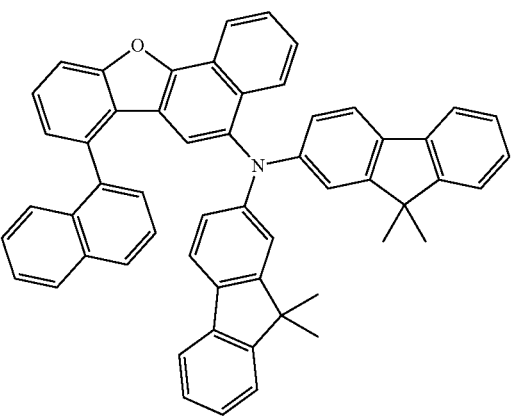
HT-406
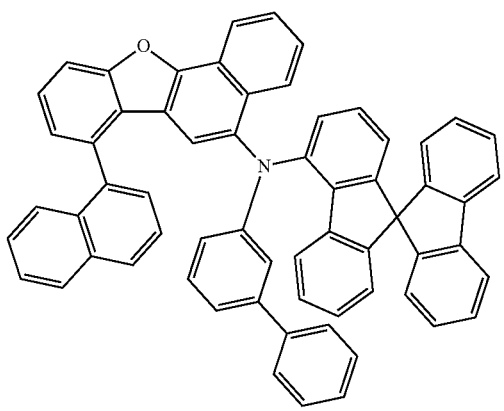
HT-409
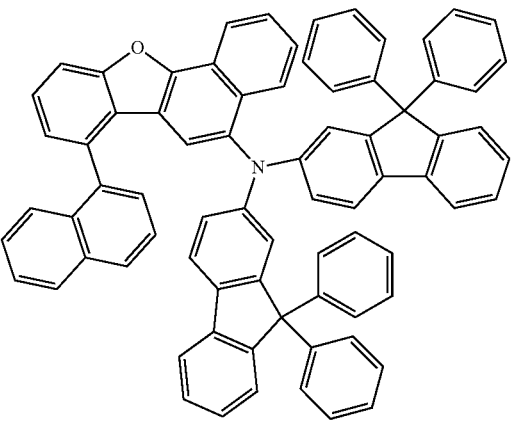

127
-continued
HT-410
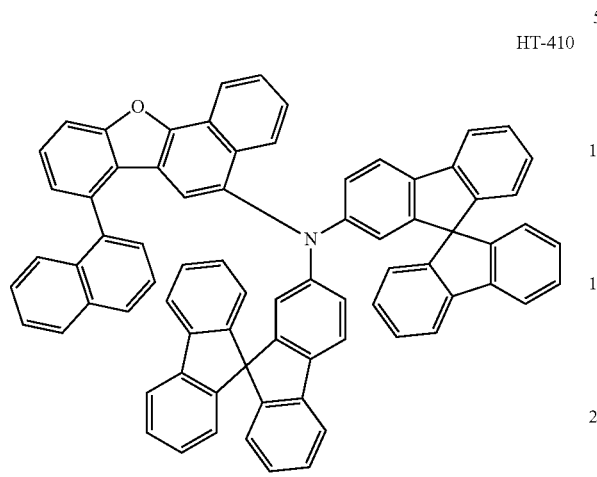
HT-411
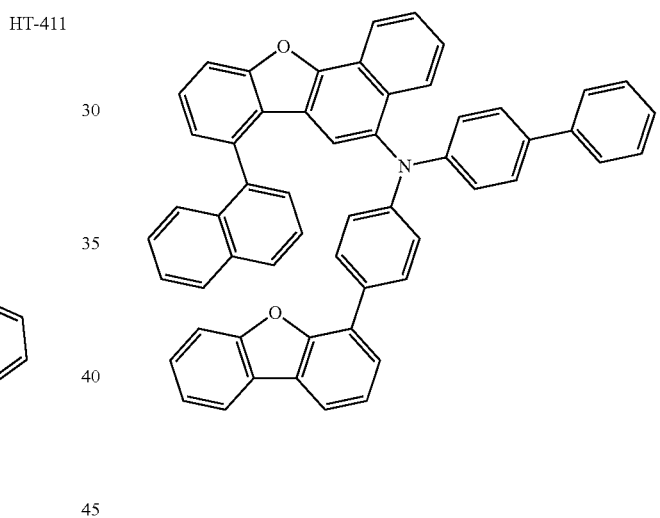
HT-412
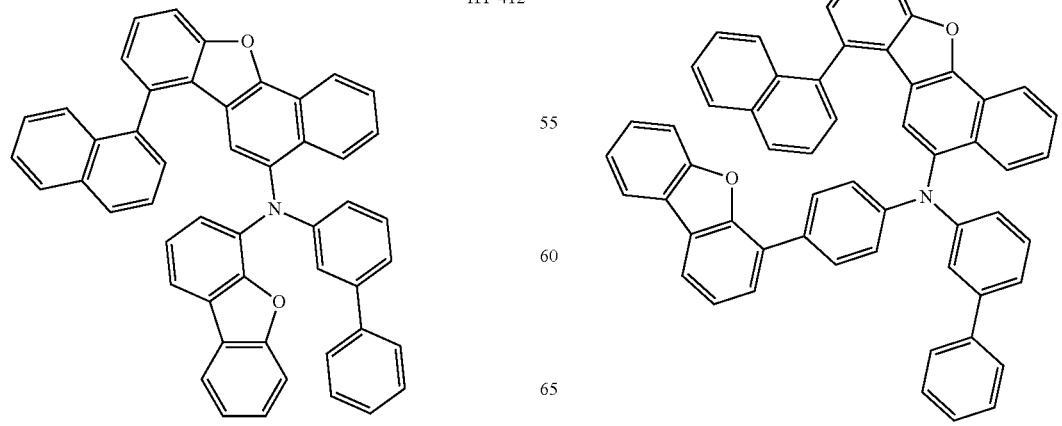
128
-continued
HT-413
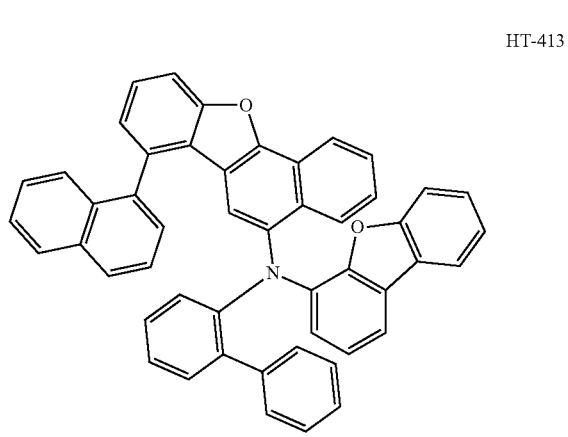
HT-414
HT-415

HT-416
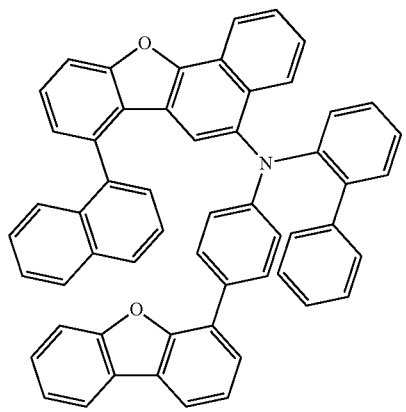
HT-417
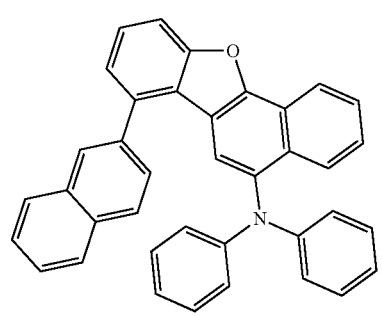
HT-418
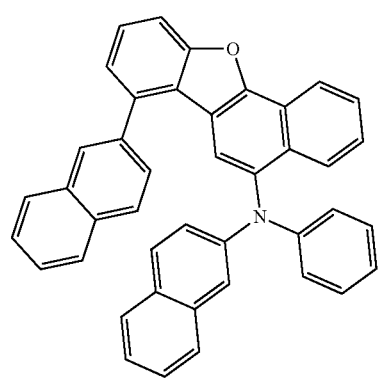
HT-419
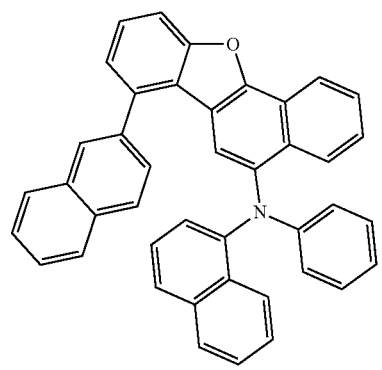
HT-420
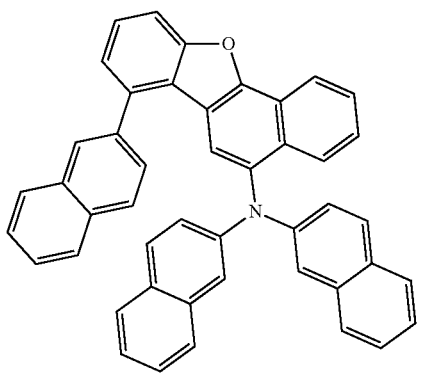
HT-421
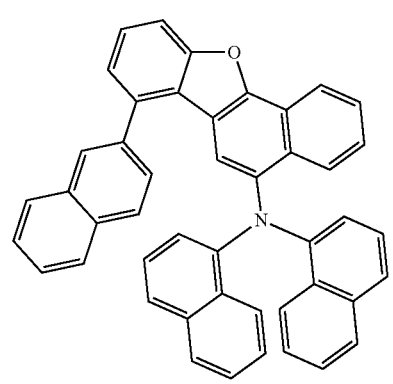
HT-422
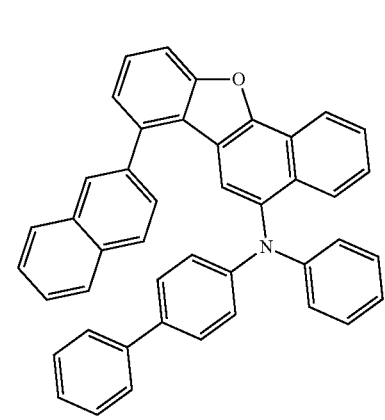
HT-423
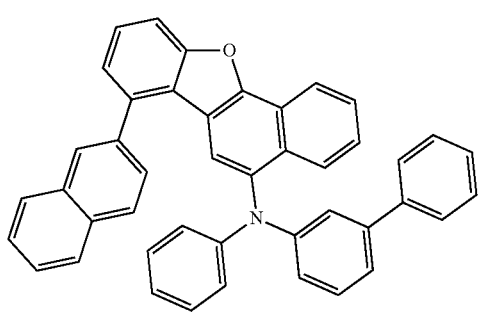

HT-424
HT-425
HT-426
HT-427
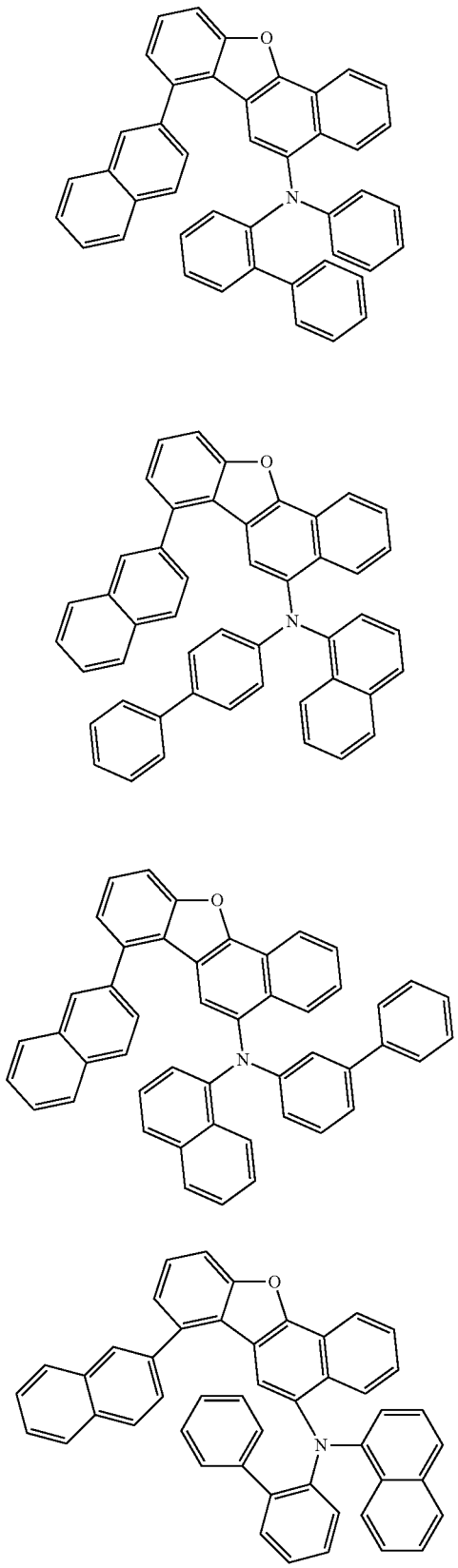
HT-428
HT-429
HT-430
HT-431
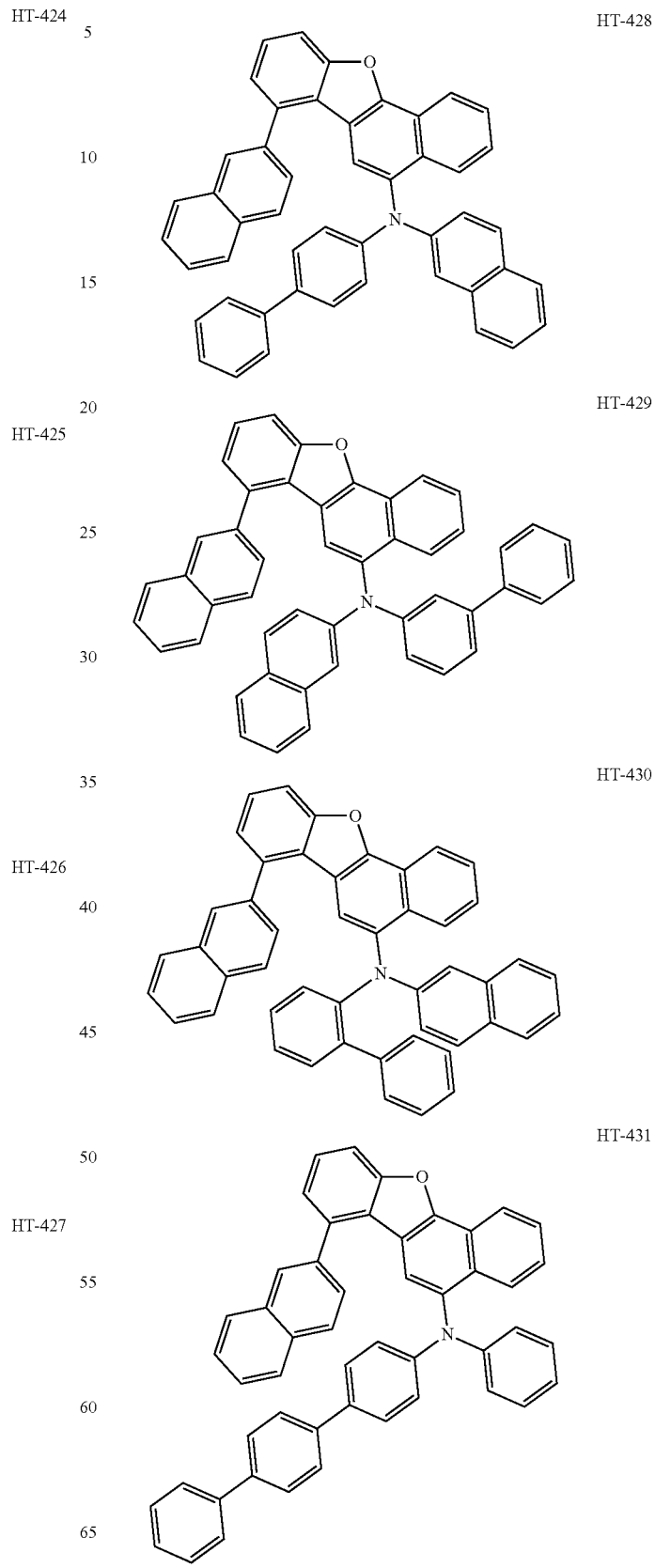

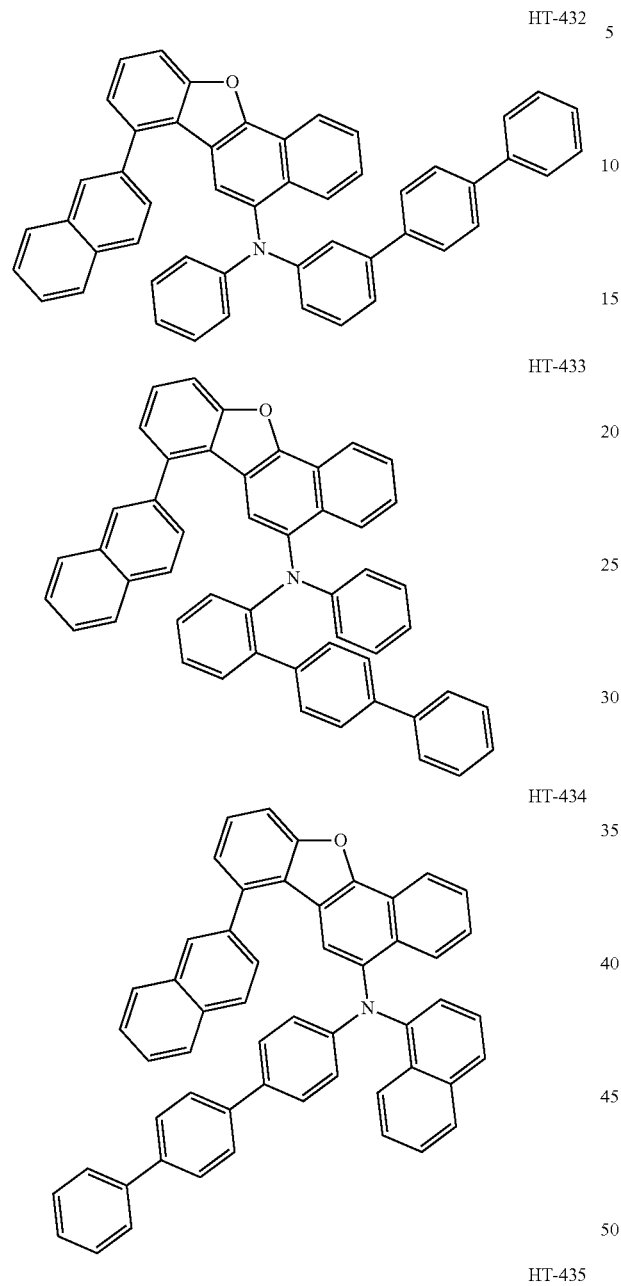
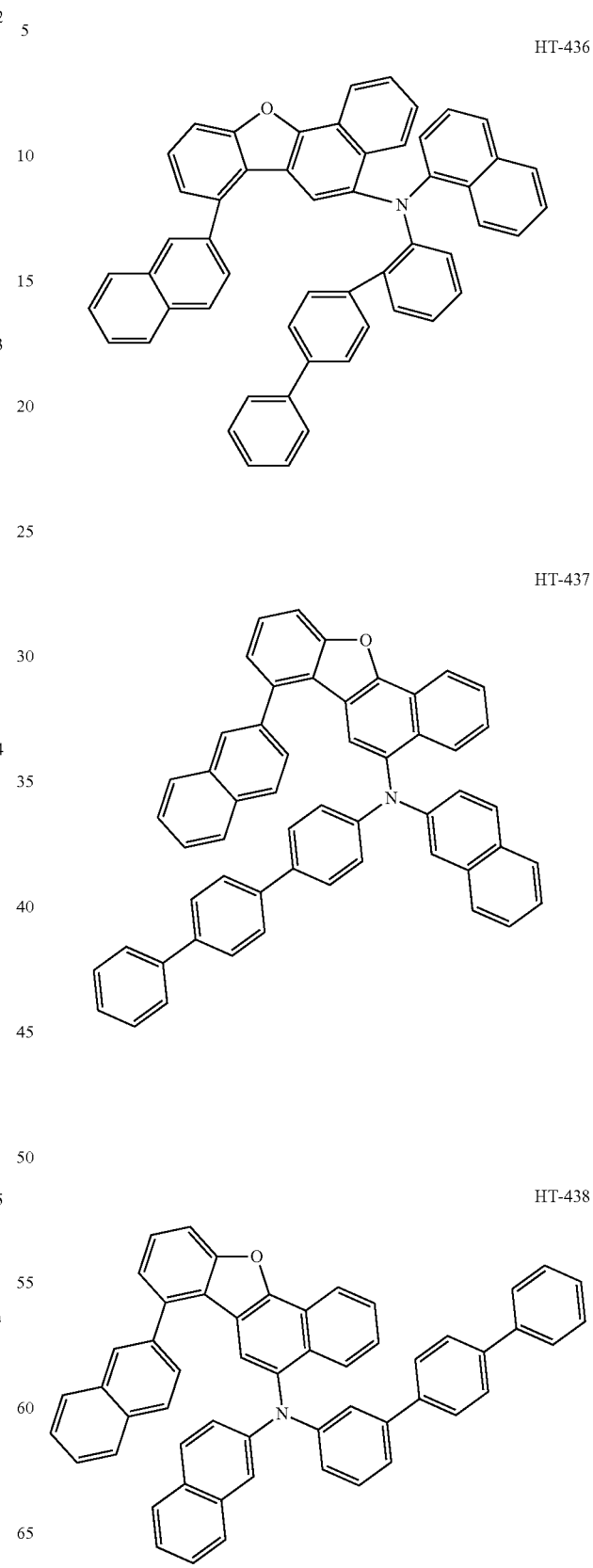

HT-439
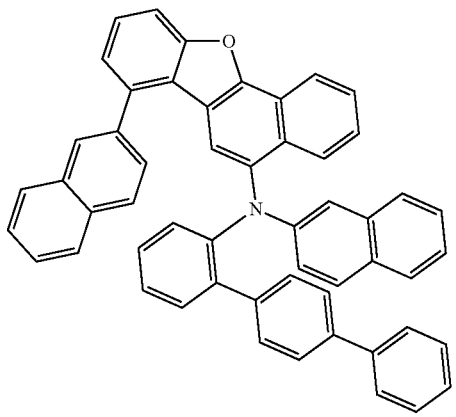
HT-440
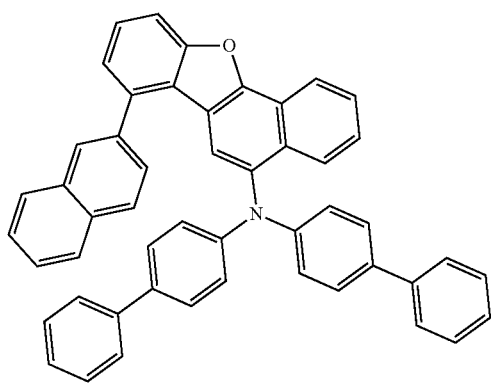
HT-441
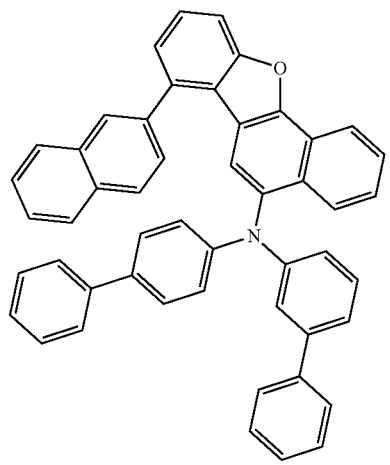
HT-442
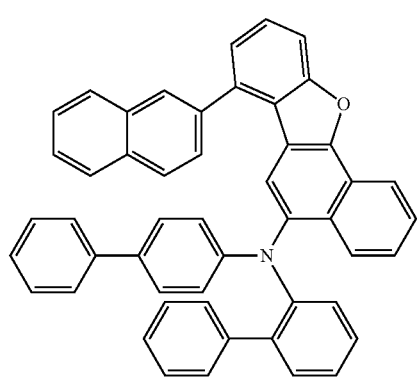
HT-443
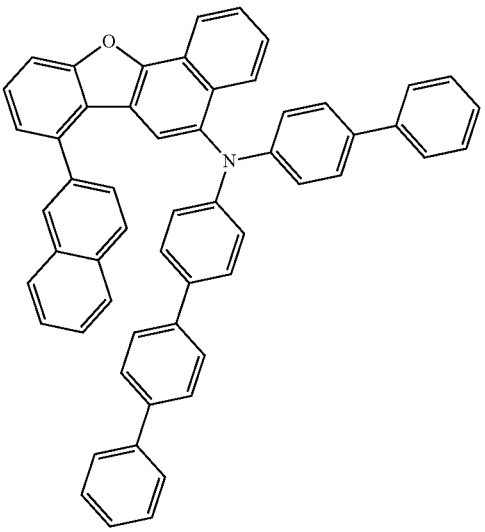
HT-444
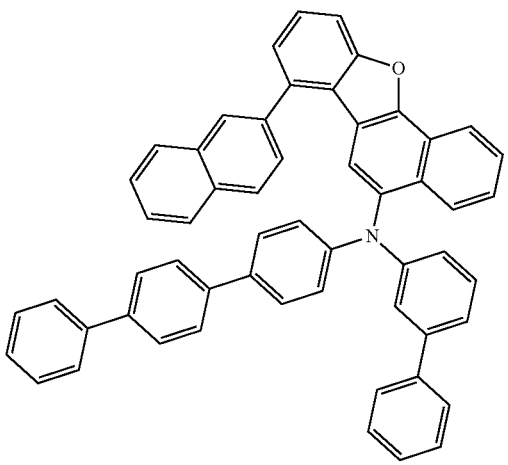
HT-445
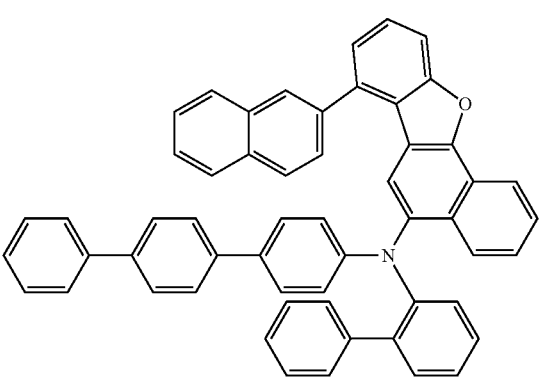

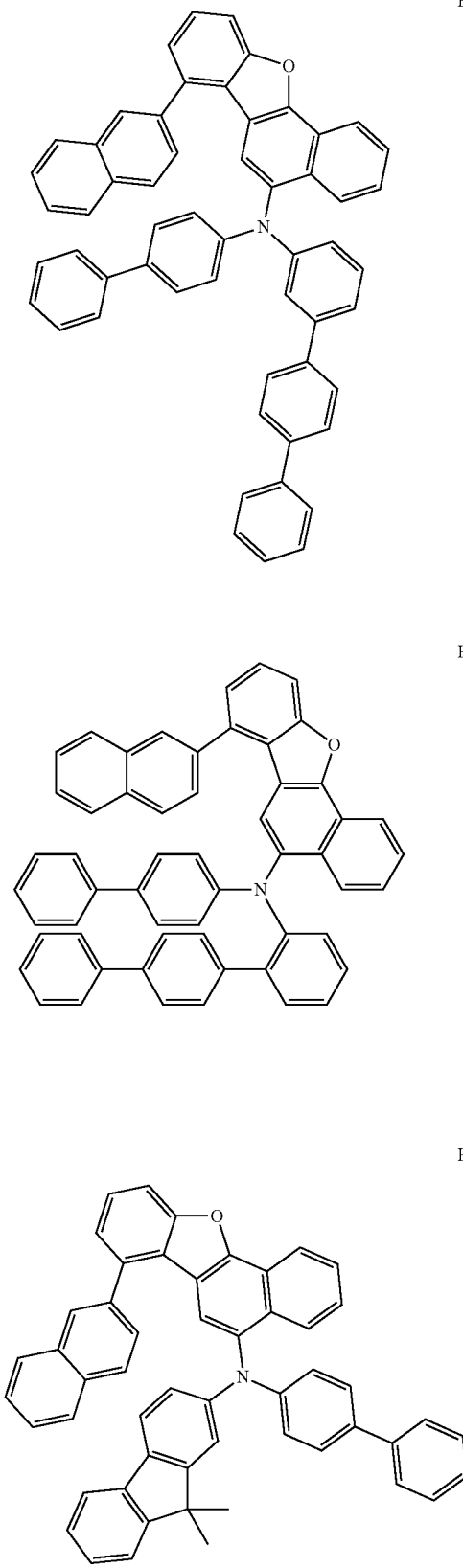
HT-446
HT-447
HT-448
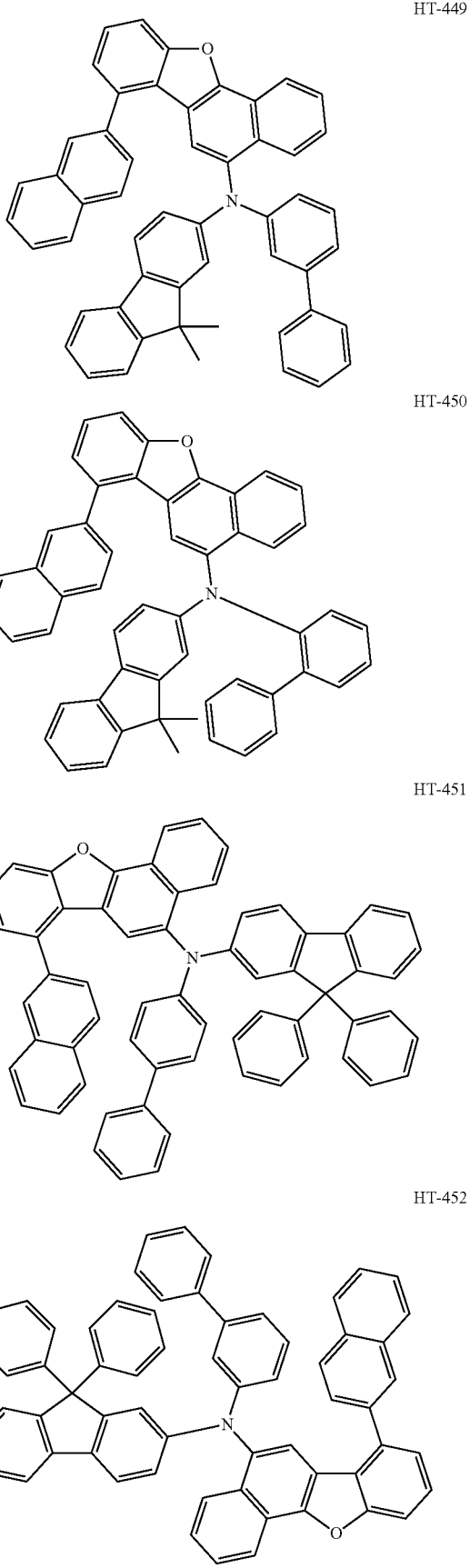
HT-449
HT-450
HT-451
HT-452

HT-453
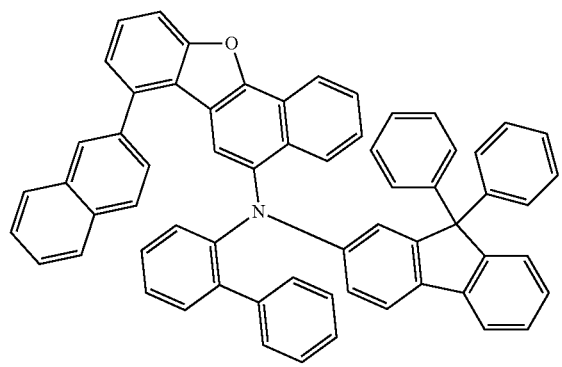
HT-454
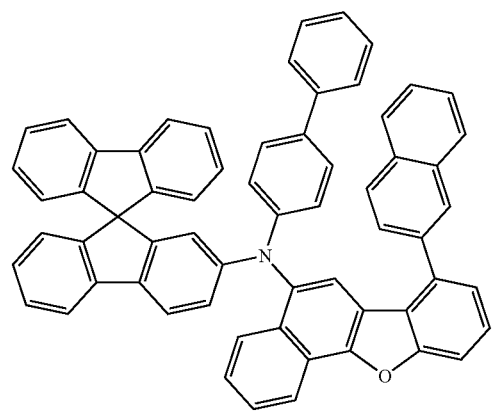
HT-455
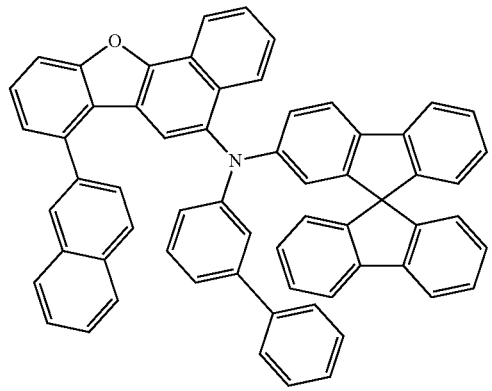
HT-456
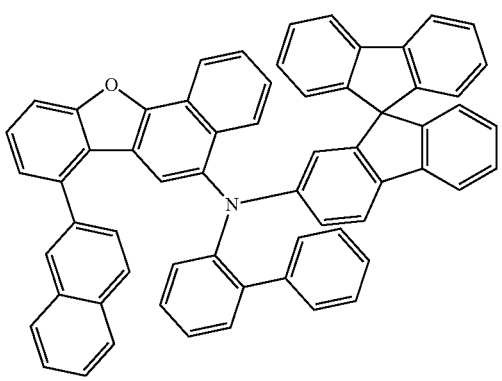
HT-457
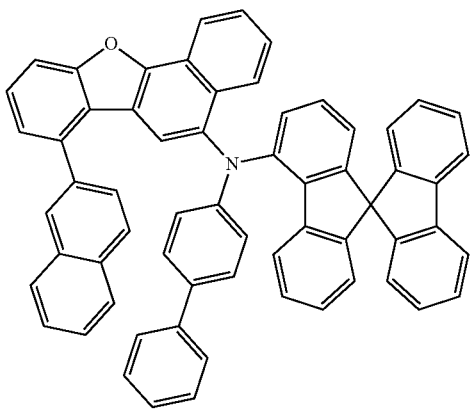
HT-458
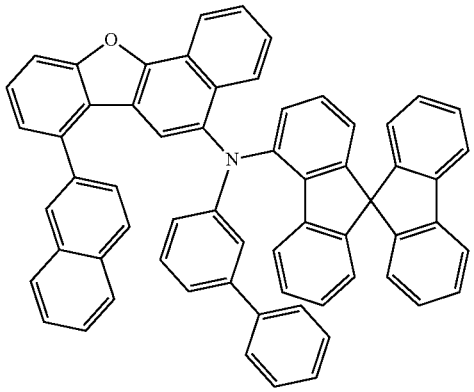
HT-459
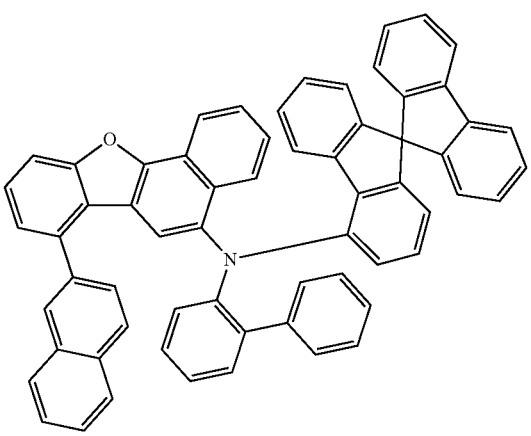

-continued
HT-460
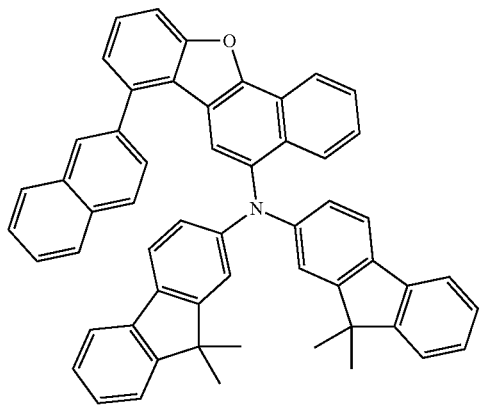
HT-461
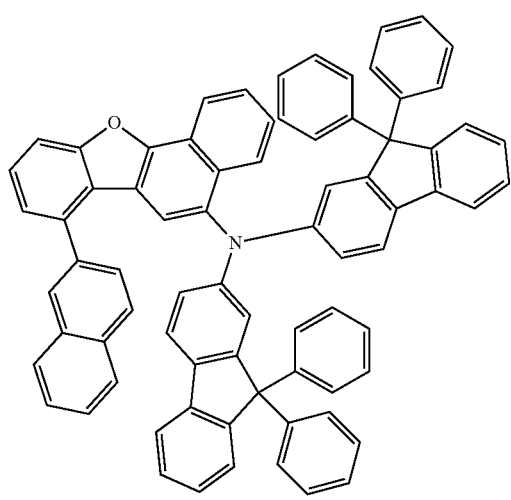
HT-462
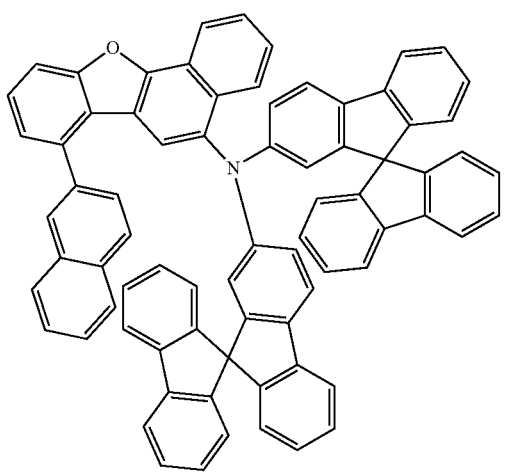
-continued
HT-463
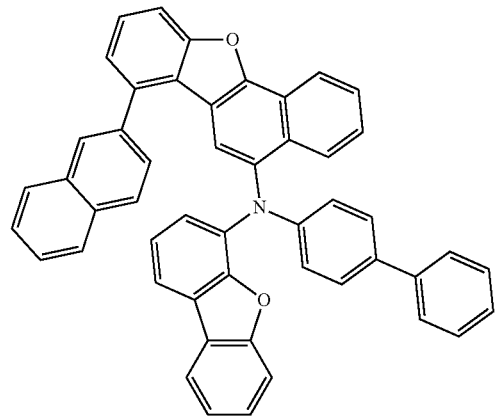
HT-464
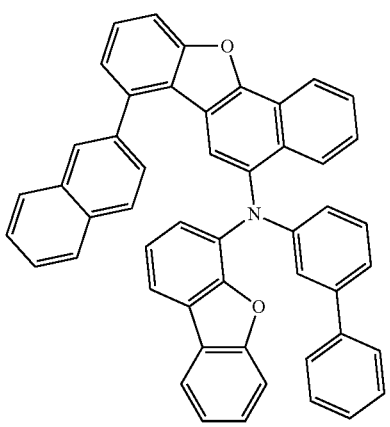
HT-465
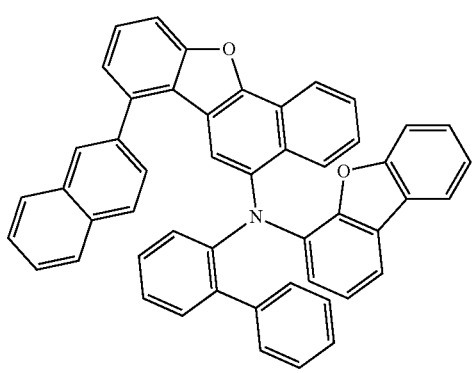

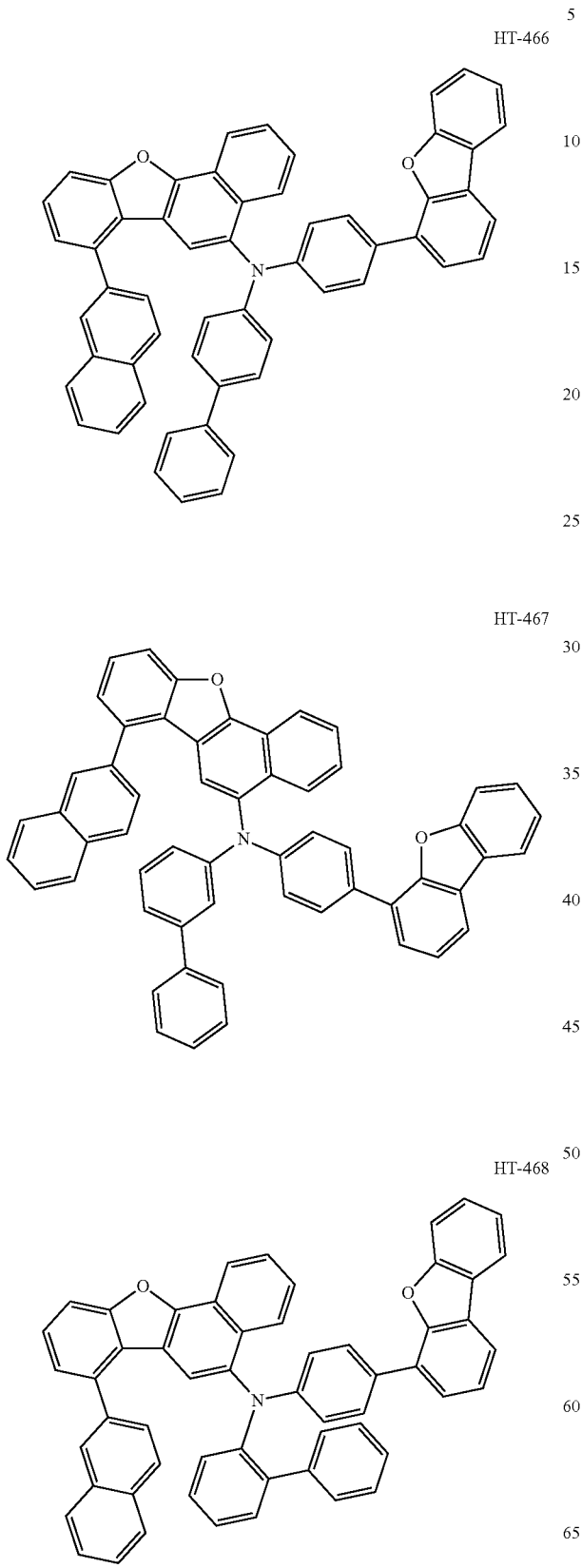
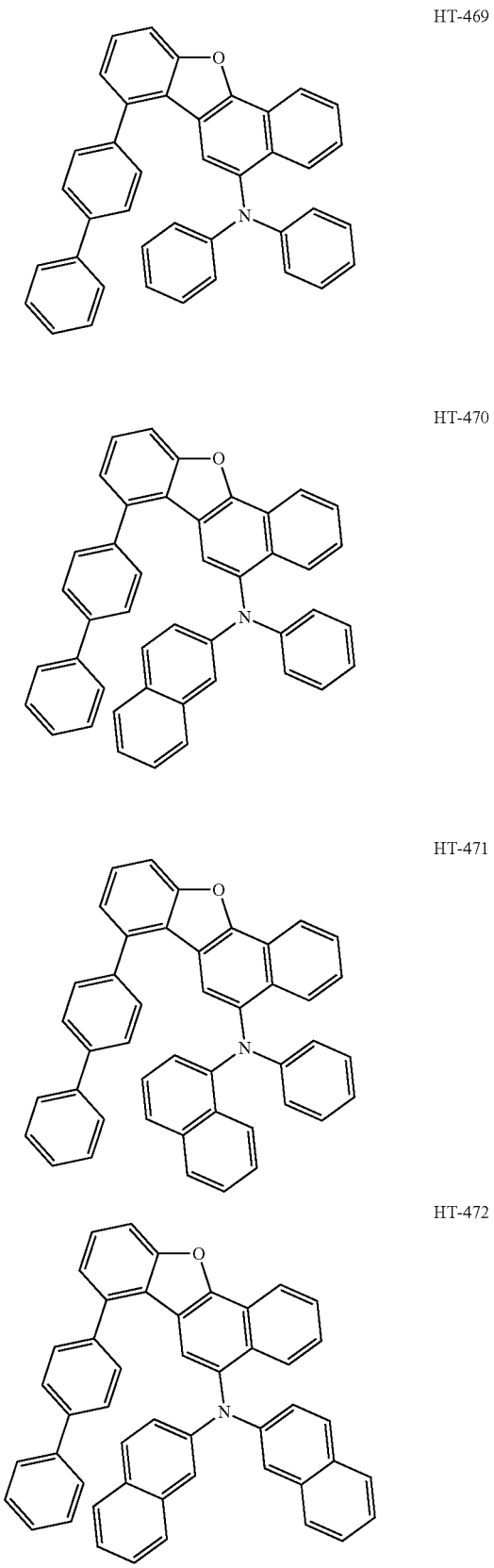

HT-473
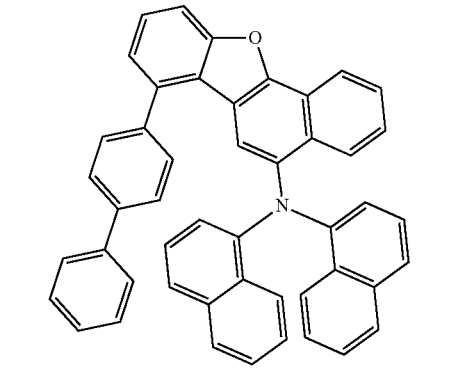
HT-474
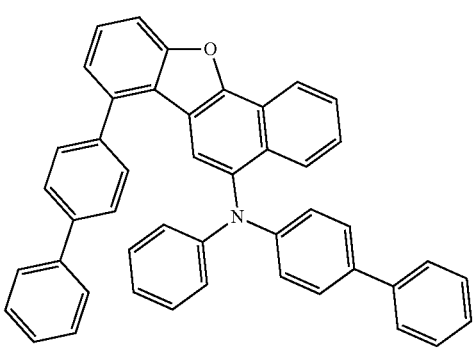
HT-475
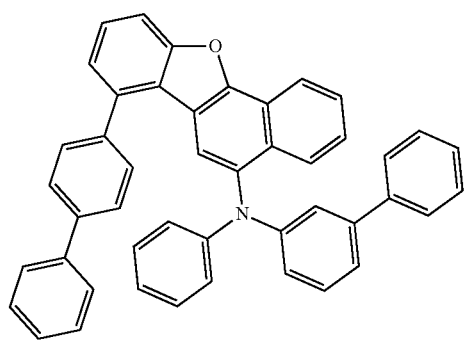
HT-476
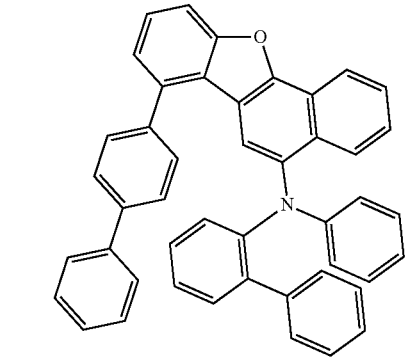
HT-477
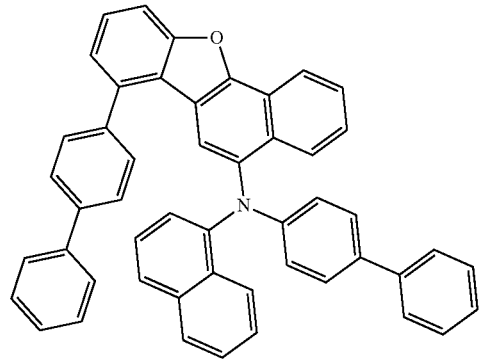
HT-478
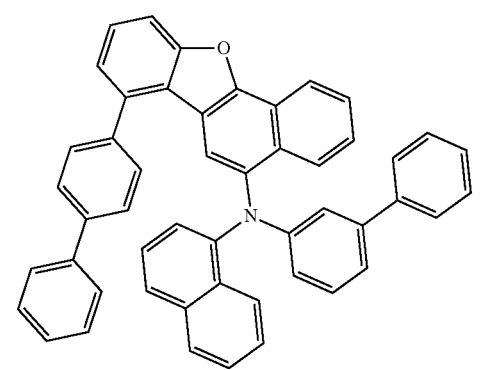
HT-479
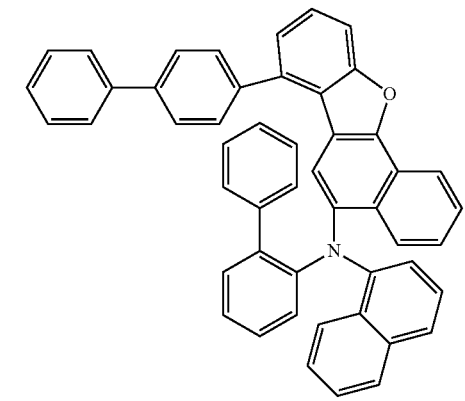
HT-480
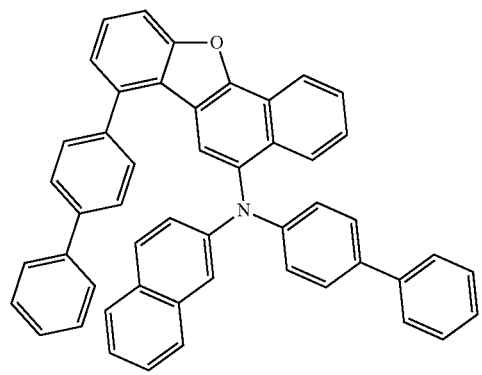

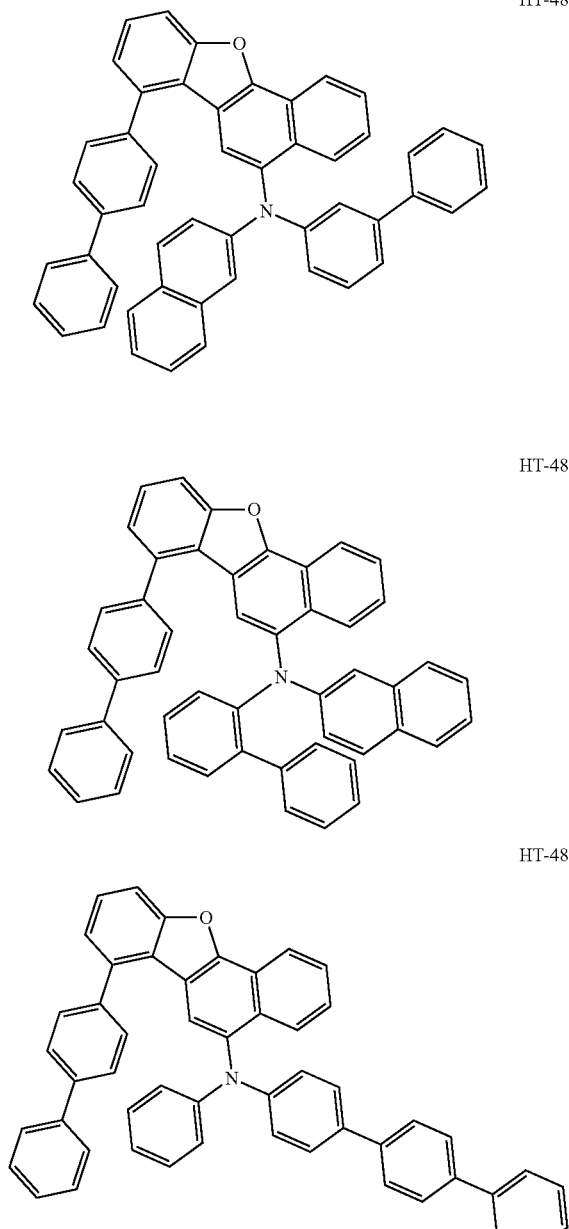
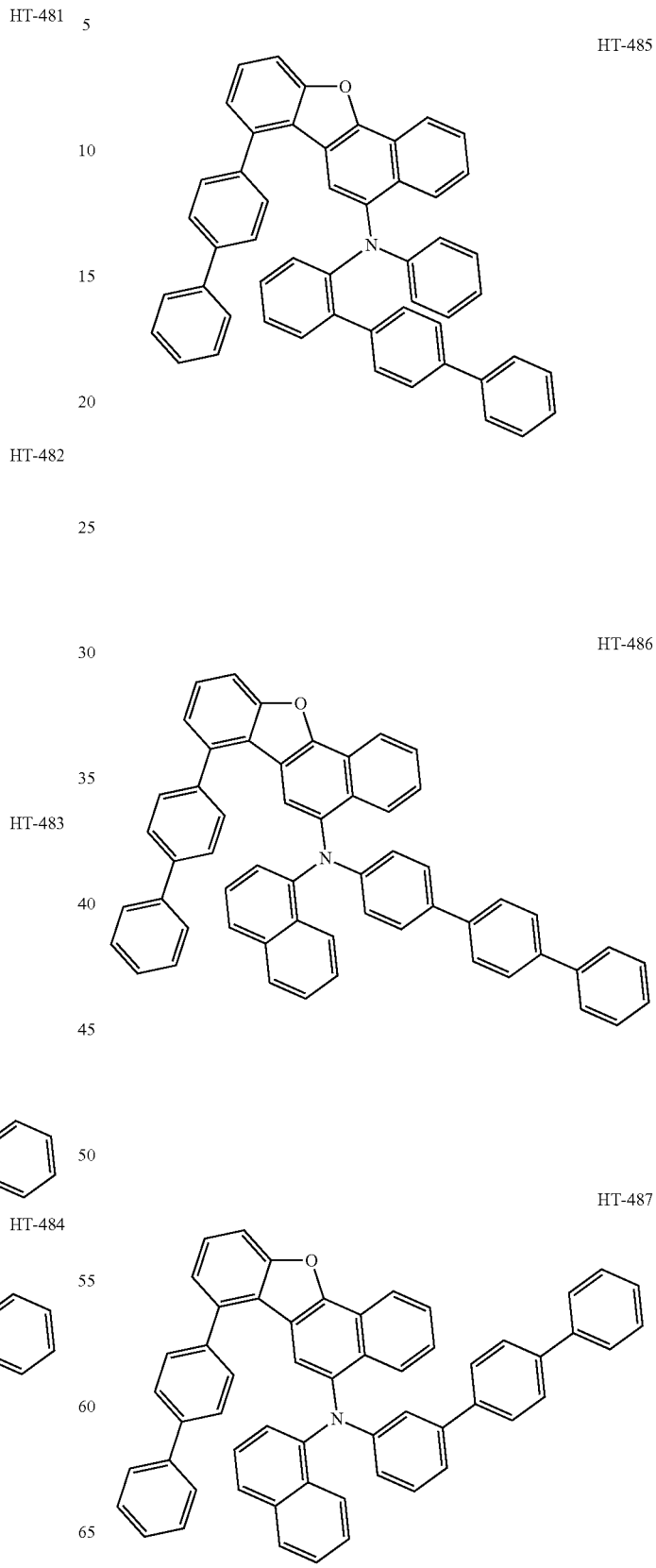

-continued
HT-488
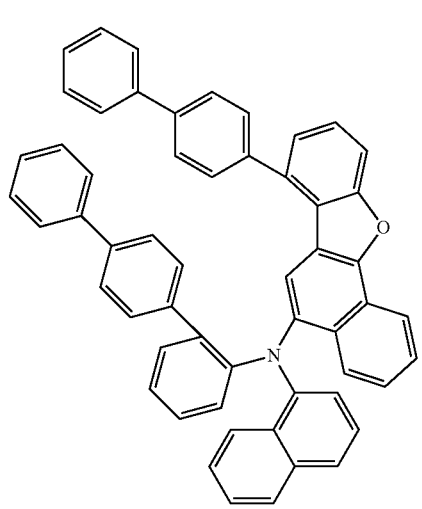
HT-489
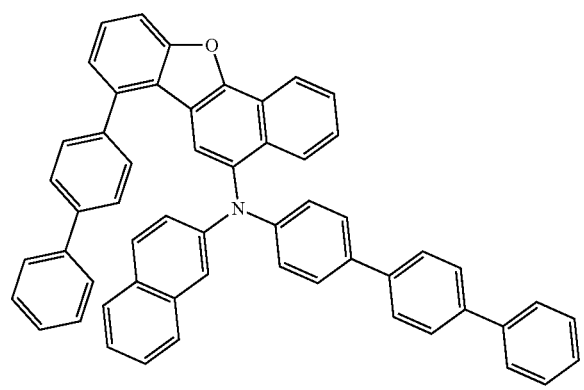
HT-490
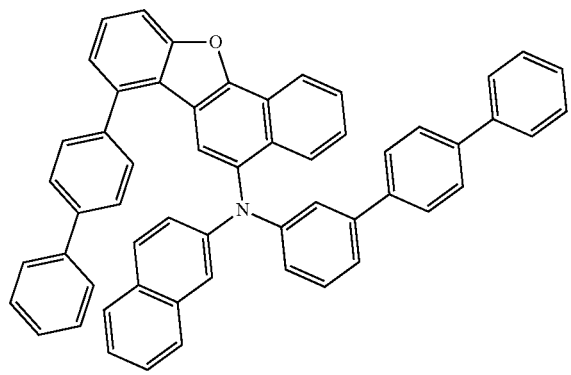
-continued
HT-491
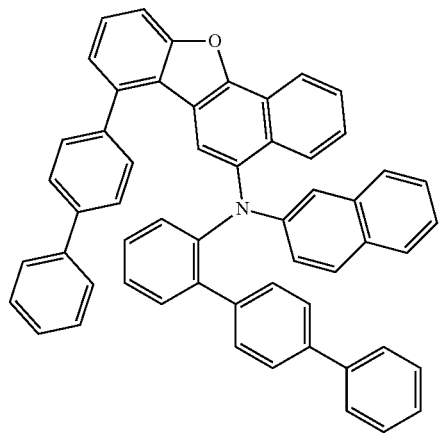
HT-492
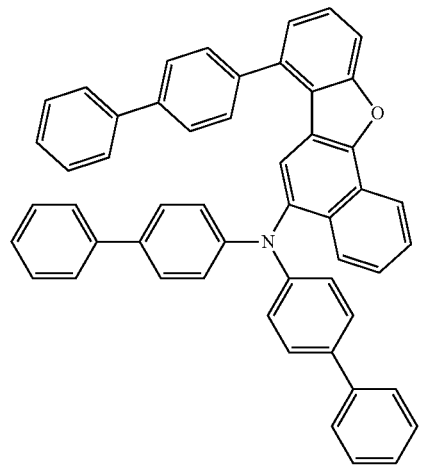
HT-493
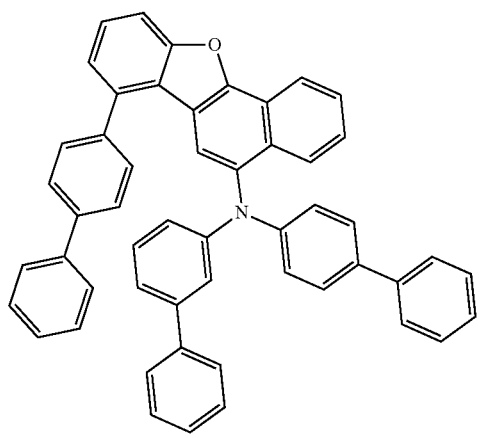

HT-494
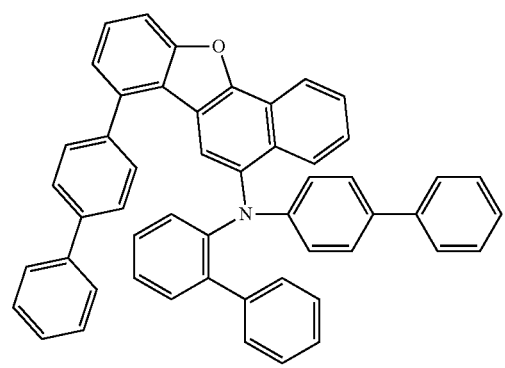
HT-495
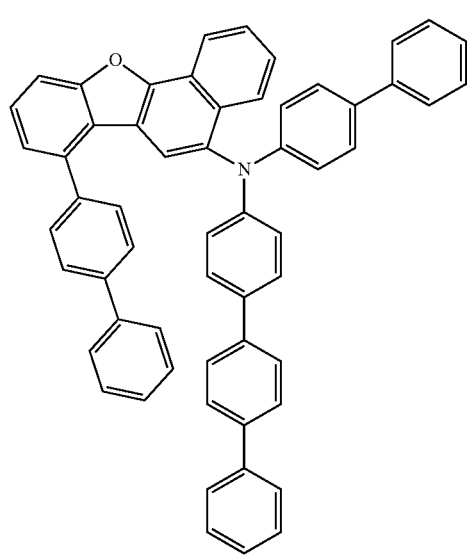
HT-496
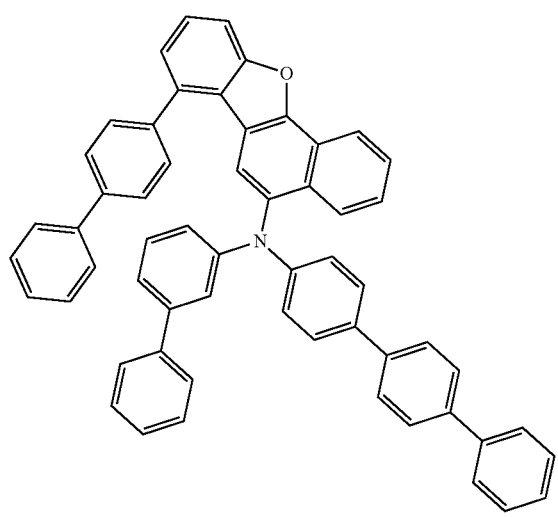
HT-497
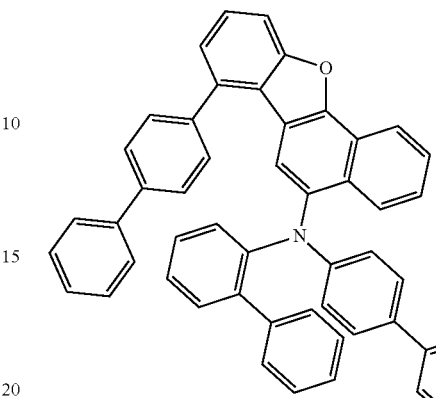
HT-498
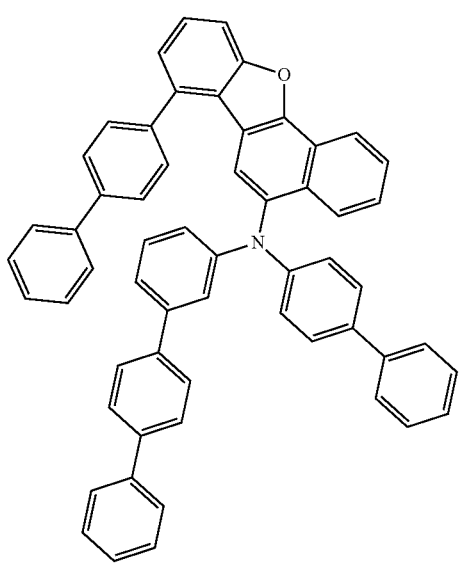
HT-499
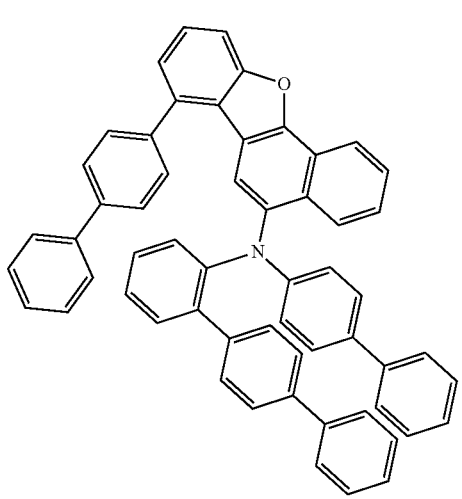

HT-501
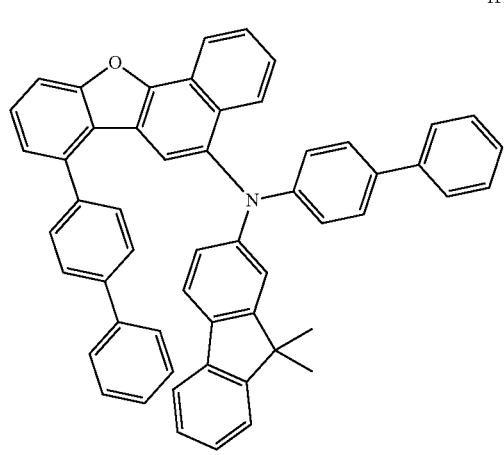
HT-504
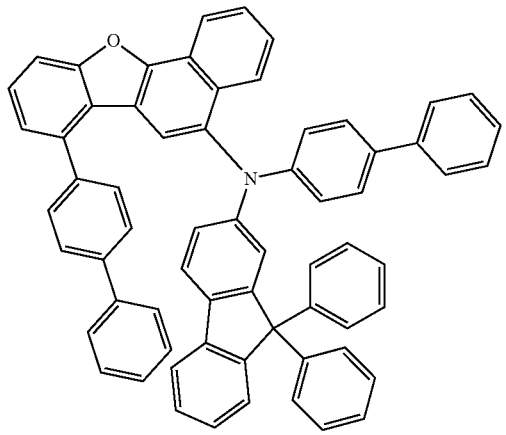
HT-502
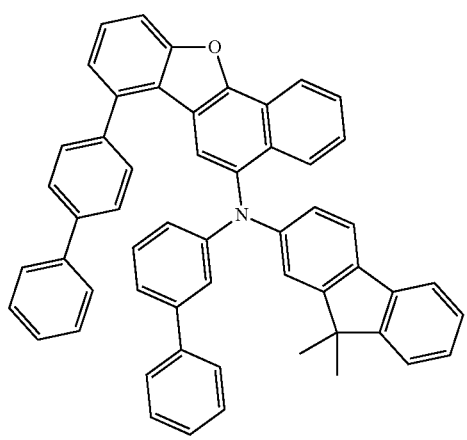
HT-505
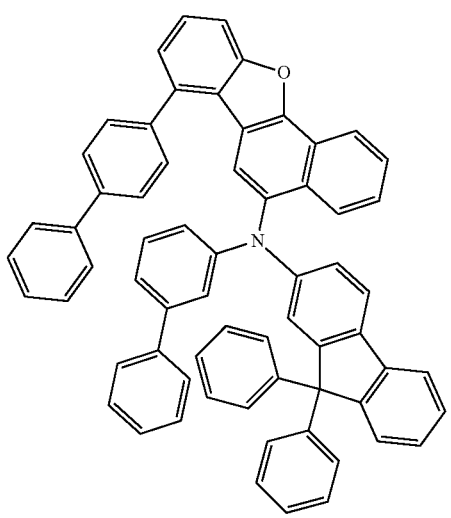
HT-503
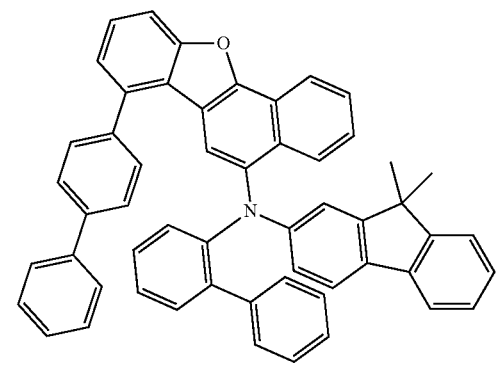
HT-506
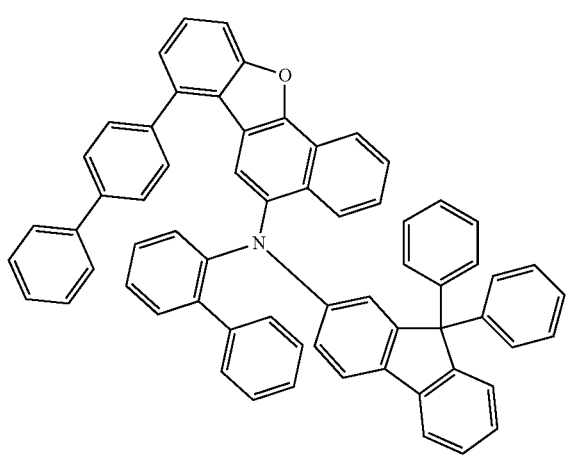

HT-507
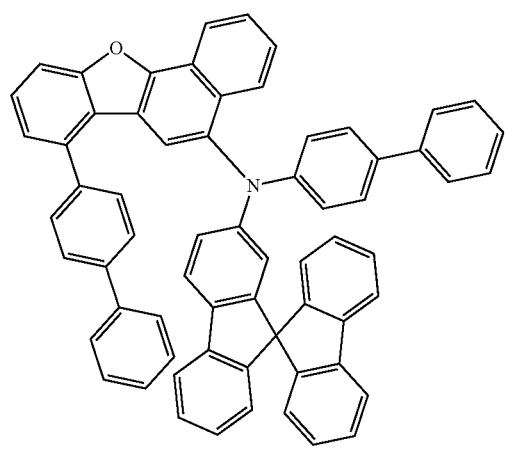
HT-508
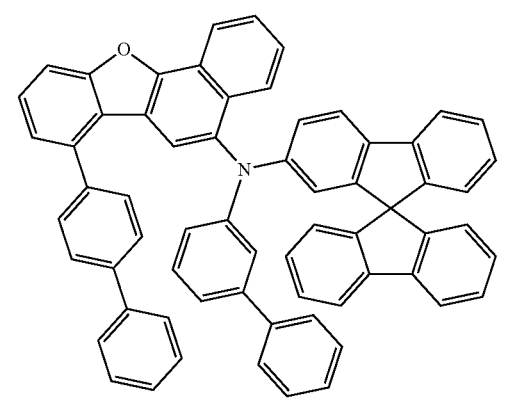
HT-509
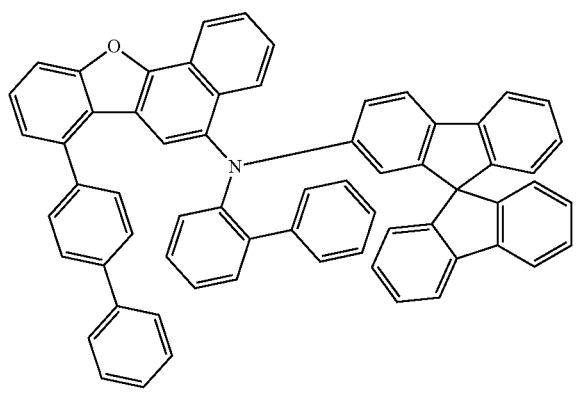
HT-510
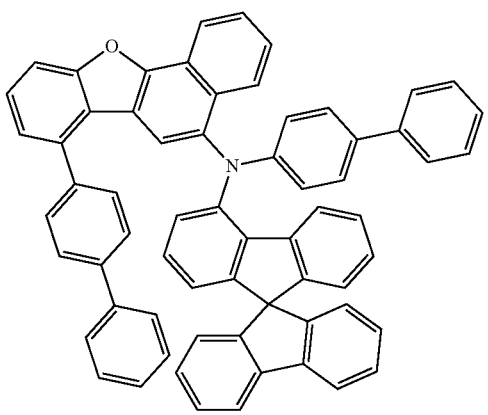
HT-511
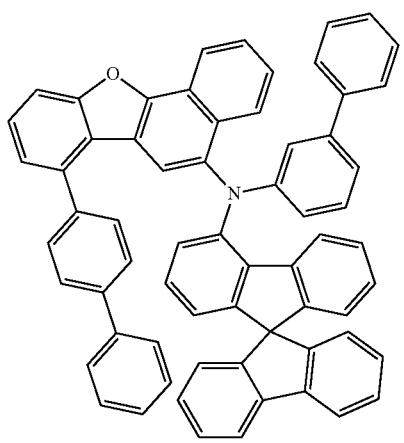
HT-512
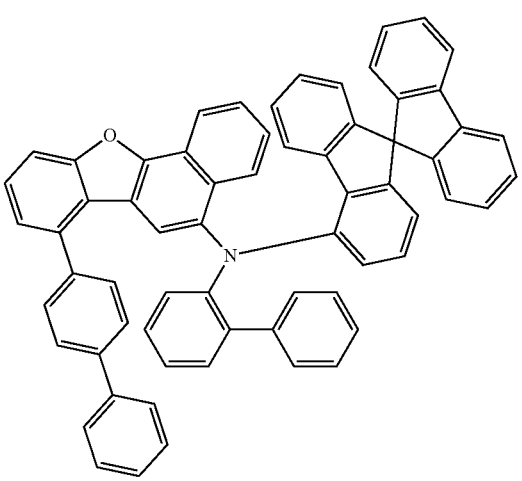

HT-513
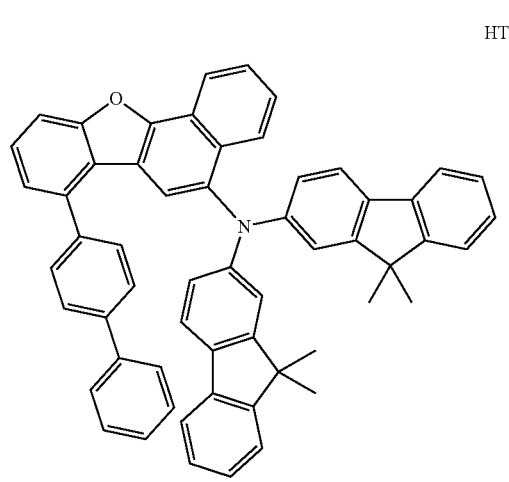
HT-516
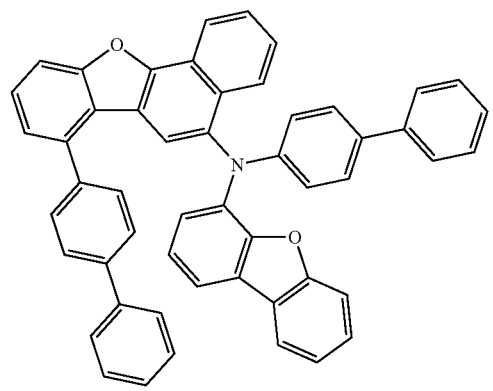
HT-514
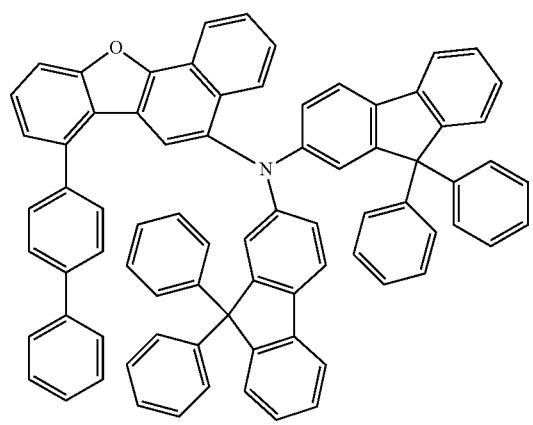
HT-517
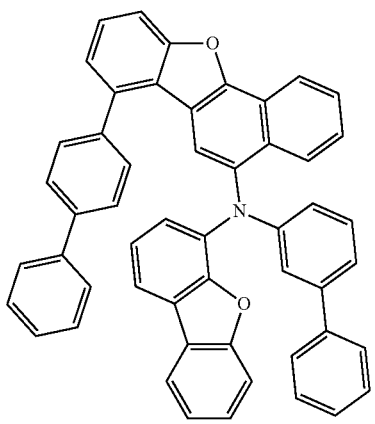
HT-515
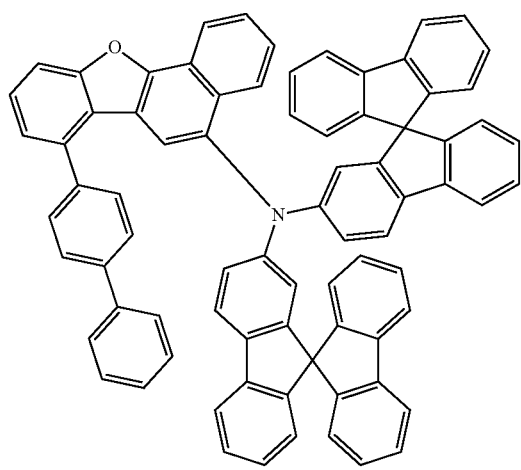
HT-518
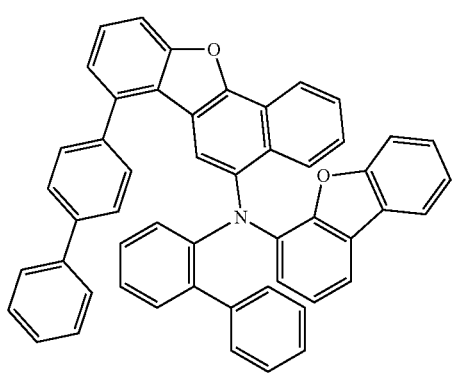

HT-519
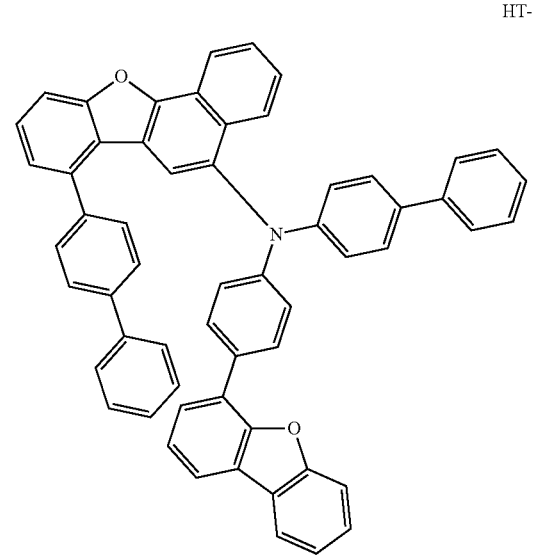
HT-520
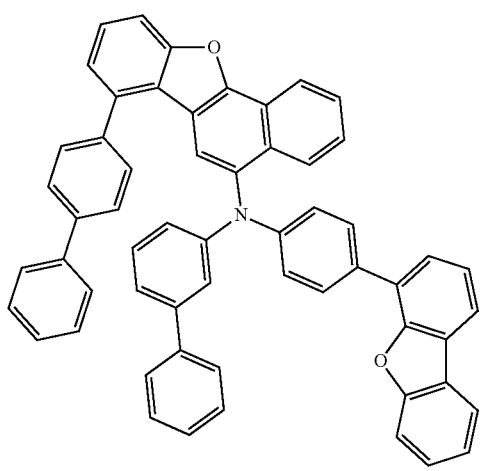
HT-521
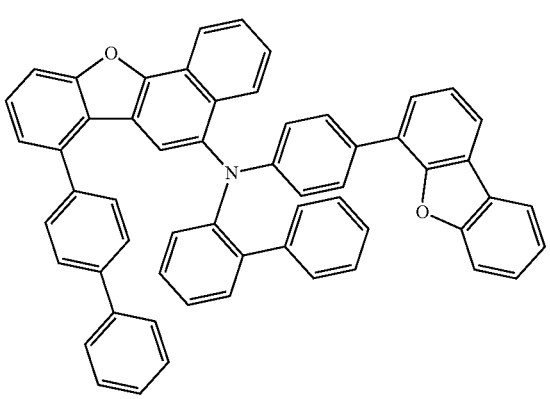
HT-522
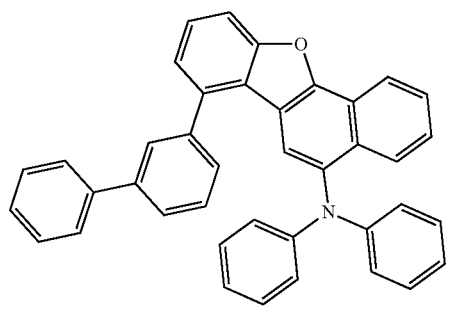
HT-523
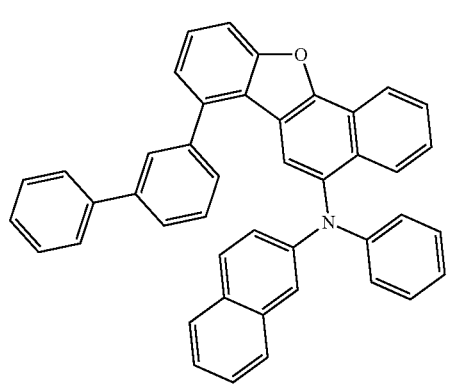
HT-524
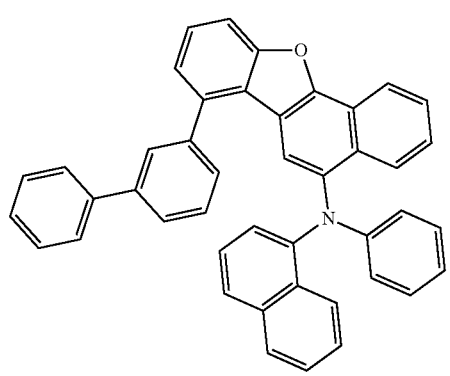
HT-525
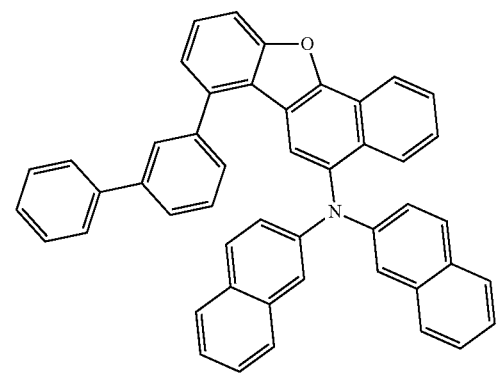

HT-526
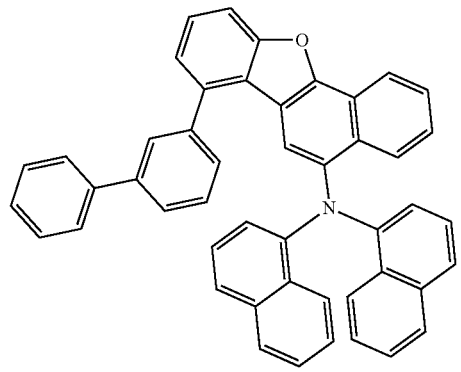
HT-527
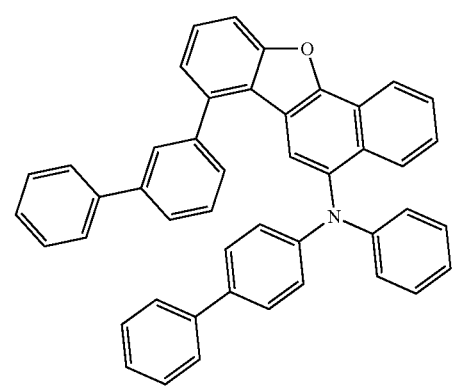
HT-528
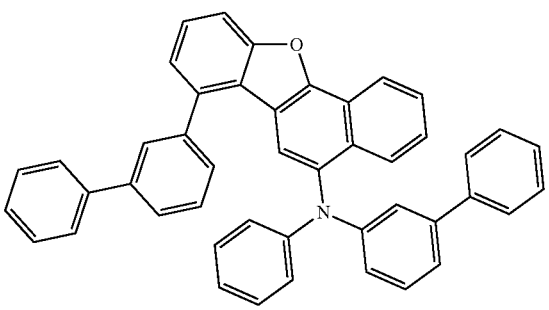
HT-529
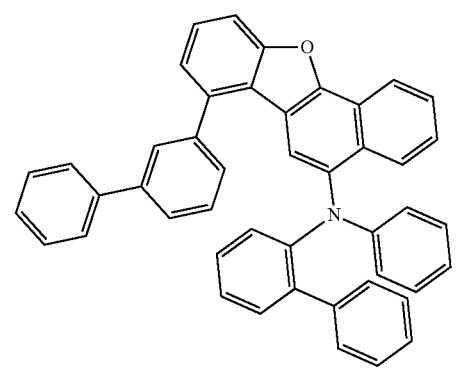
HT-530
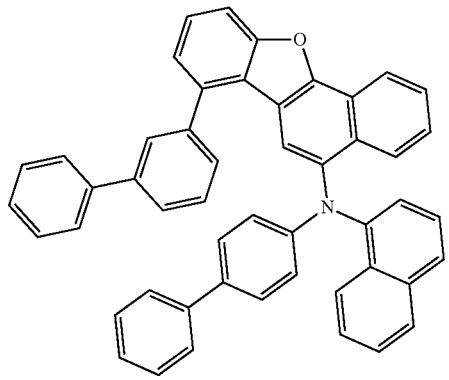
HT-531
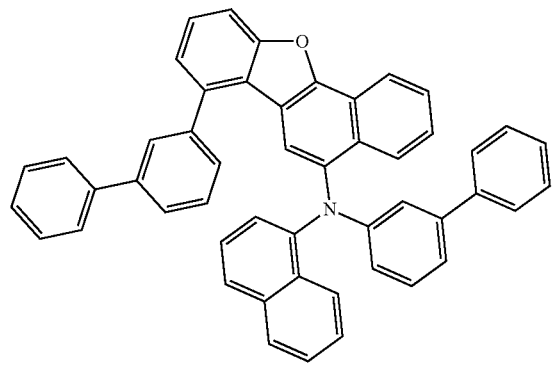
HT-532
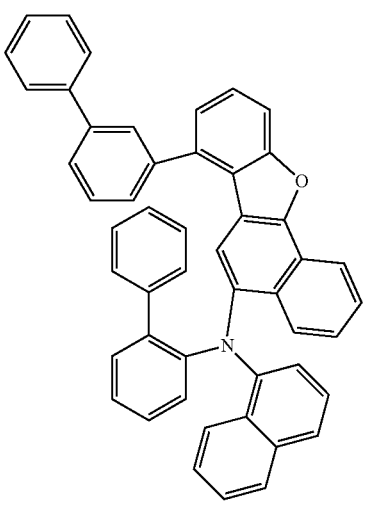

HT-533
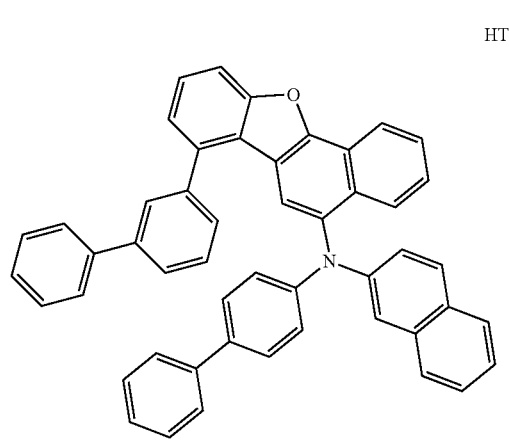
HT-536
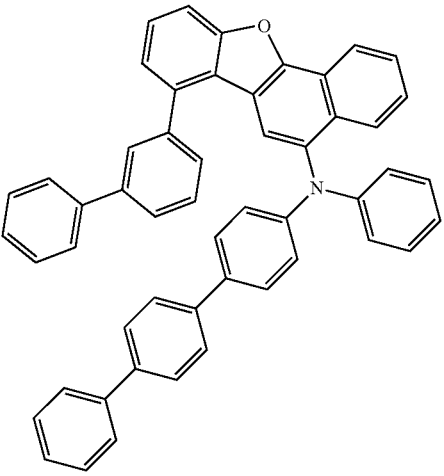
HT-534
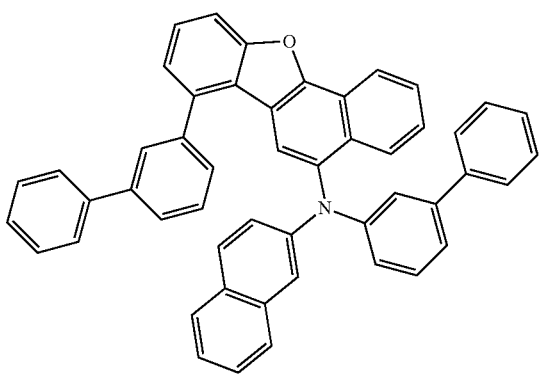
HT-537
HT-535
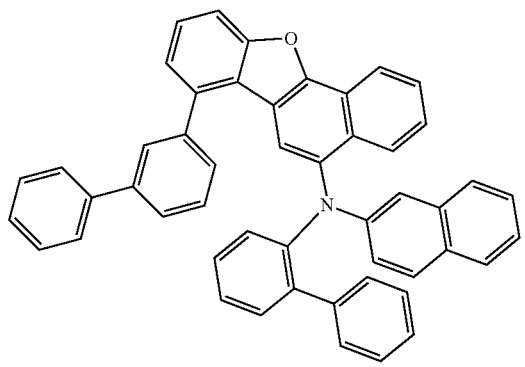
HT-538
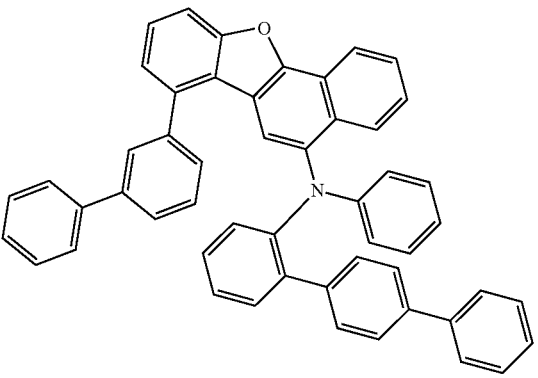

HT-539
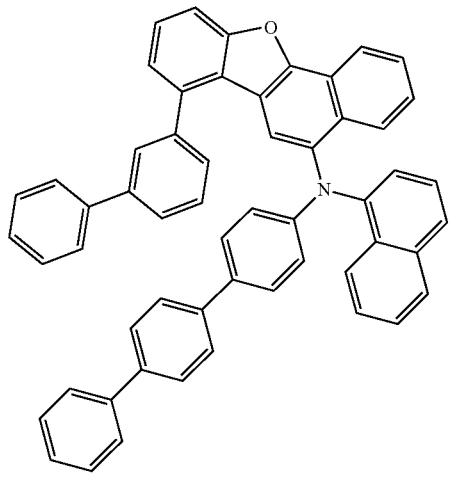
HT-542
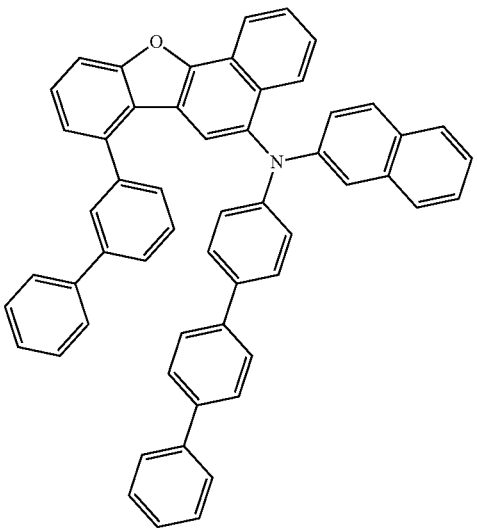
HT-540
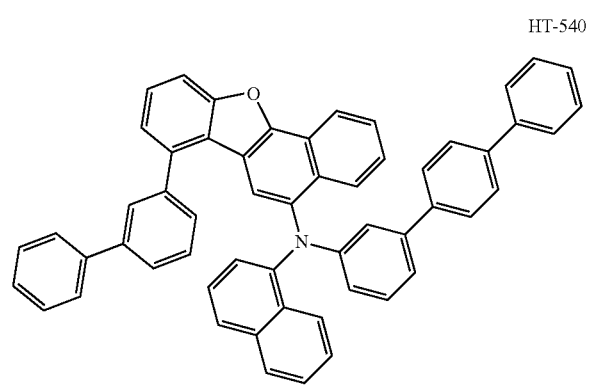
HT-543
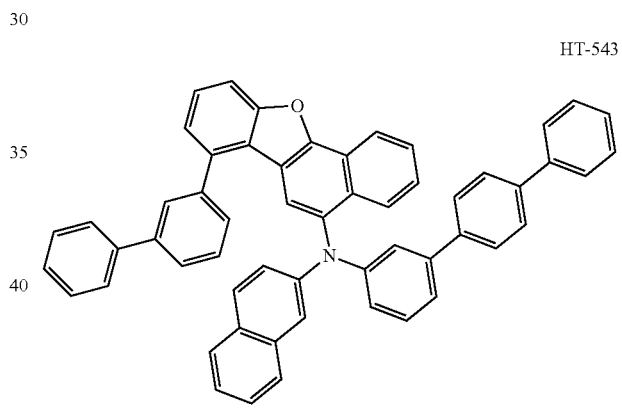
HT-541
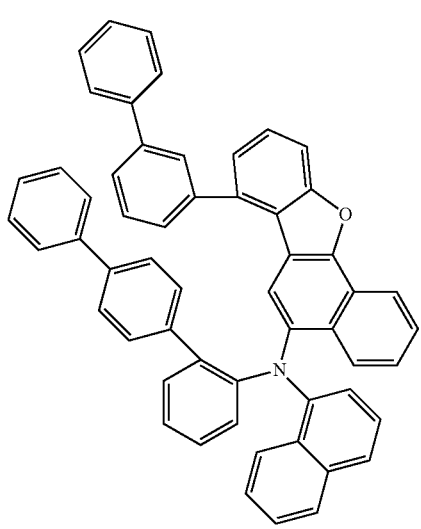
HT-544
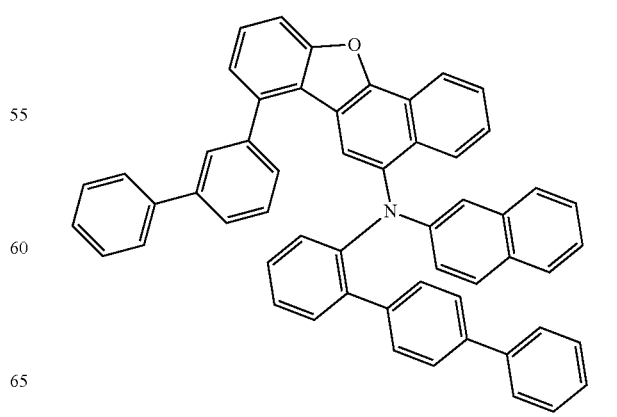

HT-545
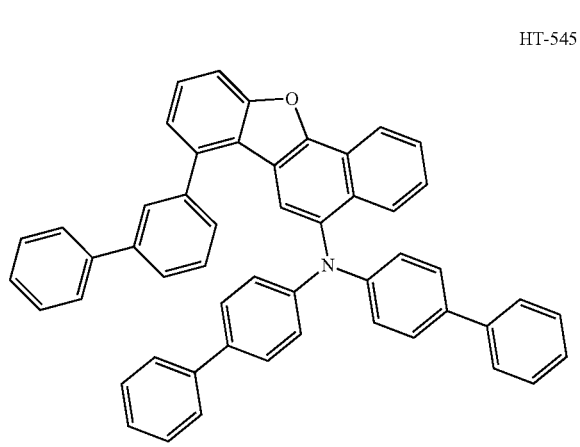
HT-546
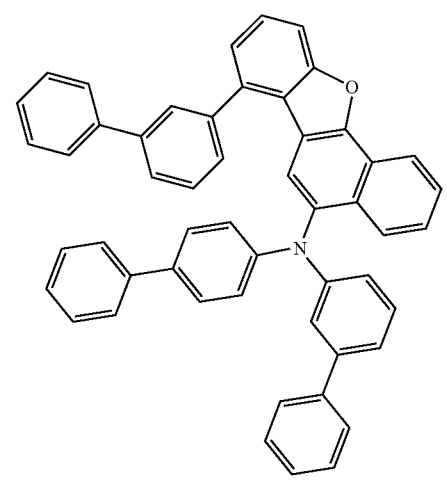
HT-547
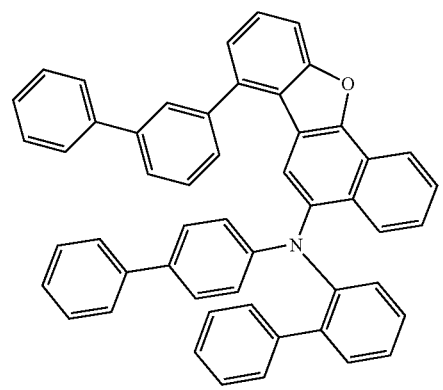
HT-548
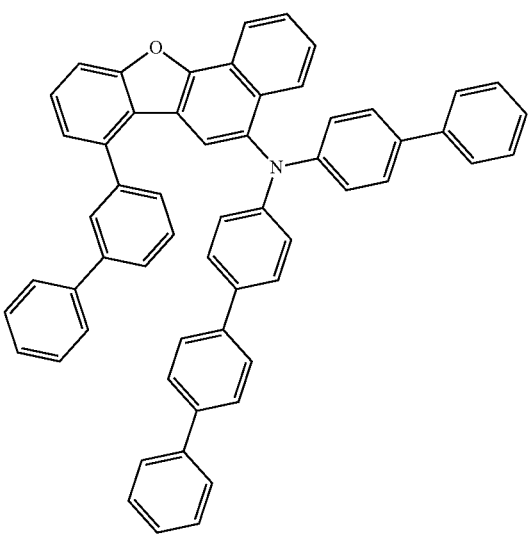
HT-549
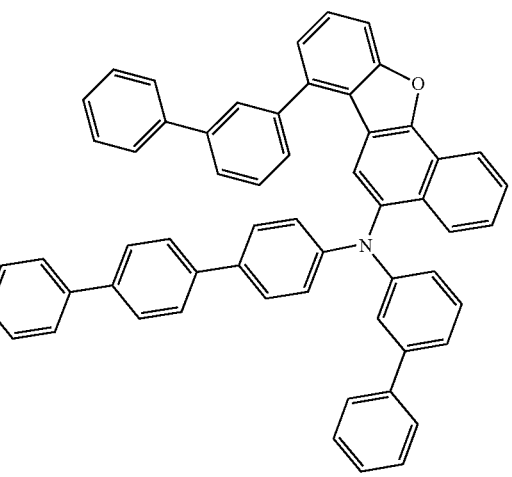
HT-550
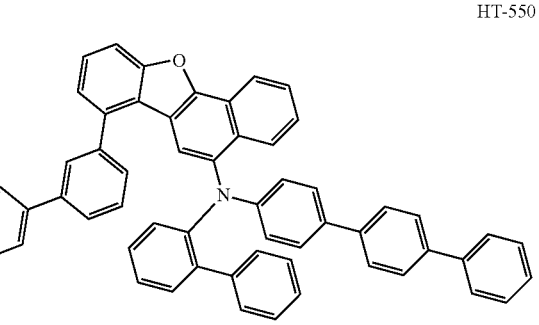

HT-551
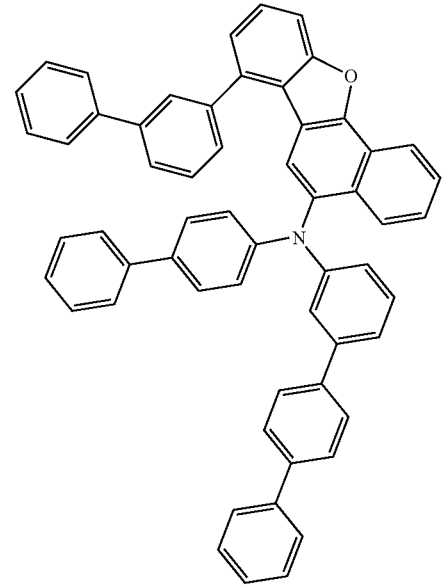
HT-552
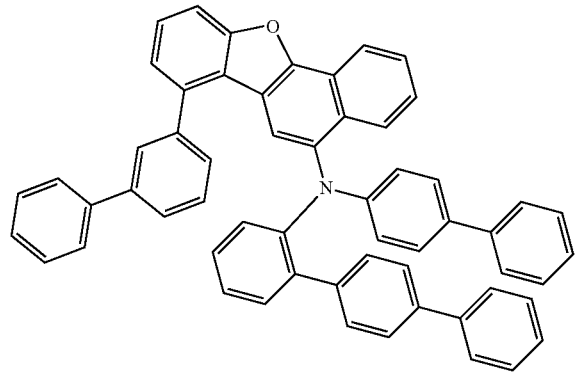
HT-553
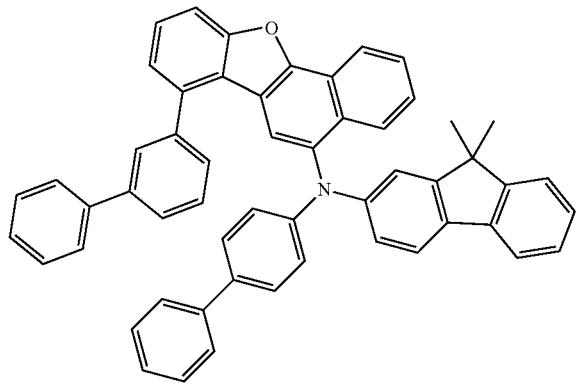
HT-554
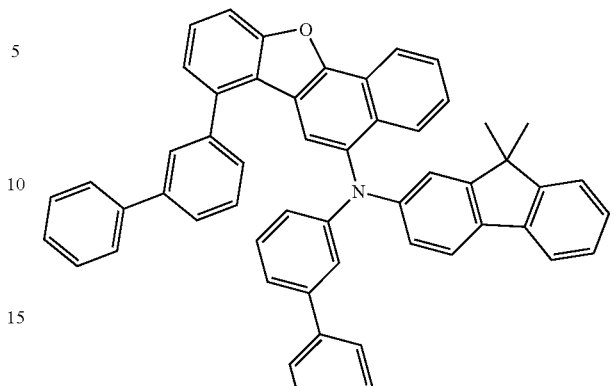
HT-555
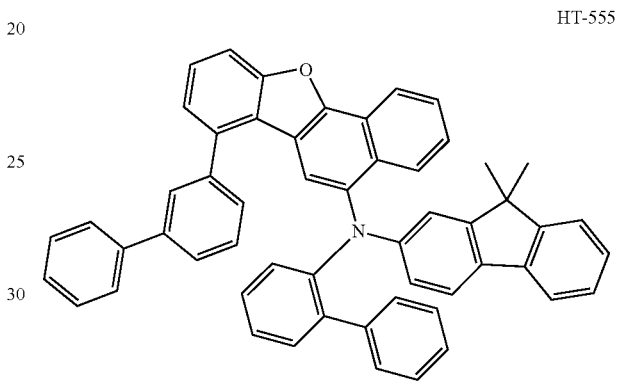
HT-556
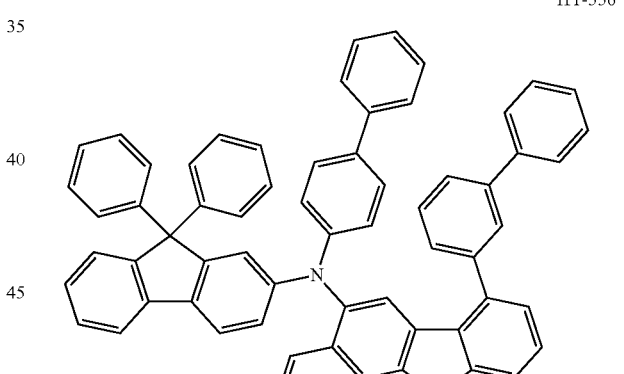
HT-557
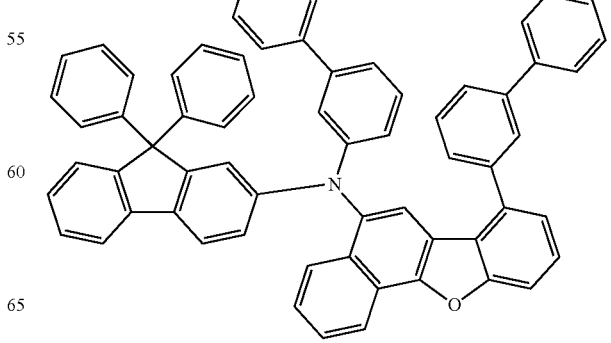

-continued
HT-558
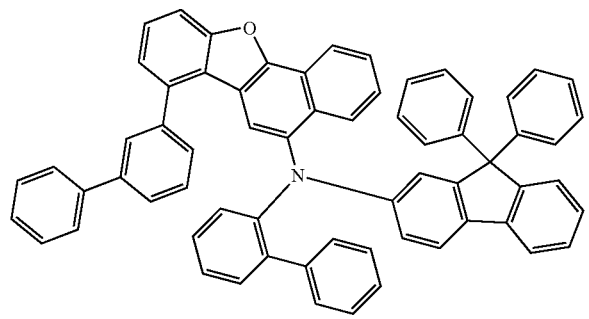
HT-559
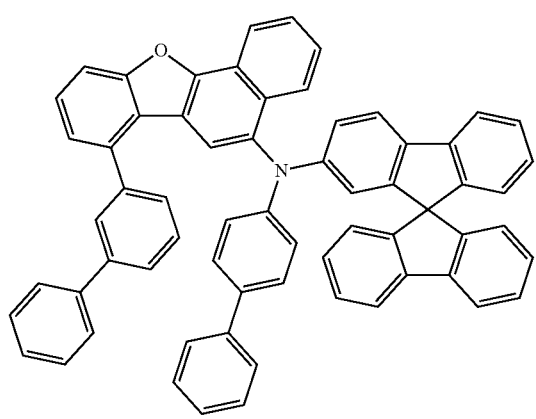
HT-560
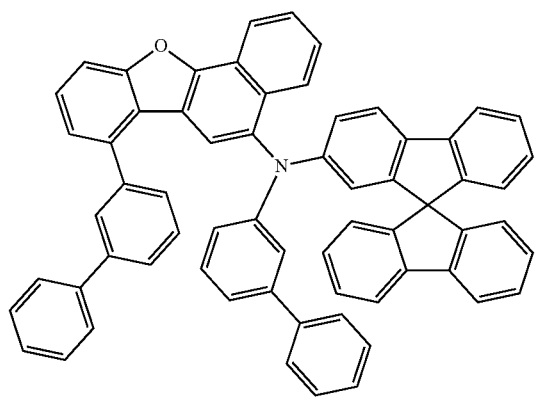
HT-561
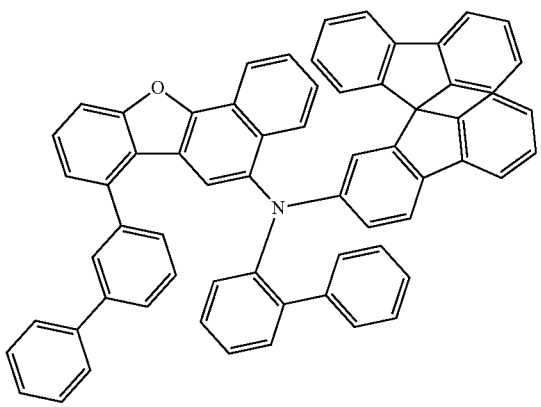
-continued
HT-562
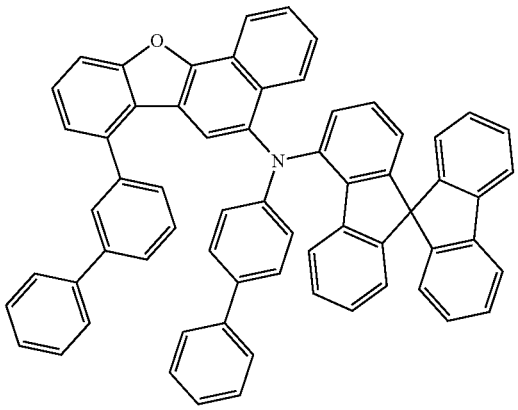
HT-563
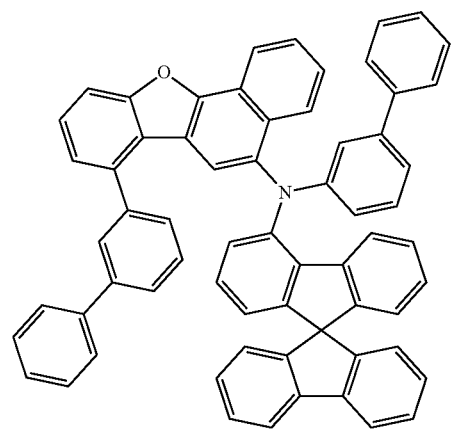
HT-564
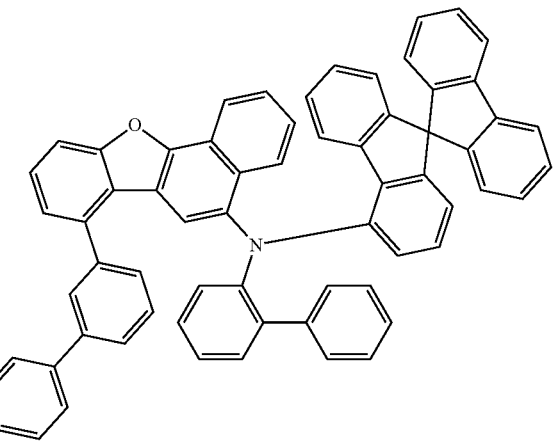

HT-565
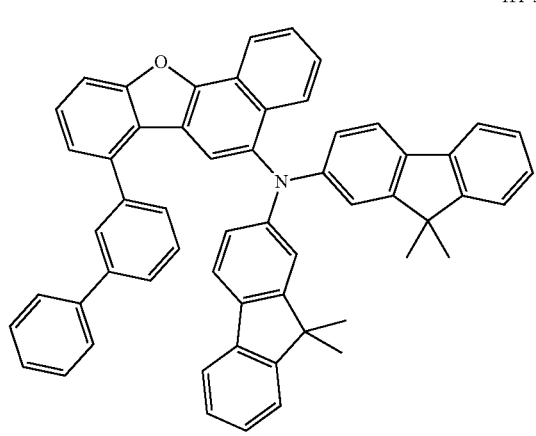
HT-566
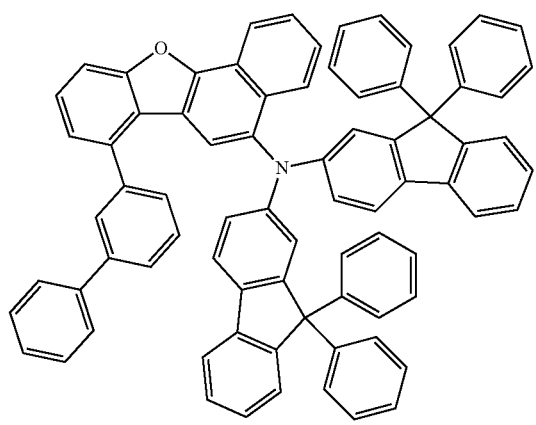
HT-567
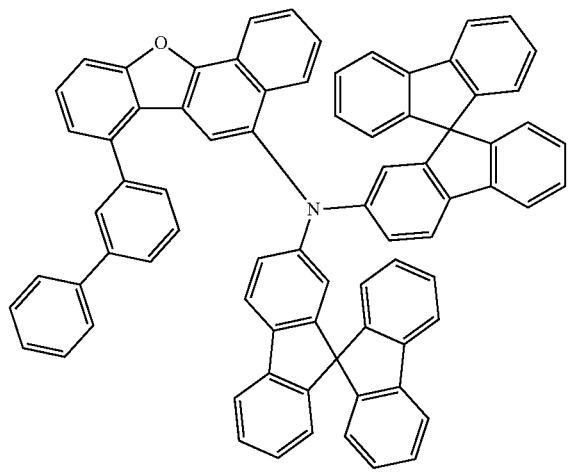
HT-568
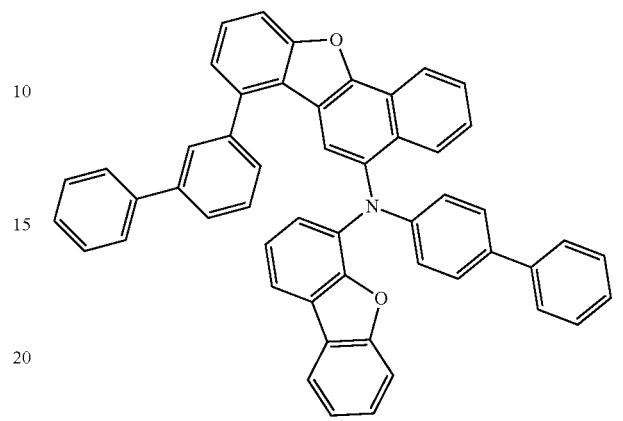
HT-569
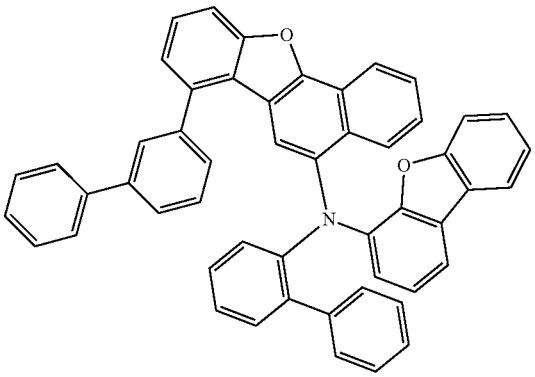
HT-570

HT-571 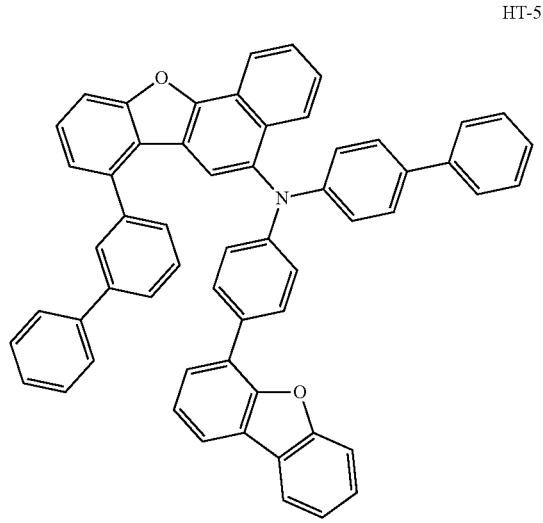
HT-572 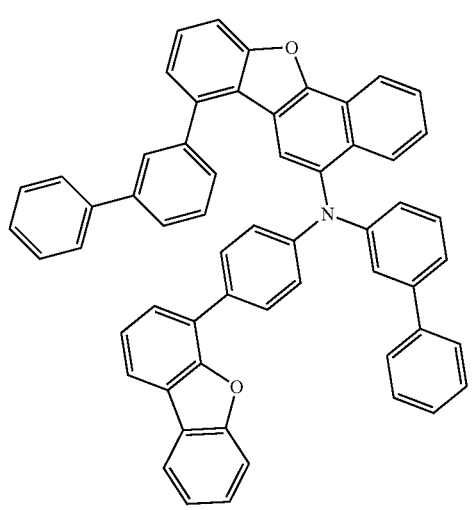
HT-573 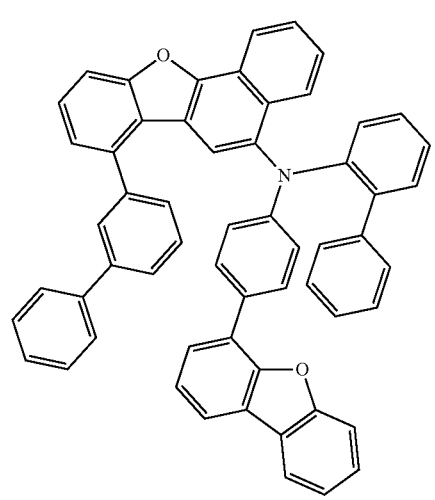
HT-574 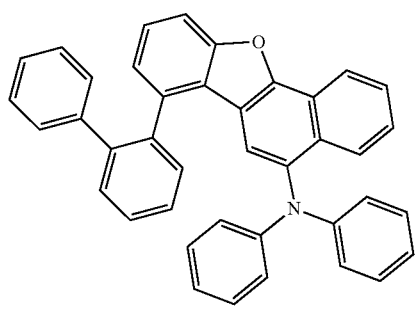
HT-575 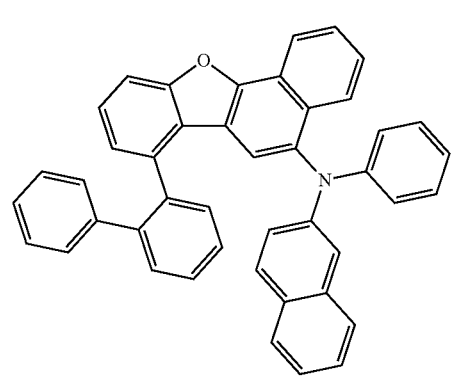
HT-576 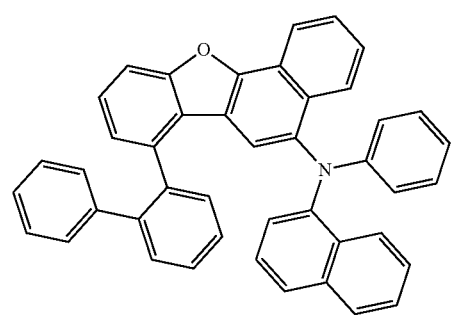
HT-577 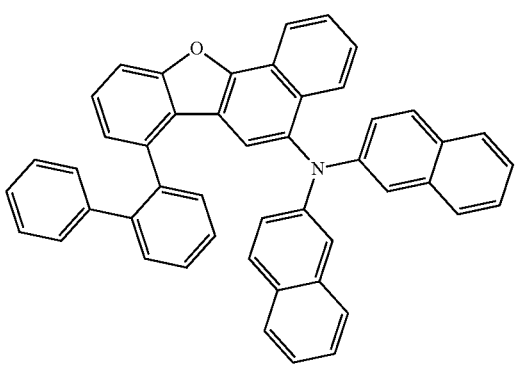

HT-578
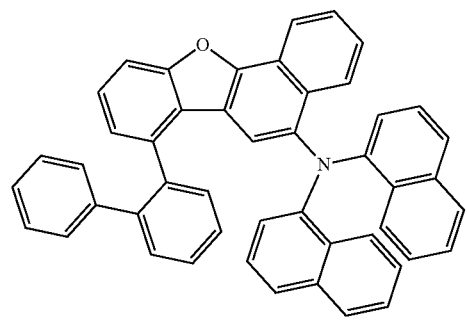
HT-579
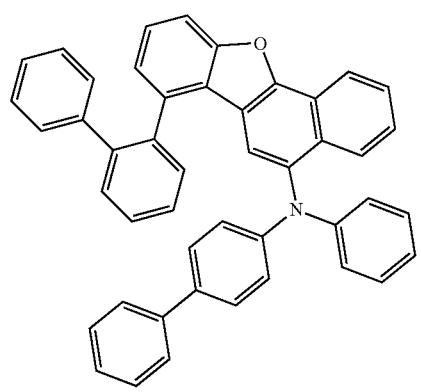
HT-580
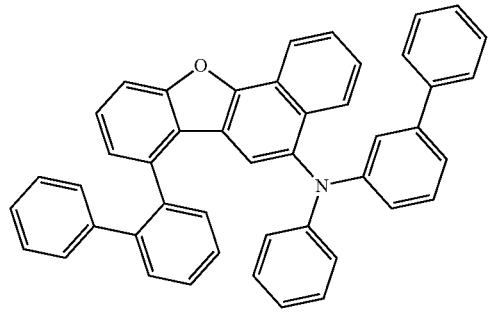
HT-581
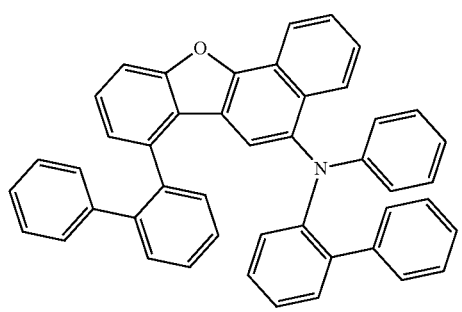
HT-582
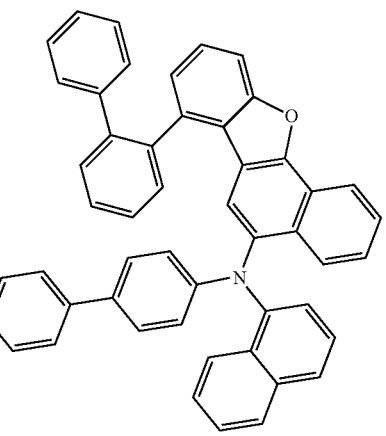
HT-583
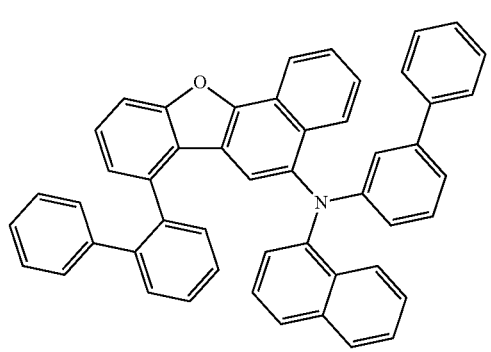
HT-584
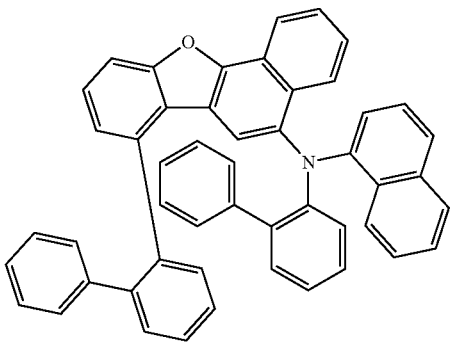
HT-585
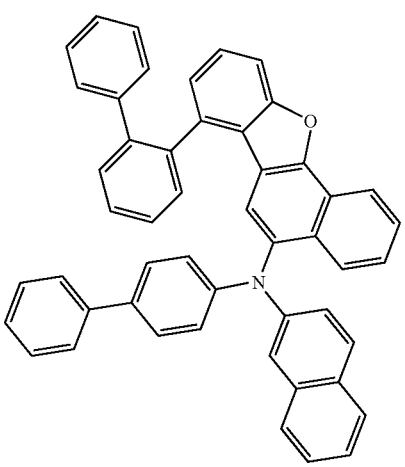

HT-586
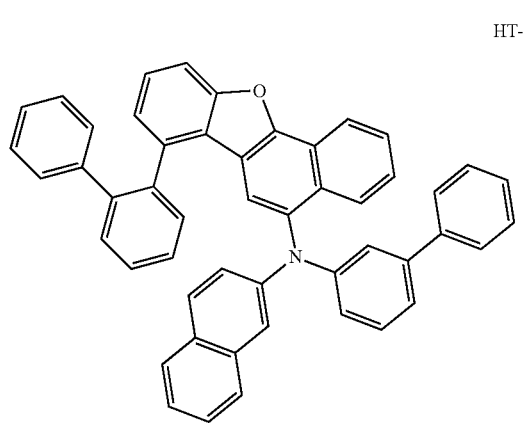
HT-587
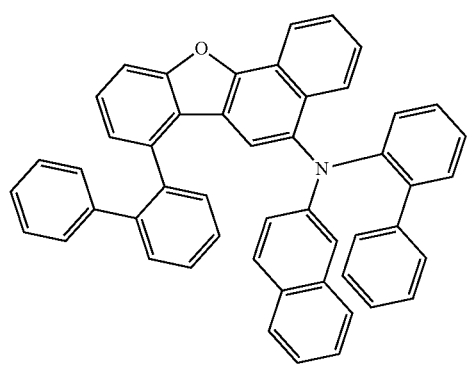
HT-588
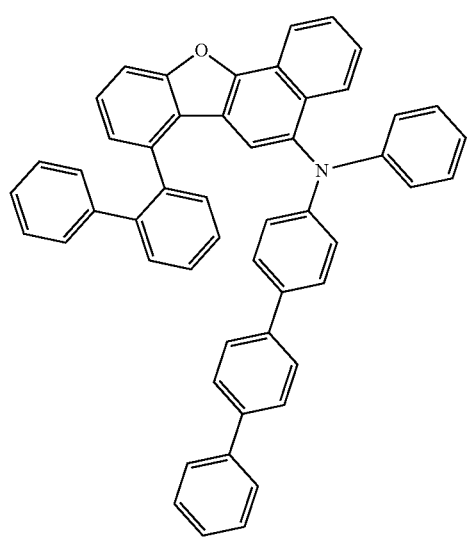
HT-589
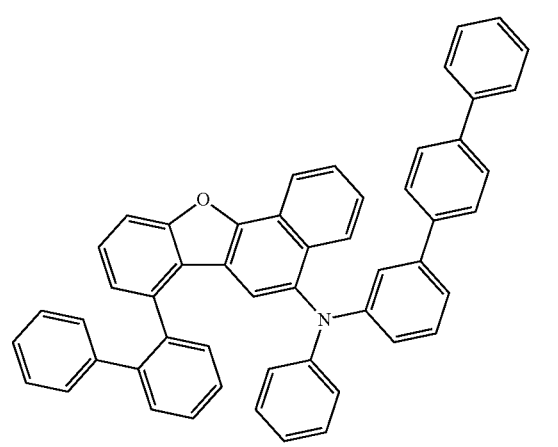
HT-590
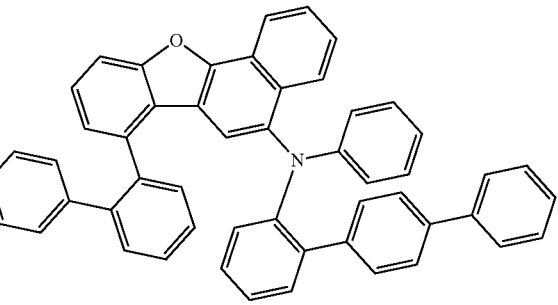
HT-591
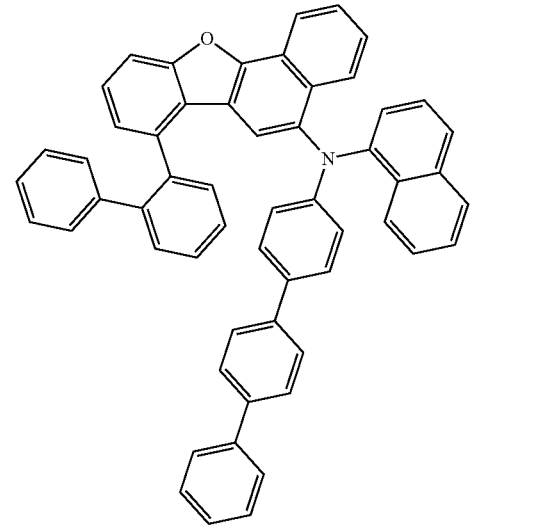

HT-592
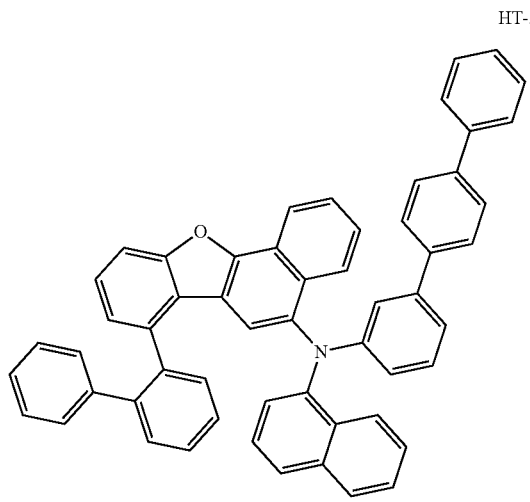
HT-595
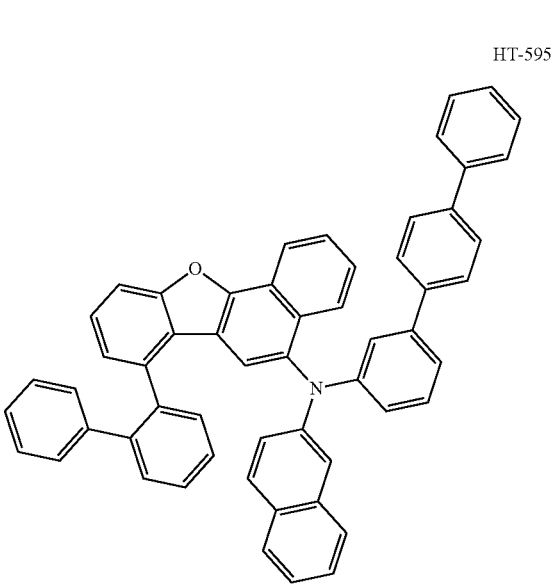
HT-593
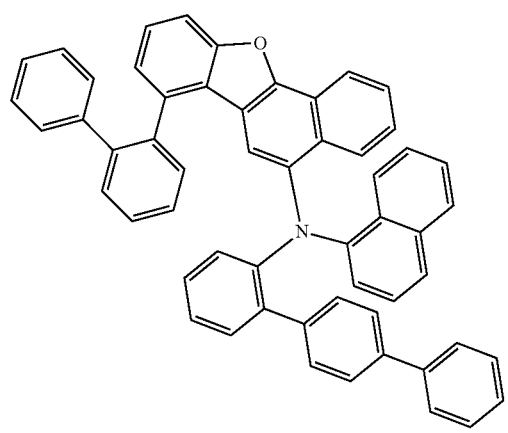
HT-596
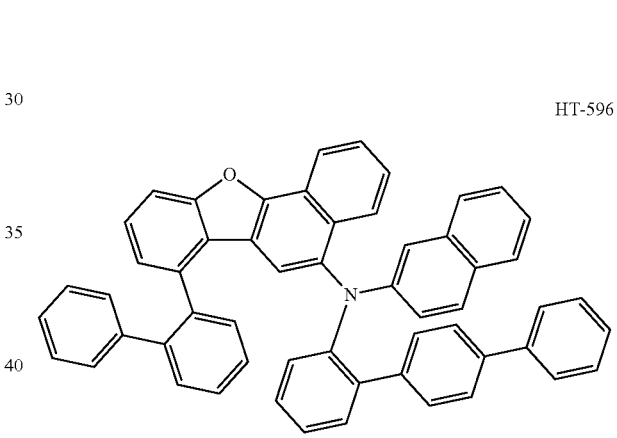
HT-594
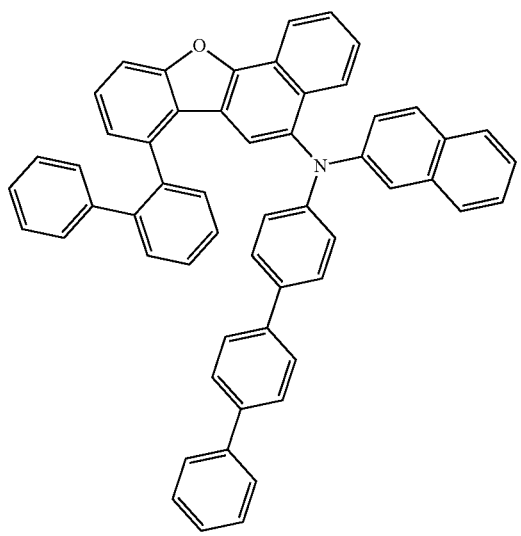
HT-597
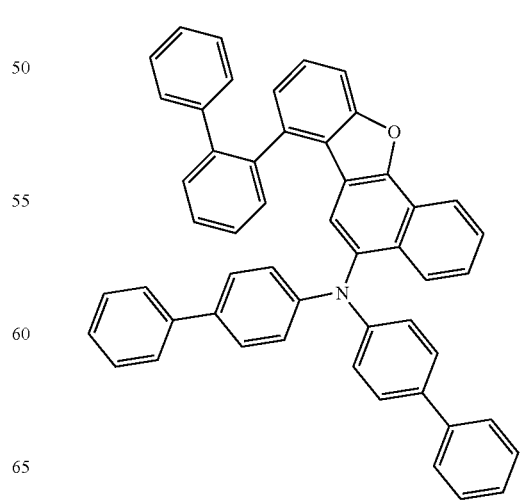

HT-598
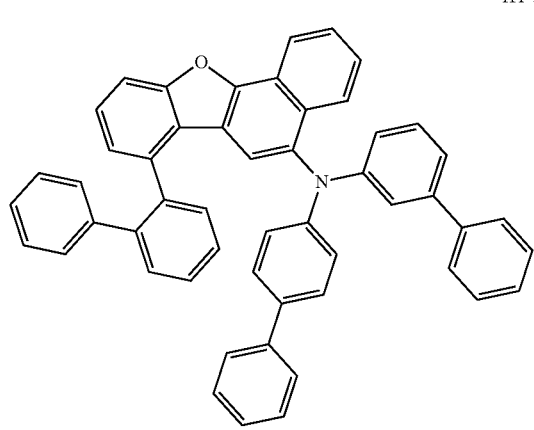
HT-599
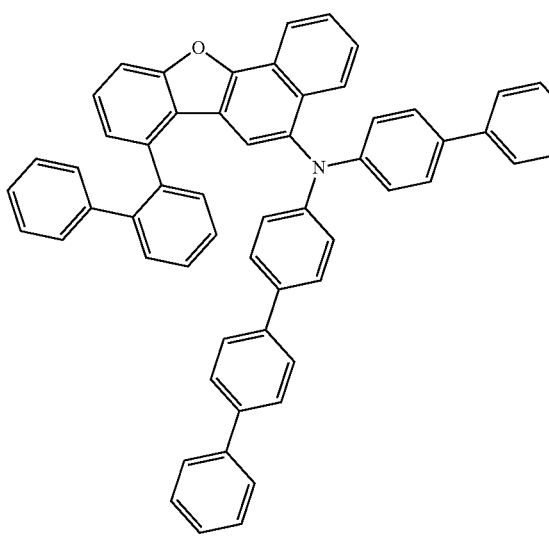
HT-600
HT-601
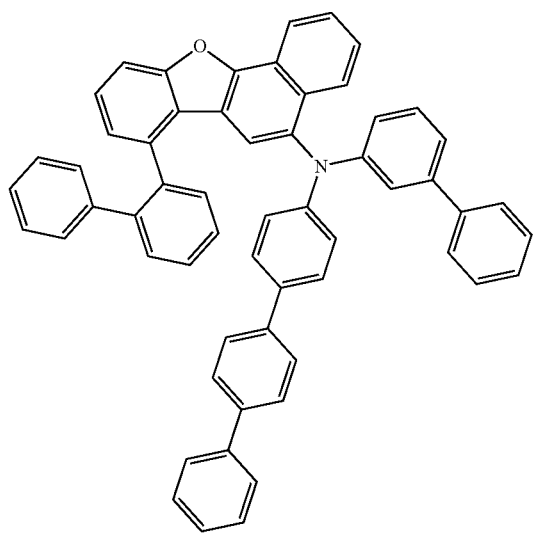
HT-602
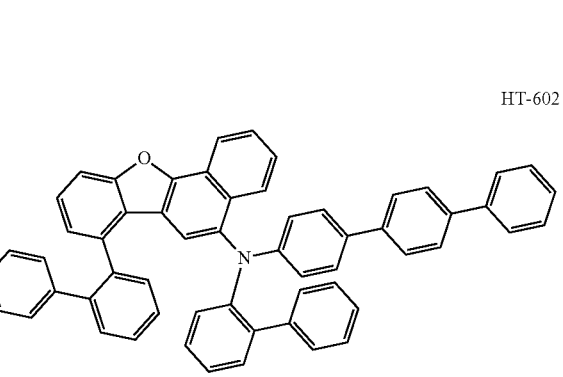
HT-603
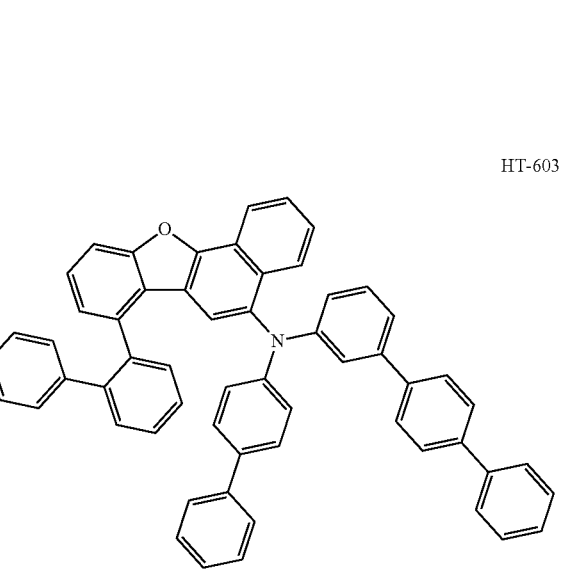

-continued
HT-604
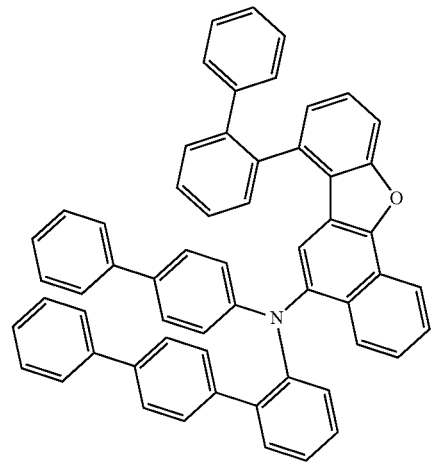
HT-605
HT-606
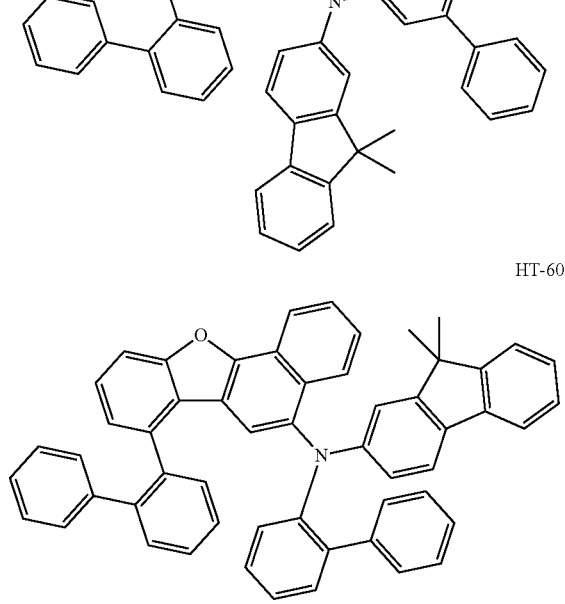
HT-607
-continued
HT-608
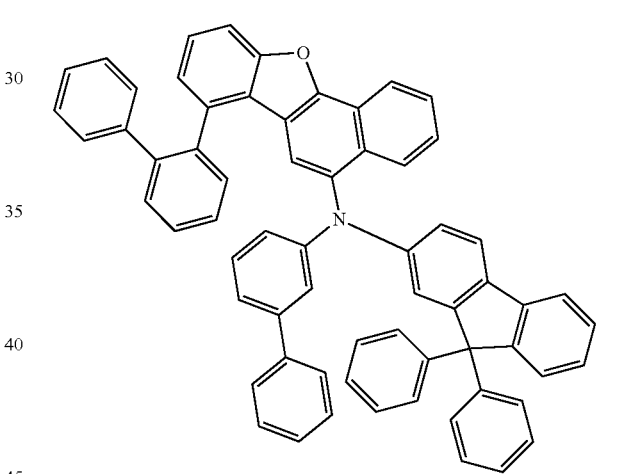
HT-609
HT-610
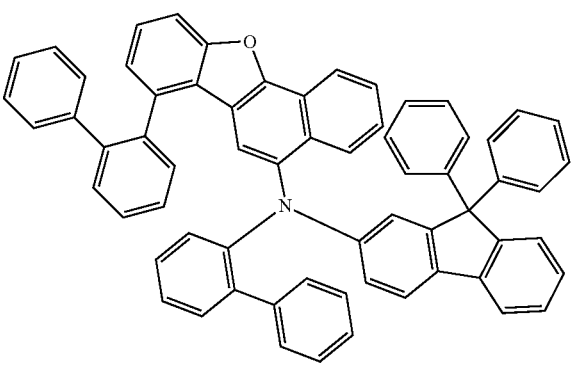

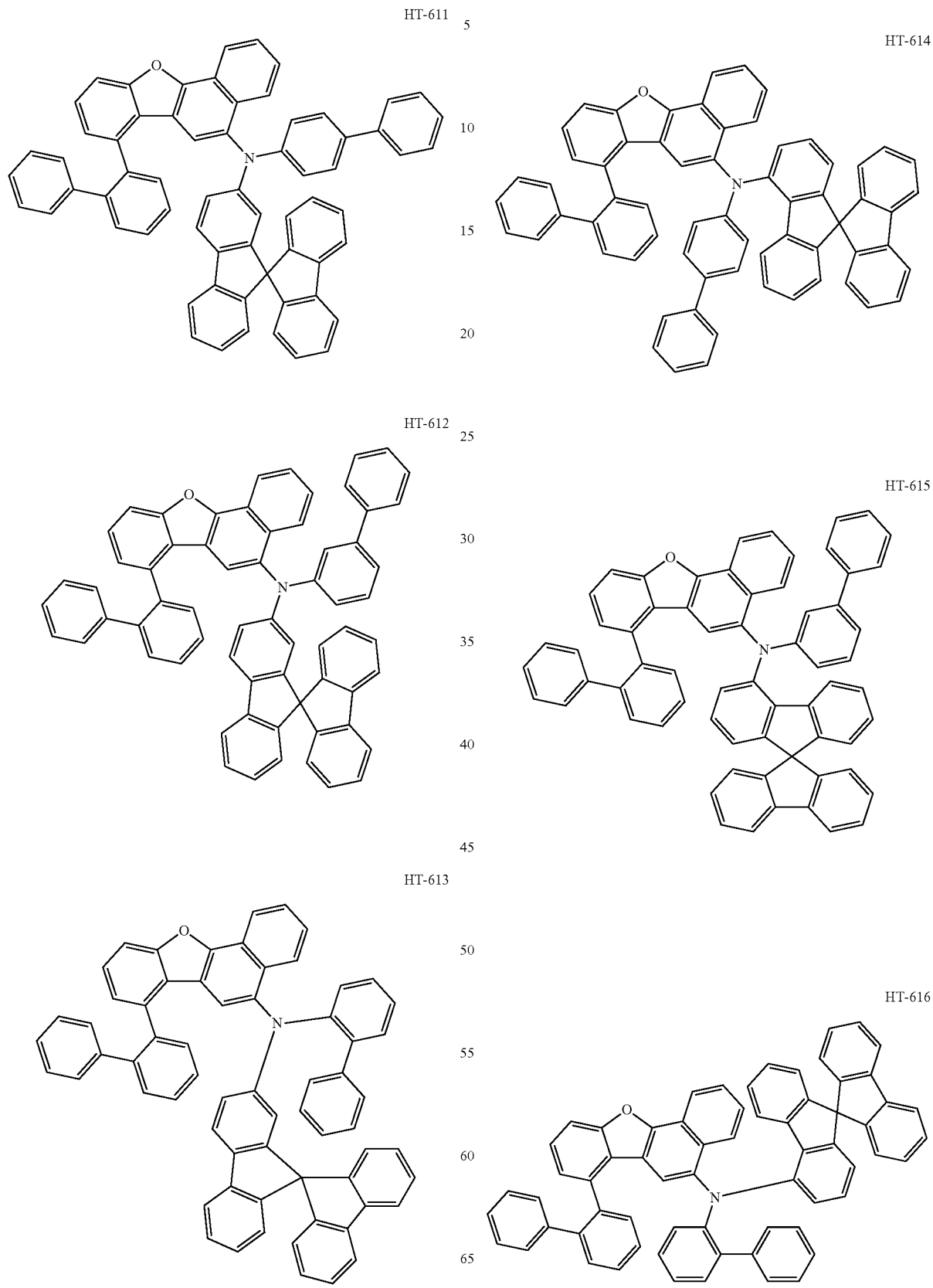

HT-617
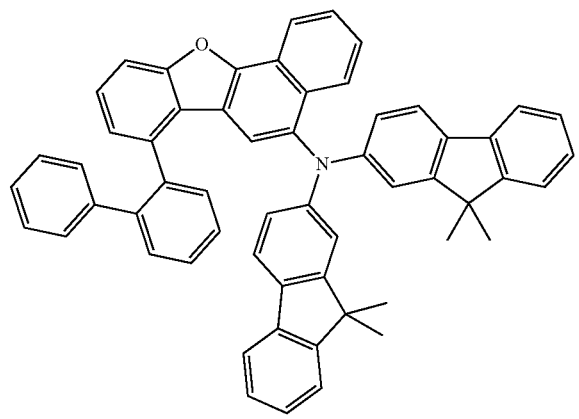
HT-618
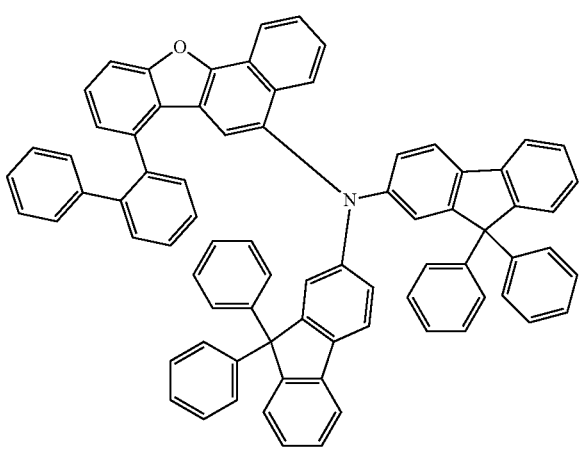
HT-619
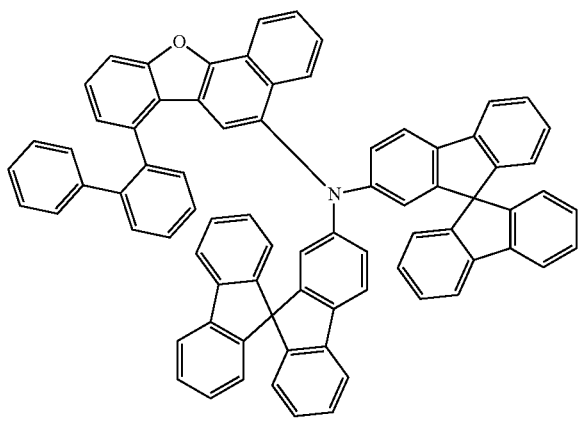
HT-620
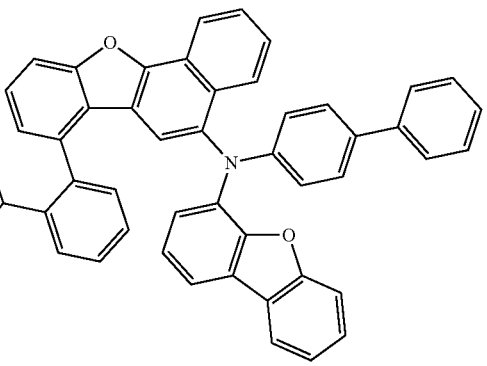
HT-621
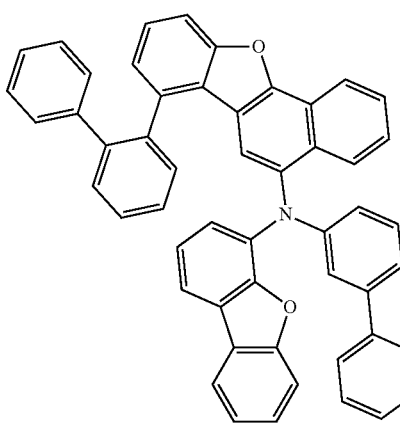
HT-622
HT-623
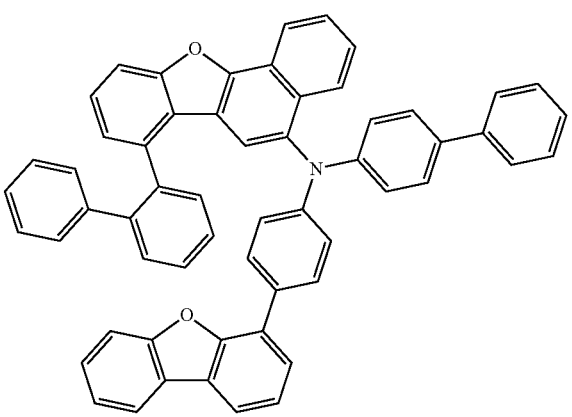

HT-624
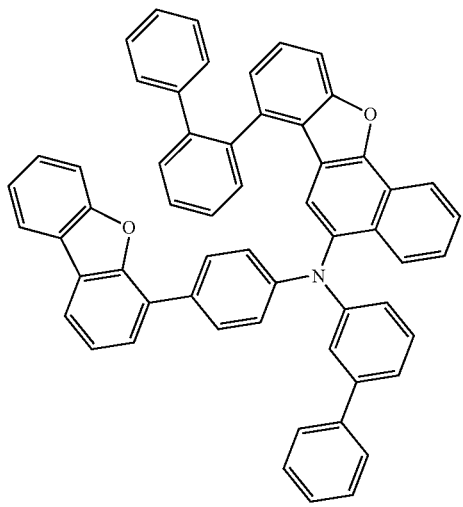
HT-625
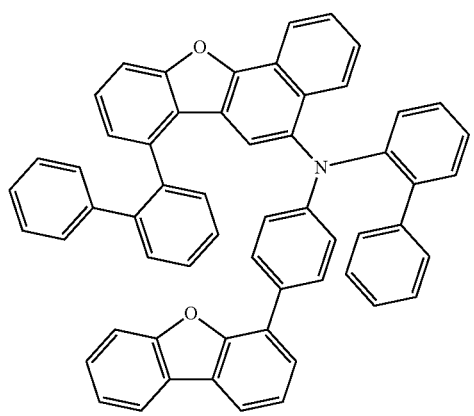
HT-626
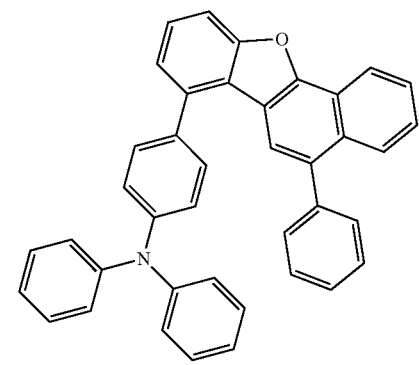
HT-627
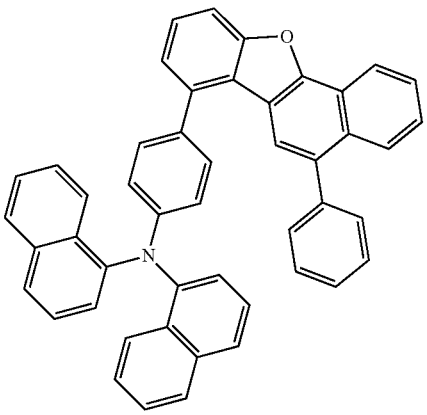
HT-628
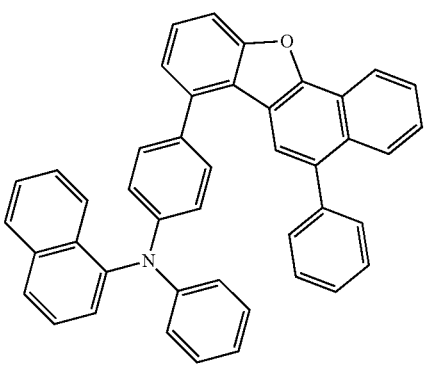
HT-629
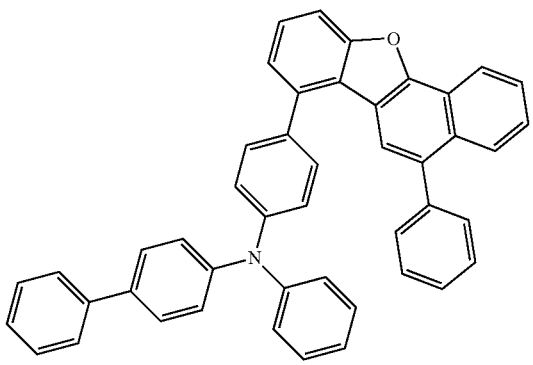
HT-630
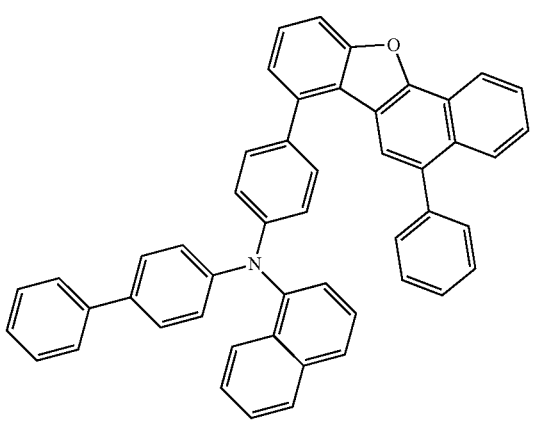 [SMILES: c1ccc(-c2ccc(N(c3ccc(-c4cccc5oc6c7ccccc7c(-c7ccccc7)cc6c45)cc3)c3cccc4ccccc34)cc2)cc1]

HT-631
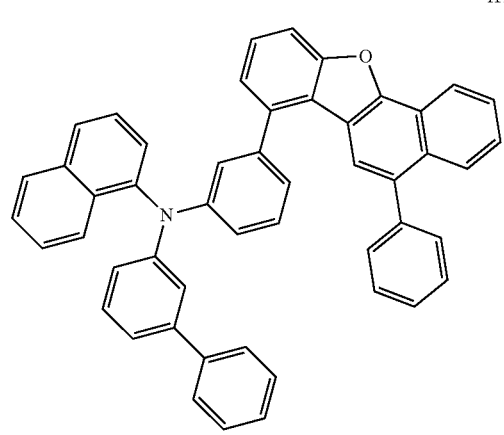
HT-634
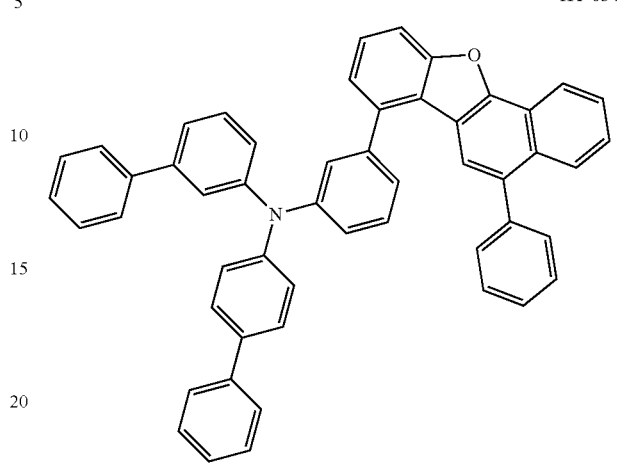
HT-632
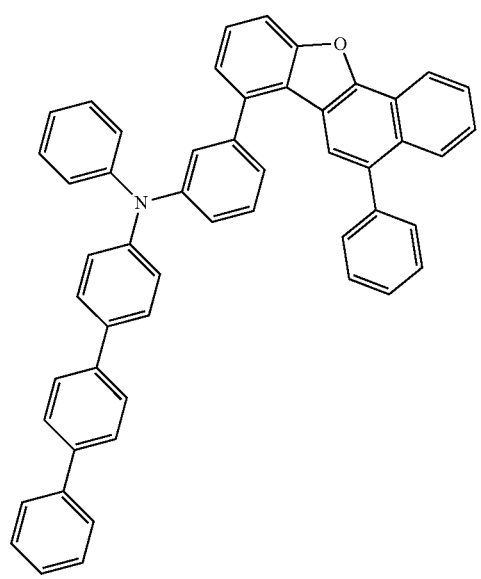 [SMILES: c1ccc(-c2ccc(-c3ccc(N(c4ccccc4)c4cccc(-c5cccc6oc7c8ccccc8c(-c8ccccc8)cc7c56)c4)cc3)cc2)cc1]
HT-635
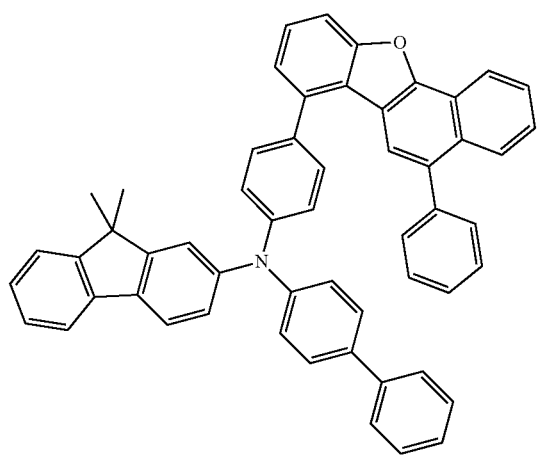 [SMILES: CC1(C)c2ccccc2-c2ccc(N(c3ccc(-c4ccccc4)cc3)c3ccc(-c4cccc5oc6c7ccccc7c(-c7ccccc7)cc6c45)cc3)cc21]
HT-633
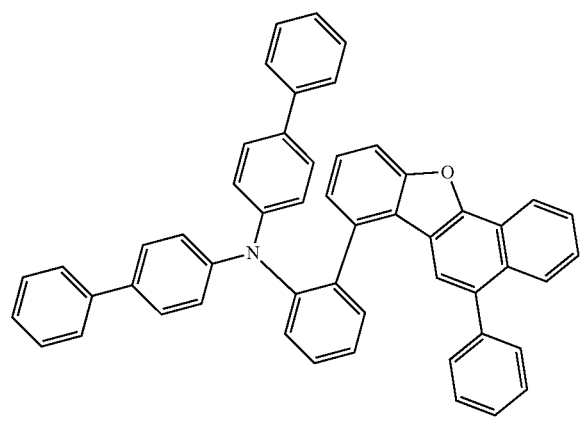
HT-636
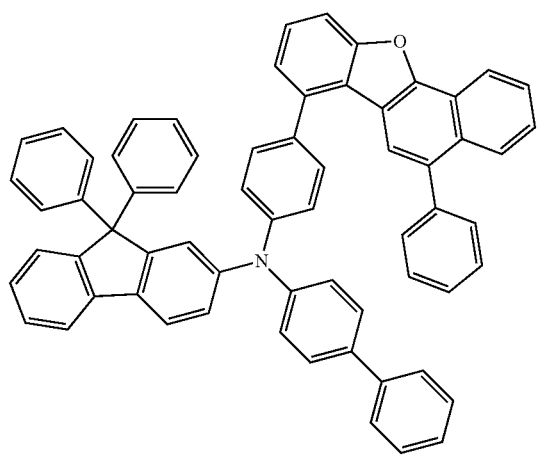

HT-637
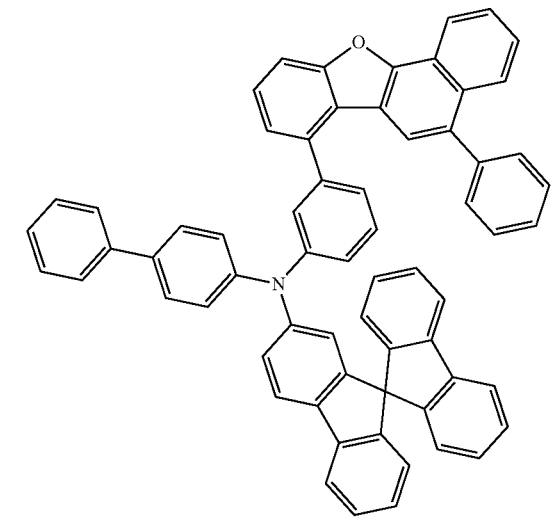
HT-638
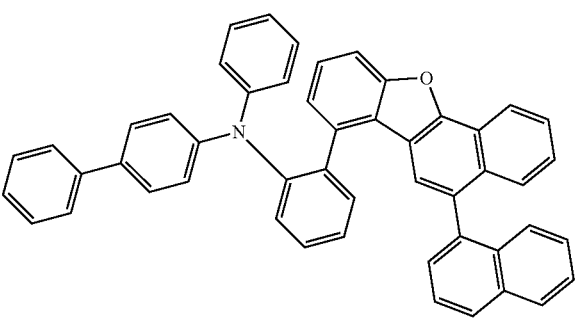
HT-639
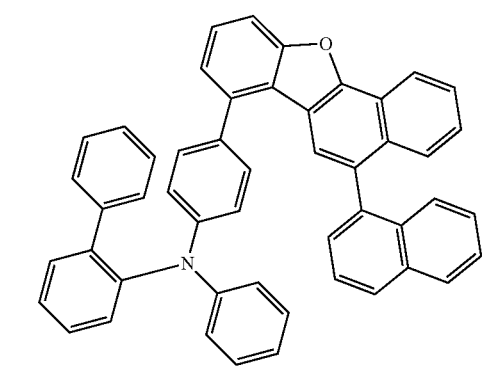
HT-640
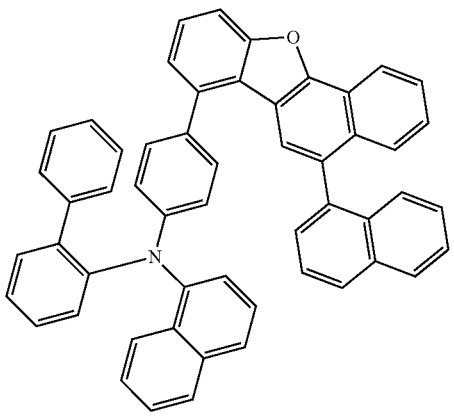
HT-641
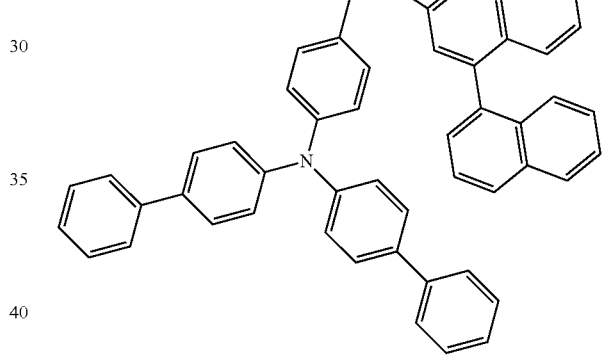
HT-642
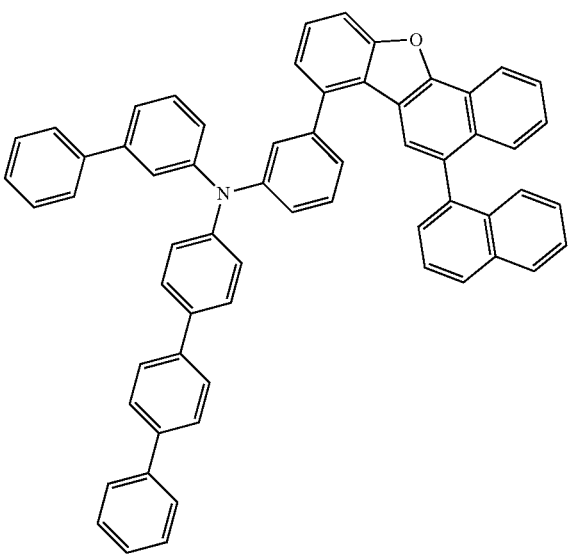

HT-643
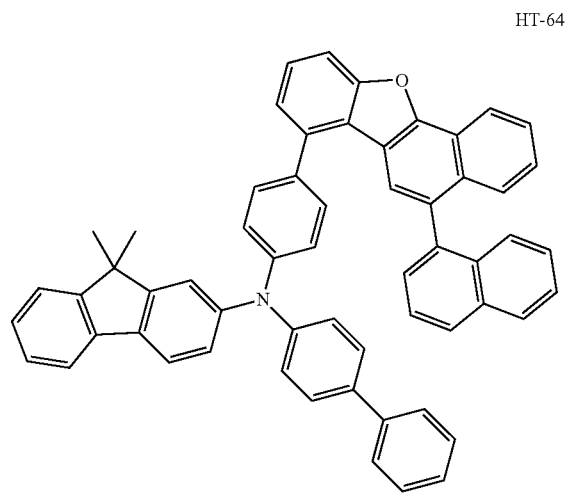
HT-644
HT-645
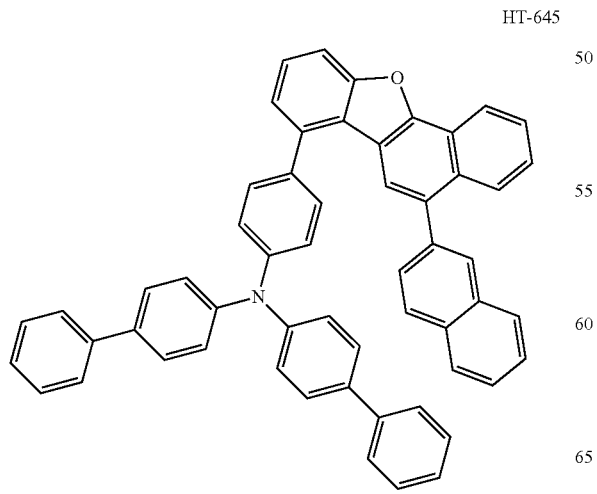
HT-646
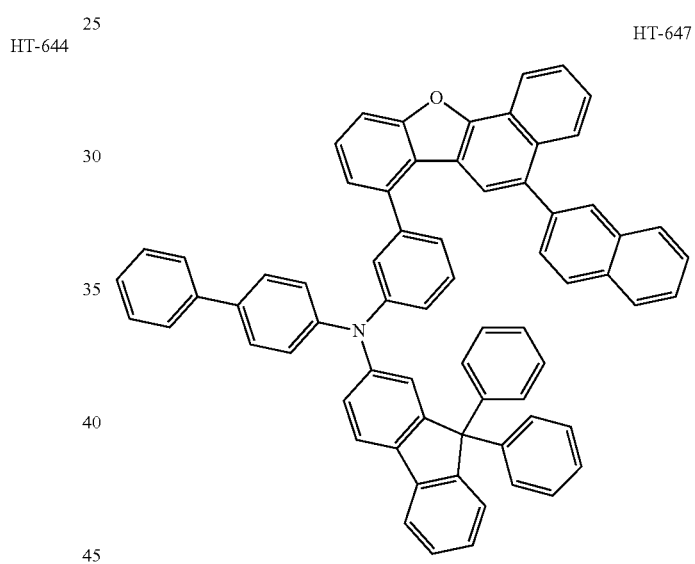
HT-647
HT-648
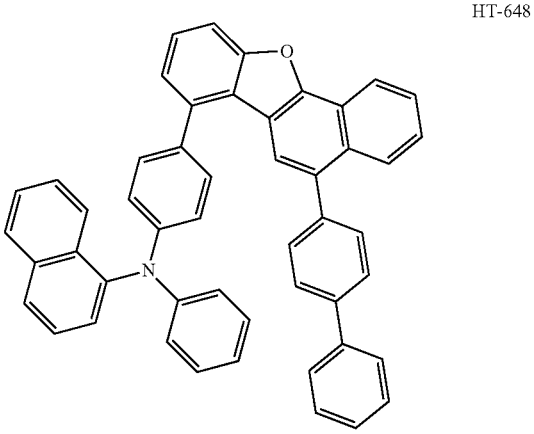

HT-649
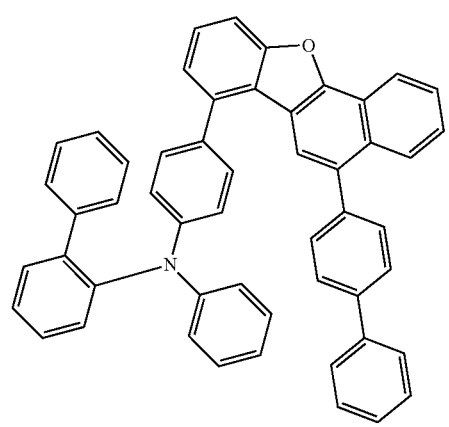
HT-650
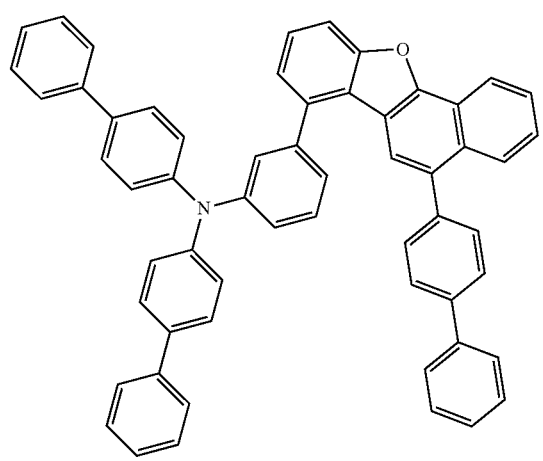
HT-651
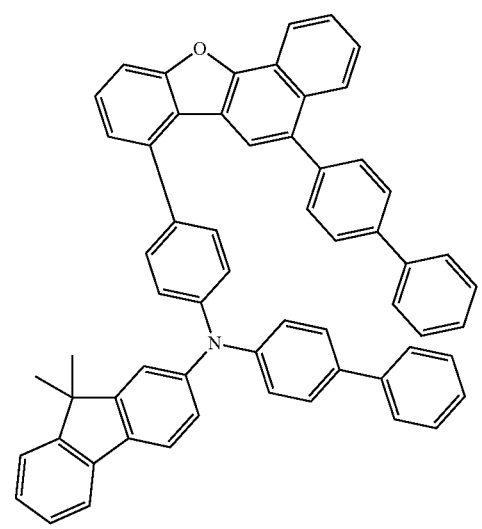
HT-652
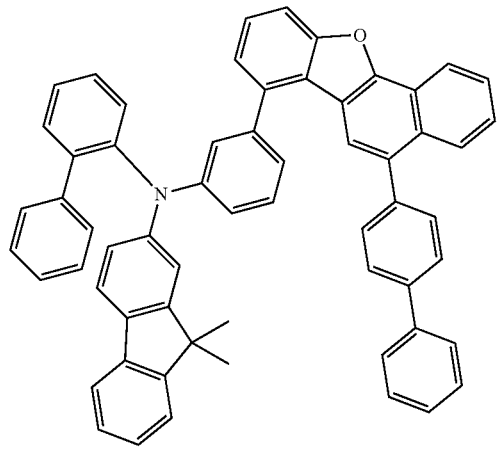
HT-653
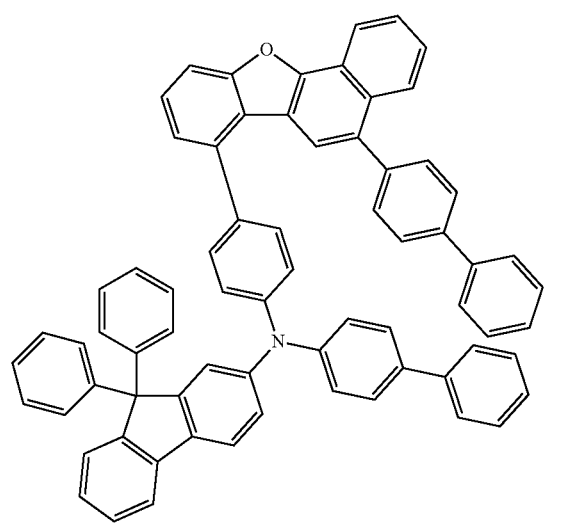
HT-654
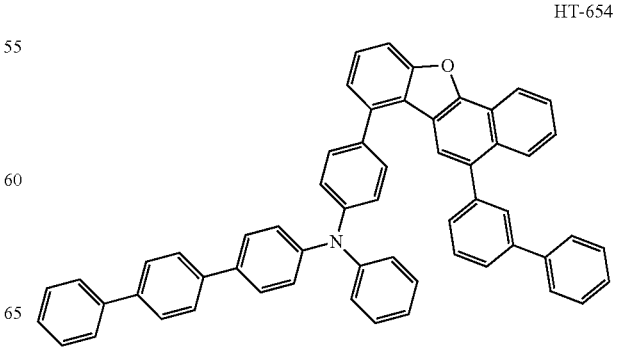

HT-655
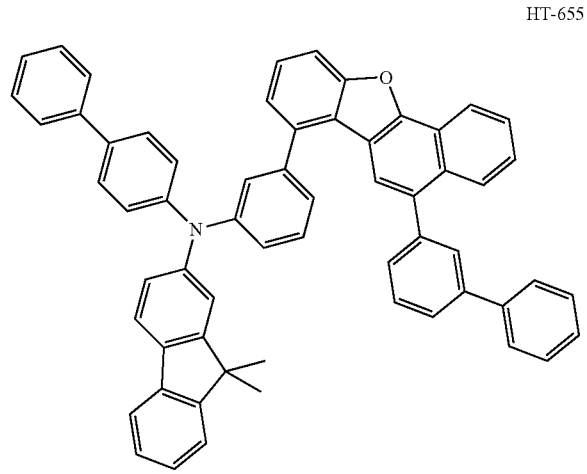
HT-656
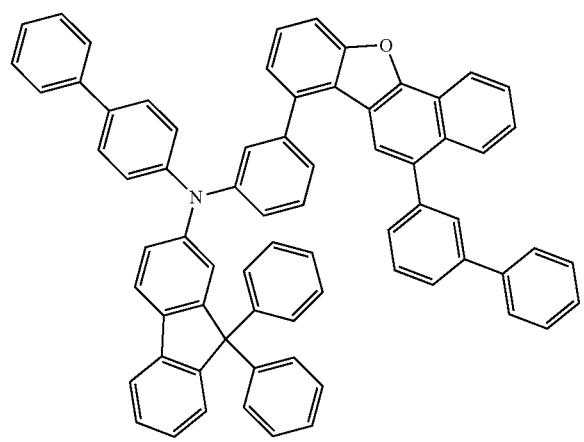
HT-657
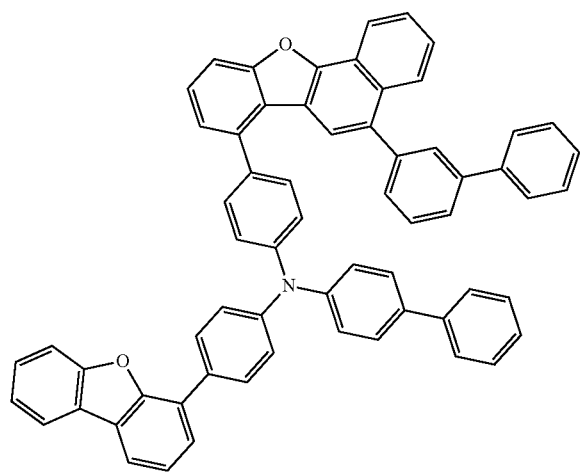
HT-658
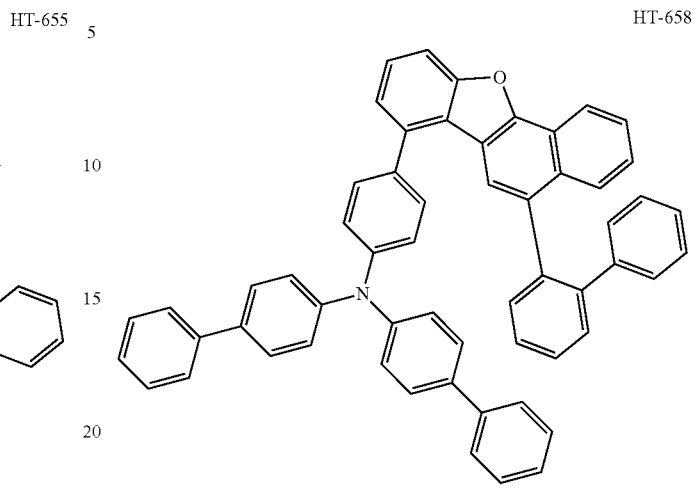
HT-659
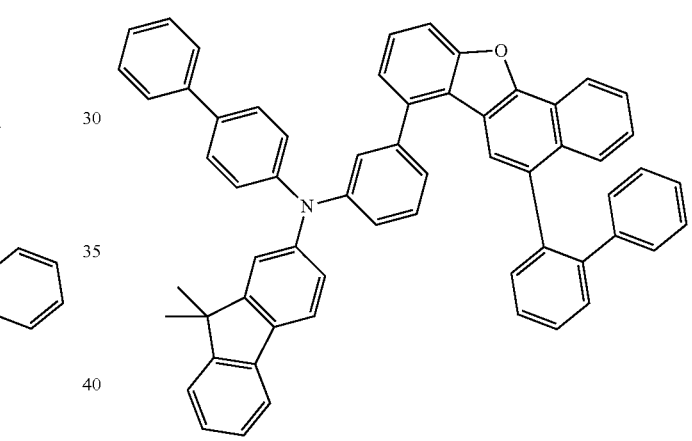
HT-660
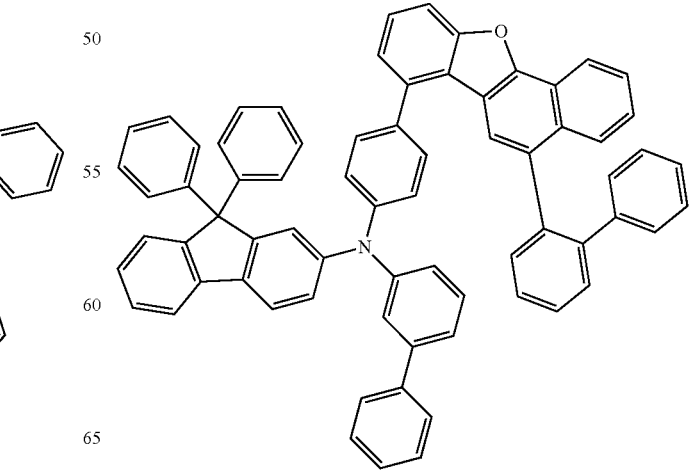

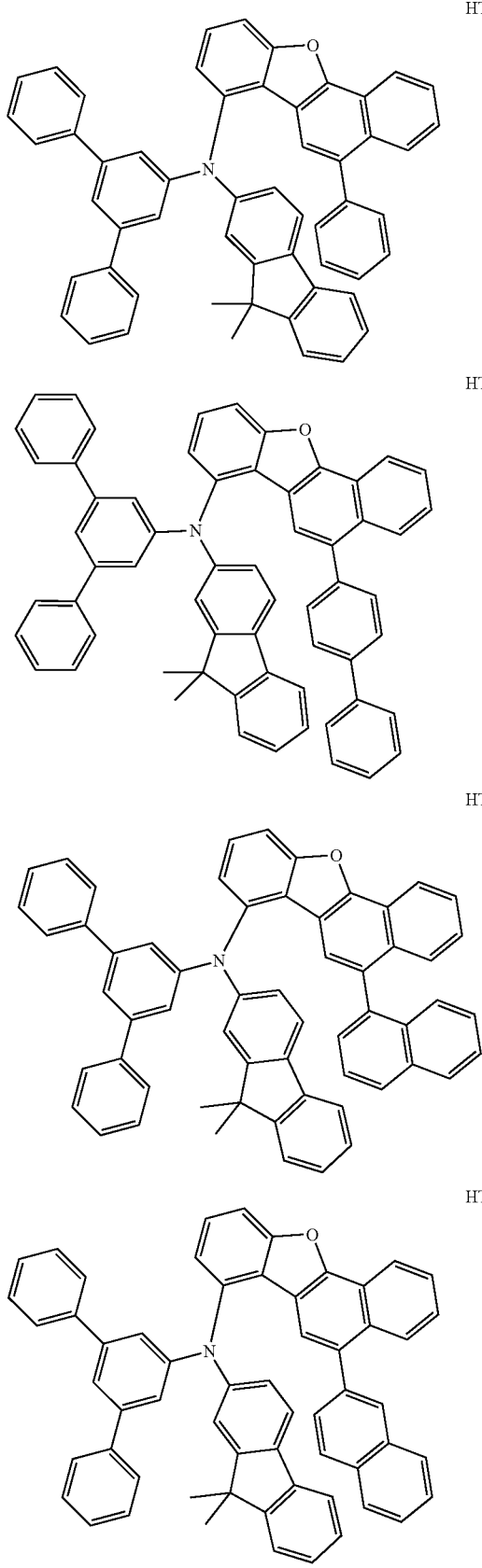
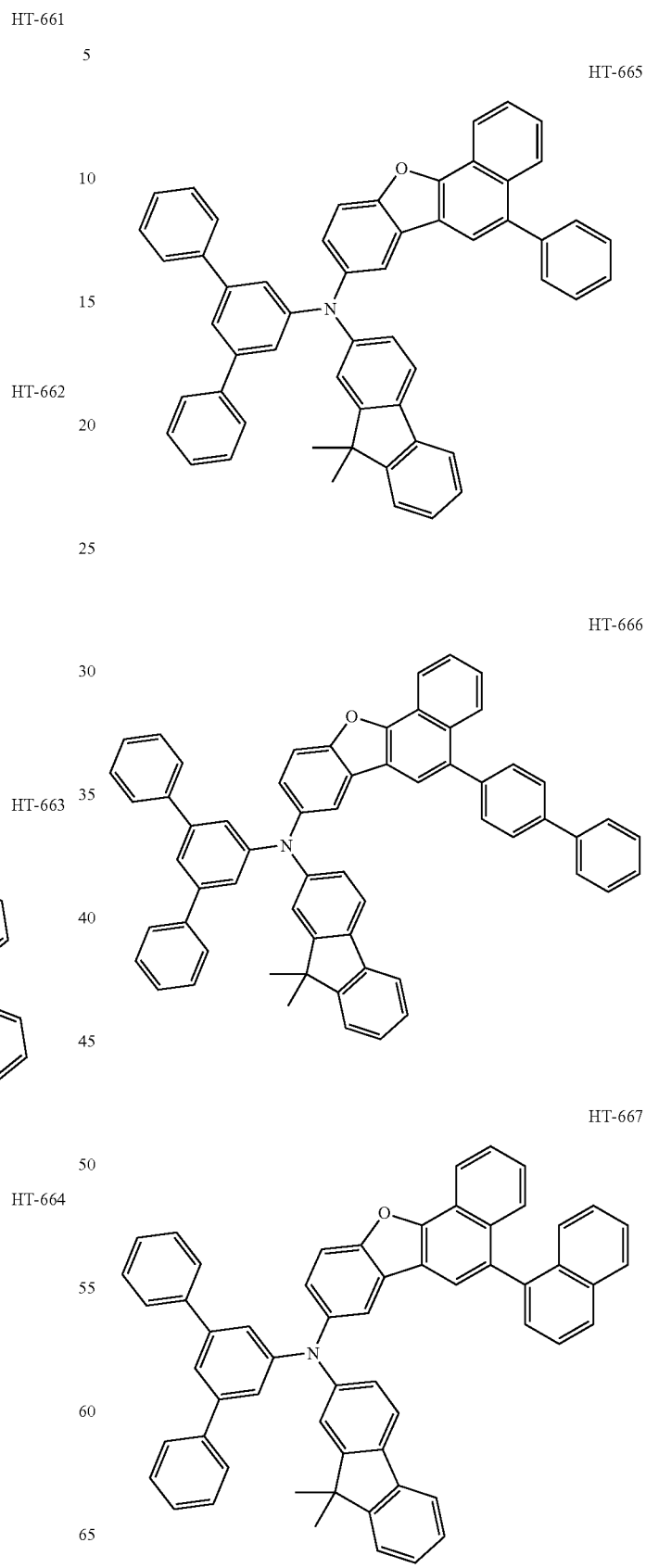

HT-668
HT-671
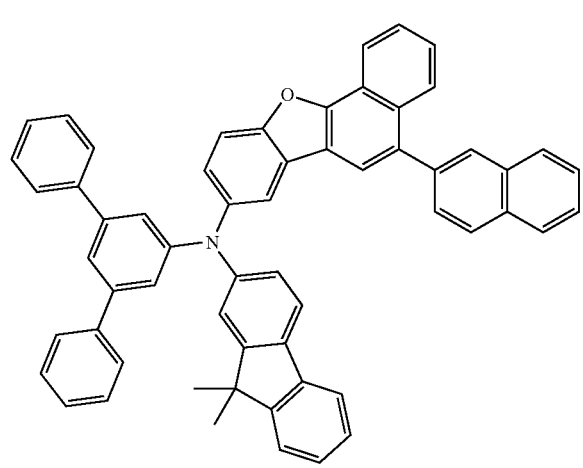
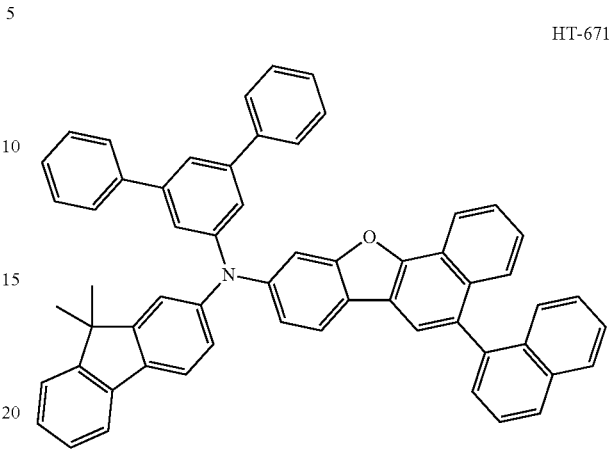
HT-669
HT-672
HT-670
HT-673
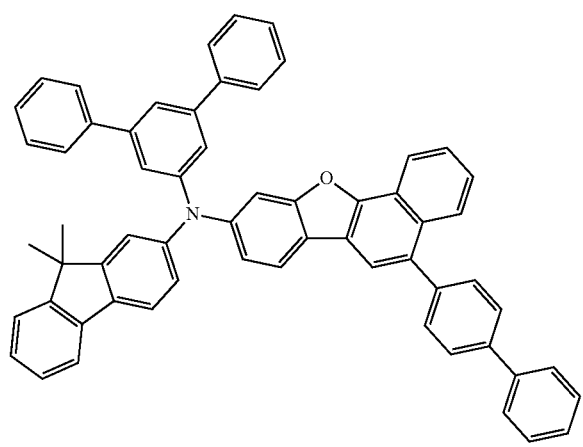
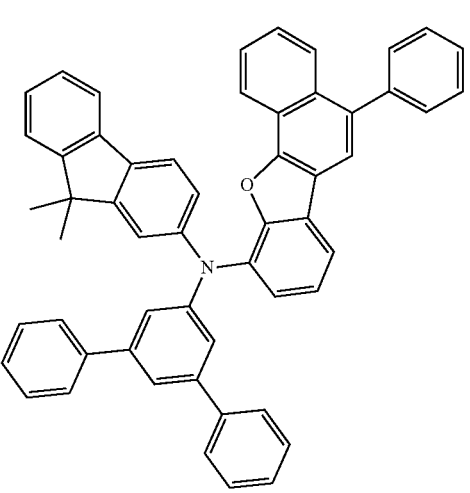

HT-674
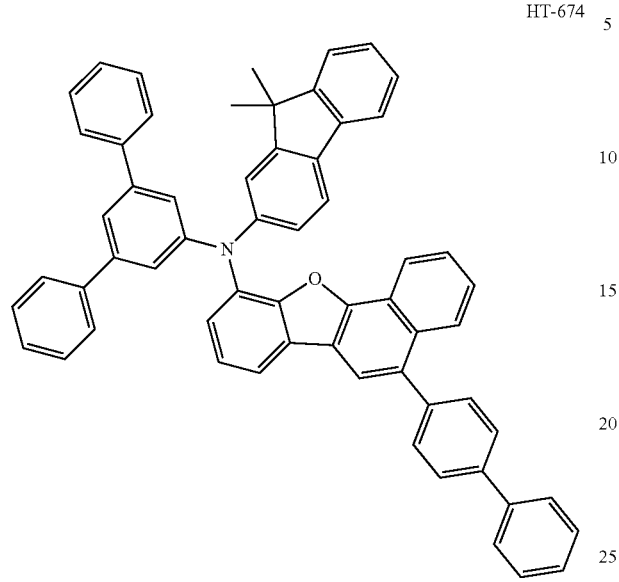
HT-677
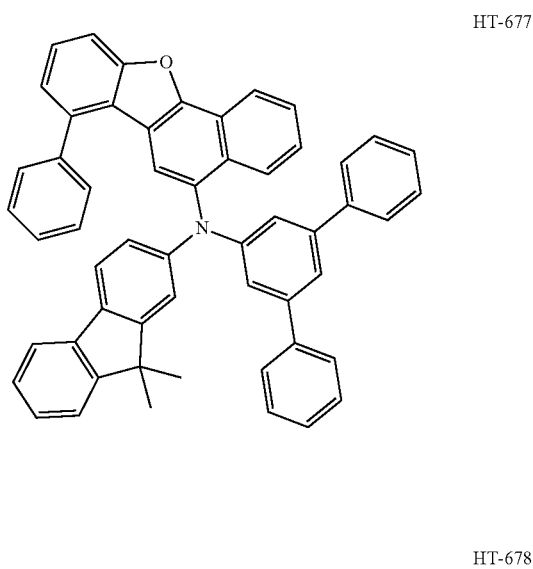
HT-675
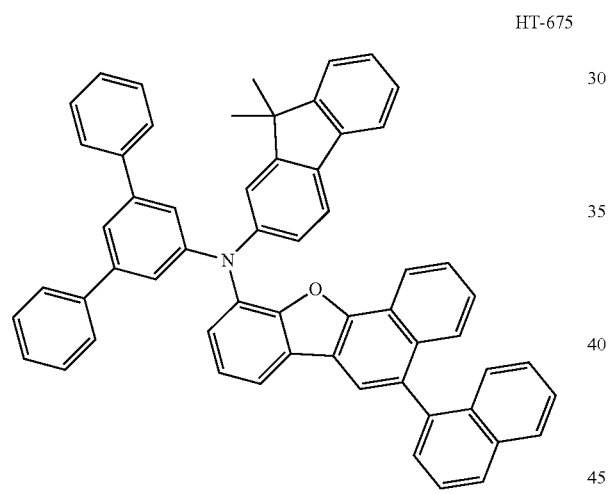
HT-678
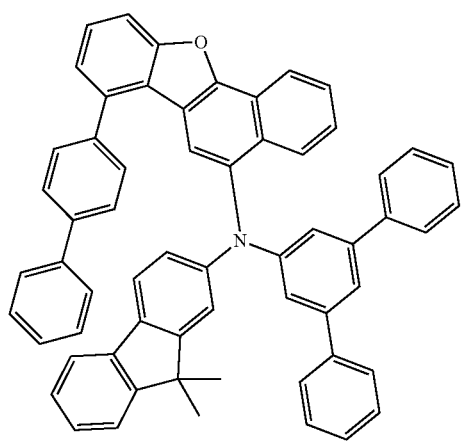
HT-676
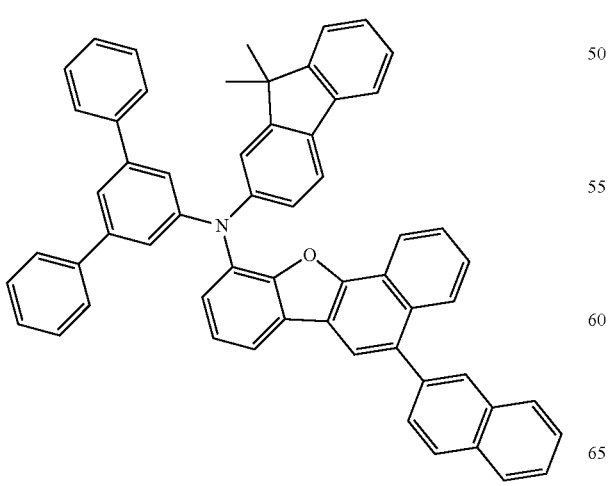
HT-679
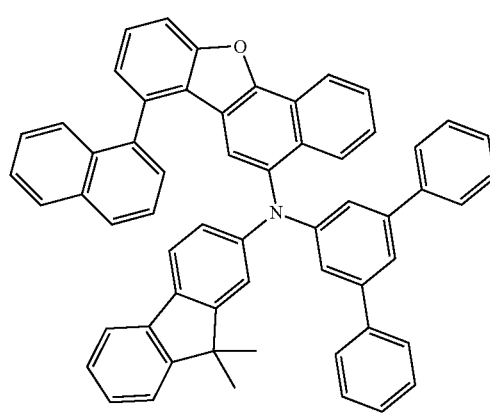

HT-680
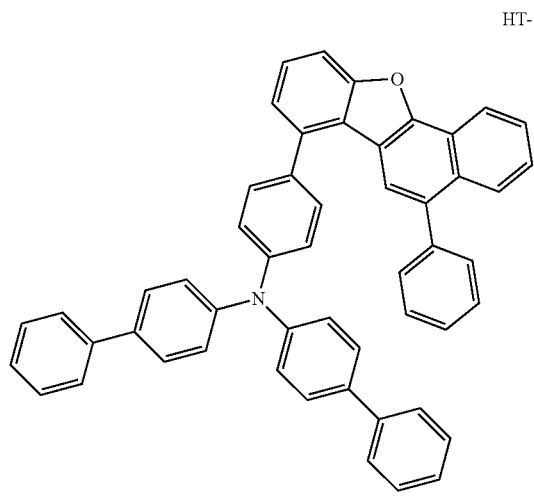
HT-683
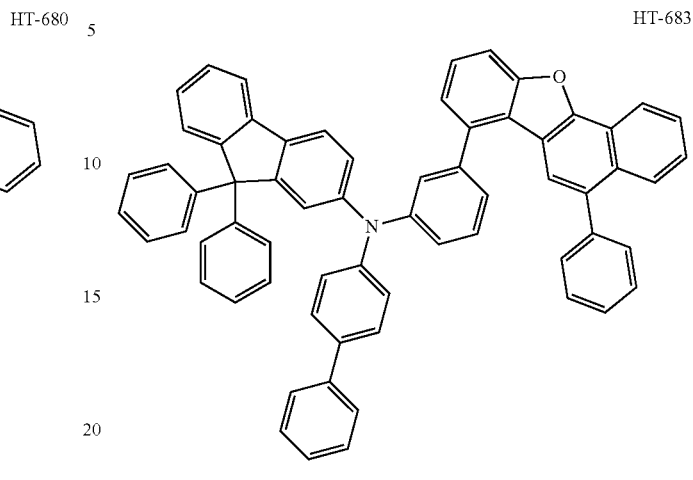
HT-681
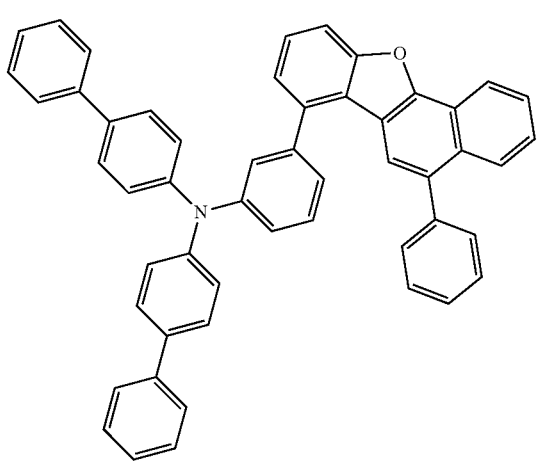
HT-684
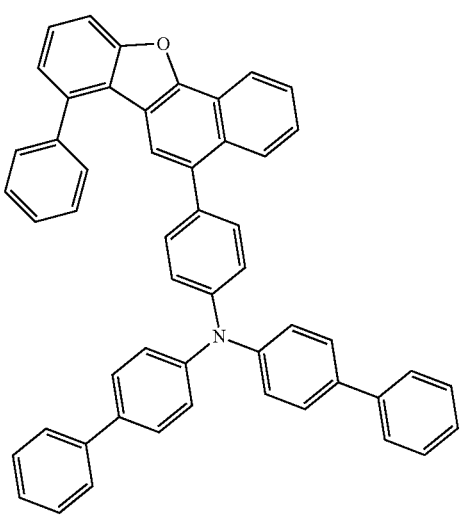
HT-682
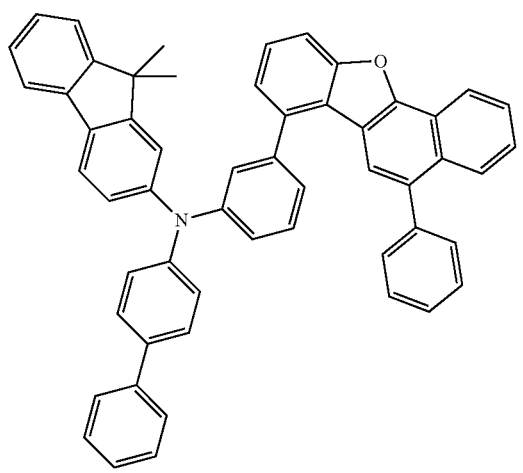
HT-685
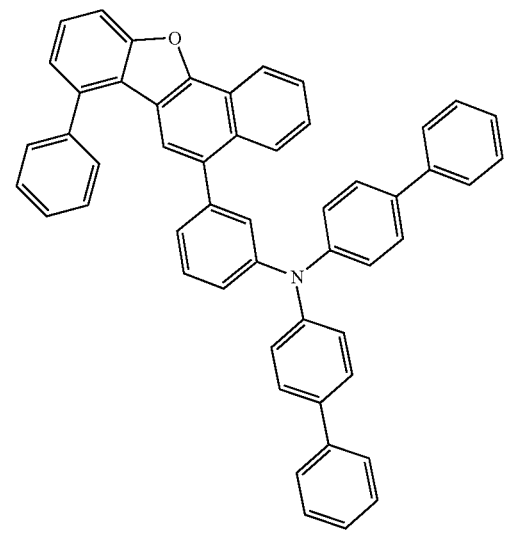

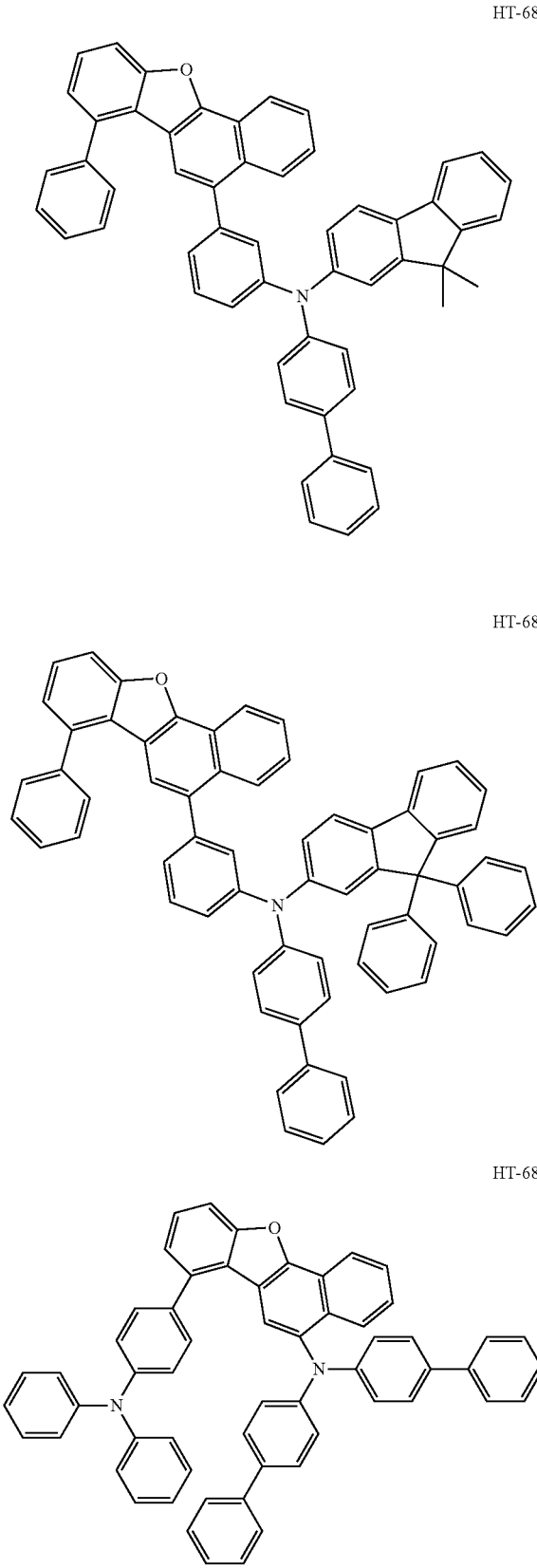
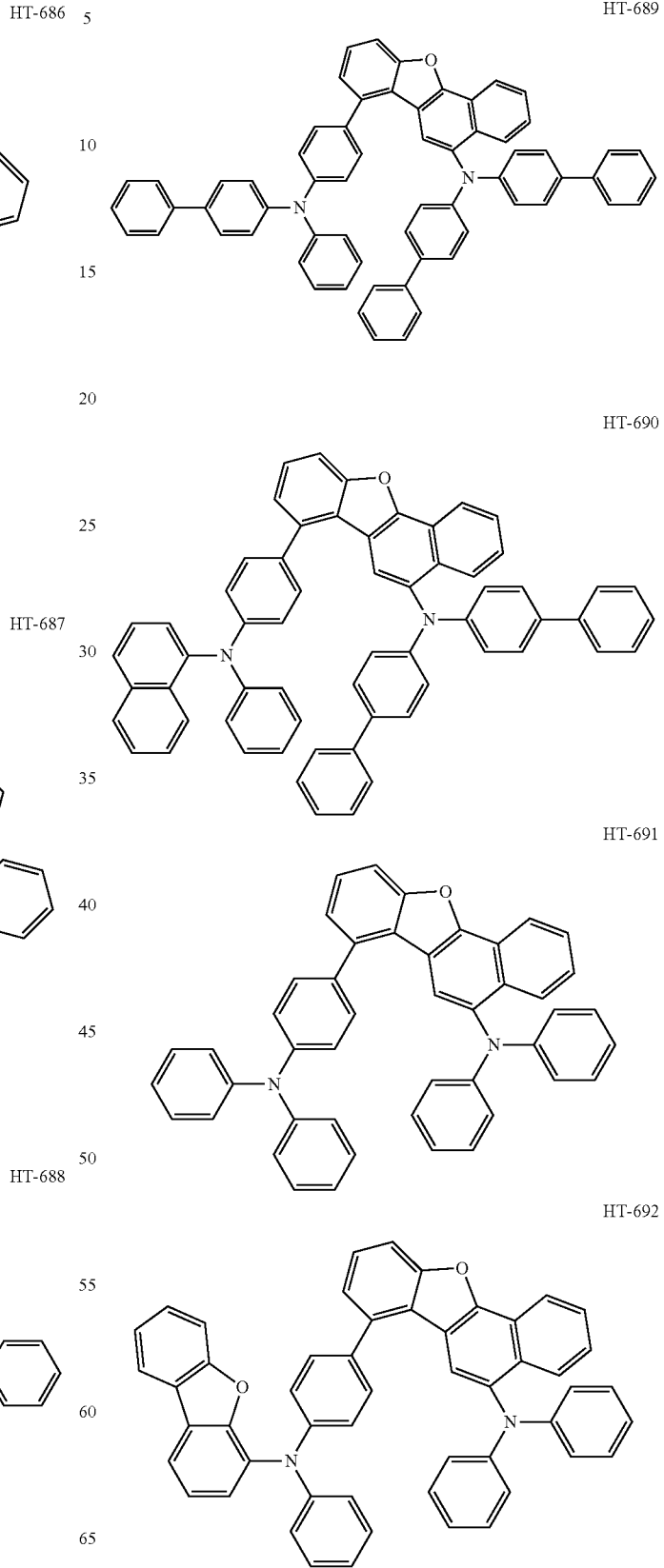

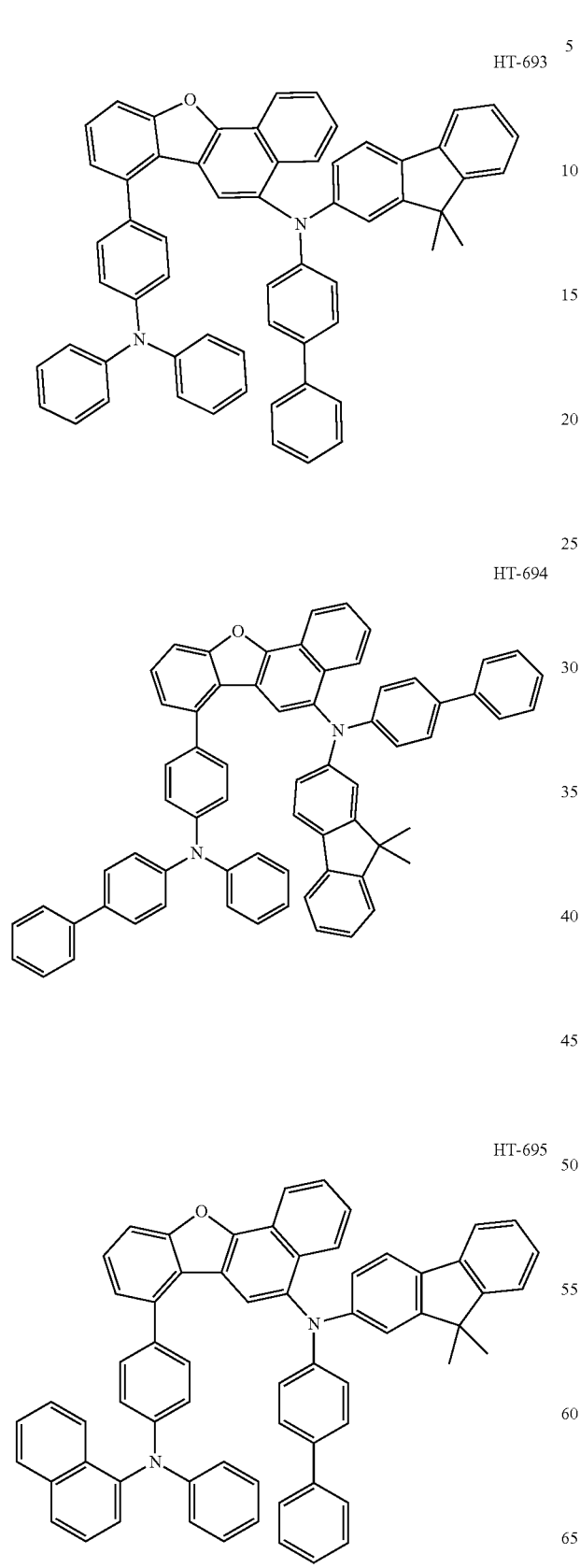
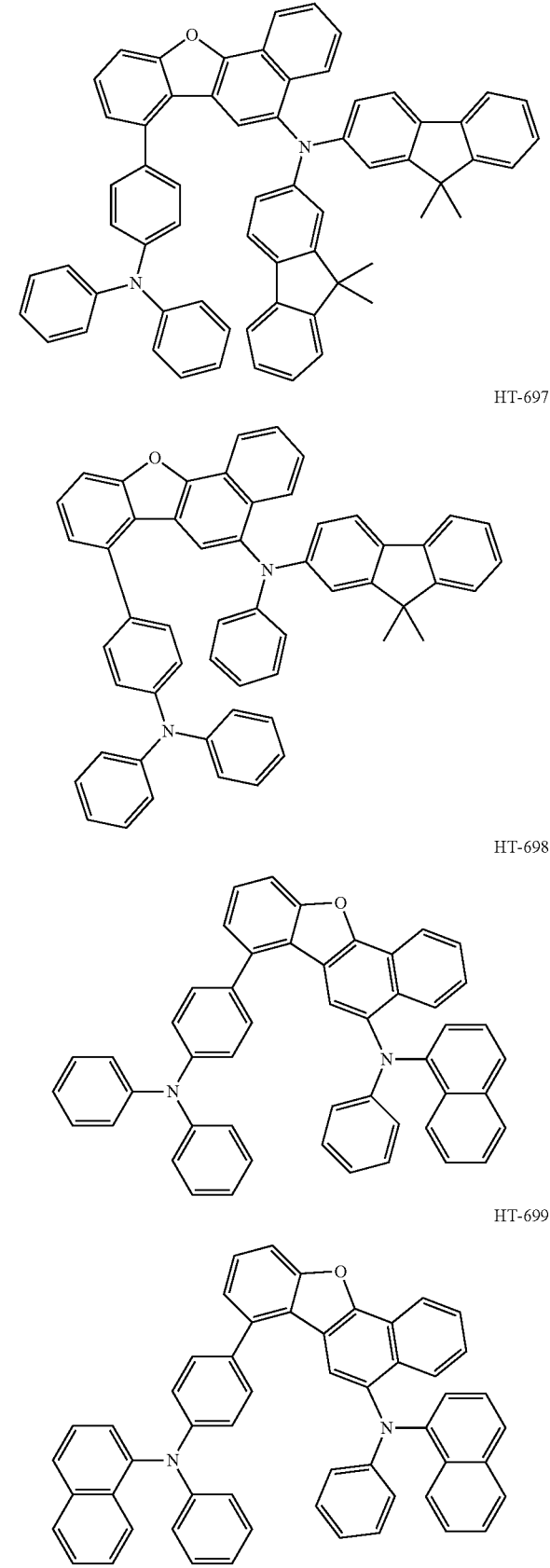

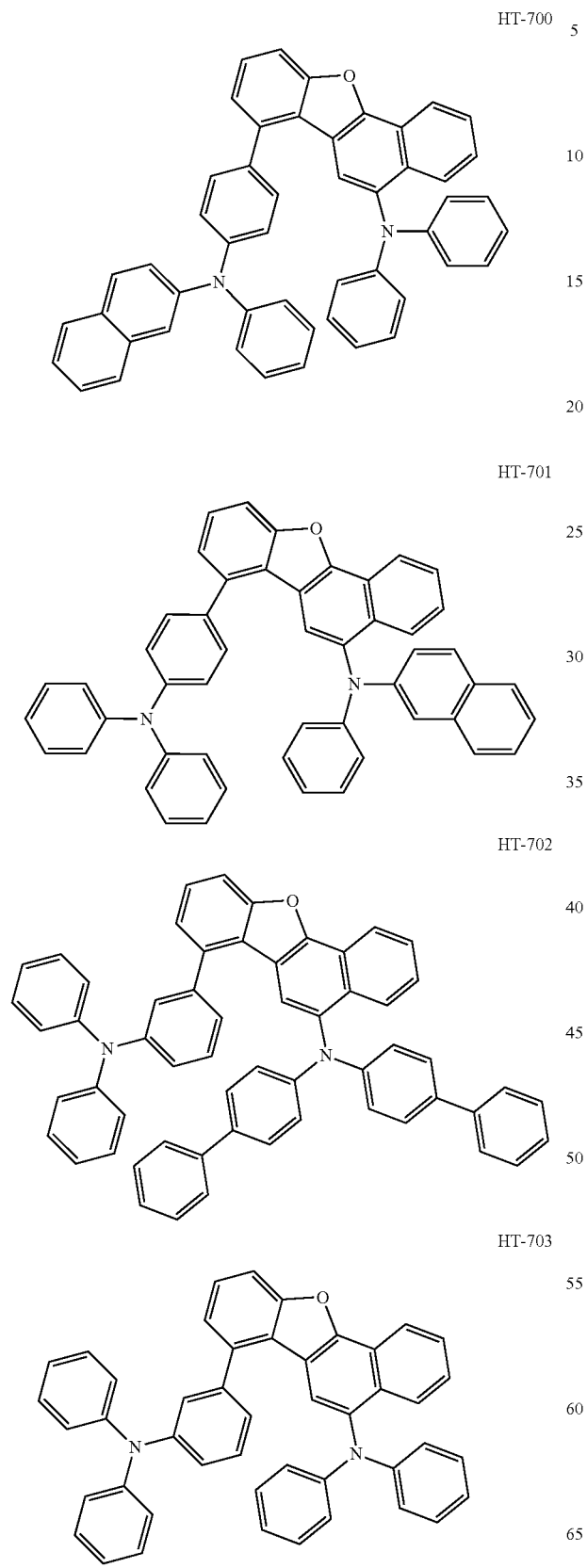

HT-707
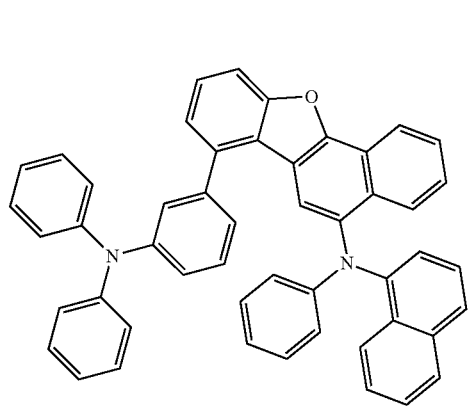
HT-708
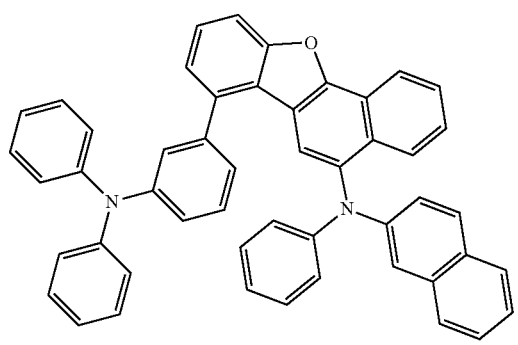
HT-709
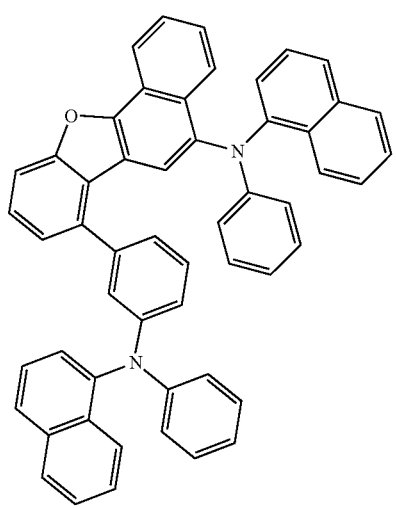
HT-710
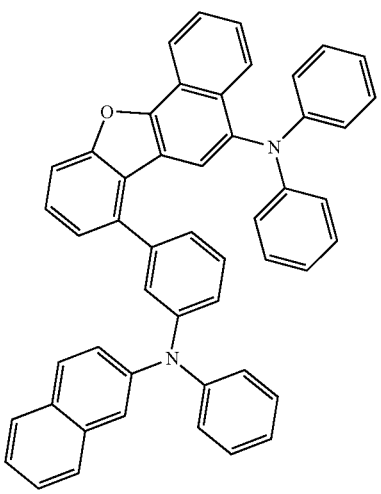
HT-711
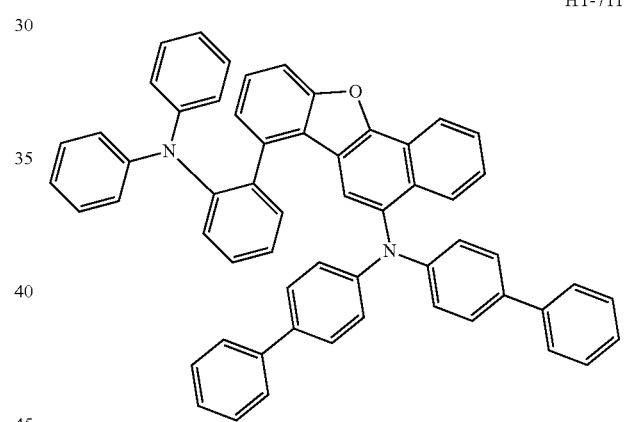
HT-712
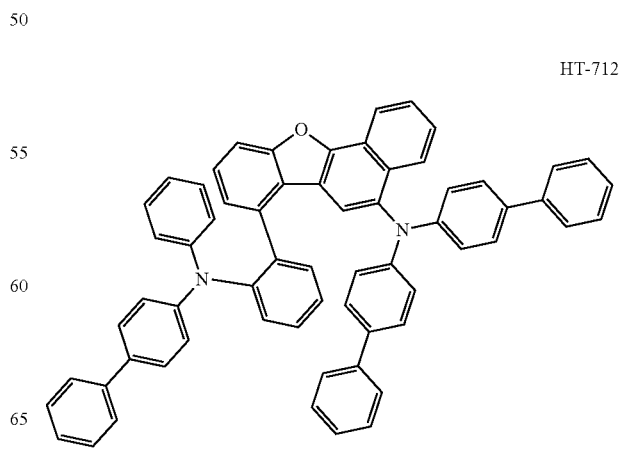

HT-713
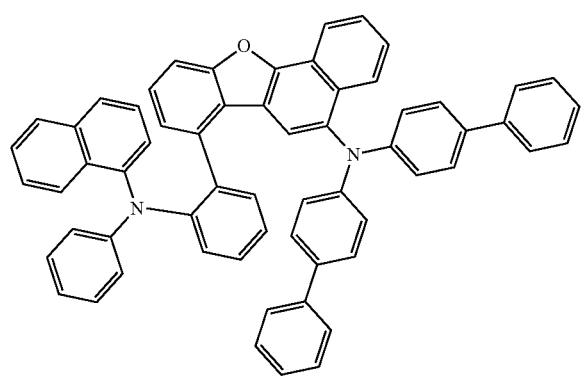

HT-714
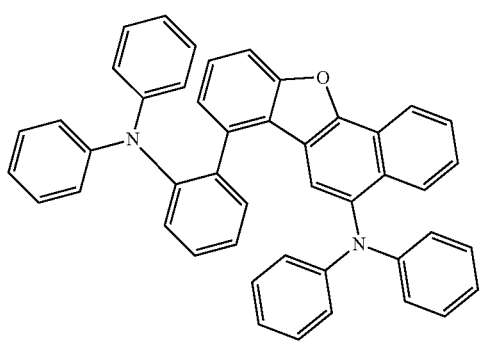

HT-715
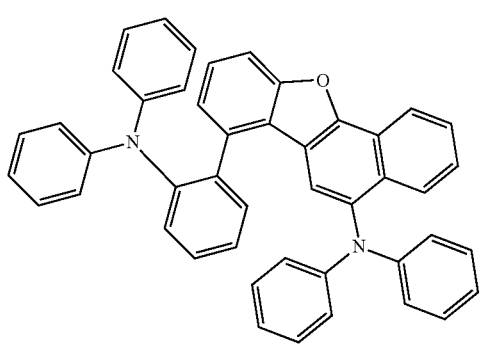

HT-716
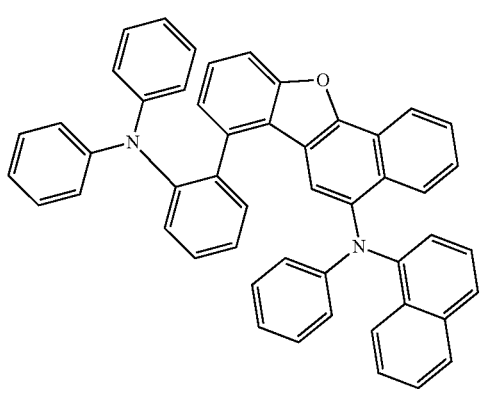

HT-717
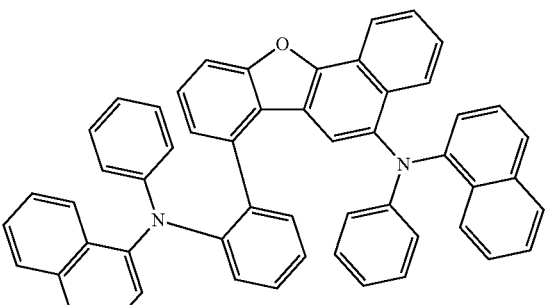

HT-718
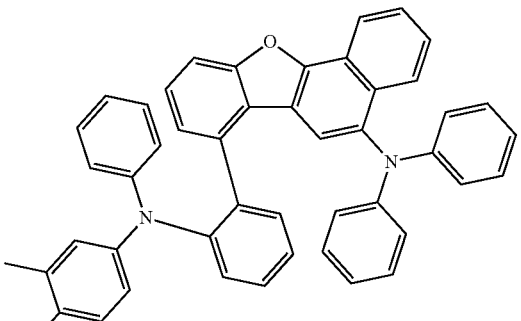

HT-719
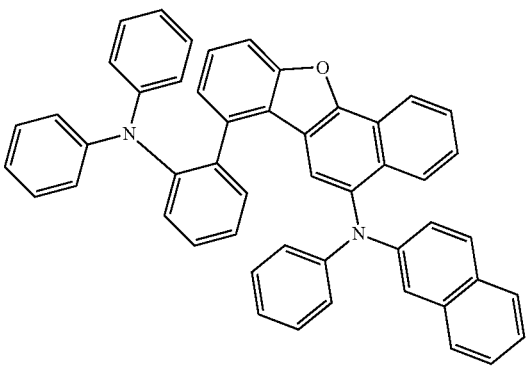

In addition, by introducing various substituents to the structure of Chemical Formula 1, compounds having unique properties of the introduced substituents may be synthesized. For example, by introducing substituents normally used as hole injection layer materials, materials for hole transfer, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the hetero-cyclic compound has a high glass transition temperature (Tg) and thereby has superior thermal stability. Such an increase in the thermal stability becomes an important factor in providing driving stability to a device.

The hetero-cyclic compound according to one embodiment of the present application may be prepared using a multi-step chemical reaction. Some intermediate compounds are prepared first, and from the intermediate compounds, the compound of Chemical Formula 1 may be prepared. More specifically, the hetero-cyclic compound according to one embodiment of the present application may be prepared based on preparation examples to describe later.

Another embodiment of the present application provides an organic light emitting device comprising the hetero-cyclic compound represented by Chemical Formula 1. The "organic light emitting device" may also be expressed in terms such as "OLED (organic light emitting diode)", "OLED device" or "organic electroluminescent device".

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present application comprises an anode, a cathode, and one or more organic material layers provided between the anode and the cathode, and one or more layers of the organic material layers comprise the hetero-cyclic compound represented by Chemical Formula 1. When comprising the hetero-cyclic compound represented by Chemical Formula 1 in the organic material layer, superior light emission efficiency and lifetime are obtained in the organic light emitting device.

The organic material layer may comprise one or more of a hole transfer layer, an electron blocking layer, a prime layer and a light emitting layer. In the present specification, the "prime layer" is a layer disposed between the hole transfer layer and the light emitting layer in the organic light emitting device, and means a functional layer used for the purpose of enhancing luminance, efficiency and lifetime properties of an organic light emitting device by preventing electrons from falling over from the opposite side of the electron transfer layer, and may also be referred to as an "electron defense layer". Materials forming the prime layer may be determined depending on light emitting materials of the light emitting layer.

The organic material layer comprises one or more hole transfer layers, and the hole transfer layer comprises the hetero-cyclic compound represented by Chemical Formula 1. When comprising the hetero-cyclic compound represented by Chemical Formula 1 in the hole transfer layer among the organic material layers, light emission efficiency and lifetime of the organic light emitting device are more superior.

In addition, the organic material layer comprises one or more electron blocking layers, and the electron blocking layer comprises the hetero-cyclic compound represented by Chemical Formula 1. When comprising the hetero-cyclic compound represented by Chemical Formula 1 in the electron blocking layer among the organic material layers, light emission efficiency and lifetime of the organic light emitting device are more superior.

In addition, the organic material layer comprises one or more prime layers, and the prime layer comprises the hetero-cyclic compound represented by Chemical Formula 1. When comprising the hetero-cyclic compound represented by Chemical Formula 1 in the prime layer among the organic material layers, light emission efficiency and lifetime of the organic light emitting device are more superior.

In addition, the organic material layer comprises one or more light emitting layers, and the light emitting layer comprises the hetero-cyclic compound represented by Chemical Formula 1. When comprising the hetero-cyclic compound represented by Chemical Formula 1 in the light emitting layer among the organic material layers, light emission efficiency and lifetime of the organic light emitting device are more superior.

The organic light emitting device according to one embodiment of the present application may be manufactured using common organic light emitting device manufacturing methods and materials except that a hole transfer layer, an electron blocking layer, a prime layer or a light emitting layer is formed using the hetero-cyclic compound described above.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, and the two or more stacks each independently comprise a light emitting layer, and a charge generation layer is included between the two or more stacks.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

The hetero-cyclic compound represented by Chemical Formula 1 alone may form one or more of the hole transfer layer or the electron blocking layer in the organic light emitting device. However, other material may be mixed as necessary to form the hole transfer layer or the electron blocking layer.

In the organic light emitting device according to one embodiment of the present application, materials other than the hetero-cyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

EXAMPLE

<Preparation Example 1> Preparation of Intermediate A

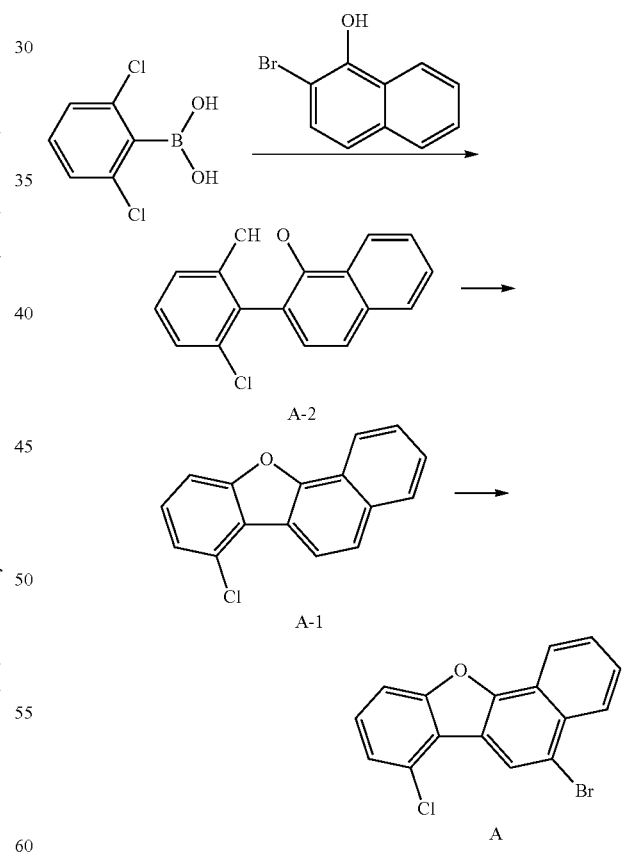

1) Preparation of Intermediate A-2

After dissolving (2,6-dichlorophenyl)boronic acid (47.05 g, 246.56 mmol) and 2-bromonaphthalen-1-ol (50 g, 224.14 mmol) in tetrahydrofuran (THF) (500 ml) and $H_2O$ (100 ml), $Pd(PPh_3)_4$ (7.77 g, 6.72 mmol) and $K_2CO_3$ (92.94 g, 672.43 mmol) were introduced thereto, and the result was stirred for 17 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Intermediate A-2 (49 g, 75%).

2) Preparation of Intermediate A-1

After dissolving Intermediate A-2 (49 g, 169.19 mmol) in dimethylacetamide (500 ml), Cs$_2$CO$_3$ (165.38 g, 507.58 mmol) was introduced thereto, and the result was stirred for 4 hours under reflux. After the reaction was completed, MC was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Intermediate A-1 (35 g, 82%).

3) Preparation of Intermediate A

After dissolving Intermediate A-1 (35 g, 138.50 mmol) in dimethylformamide (DMF) (350 ml), N-bromosuccinimide (NBS) (27.12 g, 152.35 mmol) was introduced thereto, and the result was stirred for 4 hours at room temperature. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Intermediate A (40 g, 87%).

<Preparation Example 2> Preparation of Compound HT-9

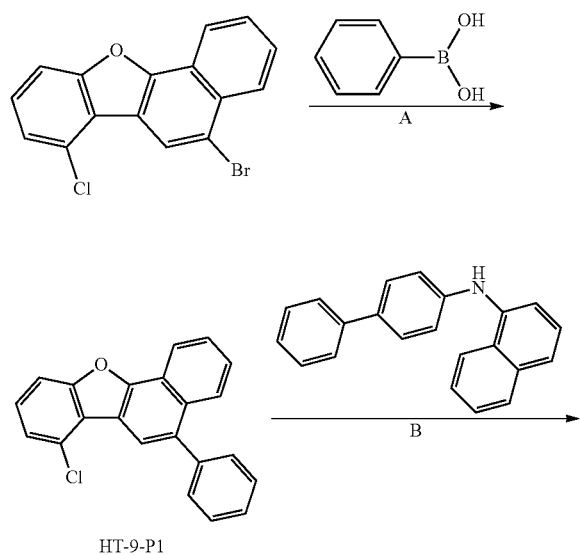

HT-9-P1

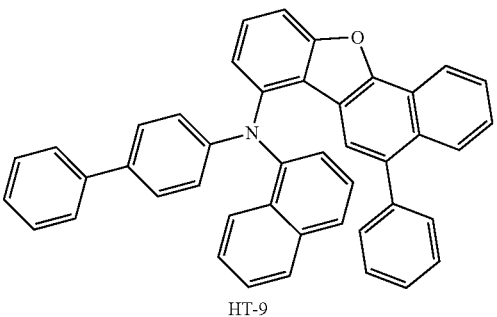

HT-9

1) Preparation of Compound HT-9-P1

After dissolving Intermediate A (20 g, 60.32 mmol) and phenylboronic acid (7.72 g, 63.33 mmol) in toluene (200 ml), ethanol (40 ml) and H$_2$O (40 ml), Pd(PPh$_3$)$_4$ (3.48 g, 3.02 mmol) and K$_3$PO$_4$ (38.41 g, 180.95 mmol) were introduced thereto, and the result was stirred for 5 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Compound HT-9-P1 (17 g, 85%).

2) Preparation of Compound HT-9

After dissolving Compound HT-9-P1 (17 g, 51.70 mmol) and N-([1,1'-biphenyl]-4-yl)naphthalen-1-amine) (18.33 g, 62.04 mmol) in toluene (200 ml), Pd(dba)$_2$ (1.49 g, 2.59 mmol), P(t-Bu)$_3$ (1.05 g, 5.17 mmol) and t-BuONa (14.9 g, 155.11 mmol) were introduced thereto, and the result was stirred for 7 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Compound HT-9 (19 g, 63%).

3) Preparation of Target Compound C

Target Compound C was prepared in the same manner as in Preparation Example 2 except that Compound A of the following Table 1 was used instead of phenylboronic acid, and Compound B of the following Table 1 was used instead of N-([1,1'-biphenyl]-4-yl)naphthalen-1-amine.

Chemical formulae of Compounds A and B used for preparing target Compound C, and compound number, chemical formula and yield of the prepared target Compound C are summarized in the following Table 1.

TABLE 1

| Compound Number | Compound A | Compound B | Target compound C | Yield |
|---|---|---|---|---|
| HT-15 | | | | 88% |
| HT-24 | | | | 75% |

TABLE 1-continued

| Compound Number | Compound A | Compound B | Target compound C | Yield |
|---|---|---|---|---|
| HT-32 | (HO)$_2$B-Ph | [structure] | [structure] | 79% |
| HT-34 | (HO)$_2$B-Ph | [structure] | [structure] | 73% |

TABLE 1-continued

| Compound Number | Compound A | Compound B | Target compound C | Yield |
|---|---|---|---|---|
| HT-35 | (HO)₂B-phenyl | [structure] | [structure] | 73% |
| HT-37 | (HO)₂B-phenyl | [structure] | [structure] | 85% |

TABLE 1-continued

| Compound Number | Compound A | Compound B | Target compound C | Yield |
|---|---|---|---|---|
| HT-38 | (HO)₂B–[phenyl] | [9,9-diphenylfluorenyl-NH-biphenyl] | [target structure] | 67% |
| HT-41 | (HO)₂B–[phenyl] | [spirobifluorenyl-NH-biphenyl] | [target structure] | 75% |

TABLE 1-continued

| Compound Number | Compound A | Compound B | Target compound C | Yield |
|---|---|---|---|---|
| HT-44 | (HO)₂B-phenyl | fluorene-NH-fluorene derivative | target structure | 90% |
| HT-50 | (HO)₂B-phenyl | dibenzofuran-phenyl-NH-biphenyl | target structure | 73% |

TABLE 1-continued

| Compound Number | Compound A | Compound B | Target compound C | Yield |
|---|---|---|---|---|
| HT-64 | (HO)₂B-naphthyl | biphenyl-NH-naphthyl | (structure) | 84% |
| HT-69 | (HO)₂B-naphthyl | phenyl-NH-biphenylphenyl | (structure) | 89% |

TABLE 1-continued

| Compound Number | Compound A | Compound B | Target compound C | Yield |
|---|---|---|---|---|
| HT-76 | | | | 67% |
| HT-78 | | | | 81% |

TABLE 1-continued

| Compound Number | Compound A | Compound B | Target compound C | Yield |
|---|---|---|---|---|
| HT-79 | (HO)₂B-naphthalene | biphenyl-NH-biphenyl-phenyl | (structure) | 83% |
| HT-84 | (HO)₂B-naphthalene | biphenyl-NH-(9,9-dimethylfluorene) | (structure) | 76% |

TABLE 1-continued

| Compound Number | Compound A | Compound B | Target compound C | Yield |
|---|---|---|---|---|
| HT-85 | (HO)₂B-naphthalene | 9,9-dimethylfluorene-NH-biphenyl (meta) | | 72% |
| HT-87 | (HO)₂B-naphthalene | 9,9-diphenylfluorene-NH-biphenyl (para) | | 79% |

TABLE 1-continued

| Compound Number | Compound A | Compound B | Target compound C | Yield |
|---|---|---|---|---|
| HT-90 | (HO)₂B-naphthyl | [structure] | [structure] | 65% |
| HT-96 | (HO)₂B-naphthyl | [structure] | [structure] | 66% |

TABLE 1-continued

| Compound Number | Compound A | Compound B | Target compound C | Yield |
|---|---|---|---|---|
| HT-128 | | | | 83% |
| HT-129 | | | | 67% |

TABLE 1-continued

| Compound Number | Compound A | Compound B | Target compound C | Yield |
|---|---|---|---|---|
| HT-136 | (HO)₂B-naphthalene | biphenyl-NH-dimethylfluorene | (structure) | 72% |
| HT-137 | (HO)₂B-naphthalene | biphenyl-NH-dimethylfluorene | (structure) | 75% |

TABLE 1-continued

| Compound Number | Compound A | Compound B | Target compound C | Yield |
|---|---|---|---|---|
| HT-139 | | | | 64% |
| HT-162 | | | | 81% |

TABLE 1-continued

| Compound Number | Compound A | Compound B | Target compound C | Yield |
|---|---|---|---|---|
| HT-171 | (HO)₂B-biphenyl | N-phenyl-4-([1,1'-biphenyl]-4-yl)aniline | (structure) | 65% |
| HT-176 | (HO)₂B-biphenyl | N-(naphthalen-1-yl)-[1,1':4',1''-terphenyl]-2-amine | (structure) | 63% |

TABLE 1-continued

| Compound Number | Compound A | Compound B | Target compound C | Yield |
|---|---|---|---|---|
| HT-180 | | | | 78% |
| HT-181 | | | | 81% |

TABLE 1-continued

| Compound Number | Compound A | Compound B | Target compound C | Yield |
|---|---|---|---|---|
| HT-188 | (HO)$_2$B-biphenyl | [structure] | [structure] | 82% |
| HT-189 | (HO)$_2$B-biphenyl | [structure] | [structure] | 74% |

TABLE 1-continued

| Compound Number | Compound A | Compound B | Target compound C | Yield |
|---|---|---|---|---|
| HT-191 | | | | 68% |
| HT-194 | | | | 54% |

TABLE 1-continued

| Compound Number | Compound A | Compound B | Target compound C | Yield |
|---|---|---|---|---|
| HT-197 | | | | 75% |
| HT-232 | | | | 68% |

TABLE 1-continued

| Compound Number | Compound A | Compound B | Target compound C | Yield |
|---|---|---|---|---|
| HT-235 | | | | 63% |
| HT-240 | | | | 81% |
| HT-241 | | | | 88% |

TABLE 1-continued

| Compound Number | Compound A | Compound B | Target compound C | Yield |
|---|---|---|---|---|
| HT-242 | | | | 73% |
| HT-246 | | | | 55% |

TABLE 1-continued

| Compound Number | Compound A | Compound B | Target compound C | Yield |
|---|---|---|---|---|
| HT-285 | | | | 68% |
| HT-292 | | | | 72% |

TABLE 1-continued

| Compound Number | Compound A | Compound B | Target compound C | Yield |
|---|---|---|---|---|
| HT-294 | | | | 52% |
| HT-295 | | | | 74% |

TABLE 1-continued

| Compound Number | Compound A | Compound B | Target compound C | Yield |
|---|---|---|---|---|
| HT-661 | phenylboronic acid | N-(3,5-diphenylphenyl)-9,9-dimethyl-9H-fluoren-2-amine | (structure) | 81% |
| HT-662 | 4-biphenylboronic acid | N-(3,5-diphenylphenyl)-9,9-dimethyl-9H-fluoren-2-amine | (structure) | 74% |

TABLE 1-continued

| Compound Number | Compound A | Compound B | Target compound C | Yield |
|---|---|---|---|---|
| HT-663 | (1-naphthaleneboronic acid, B(OH)₂) | (N-([1,1':3',1''-terphenyl]-5'-yl)-9,9-dimethyl-9H-fluoren-2-amine) | (target compound structure) | 86% |

275
<Preparation Example 3> Preparation of Compound HT-627

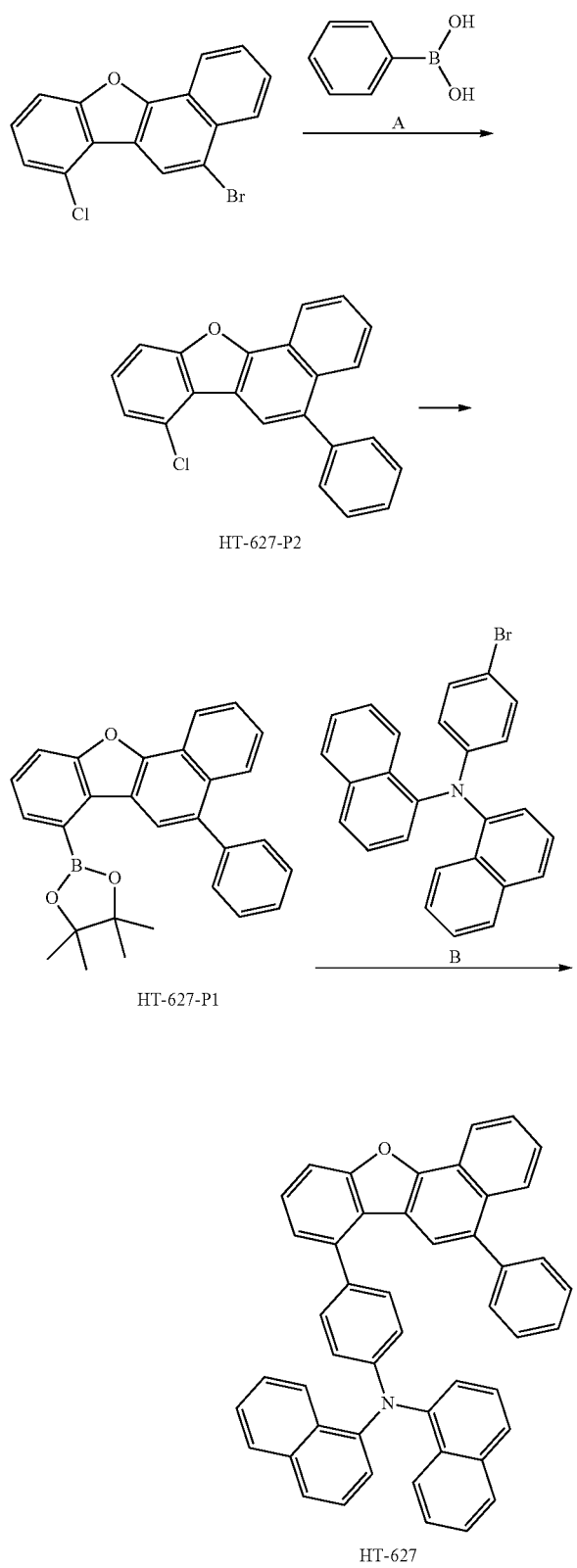

HT-627-P2

HT-627-P1

HT-627

276

1) Preparation of Compound HT-627-P2

After dissolving Intermediate A (20 g, 60.32 mmol) and phenylboronic acid (7.72 g, 63.33 mmol) in toluene (200 ml), ethanol (40 ml) and H$_2$O (40 ml), Pd(PPh$_3$)$_4$ (3.48 g, 3.02 mmol) and K$_3$PO$_4$ (38.41 g, 180.95 mmol) were introduced thereto, and the result was stirred for 5 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Compound HT-627-P2 (17 g, 85%).

2) Preparation of Compound HT-627-P1

After dissolving Compound HT-627-P2 (17 g, 51.70 mmol) and bis(pinacolato)diboron (17.07 g, 67.22 mmol) in 1,4-dioxane (170 ml), Pd(dba)$_2$ (1.49 g, 2.59 mmol), Xphos (2.46 g, 5.17 mmol) and KOAc (15.22 g, 155.11 mmol) were introduced thereto, and the result was stirred for 3 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Compound HT-627-P1 (18 g, 82%).

3) Preparation of Compound HT-627

After dissolving Compound HT-627-P1 (10 g, 23.79 mmol) and N-(4-bromophenyl)-N-(naphthalen-1-yl)naphthalen-1-amine (10.1 g, 23.79 mmol) in toluene (100 ml), ethanol (20 ml) and H$_2$O (20 ml), Pd(PPh$_3$)$_4$ (1.37 g, 1.19 mmol) and K$_3$PO$_4$ (15.15 g, 71.38 mmol) were introduced thereto, and the result was stirred for 6 hours under reflux. After the reaction was completed, methylene chloride (MC) was introduced to the reaction solution for dissolution, and the result was extracted with distilled water. After drying the organic layer with anhydrous MgSO$_4$, the solvent was removed using a rotary evaporator, and the result was purified with column chromatography using dichloromethane and hexane as a developing solvent to obtain Compound HT-627 (12 g, 79%).

4) Preparation of Target Compound D

Target Compound D was prepared in the same manner as in Preparation Example 3 except that Compound A of the following Table 2 was used instead of phenylboronic acid, and Compound B of the following Table 2 was used instead of N-(4-bromophenyl)-N-(naphthalen-1-yl)naphthalen-1-amine.

Chemical formulae of Compounds A and B used for preparing target Compound D, and compound number, chemical formula and yield of the prepared target Compound D are summarized in the following Table 2.

TABLE 2

| Compound Number | Compound A | Compound B | Target compound D | Yield |
|---|---|---|---|---|
| HT-630 | (HO)₂B-Ph | | | 76% |
| HT-632 | (HO)₂B-Ph | | | 77% |
| HT-635 | (HO)₂B-Ph | | | 81% |
| HT-637 | (HO)₂B-Ph | | | 69% |

TABLE 2-continued

| Compound Number | Compound A | Compound B | Target compound D | Yield |
|---|---|---|---|---|
| HT-639 | | | | 80% |
| HT-641 | | | | 76% |
| HT-643 | | | | 77% |
| HT-645 | | | | 77% |

TABLE 2-continued

| Compound Number | Compound A | Compound B | Target compound D | Yield |
| --- | --- | --- | --- | --- |
| HT-648 | | | | 86% |
| HT-653 | | | | 84% |
| HT-656 | | | | 69% |
| HT-680 | | | | 90% |

TABLE 2-continued
| Compound Number | Compound A | Compound B | Target compound D | Yield |
|---|---|---|---|---|
| HT-681 | | | | 75% |
| HT-682 | | | | 80% |
| HT-683 | | | | 55% |
<Preparation Example 4> Preparation of Compound HT-689
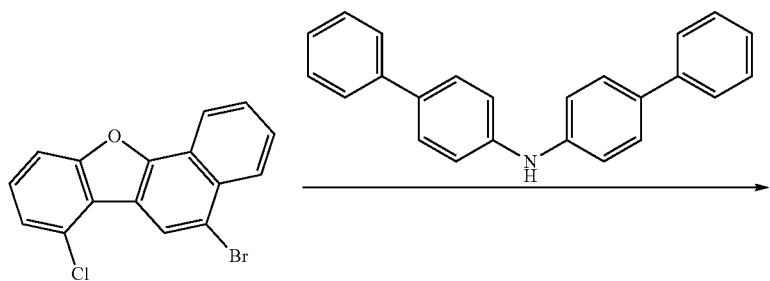

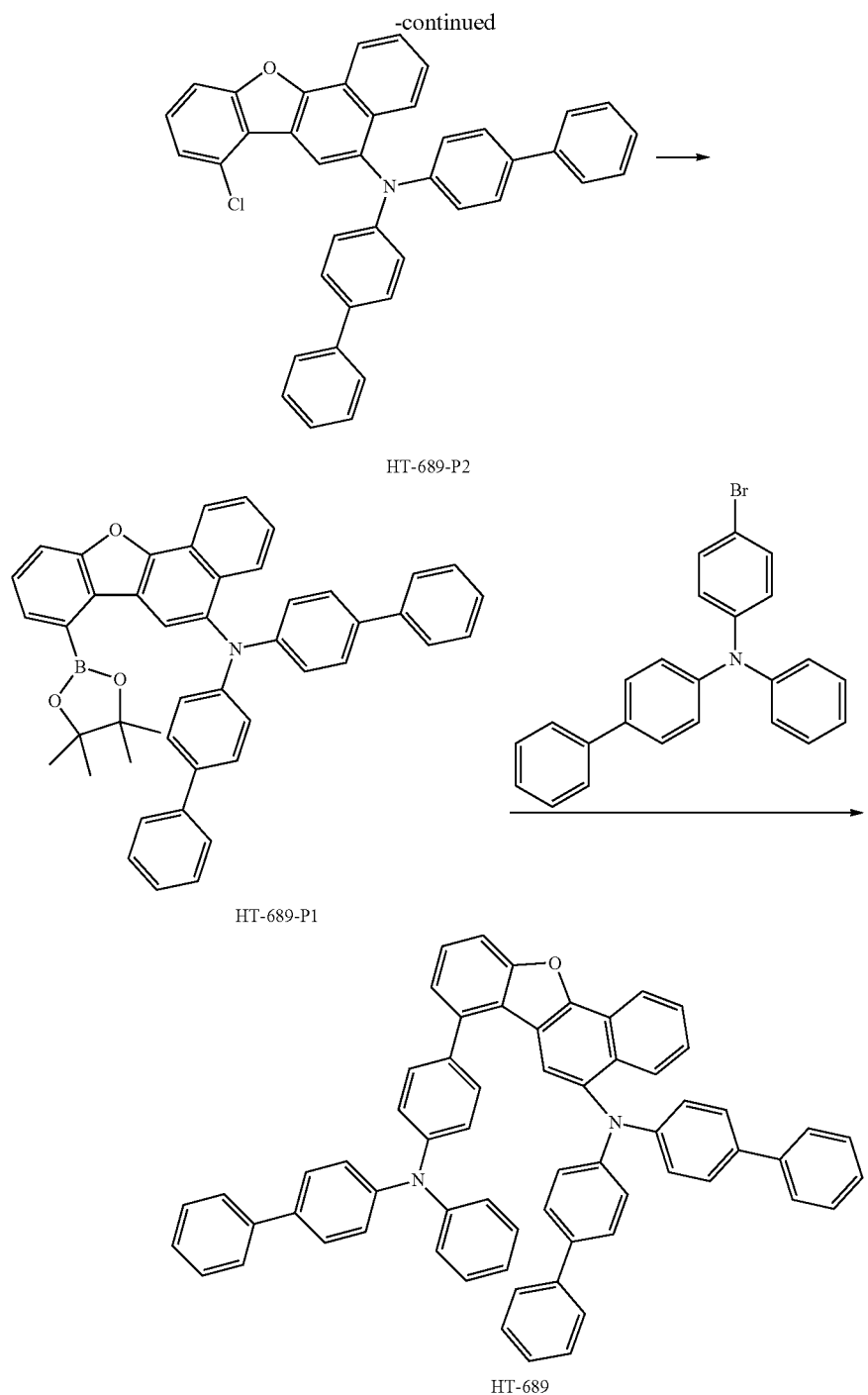

1) Preparation of Compound HT-689-P2

After dissolving Intermediate A (10 g, 30.16 mmol) and di([1,1'-biphenyl]-4-yl)amine (10.7 g, 33.18 mmol) in toluene (100 ml), Pd(dba)₂ (1.38 g, 1.51 mmol), P(t-Bu)₃ (0.6 g, 3.01 mmol) and t-BuONa (8.7 g, 90.48 mmol) were introduced thereto, and the result was stirred for 7 hours under reflux. After the reaction was completed, methylene chloride (MC) was introduced to the reaction solution for dissolution, and the result was extracted with distilled water. After drying the organic layer with anhydrous MgSO₄, the solvent was removed using a rotary evaporator, and the result was purified with column chromatography using dichloromethane and hexane as a developing solvent to obtain Compound HT-689-P2 (12 g, 70%).

2) Preparation of Compound HT-689-P1

After dissolving Compound HT-689-P2 (10 g, 17.5 mmol) and bis(pinacolato)diboron (5 g, 20.98 mmol) in 1,4-dioxane (150 ml), Pd(dba)₂ (0.8 g, 0.875 mmol), Xphos (0.83 g, 1.75 mmol) and KOAc (5.15 g, 52.5 mmol) were introduced thereto, and the result was stirred for 4 hours under reflux. After the reaction was completed, methylene chloride (MC) was introduced to the reaction solution for dissolution, and the result was extracted with distilled water. After drying the organic layer with anhydrous $MgSO_4$, the solvent was removed using a rotary evaporator, and the result was purified with column chromatography using dichloromethane and hexane as a developing solvent to obtain Compound HT-689-P1 (10 g, 86%).

3) Preparation of Compound HT-689

After dissolving Compound HT-689-P1 (10 g, 15.07 mmol) and N-(4-bromophenyl)-N-phenyl-[1,1'-biphenyl]-4-amine (7.2 g, 18.08 mmol) in toluene (100 ml), ethanol (20 ml) and $H_2O$ (20 ml), $Pd(PPh_3)_4$ (1.37 g, 1.19 mmol) and $K_3PO_4$ (9.6 g, 45.21 mmol) were introduced thereto, and the result was stirred for 6 hours under reflux. After the reaction was completed, methylene chloride (MC) was introduced to the reaction solution for dissolution, and the result was extracted with distilled water. After drying the organic layer with anhydrous $MgSO_4$, the solvent was removed using a rotary evaporator, and the result was purified with column chromatography using dichloromethane and hexane as a developing solvent to obtain Compound HT-689 (12 g, 93%).

4) Preparation of Target Compound E

Target Compound E was prepared in the same manner as in Preparation Example 4 except that Compound A of the following Table 3 was used instead of di([1,1'-biphenyl]-4-yl)amine, and Compound B of the following Table 3 was used instead of N-(4-bromophenyl)-N-phenyl-[1,1'-biphenyl]-4-amine.

Chemical formulae of Compounds A and B used for preparing target Compound E, and compound number, chemical formula and yield of the prepared target Compound E are summarized in the following Table 3.

TABLE 3
| Compound Number | Compound A | Compound B | Target compound | Yield |
|---|---|---|---|---|
| HT-691 | 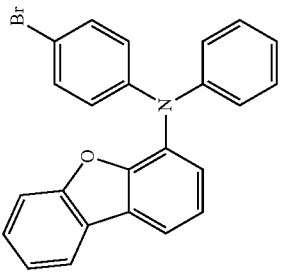 | 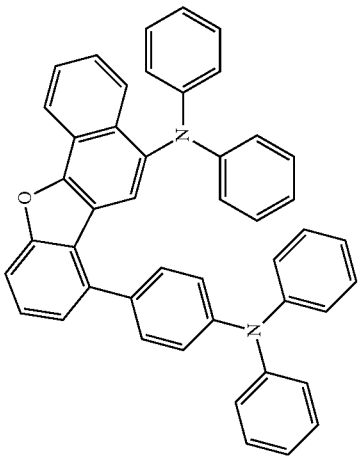 | 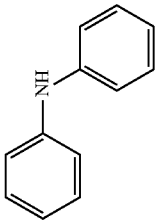 | 75% |
| HT-692 | 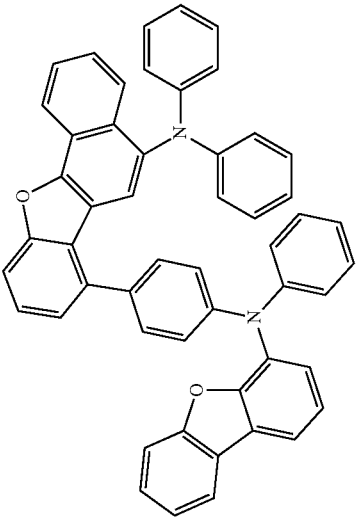 | 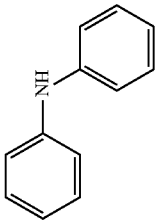 | 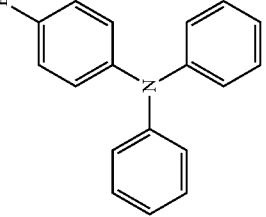 | 73% |

TABLE 3-continued

| Compound Number | Compound A | Compound B | Target compound | Yield |
|---|---|---|---|---|
| HT-694 | | | | 64% |
| HT-695 | | | | 75% |

TABLE 3-continued
| Compound Number | Compound A | Compound B | Target compound | Yield |
|---|---|---|---|---|
| HT-698 | 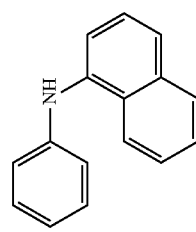 | 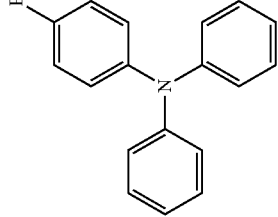 | 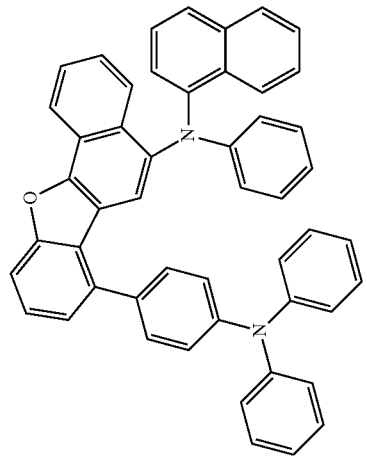 | 69% |
| HT-699 | 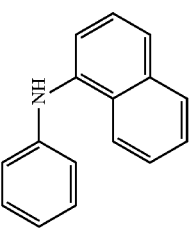 | 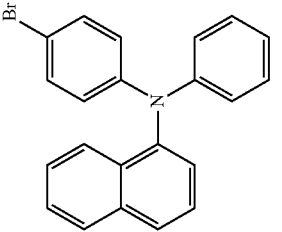 | 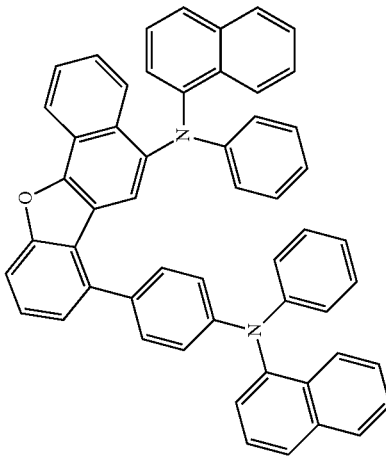 | 79% |

TABLE 3-continued
| Compound Number | Compound A | Compound B | Target compound | Yield |
|---|---|---|---|---|
| HT-701 | 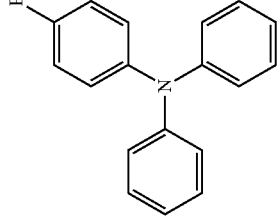 | 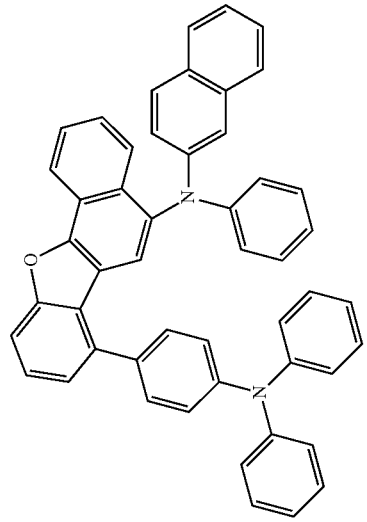 | 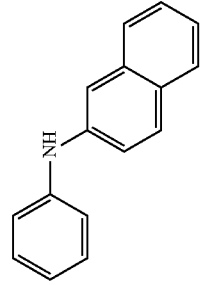 | 62% |
| HT-702 | 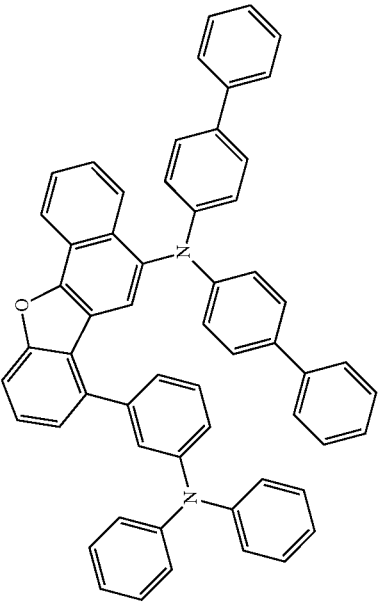 | 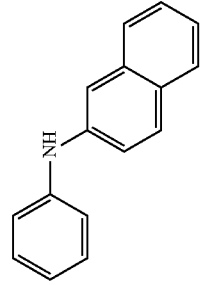 | 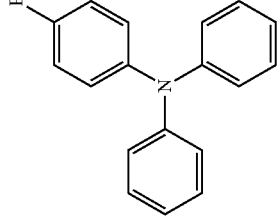 | 80% |

TABLE 3-continued
| Compound Number | Compound A | Compound B | Target compound | Yield |
|---|---|---|---|---|
| HT-709 | 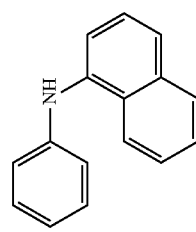 | 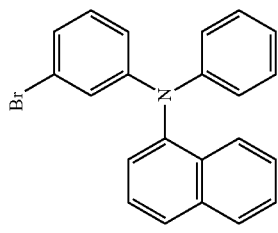 | 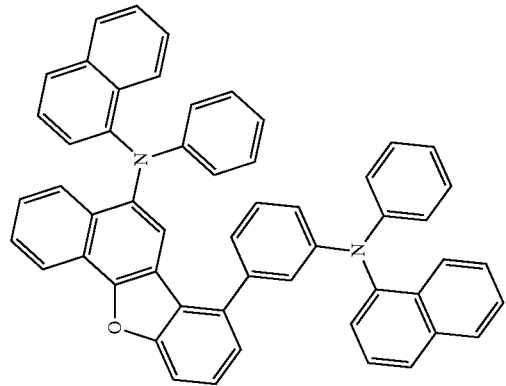 | 81% |
| HT-711 | 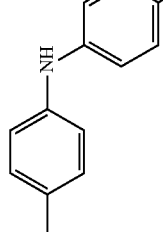 | 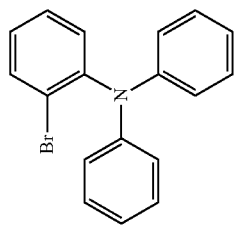 | 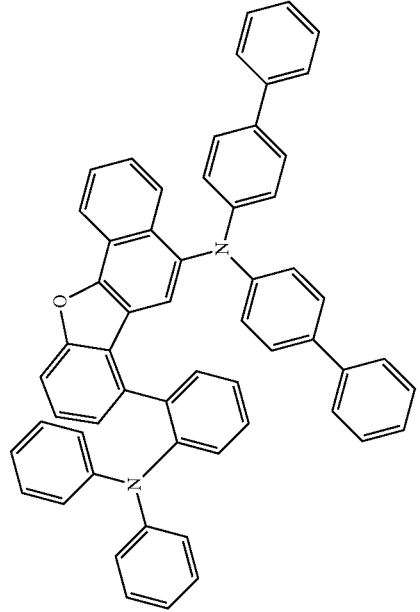 | 76% |

TABLE 3-continued

| Compound Number | Compound A | Compound B | Target compound | Yield |
|---|---|---|---|---|
| HT-714 | | | | 77% |
| HT-717 | | | | 69% |
| HT-719 | | | | 65% |

Compounds described in the present specification were prepared in the same manner as in the above-described preparation examples, and in order to identify synthesis identification results of the prepared compounds, $^1$H NMR (CDCl$_3$, 200 Mz) and FD-mass spectrometry (FD-MS: field desorption mass spectrometry) were measured, and the measured values are shown in the following Table 4 and Table 5. The following Table 4 shows $^1$H NMR (CDCl$_3$, 200 Mz) measurement values of some of the prepared compounds, and the following Table 5 shows FD-mass spectrometry (FD-MS: field desorption mass spectrometry) measurement values of the prepared compounds.

As for the compound numbers in the following Tables 4 and 5, HT- is not included. For example, when the compound number is HT-1, the compound number is described as 1 in the following Tables 4 and 5.

TABLE 4

| Compound | $^1$H NMR(CDCl$_3$, 200 Mz) |
|---|---|
| 9 | δ = 8.55(1H, d), 8.18(1H, d), 8.07-8.02(2H, m), 7.79(2H, d), 7.71(1H, s), 7.57-7.41(16H, m), 7.13(1H, t), 7.02-6.98(2H, m), 6.69(2H, d), 6.33(1H, d) |
| 15 | δ = 8.55(1H, d), 8.18(1H, d), 7.79(2H, d), 7.71(1H, s), 7.55-7.41(12H, m), 7.25-7.23(7H, m), 7.02(1H, d), 6.81(1H, t), 6.69-6.63(4H, dd)6.33(1H, d) |
| 24 | δ = 8.55(1H, d), 8.18(1H, d), 7.79(2H, d), 7.55-7.41(19H, m), 7.13(1H, t), 7.02(1H, d), 6.69(4H, d), 6.33(1H, d) |
| 32 | δ = 8.55(1H, d), 8.18(1H, d), 7.87(1H, d), 7.79(2H, d), 7.71(1H, s), 7.62-7.38(15H, m), 7.28(1H, t), 7.13(1H, t), 7.02(1H, d), 6.75(1H, s), 6.69(2H, d), 6.58(1H, d), 6.33(1H, d), 1.72(6H, s) |
| 34 | δ = 8.55(1H, d), 8.18(1H, d), 7.87(1H, d), 7.79(2H, d), 7.71(1H, s), 7.55-7.38(12H, m), 7.28(1H, t), 7.16-7.02(5H, m), 6.87(1H, t), 6.75(1H, s), 6.69(1H, d), 6.58(1H, d), 6.33(1H, d), 1.72(6H, s) |
| 35 | δ = 8.55(1H, d), 8.18(1H, d), 7.87(1H, d), 7.79(2H, d), 7.62-7.26(22H, m), 7.13-7.02(6H, m), 6.75(1H, s), 6.69(2H, d), 6.58(1H, d), 6.33(1H, d) |
| 37 | δ = 8.55(1H, d), 8.18(1H, d), 7.87(1H, d), 7.79(2H, d), 7.71(1H, s), 7.62-7.02(28H, m), 6.87(1H, t), 6.75(1H, s), 6.69(1H, d), 6.58(1H, d), 6.33(1H, d) |
| 38 | δ = 8.55(1H, d), 8.18(1H, d), 7.87(1H, d), 7.79-7.71(4H, m), 7.55-7.02(24H, m), 6.69(2H, d), 6.55(1H, s), 6.39-6.33(2H, dd) |
| 41 | δ = 8.55(1H, d), 8.18(1H, d), 7.87-7.71(6H, m), 7.55-7.13(22H, m), 7.03-7.02(2H, m), 6.91(1H, d), 6.69(1H, d), 6.58(1H, d), 6.33(1H, d) |
| 44 | δ = 8.55(1H, d), 8.18(1H, d), 7.87(2H, d), 7.79(2H, d), 7.71(1H, s), 7.62-7.51(8H, m), 7.41-7.38(3H, m), 7.28(2H, t), 7.13(1H, t), 7.02(1H, d), 6.75(2H, ss), 6.58(2H, d), 6.33(1H, d), 1.72(12H, s) |
| 50 | δ = 8.55(1H, d), 8.18(1H, d), 7.89-7.79(5H, m), 7.71-7.32(19H, m), 7.13(1H, t), 7.02(1H, d), 6.69(4H, d), 6.33(1H, d) |
| 64 | δ = 8.55(2H, d), 8.42(1H, d), 8.18(1H, d), 8.08-8.04(2H, m), 7.88-7.71(5H, m), 7.55-7.36(15H, m), 7.13(1H, t), 7.02(1H, d), 6.69(2H, d), 6.33(1H, d) |
| 69 | δ = 8.55(2H, d), 8.42(1H, d), 8.18(1H, d), 8.08-8.04(2H, m), 7.71(1H, s), 7.61-7.41(11H, m), 7.25-7.02(9H, m), 6.87-6.81(2H, m), 6.69-6.63(3H, dd), 6.33(1H, d) |
| 76 | δ = 8.55(2H, d), 8.42(1H, d), 8.18(1H, d), 8.08-8.04(2H, m), 7.71(1H, s), 7.61-7.41(19H, m), 7.13(1H, t), 7.02(1H, d), 6.69(4H, d), 6.33(1H, d) |
| 78 | δ = 8.55(2H, d), 8.42(1H, d), 8.18(1H, d), 8.08-8.04(2H, m), 7.71(1H, s), 7.61-7.41(16H, m), 7.16-7.02(5H, m), 6.87(1H, t), 6.69(4H, d), 6.33(1H, d) |
| 79 | δ = 8.55(2H, d), 8.42(1H, d), 8.18(1H, d), 8.08-8.04(2H, m), 7.71(1H, s), 7.61-7.41(19H, m), 7.25(4H, d), 7.13(1H, t), 7.02(1H, d), 6.69(4H, d), 6.33(1H, d) |
| 84 | δ = 8.55(2H, d), 8.42(1H, d), 8.18(1H, d), 8.08-8.04(2H, m), 7.87(1H, d), 7.71(1H, s), 7.61-7.41 (15H, m), 7.28(1H, t), 7.13(1H, t), 7.02(1H, d), 6.75(1H, s), 6.69(2H, d), 6.58(1H, d), 6.33(1H, d), 1.72(6H, s) |
| 85 | δ = 8.55(2H, d), 8.42(1H, d), 8.18(1H, d), 8.08-8.04(2H, m), 7.87(1H, d), 7.71(1H, s), 7.62-7.38(13H, m), 7.28(1H, t), 7.13(1H, t), 7.02(1H, d), 6.89-6.88(2H, m), 6.75(1H, s), 6.59(2H, d), 6.33(1H, d), 1.72(6H, s) |
| 87 | δ = 8.55(2H, d), 8.42(1H, d), 8.18(1H, d), 8.08-8.04(2H, m), 7.87(1H, d), 7.71(1H, s), 7.62-7.26(22H, m), 7.13-7.02(6H, m), 6.75-6.69(3H, m), 6.58(1H, d), 6.33(1H, d) |
| 90 | δ = 8.55(2H, d), 8.42(1H, d), 8.18(1H, d), 8.08-8.04(2H, m), 7.87(2H, d), 7.75-7.71(2H, m), 7.61-7.13(23H, m), 7.02(1H, d), 6.69(2H, d), 6.55(1H, d), 6.33(2H, dd) |
| 96 | δ = 8.55(2H, d), 8.42(1H, d), 8.18(1H, d), 8.08-8.04(2H, m), 7.87(2H, d), 7.71(1H, s), 7.62-7.55(9H, m), 7.38(2H, t), 7.28(2H, t), 7.13(1H, t), 7.02(1H, d), 6.75(2H, s), 6.58(2H, d), 6.33(1H, d), 1.72(12H, s) |
| 128 | δ = 8.55(1H, d), 8.18(1H, d), 8.00-7.92(3H, dd), 7.73-7.71(2H, t), 7.59-7.41(19H, m), 7.13(1H, t), 7.02(1H, d), 6.69(4H, d), 6.33(1H, d) |
| 129 | δ = 8.55(1H, d), 8.18(1H, d), 8.00-7.92(3H, dd), 7.73-7.71(2H, t), 7.59-7.41(18H, m), 7.13(1H, t), 7.02(1H, d), 6.88(2H, d), 6.69(2H, d), 6.59(1H, d), 6.33(1H, d) |
| 136 | δ = 8.55(1H, d), 8.18(1H, d), 8.00-7.92(3H, dd), 7.73-7.71(2H, t), 7.62-7.38(15H, m), 7.28(1H, t), 7.13(1H, t), 7.02(1H, d), 6.69-6.63(3H, m), 6.58(1H, t), 6.33(1H, d), 1.72(6H, s) |
| 137 | δ = 8.55(1H, d), 8.18(1H, d), 8.00-7.87(4H, m), 7.73-7.71 (2H, t), 7.59-7.38(14H, m), 7.28(1H, t), 7.13(1H, t), 7.02(1H, d), 6.89-6.88(2H, m), 6.75(1H, s), 6.59(2H, d), 6.33(1H, d), 1.72(6H, s) |
| 139 | δ = 8.55(1H, d), 8.18(1H, d), 8.00-7.87(4H, m), 7.73-7.71(2H, t), 7.59-7.26(22H, m), 7.13-7.11 (3H, m), 7.02(1H, d), 6.75-6.69(3H, m), 6.58(1H, d), 6.33(1H, d) |
| 162 | δ = 8.55(1H, d), 8.18(1H, d), 7.71(1H, s), 7.55-7.41(14H, m), 7.25-7.02(8H, m), 6.81(1H, t), 6.69-6.63(4H, m), 6.33(1H, d) |
| 171 | δ = 8.55(1H, d), 8.18(1H, d), 7.71(1H, s), 7.55-7.41(14H, m), 7.25-7.02(12H, m), 6.81(1H, t), 6.69-6.63(4H, m), 6.33(1H, d) |
| 176 | δ = 8.55(1H, d), 8.18(1H, d), 8.07-8.02(2H, dd), 7.71(1H, s), 7.57-7.41(17H, m), 7.25(8H, d), 7.16-7.02(3H, m), 6.87(1H, t), 6.69(1H, d), 6.33(1H, d) |
| 180 | δ = 8.55(1H, d), 8.18(1H, d), 7.71(1H, s), 7.55-7.41(21H, m), 7.25(4H, d), 7.13(1H, t), 7.02(1H, d), 6.69(4H, d), 6.33(1H, d) |
| 181 | δ = 8.55(1H, d), 8.18(1H, d), 7.71(1H, s), 7.55-7.41(20H, m), 7.25(4H, d), 7.13(1H, t), 7.02(1H, d), 6.89-6.88(2H, m), 6.59(1H, d), 6.33(1H, d) |

TABLE 4-continued

| Compound | ¹H NMR(CDCl₃, 200 Mz) |
|---|---|
| 188 | δ = 8.55(1H, d), 8.18(1H, d), 7.87(1H, d), 7.71(1H, s), 7.62-7.41(17H, m), 7.28-7.25(5H, m), 7.13(1H, t), 7.02(1H, d), 6.75-6.69(3H, m), 6.58(1H, d), 6.33(1H, d), 1.72(6H, s) |
| 189 | δ = 8.55(1H, d), 8.18(1H, d), 7.87(1H, d), 7.71(1H, s), 7.62-7.41(16H, m), 7.28-7.25(5H, m), 7.13(1H, t), 7.02(1H, d), 6.89-6.88(2H, m), 6.75(1H, s), 6.59-6.58(2H, dd), 6.33(1H, d), 1.72(6H, s) |
| 191 | δ = 8.55(1H, d), 8.18(1H, d), 7.87(1H, d), 7.71(1H, s), 7.62-7.02(32H, m), 6.69-6.75(3H, t), 6.58(1H, d), 6.33(1H, d) |
| 194 | δ = 8.55(1H, d), 8.18(1H, d), 7.87(2H, d), 7.75-7.71(2H, t), 7.55-7.02(30H, m), 6.69(2H, d), 6.55(1H, s), 6.39-6.33(2H, t) |
| 197 | δ = 8.55(1H, d), 8.18(1H, d), 7.87(1H, d), 7.75-7.71(3H, t), 7.55-6.91(31H, m), 6.69(2H, d), 6.58(1H, d), 6.33(1H, d) |
| 232 | δ = 8.55(1H, d), 8.18(1H, d), 7.71-7.70(2H, s), 7.57-7.41(24H, m), 7.13(1H, t), 7.02(1H, d), 6.69(4H, d), 6.33(1H, d) |
| 235 | δ = 8.55(1H, d), 8.18(1H, d), 7.71-7.70(2H, s), 7.57-7.41(24H, m), 7.25(4H, d), 7.13(1H, t), 7.02(1H, d), 6.69(4H, d), 6.33(1H, d) |
| 240 | δ = 8.55(1H, d), 8.18(1H, d), 7.87(1H, d), 7.71-7.70(2H, s), 7.62-7.38(20H, m), 7.28(1H, t), 7.13(1H, t), 7.02(1H, d), 6.75(1H, s), 6.69(2H, d), 6.58(1H, d), 6.33(1H, d), 1.72(6H, s) |
| 241 | δ = 8.55(1H, d), 8.18(1H, d), 7.87(1H, d), 7.71-7.70(2H, s), 7.62-7.38(19H, m), 7.28(1H, t), 7.13(1H, t), 7.02(1H, d), 6.89-6.88(2H, m), 6.75(1H, s), 6.59-6.58(2H, dd), 6.33(1H, d), 1.72(6H, s) |
| 242 | δ = 8.55(1H, d), 8.18(1H, d), 7.87(1H, d), 7.71-7.70(2H, s), 7.62-7.38(17H, m), 7.28(1H, t), 7.16-7.02(5H, m), 6.87(1H, t), 6.75(1H, s), 6.69(1H, d), 6.58(1H, d), 6.33(1H, d), 1.72(6H, s) |
| 246 | δ = 8.55(1H, d), 8.18(1H, d), 7.87(2H, d), 7.75-7.71(3H, m), 7.57-7.13(28H, m), 7.02(1H, d), 6.69(2H, d), 6.55(1H, s), 6.39-6.58(2H, dd) |
| 285 | δ = 8.55(1H, d), 8.18(1H, d), 7.79-7.71(5H, m), 7.55-7.41(20H, m), 7.13(1H, t), 7.02(1H, d), 6.89-6.88(2H, m), 6.69(2H, d), 6.59(1H, d), 6.33(1H, d) |
| 292 | δ = 8.55(1H, d), 8.18(1H, d), 7.87-7.79(5H, m), 7.71(H, s), 7.55-7.28(18H, m), 7.13(1H, t), 7.02(1H, d), 6.75-6.69(3H, t), 6.58(1H, d), 6.33(1H, d), 1.72(6H, s) |
| 294 | δ = 8.55(1H, d), 8.18(1H, d), 7.87-7.79(5H, m), 7.71(H, s), 7.62-7.28(15H, m), 7.16-7.02(5H, m), 6.87(1H, t), 6.75(1H, s), 6.69(1H, d), 6.58(1H, d), 6.33(1H, d), 1.72(6H, s) |
| 295 | δ = 8.55(1H, d), 8.18(1H, d), 7.87-7.79(5H, m), 7.71(H, s), 7.62-7.02(30H, m), 6.69-6.75(3H, t), 6.58(1H, d), 6.33(1H, d) |
| 336 | δ = 8.18(1H, d), 8.09(1H, d), 7.79-7.41(25H, m), 6.69(4H, d) |
| 344 | δ = 8.18(1H, d), 8.09(1H, d), 7.87-7.28(23H, m), 6.75(1H, s), 6.69(2H, d), 6.58(1H, d), 1.72(6H, s) |
| 346 | δ = 8.18(1H, d), 8.09(1H, d), 7.87-7.28(20H, m), 7.16-7.08(3H, m), 6.87(1H, t), 6.75(1H, s), 6.69(1H, d), 6.58(1H, d), 1.72(6H, s) |
| 388 | δ = 8.55(1H, d), 8.42(1H, d), 8.18(1H, d), 8.08-8.04(3H, m), 7.75-7.41(21H, m), 6.69(4H, d) |
| 396 | δ = 8.55(1H, d), 8.42(1H, d), 8.18(1H, d), 8.08-8.04(3H, m), 7.87(1H, d), 7.75(1H, d), 7.62-7.28(19H, m), 6.75(1H, s), 6.69(1H, d), 6.58(1H, d), 1.72(6H, s) |
| 398 | δ = 8.55(1H, d), 8.42(1H, d), 8.18(1H, d), 8.08-8.04(3H, m), 7.87(1H, d), 7.75(1H, d), 7.61-7.08(19H, m), 6.87(1H, t), 6.75(1H, s), 6.69(1H, d), 6.58(1H, d), 1.72(6H, s) |
| 402 | δ = 8.55(1H, d), 8.42(1H, d), 8.18(1H, d), 8.08-8.04(3H, m), 7.87(2H, d), 7.75-7.16(27H, m), 6.69(2H, d), 6.55(1H, s), 6.39(1H, d) |
| 405 | δ = 8.55(1H, d), 8.42(1H, d), 8.18(1H, d), 8.08-8.04(3H, m), 7.87(1H, d), 7.75-6.91(30H, m), 6.69(2H, d), 6.58(1H, d), |
| 440 | δ = 8.18(1H, d), 8.09(1H, d), 8.00(2H, d), 7.92(1H, d), 7.75-7.41(24H, m), 6.69(4H, d) |
| 443 | δ = 8.18(1H, d), 8.09(1H, d), 8.00(2H, d), 7.92(1H, d), 7.75-7.41(24H, m), 7.25(4H, d), 6.69(4H, d) |
| 448 | δ = 8.18(1H, d), 8.09(1H, d), 8.00(2H, d), 7.92(1H, d), 7.87(1H, d), 7.73-7.28(21H, m), 6.75(1H, s), 6.69(2H, d), 6.58(1H, d), 1.72(6H, s) |
| 450 | δ = 8.18(1H, d), 8.09(1H, d), 8.00(2H, d), 7.92(1H, d), 7.87(1H, d), 7.73-7.28(18H, m), 7.16-7.08(3H, m), 6.87(1H, t), 6.75(1H, s), 6.69(1H, d), 6.58(1H, d), 1.72(6H, s) |
| 457 | δ = 8.18(1H, d), 8.09(1H, d), 8.00(2H, d), 7.92(1H, d), 7.87(1H, d), 7.73-6.91(30H, m), 6.69(2H, d), 6.58(1H, d) |
| 460 | δ = 8.18(1H, d), 8.09(1H, d), 8.00(2H, d), 7.92(1H, d), 7.87(1H, d), 7.75-7.28(17H, m), 6.75(2H, s), 6.58(2H, d), 1.72(12H, s) |
| 492 | δ = 8.18(1H, d), 8.09(1H, d), 7.75(1H, d), 7.68(1H, s), 7.61-7.41(22H, m), 7.25(4H, d), 6.69(4H, d) |
| 494 | δ = 8.18(1H, d), 8.08(1H, d), 7.75(1H, d), 7.68(1H, s), 7.62-7.41(20H, m), 7.25(4H, d), 7.16-7.08(3H, m), 6.87(1H, t), 6.69(3H, d) |
| 501 | δ = 8.18(1H, d), 8.08(1H, d), 7.87(1H, d), 7.75-7.25(26H, m), 6.75(1H, s), 6.69(2H, d), 6.58(1H, d), 1.72(6H, s) |
| 503 | δ = 8.18(1H, d), 8.08(1H, d), 7.87(1H, d), 7.75(1H, d), 7.62-7.08(25H, m), 6.87(1H, t), 6.75(1H, s), 6.69(1H, d), 6.58(1H, d), 1.72(6H, s) |
| 507 | δ = 8.18(1H, d), 8.08(1H, d), 7.87(2H, d), 7.75(2H, d), 7.68(1H, s), 7.62-7.16(30H, m), 6.69(2H, d), 6.55(1H, s), 6.39(1H, d), |
| 545 | δ = 8.18(1H, d), 8.08(1H, d), 7.75-7.41(29H, m), 6.69(4H, d) |
| 553 | δ = 8.18(1H, d), 8.08(1H, d), 7.87(2H, d), 7.75-7.28(26H, m), 6.75(1H, s), 6.69(2H, d), 6.58(1H, d), 1.72(6H, s) |
| 555 | δ = 8.18(1H, d), 8.08(1H, d), 7.87(1H, d), 7.75-7.08(25H, m), 6.87(1H, t), 6.75(1H, s), 6.69(1H, d), 6.58(1H, d), 1.72(6H, s) |
| 597 | δ = 8.18(1H, d), 8.08(1H, d), 7.85-7.41(29H, m), 6.69(4H, d) |
| 605 | δ = 8.18(1H, d), 8.08(1H, d), 7.87-7.28(27H, m), 6.75(1H, s), 6.69(2H, d), 6.58(1H, d), 1.72(6H, s) |
| 607 | δ = 8.18(1H, d), 8.08(1H, d), 7.87-7.08(26H, m), 6.87(1H, t), 6.75(1H, s), 6.69(1H, d), 6.58(1H, d), 1.72(6H, s) |

TABLE 4-continued

| Compound | ¹H NMR(CDCl₃, 200 Mz) |
|---|---|
| 611 | δ = 8.18(1H, d), 8.08(1H, d), 7.87-7.16(35H, m), 6.69(2H, d), 6.55(1H, s), 6.39(1H, d) |
| 627 | δ = 8.55(1H, d), 8.18(1H, d), 8.07-8.02(4H, m), 7.79-7.71(4H, m), 7.62-7.41(17H, m), 6.98(2H, d), 6.69(2H, d) |
| 630 | δ = 8.55(1H, d), 8.18(1H, d), 8.07-8.02(2H, m), 7.79-7.71 (4H, m), 7.62-7.41(20H, m), 6.98(1H, d), 6.69(4H, d) |
| 632 | δ = 8.55(1H, d), 8.18(1H, d), 7.79-7.71(4H, m), 7.62-7.41(15H, m), 7.25-7.20(6H, m), 6.89-6.63(8H, m) |
| 635 | δ = 8.55(1H, d), 8.18(1H, d), 7.87(1H, d), 7.79-7.71(4H, m), 7.62-7.28(20H, m), 6.75(1H, s), 6.69(4H, d), 6.58(1H, d), 1.72(6H, s) |
| 637 | δ = 8.55(1H, d), 8.18(1H, d), 7.87(2H, d), 7.79-7.71(5H, m), 7.62-7.16(25H, m), 6.89-6.88(2H, m), 6.69(2H, d), 6.59-6.55(2H, m), 6.39(1H, d) |
| 639 | δ = 8.55(2H, d), 8.42(1H, d), 8.18(1H, d), 8.08-8.04(2H, m), 7.75-7.41(15H, m), 7.20-7.08(5H, m), 6.87-6.81(2H, m), 6.69-6.63(5H, m) |
| 641 | δ = 8.55(2H, d), 8.42(1H, d), 8.18(1H, d), 8.08-8.04(2H, m), 7.75-7.41(25H, m), 6.69(4H, d) |
| 643 | δ = 8.55(2H, d), 8.42(1H, d), 8.18(1H, d), 8.08-8.04(2H, m), 7.87-(1H, d), 7.75-7.28(22H, m), 6.75(1H, s), 6.69(4H, d), 6.58(1H, d), 1.72(6H, s) |
| 645 | δ = 8.55(1H, d), 8.18(1H, d), 8.00(2H, d), 7.92(1H, d), 7.75-7.41(26H, m), 6.69(4H, d) |
| 648 | δ = 8.55(1H, d), 8.18(1H, d), 8.07-8.02(2H, m), 7.75-7.20(21H, m), 6.98(1H, d), 6.81 (1H, t), 6.69(2H, d), 6.63(2H, d) |
| 653 | δ = 8.55(1H, d), 8.18(1H, d), 7.87(1H, d), 7.75-7.71(2H, dd), 7.62-7.11(36H, m), 6.75(1H, s), 6.69(4H, d), 6.58(1H, d) |
| 656 | δ = 8.55(1H, d), 8.18(1H, d), 7.87(1H, d), 7.75-7.11(37H, m), 6.89(1H, s), 6.88(1H, d) 6.75(1H, s), 6.69(2H, d), 6.59(1H, d), 6.58(1H, d) |
| 661 | δ = 8.97(1H, d), 8.18(1H, d), 7.75-7.90(8H, m), 7.11-7.64(21H, m), 7.16(1H, s) 6.91 (1H, s), |
| 680 | δ = 8.97(1H, d), 8.18(1H, d), 7.37-7.82(33H, m) |
| 689 | δ = 8.18(1H, d), 8.08(1H, d), 7.75-7.41(29H, m), 7.20(2H, t), 6.81(1H, t), 6.69-6.63(10H, m) |
| 691 | δ = 8.18(1H, d), 8.08(1H, d), 7.75(1H, d), 7.68(1H, s), 7.62-7.44(6H, m), 7.20(6H, t), 6.69-6.63(10H, m) |
| 692 | δ = 8.18(1H, d), 8.08(1H, d), 7.89(1H, d), 7.75(1H, d), 7.68-7.54(7H, m), 7.44-7.20(10H, m), 7.07(1H, t), 6.81(3H, t), 6.69-6.63(8H, m), 6.39(1H, d) |
| 694 | δ = 8.18(1H, d), 8.08(1H, d), 7.87(1H, d), 7.75(1H, d), 7.68(1H, s), 7.62-7.20(26H, m), 6.81-6.63(11H, m), 1.72(6H, s) |
| 695 | δ = 8.18(1H, d), 8.08-8.02(3H, m), 7.87(1H, d), 7.75(1H, d), 7.68(1H, s), 7.62-7.20(23H, m), 6.98(1H, d), 6.81-6.58(9H, m), 1.72(6H, s) |
| 698 | δ = 8.18(1H, d), 8.08-8.02(3H, m), 7.75(1H, d), 7.68(1H, s), 7.62-7.20(16H, m), 6.98(1H, d), 6.81(3H,t), 6.69-6.63(8H, m) |
| 699 | δ = 8.18(1H, d), 8.08-8.02(5H, m), 7.75(1H, d), 7.68(1H, s), 7.62-7.20(18H, m), 6.98(2H, d), 6.81(2H,t), 6.69-6.63(6H, m) |
| 701 | δ = 8.18(1H, d), 8.08(1H, d), 7.88-7.36(14H, m), 7.20(6H, t), 6.81 (3H, t), 6.69-6.63(8H, m) |
| 702 | δ = 8.18(1H, d), 8.08(1H, d), 7.75(1H, d), 7.68(1H, s), 7.62-7.20(21H, m), 6.89-6.63(13H, m) |
| 709 | δ = 8.18(1H, d), 8.08-8.02(5H, m), 7.75(1H, d), 7.68(1H, s), 7.62-7.20(17H, m), 6.98(2H, d), 6.89-6.81(4H, m), 6.63(4H, m) |
| 711 | δ = 8.18(1H, d), 8.08(1H, d), 7.75-7.41(21H, m), 7.20-7.16(5H, m), 6.87-6.63(12H, m) |
| 714 | δ = 8.18(1H, d), 8.08(1H, d), 7.75-7.44(7H, m), 7.20-7.16(9H, m), 6.87-6.63(14H, m) |
| 717 | δ = 8.18(1H, d), 8.08-8.02(5H, m), 7.75-7.16(20H, m), 6.98(2H, d), 6.87-6.81 (3H, m), 6.69-6.63(5H, m) |
| 719 | δ = 8.18(1H, d), 8.08(1H, d), 7.88-7.20(21H, m), 6.87-6.81(5H, m), 6.69-6.63(7H, m) |

TABLE 5

| Compound | FD-MS | Compound | FD-MS |
|---|---|---|---|
| 1 | m/z = 461.55 (C34H23NO = 461.18) | 2 | m/z = 511.61 (C38H25NO = 511.19) |
| 3 | m/z = 511.61 (C38H25NO = 511.19) | 4 | m/z = 561.67 (C42H27NO = 561.21) |
| 5 | m/z = 561.67 (C42H27NO = 561.21) | 6 | m/z = 537.65 (C40H27NO = 537.21) |
| 7 | m/z = 537.65 (C40H27NO = 537.21) | 8 | m/z = 537.65 (C40H27NO = 537.21) |
| 9 | m/z = 587.71 (C44H29NO = 587.22) | 10 | m/z = 587.71 (C44H29NO = 587.22) |
| 11 | m/z = 587.71 (C44H29NO = 587.22) | 12 | m/z = 587.71 (C44H29NO = 587.22) |
| 13 | m/z = 587.71 (C44H29NO = 587.22) | 14 | m/z = 587.71 (C44H29NO = 587.22) |
| 15 | m/z = 613.74 (C46H31NO = 613.24) | 16 | m/z = 613.74 (C46H31NO = 613.24) |
| 17 | m/z = 615.76 (C46H33NO = 615.26) | 18 | m/z = 663.80 (C50H33NO = 663.26) |
| 19 | m/z = 663.80 (C50H33NO = 663.26) | 20 | m/z = 663.80 (C50H33NO = 663.26) |
| 21 | m/z = 663.80 (C50H33NO = 663.26) | 22 | m/z = 663.80 (C50H33NO = 663.26) |
| 23 | m/z = 663.80 (C50H33NO = 663.26) | 24 | m/z = 613.74 (C46H31NO = 613.24) |
| 25 | m/z = 613.74 (C46H31NO = 613.24) | 26 | m/z = 613.74 (C46H31NO = 613.24) |
| 27 | m/z = 689.84 (C52H35NO = 689.27) | 28 | m/z = 689.84 (C52H35NO = 689.27) |
| 29 | m/z = 689.84 (C52H35NO = 689.27) | 30 | m/z = 689.84 (C52H35NO = 689.27) |
| 31 | m/z = 689.84 (C52H35NO = 689.27) | 32 | m/z = 653.81 (C49H35NO = 653.27) |
| 33 | m/z = 653.81 (C49H35NO = 653.27) | 34 | m/z = 653.81 (C49H35NO = 653.27) |
| 35 | m/z = 777.95 (C59H39NO = 777.30) | 36 | m/z = 777.95 (C59H39NO = 777.30) |
| 37 | m/z = 777.95 (C59H39NO = 777.30) | 38 | m/z = 775.93 (C59H37NO = 775.29) |
| 39 | m/z = 775.93 (C59H37NO = 775.29) | 40 | m/z = 775.93 (C59H37NO = 775.29) |
| 41 | m/z = 775.93 (C59H37NO = 775.29) | 42 | m/z = 775.93 (C59H37NO = 775.29) |
| 43 | m/z = 775.93 (C59H37NO = 775.29) | 44 | m/z = 693.87 (C52H39NO = 693.30) |
| 45 | m/z = 942.15 (C72H47NO = 941.37) | 46 | m/z = 938.12 (C72H43NO = 937.33) |

TABLE 5-continued

| Compound | FD-MS | Compound | FD-MS |
|---|---|---|---|
| 47 | m/z = 627.73 (C46H29NO2 = 627.22) | 48 | m/z = 627.73 (C46H29NO2 = 627.22) |
| 49 | m/z = 627.73 (C46H29NO2 = 627.22) | 50 | m/z = 703.82 (C52H33NO2 = 703.25) |
| 51 | m/z = 703.82 (C52H33NO2 = 703.25) | 52 | m/z = 703.82 (C52H33NO2 = 703.25) |
| 53 | m/z = 511.62 (C38H25NO = 511.19) | 54 | m/z = 561.67 (C42H27NO = 561.21) |
| 55 | m/z = 561.67 (C42H27NO = 561.21) | 56 | m/z = 611.73 (C46H29NO = 611.22) |
| 57 | m/z = 611.73 (C46H29NO = 611.22) | 58 | m/z = 587.71 (C44H29NO = 587.22) |
| 59 | m/z = 587.71 (C44H29NO = 587.22) | 60 | m/z = 587.71 (C44H29NO = 587.22) |
| 61 | m/z = 637.77 (C48H32NO = 637.24) | 62 | m/z = 637.77 (C48H32NO = 637.24) |
| 63 | m/z = 637.77 (C48H32NO = 637.24) | 64 | m/z = 637.77 (C48H32NO = 637.24) |
| 65 | m/z = 637.77 (C48H32NO = 637.24) | 66 | m/z = 637.77 (C48H32NO = 637.24) |
| 67 | m/z = 663.80 (C50H33NO = 663.26) | 68 | m/z = 663.80 (C50H33NO = 663.26) |
| 69 | m/z = 663.80 (C50H33NO = 663.26) | 70 | m/z = 713.86 (C54H35NO = 713.27) |
| 71 | m/z = 713.86 (C54H35NO = 713.27) | 72 | m/z = 713.86 (C54H35NO = 713.27) |
| 73 | m/z = 713.86 (C54H35NO = 713.27) | 74 | m/z = 713.86 (C54H35NO = 713.27) |
| 75 | m/z = 713.86 (C54H35NO = 713.27) | 76 | m/z = 663.80 (C50H33NO = 663.26) |
| 77 | m/z = 663.80 (C50H33NO = 663.26) | 78 | m/z = 663.80 (C50H33NO = 663.26) |
| 79 | m/z = 739.90 (C56H37NO = 739.29) | 80 | m/z = 739.90 (C56H37NO = 739.29) |
| 81 | m/z = 739.90 (C56H37NO = 739.29) | 82 | m/z = 739.90 (C56H37NO = 739.29) |
| 83 | m/z = 739.90 (C56H37NO = 739.29) | 84 | m/z = 703.87 (C53H37NO = 703.29) |
| 85 | m/z = 703.87 (C53H37NO = 703.29) | 86 | m/z = 703.87 (C53H37NO = 703.29) |
| 87 | m/z = 828.01 (C63H41NO = 827.32) | 88 | m/z = 828.01 (C63H41NO = 827.32) |
| 89 | m/z = 828.01 (C63H41NO = 827.32) | 90 | m/z = 825.99 (C63H39NO = 825.30) |
| 91 | m/z = 825.99 (C63H39NO = 825.30) | 92 | m/z = 825.99 (C63H39NO = 825.30) |
| 93 | m/z = 825.99 (C63H39NO = 825.30) | 94 | m/z = 825.99 (C63H39NO = 825.30) |
| 95 | m/z = 825.99 (C63H39NO = 825.30) | 96 | m/z = 743.93 (C56H41NO = 743.32) |
| 97 | m/z = 992.21 (C76H49NO = 991.38) | 98 | m/z = 988.18 (C76H45NO = 987.35) |
| 99 | m/z = 677.79 (C50H31NO2 = 677.24) | 100 | m/z = 677.79 (C50H31NO2 = 677.24) |
| 101 | m/z = 677.79 (C50H31NO2 = 677.24) | 102 | m/z = 753.88 (C56H35NO2 = 753.27) |
| 103 | m/z = 753.88 (C56H35NO2 = 753.27) | 104 | m/z = 753.88 (C56H35NO2 = 753.27) |
| 105 | m/z = 511.62 (C38H25NO = 511.19) | 106 | m/z = 561.67 (C42H27NO = 561.21) |
| 107 | m/z = 561.67 (C42H27NO = 561.21) | 108 | m/z = 611.73 (C46H29NO = 611.22) |
| 109 | m/z = 611.73 (C46H29NO = 611.22) | 110 | m/z = 587.71 (C44H29NO = 587.22) |
| 111 | m/z = 587.71 (C44H29NO = 587.22) | 112 | m/z = 587.71 (C44H29NO = 587.22) |
| 113 | m/z = 637.77 (C48H32NO = 637.24) | 114 | m/z = 637.77 (C48H32NO = 637.24) |
| 115 | m/z = 637.77 (C48H32NO = 637.24) | 116 | m/z = 637.77 (C48H32NO = 637.24) |
| 117 | m/z = 637.77 (C48H32NO = 637.24) | 118 | m/z = 637.77 (C48H32NO = 637.24) |
| 119 | m/z = 663.80 (C50H33NO = 663.26) | 120 | m/z = 663.80 (C50H33NO = 663.26) |
| 121 | m/z = 663.80 (C50H33NO = 663.26) | 122 | m/z = 713.86 (C54H35NO = 713.27) |
| 123 | m/z = 713.86 (C54H35NO = 713.27) | 124 | m/z = 713.86 (C54H35NO = 713.27) |
| 125 | m/z = 713.86 (C54H35NO = 713.27) | 126 | m/z = 713.86 (C54H35NO = 713.27) |
| 127 | m/z = 713.86 (C54H35NO = 713.27) | 128 | m/z = 663.80 (C50H33NO = 663.26) |
| 129 | m/z = 663.80 (C50H33NO = 663.26) | 130 | m/z = 663.80 (C50H33NO = 663.26) |
| 131 | m/z = 739.90 (C56H37NO = 739.29) | 132 | m/z = 739.90 (C56H37NO = 739.29) |
| 133 | m/z = 739.90 (C56H37NO = 739.29) | 134 | m/z = 739.90 (C56H37NO = 739.29) |
| 135 | m/z = 739.90 (C56H37NO = 739.29) | 136 | m/z = 703.87 (C53H37NO = 703.29) |
| 137 | m/z = 703.87 (C53H37NO = 703.29) | 138 | m/z = 703.87 (C53H37NO = 703.29) |
| 139 | m/z = 828.01 (C63H41NO = 827.32) | 140 | m/z = 828.01 (C63H41NO = 827.32) |
| 141 | m/z = 828.01 (C63H41NO = 827.32) | 142 | m/z = 825.99 (C63H39NO = 825.30) |
| 143 | m/z = 825.99 (C63H39NO = 825.30) | 144 | m/z = 825.99 (C63H39NO = 825.30) |
| 145 | m/z = 825.99 (C63H39NO = 825.30) | 146 | m/z = 825.99 (C63H39NO = 825.30) |
| 147 | m/z = 825.99 (C63H39NO = 825.30) | 148 | m/z = 743.93 (C56H41NO = 743.32) |
| 149 | m/z = 992.21 (C76H49NO = 991.38) | 150 | m/z = 988.18 (C76H45NO = 987.35) |
| 151 | m/z = 677.79 (C50H31NO2 = 677.24) | 152 | m/z = 677.79 (C50H31NO2 = 677.24) |
| 153 | m/z = 677.79 (C50H31NO2 = 677.24) | 154 | m/z = 753.88 (C56H35NO2 = 753.27) |
| 155 | m/z = 753.88 (C56H35NO2 = 753.27) | 156 | m/z = 753.88 (C56H35NO2 = 753.27) |
| 157 | m/z = 537.65 (C40H27NO = 537.21) | 158 | m/z = 587.71 (C44H27NO = 587.22) |
| 159 | m/z = 587.71 (C44H27NO = 587.22) | 160 | m/z = 637.77 (C48H32NO = 637.24) |
| 161 | m/z = 637.77 (C48H32NO = 637.24) | 162 | m/z = 613.74 (C46H31NO = 613.24) |
| 163 | m/z = 613.74 (C46H31NO = 613.24) | 164 | m/z = 613.74 (C46H31NO = 613.24) |
| 165 | m/z = 663.80 (C50H33NO = 663.26) | 166 | m/z = 663.80 (C50H33NO = 663.26) |
| 167 | m/z = 663.80 (C50H33NO = 663.26) | 168 | m/z = 663.80 (C50H33NO = 663.26) |
| 169 | m/z = 663.80 (C50H33NO = 663.26) | 170 | m/z = 663.80 (C50H33NO = 663.26) |
| 171 | m/z = 689.84 (C52H35NO = 689.27) | 172 | m/z = 689.84 (C52H35NO = 689.27) |
| 173 | m/z = 689.84 (C52H35NO = 689.27) | 174 | m/z = 739.90 (C56H37NO = 739.29) |
| 175 | m/z = 739.90 (C56H37NO = 739.29) | 176 | m/z = 739.90 (C56H37NO = 739.29) |
| 177 | m/z = 739.90 (C56H37NO = 739.29) | 178 | m/z = 739.90 (C56H37NO = 739.29) |
| 179 | m/z = 739.90 (C56H37NO = 739.29) | 180 | m/z = 689.84 (C52H35NO = 689.27) |
| 181 | m/z = 689.84 (C52H35NO = 689.27) | 182 | m/z = 689.84 (C52H35NO = 689.27) |
| 183 | m/z = 765.94 (C58H39NO = 765.30) | 184 | m/z = 765.94 (C58H39NO = 765.30) |
| 185 | m/z = 765.94 (C58H39NO = 765.30) | 186 | m/z = 765.94 (C58H39NO = 765.30) |
| 187 | m/z = 765.94 (C58H39NO = 765.30) | 188 | m/z = 765.94 (C58H39NO = 765.30) |
| 189 | m/z = 729.90 (C5H39NO = 729.30) | 190 | m/z = 729.90 (C5H39NO = 729.30) |
| 191 | m/z = 854.04 (C65H43NO = 854.34) | 192 | m/z = 854.04 (C65H43NO = 854.34) |
| 193 | m/z = 854.04 (C65H43NO = 854.34) | 194 | m/z = 852.03 (C65H41NO = 851.32) |
| 195 | m/z = 852.03 (C65H41NO = 851.32) | 196 | m/z = 852.03 (C65H41NO = 851.32) |
| 197 | m/z = 852.03 (C65H41NO = 851.32) | 198 | m/z = 852.03 (C65H41NO = 851.32) |
| 199 | m/z = 852.03 (C65H41NO = 851.32) | 200 | m/z = 769.97 (C58H43NO = 769.33) |
| 201 | m/z = 1028.25 (C78H51NO = 1017.40) | 202 | m/z = 1014.21 (C78H47NO = 1013.37) |

TABLE 5-continued

| Compound | FD-MS | Compound | FD-MS |
|---|---|---|---|
| 203 | m/z = 703.82 (C52H33NO2 = 703.25) | 204 | m/z = 703.82 (C52H33NO2 = 703.25) |
| 205 | m/z = 703.82 (C52H33NO2 = 703.25) | 206 | m/z = 779.92 (C58H37NO2 = 779.28) |
| 207 | m/z = 779.92 (C58H37NO2 = 779.28) | 208 | m/z = 779.92 (C58H37NO2 = 779.28) |
| 209 | m/z = 537.65 (C40H27NO = 537.21) | 210 | m/z = 587.71 (C44H27NO = 587.22) |
| 211 | m/z = 587.71 (C44H27NO = 587.22) | 212 | m/z = 637.77 (C48H32NO = 637.24) |
| 213 | m/z = 637.77 (C48H32NO = 637.24) | 214 | m/z = 613.74 (C46H31NO = 613.24) |
| 215 | m/z = 613.74 (C46H31NO = 613.24) | 216 | m/z = 613.74 (C46H31NO = 613.24) |
| 217 | m/z = 663.80 (C50H33NO = 663.26) | 218 | m/z = 663.80 (C50H33NO = 663.26) |
| 219 | m/z = 663.80 (C50H33NO = 663.26) | 220 | m/z = 663.80 (C50H33NO = 663.26) |
| 221 | m/z = 663.80 (C50H33NO = 663.26) | 222 | m/z = 663.80 (C50H33NO = 663.26) |
| 223 | m/z = 689.84 (C52H35NO = 689.27) | 224 | m/z = 689.84 (C52H35NO = 689.27) |
| 225 | m/z = 689.84 (C52H35NO = 689.27) | 226 | m/z = 739.90 (C56H37NO = 739.29) |
| 227 | m/z = 739.90 (C56H37NO = 739.29) | 228 | m/z = 739.90 (C56H37NO = 739.29) |
| 229 | m/z = 739.90 (C56H37NO = 739.29) | 230 | m/z = 739.90 (C56H37NO = 739.29) |
| 231 | m/z = 739.90 (C56H37NO = 739.29) | 232 | m/z = 689.84 (C52H35NO = 689.27) |
| 233 | m/z = 689.84 (C52H35NO = 689.27) | 234 | m/z = 689.84 (C52H35NO = 689.27) |
| 235 | m/z = 765.94 (C58H39NO = 765.30) | 236 | m/z = 765.94 (C58H39NO = 765.30) |
| 237 | m/z = 765.94 (C58H39NO = 765.30) | 238 | m/z = 765.94 (C58H39NO = 765.30) |
| 239 | m/z = 765.94 (C58H39NO = 765.30) | 240 | m/z = 765.94 (C58H39NO = 765.30) |
| 241 | m/z = 729.90 (C5H39NO = 729.30) | 242 | m/z = 729.90 (C5H39NO = 729.30) |
| 243 | m/z = 854.04 (C65H43NO = 854.34) | 244 | m/z = 854.04 (C65H43NO = 854.34) |
| 245 | m/z = 854.04 (C65H43NO = 854.34) | 246 | m/z = 852.03 (C65H41NO = 851.32) |
| 247 | m/z = 852.03 (C65H41NO = 851.32) | 248 | m/z = 852.03 (C65H41NO = 851.32) |
| 249 | m/z = 852.03 (C65H41NO = 851.32) | 250 | m/z = 852.03 (C65H41NO = 851.32) |
| 251 | m/z = 852.03 (C65H41NO = 851.32) | 252 | m/z = 769.97 (C58H43NO = 769.33) |
| 253 | m/z = 1028.25 (C78H51NO = 1017.40) | 254 | m/z = 1014.21 (C78H47NO = 1013.37) |
| 255 | m/z = 703.82 (C52H33NO2 = 703.25) | 256 | m/z = 703.82 (C52H33NO2 = 703.25) |
| 257 | m/z = 703.82 (C52H33NO2 = 703.25) | 258 | m/z = 779.92 (C58H37NO2 = 779.28) |
| 259 | m/z = 779.92 (C58H37NO2 = 779.28) | 260 | m/z = 779.92 (C58H37NO2 = 779.28) |
| 261 | m/z = 537.65 (C40H27NO = 537.21) | 262 | m/z = 587.71 (C44H27NO = 587.22) |
| 263 | m/z = 587.71 (C44H27NO = 587.22) | 264 | m/z = 637.77 (C48H32NO = 637.24) |
| 265 | m/z = 637.77 (C48H32NO = 637.24) | 266 | m/z = 613.74 (C46H31NO = 613.24) |
| 267 | m/z = 613.74 (C46H31NO = 613.24) | 268 | m/z = 613.74 (C46H31NO = 613.24) |
| 269 | m/z = 663.80 (C50H33NO = 663.26) | 270 | m/z = 663.80 (C50H33NO = 663.26) |
| 271 | m/z = 663.80 (C50H33NO = 663.26) | 272 | m/z = 663.80 (C50H33NO = 663.26) |
| 273 | m/z = 663.80 (C50H33NO = 663.26) | 274 | m/z = 663.80 (C50H33NO = 663.26) |
| 275 | m/z = 689.84 (C52H35NO = 689.27) | 276 | m/z = 689.84 (C52H35NO = 689.27) |
| 277 | m/z = 689.84 (C52H35NO = 689.27) | 278 | m/z = 739.90 (C56H37NO = 739.29) |
| 279 | m/z = 739.90 (C56H37NO = 739.29) | 280 | m/z = 739.90 (C56H37NO = 739.29) |
| 281 | m/z = 739.90 (C56H37NO = 739.29) | 282 | m/z = 739.90 (C56H37NO = 739.29) |
| 283 | m/z = 739.90 (C56H37NO = 739.29) | 284 | m/z = 689.84 (C52H35NO = 689.27) |
| 285 | m/z = 689.84 (C52H35NO = 689.27) | 286 | m/z = 689.84 (C52H35NO = 689.27) |
| 287 | m/z = 765.94 (C58H39NO = 765.30) | 288 | m/z = 765.94 (C58H39NO = 765.30) |
| 289 | m/z = 765.94 (C58H39NO = 765.30) | 290 | m/z = 765.94 (C58H39NO = 765.30) |
| 291 | m/z = 765.94 (C58H39NO = 765.30) | 292 | m/z = 765.94 (C58H39NO = 765.30) |
| 293 | m/z = 729.90 (C5H39NO = 729.30) | 294 | m/z = 729.90 (C5H39NO = 729.30) |
| 295 | m/z = 854.04 (C65H43NO = 854.34) | 296 | m/z = 854.04 (C65H43NO = 854.34) |
| 297 | m/z = 854.04 (C65H43NO = 854.34) | 298 | m/z = 852.03 (C65H41NO = 851.32) |
| 299 | m/z = 852.03 (C65H41NO = 851.32) | 300 | m/z = 852.03 (C65H41NO = 851.32) |
| 301 | m/z = 852.03 (C65H41NO = 851.32) | 302 | m/z = 852.03 (C65H41NO = 851.32) |
| 303 | m/z = 852.03 (C65H41NO = 851.32) | 304 | m/z = 769.97 (C58H43NO = 769.33) |
| 305 | m/z = 1028.25 (C78H51NO = 1017.40) | 306 | m/z = 1014.21 (C78H47NO = 1013.37) |
| 307 | m/z = 703.82 (C52H33NO2 = 703.25) | 308 | m/z = 703.82 (C52H33NO2 = 703.25) |
| 309 | m/z = 703.82 (C52H33NO2 = 703.25) | 310 | m/z = 779.92 (C58H37NO2 = 779.28) |
| 311 | m/z = 779.92 (C58H37NO2 = 779.28) | 312 | m/z = 779.92 (C58H37NO2 = 779.28) |
| 313 | m/z = 461.55 (C34H23NO = 461.18) | 314 | m/z = 511.61 (C38H25NO = 511.19) |
| 315 | m/z = 511.61 (C38H25NO = 511.19) | 316 | m/z = 561.67 (C42H27NO = 561.21) |
| 317 | m/z = 561.67 (C42H27NO = 561.21) | 318 | m/z = 537.65 (C40H27NO = 537.21) |
| 319 | m/z = 537.65 (C40H27NO = 537.21) | 320 | m/z = 537.65 (C40H27NO = 537.21) |
| 321 | m/z = 587.71 (C44H29NO = 587.22) | 322 | m/z = 587.71 (C44H29NO = 587.22) |
| 323 | m/z = 587.71 (C44H29NO = 587.22) | 324 | m/z = 587.71 (C44H29NO = 587.22) |
| 325 | m/z = 587.71 (C44H29NO = 587.22) | 326 | m/z = 587.71 (C44H29NO = 587.22) |
| 327 | m/z = 613.74 (C46H31NO = 613.24) | 328 | m/z = 613.74 (C46H31NO = 613.24) |
| 329 | m/z = 615.76 (C46H33NO = 615.26) | 330 | m/z = 663.80 (C50H33NO = 663.26) |
| 331 | m/z = 663.80 (C50H33NO = 663.26) | 332 | m/z = 663.80 (C50H33NO = 663.26) |
| 333 | m/z = 663.80 (C50H33NO = 663.26) | 334 | m/z = 663.80 (C50H33NO = 663.26) |
| 335 | m/z = 663.80 (C50H33NO = 663.26) | 336 | m/z = 613.74 (C46H31NO = 613.24) |
| 337 | m/z = 613.74 (C46H31NO = 613.24) | 338 | m/z = 613.74 (C46H31NO = 613.24) |
| 339 | m/z = 689.84 (C52H35NO = 689.27) | 340 | m/z = 689.84 (C52H35NO = 689.27) |
| 341 | m/z = 689.84 (C52H35NO = 689.27) | 342 | m/z = 689.84 (C52H35NO = 689.27) |
| 343 | m/z = 689.84 (C52H35NO = 689.27) | 344 | m/z = 653.81 (C49H35NO = 653.27) |
| 345 | m/z = 653.81 (C49H35NO = 653.27) | 346 | m/z = 653.81 (C49H35NO = 653.27) |
| 347 | m/z = 777.95 (C59H39NO = 777.30) | 348 | m/z = 777.95 (C59H39NO = 777.30) |
| 349 | m/z = 777.95 (C59H39NO = 777.30) | 350 | m/z = 775.93 (C59H37NO = 775.29) |
| 351 | m/z = 775.93 (C59H37NO = 775.29) | 352 | m/z = 775.93 (C59H37NO = 775.29) |
| 353 | m/z = 775.93 (C59H37NO = 775.29) | 354 | m/z = 775.93 (C59H37NO = 775.29) |
| 355 | m/z = 775.93 (C59H37NO = 775.29) | 356 | m/z = 693.87 (C52H39NO = 693.30) |
| 357 | m/z = 942.15 (C72H47NO = 941.37) | 358 | m/z = 938.12 (C72H43NO = 937.33) |

TABLE 5-continued

| Compound | FD-MS | Compound | FD-MS |
|---|---|---|---|
| 359 | m/z = 627.73 (C46H29NO2 = 627.22) | 360 | m/z = 627.73 (C46H29NO2 = 627.22) |
| 361 | m/z = 627.73 (C46H29NO2 = 627.22) | 362 | m/z = 703.82 (C52H33NO2 = 703.25) |
| 363 | m/z = 703.82 (C52H33NO2 = 703.25) | 364 | m/z = 703.82 (C52H33NO2 = 703.25) |
| 365 | m/z = 511.62 (C38H25NO = 511.19) | 366 | m/z = 561.67 (C42H27NO = 561.21) |
| 367 | m/z = 561.67 (C42H27NO = 561.21) | 368 | m/z = 611.73 (C46H29NO = 611.22) |
| 369 | m/z = 611.73 (C46H29NO = 611.22) | 370 | m/z = 587.71 (C44H29NO = 587.22) |
| 371 | m/z = 587.71 (C44H29NO = 587.22) | 372 | m/z = 587.71 (C44H29NO = 587.22) |
| 373 | m/z = 637.77 (C48H32NO = 637.24) | 374 | m/z = 637.77 (C48H32NO = 637.24) |
| 375 | m/z = 637.77 (C48H32NO = 637.24) | 376 | m/z = 637.77 (C48H32NO = 637.24) |
| 377 | m/z = 637.77 (C48H32NO = 637.24) | 378 | m/z = 637.77 (C48H32NO = 637.24) |
| 379 | m/z = 663.80 (C50H33NO = 663.26) | 380 | m/z = 663.80 (C50H33NO = 663.26) |
| 381 | m/z = 663.80 (C50H33NO = 663.26) | 382 | m/z = 713.86 (C54H35NO = 713.27) |
| 383 | m/z = 713.86 (C54H35NO = 713.27) | 384 | m/z = 713.86 (C54H35NO = 713.27) |
| 385 | m/z = 713.86 (C54H35NO = 713.27) | 386 | m/z = 713.86 (C54H35NO = 713.27) |
| 387 | m/z = 713.86 (C54H35NO = 713.27) | 388 | m/z = 663.80 (C50H33NO = 663.26) |
| 389 | m/z = 663.80 (C50H33NO = 663.26) | 390 | m/z = 663.80 (C50H33NO = 663.26) |
| 391 | m/z = 739.90 (C56H37NO = 739.29) | 392 | m/z = 739.90 (C56H37NO = 739.29) |
| 393 | m/z = 739.90 (C56H37NO = 739.29) | 394 | m/z = 739.90 (C56H37NO = 739.29) |
| 395 | m/z = 739.90 (C56H37NO = 739.29) | 396 | m/z = 703.87 (C53H37NO = 703.29) |
| 397 | m/z = 703.87 (C53H37NO = 703.29) | 398 | m/z = 703.87 (C53H37NO = 703.29) |
| 399 | m/z = 828.01 (C63H41NO = 827.32) | 400 | m/z = 828.01 (C63H41NO = 827.32) |
| 401 | m/z = 828.01 (C63H41NO = 827.32) | 402 | m/z = 825.99 (C63H39NO = 825.30) |
| 403 | m/z = 825.99 (C63H39NO = 825.30) | 404 | m/z = 825.99 (C63H39NO = 825.30) |
| 405 | m/z = 825.99 (C63H39NO = 825.30) | 406 | m/z = 825.99 (C63H39NO = 825.30) |
| 407 | m/z = 825.99 (C63H39NO = 825.30) | 408 | m/z = 743.93 (C56H41NO = 743.32) |
| 409 | m/z = 992.21 (C76H49NO = 991.38) | 410 | m/z = 988.18 (C76H45NO = 987.35) |
| 411 | m/z = 677.79 (C50H31NO2 = 677.24) | 412 | m/z = 677.79 (C50H31NO2 = 677.24) |
| 413 | m/z = 677.79 (C50H31NO2 = 677.24) | 414 | m/z = 753.88 (C56H35NO2 = 753.27) |
| 415 | m/z = 753.88 (C56H35NO2 = 753.27) | 416 | m/z = 753.88 (C56H35NO2 = 753.27) |
| 417 | m/z = 511.62 (C38H25NO = 511.19) | 418 | m/z = 561.67 (C42H27NO = 561.21) |
| 419 | m/z = 561.67 (C42H27NO = 561.21) | 420 | m/z = 611.73 (C46H29NO = 611.22) |
| 421 | m/z = 611.73 (C46H29NO = 611.22) | 422 | m/z = 587.71 (C44H29NO = 587.22) |
| 423 | m/z = 587.71 (C44H29NO = 587.22) | 424 | m/z = 587.71 (C44H29NO = 587.22) |
| 425 | m/z = 637.77 (C48H32NO = 637.24) | 426 | m/z = 637.77 (C48H32NO = 637.24) |
| 427 | m/z = 637.77 (C48H32NO = 637.24) | 428 | m/z = 637.77 (C48H32NO = 637.24) |
| 429 | m/z = 637.77 (C48H32NO = 637.24) | 430 | m/z = 637.77 (C48H32NO = 637.24) |
| 431 | m/z = 663.80 (C50H33NO = 663.26) | 432 | m/z = 663.80 (C50H33NO = 663.26) |
| 433 | m/z = 663.80 (C50H33NO = 663.26) | 434 | m/z = 713.86 (C54H35NO = 713.27) |
| 435 | m/z = 713.86 (C54H35NO = 713.27) | 436 | m/z = 713.86 (C54H35NO = 713.27) |
| 437 | m/z = 713.86 (C54H35NO = 713.27) | 438 | m/z = 713.86 (C54H35NO = 713.27) |
| 439 | m/z = 713.86 (C54H35NO = 713.27) | 440 | m/z = 663.80 (C50H33NO = 663.26) |
| 441 | m/z = 663.80 (C50H33NO = 663.26) | 442 | m/z = 663.80 (C50H33NO = 663.26) |
| 443 | m/z = 739.90 (C56H37NO = 739.29) | 444 | m/z = 739.90 (C56H37NO = 739.29) |
| 445 | m/z = 739.90 (C56H37NO = 739.29) | 446 | m/z = 739.90 (C56H37NO = 739.29) |
| 447 | m/z = 739.90 (C56H37NO = 739.29) | 448 | m/z = 703.87 (C53H37NO = 703.29) |
| 449 | m/z = 703.87 (C53H37NO = 703.29) | 450 | m/z = 703.87 (C53H37NO = 703.29) |
| 451 | m/z = 828.01 (C63H41NO = 827.32) | 452 | m/z = 828.01 (C63H41NO = 827.32) |
| 453 | m/z = 828.01 (C63H41NO = 827.32) | 454 | m/z = 825.99 (C63H39NO = 825.30) |
| 455 | m/z = 825.99 (C63H39NO = 825.30) | 456 | m/z = 825.99 (C63H39NO = 825.30) |
| 457 | m/z = 825.99 (C63H39NO = 825.30) | 458 | m/z = 825.99 (C63H39NO = 825.30) |
| 459 | m/z = 825.99 (C63H39NO = 825.30) | 460 | m/z = 743.93 (C56H41NO = 743.32) |
| 461 | m/z = 992.21 (C76H49NO = 991.38) | 462 | m/z = 988.18 (C76H45NO = 987.35) |
| 463 | m/z = 677.79 (C50H31NO2 = 677.24) | 464 | m/z = 677.79 (C50H31NO2 = 677.24) |
| 465 | m/z = 677.79 (C50H31NO2 = 677.24) | 466 | m/z = 753.88 (C56H35NO2 = 753.27) |
| 467 | m/z = 753.88 (C56H35NO2 = 753.27) | 468 | m/z = 753.88 (C56H35NO2 = 753.27) |
| 469 | m/z = 537.65 (C40H27NO = 537.21) | 470 | m/z = 587.71 (C44H27NO = 587.22) |
| 471 | m/z = 587.71 (C44H29NO = 587.22) | 472 | m/z = 637.77 (C48H32NO = 637.24) |
| 473 | m/z = 637.77 (C48H32NO = 637.24) | 474 | m/z = 613.74 (C46H31NO = 613.24) |
| 475 | m/z = 613.74 (C46H31NO = 613.24) | 476 | m/z = 613.74 (C46H31NO = 613.24) |
| 477 | m/z = 663.80 (C50H33NO = 663.26) | 478 | m/z = 663.80 (C50H33NO = 663.26) |
| 479 | m/z = 663.80 (C50H33NO = 663.26) | 480 | m/z = 663.80 (C50H33NO = 663.26) |
| 481 | m/z = 663.80 (C50H33NO = 663.26) | 482 | m/z = 663.80 (C50H33NO = 663.26) |
| 483 | m/z = 689.84 (C52H35NO = 689.27) | 484 | m/z = 689.84 (C52H35NO = 689.27) |
| 485 | m/z = 689.84 (C52H35NO = 689.27) | 486 | m/z = 739.90 (C56H37NO = 739.29) |
| 487 | m/z = 739.90 (C56H37NO = 739.29) | 488 | m/z = 739.90 (C56H37NO = 739.29) |
| 489 | m/z = 739.90 (C56H37NO = 739.29) | 490 | m/z = 739.90 (C56H37NO = 739.29) |
| 491 | m/z = 739.90 (C56H37NO = 739.29) | 492 | m/z = 689.84 (C52H35NO = 689.27) |
| 493 | m/z = 689.84 (C52H35NO = 689.27) | 494 | m/z = 689.84 (C52H35NO = 689.27) |
| 495 | m/z = 765.94 (C58H39NO = 765.30) | 496 | m/z = 765.94 (C58H39NO = 765.30) |
| 497 | m/z = 765.94 (C58H39NO = 765.30) | 498 | m/z = 765.94 (C58H39NO = 765.30) |
| 499 | m/z = 765.94 (C58H39NO = 765.30) | 500 | m/z = 765.94 (C58H39NO = 765.30) |
| 501 | m/z = 729.90 (C5H39NO = 729.30) | 502 | m/z = 729.90 (C5H39NO = 729.30) |
| 503 | m/z = 854.04 (C65H43NO = 854.34) | 504 | m/z = 854.04 (C65H43NO = 854.34) |
| 505 | m/z = 854.04 (C65H43NO = 854.34) | 506 | m/z = 852.03 (C65H41NO = 851.32) |
| 507 | m/z = 852.03 (C65H41NO = 851.32) | 508 | m/z = 852.03 (C65H41NO = 851.32) |
| 509 | m/z = 852.03 (C65H41NO = 851.32) | 510 | m/z = 852.03 (C65H41NO = 851.32) |
| 511 | m/z = 852.03 (C65H41NO = 851.32) | 512 | m/z = 769.97 (C58H43NO = 769.33) |
| 513 | m/z = 1028.25 (C78H51NO = 1017.40) | 514 | m/z = 1014.21 (C78H47NO = 1013.37) |

TABLE 5-continued

| Compound | FD-MS | Compound | FD-MS |
|---|---|---|---|
| 515 | m/z = 703.82 (C52H33NO2 = 703.25) | 516 | m/z = 703.82 (C52H33NO2 = 703.25) |
| 517 | m/z = 703.82 (C52H33NO2 = 703.25) | 518 | m/z = 779.92 (C58H37NO2 = 779.28) |
| 519 | m/z = 779.92 (C58H37NO2 = 779.28) | 520 | m/z = 779.92 (C58H37NO2 = 779.28) |
| 521 | m/z = 537.65 (C40H27NO = 537.21) | 522 | m/z = 587.71 (C44H27NO = 587.22) |
| 523 | m/z = 587.71 (C44H27NO = 587.22) | 524 | m/z = 637.77 (C48H32NO = 637.24) |
| 525 | m/z = 637.77 (C48H32NO = 637.24) | 526 | m/z = 613.74 (C46H31NO = 613.24) |
| 527 | m/z = 613.74 (C46H31NO = 613.24) | 528 | m/z = 613.74 (C46H31NO = 613.24) |
| 529 | m/z = 663.80 (C50H33NO = 663.26) | 530 | m/z = 663.80 (C50H33NO = 663.26) |
| 531 | m/z = 663.80 (C50H33NO = 663.26) | 532 | m/z = 663.80 (C50H33NO = 663.26) |
| 533 | m/z = 663.80 (C50H33NO = 663.26) | 534 | m/z = 663.80 (C50H33NO = 663.26) |
| 535 | m/z = 689.84 (C52H35NO = 689.27) | 536 | m/z = 689.84 (C52H35NO = 689.27) |
| 537 | m/z = 689.84 (C52H35NO = 689.27) | 538 | m/z = 739.90 (C56H37NO = 739.29) |
| 539 | m/z = 739.90 (C56H37NO = 739.29) | 540 | m/z = 739.90 (C56H37NO = 739.29) |
| 541 | m/z = 739.90 (C56H37NO = 739.29) | 542 | m/z = 739.90 (C56H37NO = 739.29) |
| 543 | m/z = 739.90 (C56H37NO = 739.29) | 544 | m/z = 689.84 (C52H35NO = 689.27) |
| 545 | m/z = 689.84 (C52H35NO = 689.27) | 546 | m/z = 689.84 (C52H35NO = 689.27) |
| 547 | m/z = 765.94 (C58H39NO = 765.30) | 548 | m/z = 765.94 (C58H39NO = 765.30) |
| 549 | m/z = 765.94 (C58H39NO = 765.30) | 550 | m/z = 765.94 (C58H39NO = 765.30) |
| 551 | m/z = 765.94 (C58H39NO = 765.30) | 552 | m/z = 765.94 (C58H39NO = 765.30) |
| 553 | m/z = 729.90 (C5H39NO = 729.30) | 554 | m/z = 729.90 (C5H39NO = 729.30) |
| 555 | m/z = 854.04 (C65H43NO = 854.34) | 556 | m/z = 854.04 (C65H43NO = 854.34) |
| 557 | m/z = 854.04 (C65H43NO = 854.34) | 558 | m/z = 852.03 (C65H41NO = 851.32) |
| 559 | m/z = 852.03 (C65H41NO = 851.32) | 560 | m/z = 852.03 (C65H41NO = 851.32) |
| 561 | m/z = 852.03 (C65H41NO = 851.32) | 562 | m/z = 852.03 (C65H41NO = 851.32) |
| 563 | m/z = 852.03 (C65H41NO = 851.32) | 564 | m/z = 769.97 (C58H43NO = 769.33) |
| 565 | m/z = 1028.25 (C78H51NO = 1017.40) | 566 | m/z = 1014.21 (C78H47NO = 1013.37) |
| 567 | m/z = 703.82 (C52H33NO2 = 703.25) | 568 | m/z = 703.82 (C52H33NO2 = 703.25) |
| 569 | m/z = 703.82 (C52H33NO2 = 703.25) | 570 | m/z = 779.92 (C58H37NO2 = 779.28) |
| 571 | m/z = 779.92 (C58H37NO2 = 779.28) | 572 | m/z = 779.92 (C58H37NO2 = 779.28) |
| 573 | m/z = 537.65 (C40H27NO = 537.21) | 574 | m/z = 587.71 (C44H27NO = 587.22) |
| 575 | m/z = 587.71 (C44H27NO = 587.22) | 576 | m/z = 637.77 (C48H32NO = 637.24) |
| 577 | m/z = 637.77 (C48H32NO = 637.24) | 578 | m/z = 613.74 (C46H31NO = 613.24) |
| 579 | m/z = 613.74 (C46H31NO = 613.24) | 580 | m/z = 613.74 (C46H31NO = 613.24) |
| 581 | m/z = 663.80 (C50H33NO = 663.26) | 582 | m/z = 663.80 (C50H33NO = 663.26) |
| 583 | m/z = 663.80 (C50H33NO = 663.26) | 584 | m/z = 663.80 (C50H33NO = 663.26) |
| 585 | m/z = 663.80 (C50H33NO = 663.26) | 586 | m/z = 663.80 (C50H33NO = 663.26) |
| 587 | m/z = 689.84 (C52H35NO = 689.27) | 588 | m/z = 689.84 (C52H35NO = 689.27) |
| 589 | m/z = 689.84 (C52H35NO = 689.27) | 590 | m/z = 739.90 (C56H37NO = 739.29) |
| 591 | m/z = 739.90 (C56H37NO = 739.29) | 592 | m/z = 739.90 (C56H37NO = 739.29) |
| 593 | m/z = 739.90 (C56H37NO = 739.29) | 594 | m/z = 739.90 (C56H37NO = 739.29) |
| 595 | m/z = 739.90 (C56H37NO = 739.29) | 596 | m/z = 739.90 (C56H37NO = 739.29) |
| 597 | m/z = 689.84 (C52H35NO = 689.27) | 598 | m/z = 689.84 (C52H35NO = 689.27) |
| 599 | m/z = 765.94 (C58H39NO = 765.30) | 600 | m/z = 765.94 (C58H39NO = 765.30) |
| 601 | m/z = 765.94 (C58H39NO = 765.30) | 602 | m/z = 765.94 (C58H39NO = 765.30) |
| 603 | m/z = 765.94 (C58H39NO = 765.30) | 604 | m/z = 765.94 (C58H39NO = 765.30) |
| 605 | m/z = 729.90 (C5H39NO = 729.30) | 606 | m/z = 729.90 (C5H39NO = 729.30) |
| 607 | m/z = 729.90 (C5H39NO = 729.30) | 608 | m/z = 854.04 (C65H43NO = 854.34) |
| 609 | m/z = 854.04 (C65H43NO = 854.34) | 610 | m/z = 854.03 (C65H41NO = 853.33) |
| 611 | m/z = 852.03 (C65H41NO = 851.32) | 612 | m/z = 852.03 (C65H41NO = 851.32) |
| 613 | m/z = 852.03 (C65H41NO = 851.32) | 614 | m/z = 852.03 (C65H41NO = 851.32) |
| 615 | m/z = 852.03 (C65H41NO = 851.32) | 616 | m/z = 852.03 (C65H41NO = 851.32) |
| 617 | m/z = 769.97 (C58H43NO = 769.33) | 618 | m/z = 1018.25 (C78H51NO = 1017.40) |
| 619 | m/z = 1014.21 (C78H47NO = 1013.37) | 620 | m/z = 703.82 (C52H33NO2 = 703.25) |
| 621 | m/z = 703.82 (C52H33NO2 = 703.25) | 622 | m/z = 703.82 (C52H33NO2 = 703.25) |
| 623 | m/z = 779.92 (C58H37NO2 = 779.28) | 624 | m/z = 779.92 (C58H37NO2 = 779.28) |
| 625 | m/z = 779.92 (C58H37NO2 = 779.28) | 626 | m/z = 613.74 (C46H31NO = 613.24) |
| 627 | m/z = 637.77 (C48H32NO = 637.24) | 628 | m/z = 587.71 (C44H29NO = 587.22) |
| 629 | m/z = 613.74 (C46H31NO = 613.24) | 630 | m/z = 663.80 (C50H33NO = 663.26) |
| 631 | m/z = 663.80 (C50H33NO = 663.26) | 632 | m/z = 689.84 (C52H35NO = 689.27) |
| 633 | m/z = 689.84 (C52H35NO = 689.27) | 634 | m/z = 689.84 (C52H35NO = 689.27) |
| 635 | m/z = 729.90 (C55H39NO = 729.30) | 636 | m/z = 854.04 (C65H43NO = 853.33) |
| 637 | m/z = 852.03 (C65H41NO = 851.32) | 638 | m/z = 663.80 (C50H33NO = 663.26) |
| 639 | m/z = 663.80 (C50H33NO = 663.26) | 640 | m/z = 713.86 (C54H35NO = 713.27) |
| 641 | m/z = 739.90 (C56H37NO = 739.29) | 642 | m/z = 816.00 (C62H41NO = 815.32) |
| 643 | m/z = 779.96 (C59H41NO = 779.32) | 644 | m/z = 820.03 (C62H45NO = 819.35) |
| 645 | m/z = 739.90 (C56H37NO = 739.29) | 646 | m/z = 779.96 (C59H41NO = 779.32) |
| 647 | m/z = 904.10 (C69H45NO = 903.35) | 648 | m/z = 663.80 (C50H33NO = 663.26) |
| 649 | m/z = 689.84 (C52H35NO = 689.27) | 650 | m/z = 765.94 (C58H39NO = 765.30) |
| 651 | m/z = 806.00 (C71H47NO = 929.37) | 652 | m/z = 806.00 (C61H43NO = 805.33) |
| 653 | m/z = 930.14 (C46H31NO = 613.24) | 654 | m/z = 765.94 (C58H39NO = 765.30) |
| 655 | m/z = 806.00 (C71H47NO = 929.37) | 656 | m/z = 930.14 (C46H31NO = 613.24) |
| 657 | m/z = 856.02 (C64H41NO2 = 855.31) | 658 | m/z = 765.94 (C58H39NO = 765.30) |
| 659 | m/z = 806.00 (C61H43NO = 805.33) | 660 | m/z = 930.14 (C46H31NO = 613.24) |
| 661 | m/z = 729.30 (C55H39NO = 729.92) | 680 | m/z = 689.27 (C52H35NO = 689.86) |
| 688 | m/z = 780.95 (C58H40N2O = 780.31) | 689 | m/z = 857.05 (C64H44N2O = 856.35) |
| 690 | m/z = 831.01 (C62H42N2O = 830.33) | 691 | m/z = 628.76 (C46H32N2O = 628.25) |
| 692 | m/z = 718.84 (C52H34N2O2 = 718.84) | 693 | m/z = 821.01 (C61H44N2O = 820.35) |
| 694 | m/z = 897.11 (C67H48N2O = 896.38) | 695 | m/z = 871.07 (C65H46N2O = 870.36) |

TABLE 5-continued

| Compound | FD-MS | Compound | FD-MS |
|---|---|---|---|
| 696 | m/z = 861.08 (C64H48N2O = 860.38) | 697 | m/z = 744.92 (C55H40N2O = 744.31) |
| 698 | m/z = 678.82 (C50H34N2O = 678.27) | 699 | m/z = 728.88 (C54H36N2O = 728.28) |
| 700 | m/z = 678.82 (C50H34N2O = 678.27) | 701 | m/z = 678.82 (C50H34N2O = 678.27) |
| 702 | m/z = 780.95 (C58H40N2O = 780.31) | 703 | m/z = 628.76 (C46H32N2O = 628.25) |
| 704 | m/z = 857.05 (C64H44N2O = 856.35) | 705 | m/z = 831.01 (C62H42N2O = 830.33) |
| 706 | m/z = 628.76 (C46H32N2O = 628.25) | 707 | m/z = 678.82 (C50H34N2O = 678.27) |
| 708 | m/z = 678.82 (C50H34N2O = 678.27) | 709 | m/z = 728.88 (C54H36N2O = 728.28) |
| 710 | m/z = 678.82 (C50H34N2O = 678.27) | 711 | m/z = 780.95 (C58H40N2O = 780.31) |
| 712 | m/z = 857.05 (C64H44N2O = 856.35) | 713 | m/z = 831.01 (C62H42N2O = 830.33) |
| 714 | m/z = 628.76 (C46H32N2O = 628.25) | 715 | m/z = 628.76 (C46H32N2O = 628.25) |
| 716 | m/z = 678.82 (C50H34N2O = 678.27) | 717 | m/z = 728.88 (C54H36N2O = 728.28) |
| 718 | m/z = 678.82 (C50H34N2O = 678.27) | 719 | m/z = 678.82 (C50H34N2O = 678.27) |

EXPERIMENTAL EXAMPLE

Experimental Example 1

(1) Manufacture of Organic Light Emitting Device A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and WO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

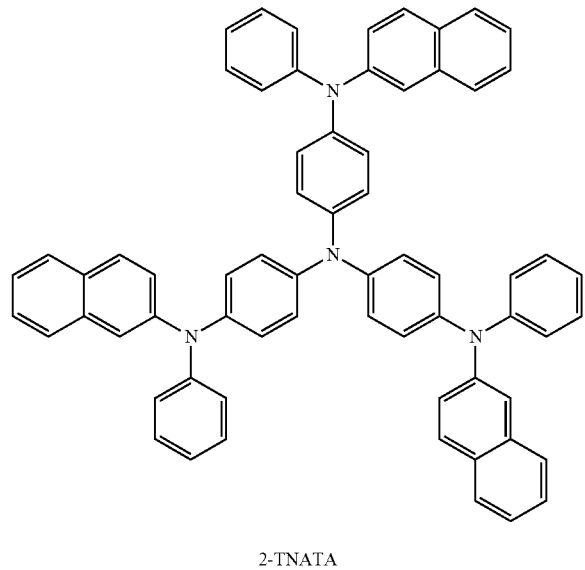 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

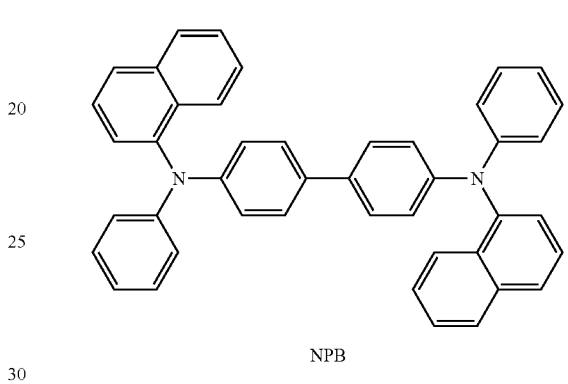

NPB

A light emitting layer was thermal vacuum deposited thereon as follows. As the light emitting layer, a compound of 9-[4-(4,6-diphenyl-1,3,5-triazin-2-yl)phenyl]-9'-phenyl-3,3'-Bi-9H-carbazole was deposited to 400 Å as a host, and Ir(ppy)$_3$ was 7% doped and deposited as a green phosphorescent dopant. After that, BCP was deposited to a thickness of 60 Å as a hole blocking layer, and Alq$_3$ was deposited to a thickness of 200 Å thereon as an electron transfer layer. Lastly, an electron injection layer was formed on the electron transfer layer by depositing lithium fluoride (LiF) to a thickness of 10 Å, and a cathode was formed on the electron injection layer by depositing an aluminum (Al) cathode to a thickness of 1,200 Å, and as a result, an organic light emitting device (hereinafter, Comparative Example 1) was manufactured.

Meanwhile, all the organic compounds required to manufacture the organic light emitting device were vacuum sublimation purified under $10^{-6}$ torr to $10^{-8}$ torr for each material to be used in the organic light emitting device manufacture.

In addition, organic light emitting devices of Examples 1 to 63 were manufactured in the same manner as in the method for manufacturing the organic light emitting device of Comparative Example 1 except that compounds of Examples 1 to 63 of the following Table 6 were used instead of the compound NPB used for forming the hole transfer layer in Comparative Example 1.

In addition, organic light emitting devices of Comparative Examples 2 to 4 were manufactured in the same manner as in the method for manufacturing the organic light emitting device of Comparative Example 1 except that compounds of M1 to M3 of Comparative Examples 2 to 4 of the following Table 6 were used instead of the compound NPB used for forming the hole transfer layer in Comparative Example 1.

Herein, Compounds M1 to M3, the hole transfer compounds of Comparative Examples 2 to 4, are as follows.

M1

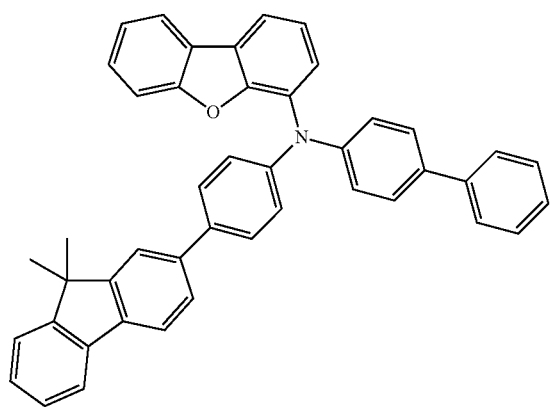

Molecular Weight: 603.77

M2

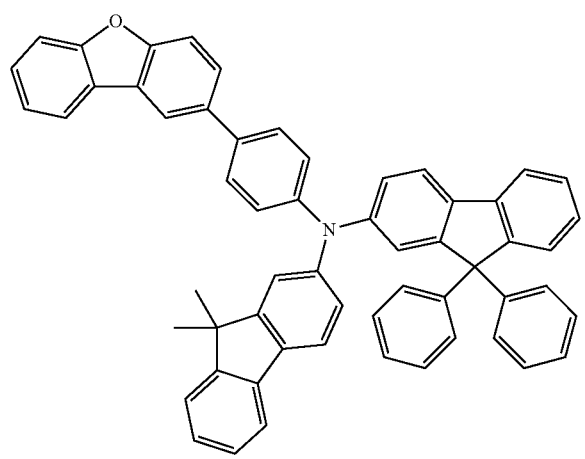

Molecular Weight: 767.97

-continued

M3

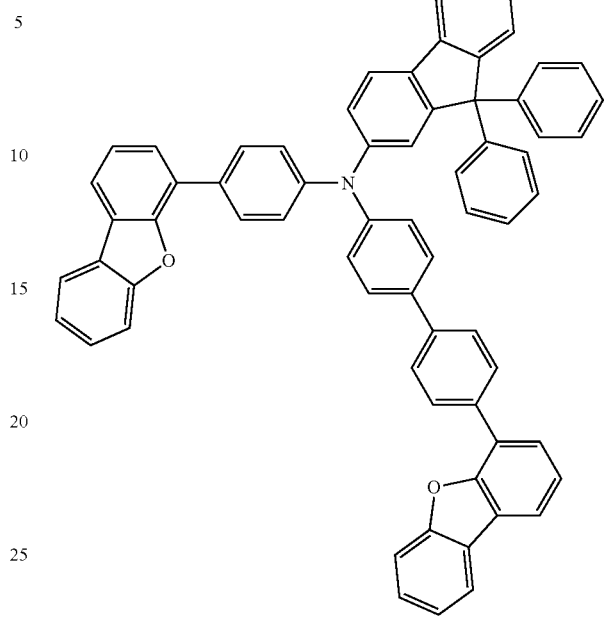

Molecular Weight: 894.09

(2) Driving Voltage and Light Emission Efficiency of Organic Light Emitting Device For each of the organic light emitting devices of Examples 1 to 63 and Comparative Examples 1 to 4 manufactured as above, electroluminescent (EL) properties were measured using M7000 manufactured by McScience Inc., and with the measurement results, a lifetime $T_{90}$ (unit: h, time) that is a time taken to be 90% with respect to initial luminance was measured when standard luminance was 6,000 $cd/m^2$ through a lifetime measurement system (M6000) manufactured by McScience Inc.

Properties of the organic light emitting devices of the present disclosure obtained by the above-described measurement results are as shown in the following Table 6.

TABLE 6

|  | Compound | Driving Voltage (V) | Light Emission Efficiency (cd/A) | Lifetime ($T_{90}$) |
|---|---|---|---|---|
| Comparative Example 1 | NPB | 4.51 | 110.59 | 150 |
| Example 1 | HT-24 | 4.25 | 120.92 | 231 |
| Example 2 | HT-25 | 4.23 | 119.32 | 230 |
| Example 3 | HT-26 | 4.29 | 122.54 | 235 |
| Example 4 | HT-32 | 4.24 | 124.32 | 244 |
| Example 5 | HT-33 | 4.12 | 120.33 | 200 |
| Example 6 | HT-34 | 4.36 | 118.99 | 253 |
| Example 7 | HT-35 | 4.19 | 125.71 | 266 |
| Example 8 | HT-36 | 4.68 | 123.68 | 238 |
| Example 9 | HT-37 | 3.99 | 124.23 | 246 |
| Example 10 | HT-38 | 4.27 | 130.12 | 249 |
| Example 11 | HT-39 | 3.79 | 126.84 | 250 |
| Example 12 | HT-40 | 3.88 | 129.52 | 251 |
| Example 13 | HT-44 | 4.49 | 124.33 | 238 |
| Example 14 | HT-45 | 4.42 | 128.17 | 231 |

TABLE 6-continued

|  | Compound | Driving Voltage (V) | Light Emission Efficiency (cd/A) | Lifetime ($T_{90}$) |
|---|---|---|---|---|
| Example 15 | HT-46 | 4.68 | 132.81 | 222 |
| Example 16 | HT-47 | 4.22 | 138.67 | 210 |
| Example 17 | HT-48 | 3.87 | 128.76 | 200 |
| Example 18 | HT-49 | 3.92 | 128.11 | 203 |
| Example 19 | HT-50 | 3.5 | 126.08 | 267 |
| Example 20 | HT-51 | 3.66 | 126.79 | 209 |
| Example 21 | HT-52 | 4.69 | 123.97 | 211 |
| Example 22 | HT-180 | 4.28 | 140.11 | 210 |
| Example 23 | HT-181 | 4.11 | 138.62 | 222 |
| Example 24 | HT-182 | 3.72 | 137.55 | 238 |
| Example 25 | HT-188 | 3.88 | 130.79 | 251 |
| Example 26 | HT-189 | 3.91 | 129.34 | 263 |
| Example 27 | HT-190 | 4.67 | 128.59 | 241 |
| Example 28 | HT-191 | 4.11 | 129.19 | 253 |
| Example 29 | HT-192 | 4.20 | 123.55 | 231 |
| Example 30 | HT-193 | 3.77 | 137.26 | 264 |
| Example 31 | HT-194 | 3.69 | 129.87 | 222 |
| Example 32 | HT-195 | 3.97 | 129.58 | 210 |
| Example 33 | HT-196 | 3.92 | 132.99 | 253 |
| Example 34 | HT-197 | 3.91 | 134.59 | 240 |
| Example 35 | HT-198 | 3.67 | 127.85 | 250 |
| Example 36 | HT-199 | 3.77 | 125.71 | 273 |
| Example 37 | HT-200 | 3.99 | 126.85 | 268 |
| Example 38 | HT-201 | 4.10 | 126.29 | 266 |
| Example 39 | HT-202 | 4.10 | 127.62 | 190 |
| Example 40 | HT-203 | 4.27 | 130.16 | 173 |
| Example 41 | HT-204 | 3.54 | 131.76 | 216 |
| Example 42 | HT-205 | 3.86 | 132.99 | 237 |
| Example 43 | HT-336 | 3.88 | 130.86 | 256 |
| Example 44 | HT-344 | 3.98 | 126.88 | 233 |
| Example 45 | HT-347 | 3.91 | 126.05 | 261 |
| Example 46 | HT-350 | 3.79 | 130.28 | 186 |
| Example 47 | HT-356 | 3.99 | 139.69 | 197 |
| Example 48 | HT-359 | 4.00 | 138.62 | 266 |
| Example 49 | HT-362 | 4.03 | 138.73 | 234 |
| Example 50 | HT-492 | 4.23 | 139.88 | 236 |
| Example 51 | HT-501 | 4.01 | 135.36 | 208 |
| Example 52 | HT-504 | 3.97 | 137.14 | 244 |
| Example 53 | HT-507 | 4.30 | 135.29 | 197 |
| Example 54 | HT-513 | 3.88 | 130.89 | 266 |
| Example 55 | HT-516 | 3.91 | 131.50 | 177 |
| Example 56 | HT-519 | 3.90 | 134.63 | 194 |
| Example 57 | HT-661 | 4.00 | 139.54 | 200 |
| Example 58 | HT-662 | 3.73 | 129.17 | 238 |
| Example 59 | HT-665 | 3.94 | 129.33 | 267 |
| Example 60 | HT-666 | 4.00 | 128.66 | 198 |
| Example 61 | HT-680 | 4.32 | 124.59 | 200 |
| Example 62 | HT-681 | 4.11 | 115.55 | 199 |
| Example 63 | HT-682 | 4.23 | 125.75 | 198 |
| Example 63 | HT-683 | 4.28 | 125.75 | 198 |
| Comparative Example 2 | M1 | 4.49 | 117.62 | 181 |
| Comparative Example 3 | M2 | 4.37 | 116.20 | 192 |
| Comparative Example 4 | M3 | 4.46 | 118.92 | 177 |

From Experimental Example 1, it was identified that, by having a structure in which naphthobenzofuran is disubstituted with specific substituents such as an amine group, and thereby increasing a hole transfer ability through delocalizing a highest occupied molecular orbital (HOMO) energy level and stabilizing HOMO energy, the organic light emitting devices of Examples 1 to 63 using the compounds according to the present application when forming the hole transfer layer had superior light emission efficiency and lifetime compared to the organic light emitting devices of Comparative Examples 1 to 4 not using the compounds according to the present application when forming the hole transfer layer.

Experimental Example 2

(1) Manufacture of Organic Light Emitting Device

A transparent ITO electrode thin film obtained from glass for an organic light emitting device (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

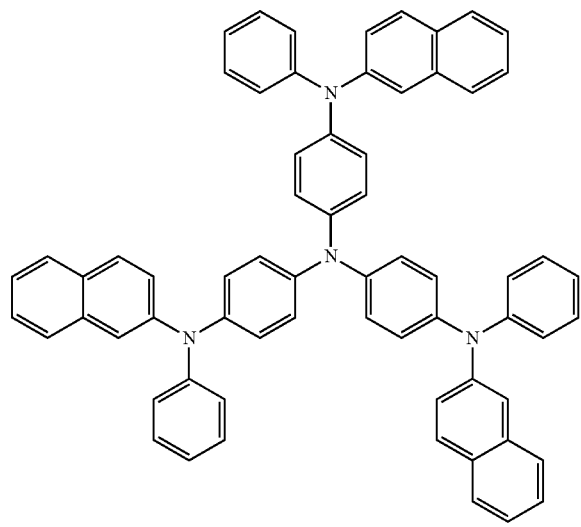

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

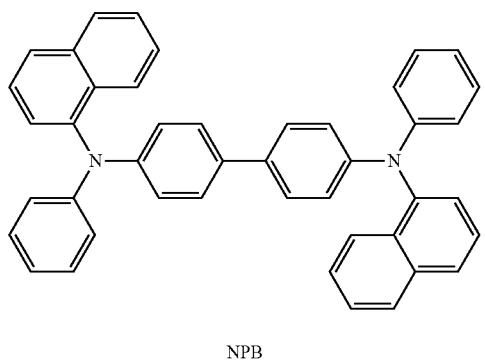 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

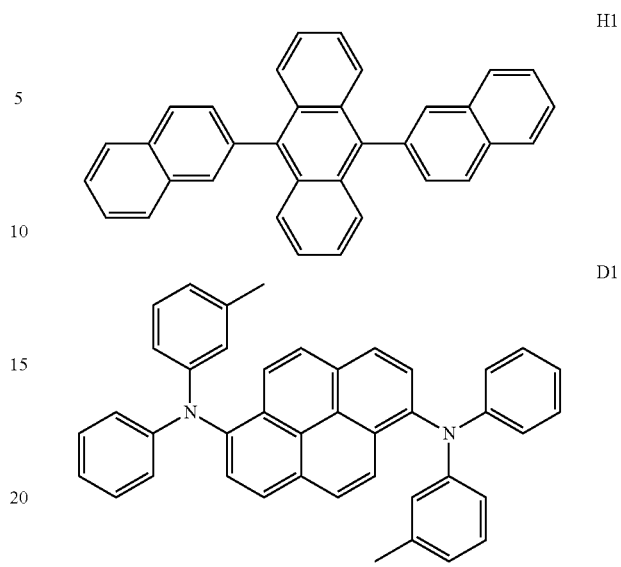

Subsequently, a compound of the following Structural Formula E1 was deposited to a thickness of 300 Å as an electron transfer layer.

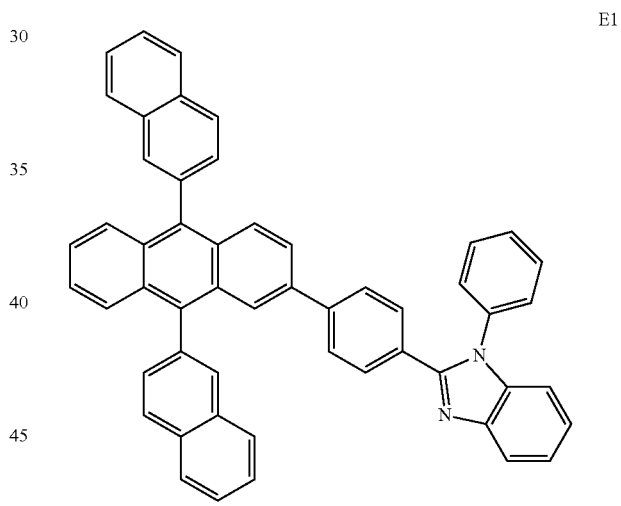

As an electron injection layer, lithium fluoride (LiF) was deposited to a thickness of 10 Å, and an Al cathode was employed to a thickness of 1,000 Å, and as a result, an organic light emitting device (hereinafter, Comparative Example 5) was manufactured. Meanwhile, all the organic compounds required to manufacture the OLED were vacuum sublimation purified under $10^{-6}$ torr to $10^{-8}$ torr by each material to be used in the organic light emitting device manufacture.

In addition, organic light emitting devices were manufactured in the same manner as in the method for manufacturing the organic light emitting device of Comparative Example 5 except that, after forming the organic hole transfer layer NPB to a thickness of 150 Å, an electron blocking layer having a thickness of 50 Å was formed on the hole transfer layer using compounds of Examples 64 to 141 and Comparative Examples 5 to 7 of the following Table 7.

Herein, the electron blocking layer compounds M4 to M6 of Comparative Examples 5 to 7 are as follows.

M4

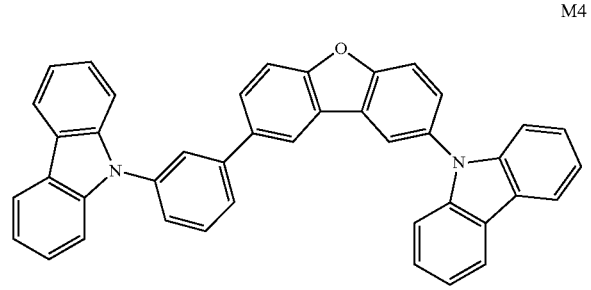

Molecular Weight: 574.68

M5

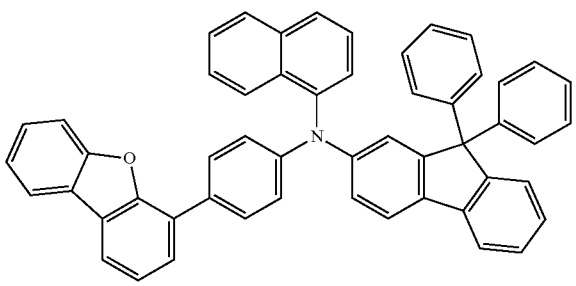

Molecular Weight: 701.87

M6

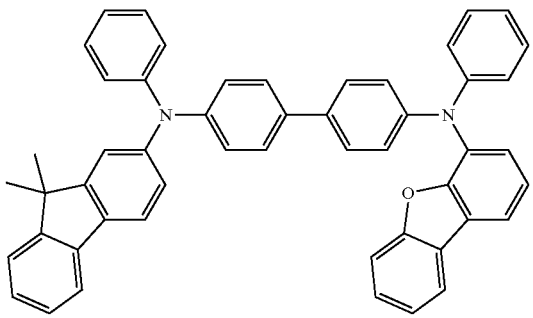

Molecular Weight: 694.88

(2) Driving Voltage and Light Emission Efficiency of Organic Light Emitting Device For each of the organic light emitting devices of Examples 64 to 141 and Comparative Examples 5 to 7 manufactured as above, electroluminescent (EL) properties were measured using M7000 manufactured by McScience Inc., and with the measurement results, a lifetime T95 (unit: h, time) that is a time taken to be 95% with respect to initial luminance was measured when standard luminance was 6,000 cd/m² through a lifetime measurement system (M6000) manufactured by McScience Inc.

Properties of the organic light emitting devices of the present disclosure obtained by the above-described measurement results are as shown in the following Table 7.

TABLE 7

| | Compound | Driving Voltage (V) | Light Emission Efficiency (cd/A) | Lifetime ($T_{95}$) |
|---|---|---|---|---|
| Example 64 | HT-24 | 4.71 | 6.09 | 55 |
| Example 65 | HT-25 | 4.73 | 6.33 | 51 |
| Example 66 | HT-26 | 4.64 | 6.41 | 46 |
| Example 67 | HT-32 | 4.19 | 6.28 | 53 |
| Example 68 | HT-33 | 4.89 | 6.87 | 55 |
| Example 69 | HT-34 | 4.93 | 6.66 | 55 |
| Example 70 | HT-35 | 4.88 | 5.99 | 55 |
| Example 71 | HT-36 | 4.61 | 6.78 | 58 |
| Example 72 | HT-37 | 4.82 | 6.18 | 51 |
| Example 73 | HT-38 | 4.67 | 6.92 | 50 |
| Example 74 | HT-39 | 4.92 | 6.71 | 51 |
| Example 75 | HT-40 | 4.66 | 6.52 | 51 |
| Example 76 | HT-44 | 4.08 | 6.79 | 53 |
| Example 77 | HT-45 | 4.41 | 6.44 | 57 |
| Example 78 | HT-46 | 4.69 | 6.81 | 57 |
| Example 79 | HT-47 | 4.88 | 6.29 | 59 |
| Example 80 | HT-48 | 4.85 | 6.87 | 53 |
| Example 81 | HT-49 | 5.11 | 6.27 | 51 |
| Example 82 | HT-50 | 5.10 | 6.90 | 52 |
| Example 83 | HT-51 | 4.78 | 6.66 | 57 |
| Example 84 | HT-52 | 4.94 | 6.51 | 51 |
| Example 85 | HT-180 | 5.09 | 6.17 | 53 |
| Example 86 | HT-181 | 4.83 | 6.61 | 44 |
| Example 87 | HT-182 | 4.77 | 6.07 | 52 |
| Example 88 | HT-188 | 4.69 | 6.30 | 50 |
| Example 89 | HT-189 | 4.99 | 6.11 | 50 |
| Example 90 | HT-190 | 4.81 | 6.00 | 46 |
| Example 91 | HT-191 | 4.48 | 5.95 | 49 |
| Example 92 | HT-192 | 4.72 | 6.40 | 46 |
| Example 93 | HT-193 | 4.97 | 6.28 | 47 |
| Example 94 | HT-194 | 5.11 | 6.09 | 41 |

TABLE 7-continued

| | Compound | Driving Voltage (V) | Light Emission Efficiency (cd/A) | Lifetime ($T_{95}$) |
|---|---|---|---|---|
| Example 95 | HT-195 | 4.73 | 6.67 | 45 |
| Example 96 | HT-196 | 4.87 | 6.81 | 52 |
| Example 97 | HT-197 | 5.37 | 6.02 | 55 |
| Example 98 | HT-198 | 5.15 | 5.86 | 50 |
| Example 99 | HT-199 | 5.13 | 6.02 | 62 |
| Example 100 | HT-200 | 5.49 | 6.07 | 48 |
| Example 101 | HT-201 | 5.36 | 5.69 | 43 |
| Example 102 | HT-202 | 5.41 | 5.85 | 44 |
| Example 103 | HT-203 | 4.78 | 6.07 | 52 |
| Example 104 | HT-204 | 4.69 | 6.30 | 48 |
| Example 105 | HT-205 | 4.92 | 6.11 | 46 |
| Example 106 | HT-336 | 4.81 | 6.08 | 57 |
| Example 107 | HT-344 | 4.13 | 5.55 | 43 |
| Example 108 | HT-347 | 4.48 | 6.95 | 41 |
| Example 109 | HT-350 | 4.65 | 6.76 | 57 |
| Example 110 | HT-356 | 5.02 | 6.16 | 55 |
| Example 111 | HT-359 | 4.98 | 6.41 | 49 |
| Example 112 | HT-362 | 4.79 | 6.07 | 52 |
| Example 113 | HT-492 | 4.46 | 6.13 | 50 |
| Example 114 | HT-501 | 4.99 | 6.11 | 50 |
| Example 115 | HT-504 | 4.81 | 6.00 | 46 |
| Example 116 | HT-507 | 4.49 | 6.23 | 49 |
| Example 117 | HT-513 | 4.70 | 6.40 | 46 |
| Example 118 | HT-516 | 4.06 | 6.28 | 47 |
| Example 119 | HT-519 | 5.44 | 6.09 | 41 |
| Example 120 | HT-661 | 4.75 | 6.67 | 45 |
| Example 121 | HT-662 | 4.80 | 6.81 | 52 |
| Example 122 | HT-665 | 5.16 | 6.02 | 55 |
| Example 123 | HT-666 | 5.04 | 6.31 | 50 |
| Example 124 | HT-680 | 5.01 | 6.02 | 62 |
| Example 125 | HT-681 | 4.43 | 6.07 | 48 |
| Example 126 | HT-682 | 5.76 | 6.21 | 43 |
| Example 127 | HT-683 | 5.12 | 6.12 | 44 |
| Example 128 | HT-689 | 6.09 | 5.75 | 40 |
| Example 129 | HT-691 | 6.14 | 5.86 | 41 |
| Example 130 | HT-692 | 6.29 | 5.46 | 39 |
| Example 131 | HT-694 | 6.12 | 5.53 | 38 |
| Example 132 | HT-695 | 6.23 | 5.64 | 39 |
| Example 133 | HT-698 | 6.30 | 5.43 | 34 |
| Example 134 | HT-699 | 6.05 | 5.95 | 39 |
| Example 135 | HT-701 | 6.04 | 5.42 | 36 |
| Example 136 | HT-702 | 6.11 | 5.83 | 40 |
| Example 137 | HT-709 | 6.11 | 5.93 | 41 |
| Example 138 | HT-711 | 6.37 | 5.92 | 39 |
| Example 139 | HT-714 | 6.19 | 5.62 | 40 |
| Example 140 | HT-717 | 6.37 | 5.82 | 42 |
| Example 141 | HT-719 | 6.15 | 5.95 | 41 |
| Comparative Example 5 | M4 | 6.49 | 6.07 | 39 |
| Comparative Example 6 | M5 | 6.36 | 5.69 | 43 |
| Comparative Example 7 | M6 | 6.41 | 5.85 | 40 |

From Experimental Example 2, it was identified that, by having a structure in which naphthobenzofuran is disubstituted with specific substituents such as an amine group, and thereby having a superior electron blocking ability through delocalizing a highest occupied molecular orbital (HOMO) energy level and stabilizing HOMO energy, the organic light emitting devices of Examples 64 to 141 using the compounds according to the present application when forming the electron blocking layer had superior light emission efficiency and lifetime compared to the organic light emitting devices of Comparative Examples 5 to 7 not using the compounds according to the present application when forming the electron blocking layer.

Experimental Example 3

(1) Manufacture of Organic Light Emitting Device

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and WO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

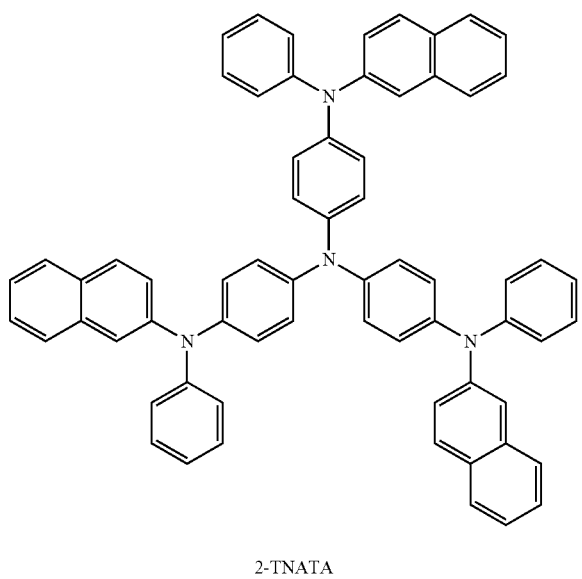 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer. After that, M7 was deposited to a thickness of 100 Å as a prime layer, and

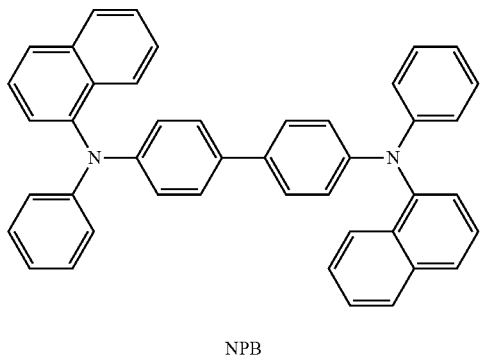 [SMILES: c1ccc(N(c2ccc(-c3ccc(N(c4ccccc4)c4cccc5ccccc45)cc3)cc2)c2cccc3ccccc23)cc1 ; "NPB"]

NPB a light emitting layer was thermal vacuum deposited thereon as follows. As the light emitting layer, a compound of 9-[4-(4,6-diphenyl-1,3,5-triazin-2-yl)phenyl]-9'-phenyl-3,3'-Bi-9H-carbazole was deposited to 400 Å as a host, and Ir(ppy)$_3$ was 7% doped and deposited as a green phosphorescent dopant. After that, BCP was deposited to a thickness of 60 Å as a hole blocking layer, and Alq$_3$ was deposited to a thickness of 200 Å thereon as an electron transfer layer. Lastly, an electron injection layer was formed on the electron transfer layer by depositing lithium fluoride (LiF) to a thickness of 10 Å, and a cathode was formed on the electron injection layer by depositing an aluminum (Al) cathode to a thickness of 1,200 Å, and as a result, an organic light emitting device (hereinafter, Comparative Example 8) was manufactured.

Meanwhile, all the organic compounds required to manufacture the organic light emitting device were vacuum sublimation purified under $10^{-6}$ torr to $10^{-8}$ torr for each material to be used in the organic light emitting device manufacture.

In addition, organic light emitting devices of Examples 142 to 205 and Comparative Examples 9 and 10 were manufactured in the same manner as in the method for manufacturing the organic light emitting device of Comparative Example 8 except that compounds of Examples 142 to 205 and Comparative Examples 9 and 10 of the following Table 8 were used instead of Compound M7 used for forming the prime layer in Comparative Example 8.

Herein, the prime layer compounds M7 to M9 of Comparative Examples 8 to 10 are as follows.

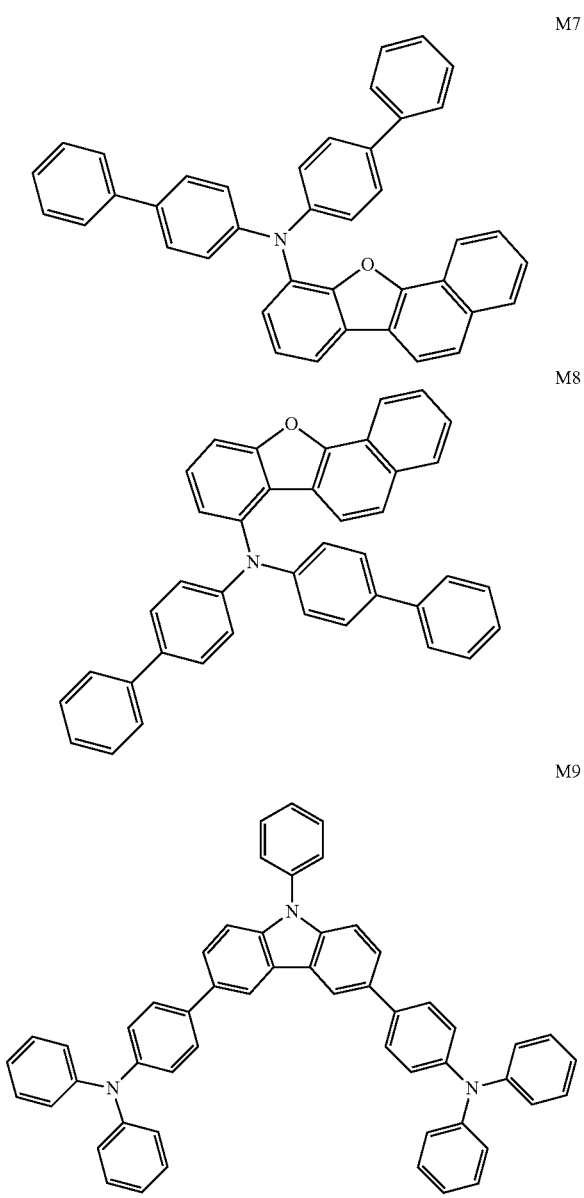

(2) Driving Voltage and Light Emission Efficiency of Organic Light Emitting Device For each of the organic light emitting devices of Examples 142 to 205 and Comparative Examples 8 to 10 manufactured as above, electroluminescent (EL) properties were measured using M7000 manufactured by McScience Inc., and with the measurement results, a lifetime $T_{90}$ (unit: h, time) that is a time taken to be 90% with respect to initial luminance was measured when standard luminance was 6,000 cd/m² through a lifetime measurement system (M6000) manufactured by McScience Inc.

Properties of the organic light emitting devices of the present disclosure obtained by the above-described measurement results are as shown in the following Table 8.

TABLE 8

|  | Compound | Driving Voltage (V) | Light Emission Efficiency (cd/A) | Lifetime ($T_{90}$) |
|---|---|---|---|---|
| Example 142 | HT-24 | 4.78 | 124.92 | 212 |
| Example 143 | HT-25 | 4.23 | 114.13 | 230 |
| Example 144 | HT-26 | 4.22 | 124.64 | 235 |
| Example 145 | HT-32 | 4.04 | 124.21 | 244 |
| Example 146 | HT-33 | 4.13 | 119.46 | 215 |
| Example 147 | HT-34 | 4.46 | 118.46 | 213 |
| Example 148 | HT-35 | 4.25 | 127.46 | 210 |
| Example 149 | HT-36 | 4.68 | 116.78 | 238 |
| Example 150 | HT-37 | 3.97 | 125.67 | 246 |
| Example 151 | HT-38 | 4.27 | 122.67 | 249 |
| Example 152 | HT-39 | 3.46 | 127.82 | 250 |
| Example 153 | HT-40 | 3.24 | 124.16 | 251 |
| Example 154 | HT-44 | 4.25 | 115.97 | 238 |
| Example 155 | HT-45 | 4.21 | 128.17 | 231 |
| Example 156 | HT-46 | 4.12 | 130.01 | 220 |
| Example 157 | HT-47 | 4.03 | 134.24 | 210 |
| Example 158 | HT-48 | 3.24 | 128.46 | 220 |
| Example 159 | HT-49 | 3.26 | 128.10 | 223 |
| Example 160 | HT-50 | 3.42 | 124.12 | 267 |
| Example 161 | HT-51 | 3.28 | 123.64 | 209 |
| Example 162 | HT-52 | 4.69 | 123.97 | 211 |
| Example 163 | HT-180 | 4.28 | 137.46 | 210 |
| Example 164 | HT-181 | 4.11 | 131.65 | 222 |
| Example 165 | HT-182 | 3.72 | 136.91 | 227 |
| Example 166 | HT-188 | 3.88 | 131.42 | 215 |
| Example 167 | HT-189 | 3.91 | 120.16 | 242 |
| Example 168 | HT-190 | 4.13 | 127.45 | 218 |
| Example 169 | HT-191 | 4.11 | 129.19 | 253 |
| Example 170 | HT-192 | 4.20 | 123.55 | 230 |
| Example 171 | HT-193 | 3.68 | 137.26 | 213 |
| Example 172 | HT-194 | 3.95 | 129.87 | 197 |
| Example 173 | HT-195 | 3.97 | 130.12 | 220 |
| Example 174 | HT-196 | 3.92 | 130.45 | 210 |
| Example 175 | HT-197 | 3.91 | 130.12 | 240 |
| Example 176 | HT-198 | 3.76 | 129.45 | 260 |
| Example 177 | HT-199 | 3.77 | 125.71 | 213 |
| Example 178 | HT-200 | 3.99 | 127.77 | 241 |
| Example 179 | HT-201 | 4.24 | 122.13 | 242 |
| Example 180 | HT-202 | 4.12 | 126.45 | 188 |
| Example 181 | HT-203 | 4.24 | 129.45 | 182 |
| Example 182 | HT-204 | 3.64 | 130.45 | 233 |
| Example 183 | HT-205 | 3.75 | 130.35 | 236 |
| Example 184 | HT-336 | 3.88 | 130.86 | 234 |
| Example 185 | HT-344 | 3.99 | 120.14 | 243 |
| Example 186 | HT-347 | 3.91 | 127.65 | 242 |
| Example 187 | HT-350 | 3.98 | 130.28 | 191 |
| Example 188 | HT-356 | 3.99 | 134.65 | 197 |
| Example 189 | HT-359 | 4.12 | 130.12 | 272 |
| Example 190 | HT-362 | 4.03 | 127.12 | 245 |
| Example 191 | HT-492 | 4.23 | 129.11 | 265 |
| Example 192 | HT-501 | 4.01 | 130.12 | 214 |
| Example 193 | HT-504 | 3.97 | 137.14 | 201 |
| Example 194 | HT-507 | 4.24 | 135.29 | 190 |
| Example 195 | HT-513 | 3.91 | 130.89 | 250 |
| Example 196 | HT-516 | 3.91 | 131.50 | 191 |
| Example 197 | HT-519 | 3.90 | 134.63 | 186 |
| Example 198 | HT-661 | 4.00 | 139.54 | 204 |
| Example 199 | HT-662 | 3.73 | 129.17 | 239 |
| Example 200 | HT-665 | 3.94 | 129.33 | 264 |
| Example 201 | HT-686 | 4.21 | 118.16 | 190 |
| Example 202 | HT-688 | 4.54 | 120.14 | 188 |
| Example 203 | HT-692 | 4.31 | 125.45 | 179 |
| Example 204 | HT-702 | 4.42 | 124.75 | 185 |
| Example 205 | HT-712 | 4.47 | 122.75 | 180 |
| Comparative Example 8 | M7 | 4.79 | 117.62 | 171 |
| Comparative Example 9 | M8 | 4.67 | 116.20 | 182 |
| Comparative Example 10 | M9 | 4.86 | 118.92 | 167 |

From Experimental Example 3, it was identified that, by having a structure in which naphthobenzofuran is disubstituted with specific substituents such as an amine group, and thereby effectively preventing electrons from falling over from the opposite side of the electron transfer layer through delocalizing a highest occupied molecular orbital (HOMO) energy level and stabilizing HOMO energy, the organic light emitting devices of Examples 142 to 205 using the compounds according to the present application when forming the prime layer had superior light emission efficiency and lifetime compared to the organic light emitting devices of Comparative Examples 8 to 10 not using the compounds according to the present application when forming the prime layer.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A hetero-cyclic compound represented by the following Chemical Formula 3 or 4:

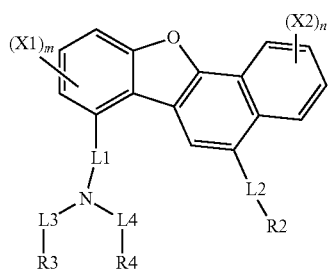

[Chemical Formula 3]

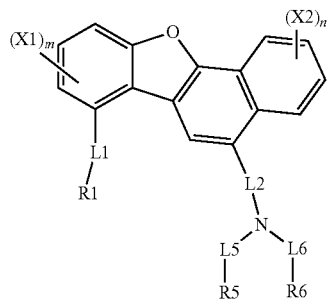

[Chemical Formula 4]

in Chemical Formulae 3 and 4,

L1 is a direct bond; a substituted or unsubstituted arylene group having 6 to 60 carbon atoms; or a substituted or unsubstituted heteroarylene group having 2 to 60 carbon atoms, L2 is a direct bond; or a substituted or unsubstituted arylene group having 6 to 60 carbon atoms, R1 is a substituted or unsubstituted aryl group having 6 to 60 carbon atoms; a substituted or unsubstituted heteroaryl group having 2 to 60 carbon atoms; or a substituted or unsubstituted amine group, R2 is a substituted or unsubstituted aryl group having 6 to 60 carbon atoms; or a substituted or unsubstituted amine group, X1 and X2 are each independently hydrogen; deuterium; a halogen group; a substituted or unsubstituted alkyl group having 61 to 60 carbon atoms; a substituted or unsubstituted cycloalkyl group having 3 to 60 carbon atoms; a substituted or unsubstituted aryl group having 6 to 60 carbon atoms; or a substituted or unsubstituted hetero-cyclic group having 2 to 60 carbon atoms, m and n are each an integer of 1 to 4, and when m and n are 2 or greater, substituents in the parentheses are the same as or different from each other, m and n are m+n≤7, L3 to L6 are each independently a direct bond; or a substituted or unsubstituted arylene group having 6 to 60 carbon atoms, R3 and R4 are each independently a substituted or unsubstituted aryl group having 6 to 60 carbon atoms; or a substituted or unsubstituted heteroaryl group having 2 to 60 carbon atoms, and R5 and R6 are each independently a substituted or unsubstituted aryl group having 6 to 60 carbon atoms.

2. The hetero-cyclic compound of claim 1, wherein Chemical Formula 3 or 4 is represented by any one of the following compounds:

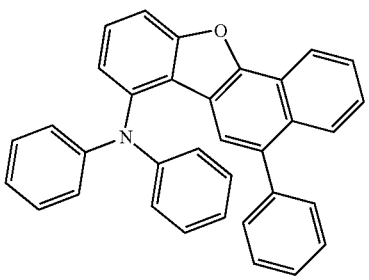

HT-1

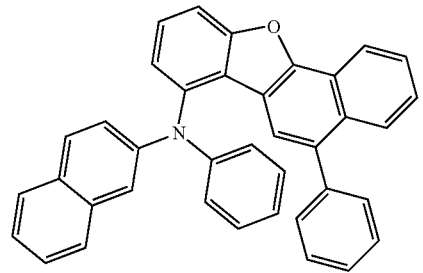

HT-2

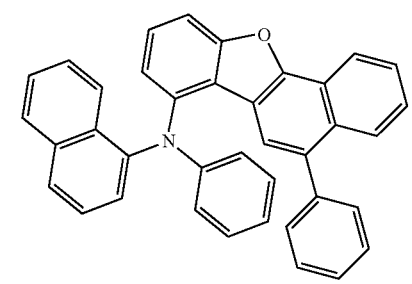

HT-3

333
-continued
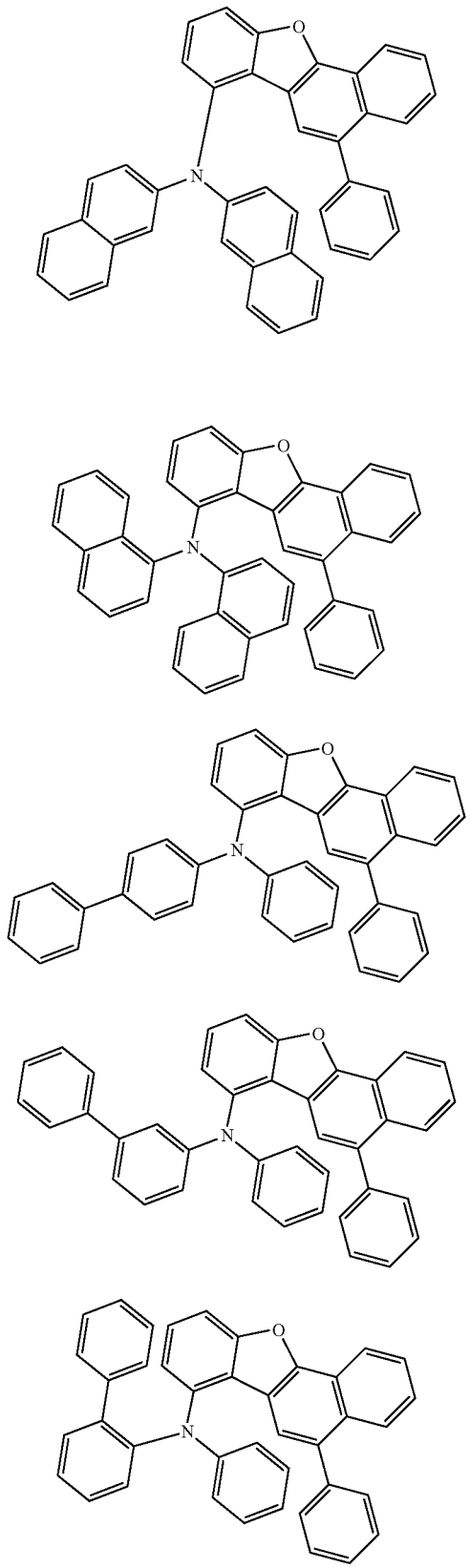
334
-continued
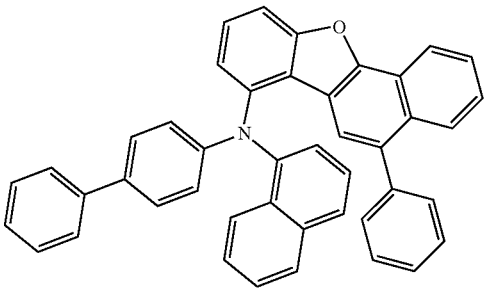
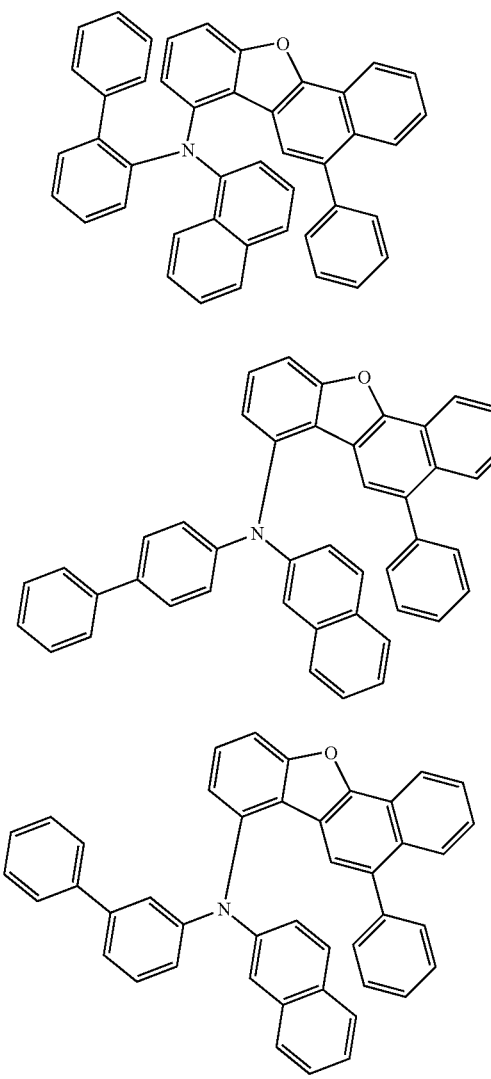

HT-14
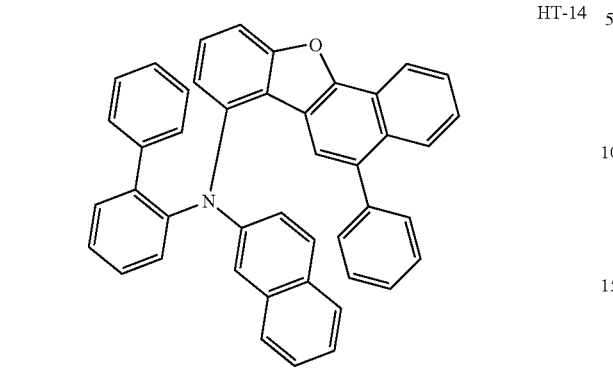
HT-15
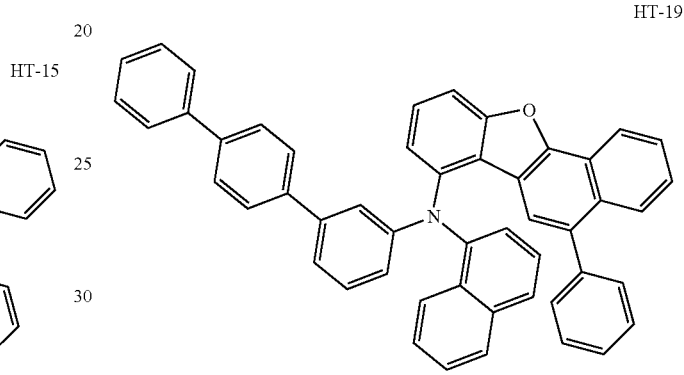
HT-16
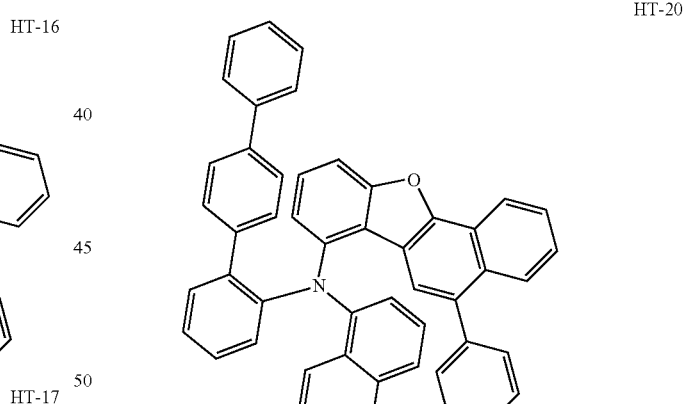
HT-17
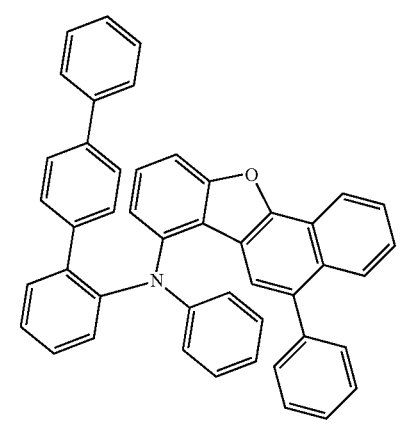
HT-18
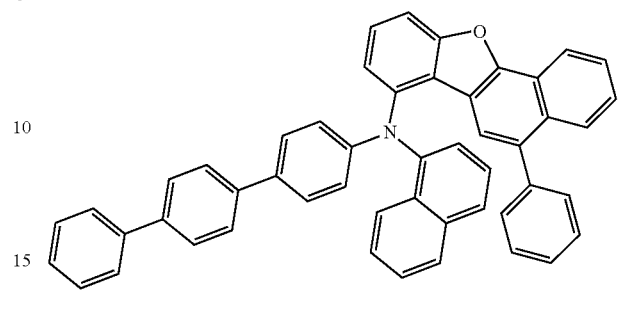
HT-19
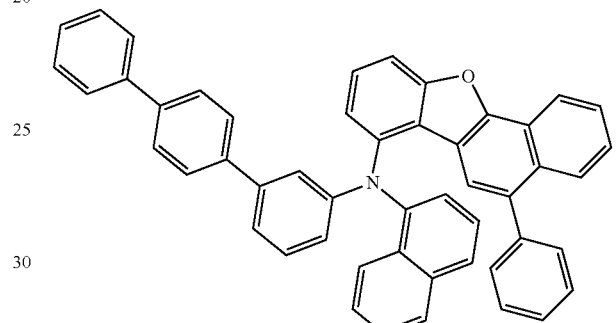
HT-20
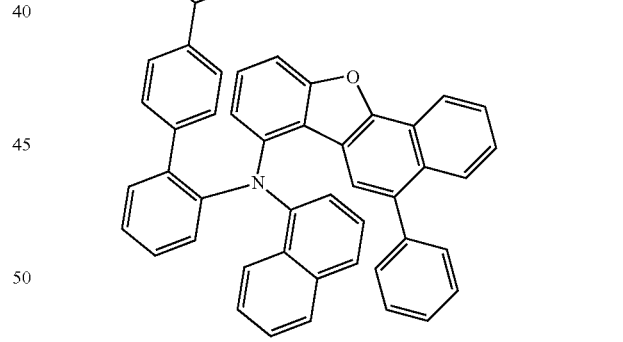
HT-21
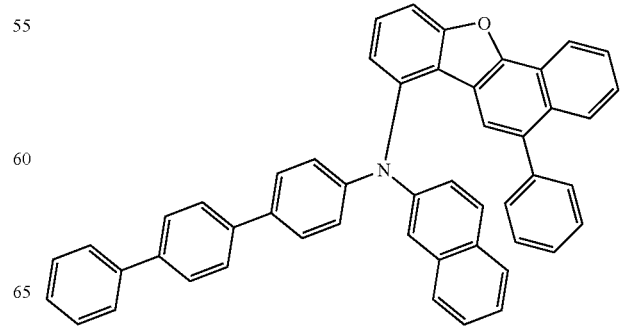

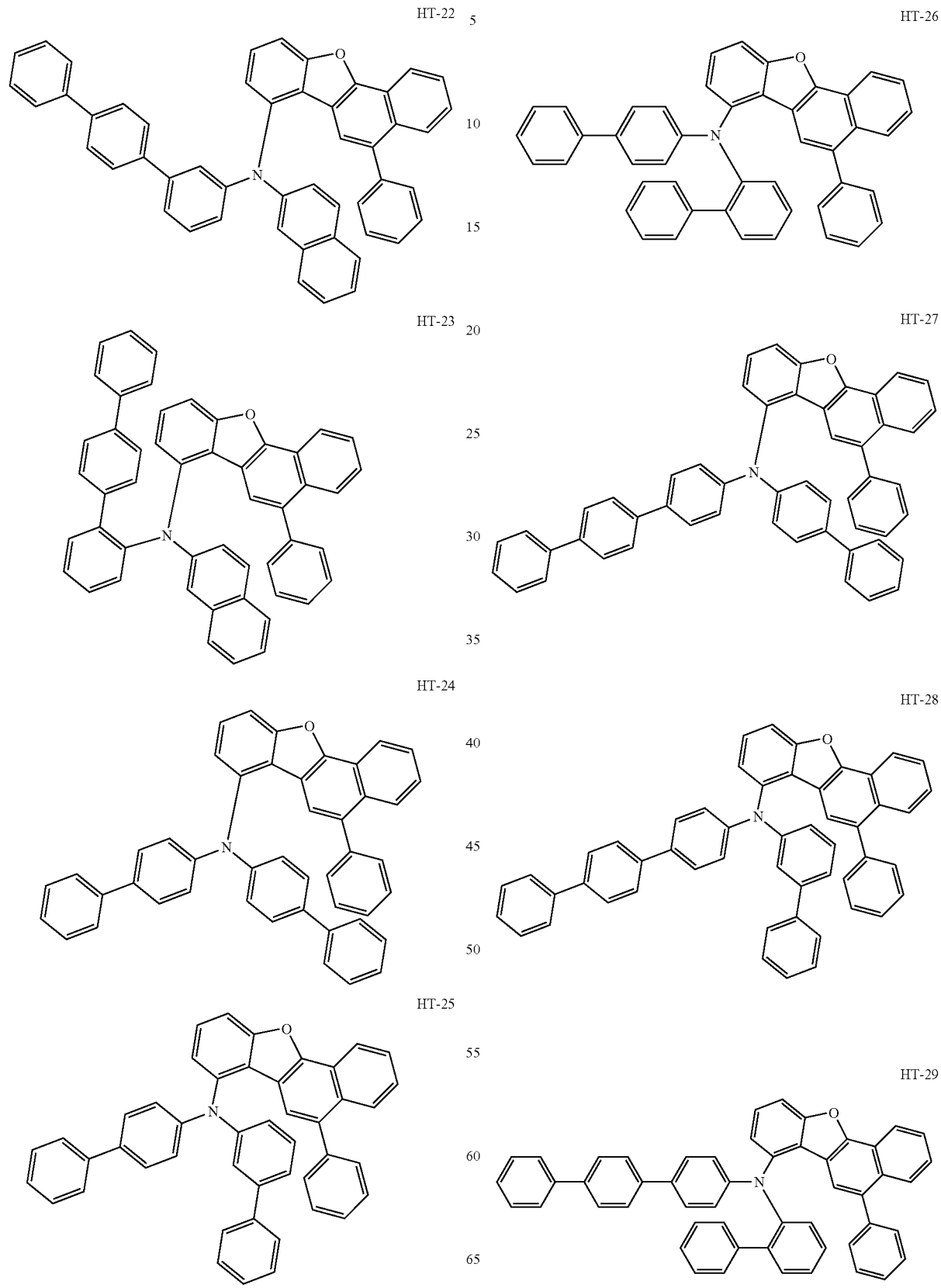

-continued
HT-30
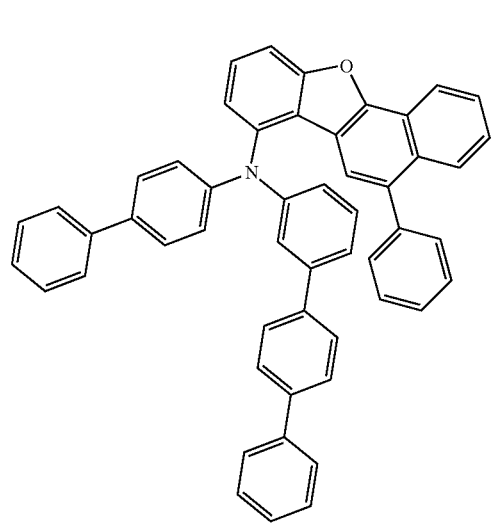
HT-31
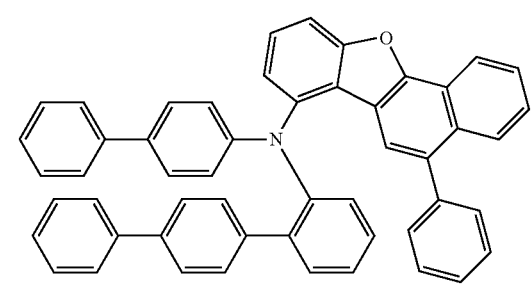
HT-32
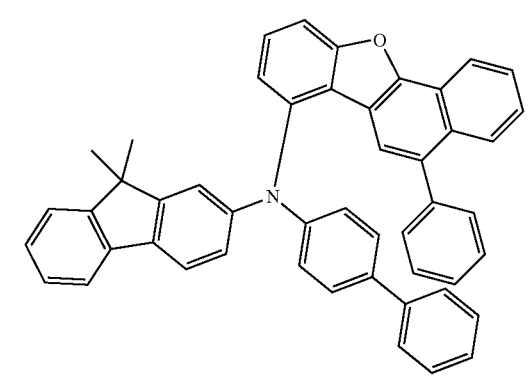
HT-33
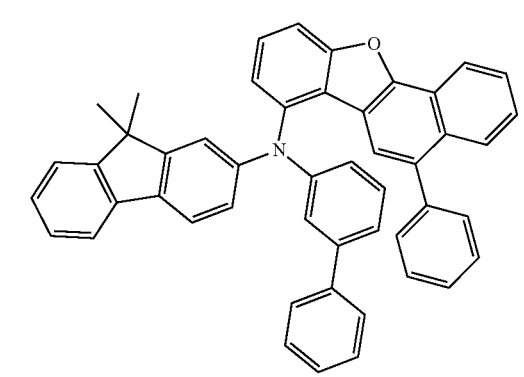
-continued
HT-34
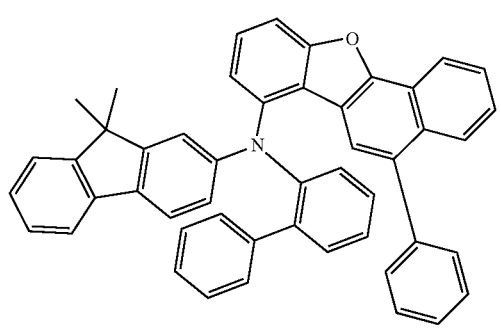
HT-35
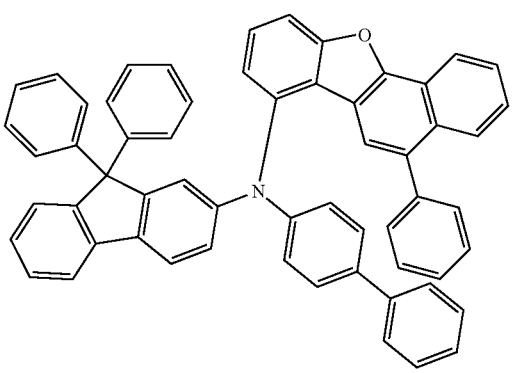
HT-36
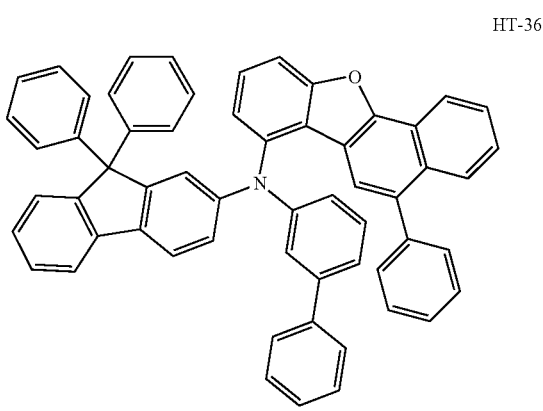
HT-37
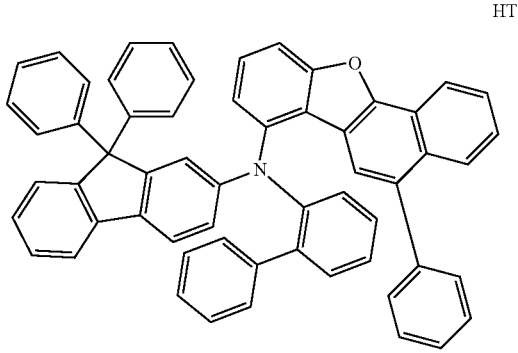

HT-38
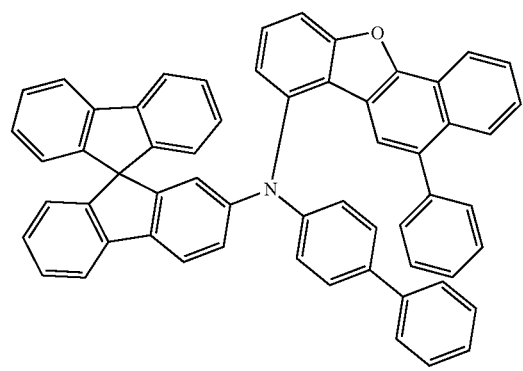
HT-39
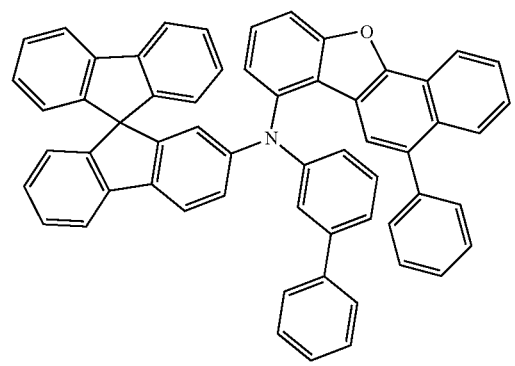
HT-40
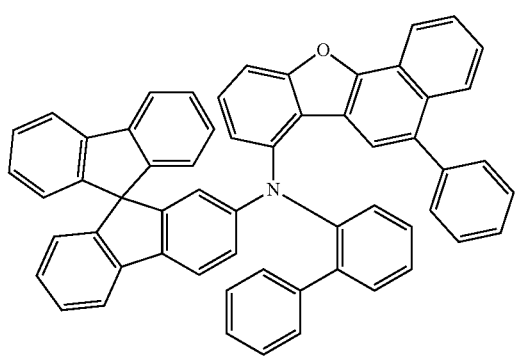
HT-41
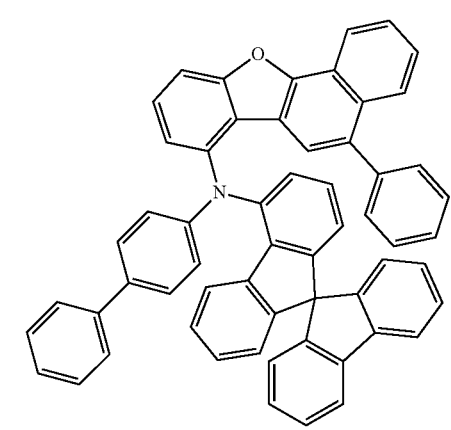
HT-42
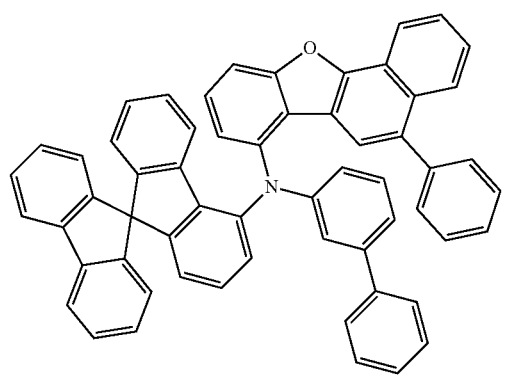
HT-43
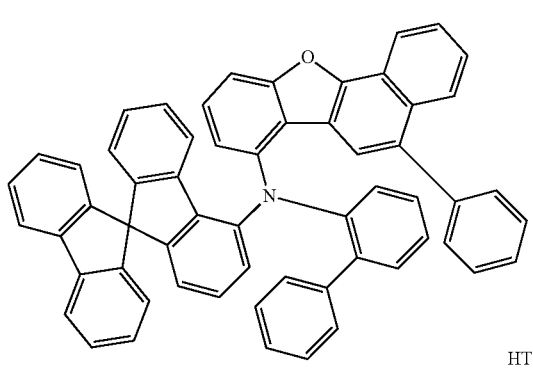
HT-44
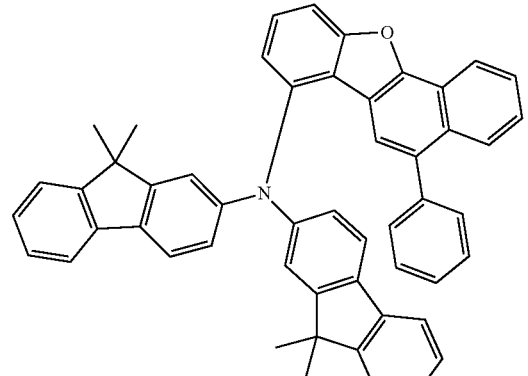
HT-45
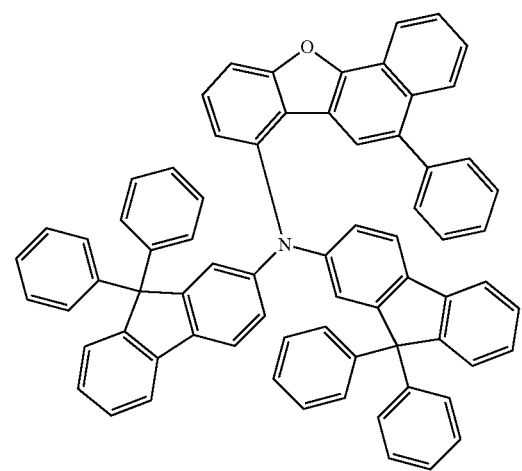

HT-46
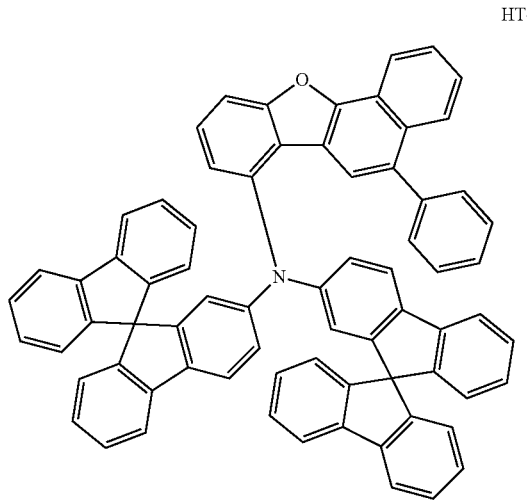
HT-47
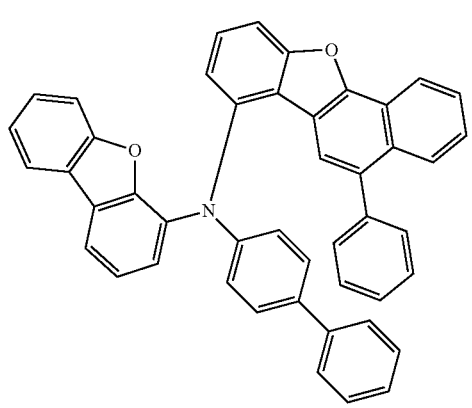
HT-48
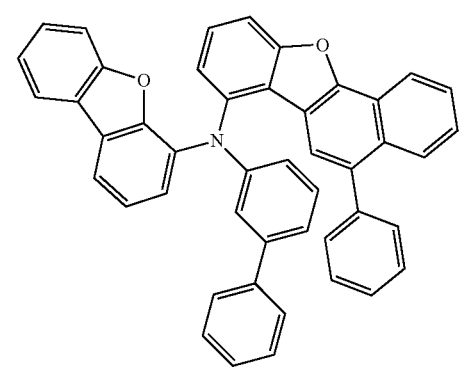
HT-49
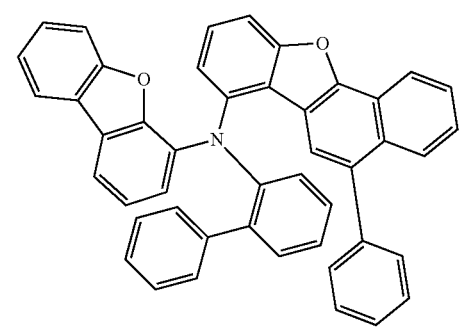
HT-50
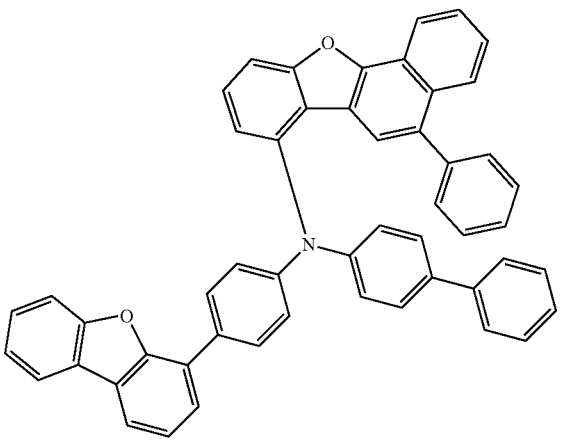
HT-51
HT-52
HT-53
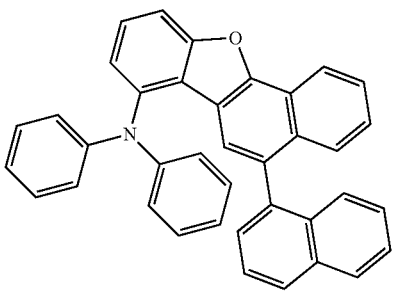

HT-54
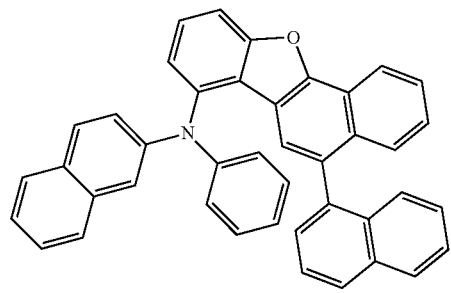
HT-55
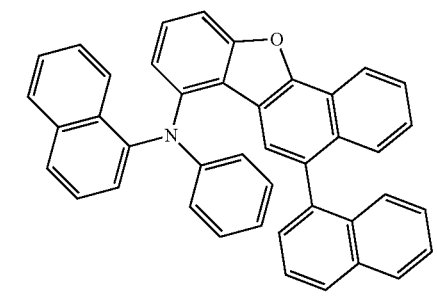
HT-56
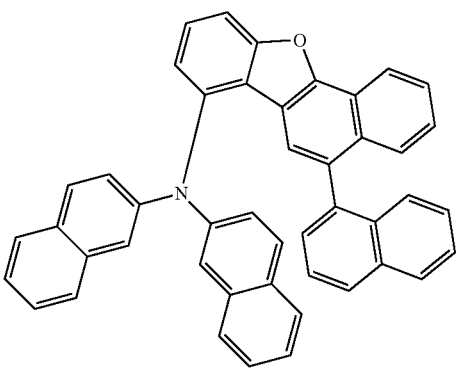
HT-57
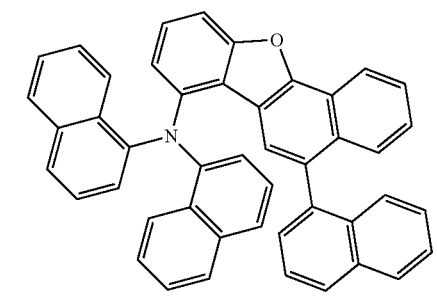
HT-58
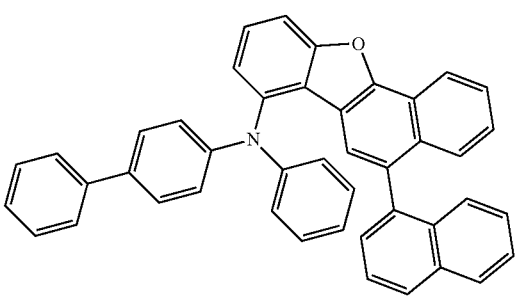
HT-59
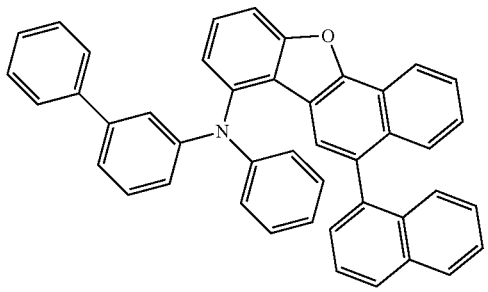
HT-60
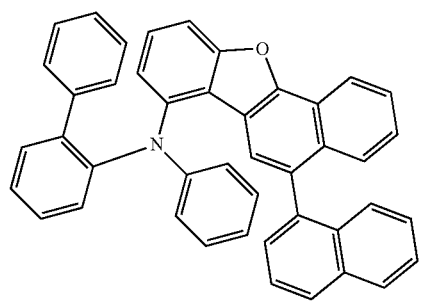
HT-61
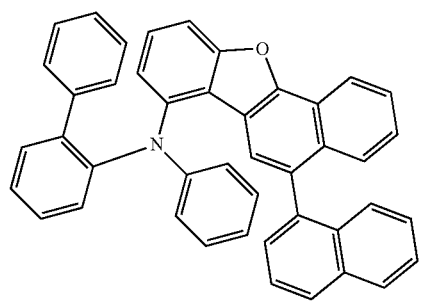
HT-62
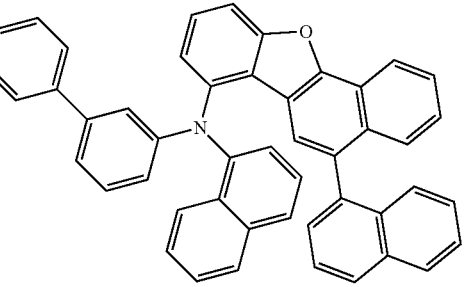
HT-63
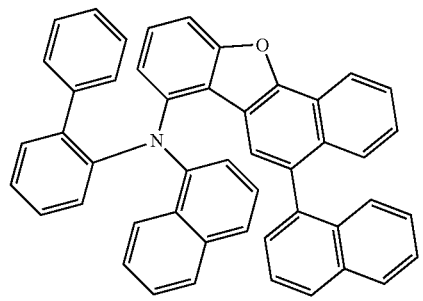

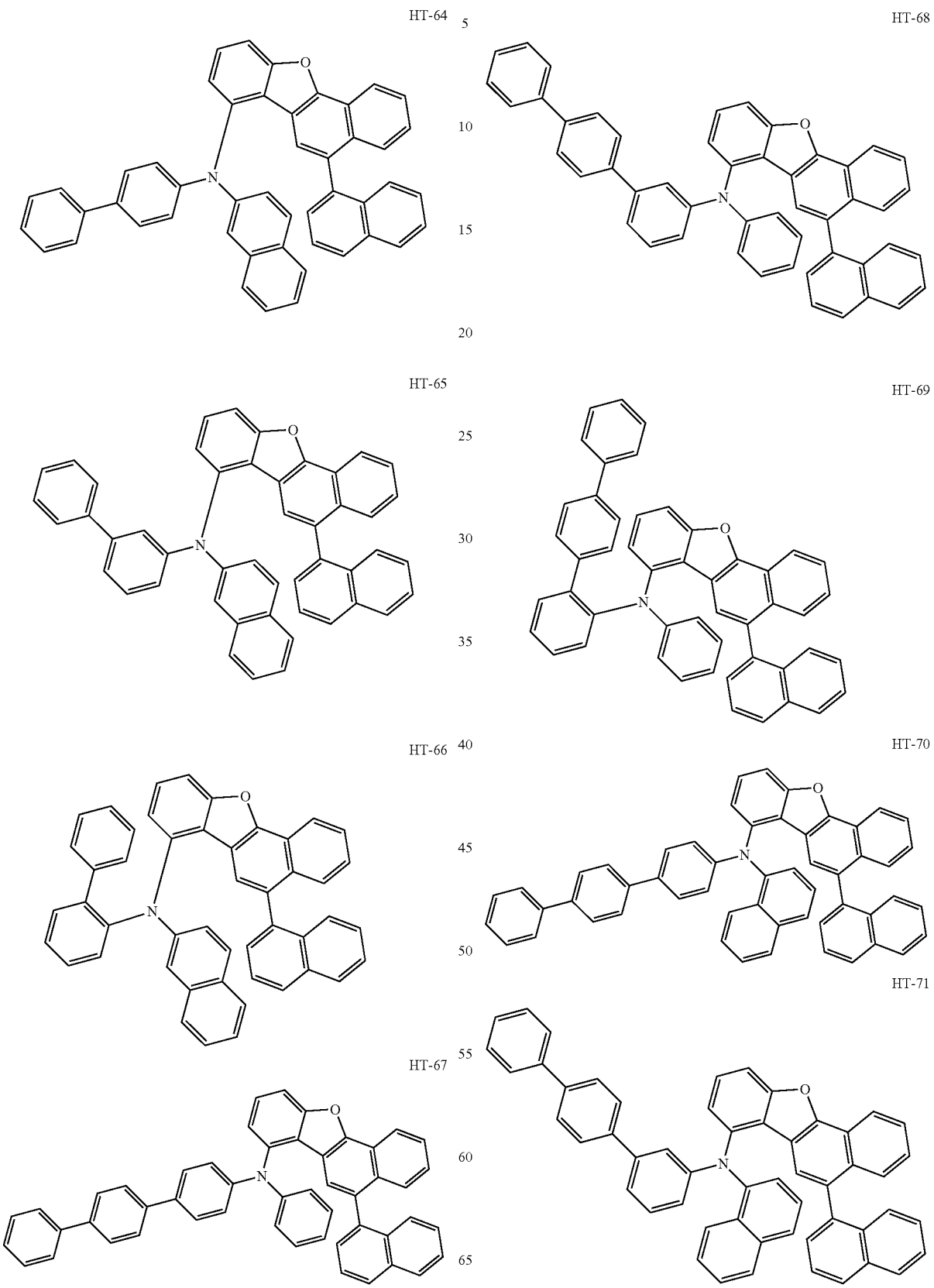

HT-72
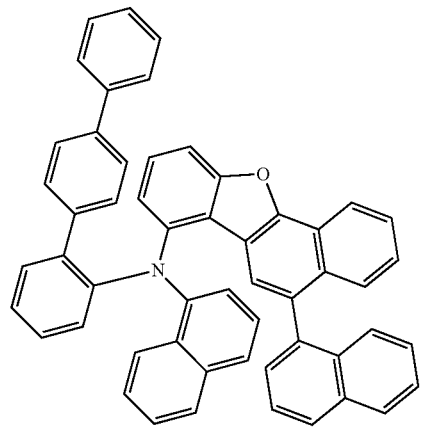
HT-73
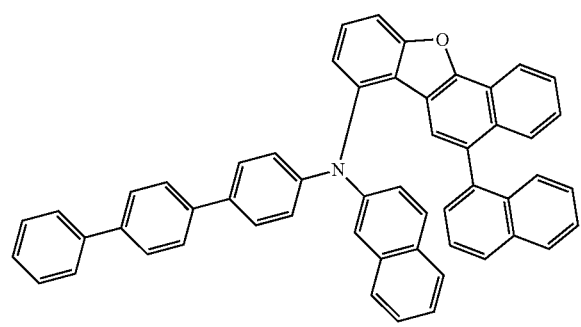
HT-74
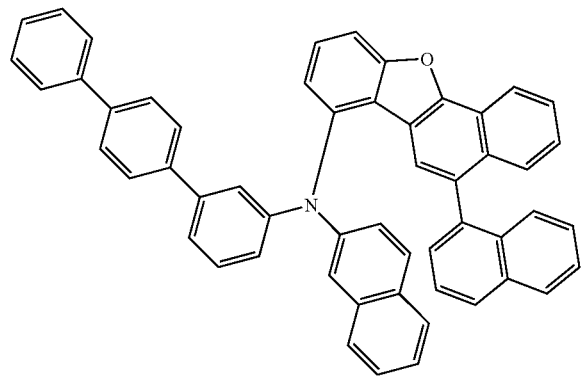
HT-75
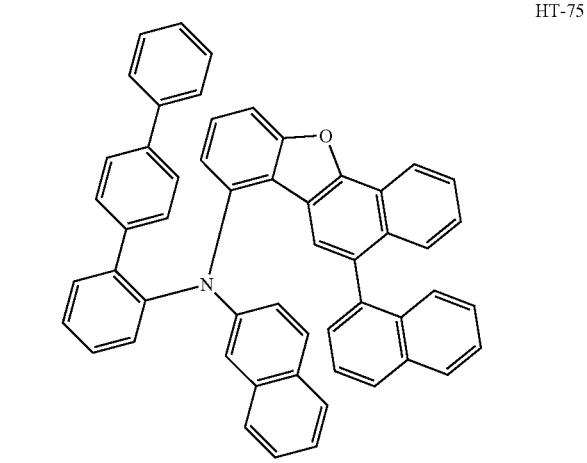
HT-76
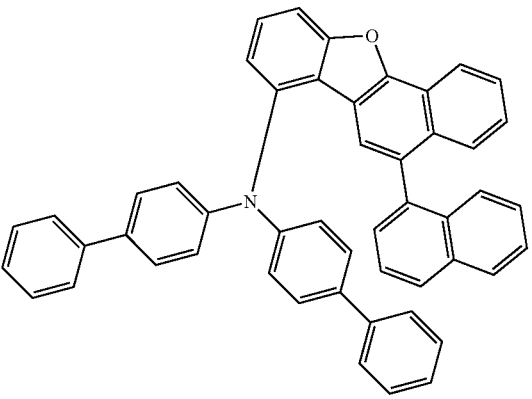
HT-77
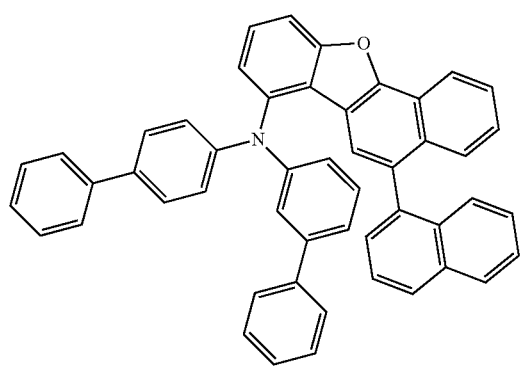
HT-78
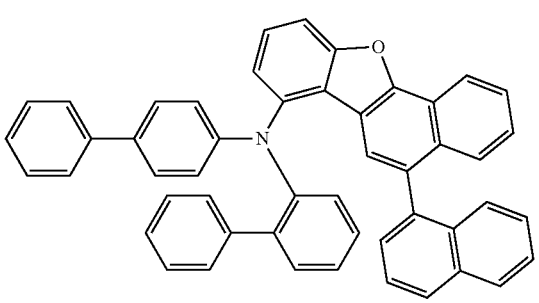
HT-79
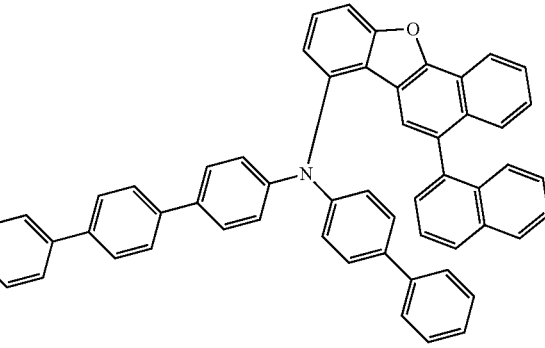

-continued
HT-80
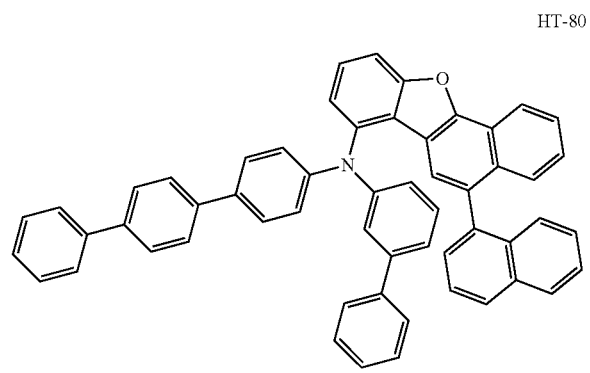
HT-81
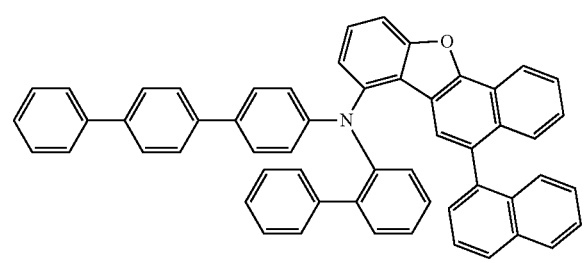
HT-82
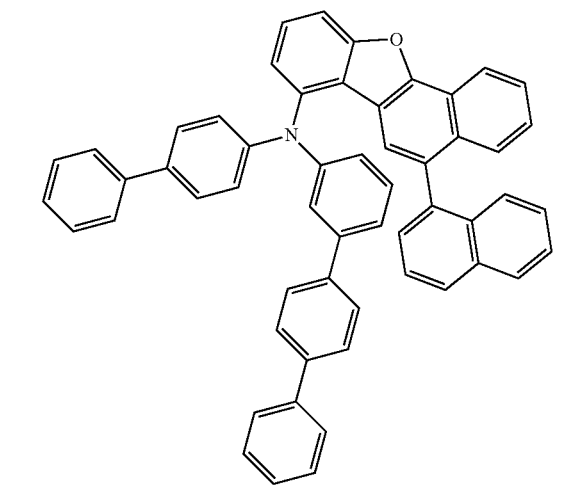
HT-83
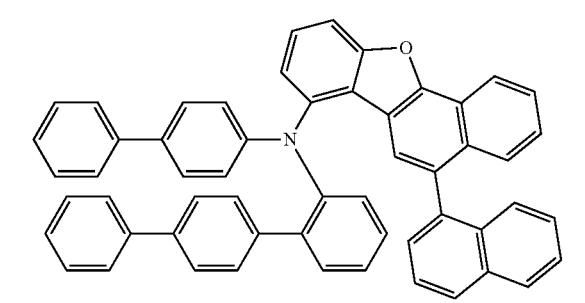
-continued
HT-84
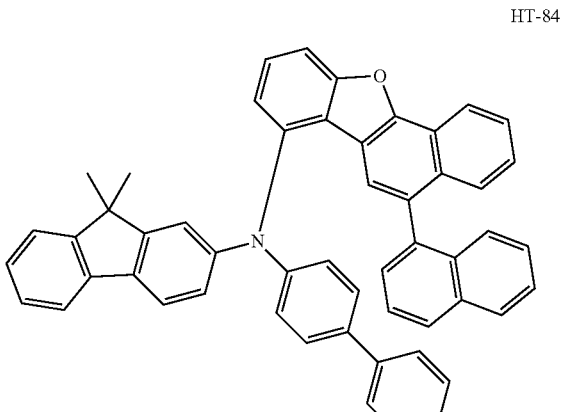
HT-85
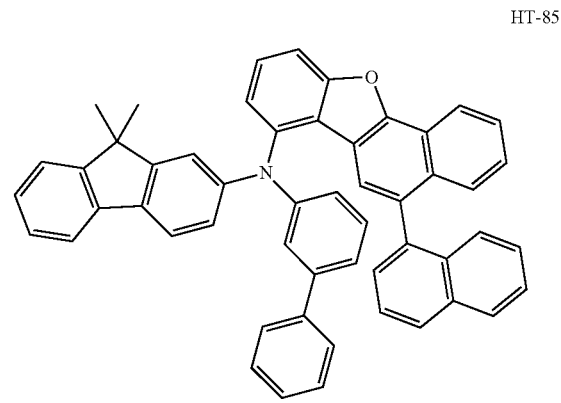
HT-86
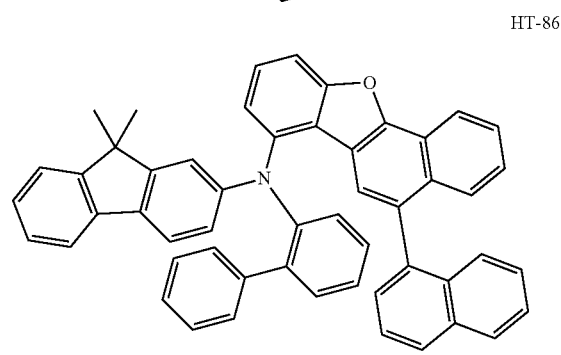
HT-87
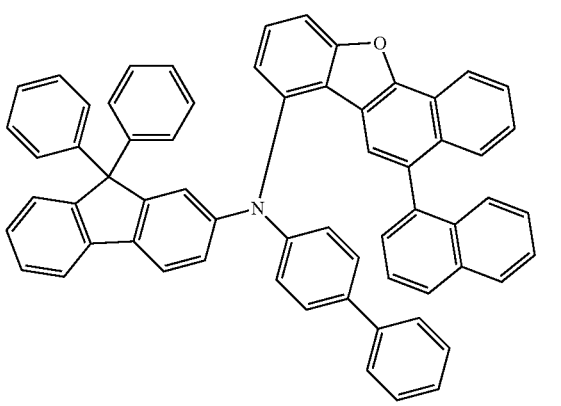

-continued
HT-88
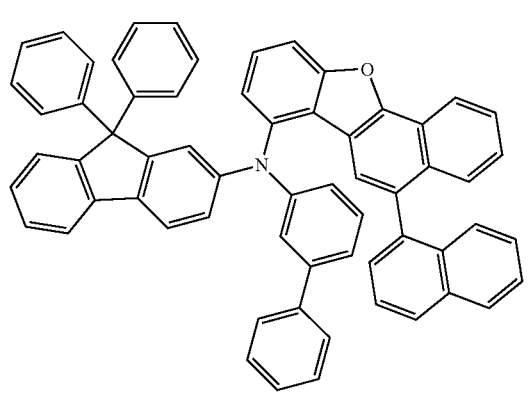
HT-89
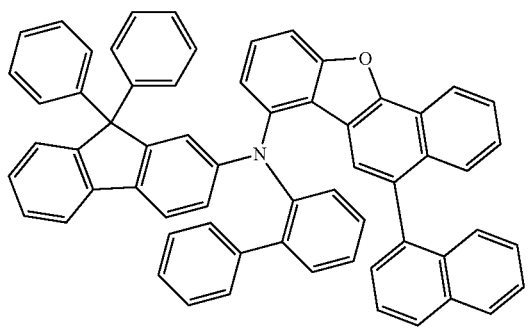
HT-90
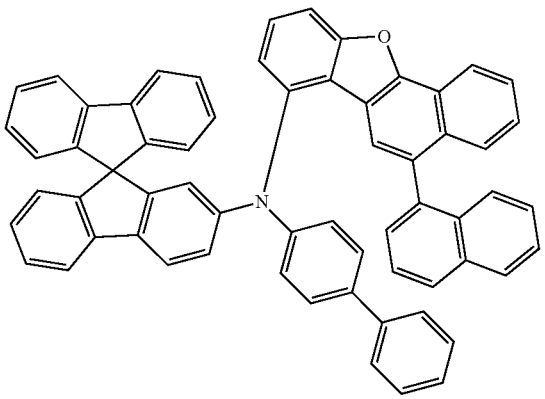
HT-91
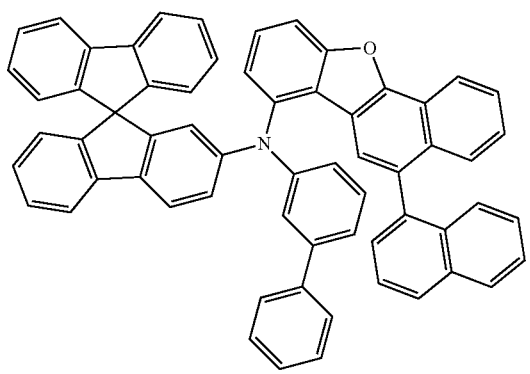
-continued
HT-92
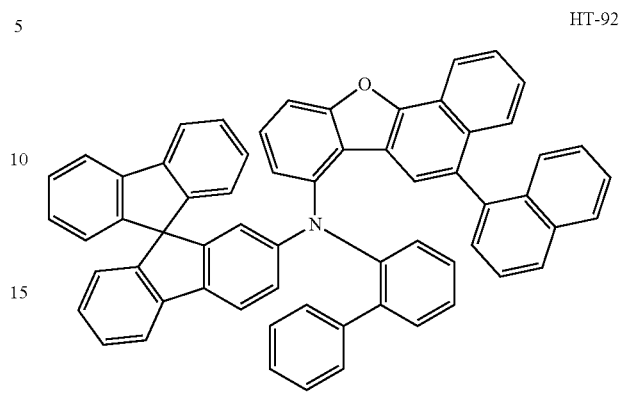
HT-93
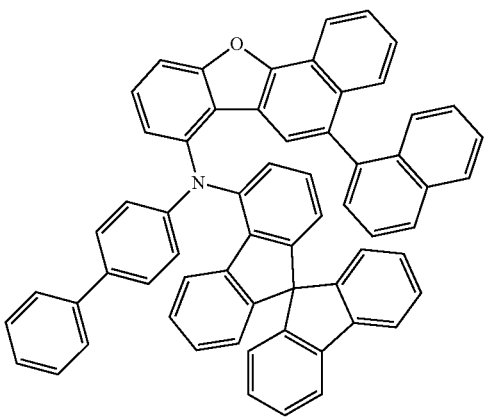
HT-94
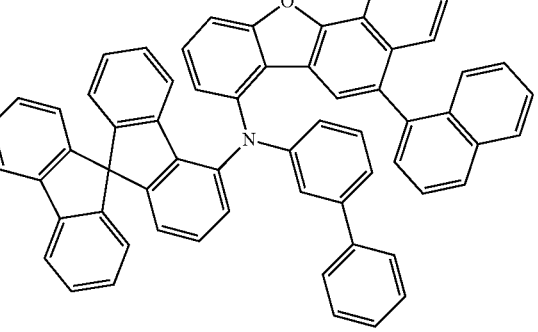
HT-95
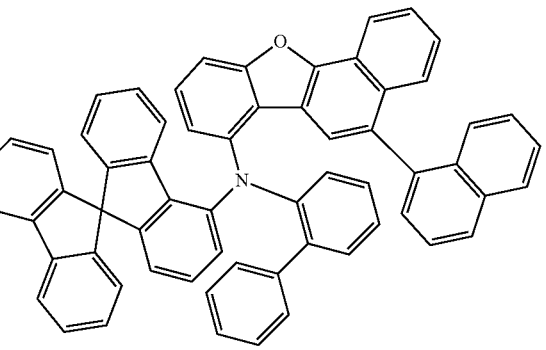

HT-96
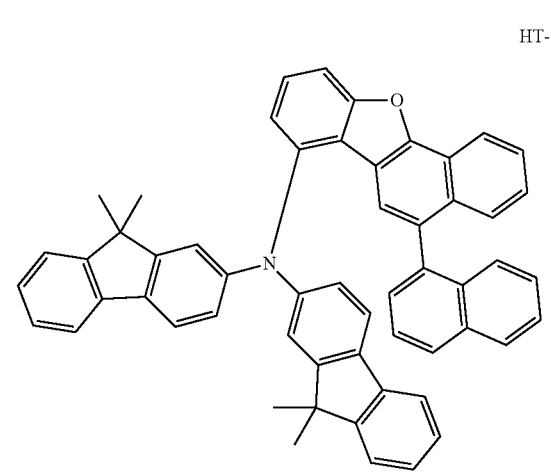
HT-97
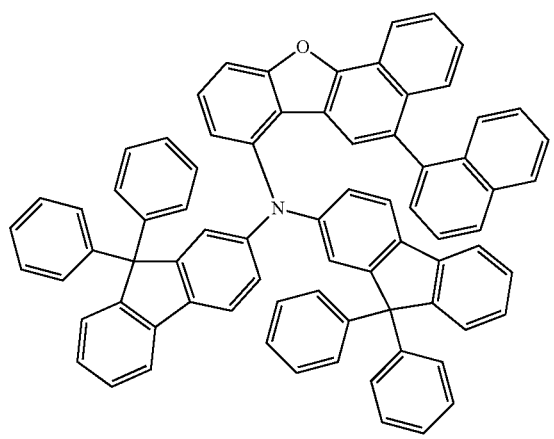
HT-98
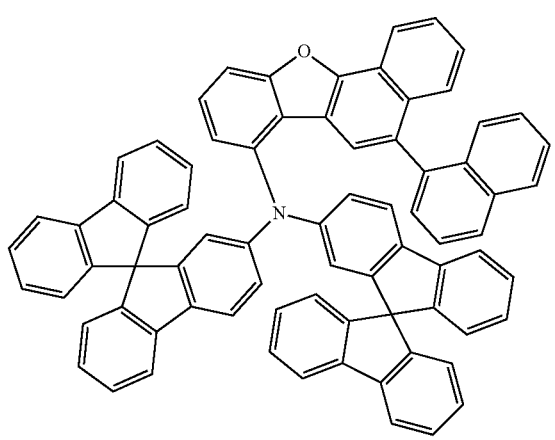
HT-99
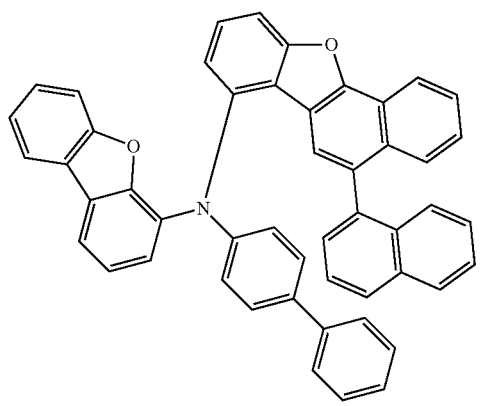
HT-100
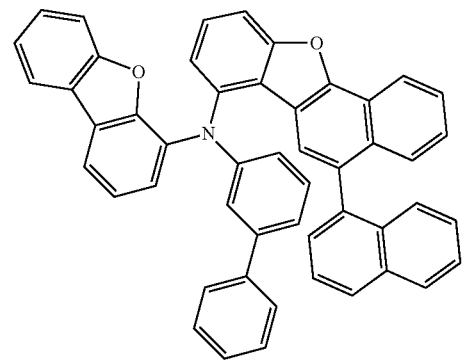
HT-101
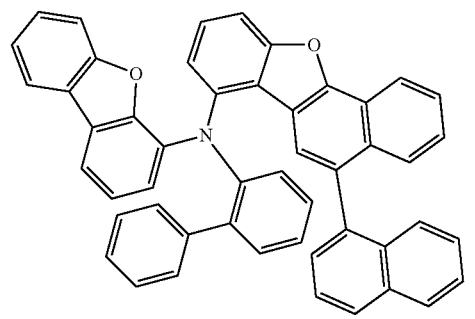
HT-102
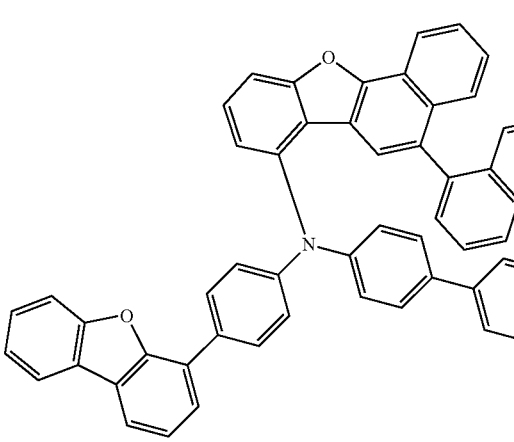

-continued
HT-103
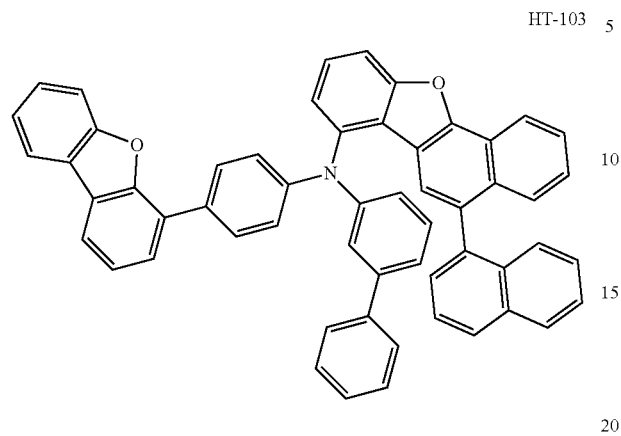
HT-104
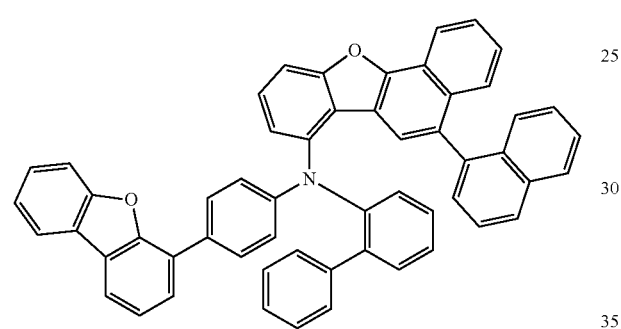
HT-105
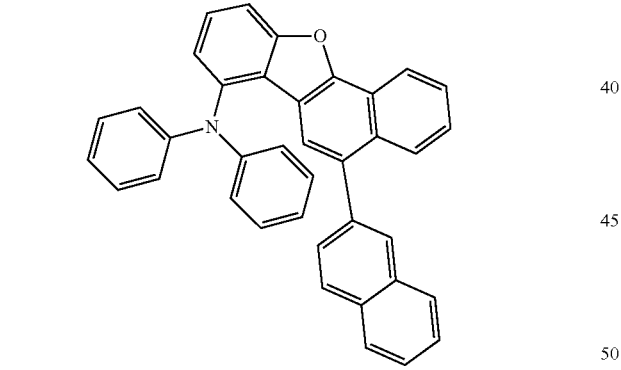
HT-106
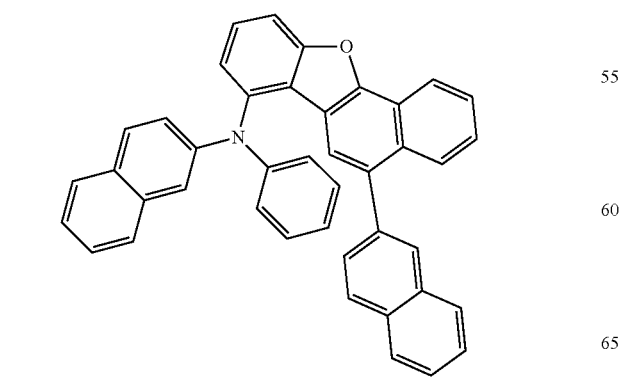
-continued
HT-107
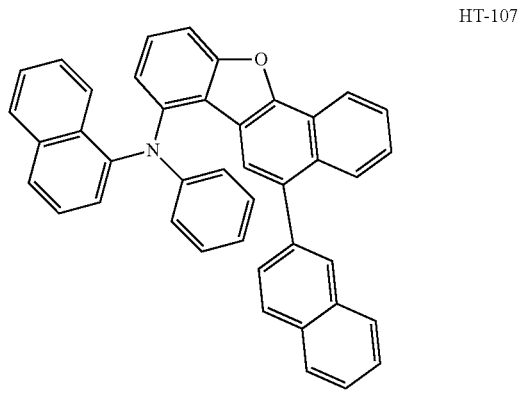
HT-108
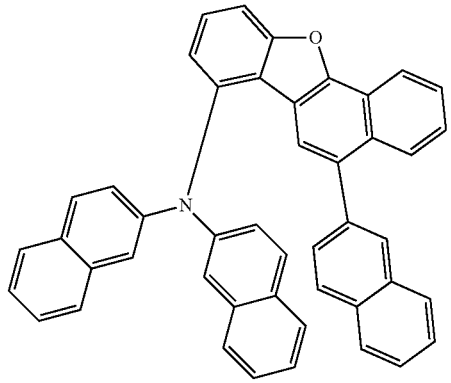
HT-109
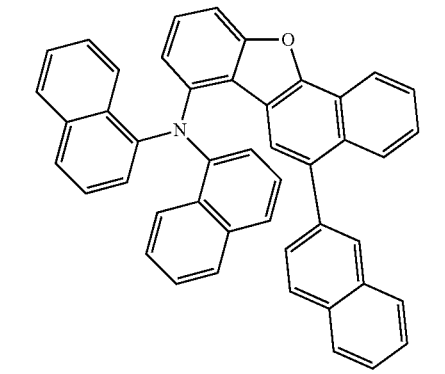
HT-110
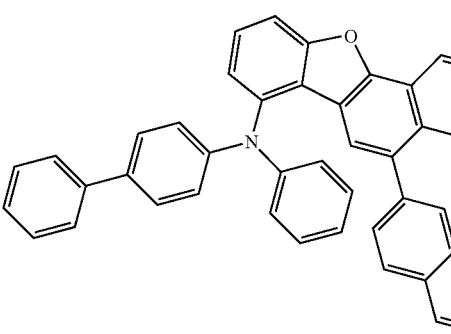

HT-111
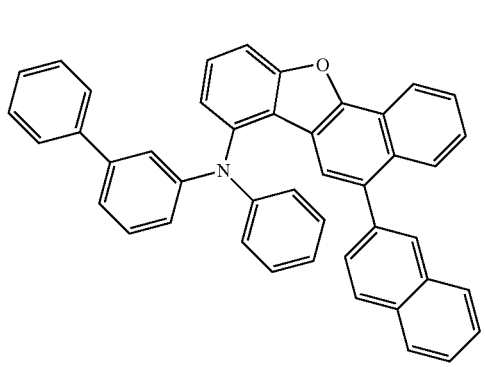
HT-112
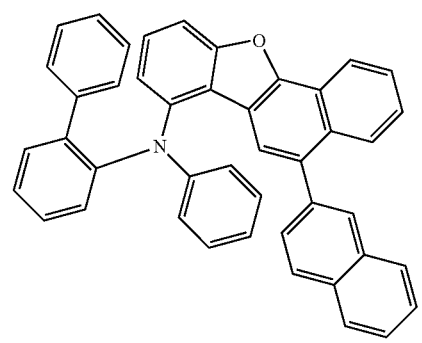
HT-113
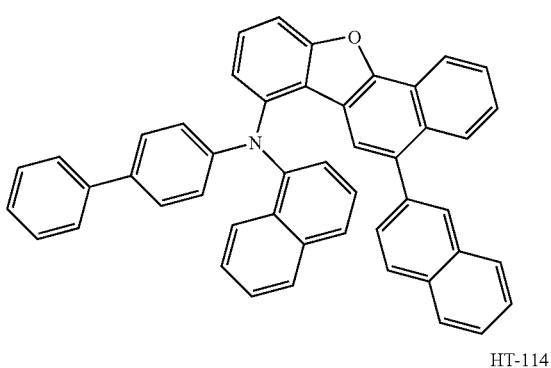
HT-114
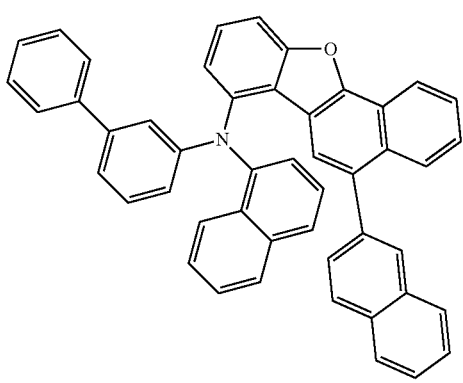
HT-115
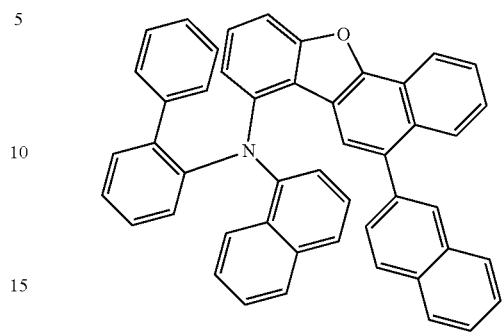
HT-116
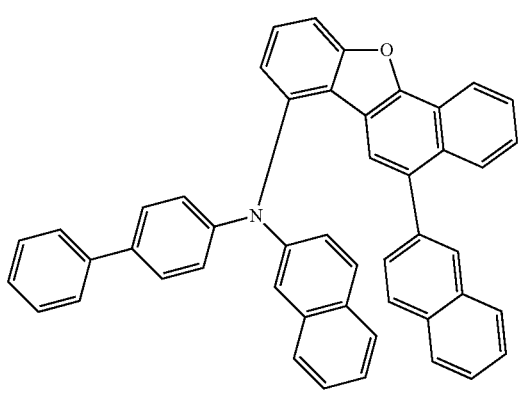
HT-117
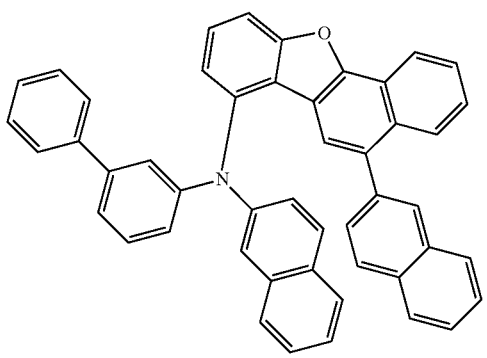
HT-118
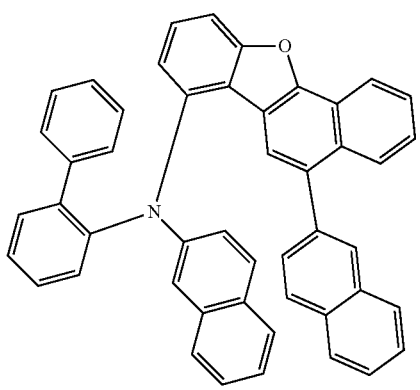

HT-119
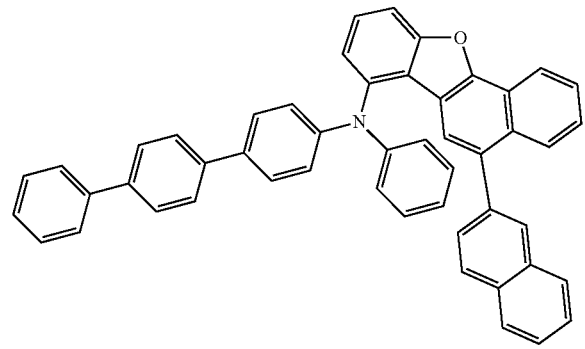
HT-120
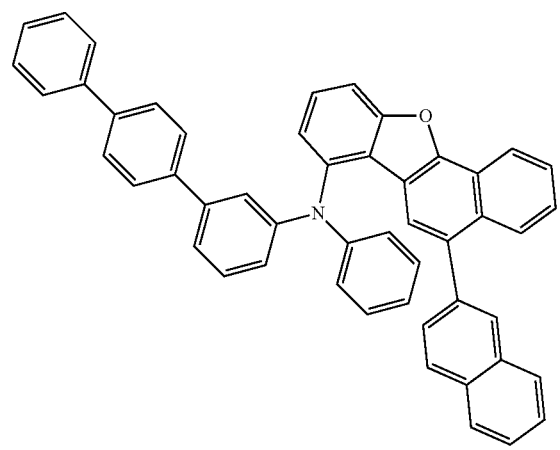
HT-121
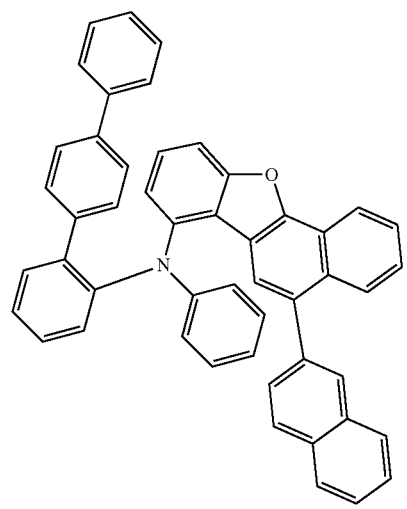
HT-122
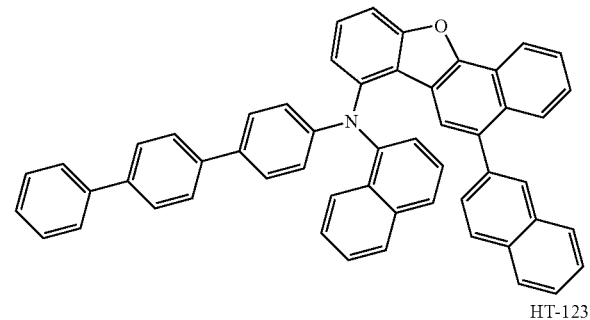
HT-123
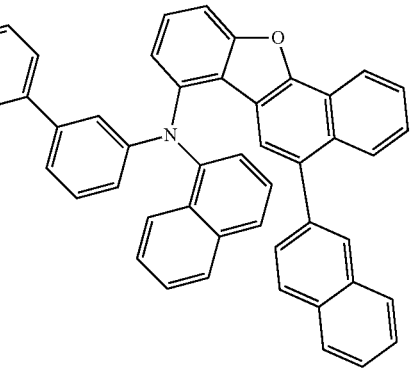
HT-124
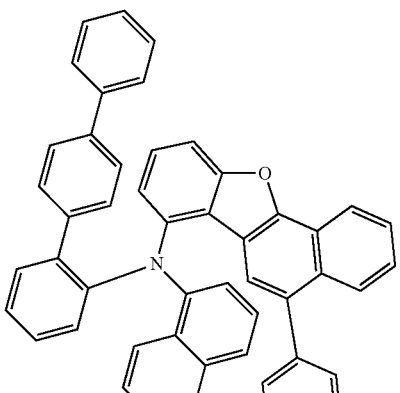
HT-125
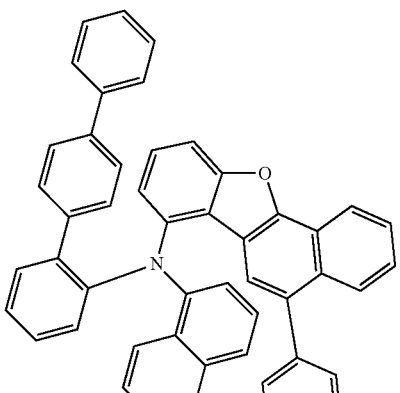

HT-126
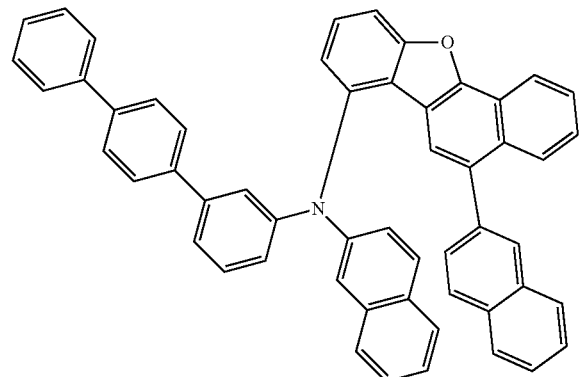
HT-130
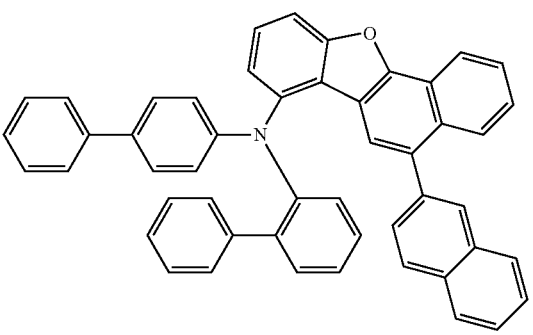
HT-127
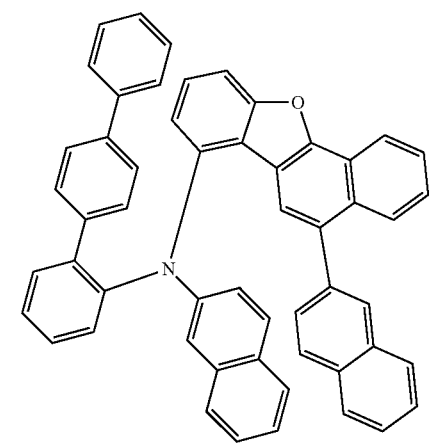
HT-131
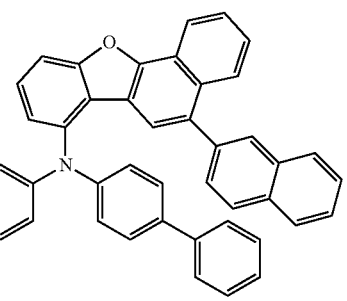
HT-128
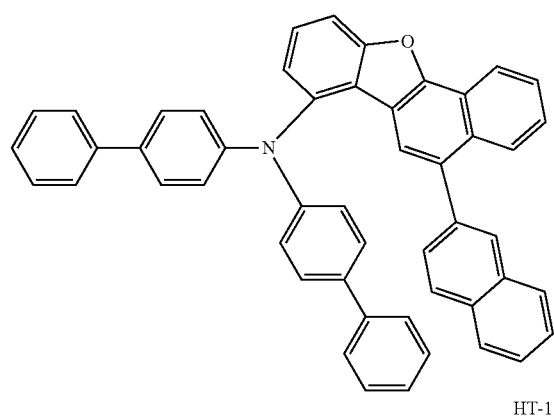
HT-132
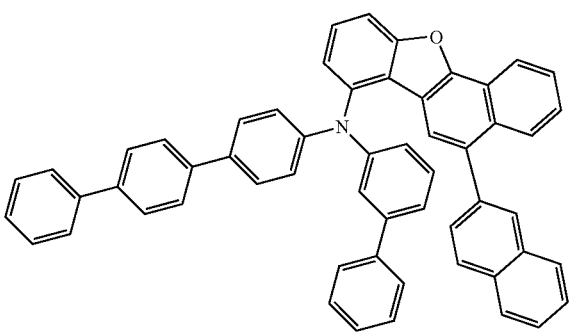
HT-129
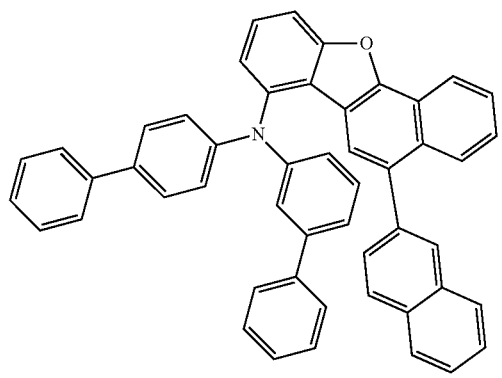
HT-133
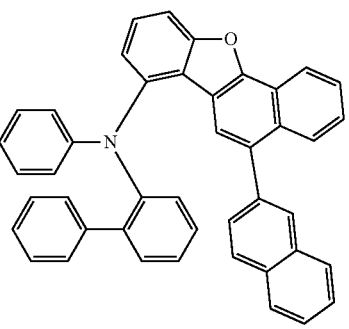

HT-134
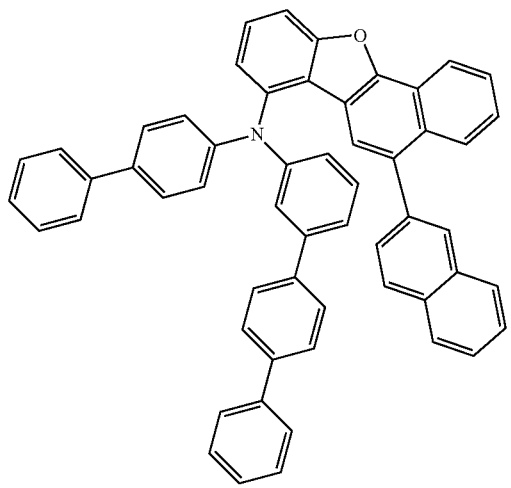
HT-135
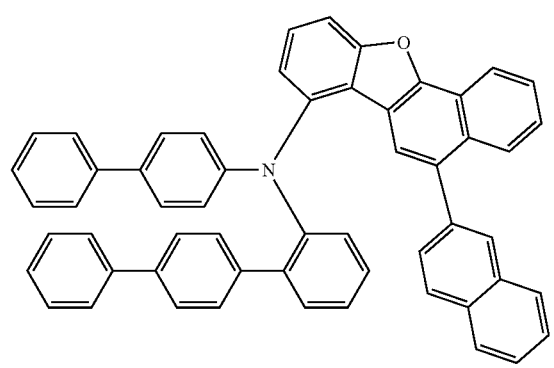
HT-136
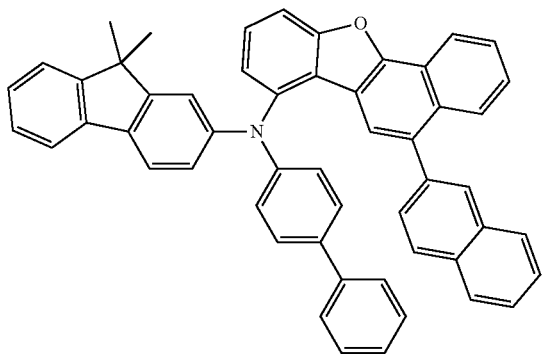
HT-137
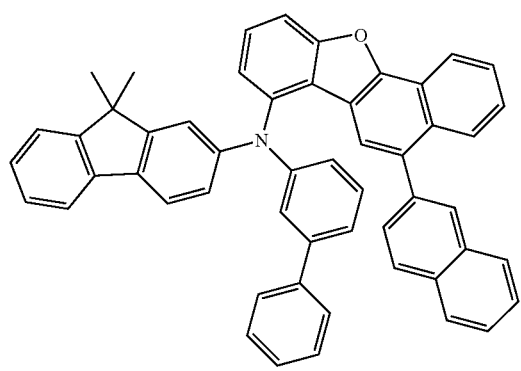
HT-138
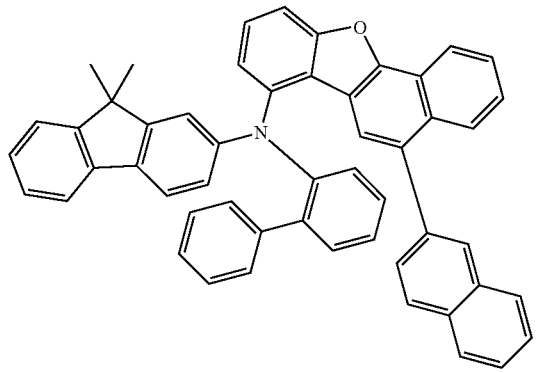
HT-139
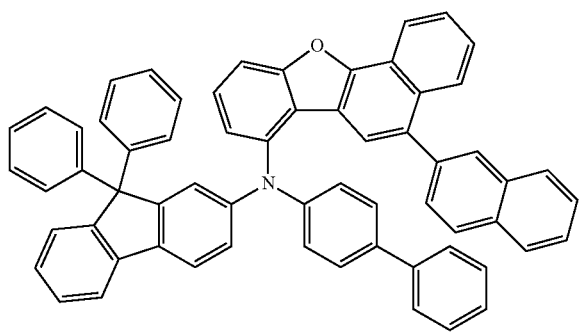
HT-140
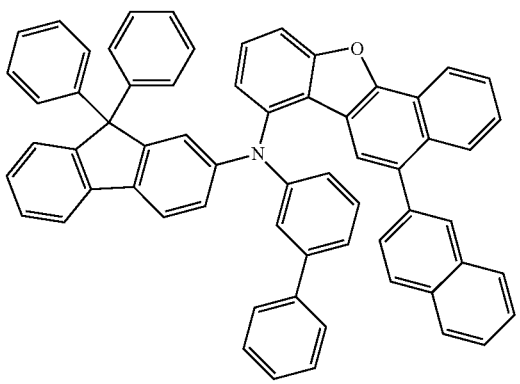
HT-141
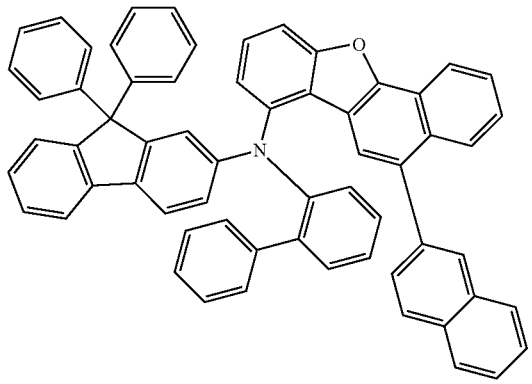

HT-142
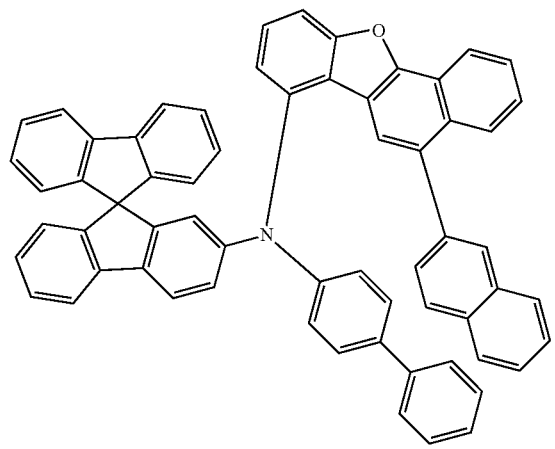
HT-143
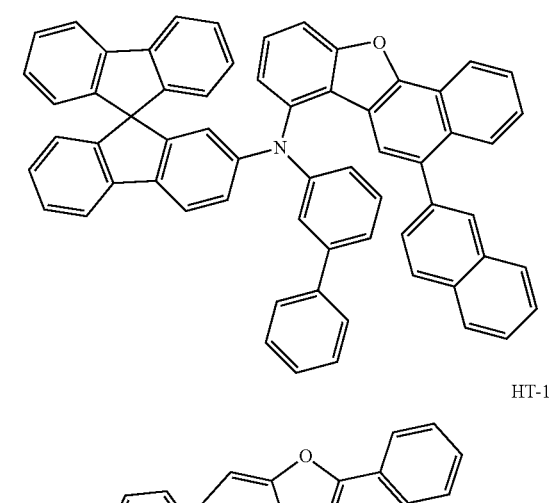
HT-144
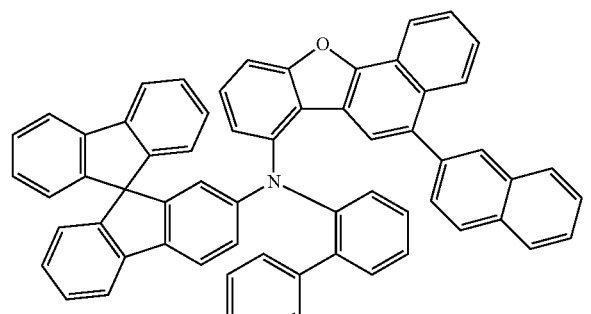
HT-145
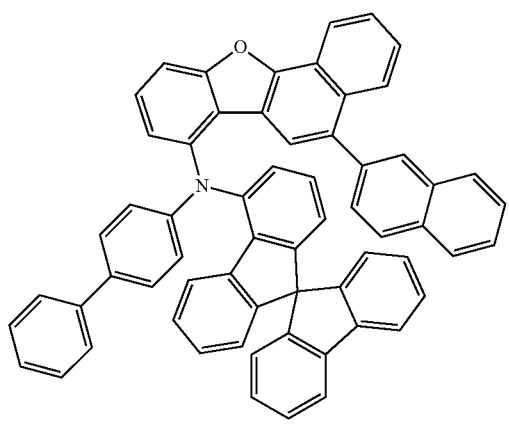
HT-146
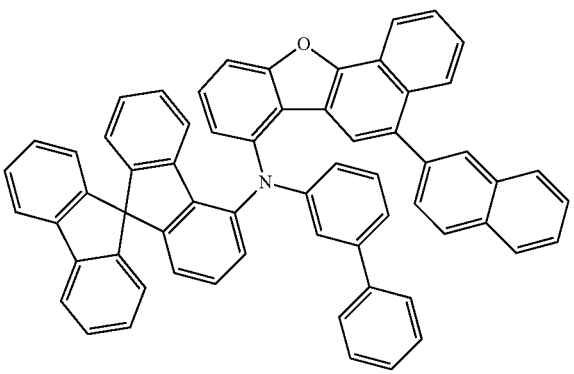
HT-147
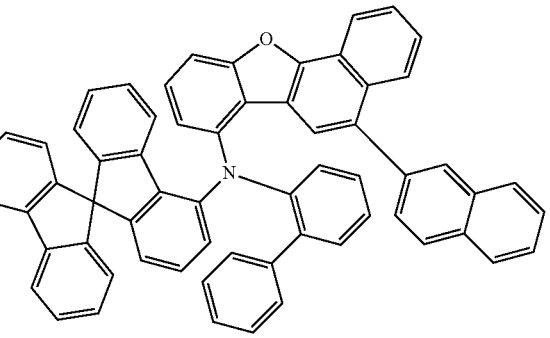
HT-148
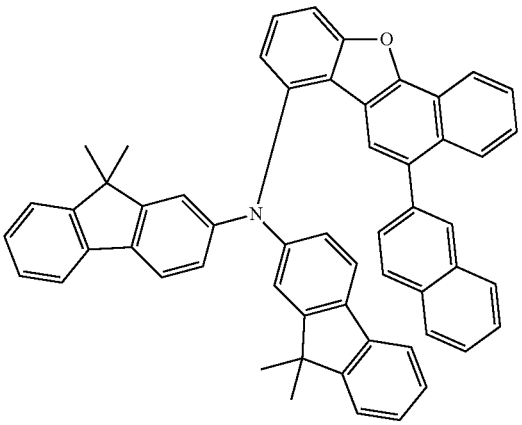

-continued
HT-149
HT-150
HT-151
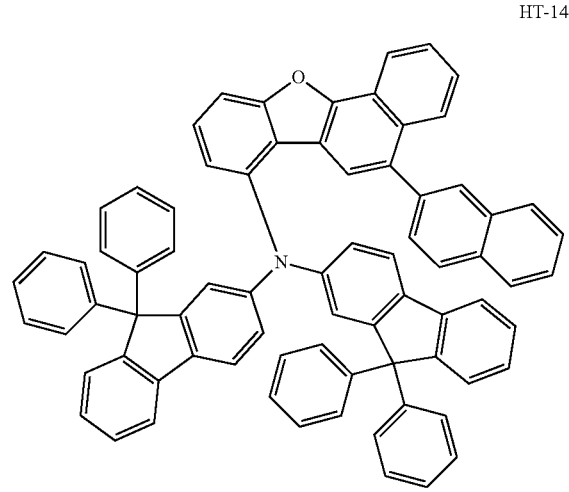
-continued
HT-152
HT-153
HT-154
HT-155
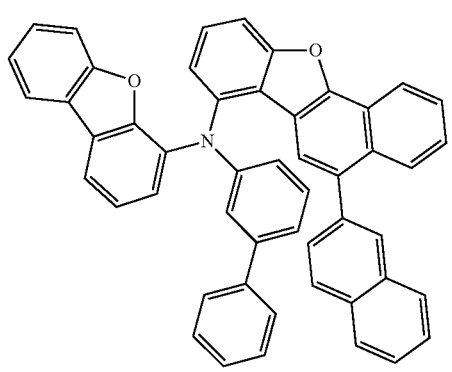

HT-156
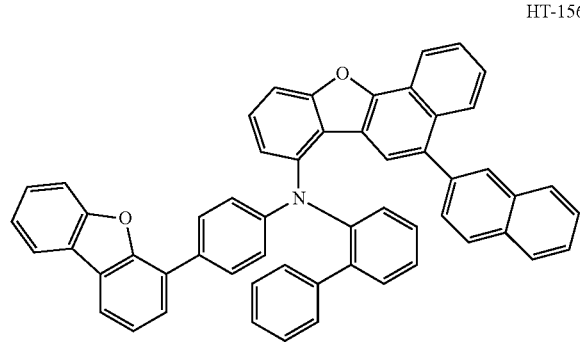
HT-157
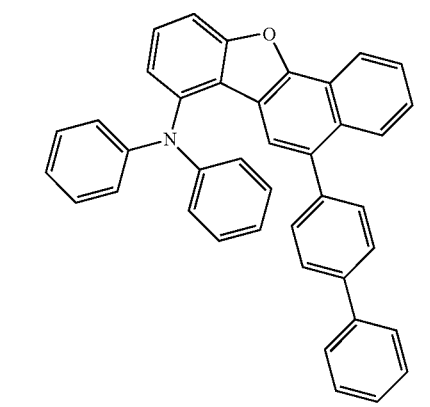
HT-158
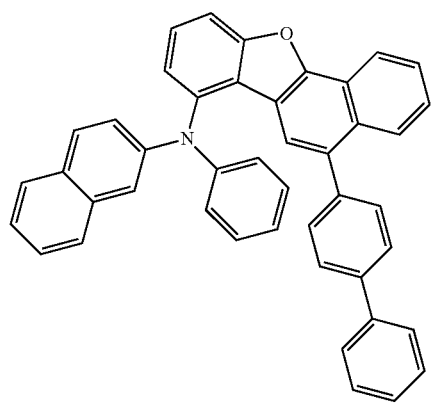
HT-160
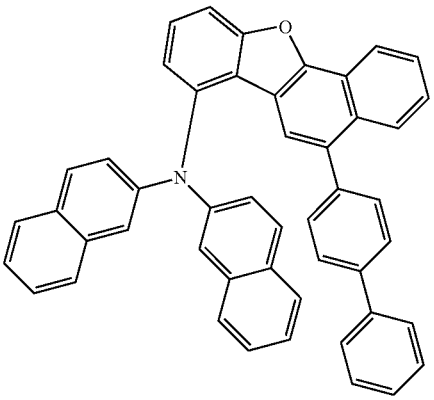
HT-161
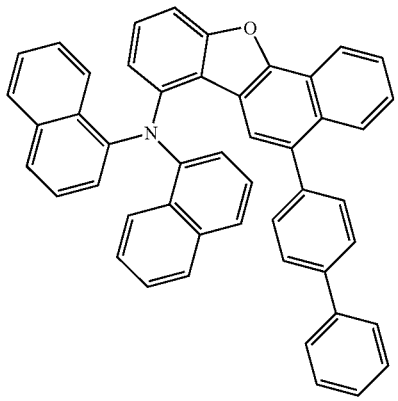
HT-162
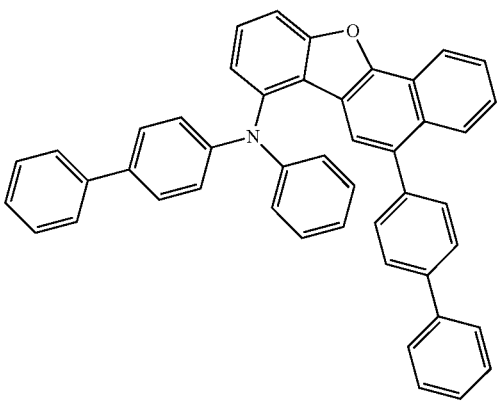
HT-159
HT-163

HT-164
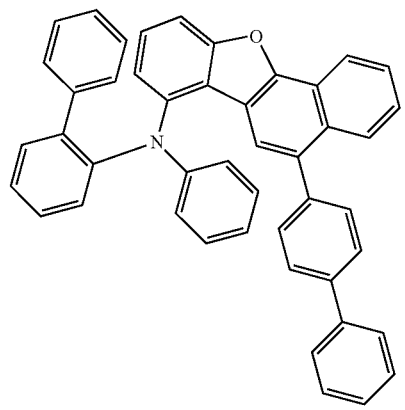
HT-165
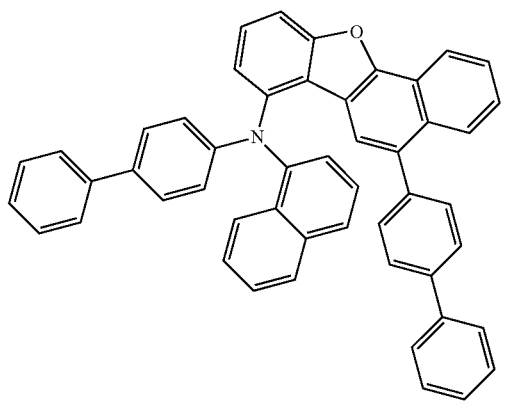
HT-166
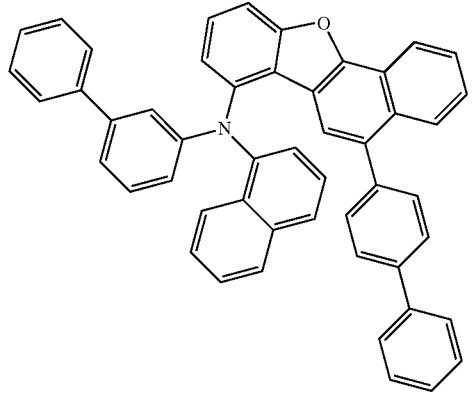
HT-167
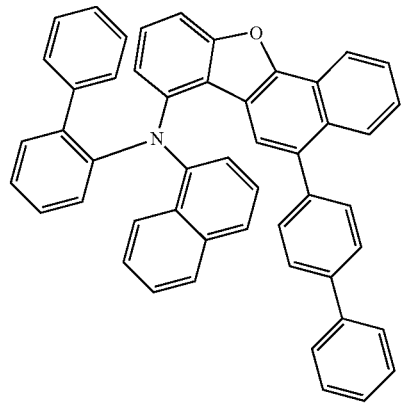
HT-168
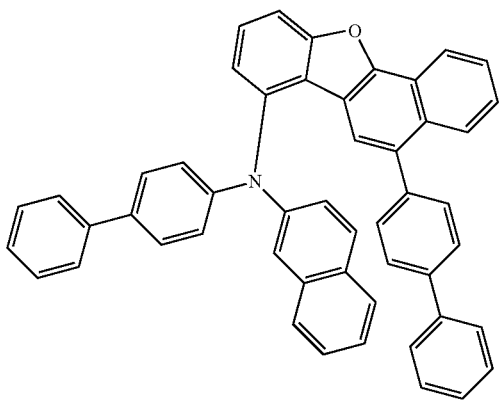
HT-169
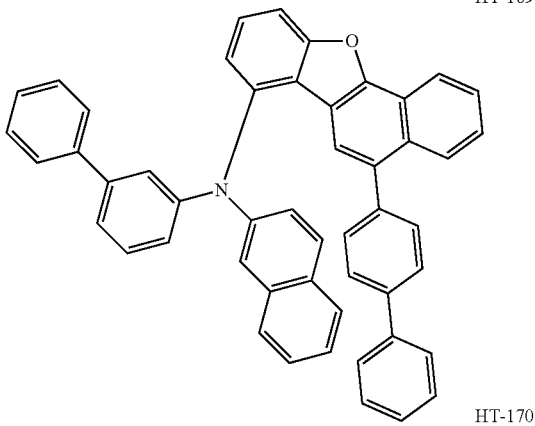
HT-170
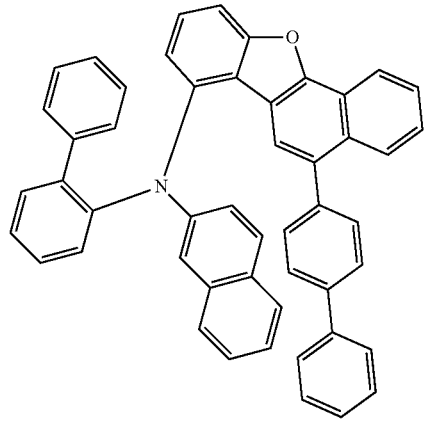
HT-171
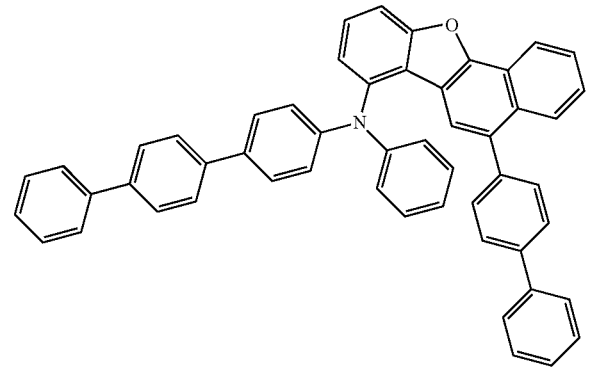

HT-172
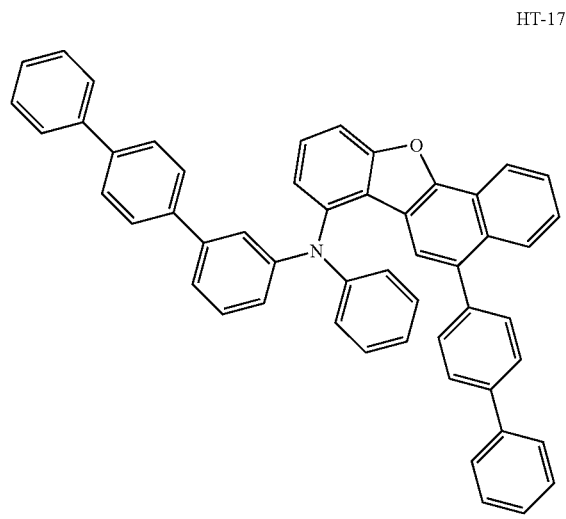
HT-175
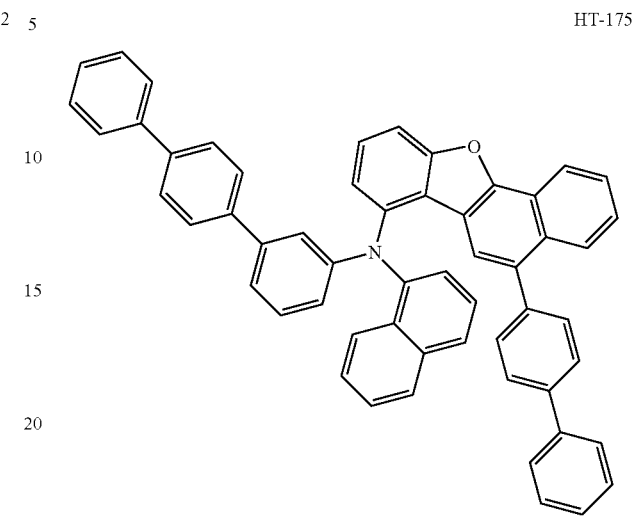
HT-173
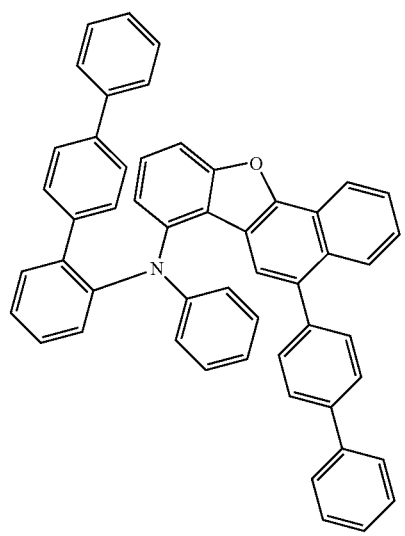
HT-176
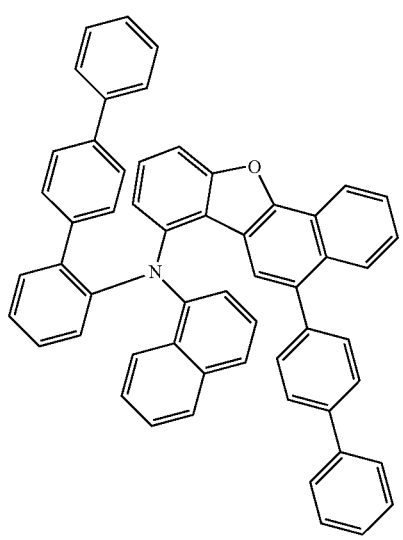
HT-174
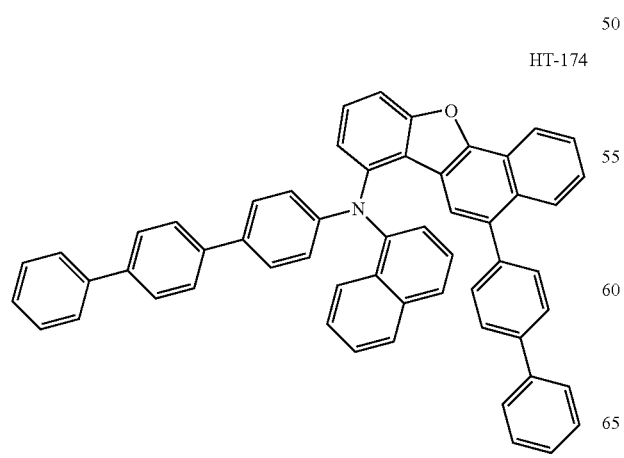
HT-177
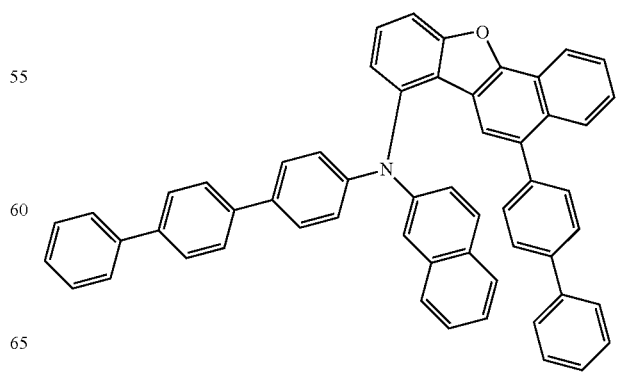

HT-178
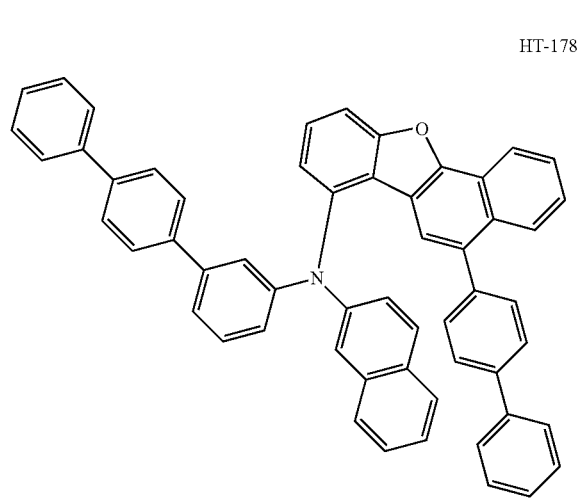
HT-179
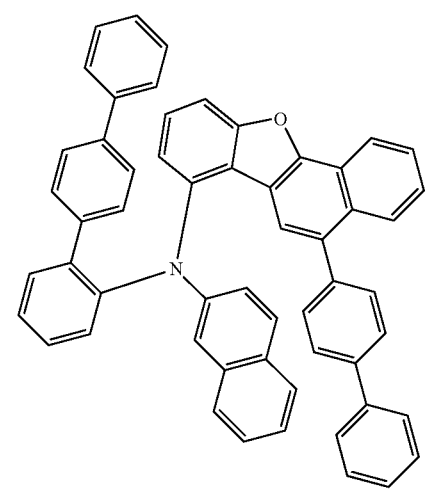
HT-180
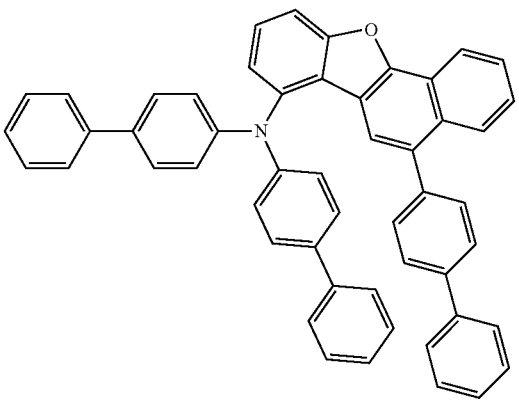
HT-181
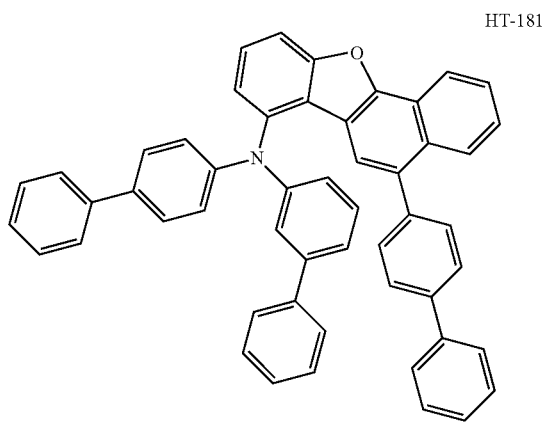
HT-182
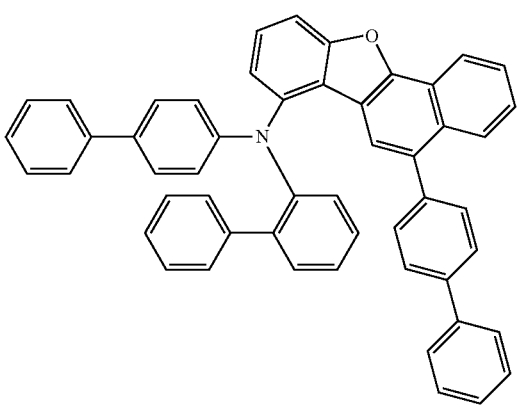
HT-183
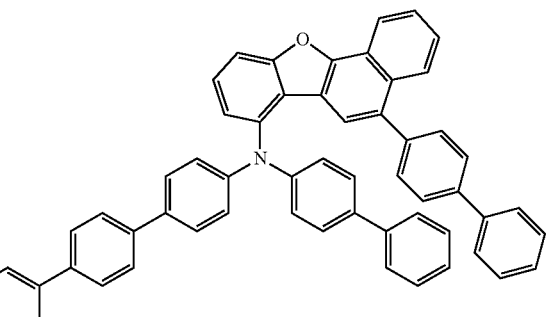
HT-184
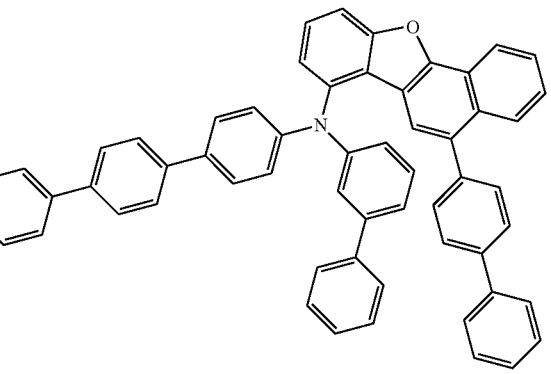

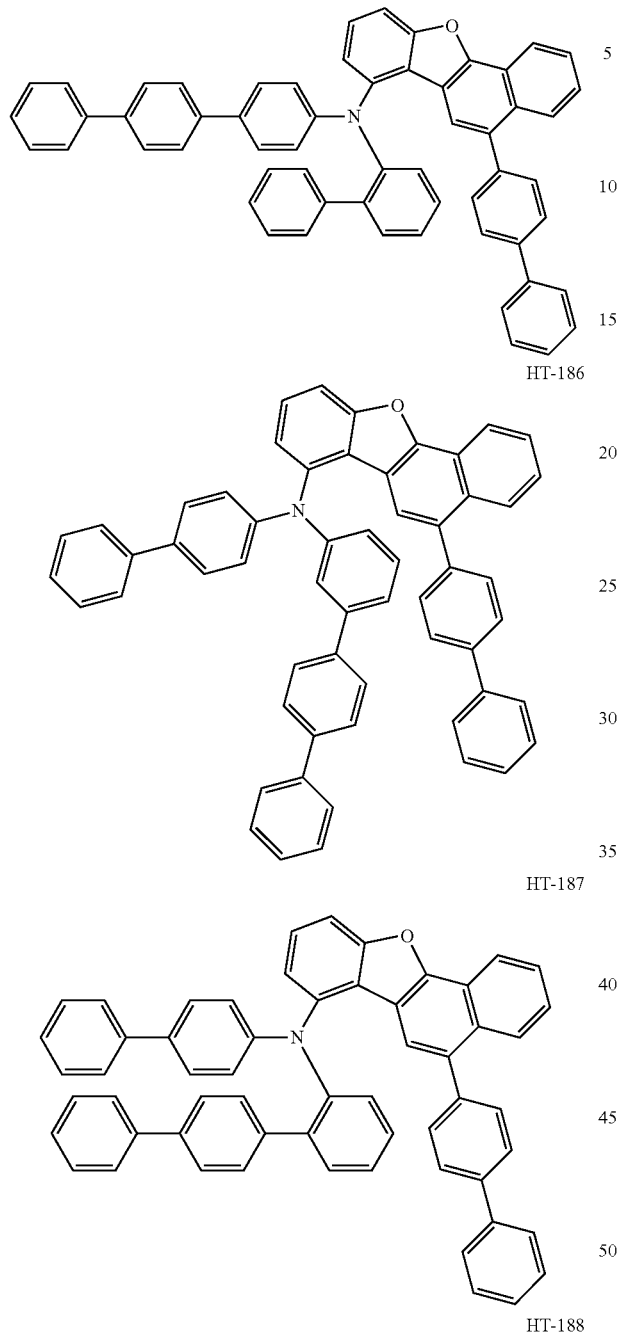
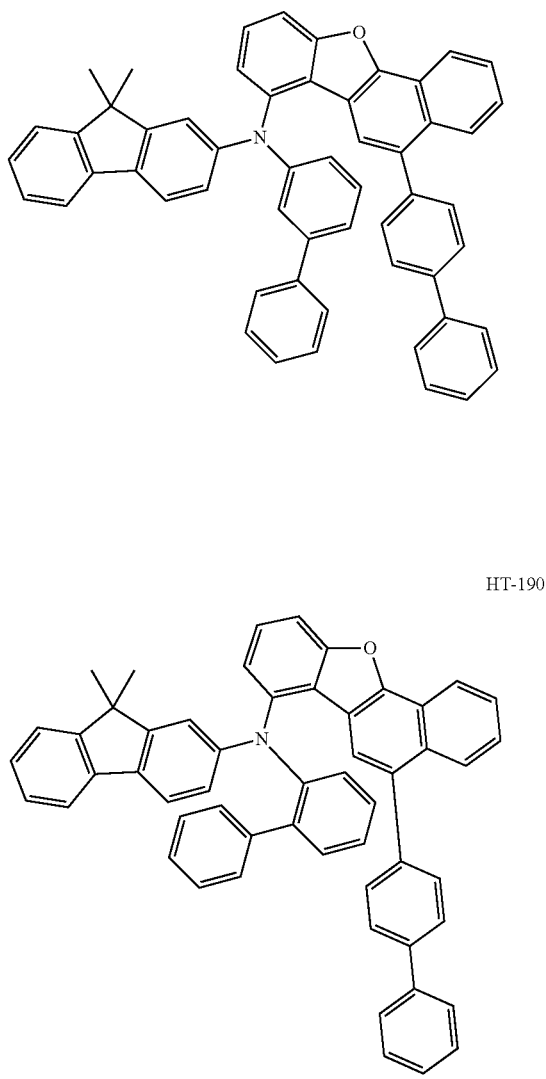
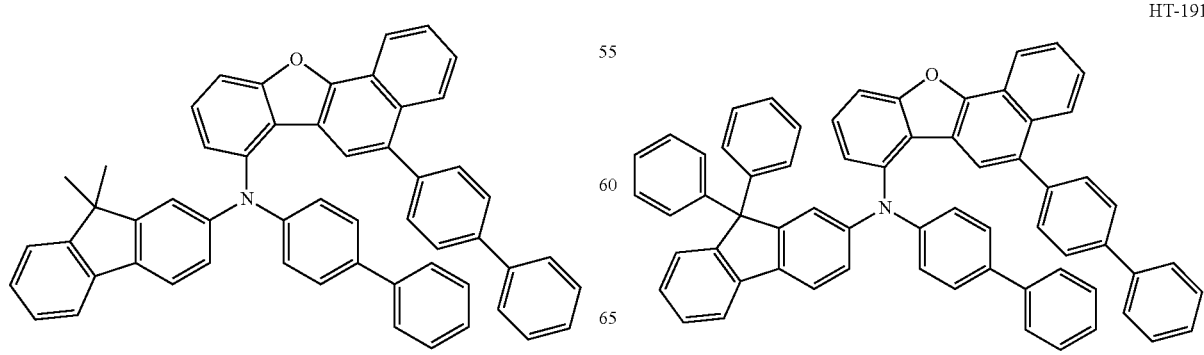

HT-192
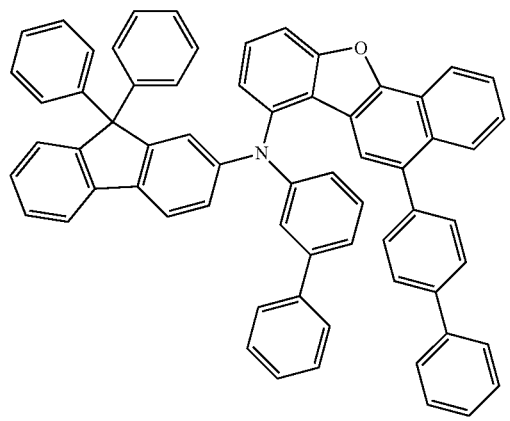
HT-193
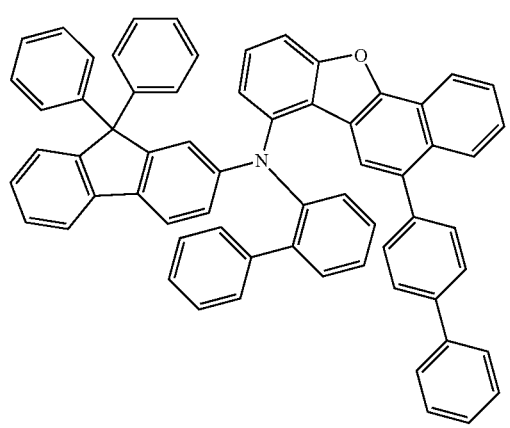
HT-194
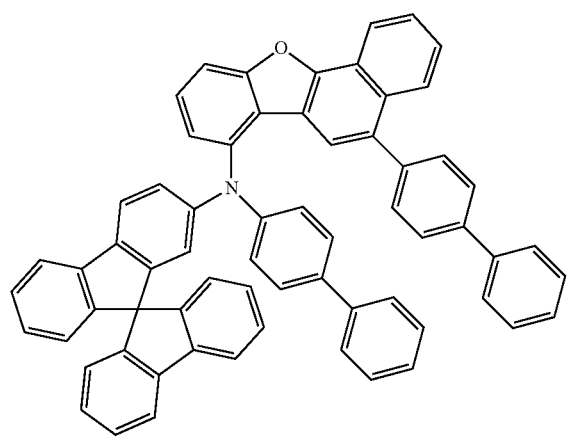
HT-195
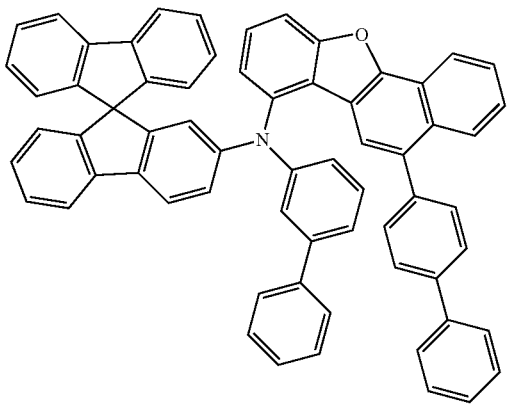
HT-196
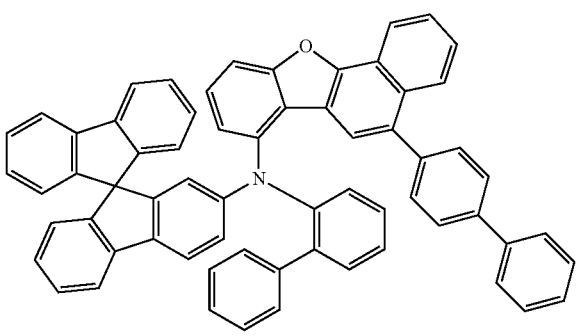
HT-197
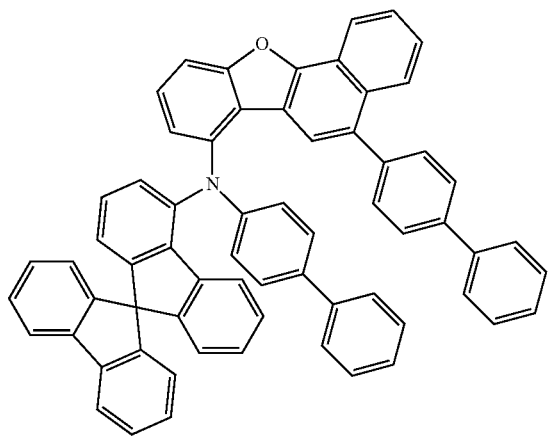
HT-198
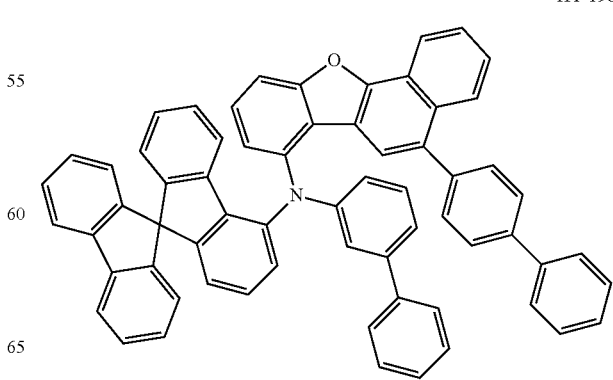

HT-199
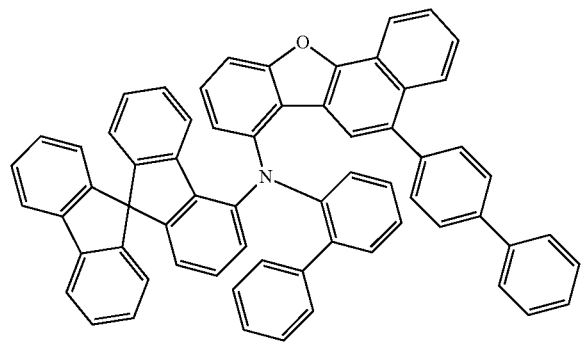
HT-200
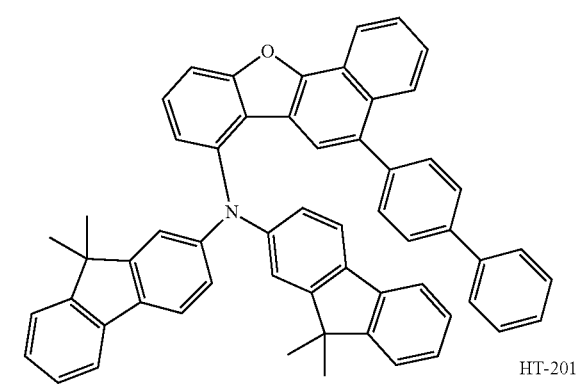
HT-201
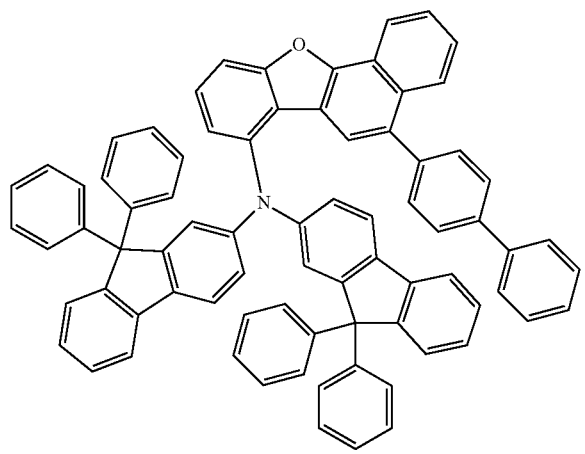
HT-202
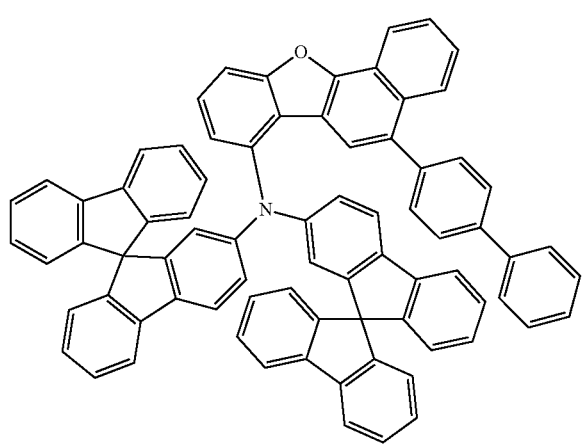
HT-203
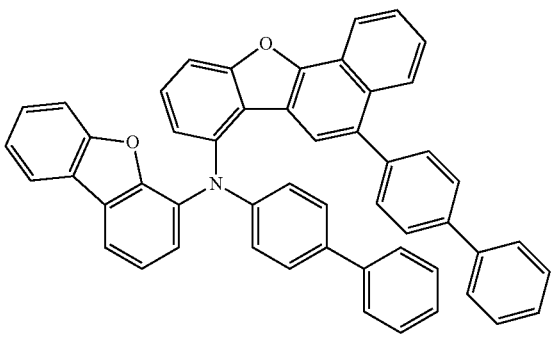
HT-204
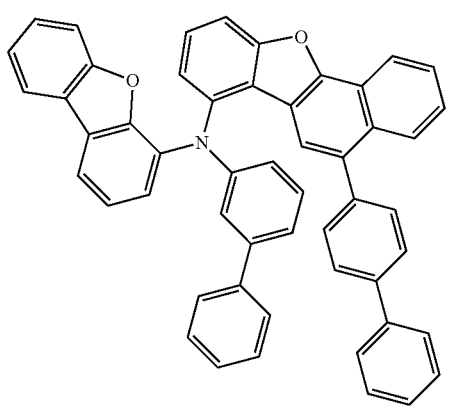
HT-205
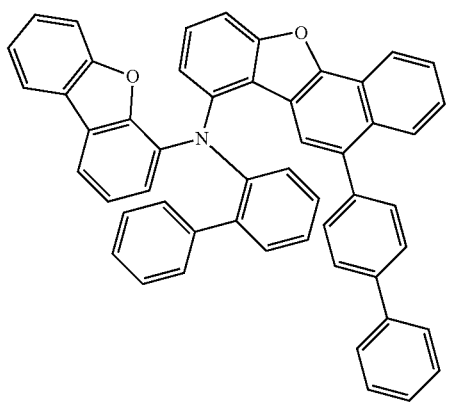
HT-206
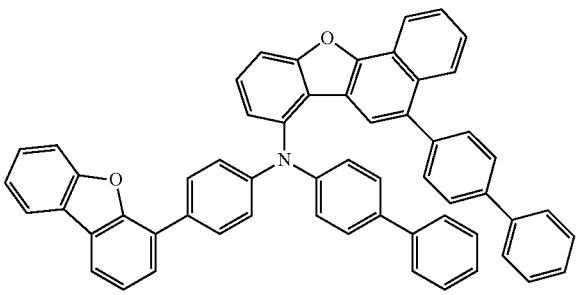

HT-207
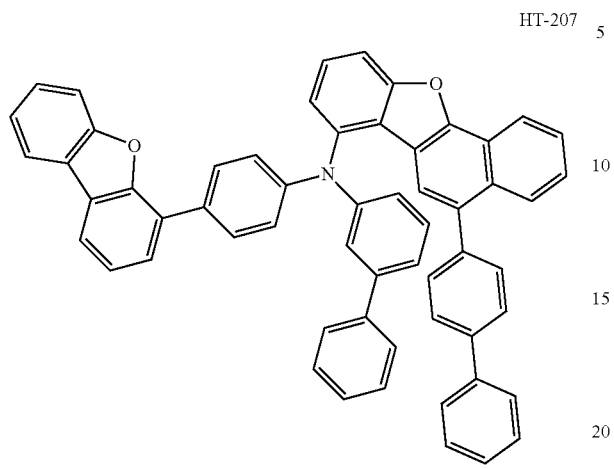
HT-208
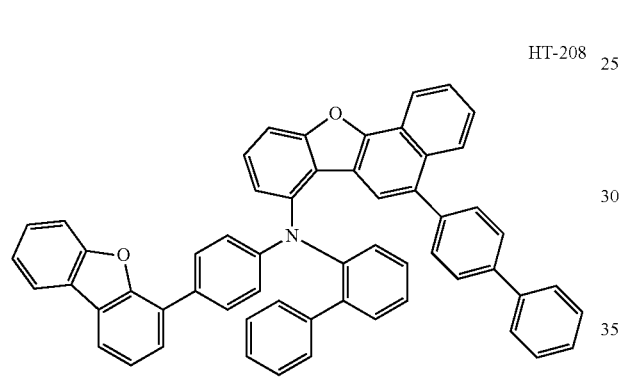
HT-209
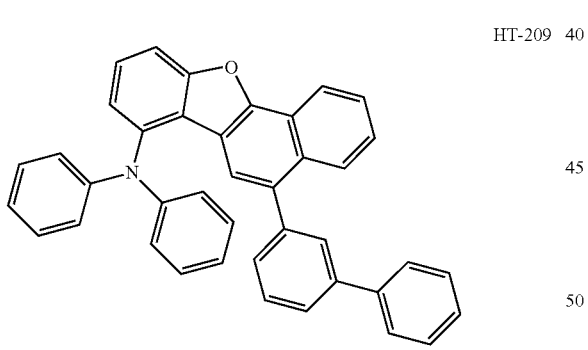
HT-210
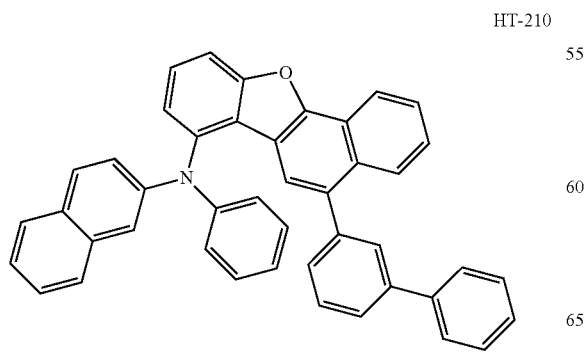
HT-211
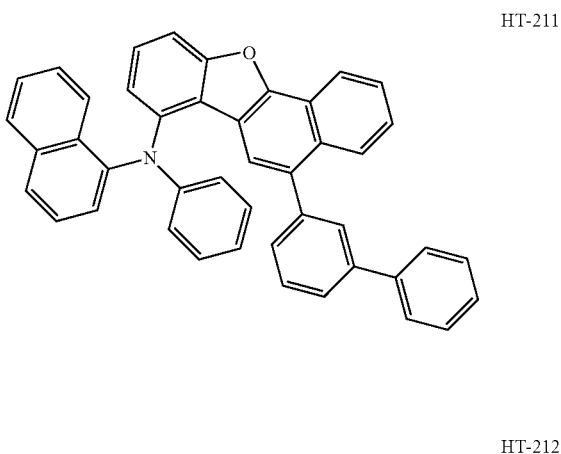
HT-212
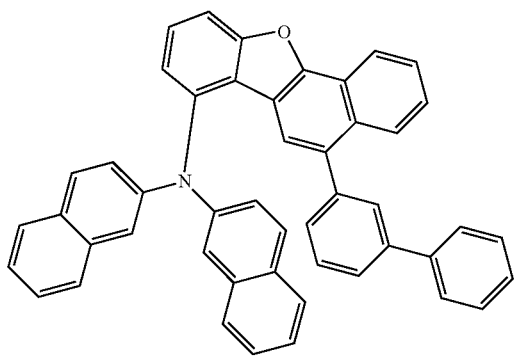
HT-213
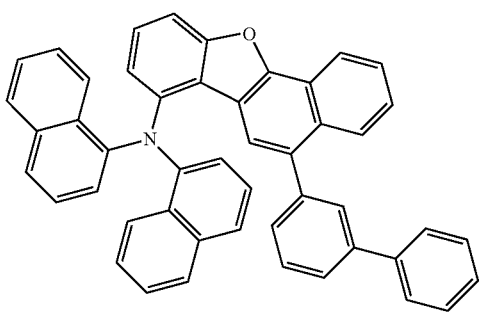
HT-214
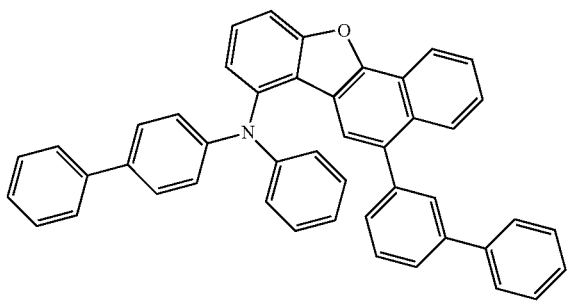

387
-continued
HT-215
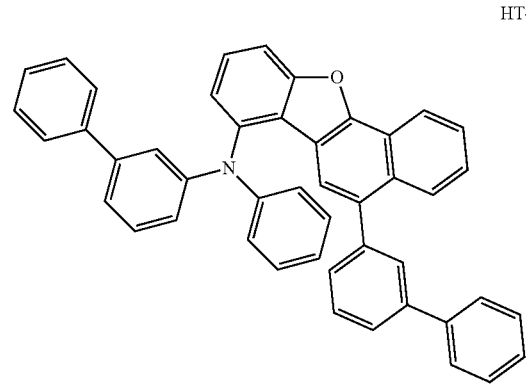
HT-216
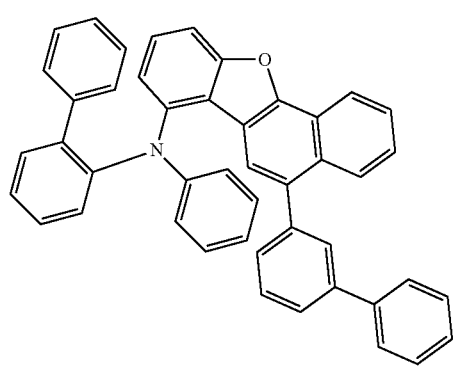
HT-217
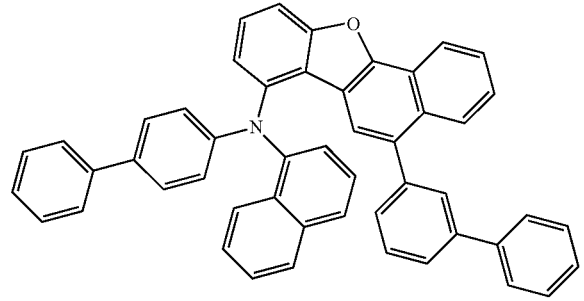
HT-218
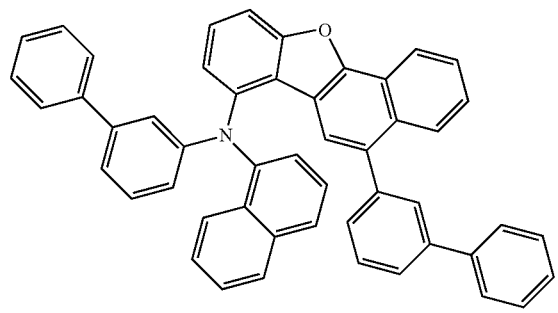
388
-continued
HT-219
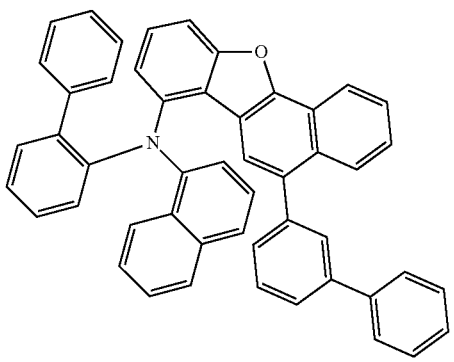
HT-220
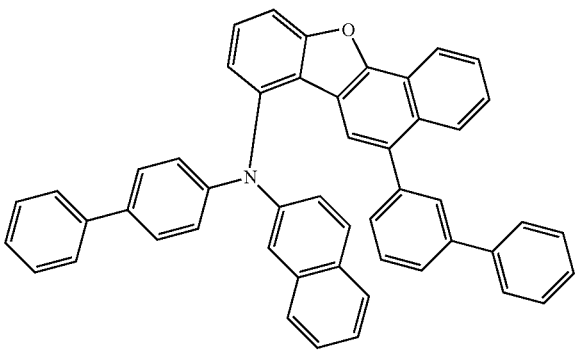
HT-221
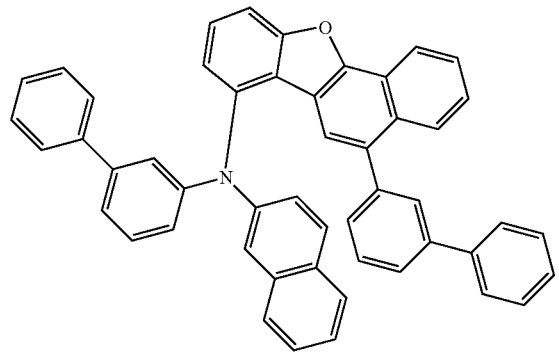
HT-222
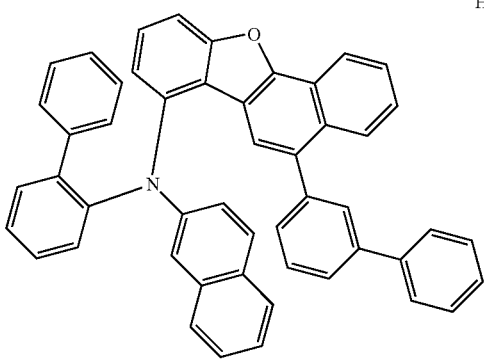

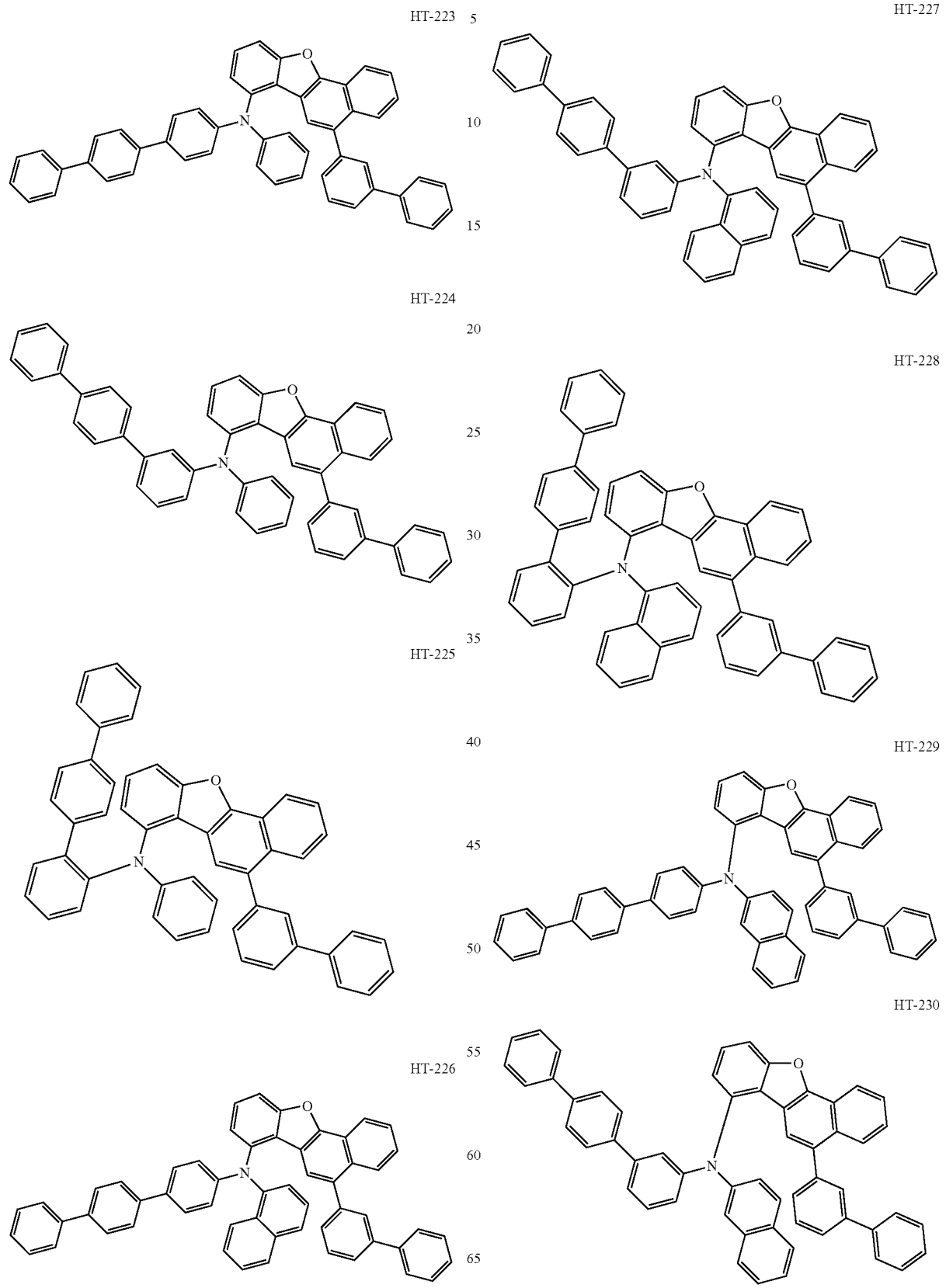

HT-231
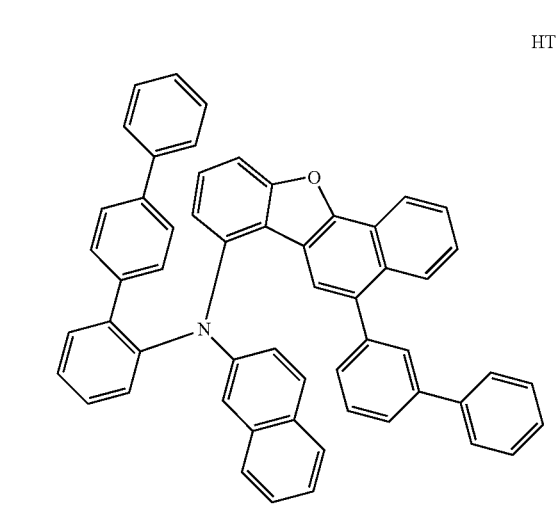
HT-232
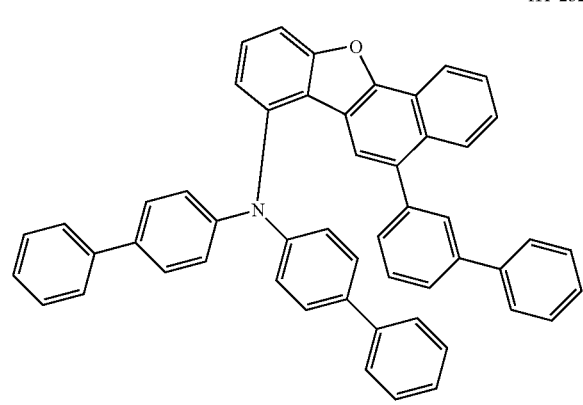
HT-233
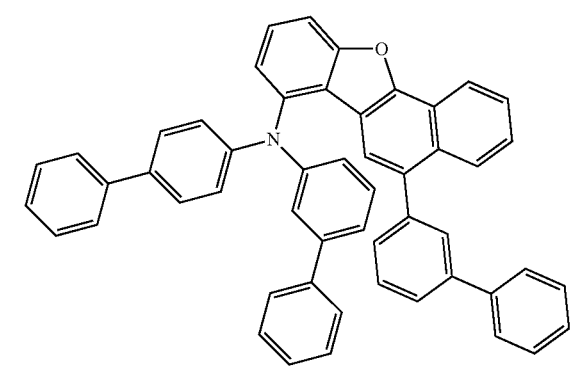
HT-234
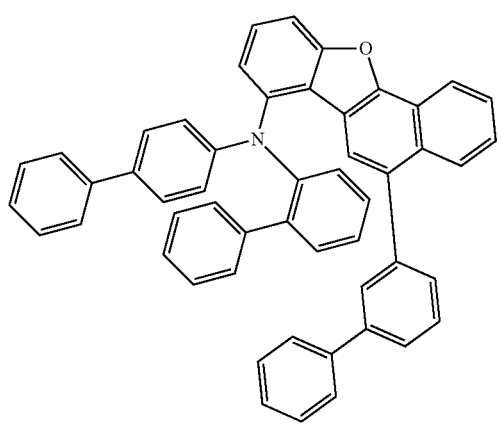
HT-235
HT-236
HT-237
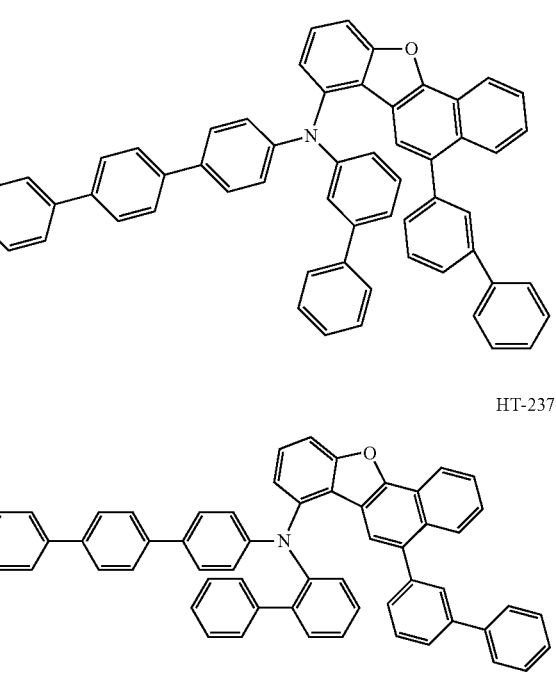

HT-238
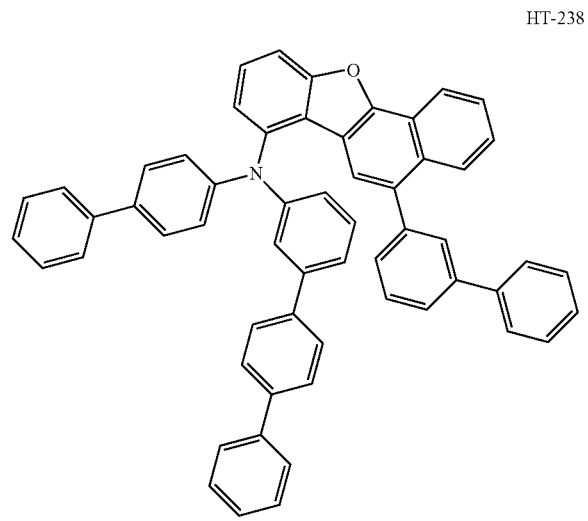
HT-239
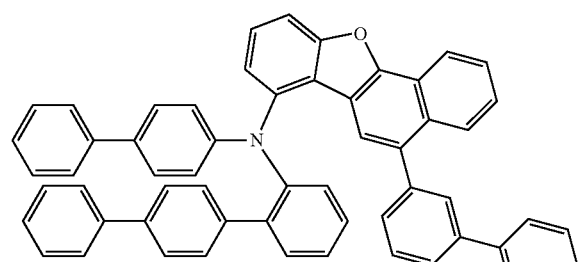
HT-240
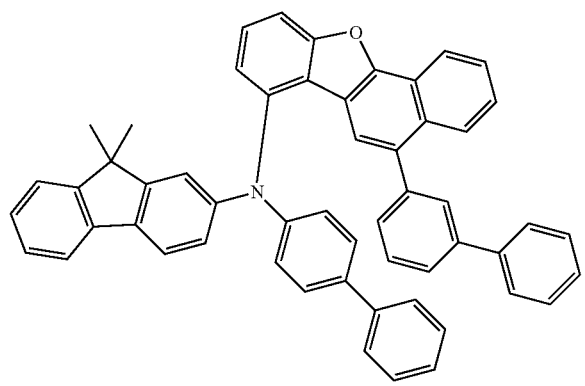
HT-241
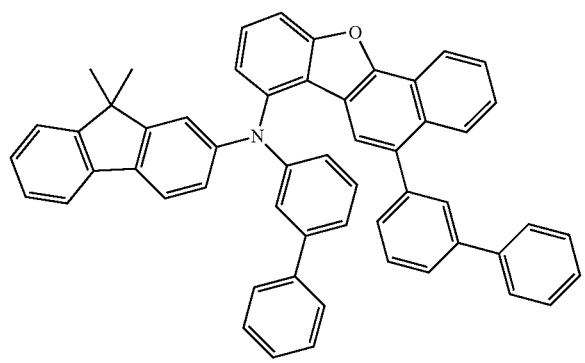
HT-242
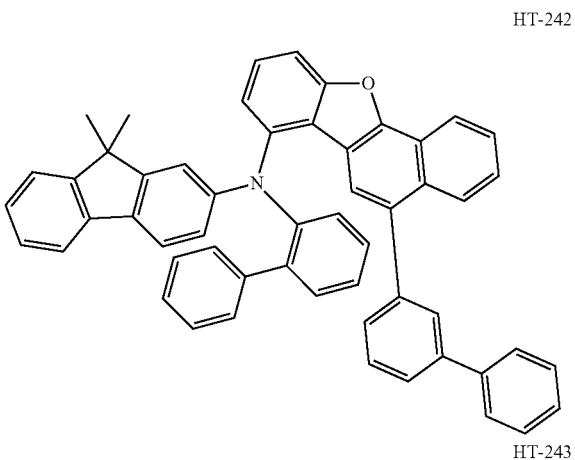
HT-243
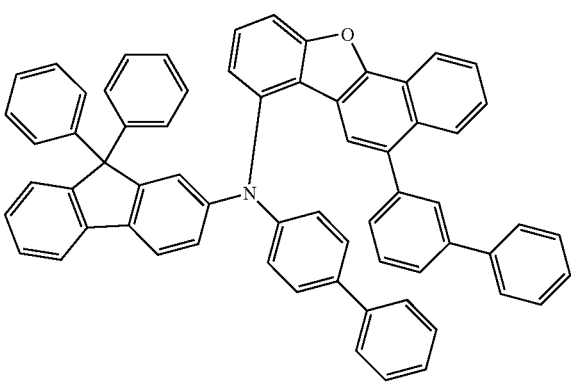
HT-244
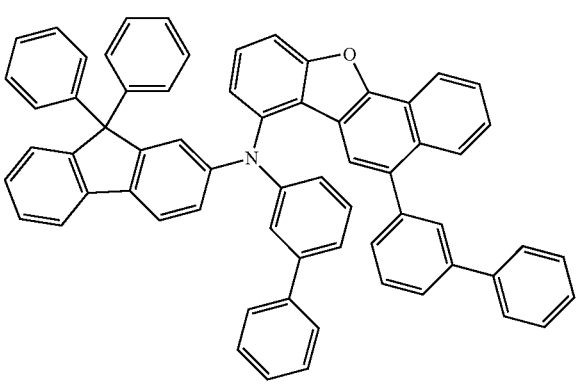
HT-245
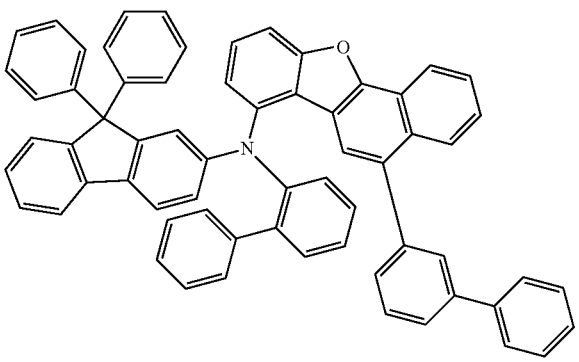

HT-246
HT-247
HT-248
HT-249
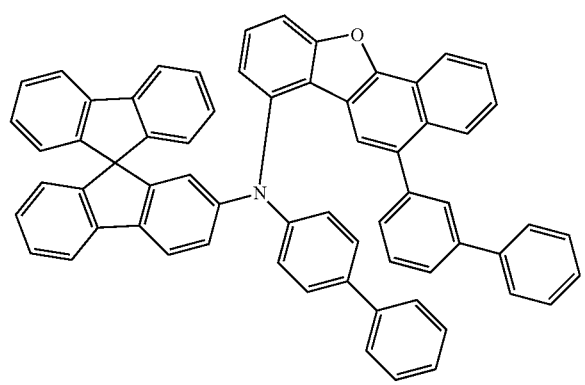
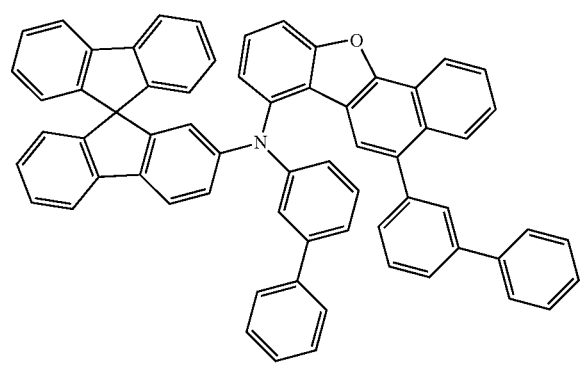
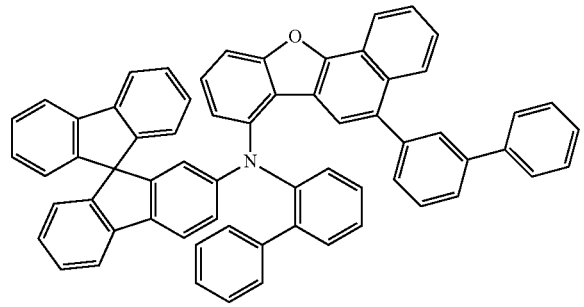
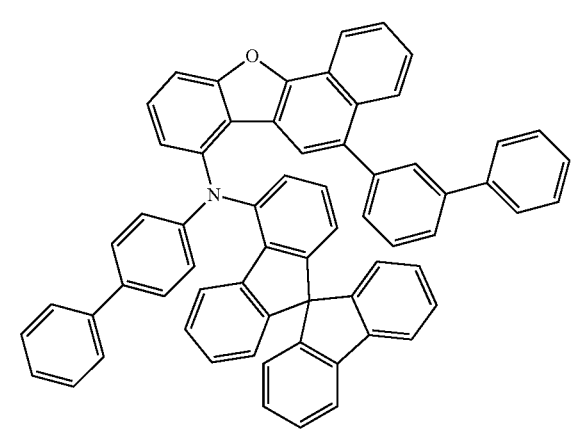
HT-250
HT-251
HT-252
HT-253

HT-254
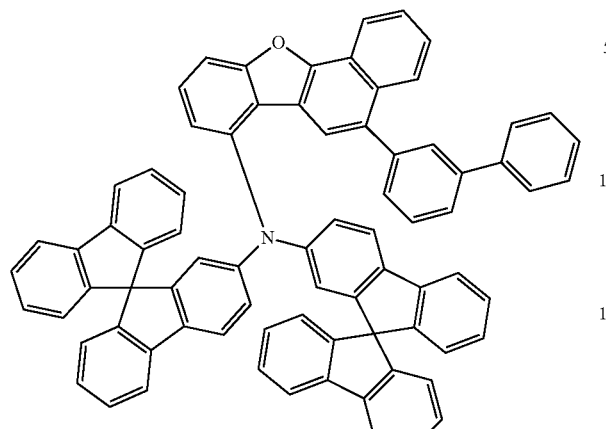
HT-255
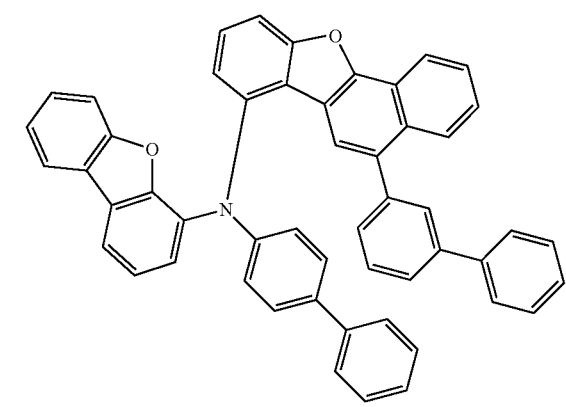
HT-256
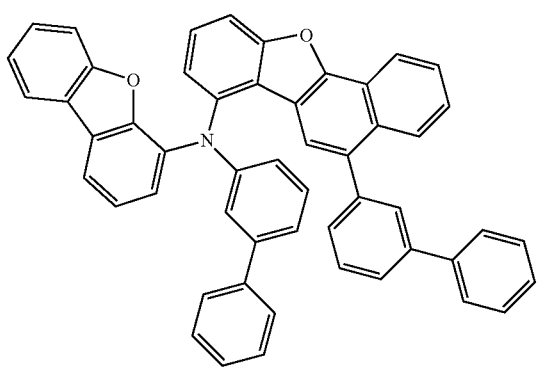
HT-257
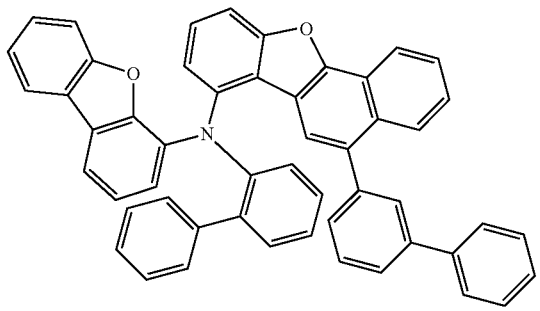
HT-258
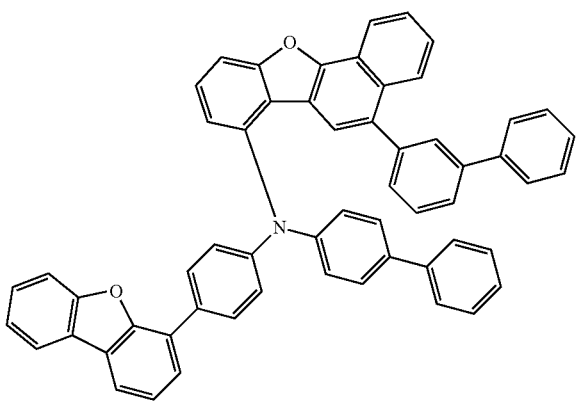
HT-259
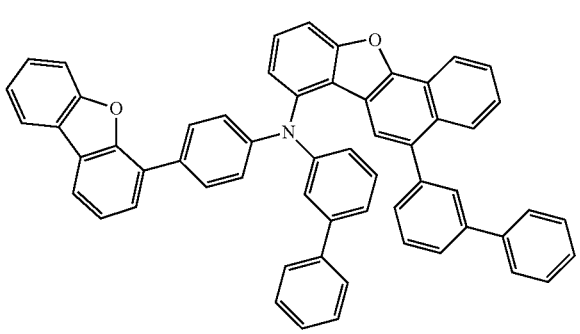
HT-260
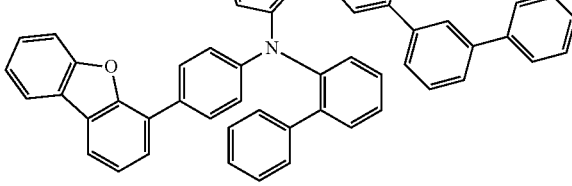
HT-261
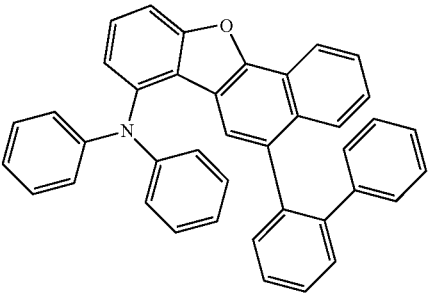

HT-262
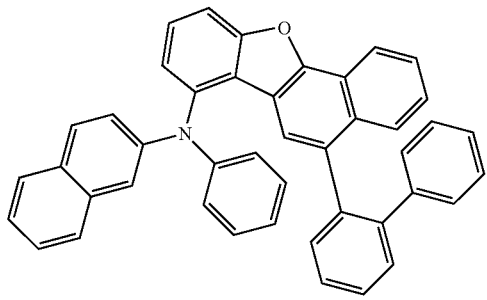
HT-263
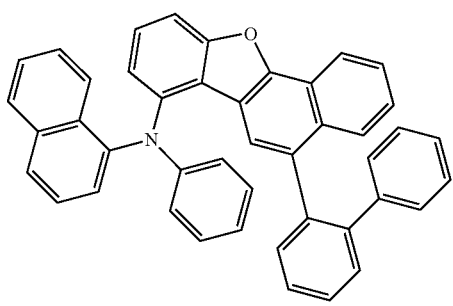
HT-264
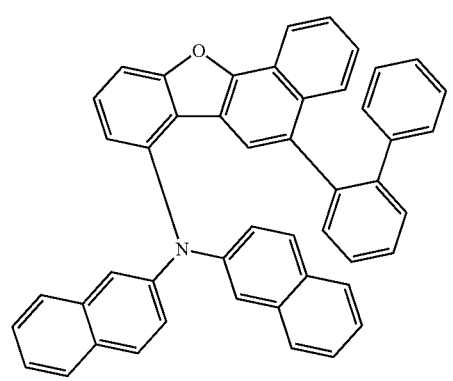
HT-265
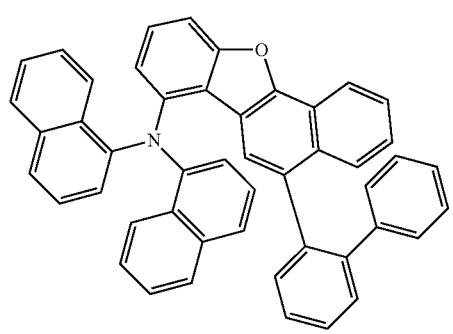
HT-266
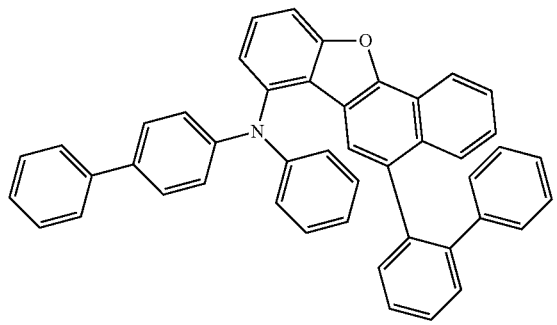
HT-267
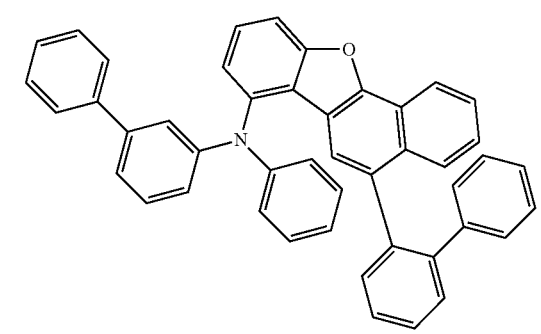
HT-268
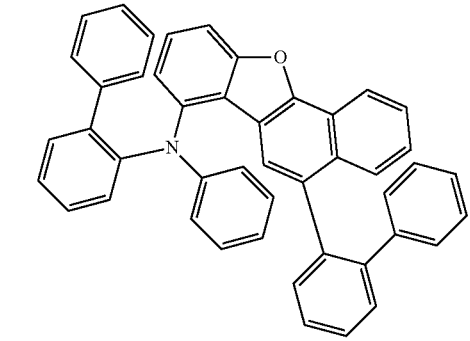
HT-269
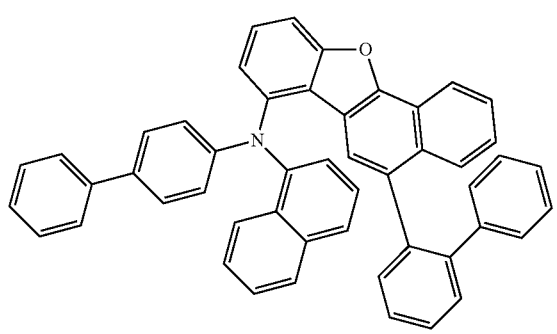

HT-270
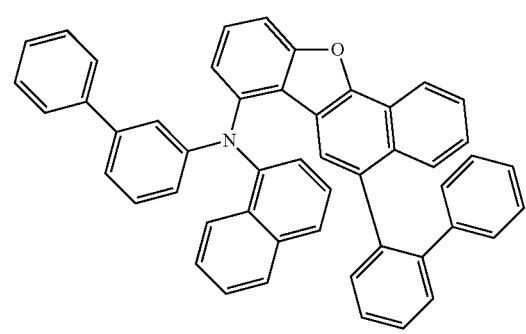
HT-271
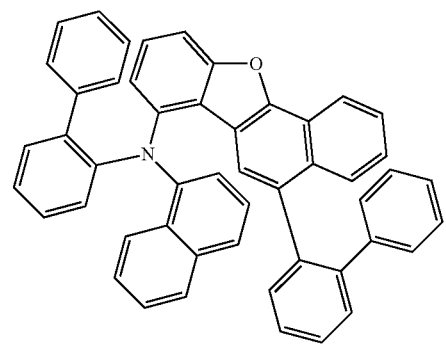
HT-272
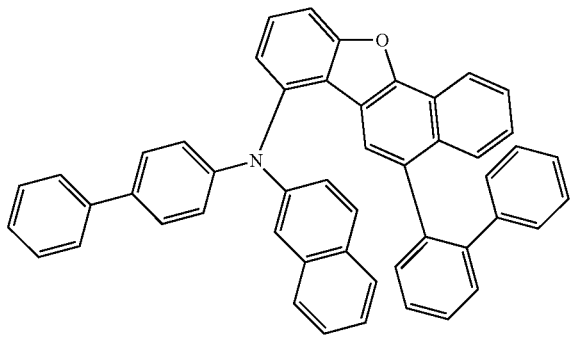
HT-273
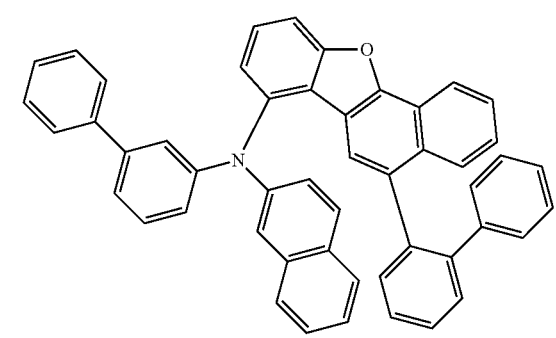
HT-274
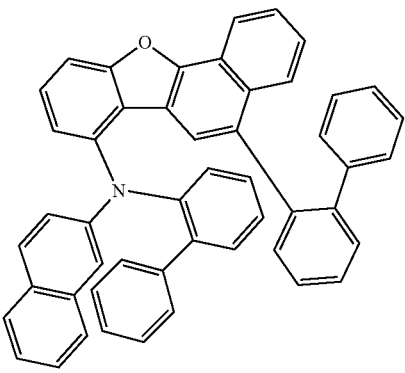
HT-275
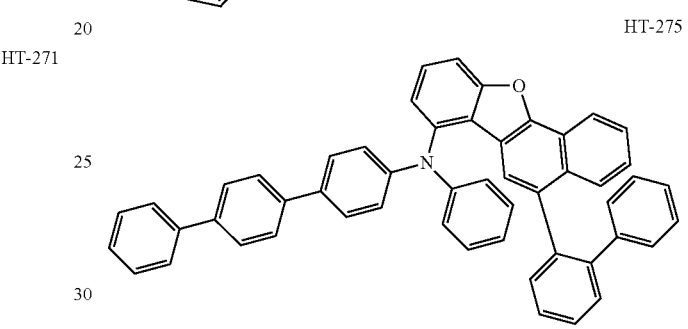
HT-276
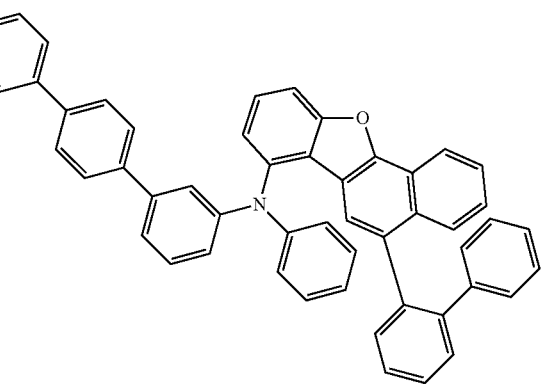
HT-277
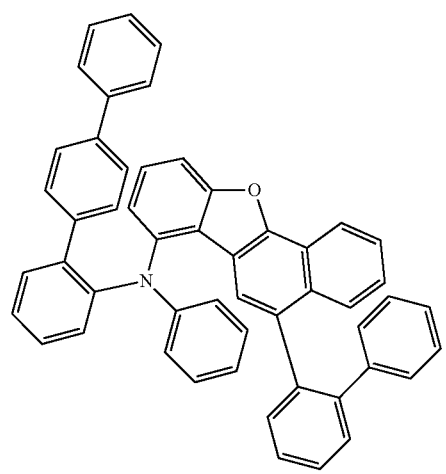

HT-278
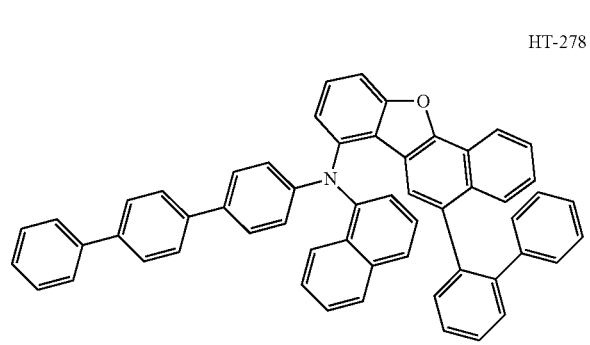
HT-279
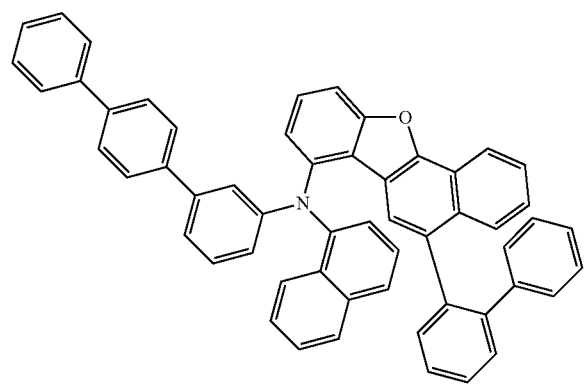
HT-280
HT-281
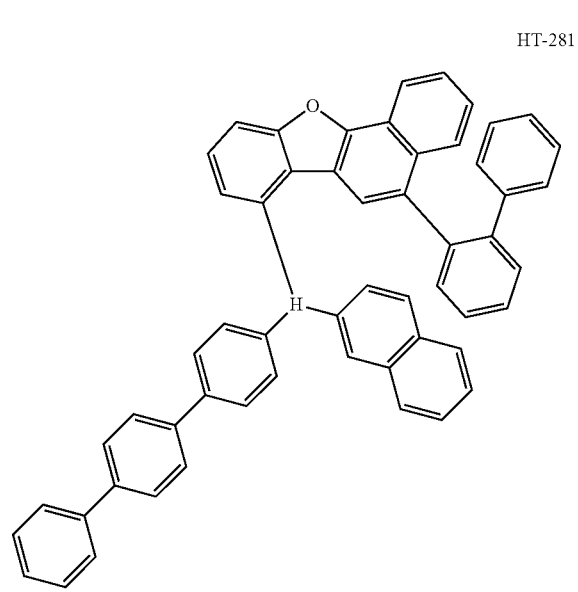
HT-282
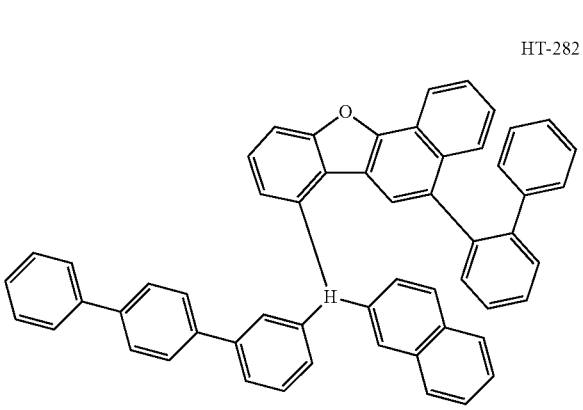
HT-283
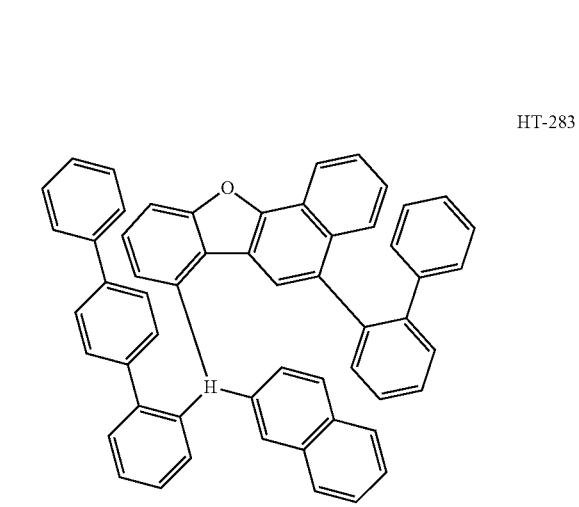

-continued
HT-285
HT-285
HT-286
HT-287
-continued
HT-288
HT-289
HT-290
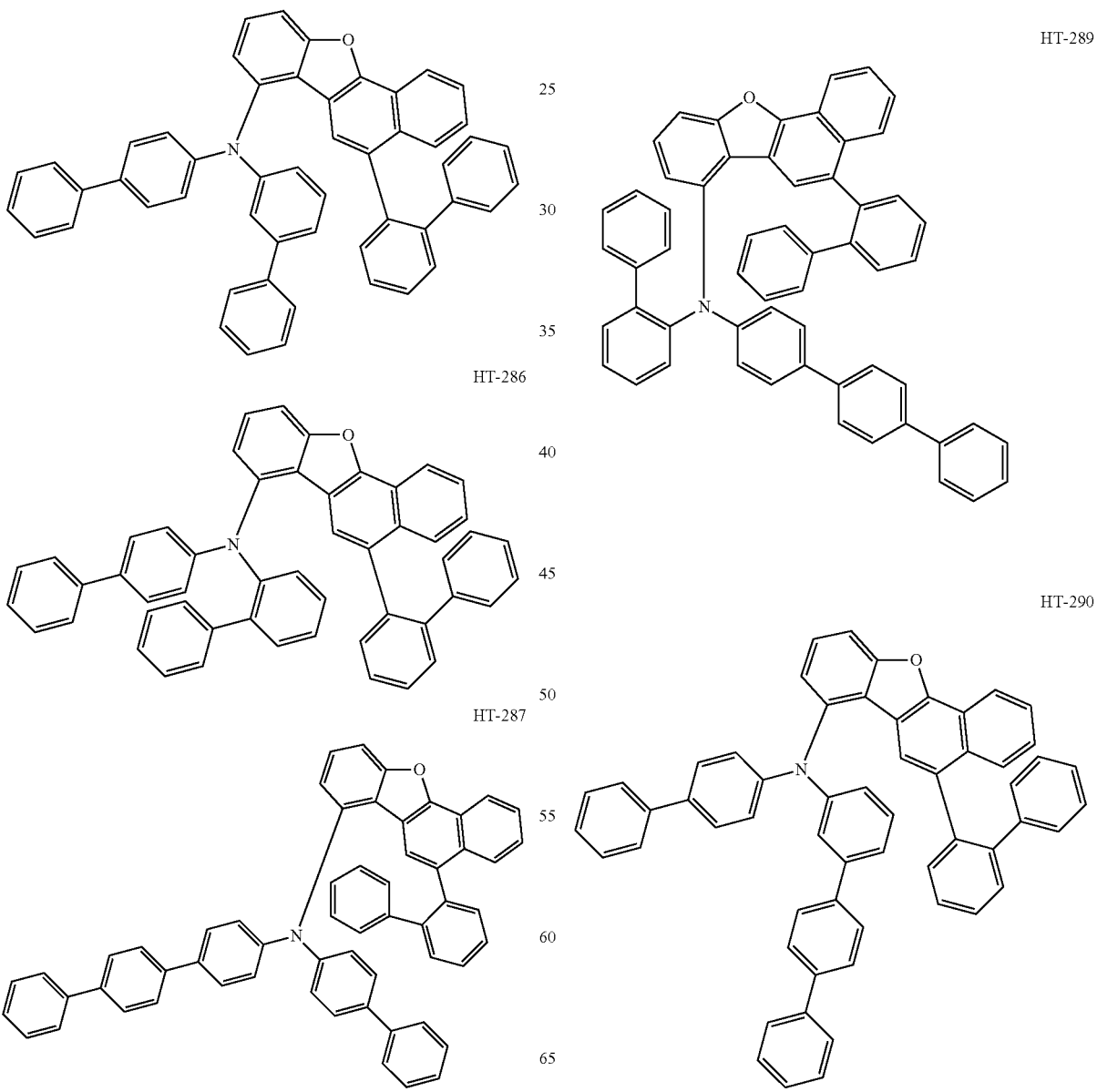

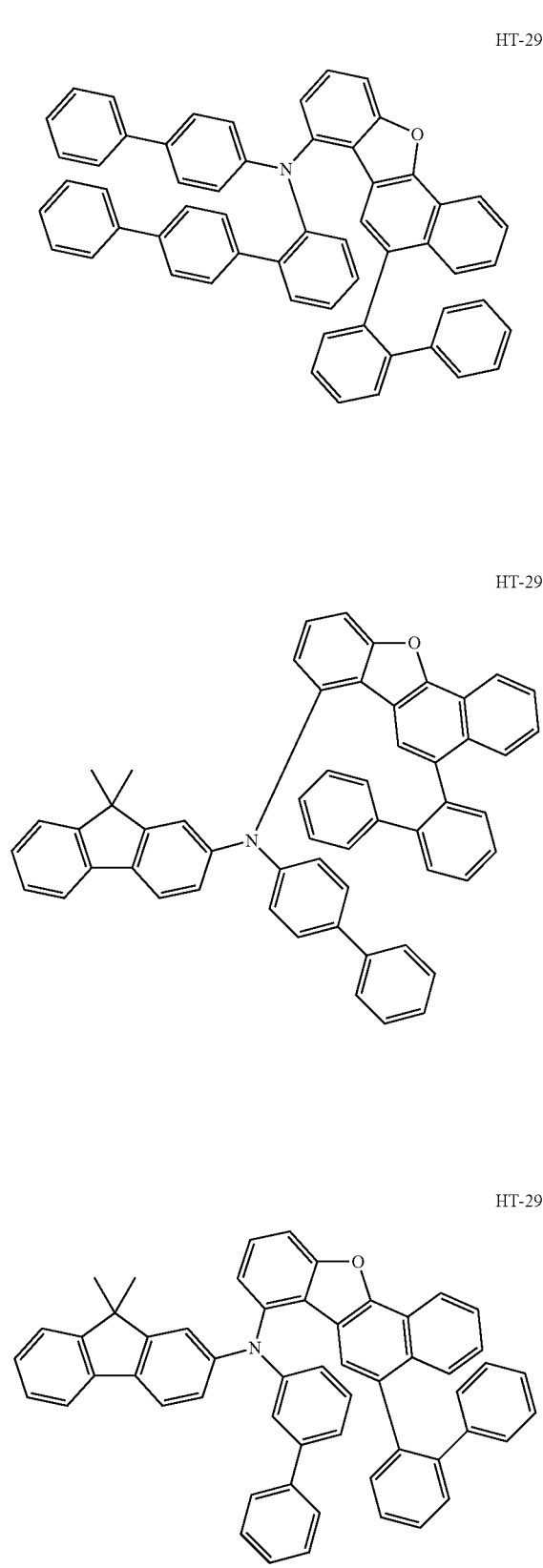
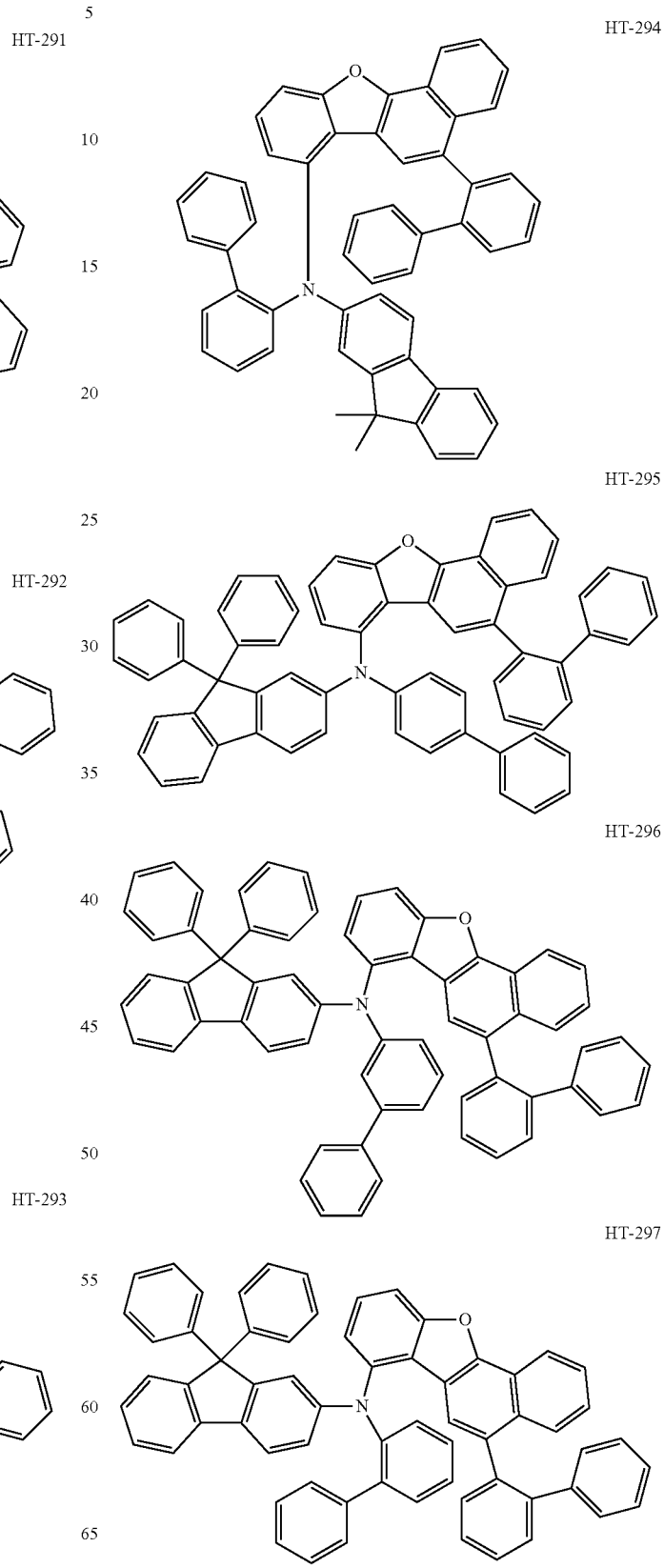

HT-298
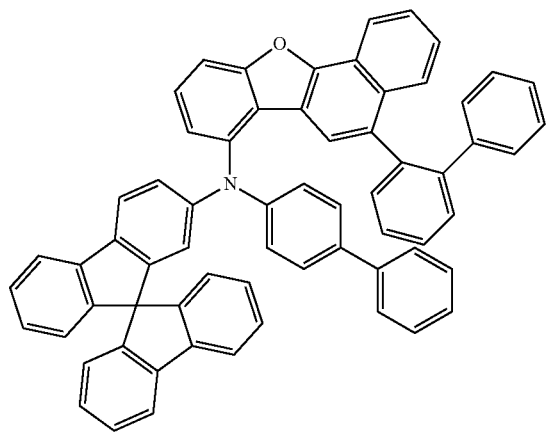
HT-302
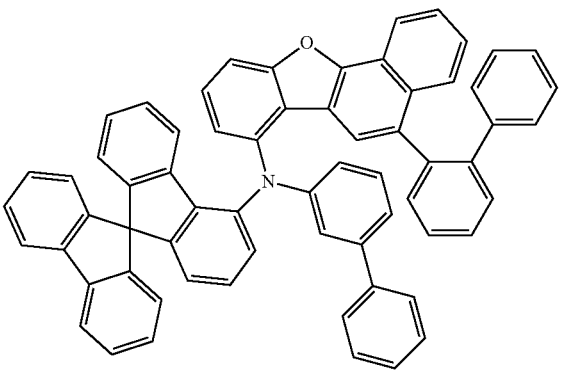
HT-299
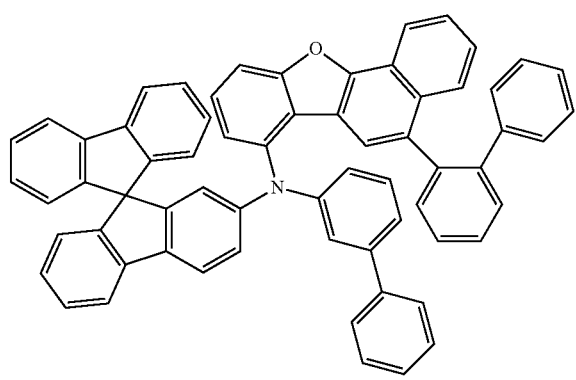
HT-303
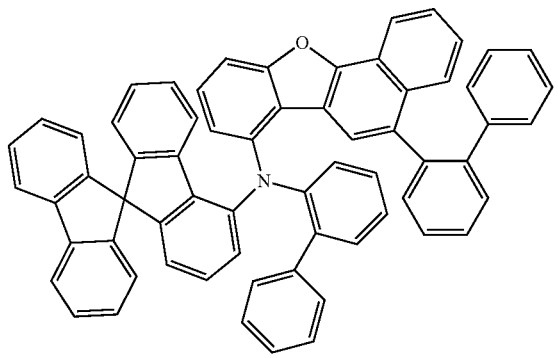
HT-300
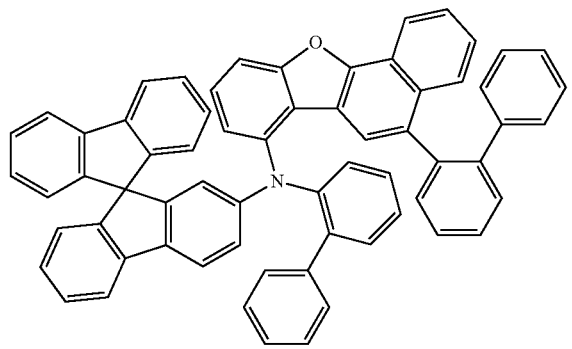
HT-301
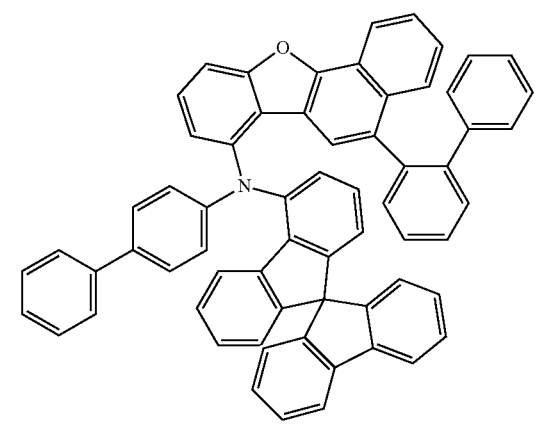
HT-304
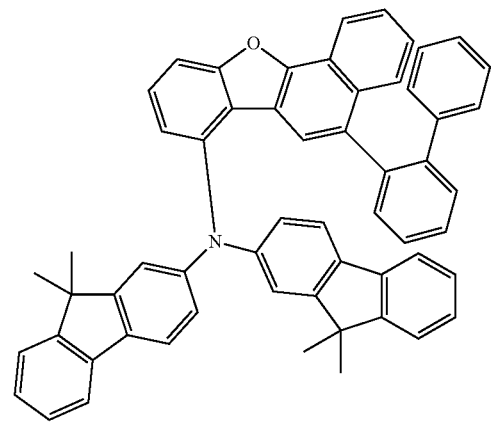

-continued
HT-305
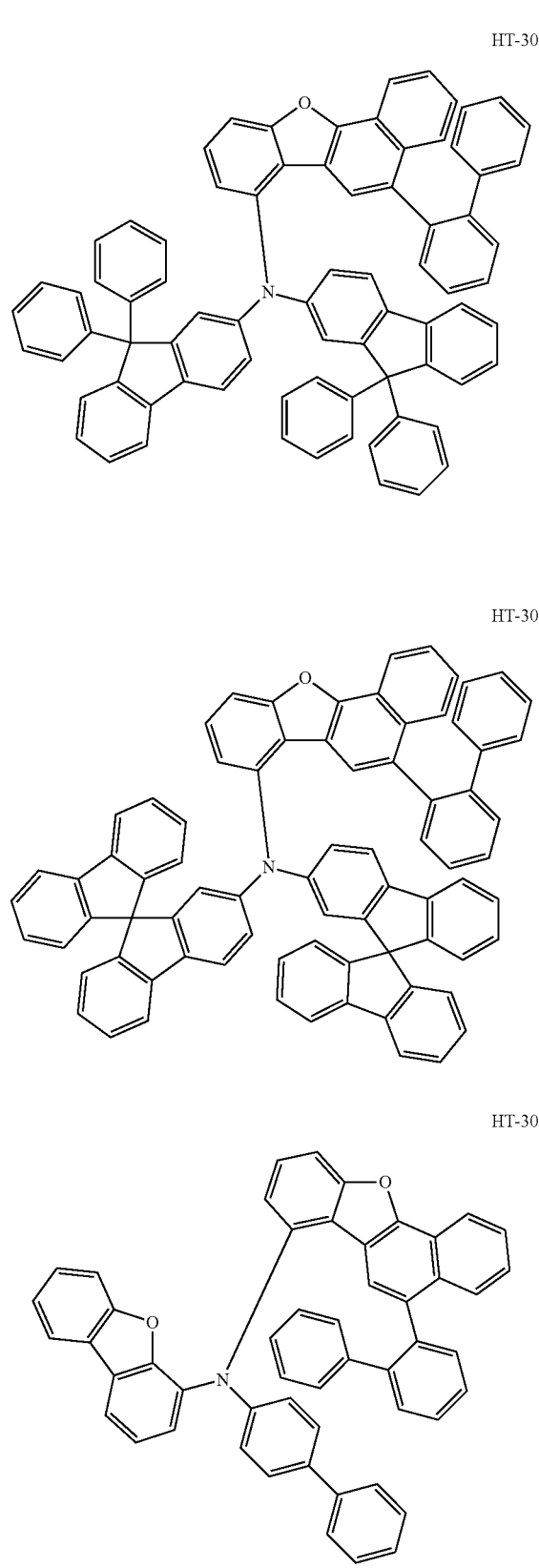
HT-306
HT-307
-continued
HT-308
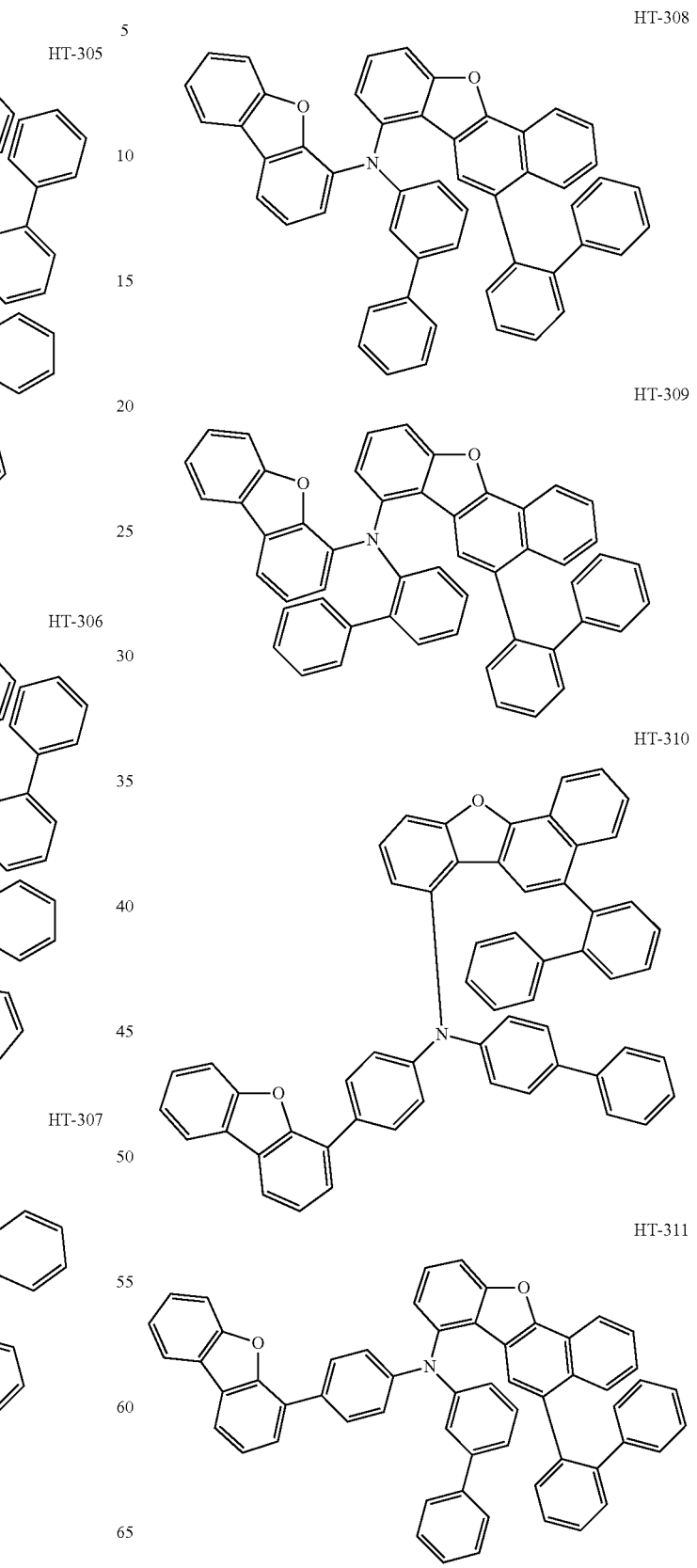
HT-309
HT-310
HT-311

HT-312
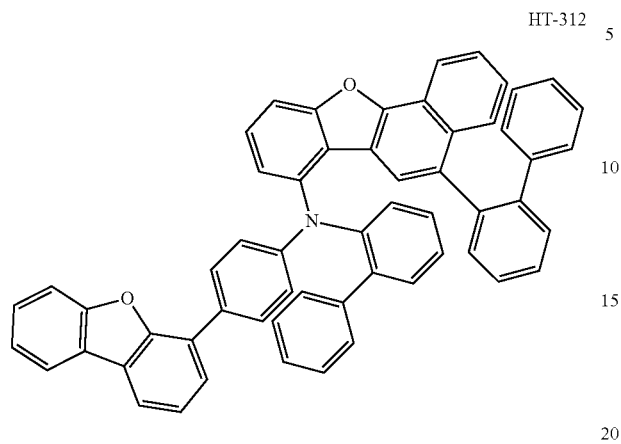
HT-313
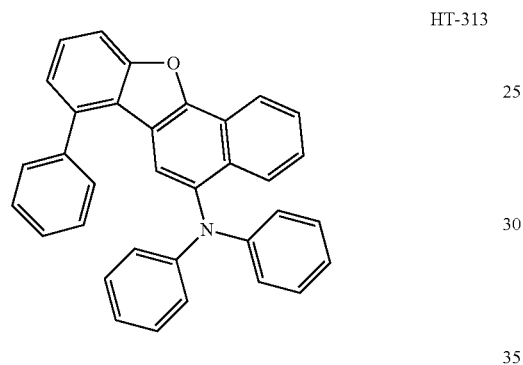
HT-314
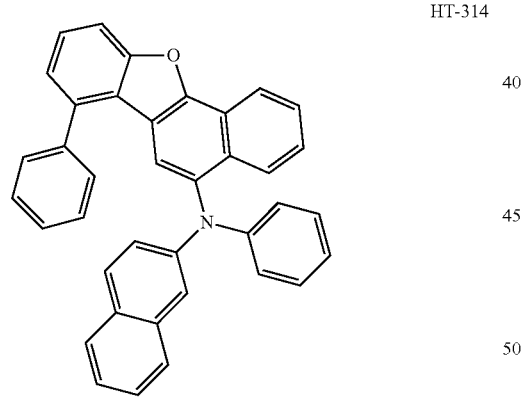
HT-315
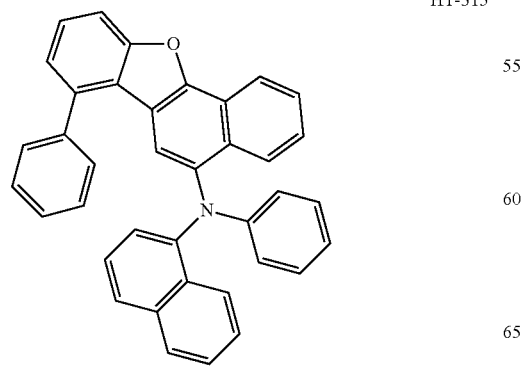
HT-316
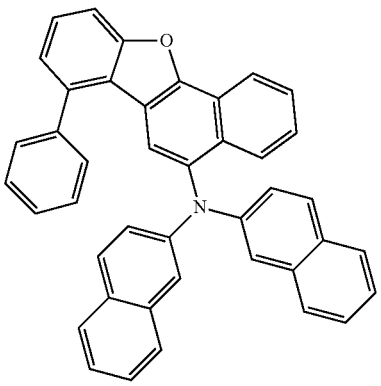
HT-317
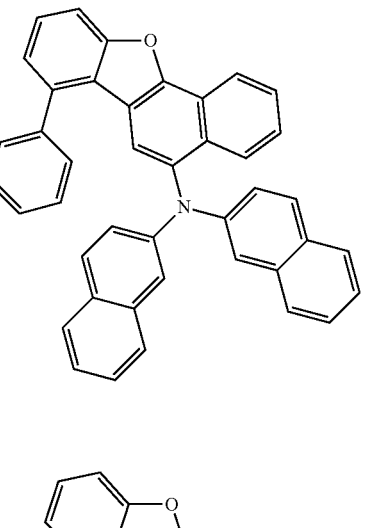
HT-318
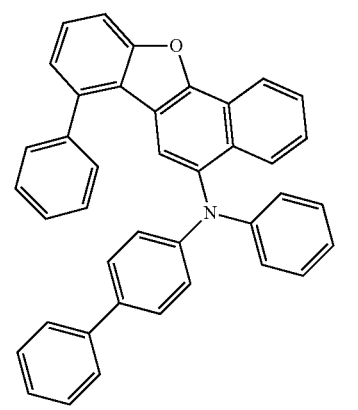
HT-319
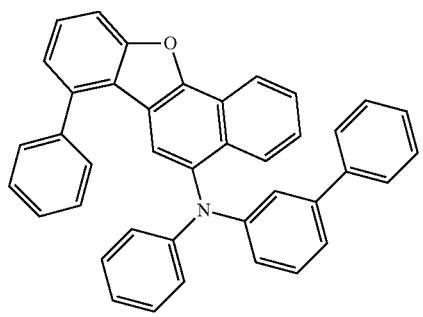

415
-continued
HT-320
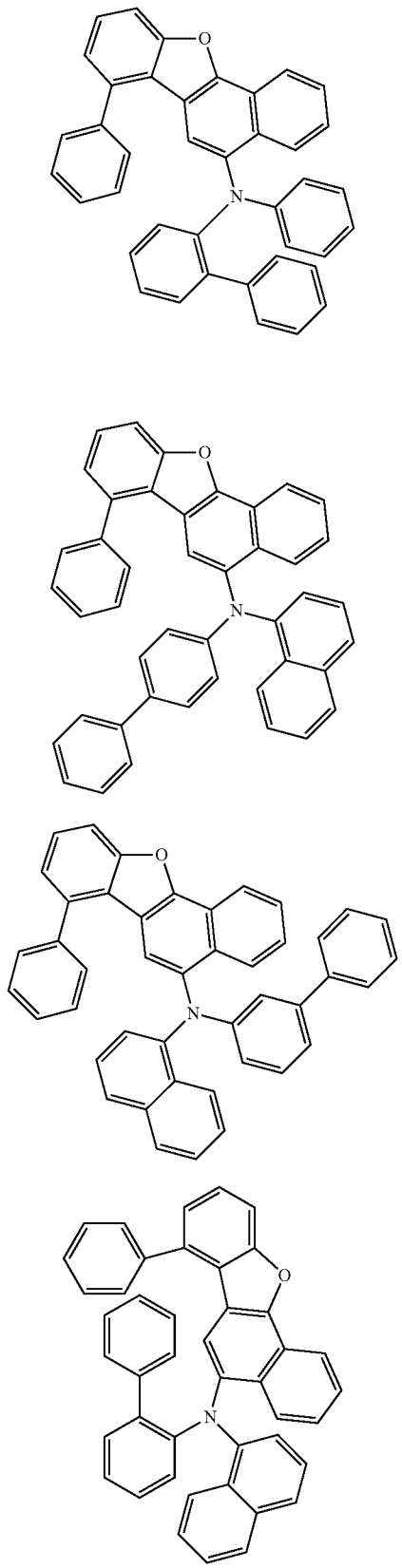
HT-321
HT-322
HT-323
416
-continued
HT-324
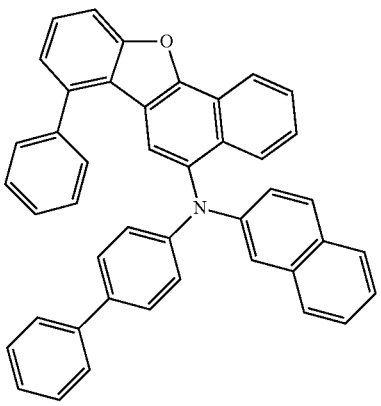
HT-325
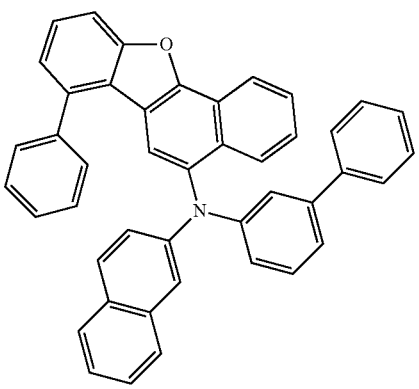
HT-326
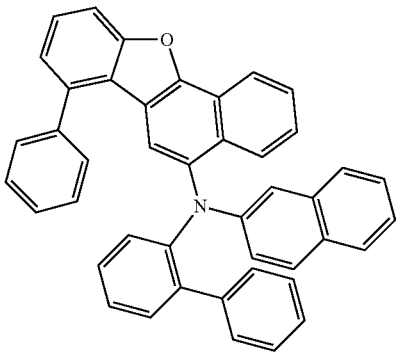
HT-327
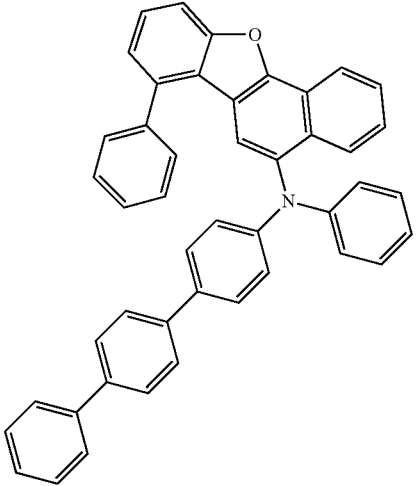

HT-328
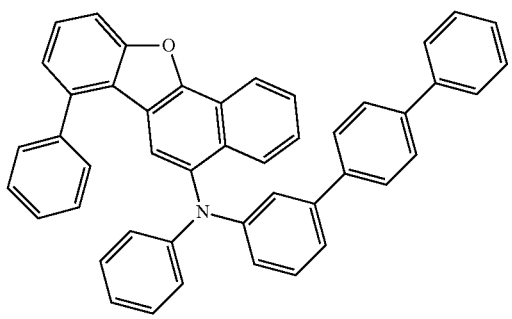
HT-329
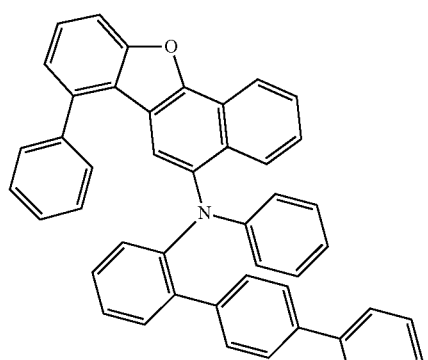
HT-330
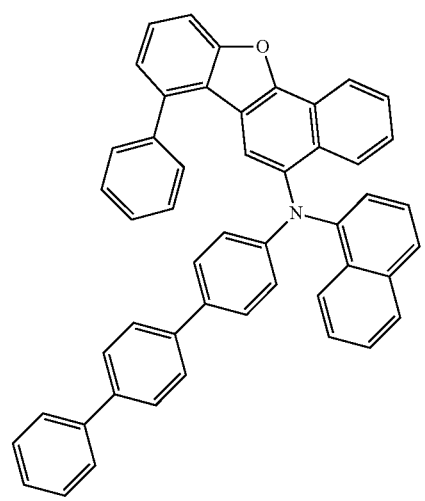
HT-331
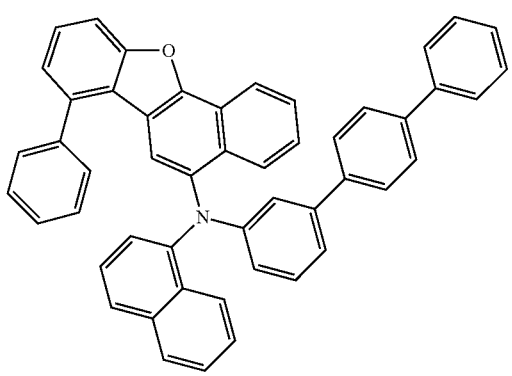
HT-332
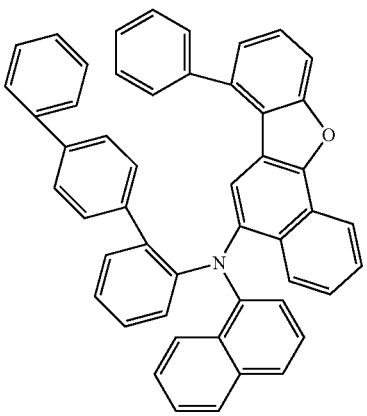
HT-333
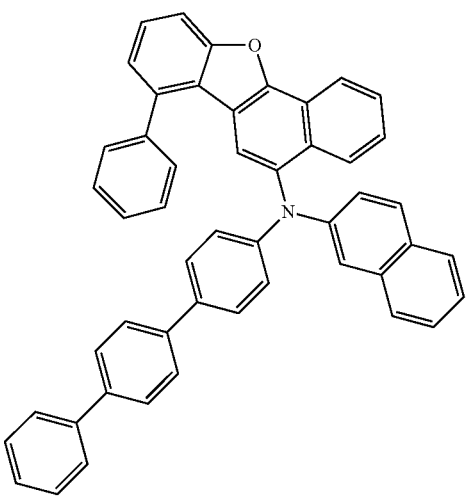
HT-334
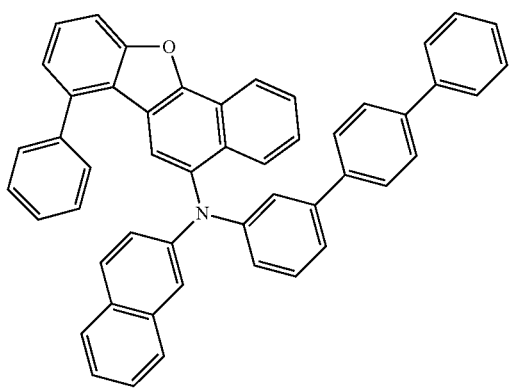

HT-335
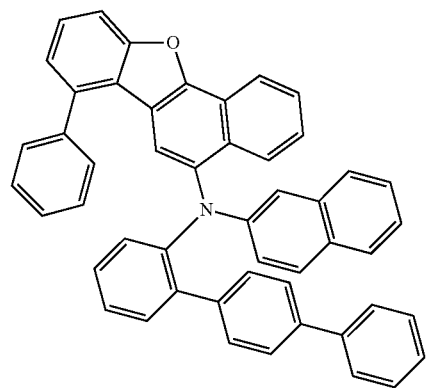
HT-336
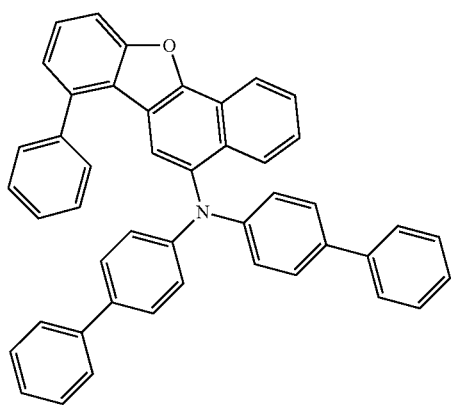
HT-337
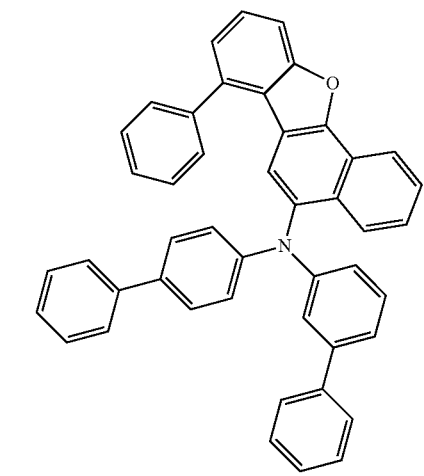
HT-338
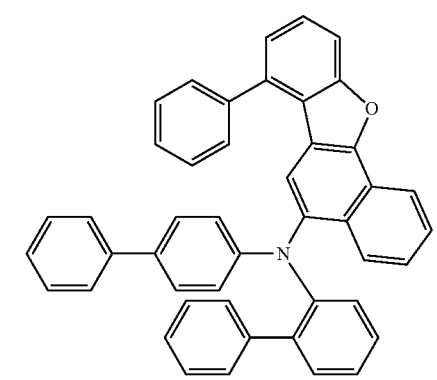
HT-339
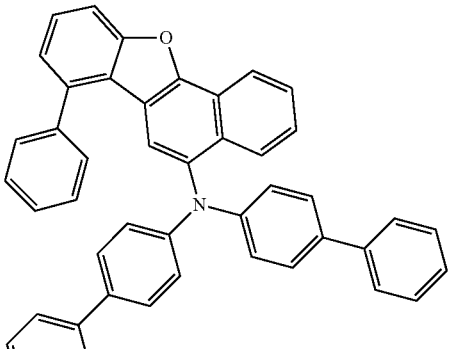
HT-340
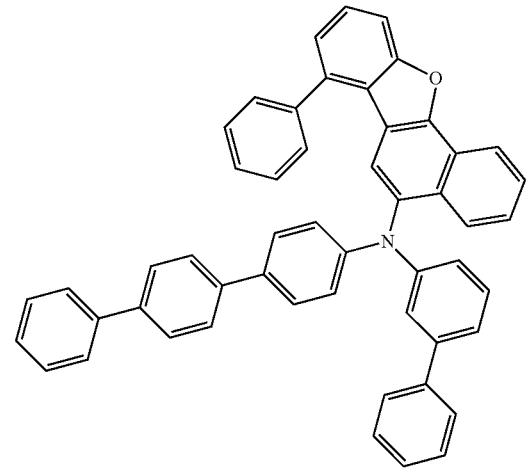
HT-341
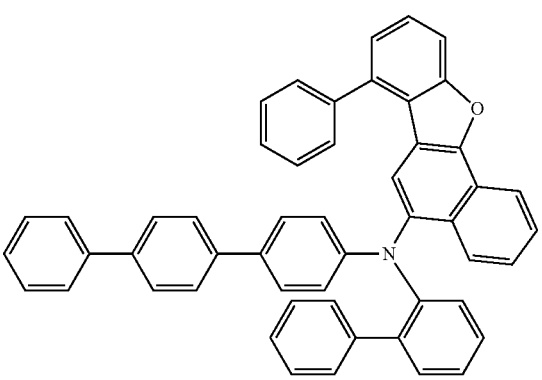

421
-continued
HT-342
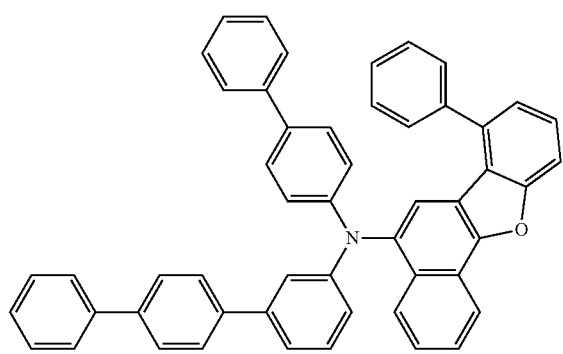
HT-343
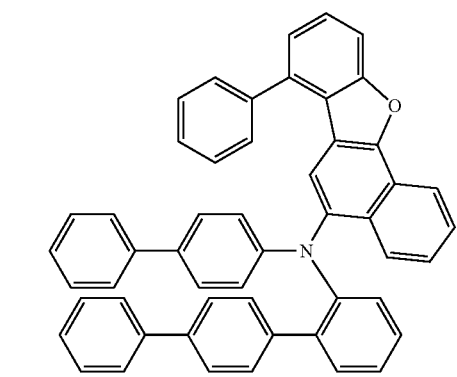
HT-344
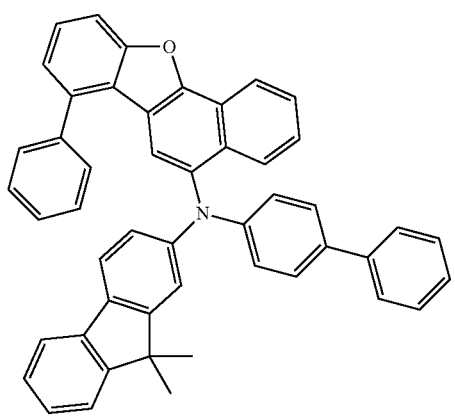
HT-345
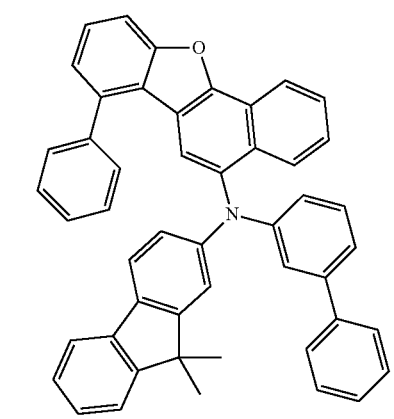
422
-continued
HT-346
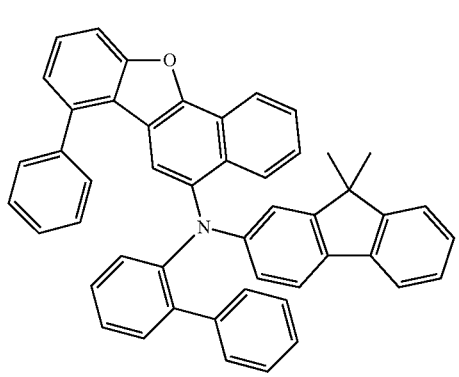
HT-347
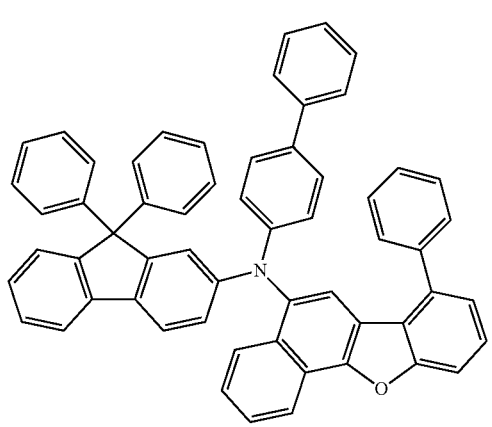
HT-348
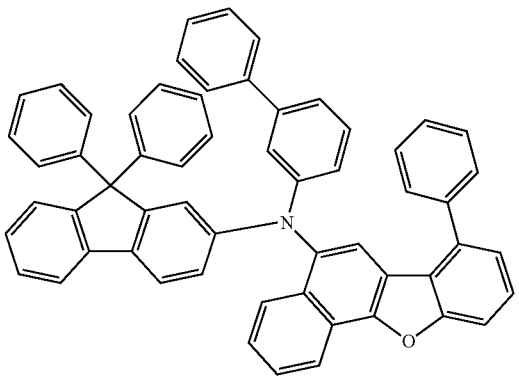
HT-349
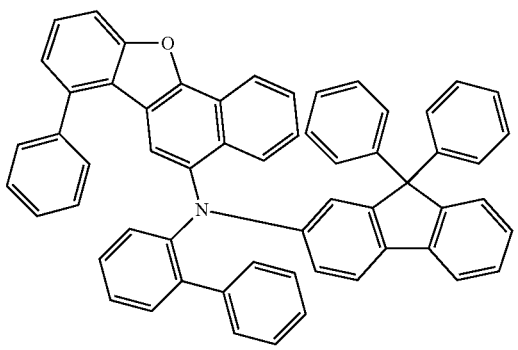

HT-350
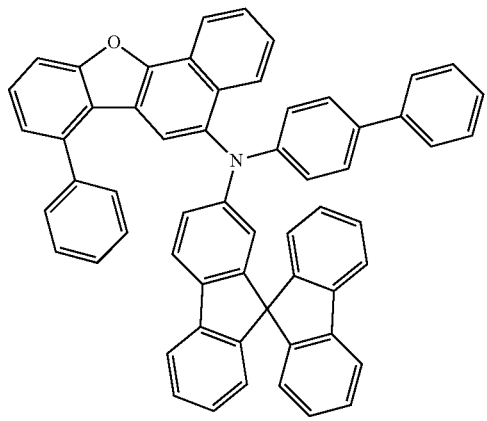
HT-351
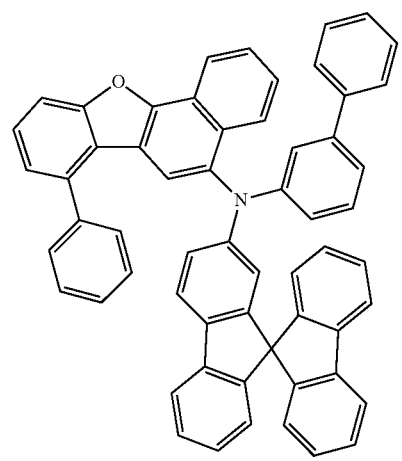
HT-352
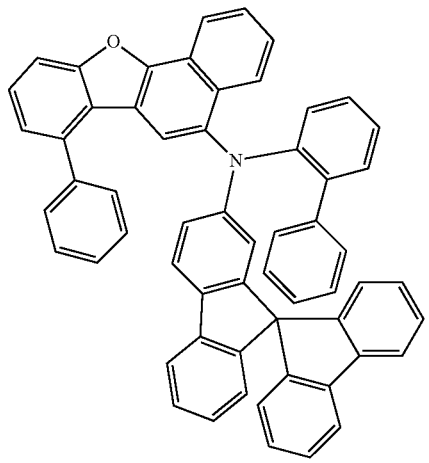
HT-353
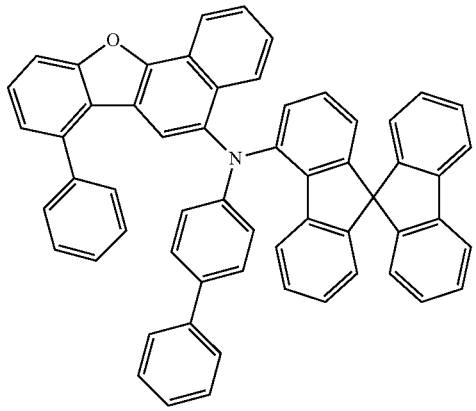
HT-354
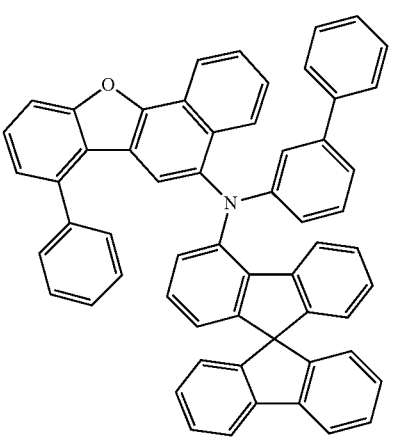
HT-355
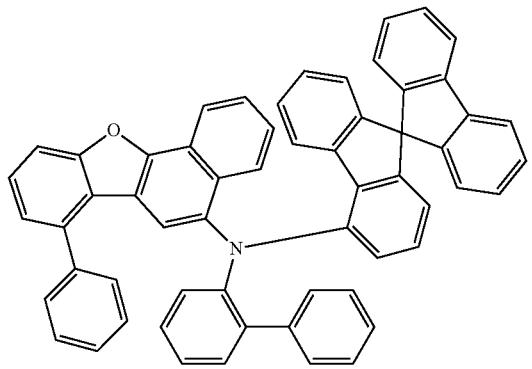
HT-356
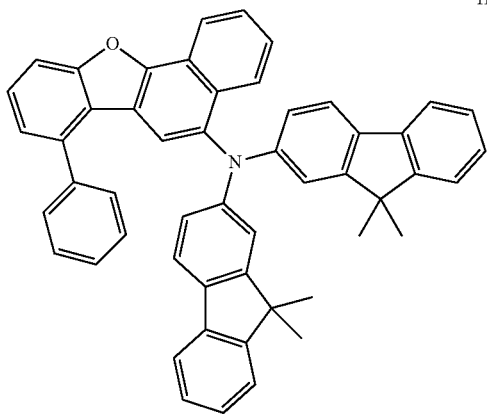

HT-357
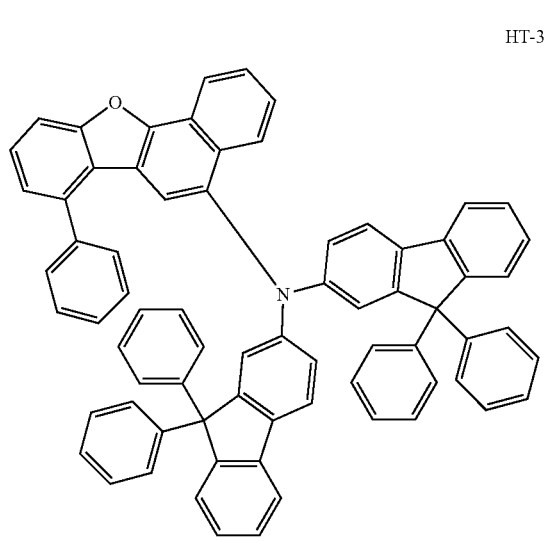
HT-360
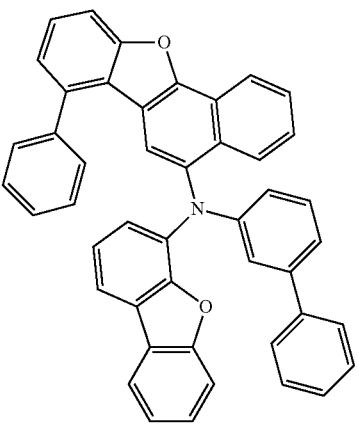
HT-358
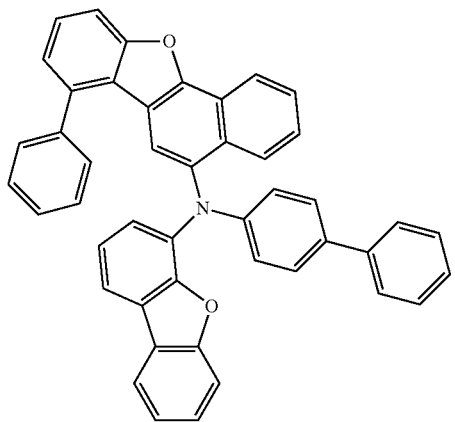
HT-361
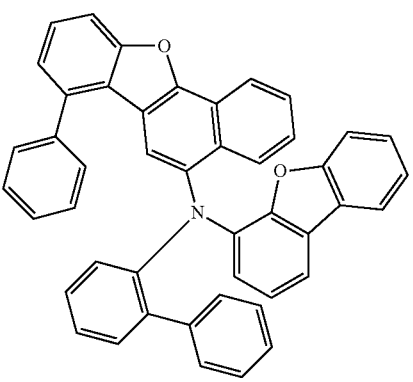
HT-359
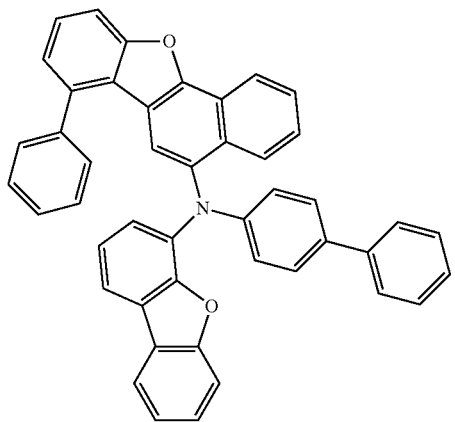
HT-362
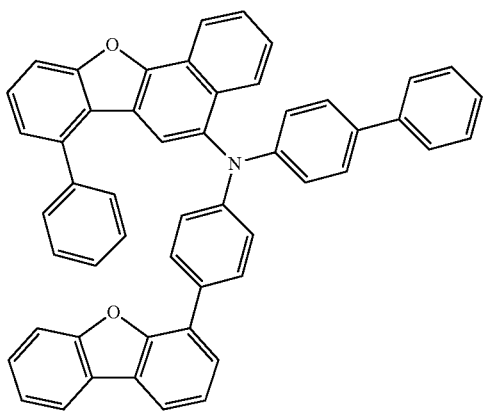

HT-363
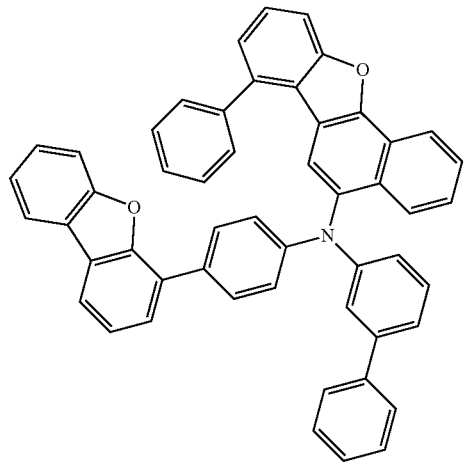
HT-364
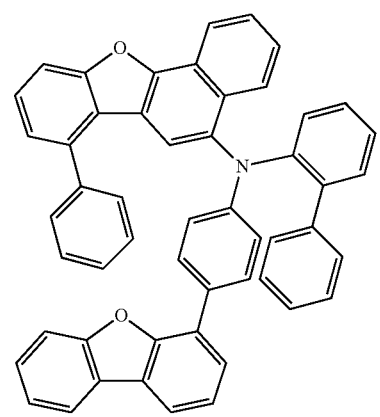
HT-365
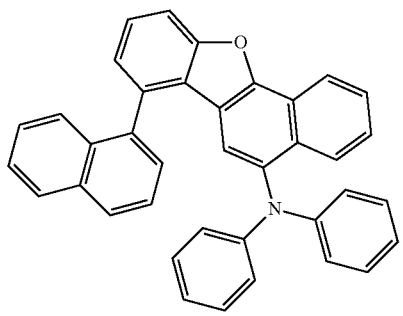
HT-366
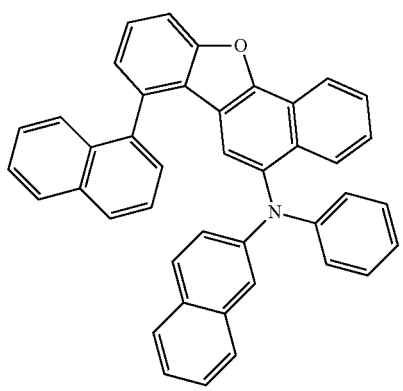
HT-367
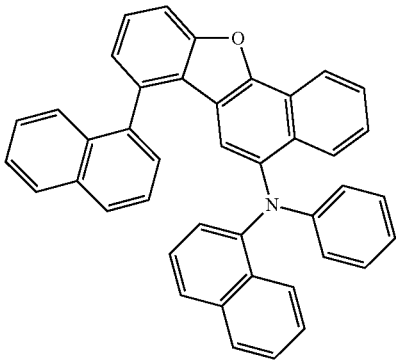
HT-368
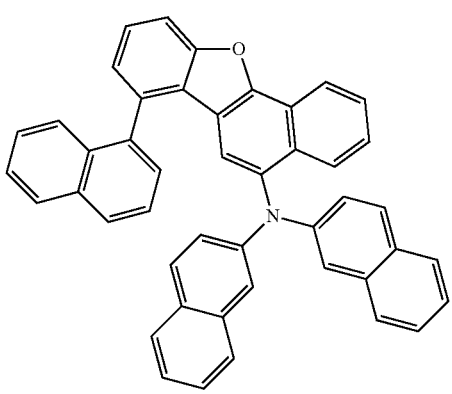
HT-369
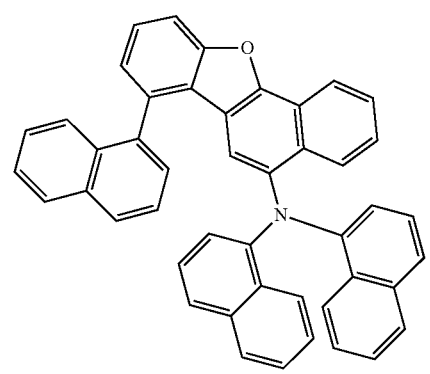
HT-370
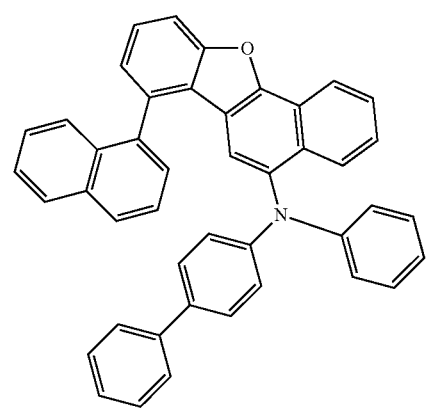

429
-continued
HT-371
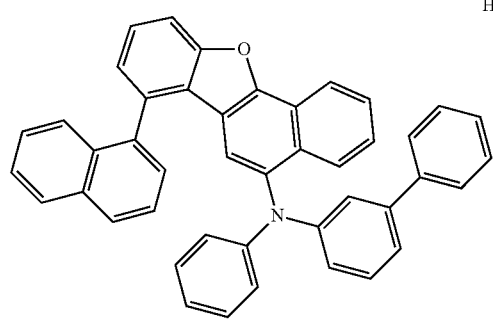
HT-372
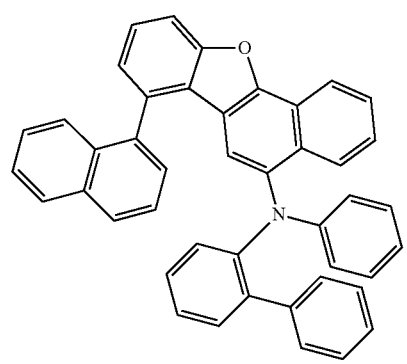
HT-373
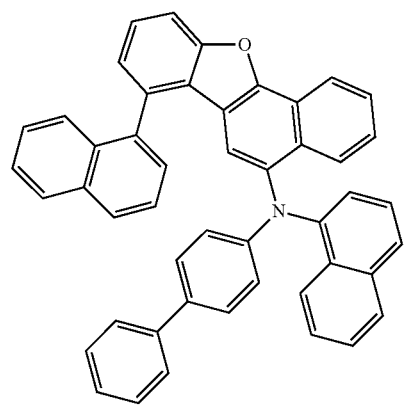
HT-374
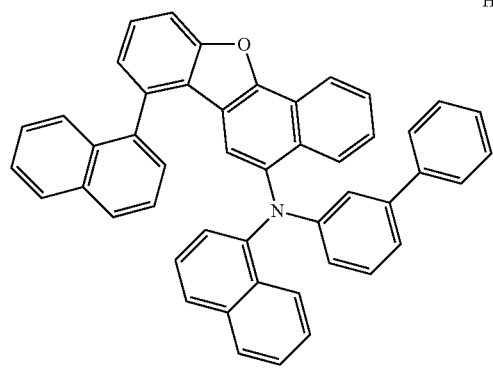
430
-continued
HT-375
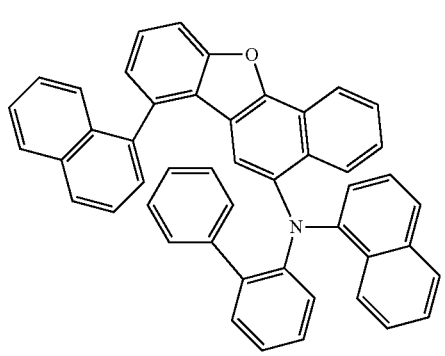
HT-376
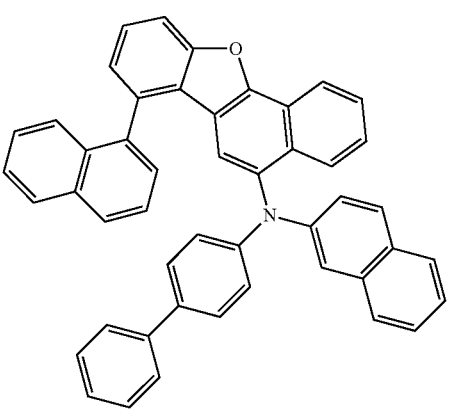
HT-377
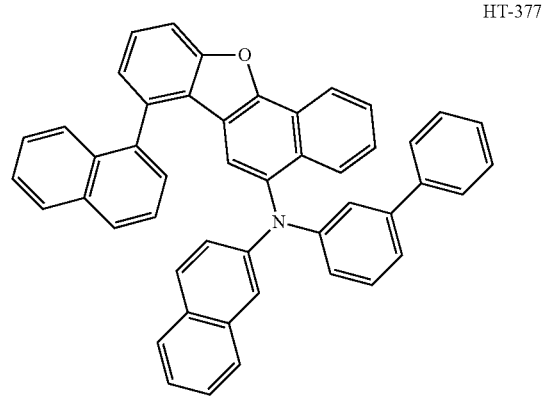
HT-378
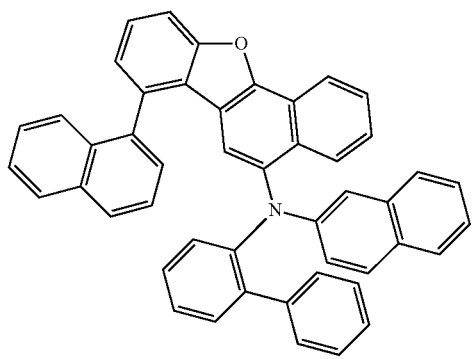

HT-379
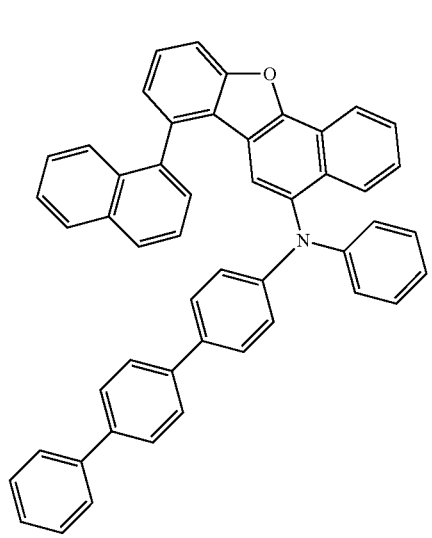
HT-382
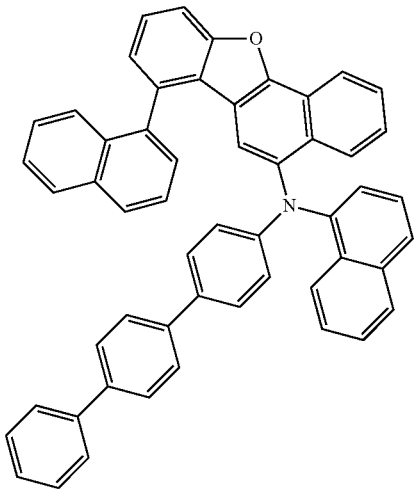
HT-380
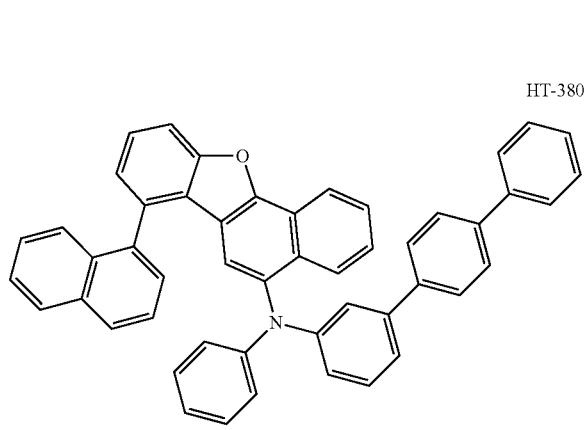
HT-383
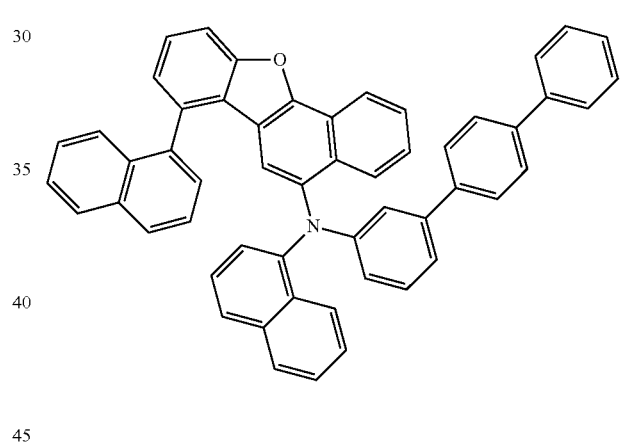
HT-381
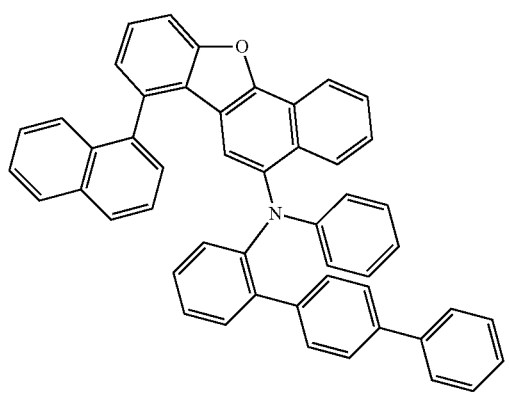
HT-384
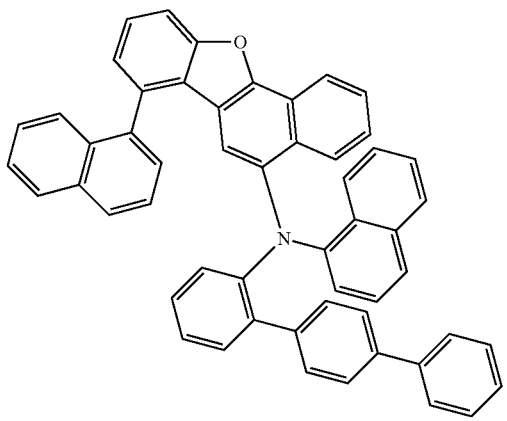

HT-385
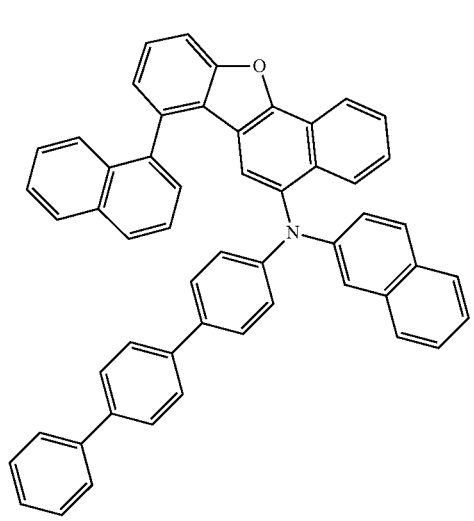
HT-388
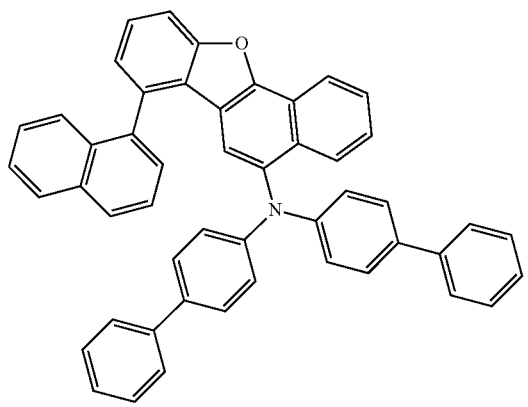
HT-386
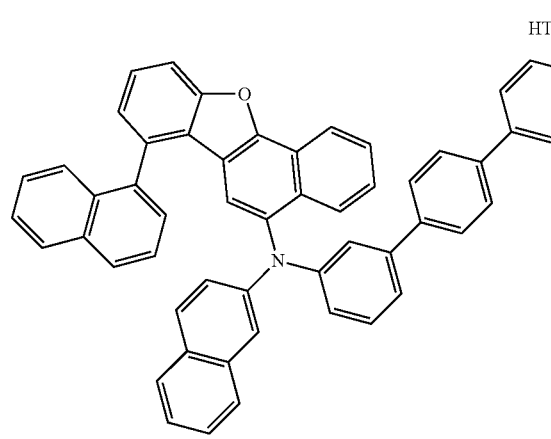
HT-389
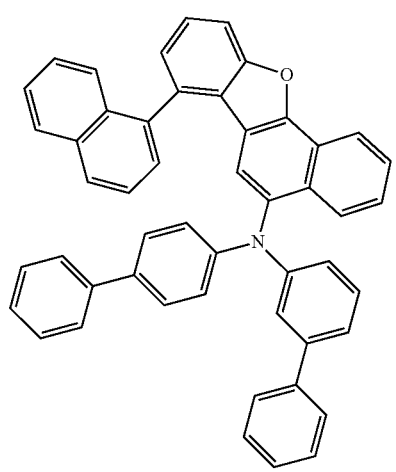
HT-387
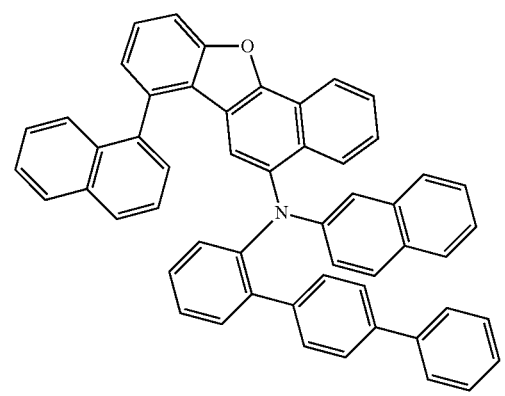
HT-390
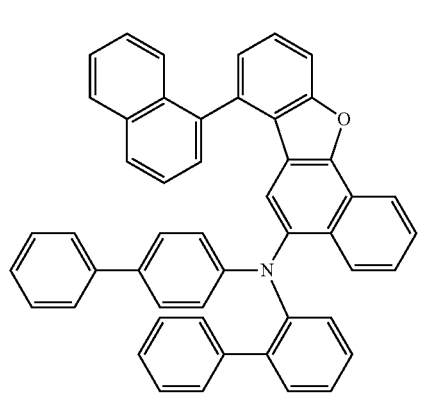

-continued
HT-391
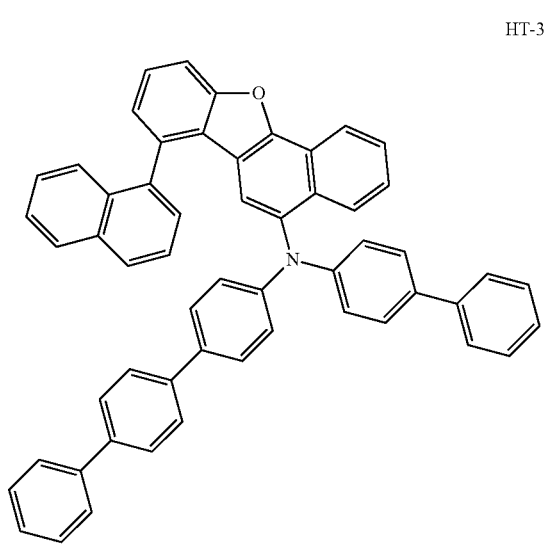
HT-392
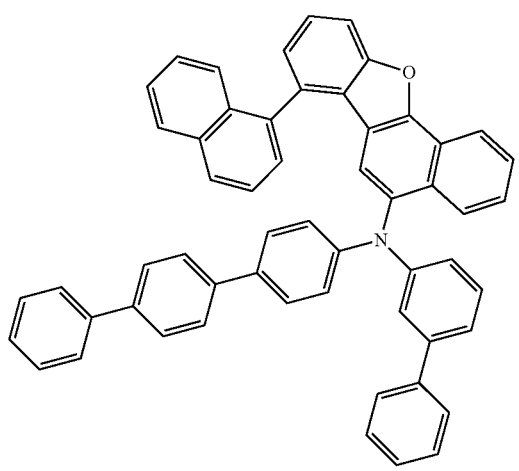
HT-393
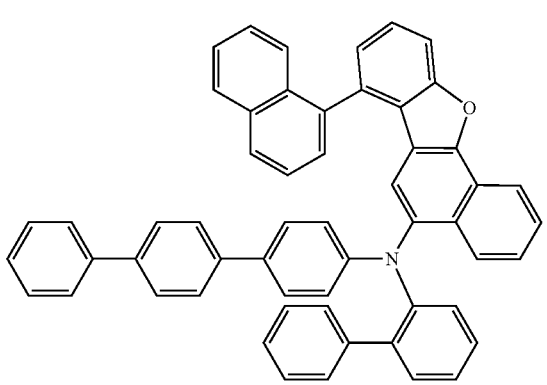
-continued
HT-394
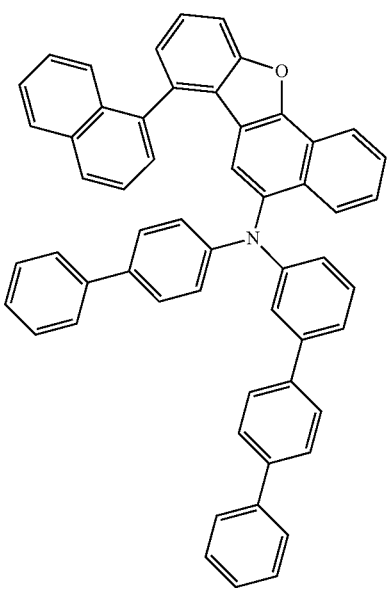
HT-395
HT-396
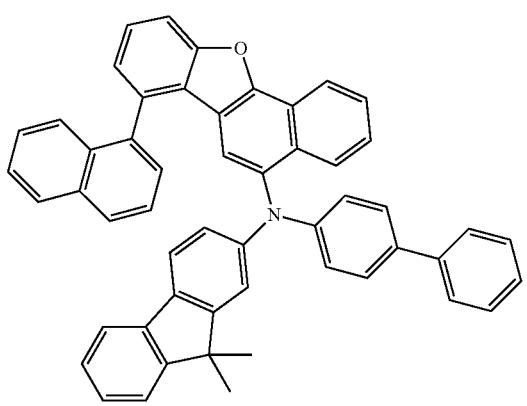

HT-397
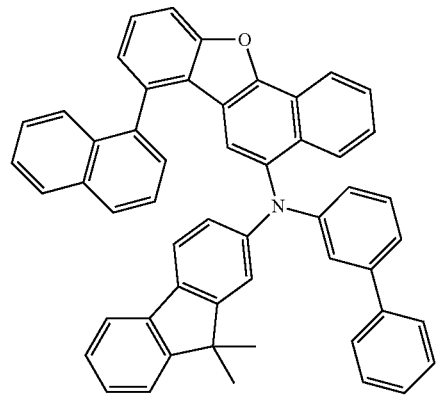
HT-398
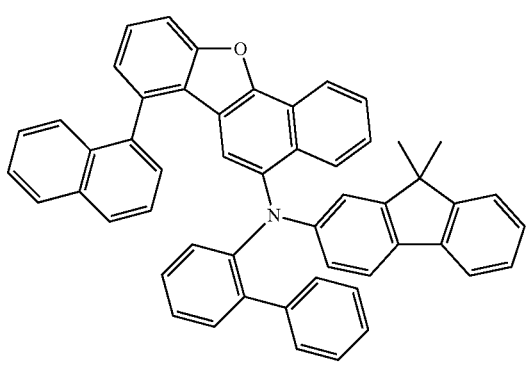
HT-399
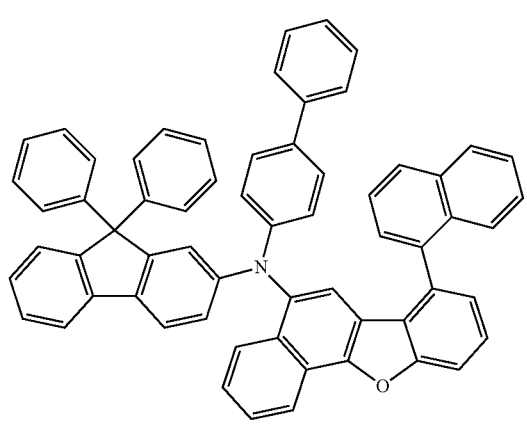
HT-400
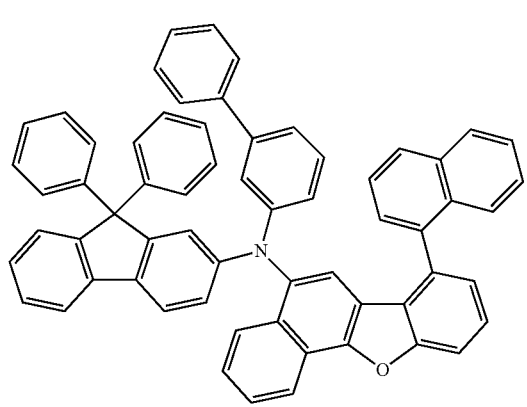
HT-401
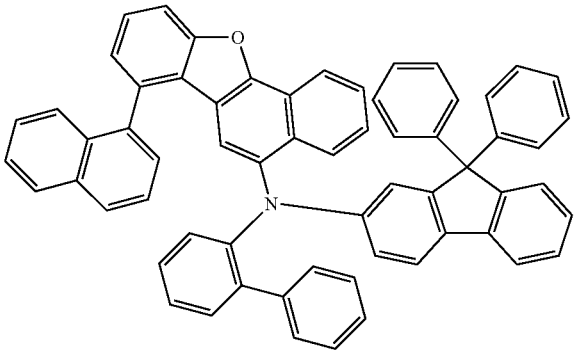
HT-402
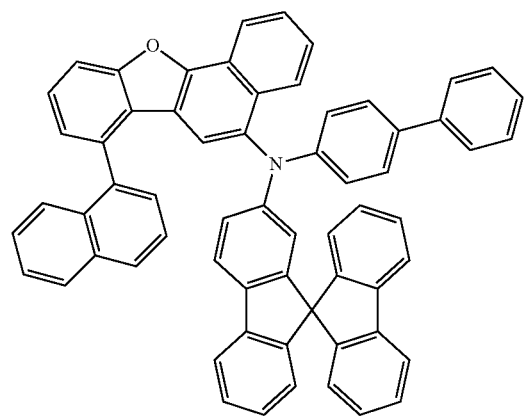
HT-403
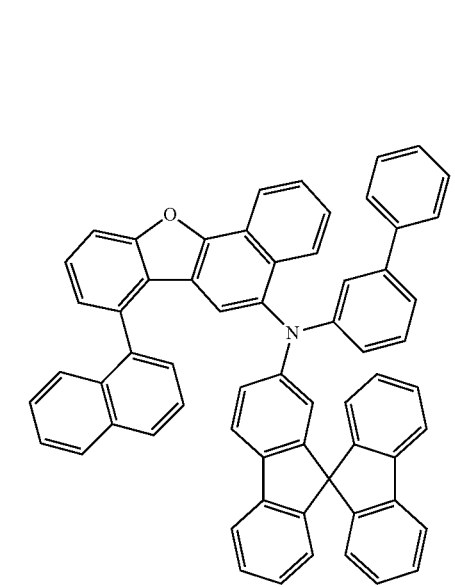

-continued
HT-404
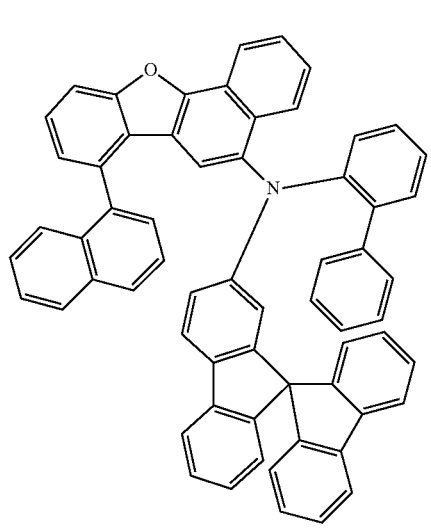
HT-405
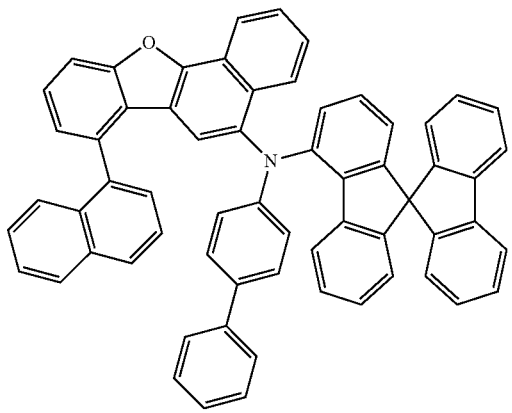
HT-406
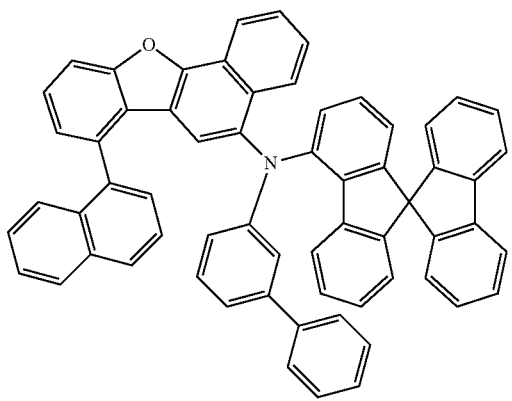
-continued
HT-407
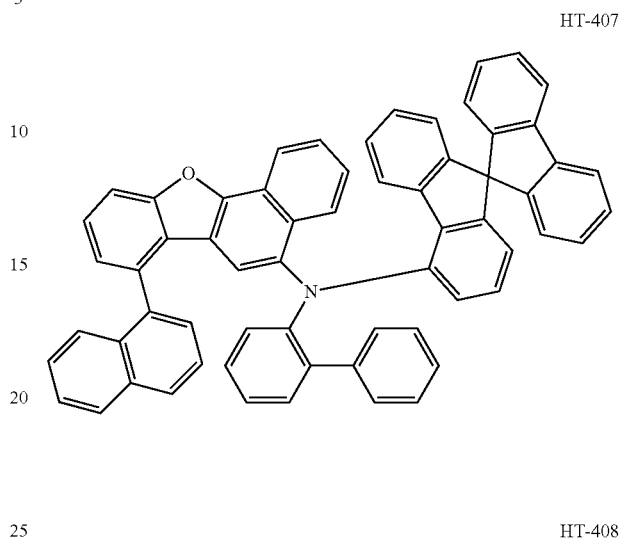
HT-408
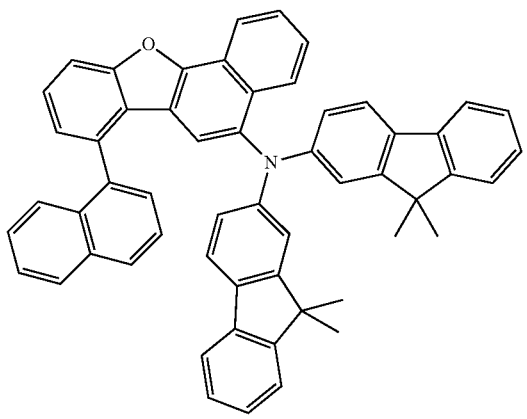
HT-409
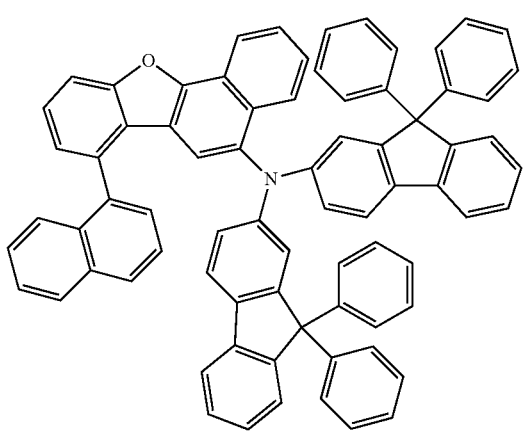

HT-410
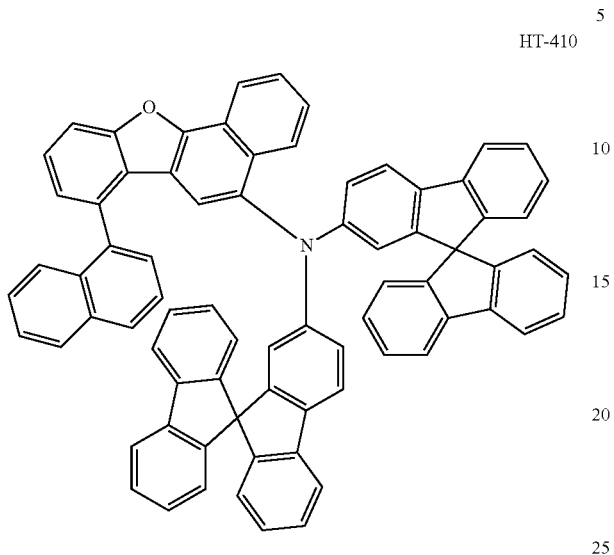
HT-411
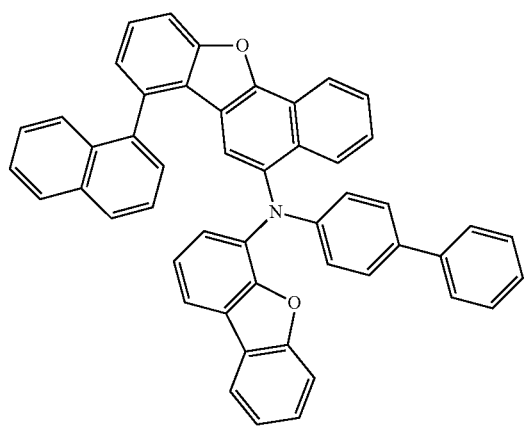
HT-412
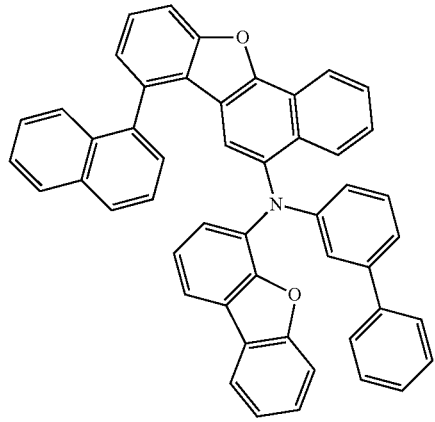
HT-413
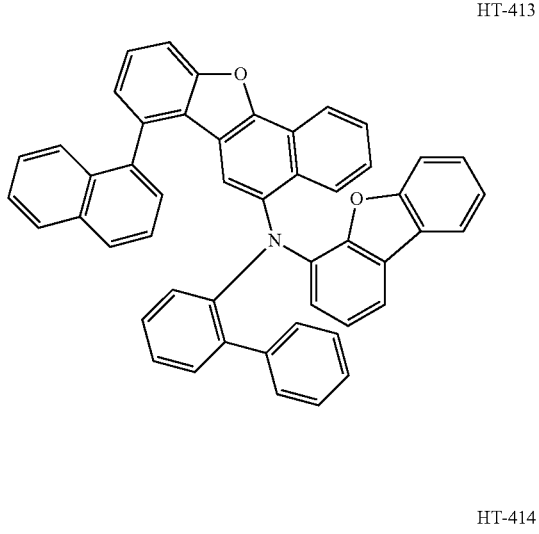
HT-414
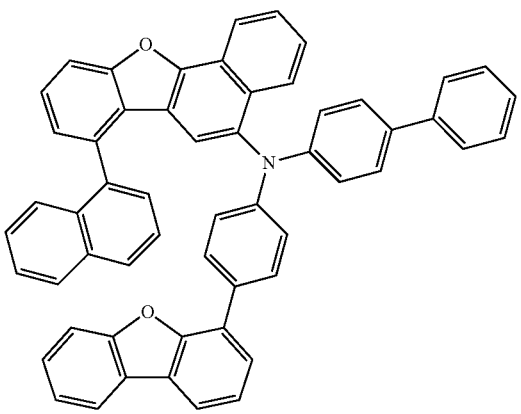
HT-415
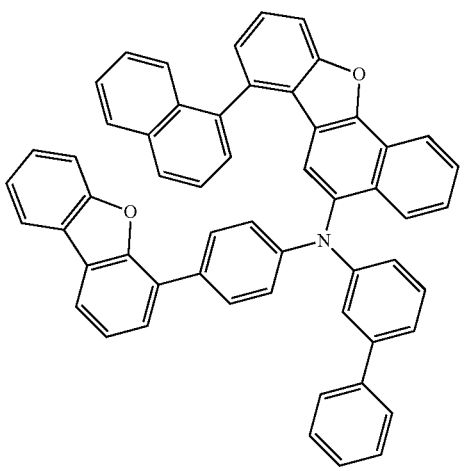

HT-416
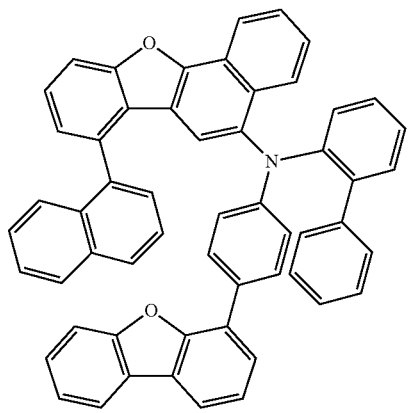
HT-417
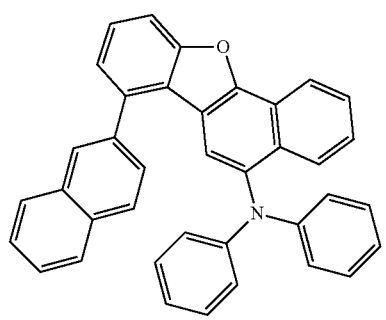
HT-418
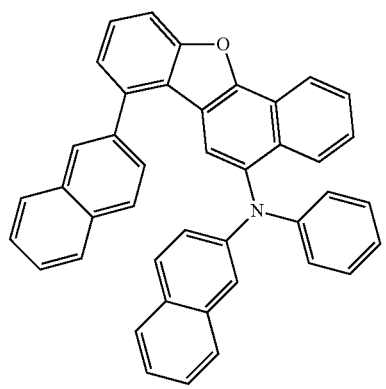
HT-419
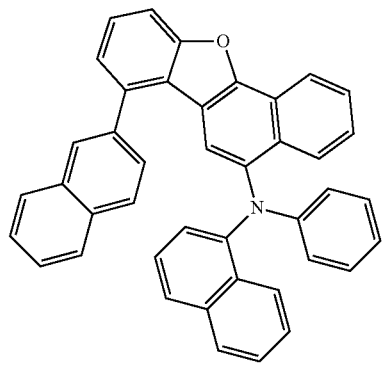
HT-420
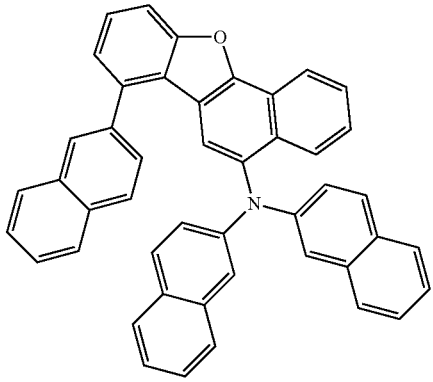
HT-421
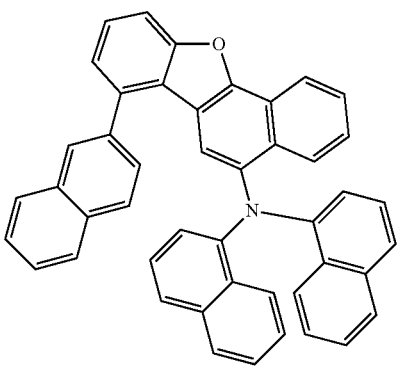
HT-422
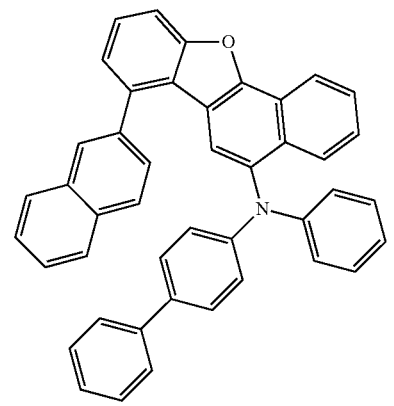
HT-423
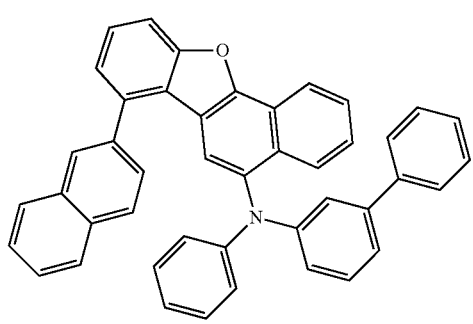

-continued
HT-424
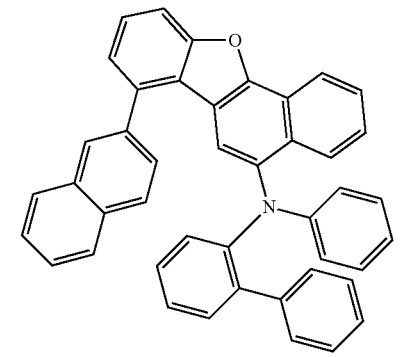
HT-425
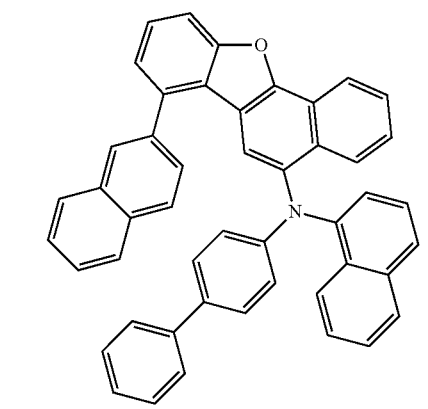
HT-426
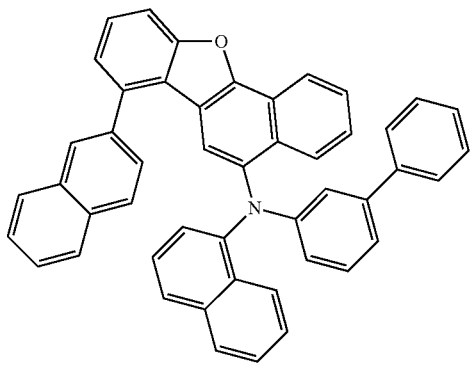
HT-427
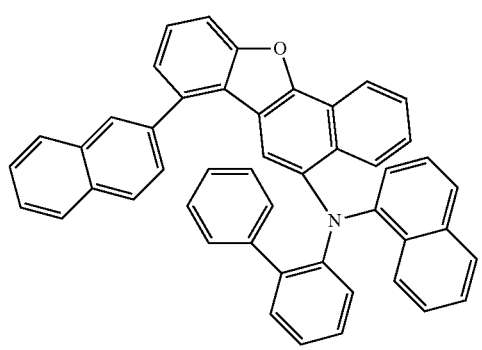
-continued
HT-428
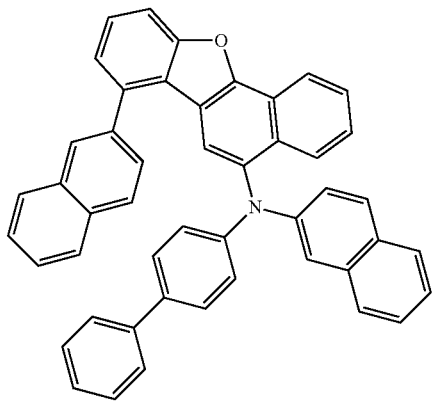
HT-429
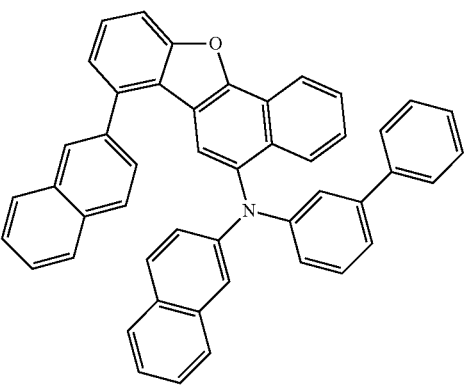
HT-430
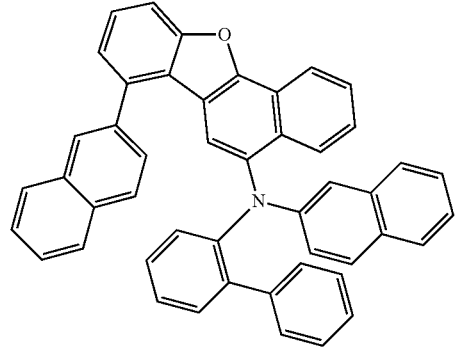
HT-431
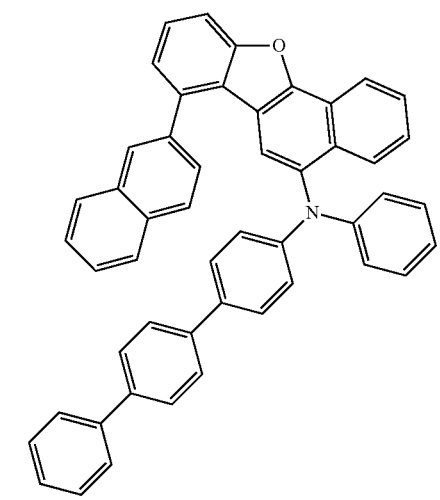

HT-432
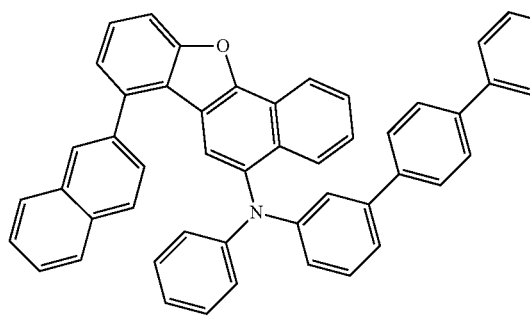
HT-433
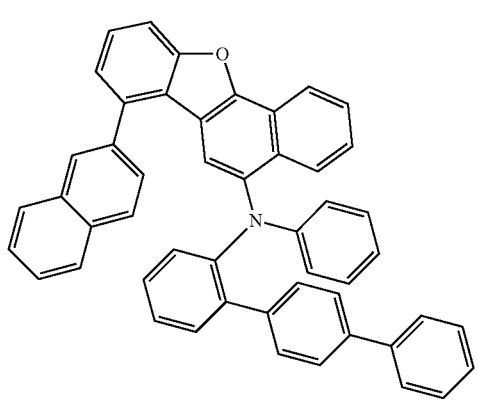
HT-434
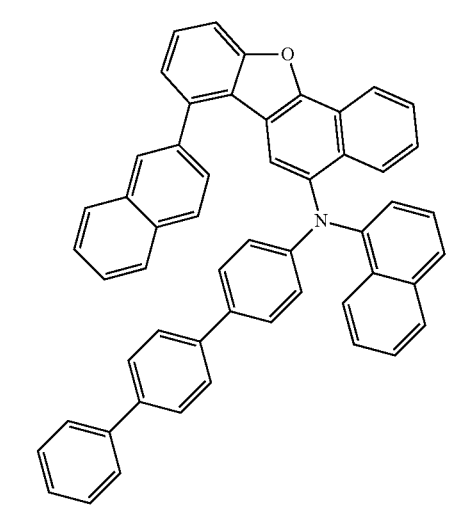
HT-435
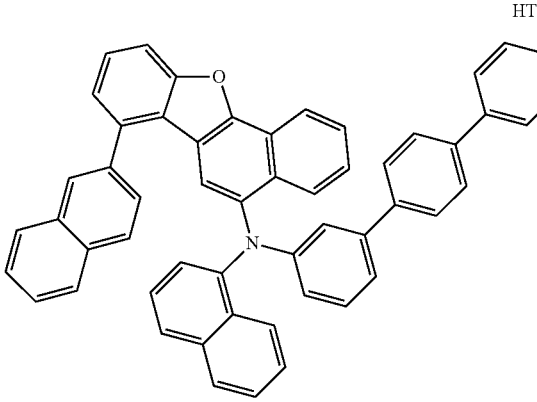
HT-436
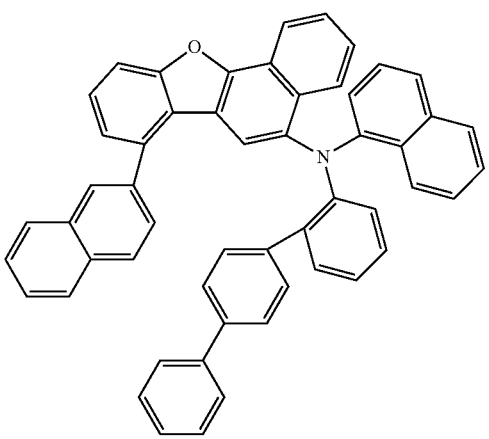
HT-437
HT-438

-continued
HT-439
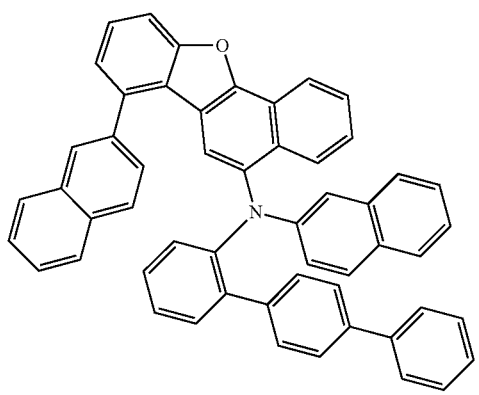
HT-442
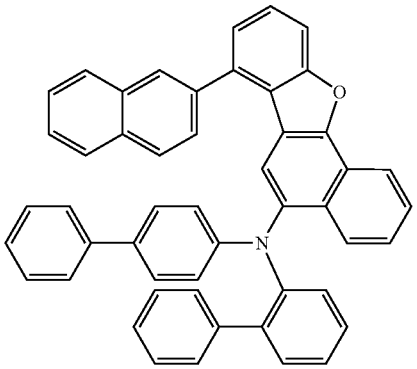
HT-440
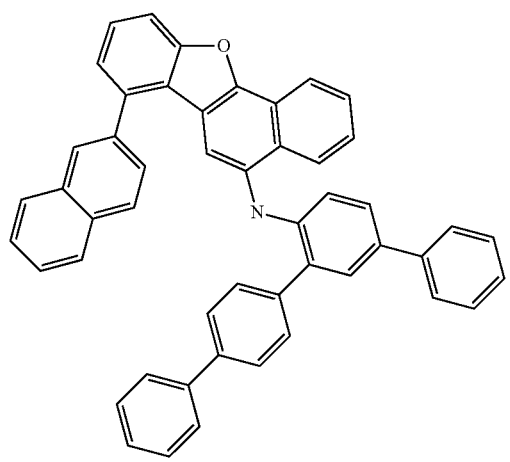
HT-443
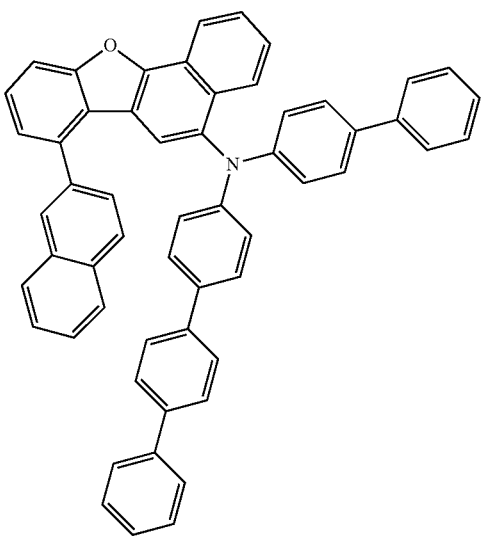
HT-441
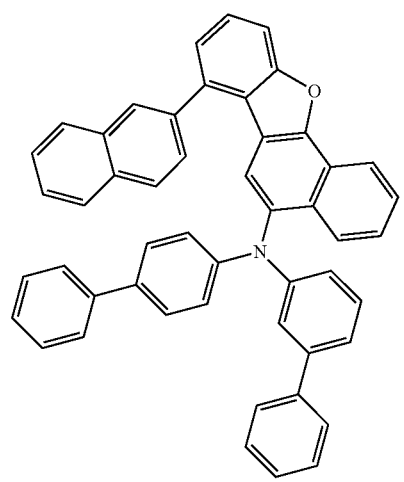
HT-444
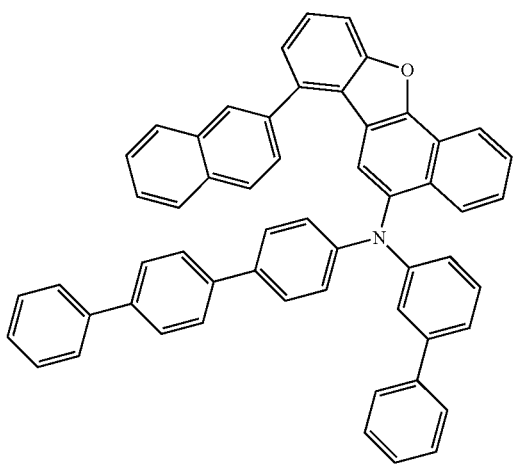

451
-continued
HT-445
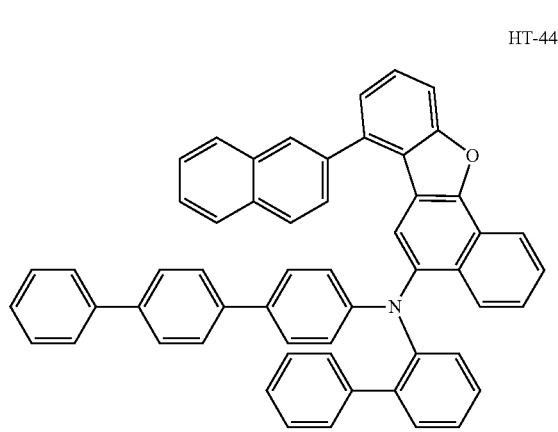
HT-446
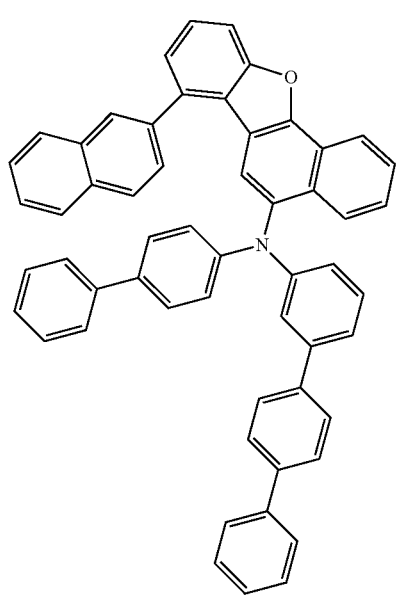
HT-447
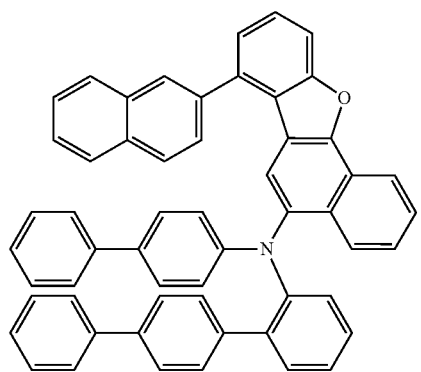
452
-continued
HT-448
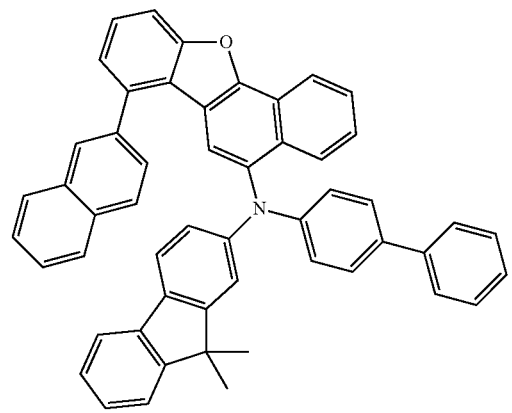
HT-449
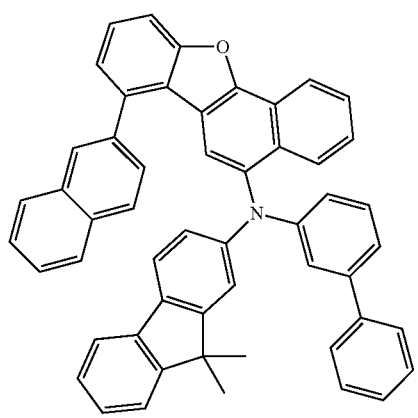
HT-450
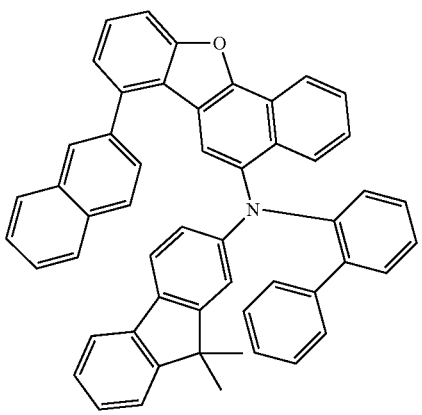

HT-451
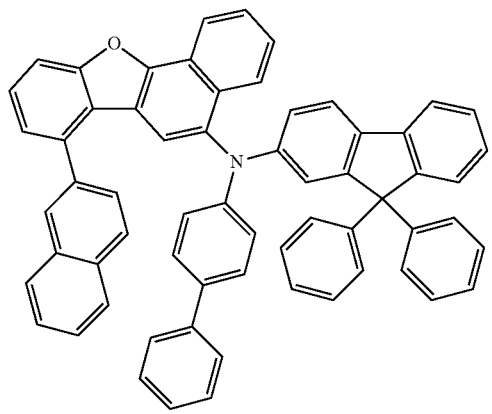
HT-452
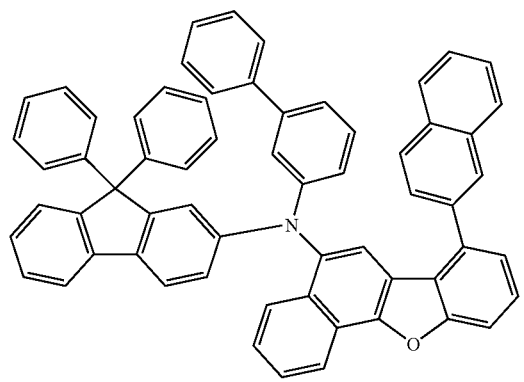
HT-453
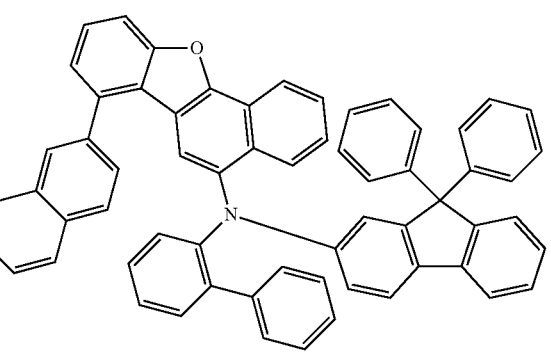
HT-454
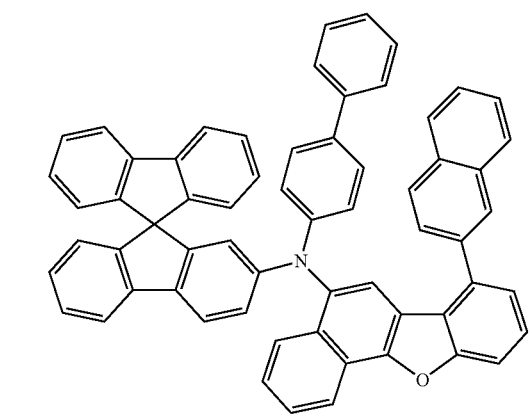
HT-455
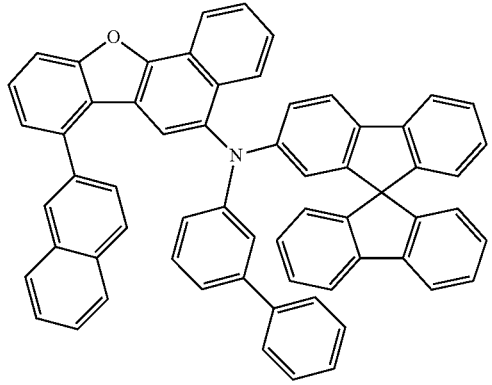
HT-456
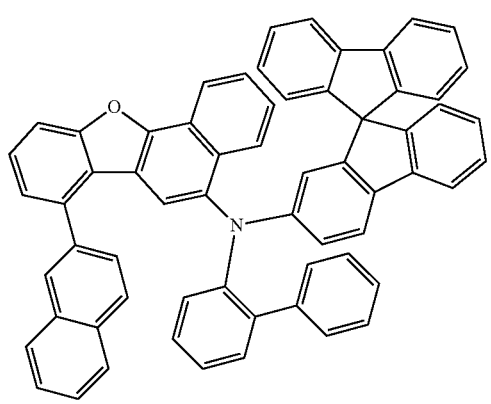
HT-457
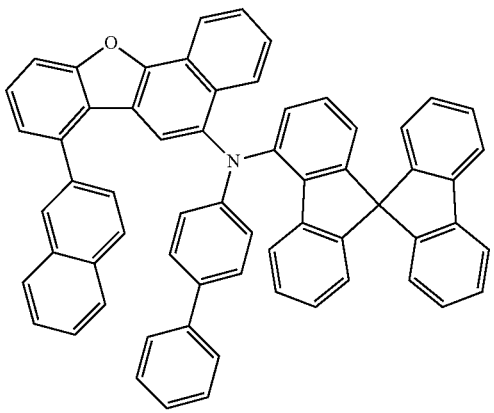
HT-458
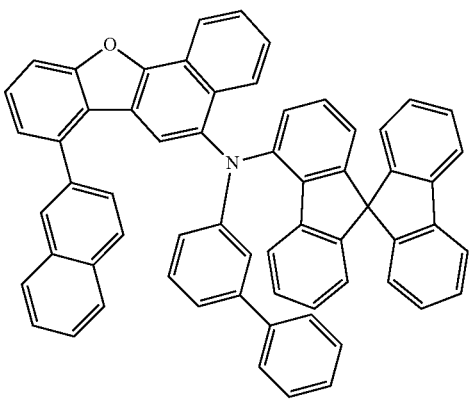

HT-459
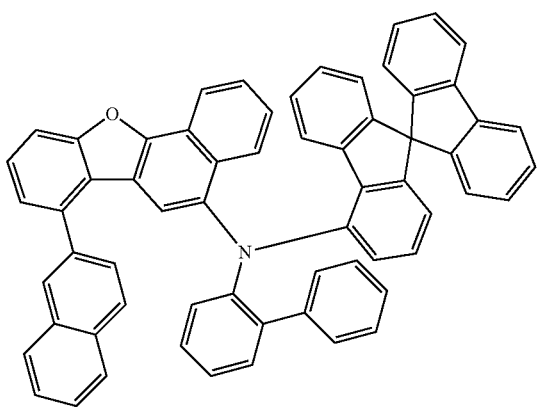
HT-460
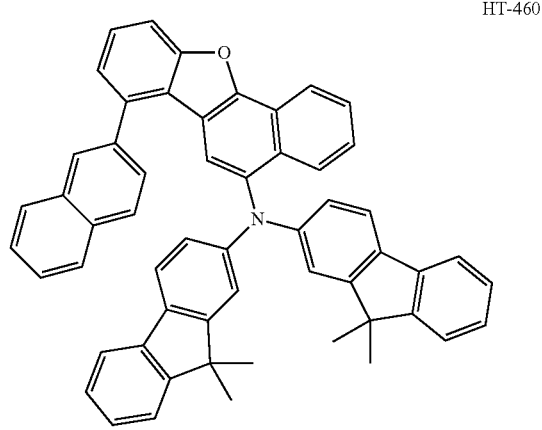
HT-461
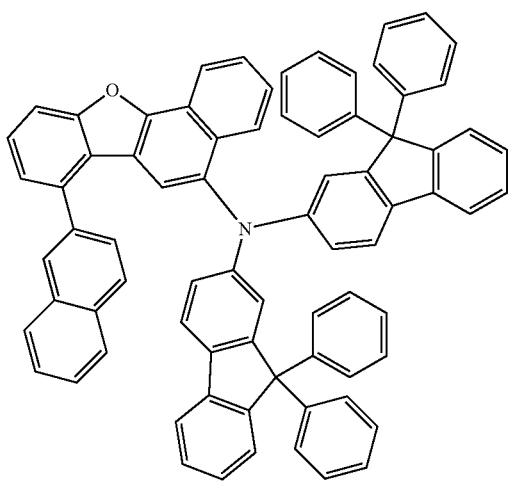
HT-462
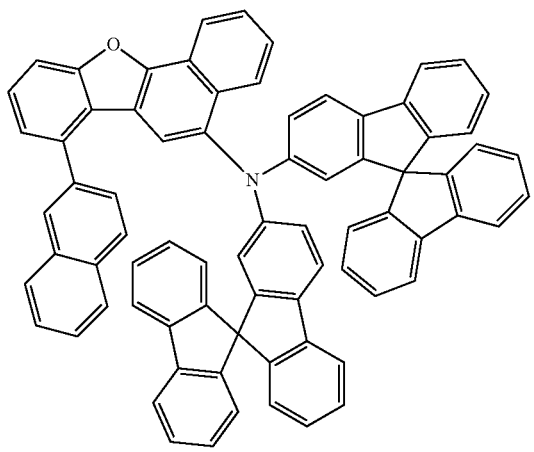
HT-463
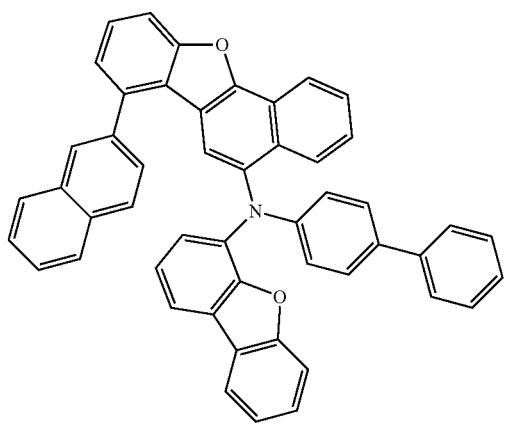
HT-464
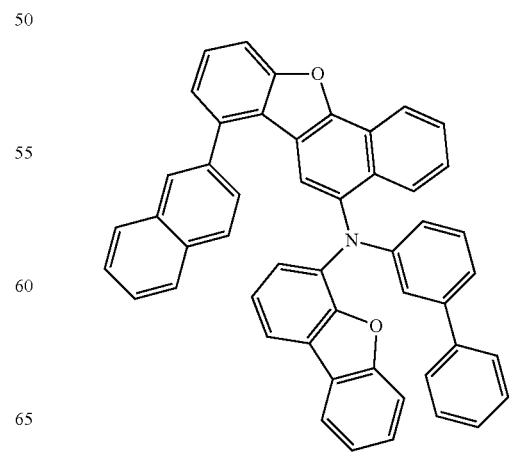

HT-465
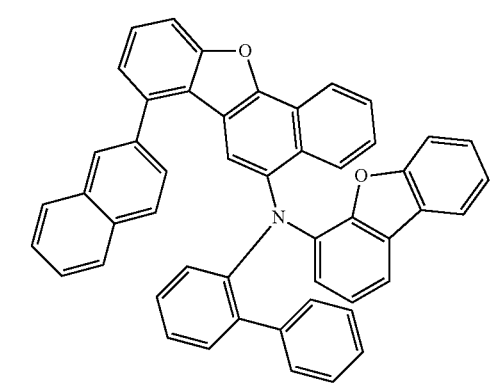
HT-468
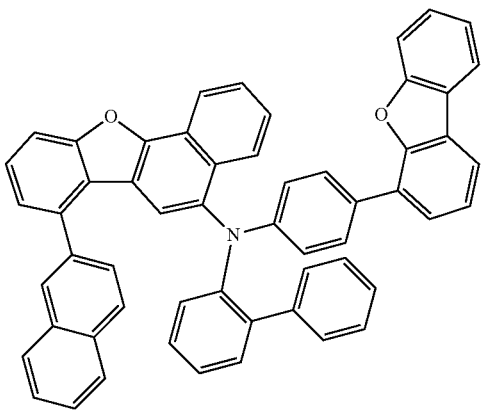
HT-466
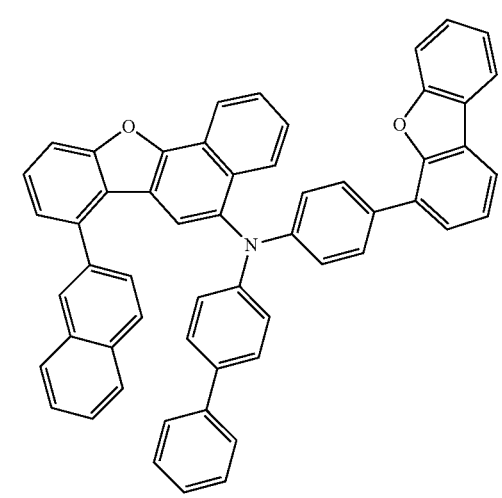
HT-469
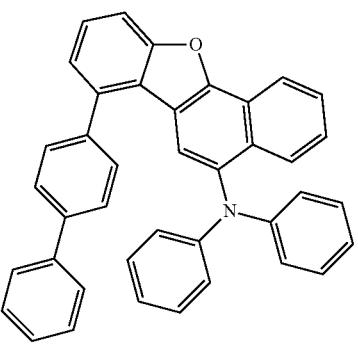
HT-470
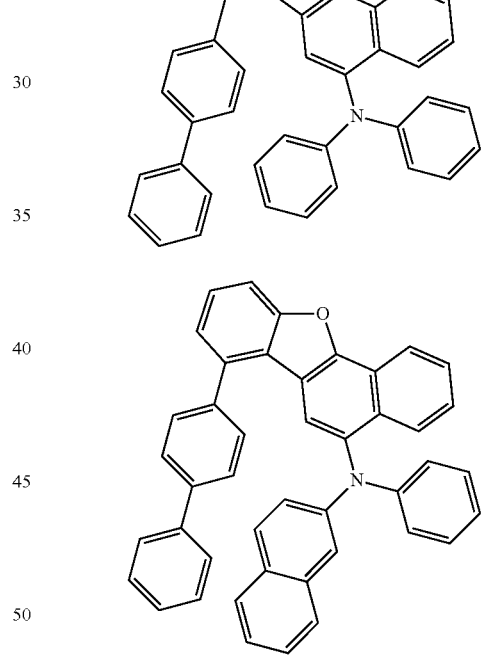
HT-467
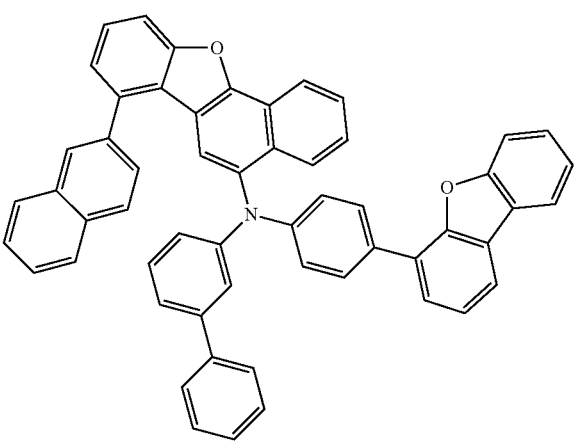
HT-471
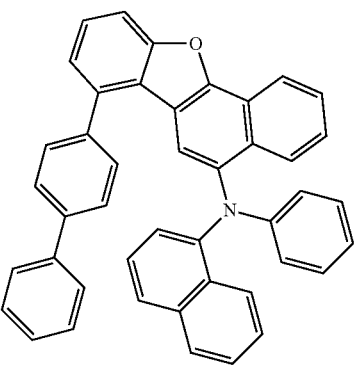

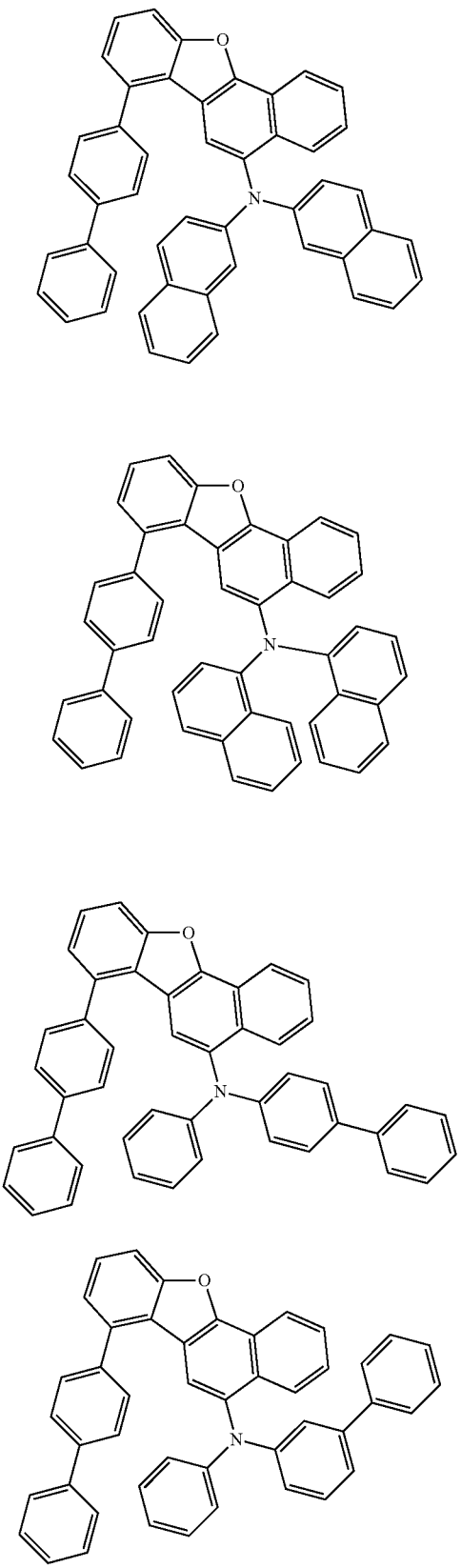
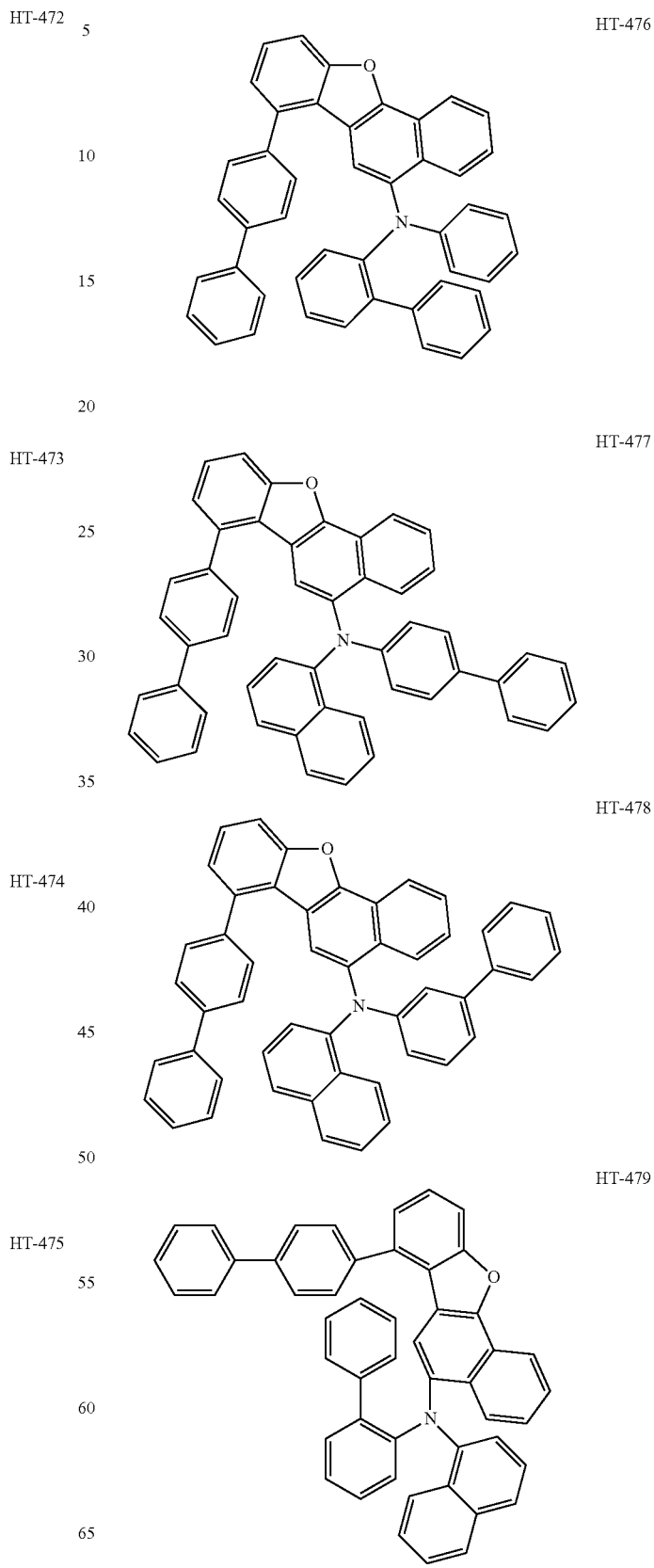

461
-continued
HT-480
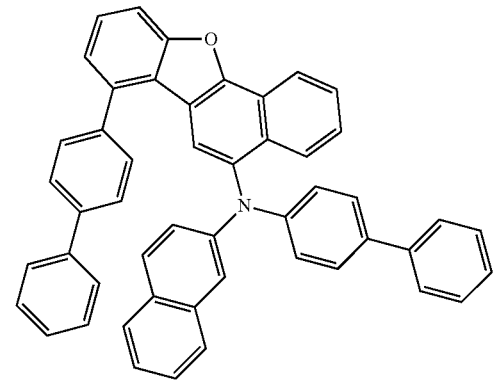
HT-481
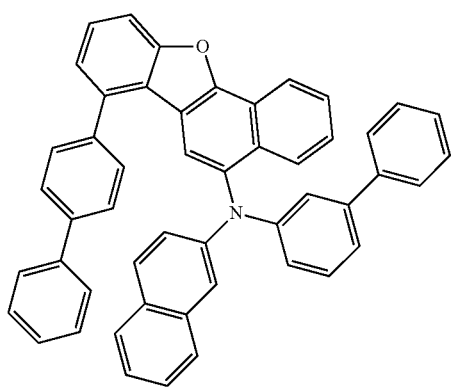
HT-482
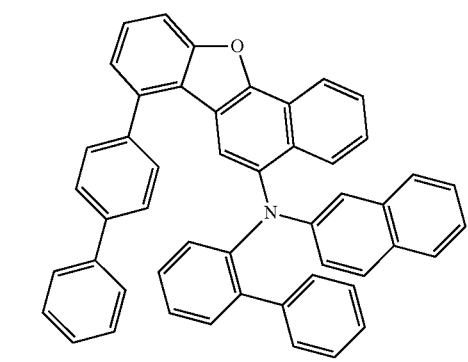
HT-483
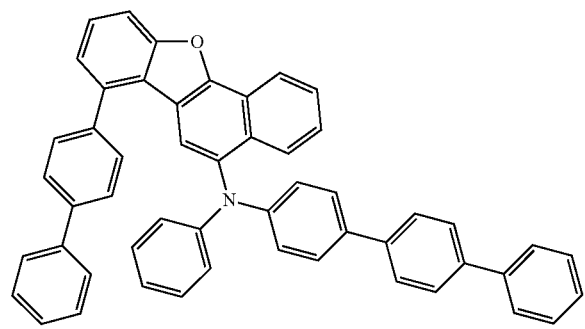
462
-continued
HT-484
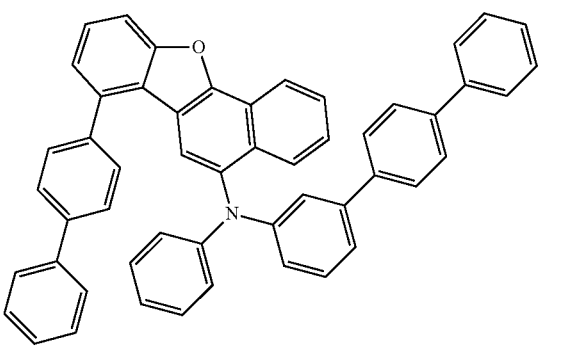
HT-485
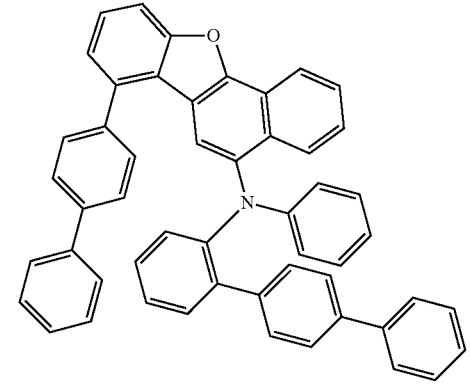
HT-486
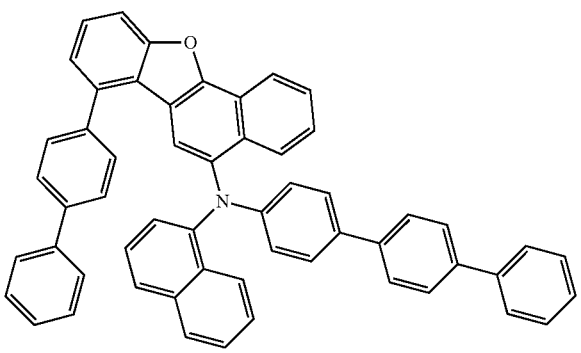
HT-487
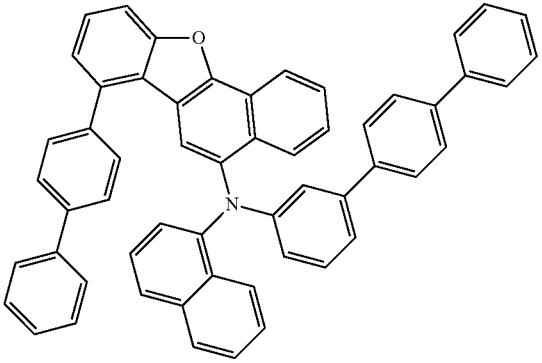

-continued
HT-488
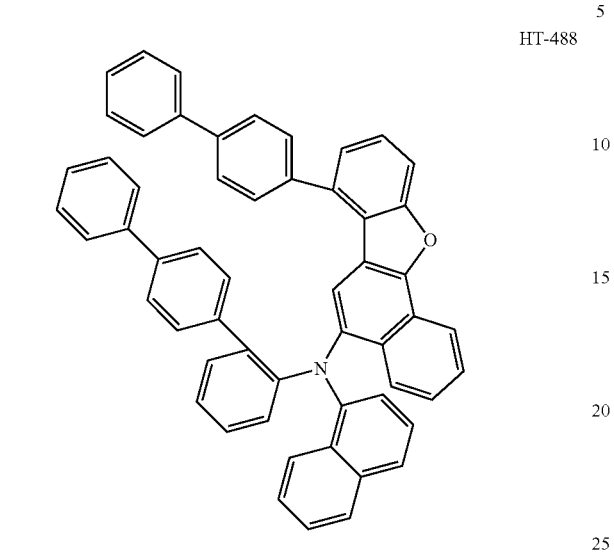
HT-489
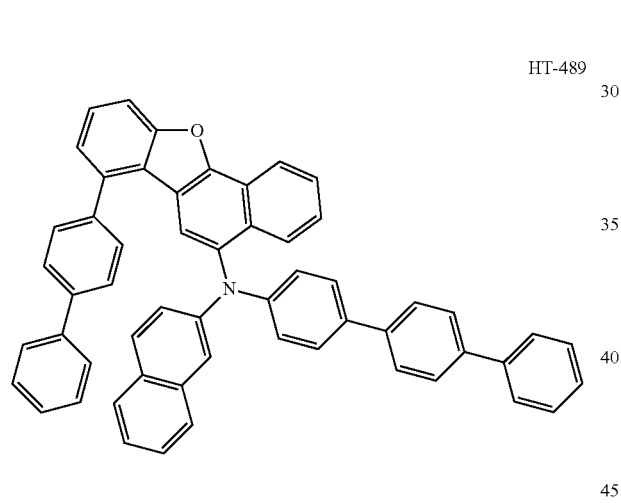
HT-490
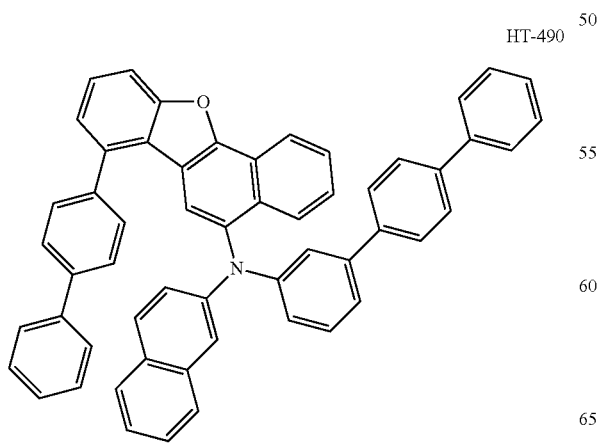
-continued
HT-491
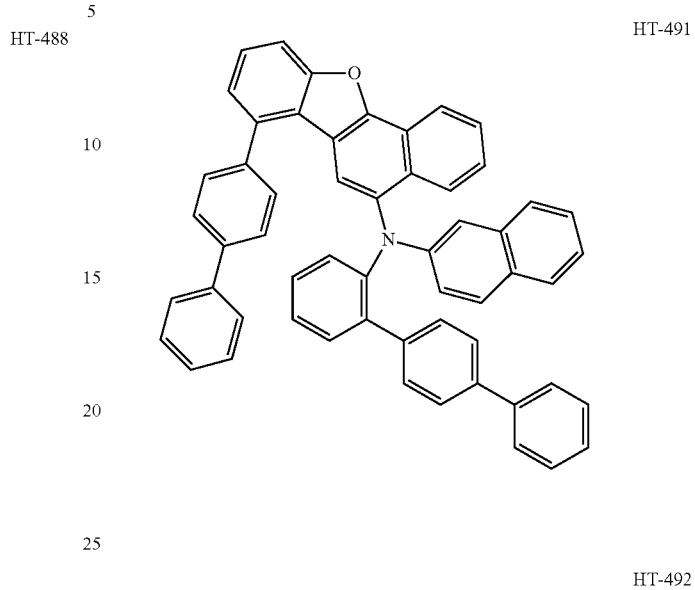
HT-492
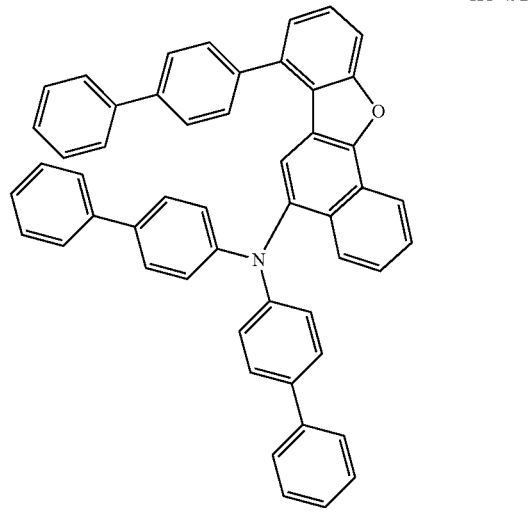
HT-493
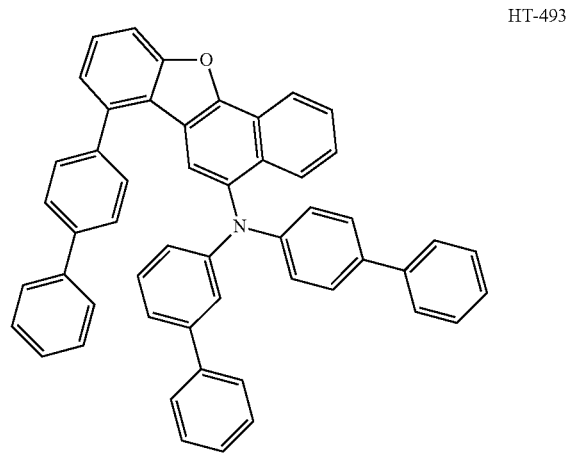

HT-494
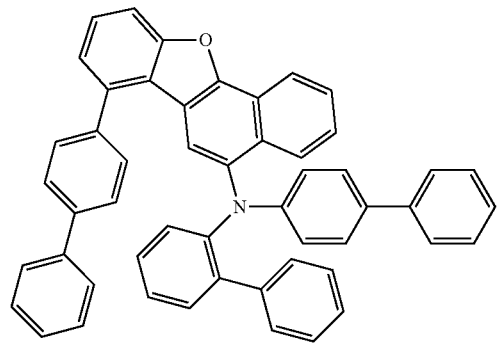
HT-497
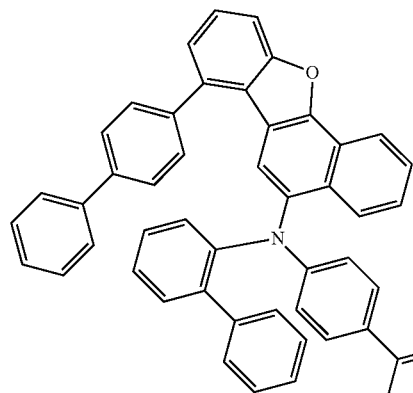
HT-495
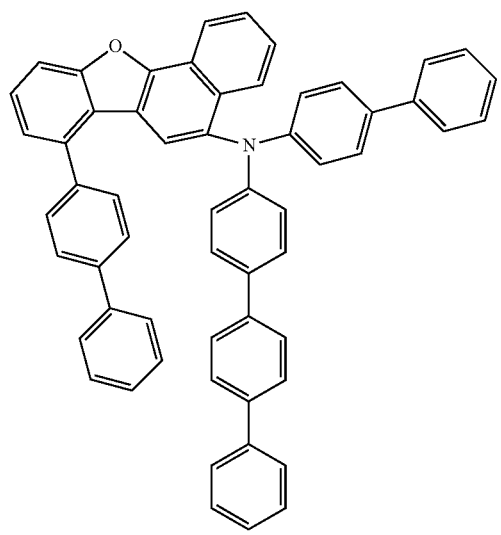
HT-498
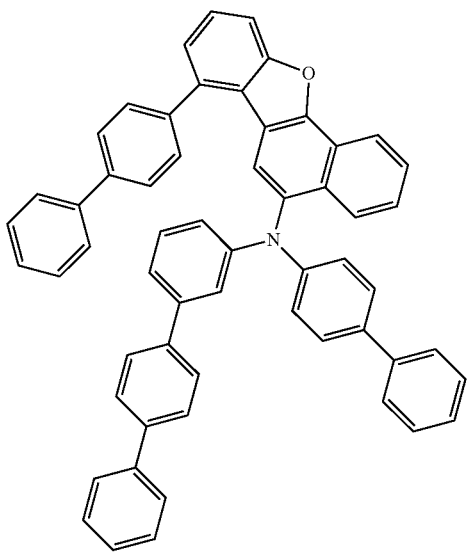
HT-496
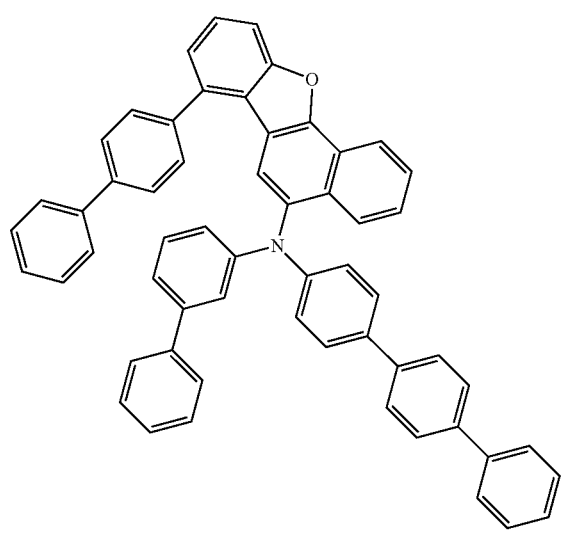
HT-499
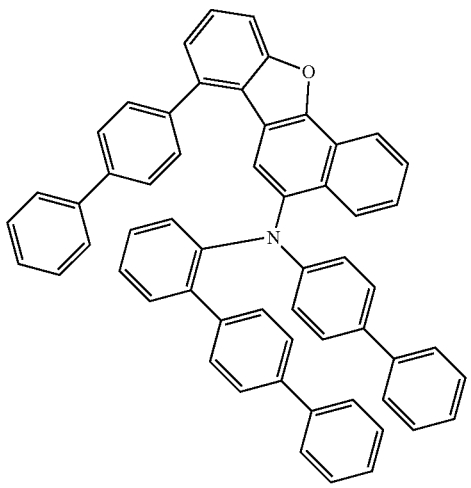

-continued
HT-501
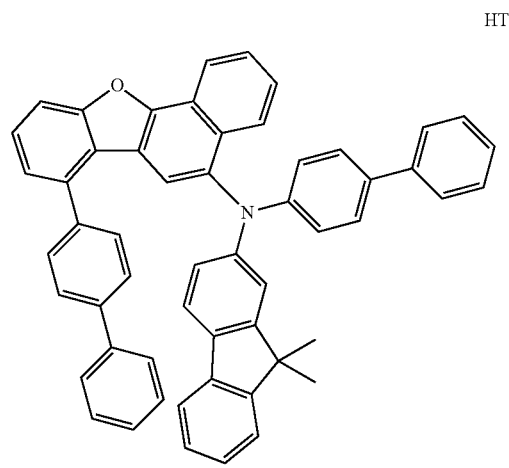
HT-502
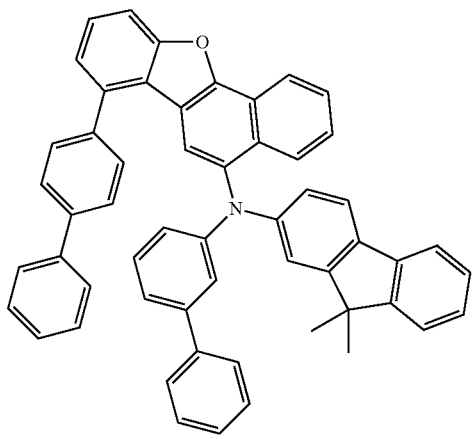
HT-503
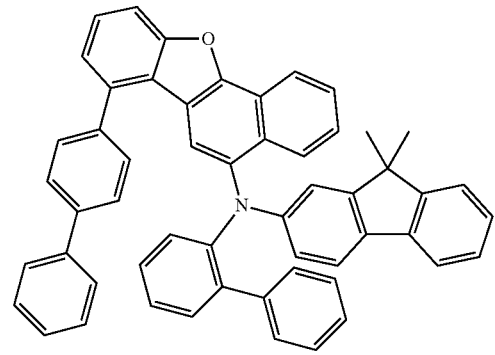
-continued
HT-504
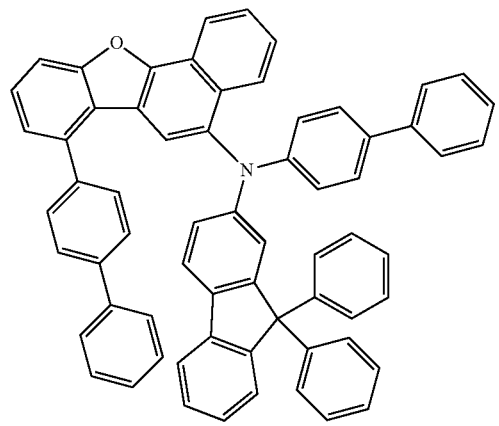
HT-505
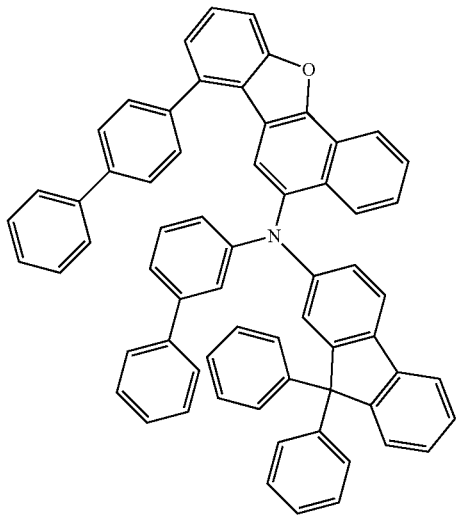
HT-506
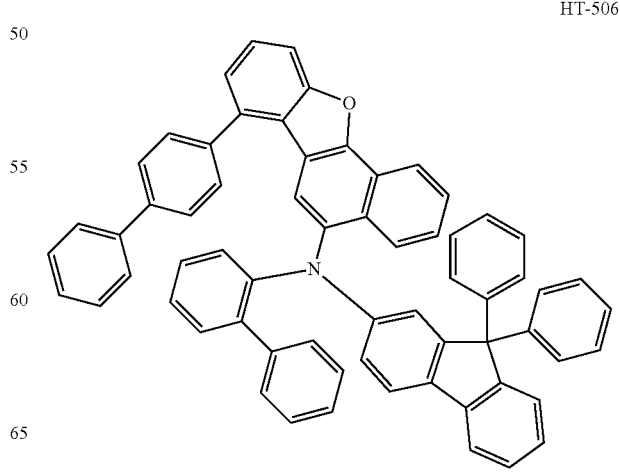

469
-continued
HT-507
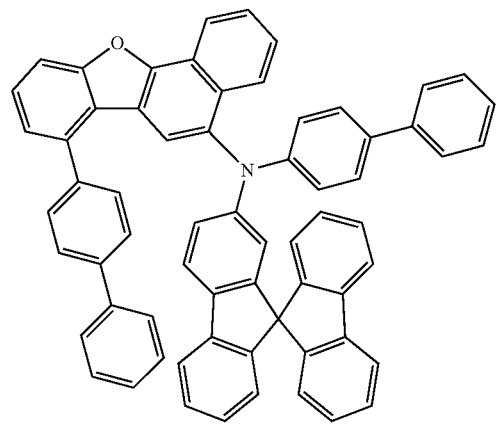
HT-508
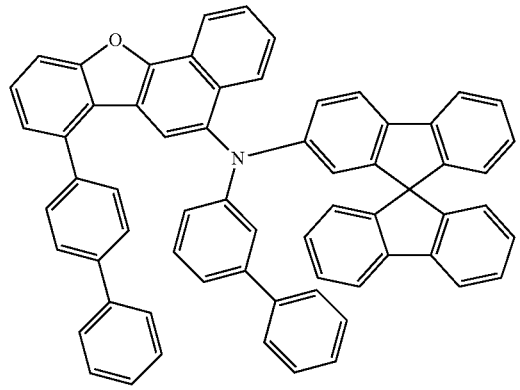
HT-509
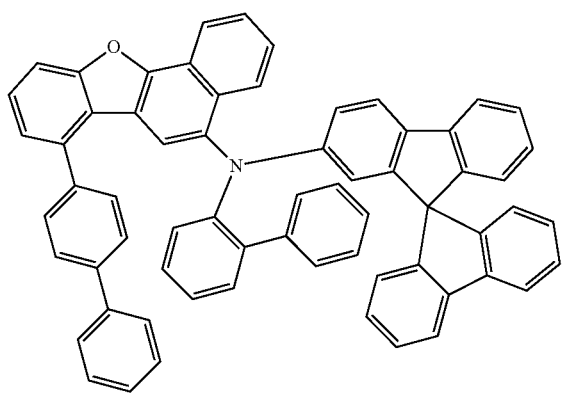
470
-continued
HT-510
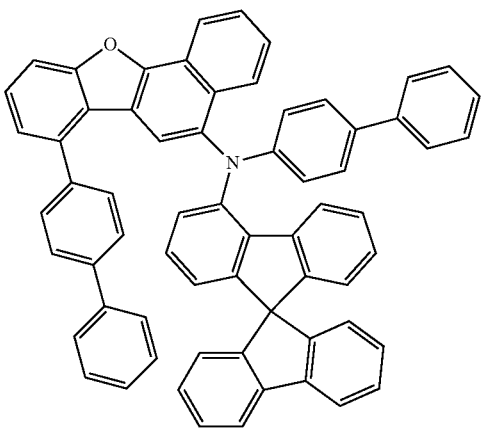
HT-511
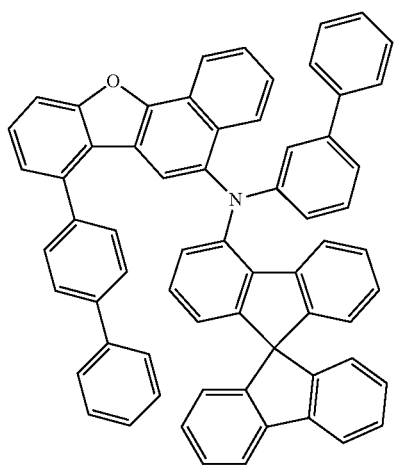
HT-512
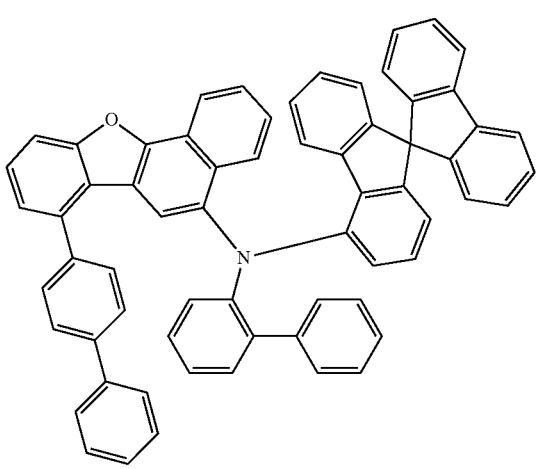

471
-continued
HT-513
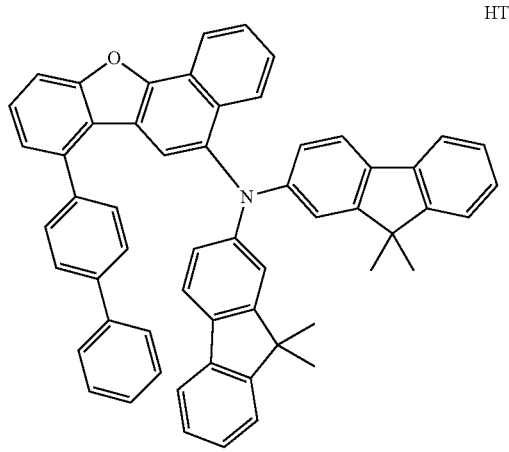
HT-514
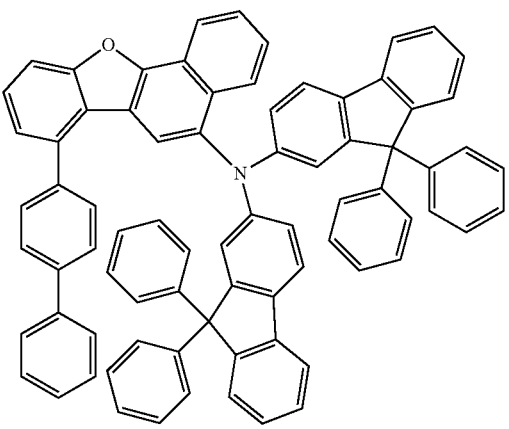
HT-515
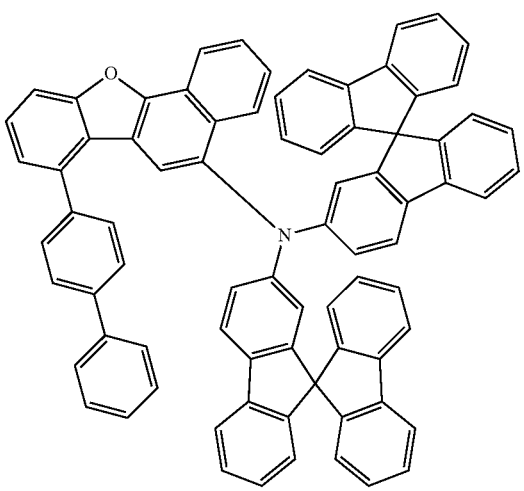
472
-continued
HT-516
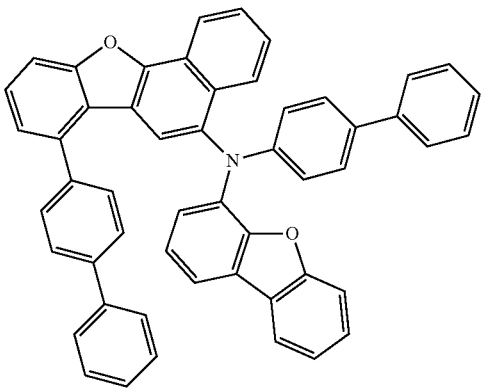
HT-517
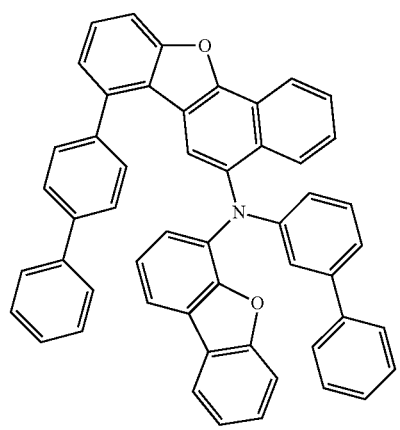
HT-518
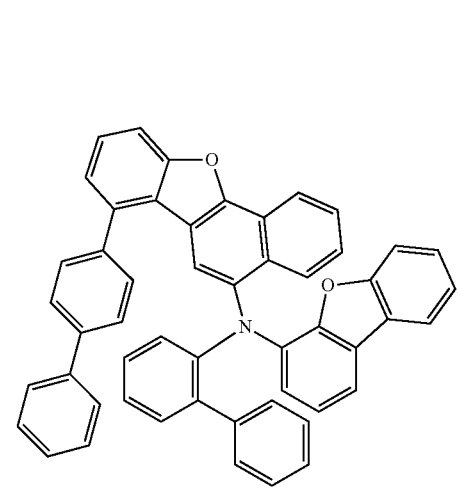

HT-519
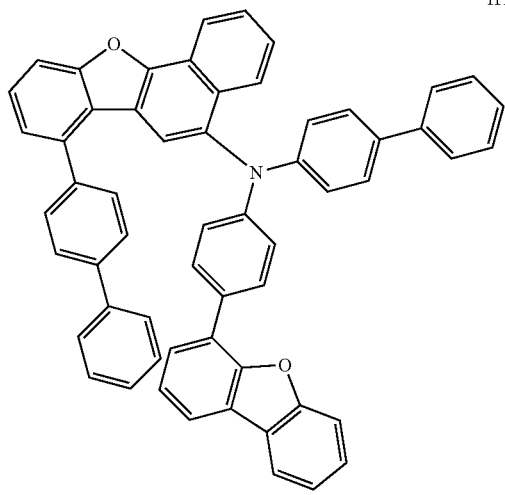
HT-520
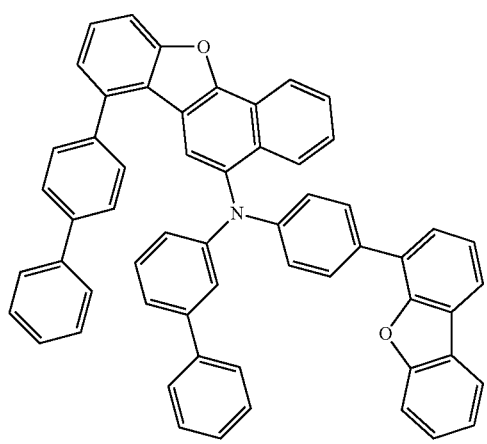
HT-521
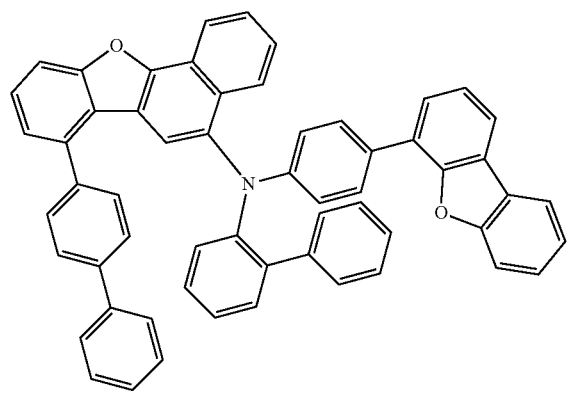
HT-522
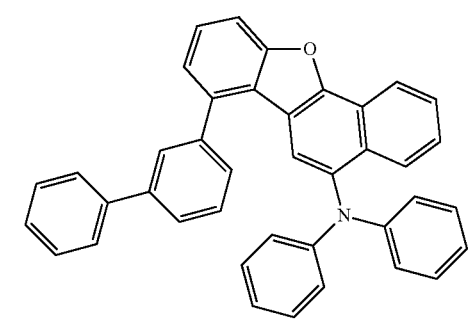
HT-523
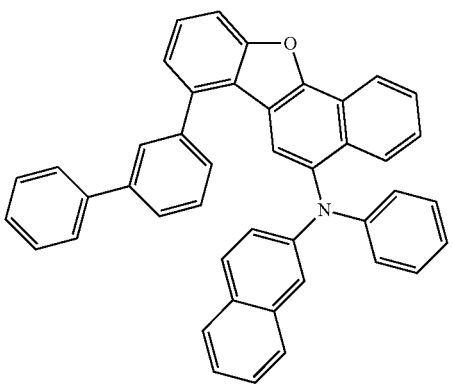
HT-524
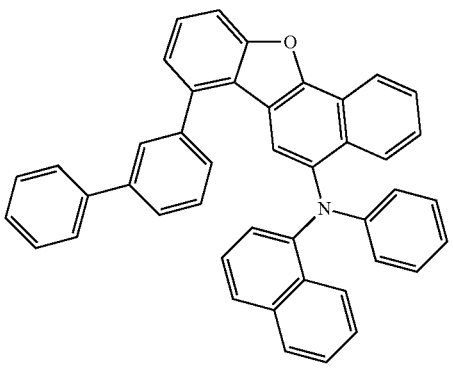
HT-525
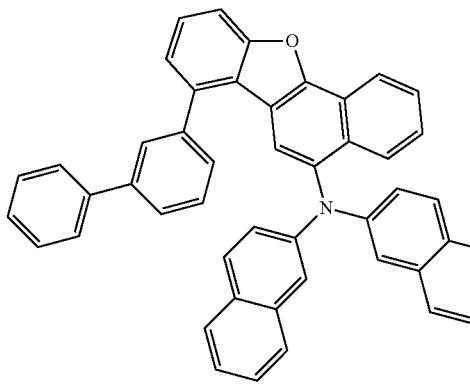
HT-526
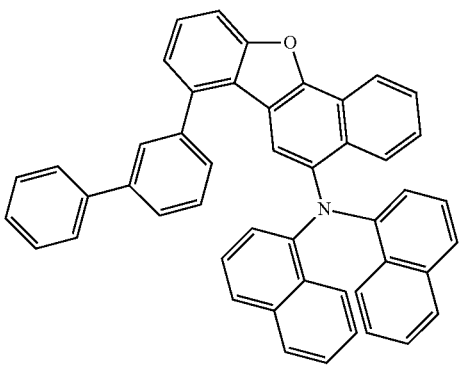

HT-527
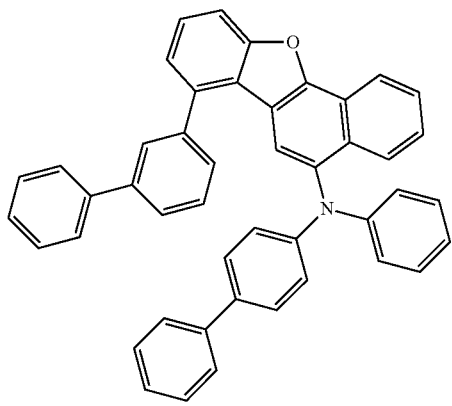
HT-528
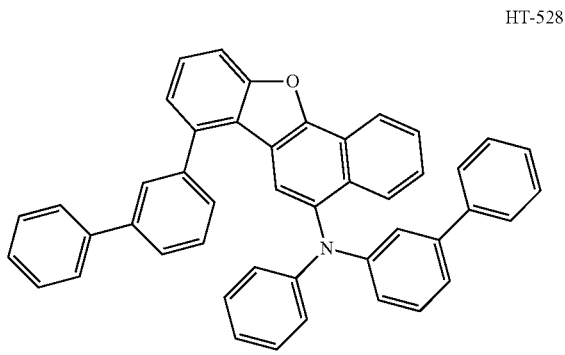
HT-529
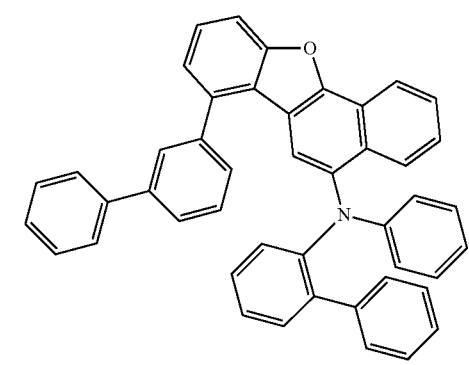
HT-530
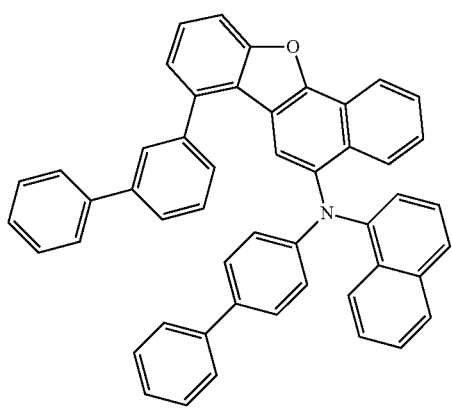
HT-531
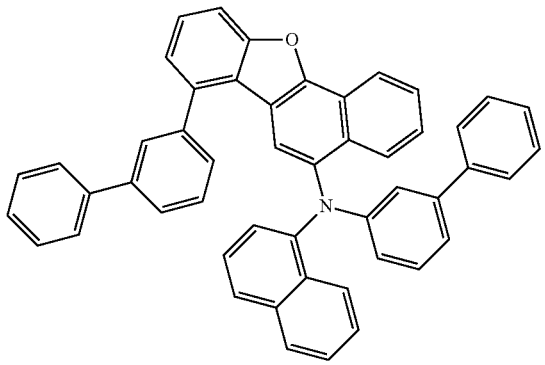
HT-532
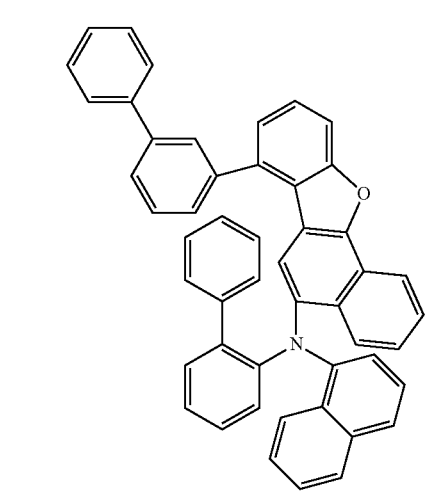
HT-533
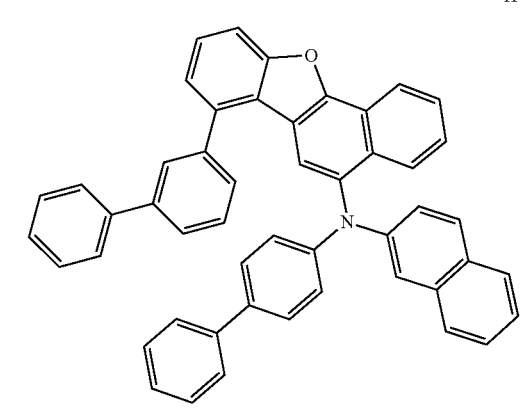

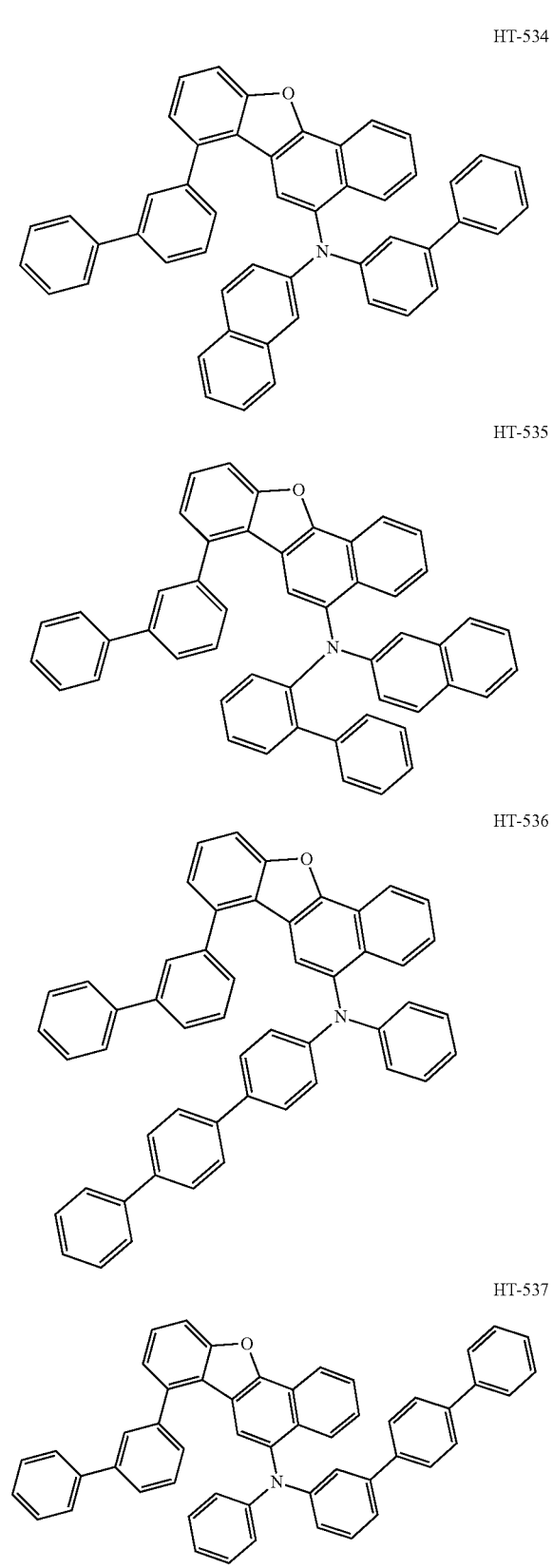
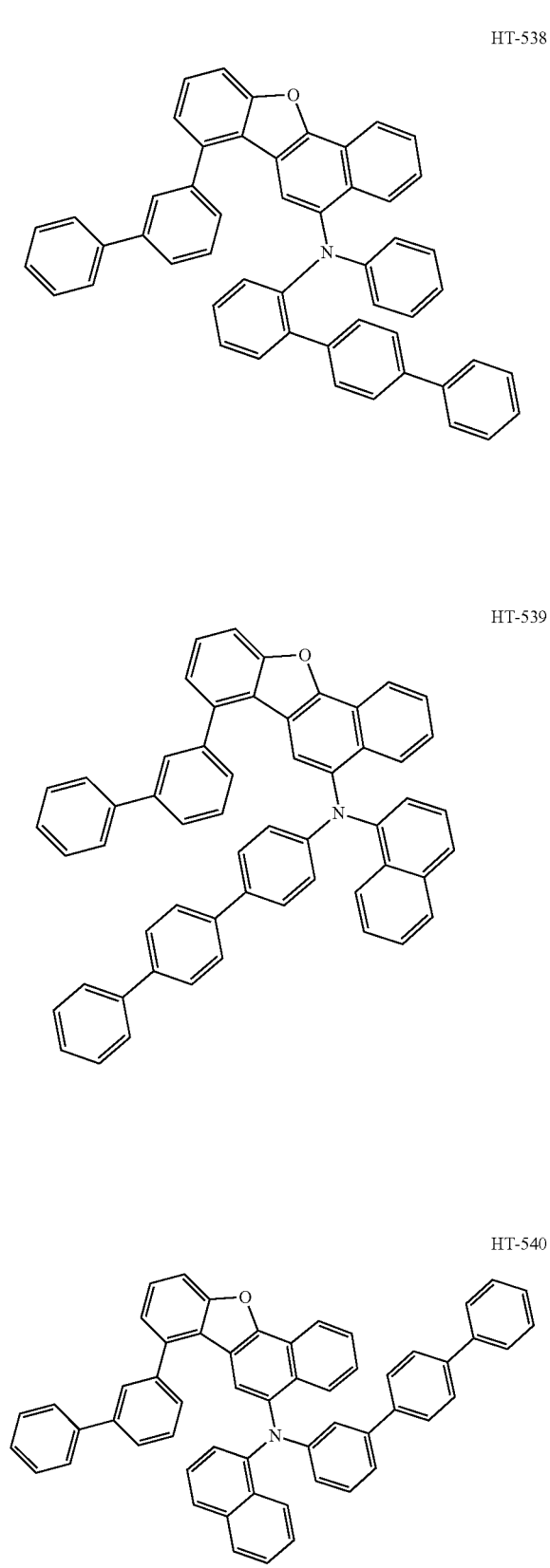

HT-541
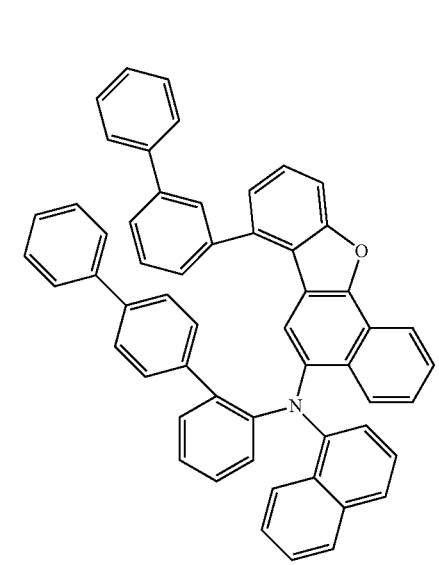
HT-544
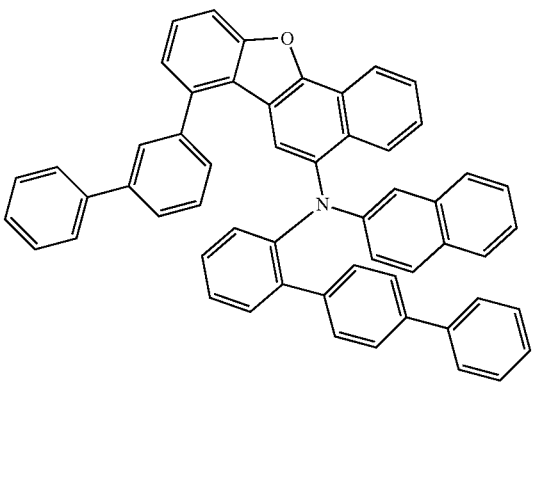
HT-542
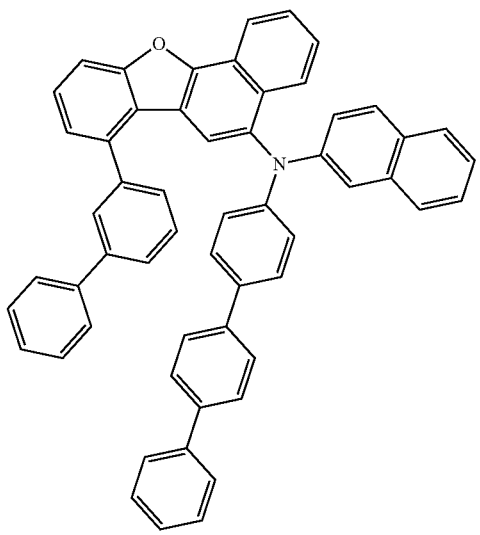
HT-545
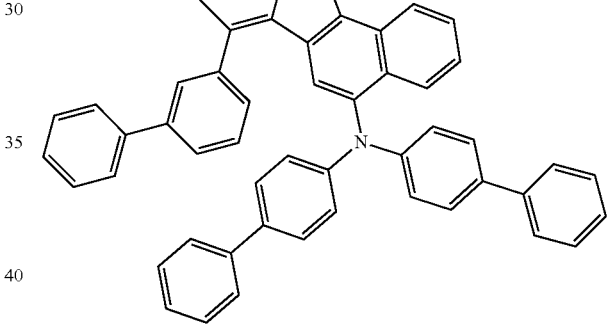
HT-543
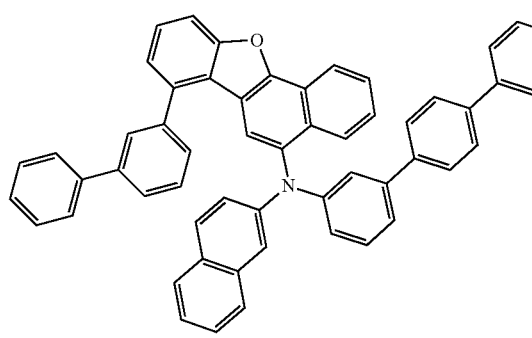
HT-546
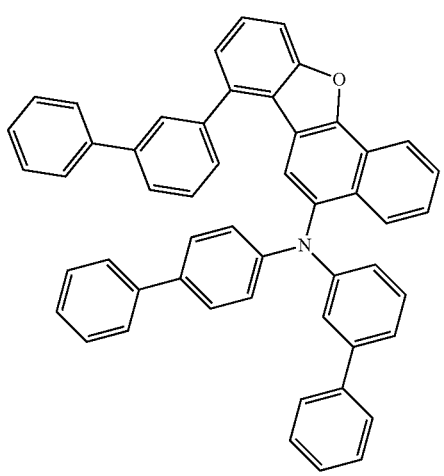

HT-547
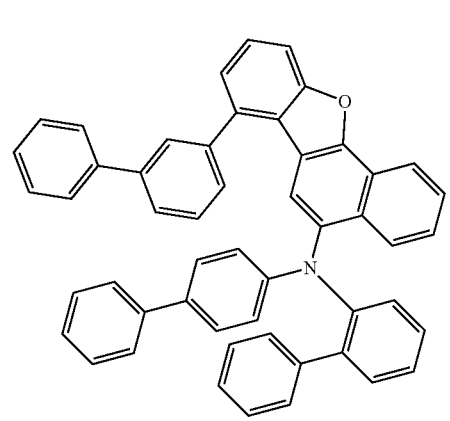
HT-548
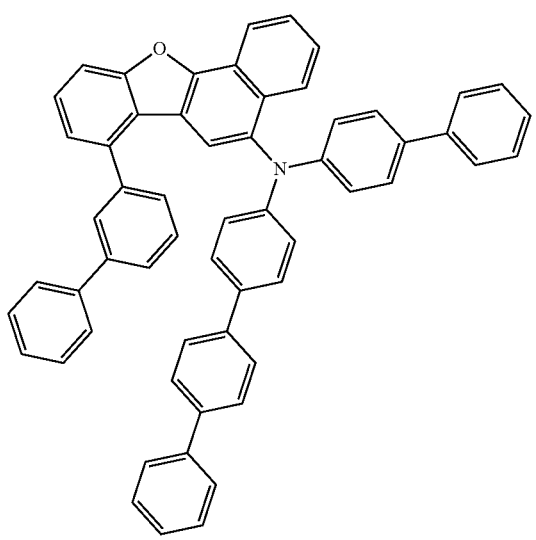
HT-549
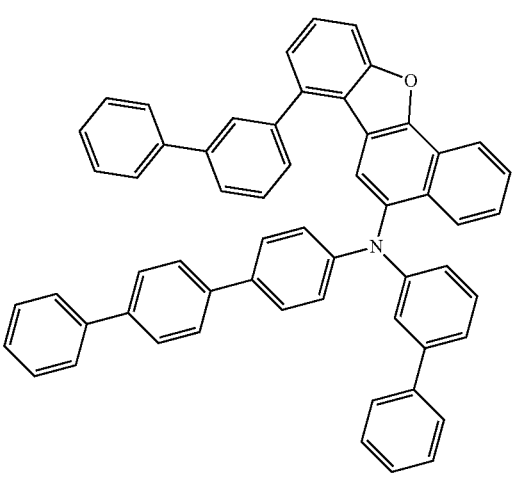
HT-550
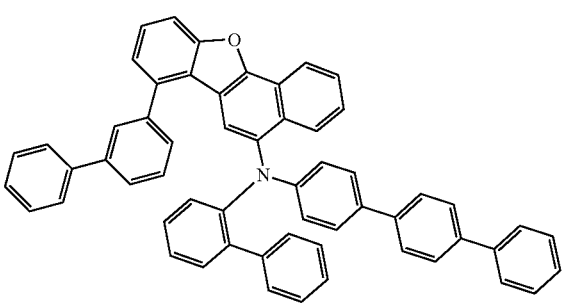
HT-551
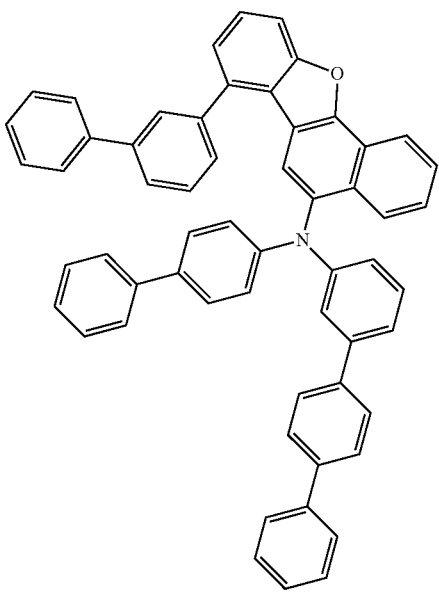
HT-552
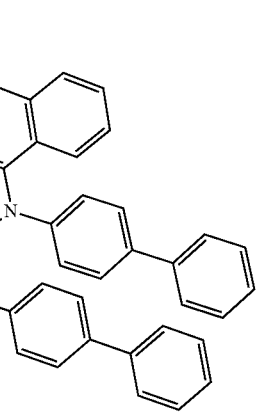

HT-553
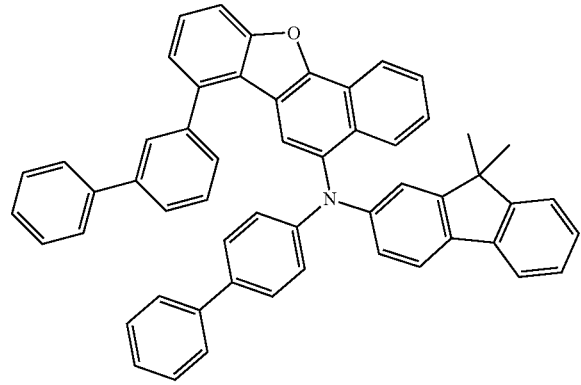
HT-554
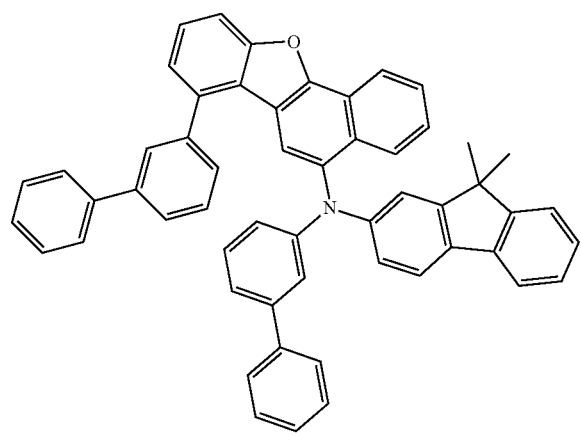
HT-555
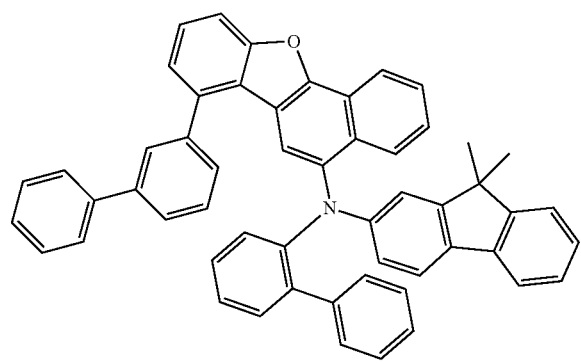
HT-556
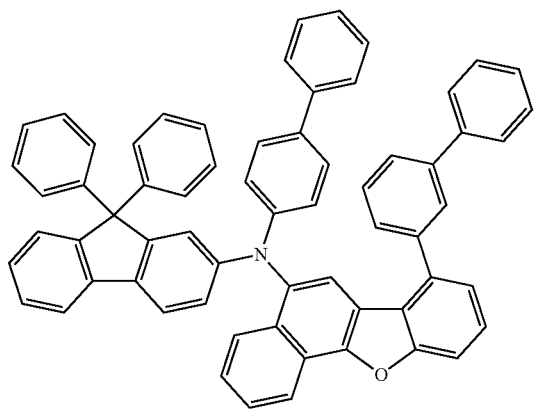
HT-557
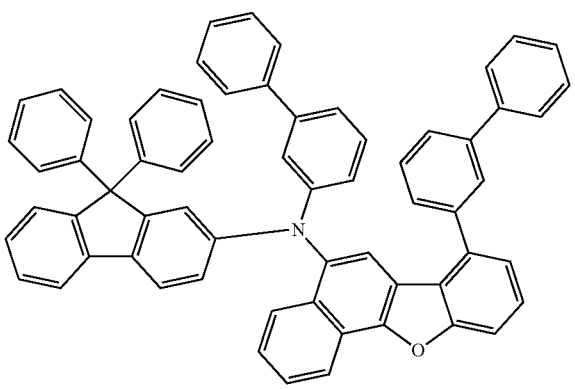
HT-558
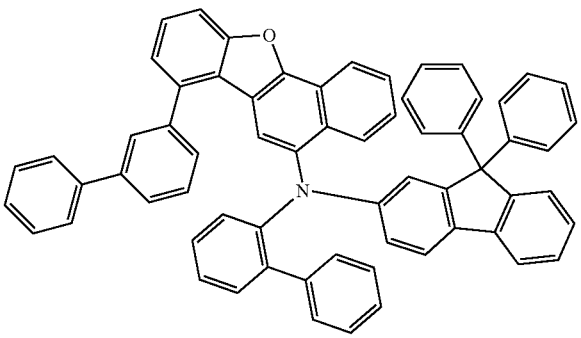
HT-559
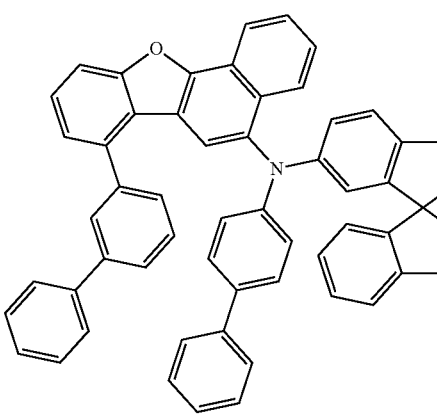

-continued
HT-560
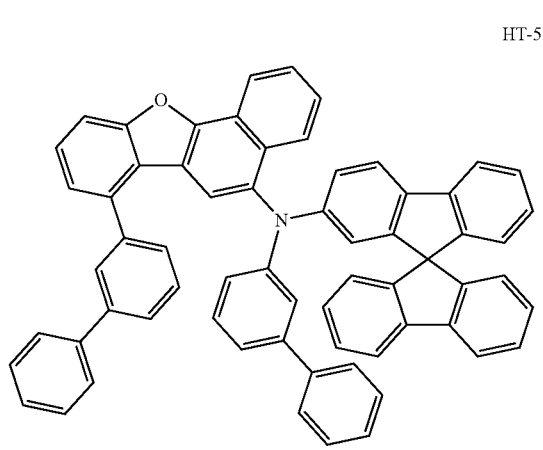
HT-561
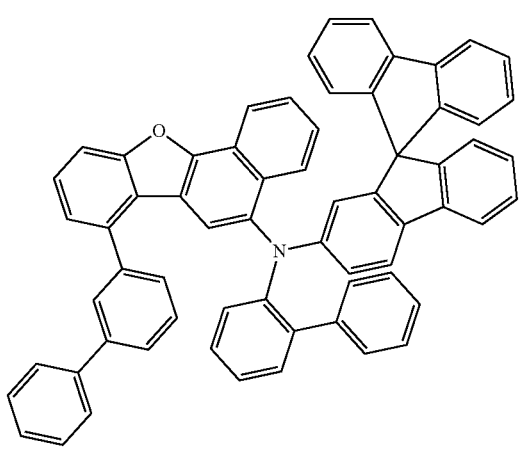
HT-562
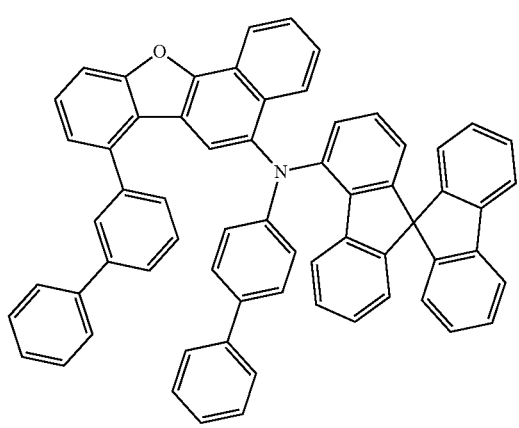
-continued
HT-563
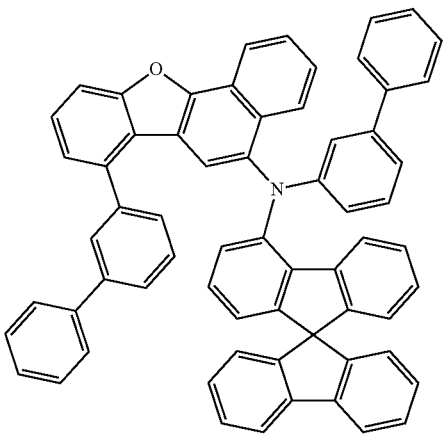
HT-564
HT-565
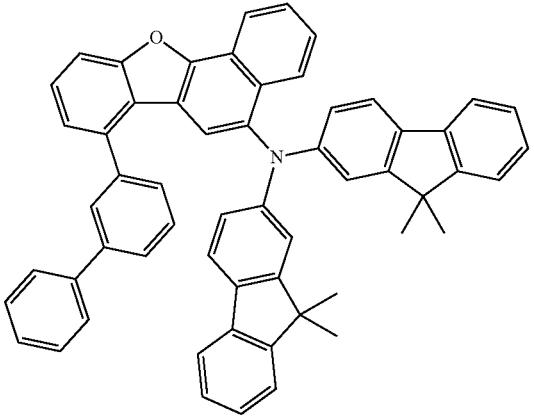

HT-566
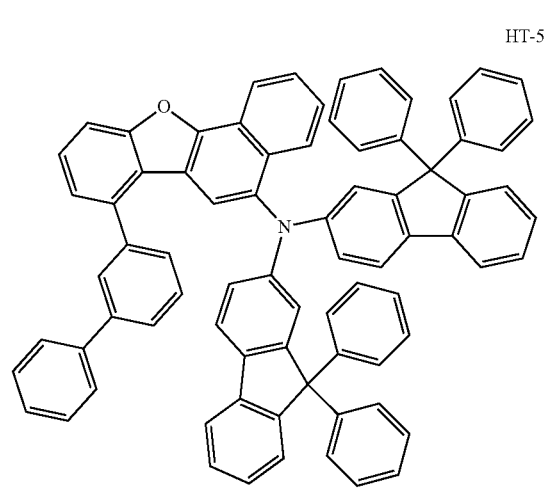
HT-567
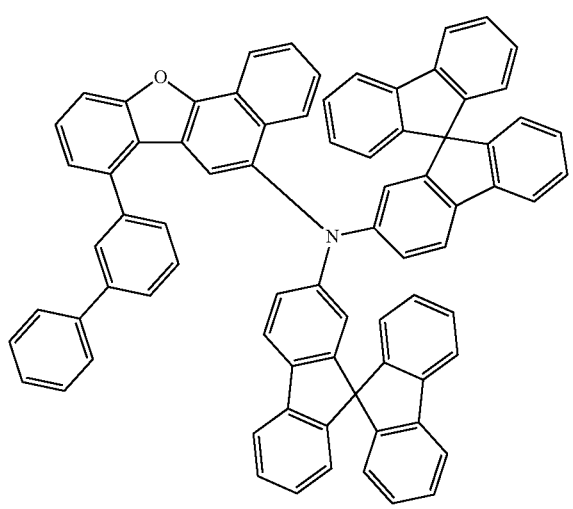
HT-568
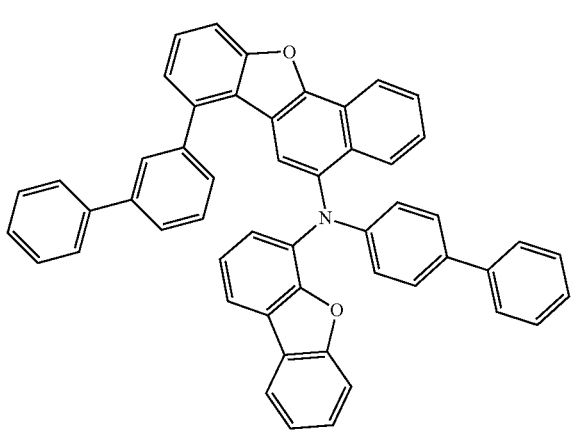
HT-569
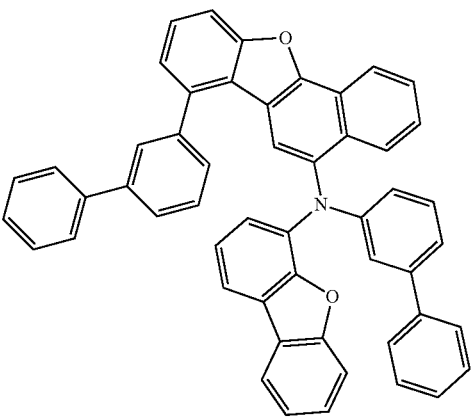
HT-570
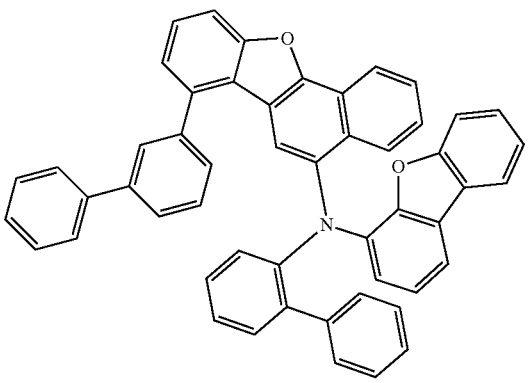
HT-571
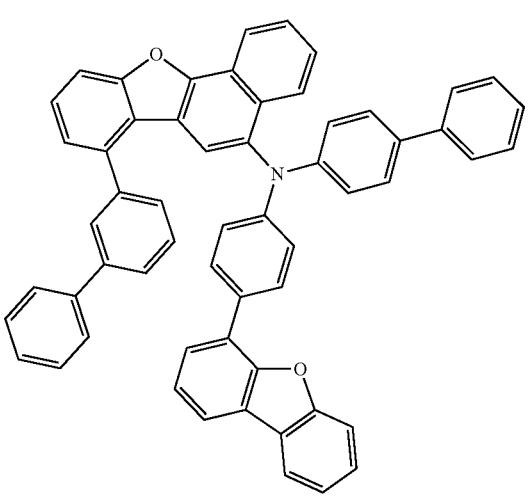

HT-572
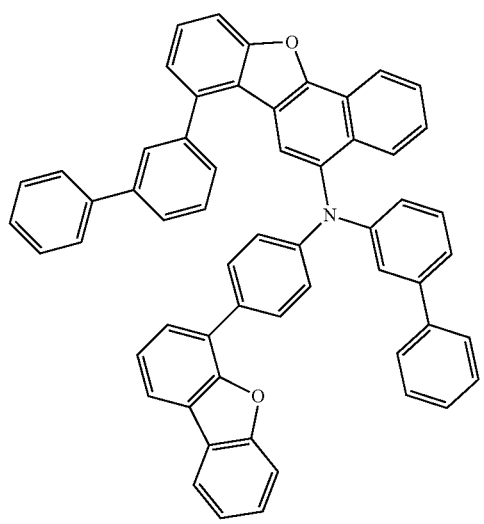
HT-573
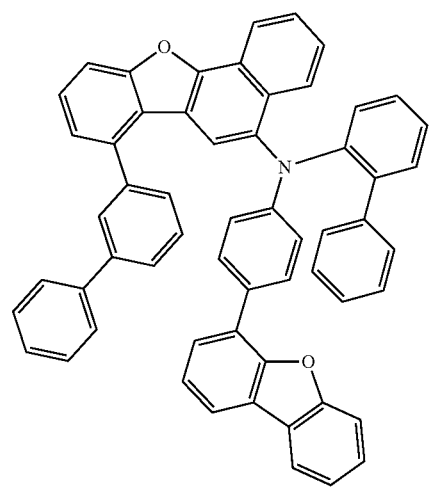
HT-574
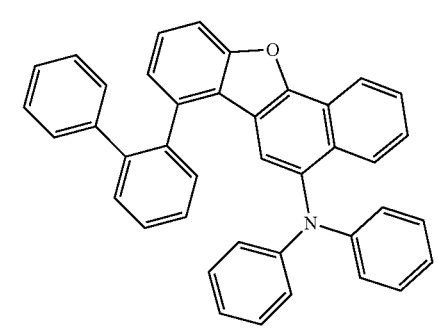
HT-575
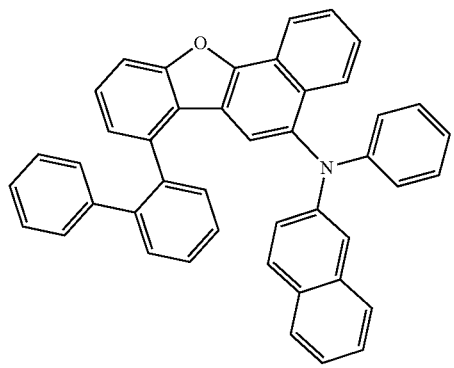
HT-576
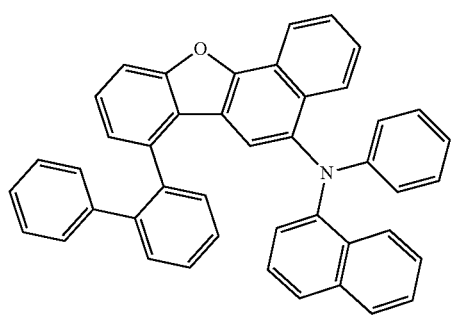
HT-577
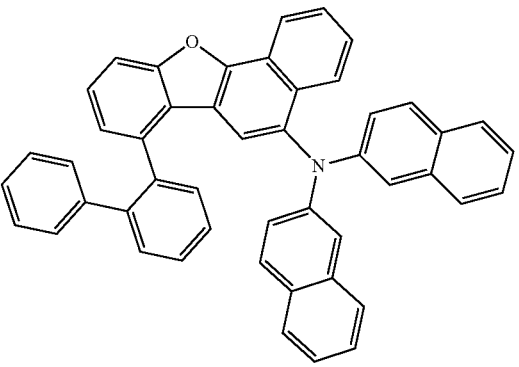
HT-578
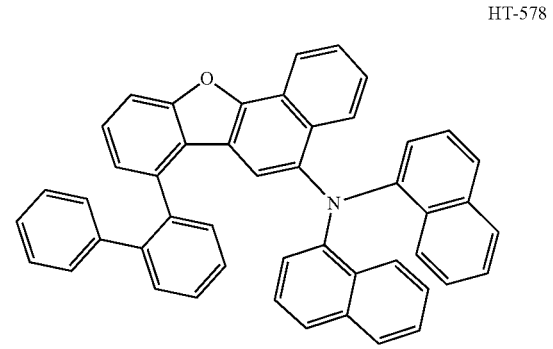

491
-continued
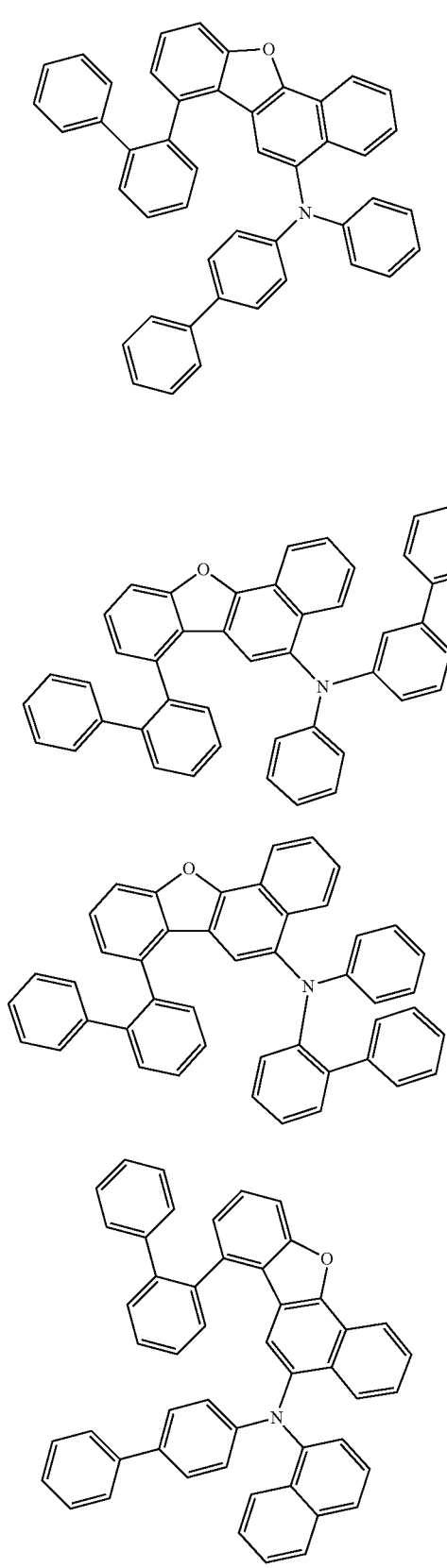
HT-579
HT-580
HT-581
HT-582
492
-continued
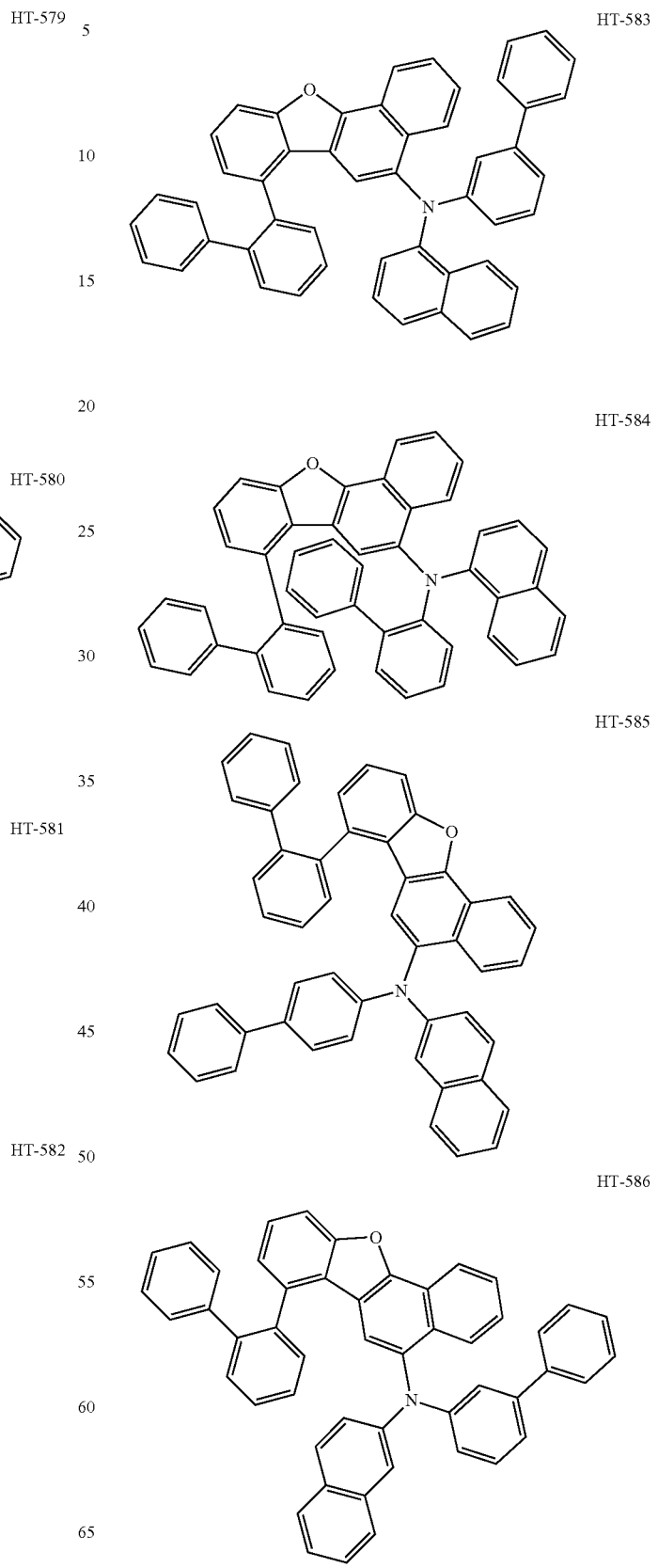
HT-583
HT-584
HT-585
HT-586

HT-587
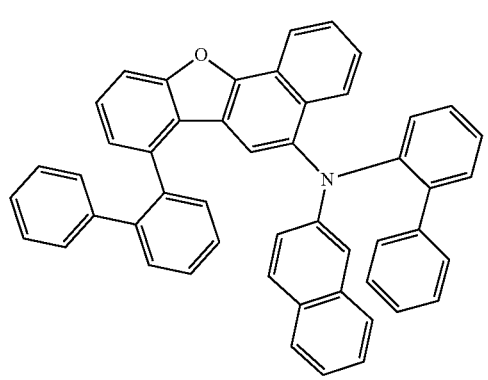
HT-590
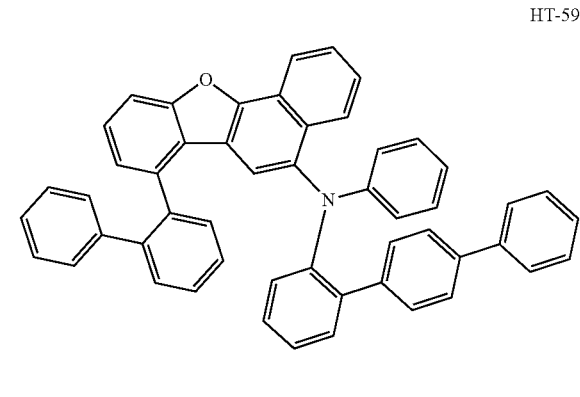
HT-588
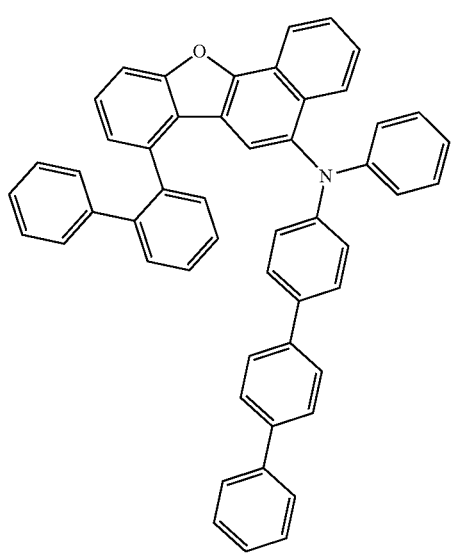
HT-591
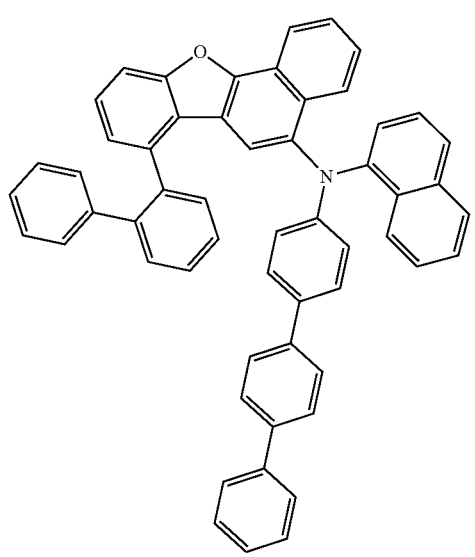
HT-589
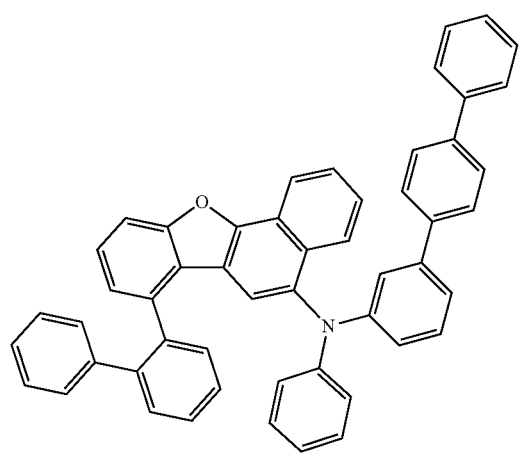
HT-592
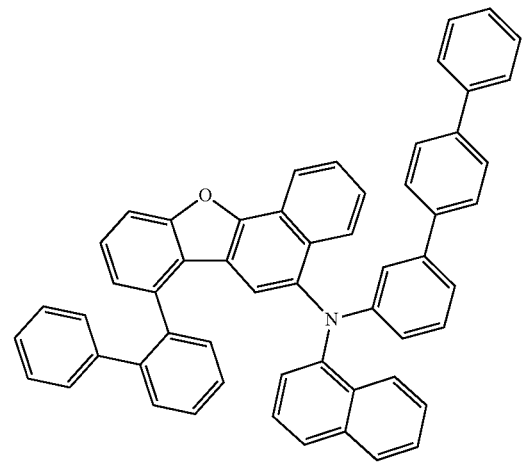

HT-593
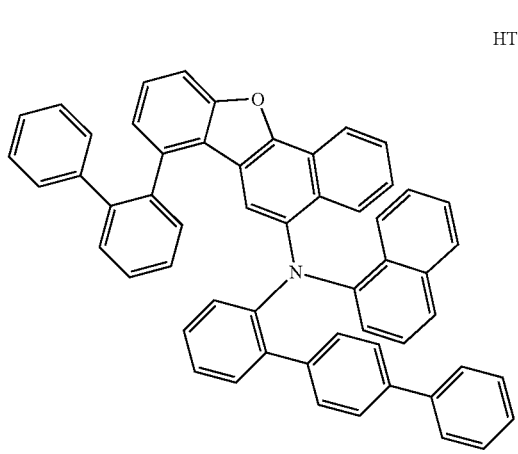
HT-594
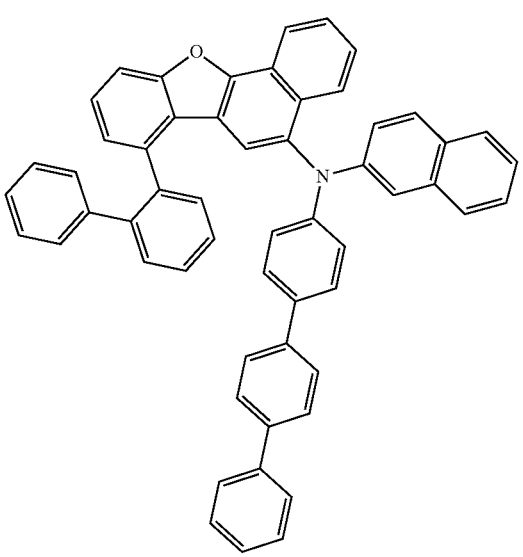
HT-595
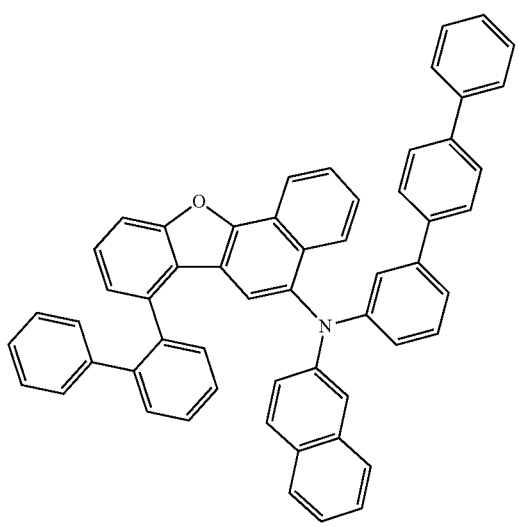
HT-596
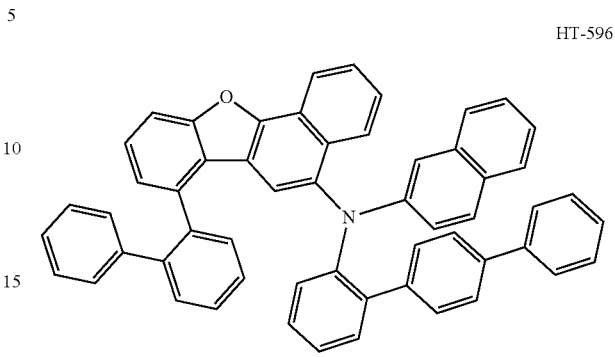
HT-597
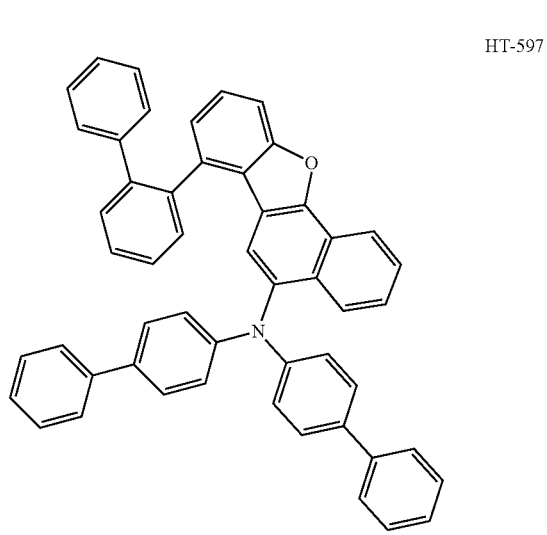
HT-598
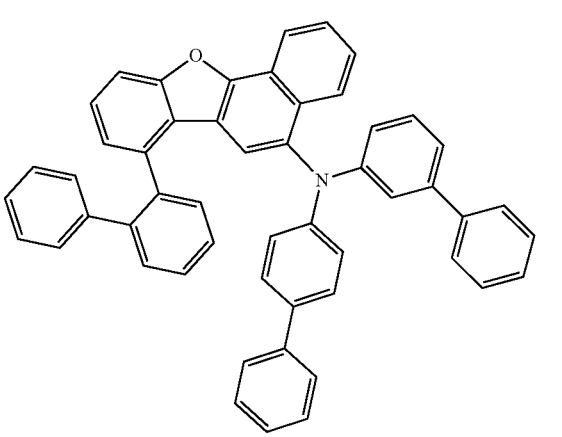

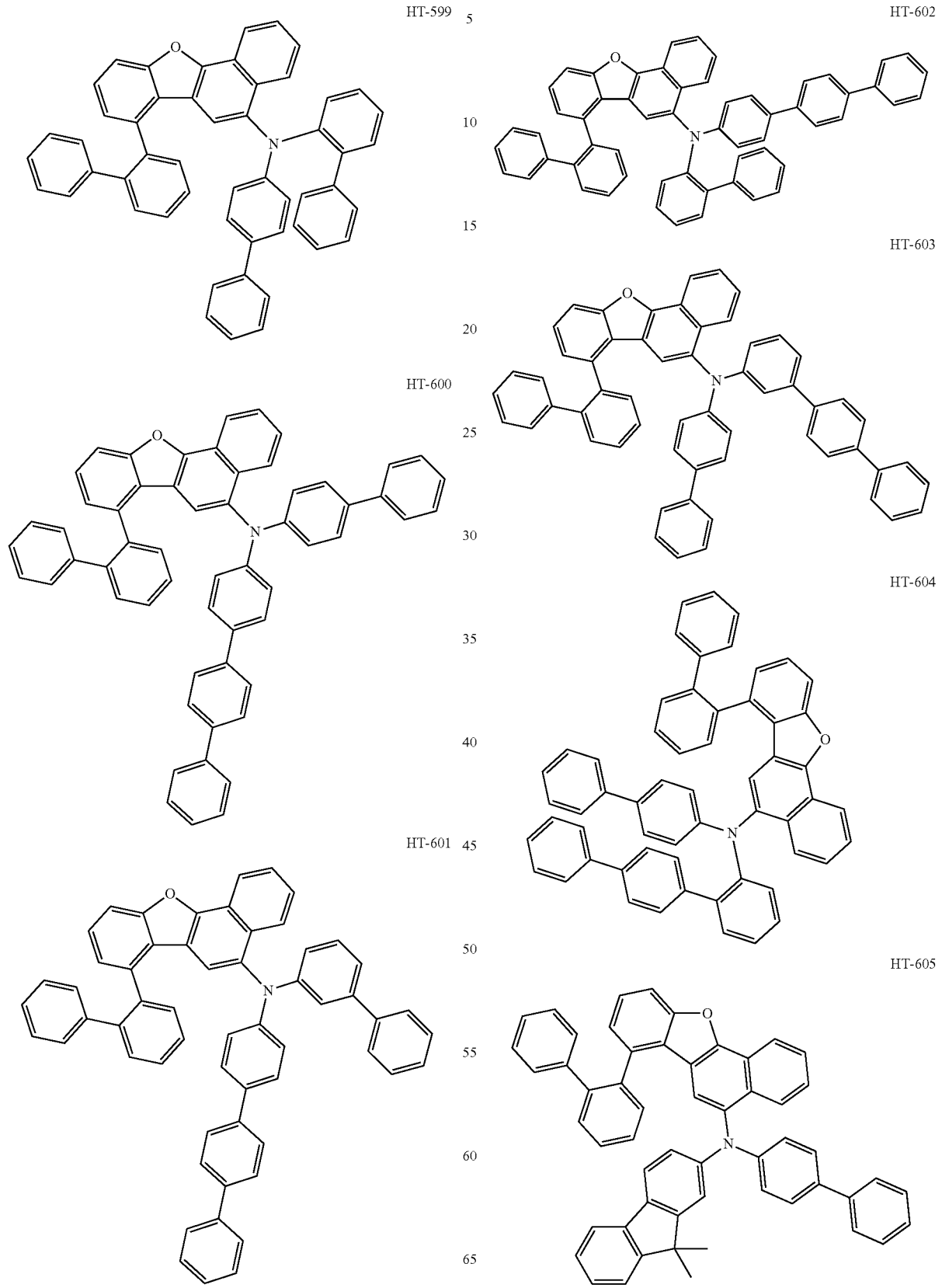

-continued
HT-606
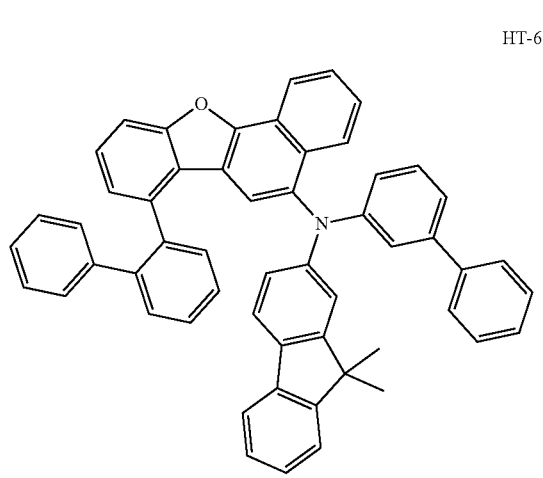
HT-607
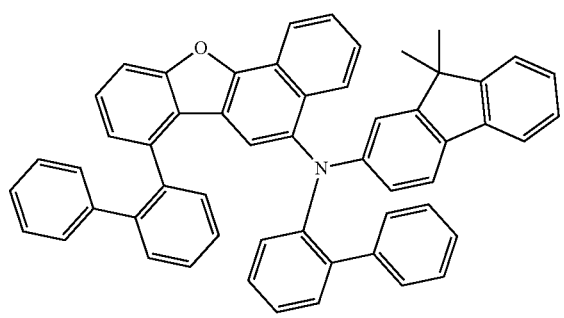
HT-608
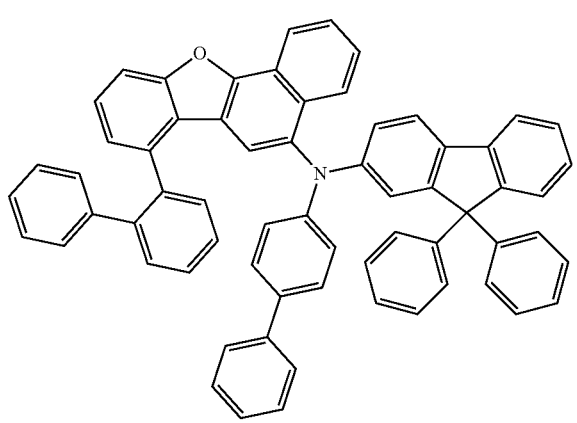
-continued
HT-609
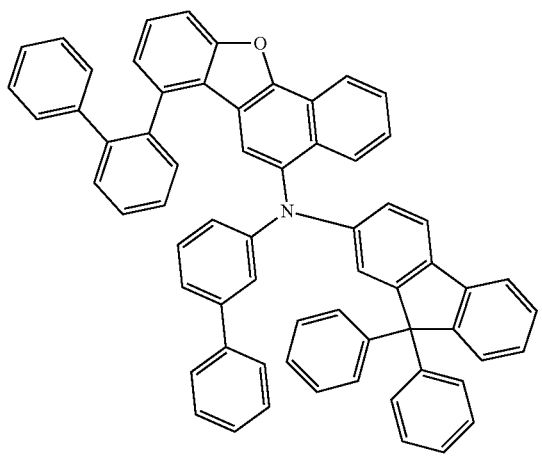
HT-610
HT-611
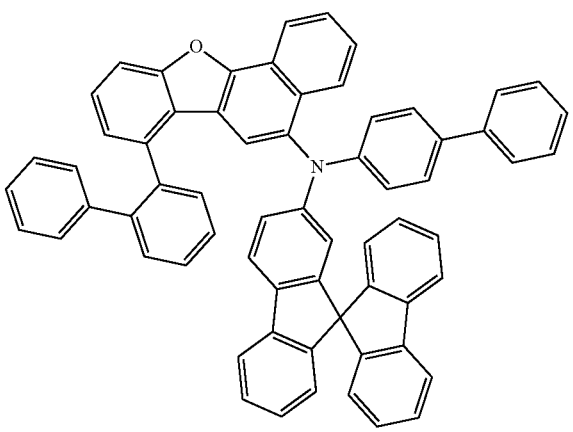

HT-612
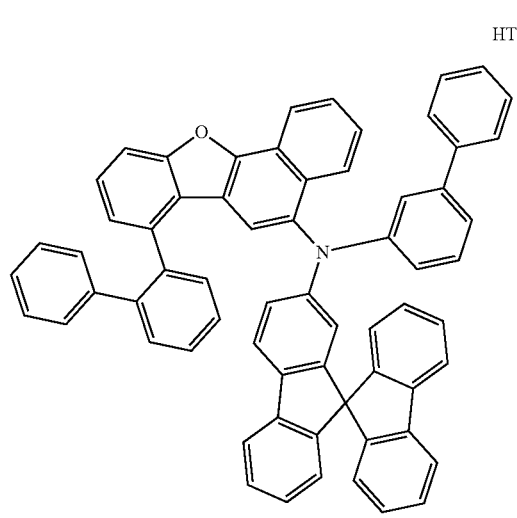
HT-615
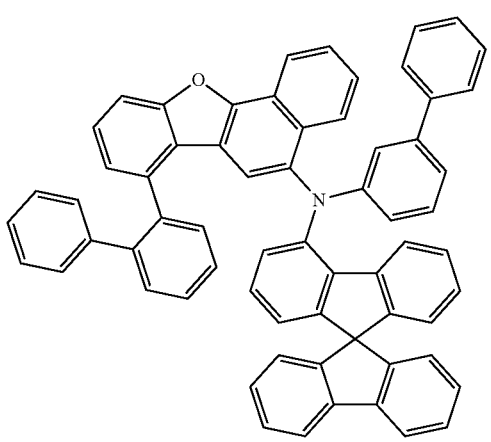
HT-613
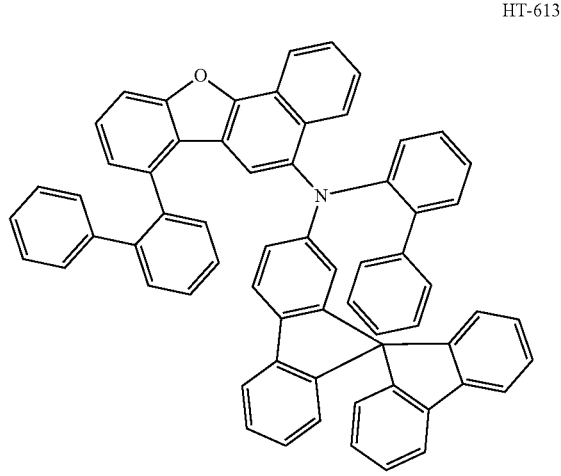
HT-616
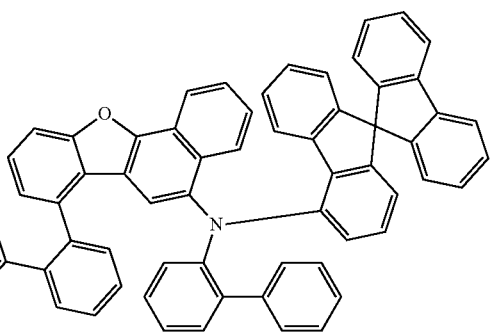
HT-614
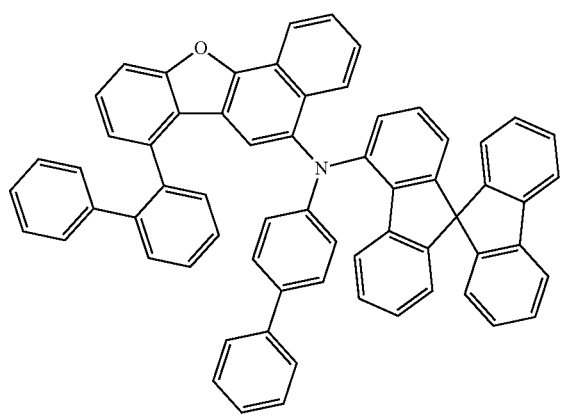
HT-617
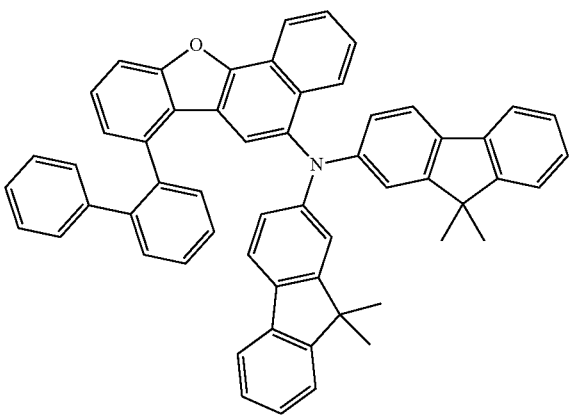

HT-618
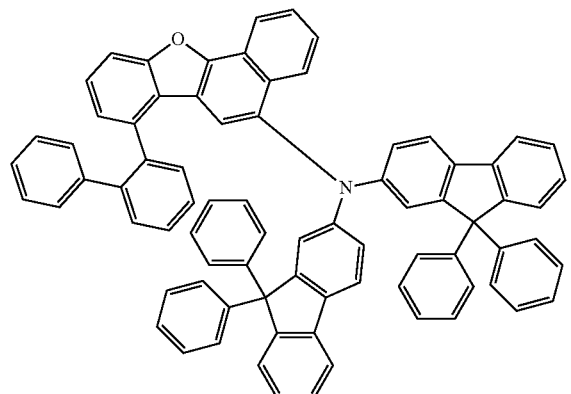
HT-619
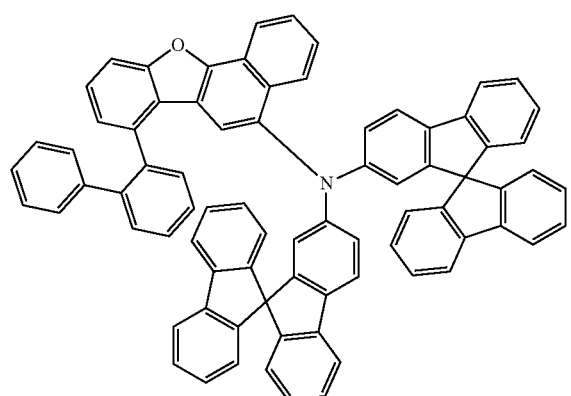
HT-620
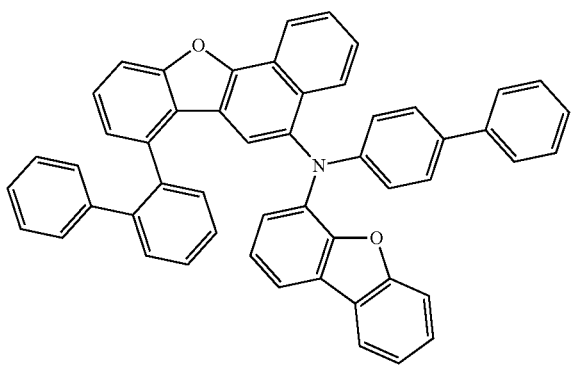
HT-621
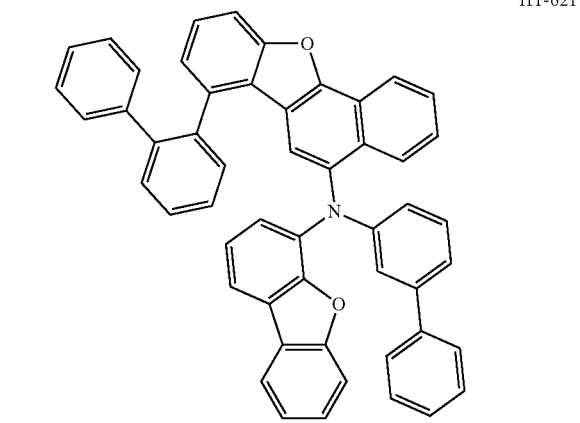
HT-622
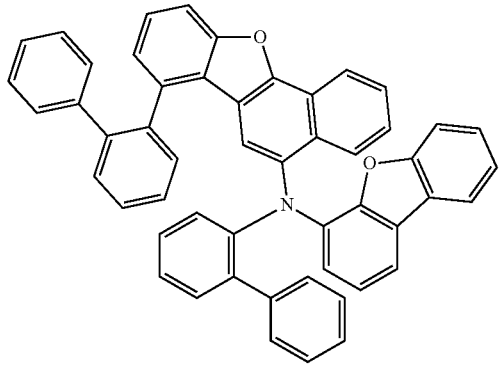
HT-623
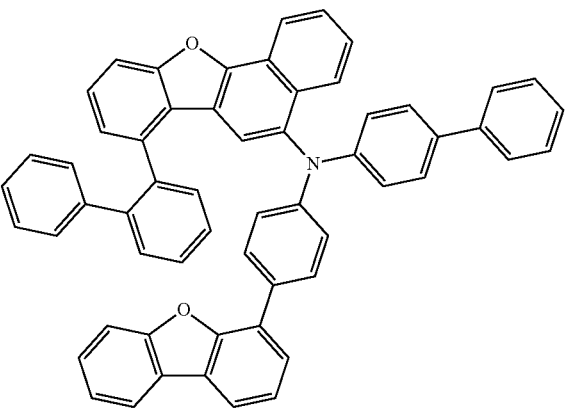
HT-624
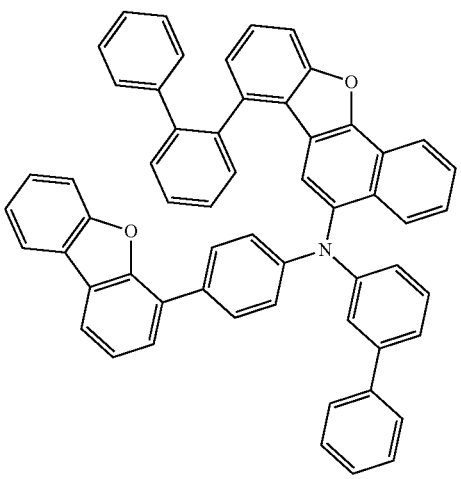

HT-625
HT-626
HT-627
HT-628
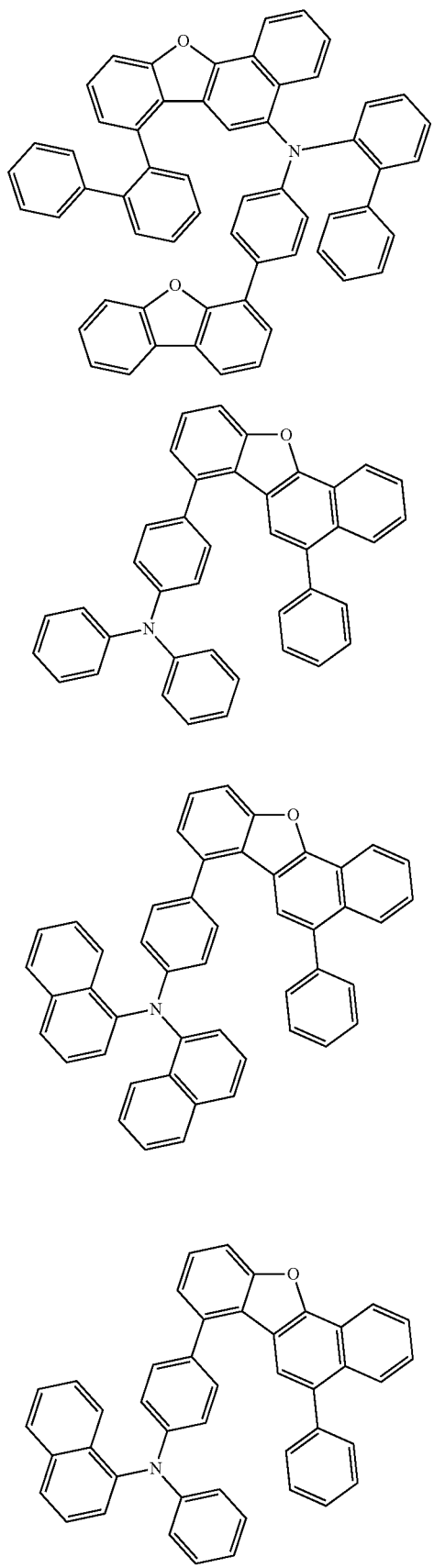
HT-629
HT-630
HT-631
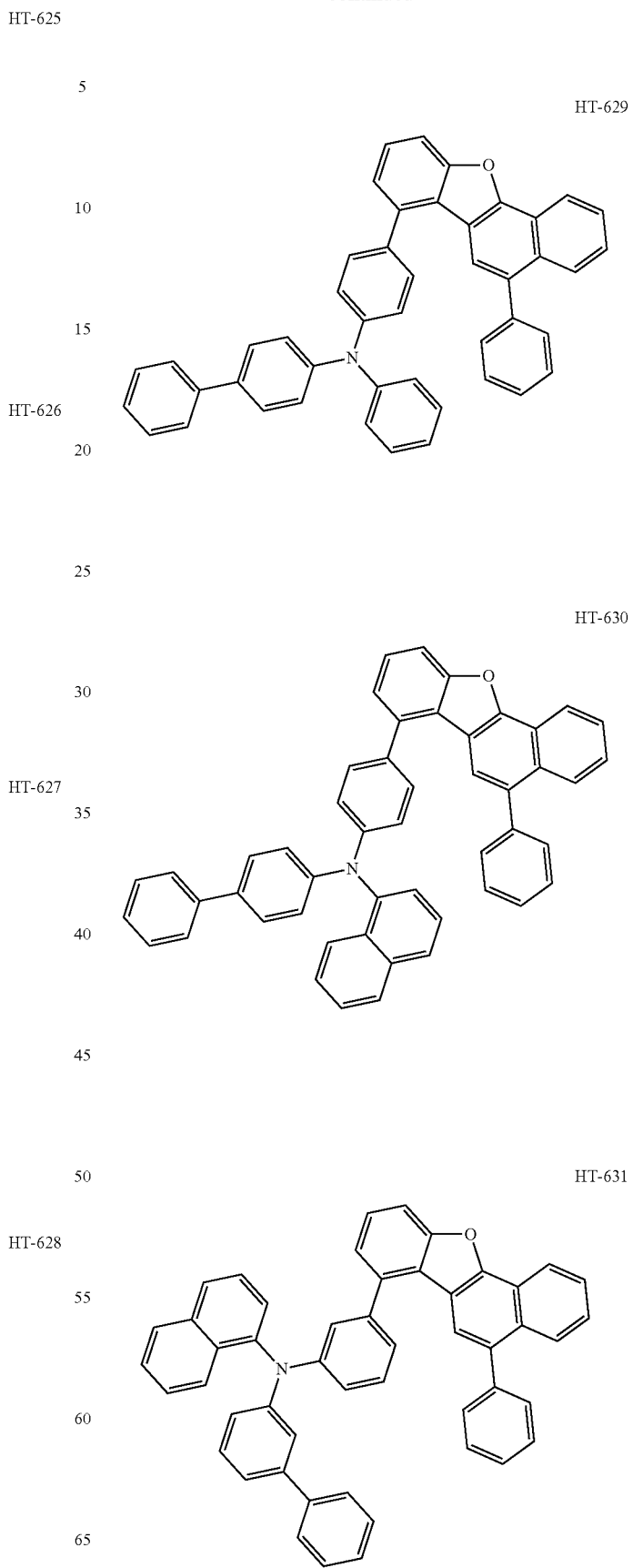

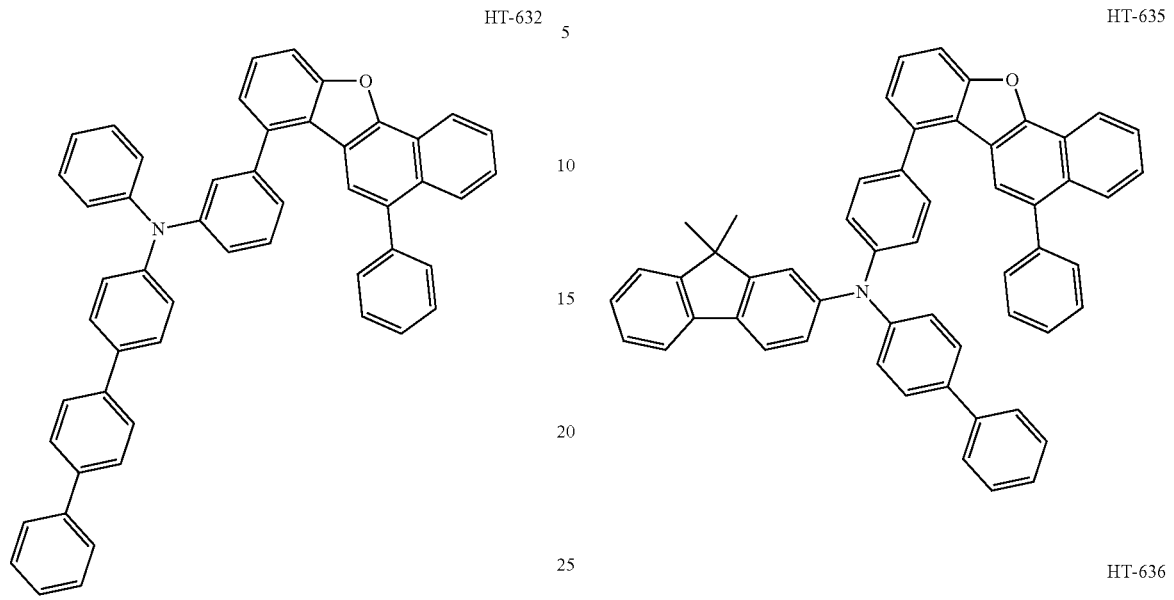
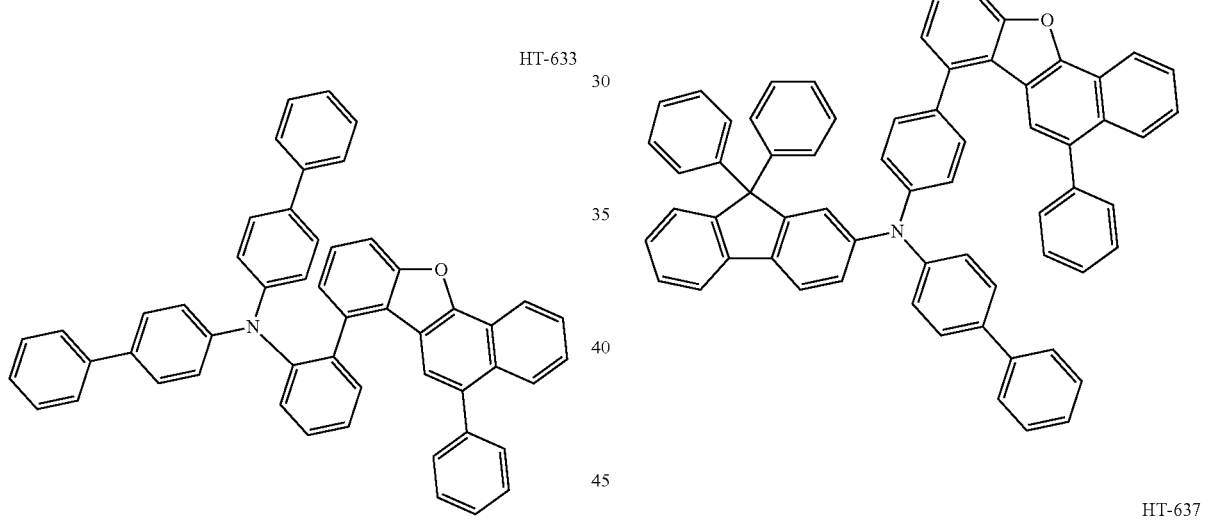
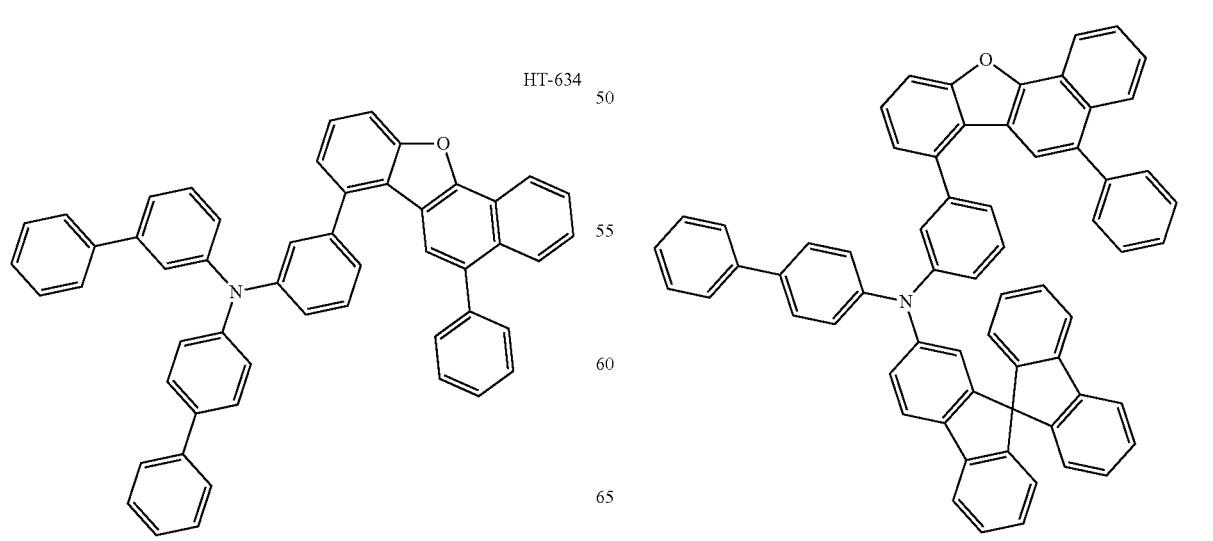

509
-continued
HT-638
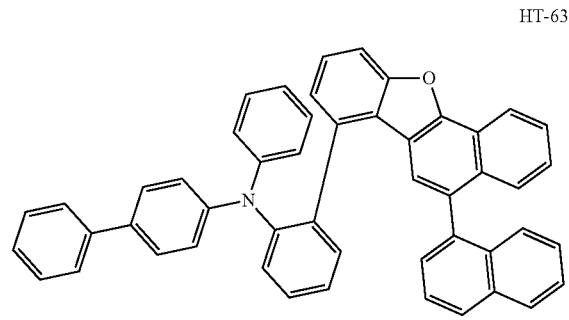
HT-639
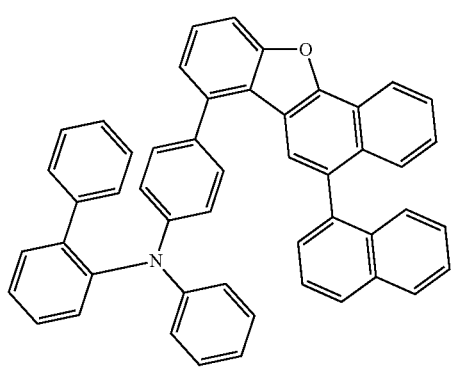
HT-640
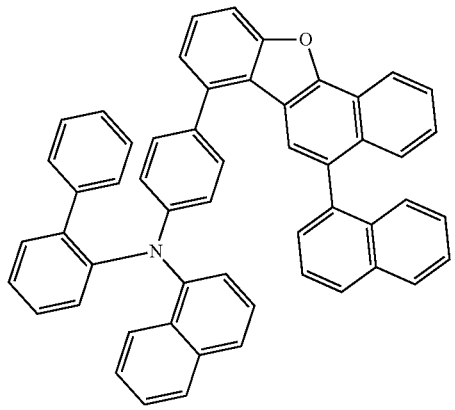
HT-641
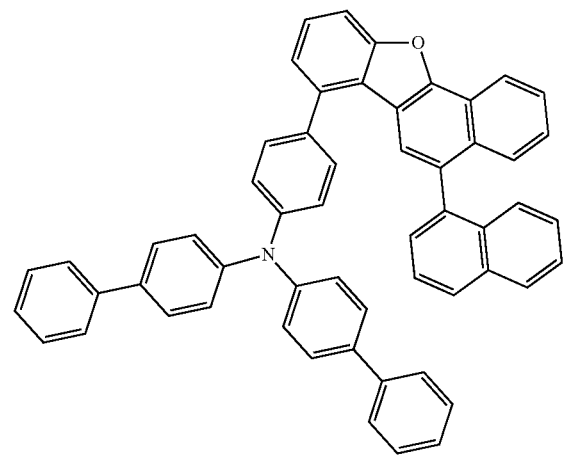
510
-continued
HT-642
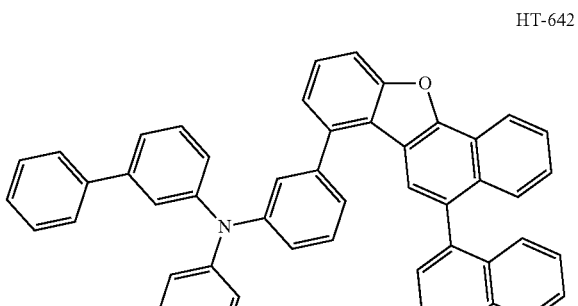
HT-643
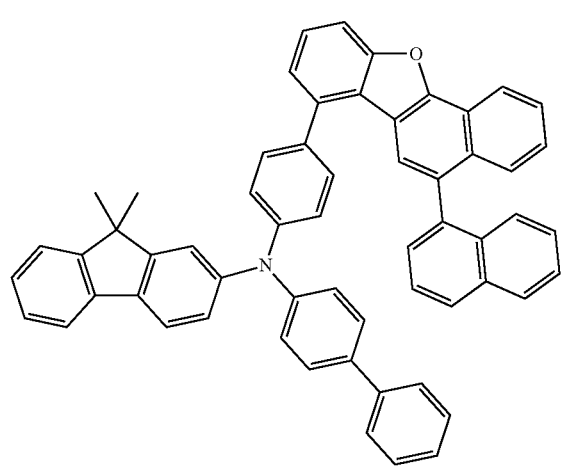
HT-644
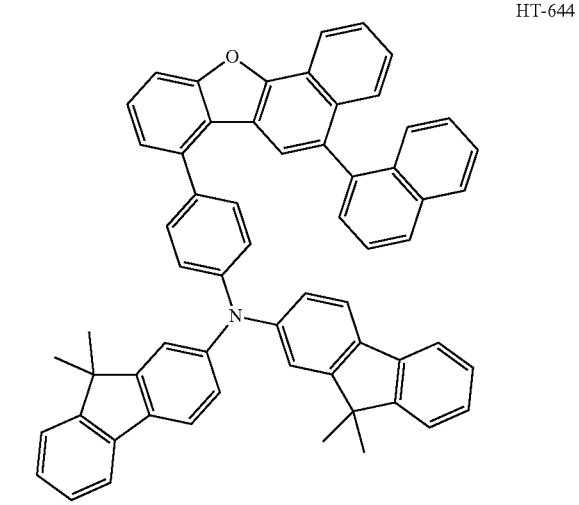

511
-continued
512
-continued
HT-645
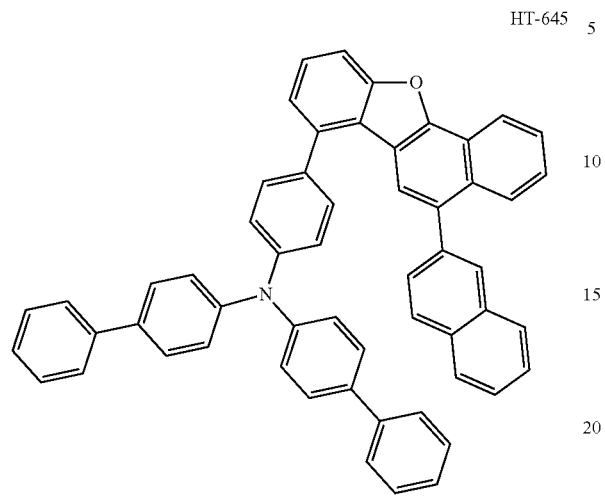
HT-648
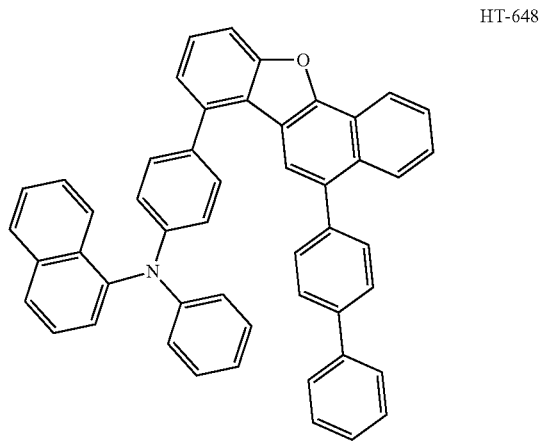
HT-646
HT-649
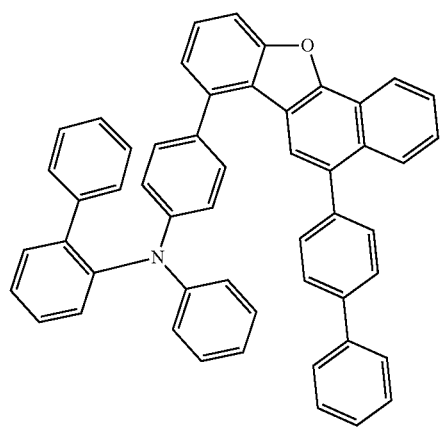
HT-647
HT-650
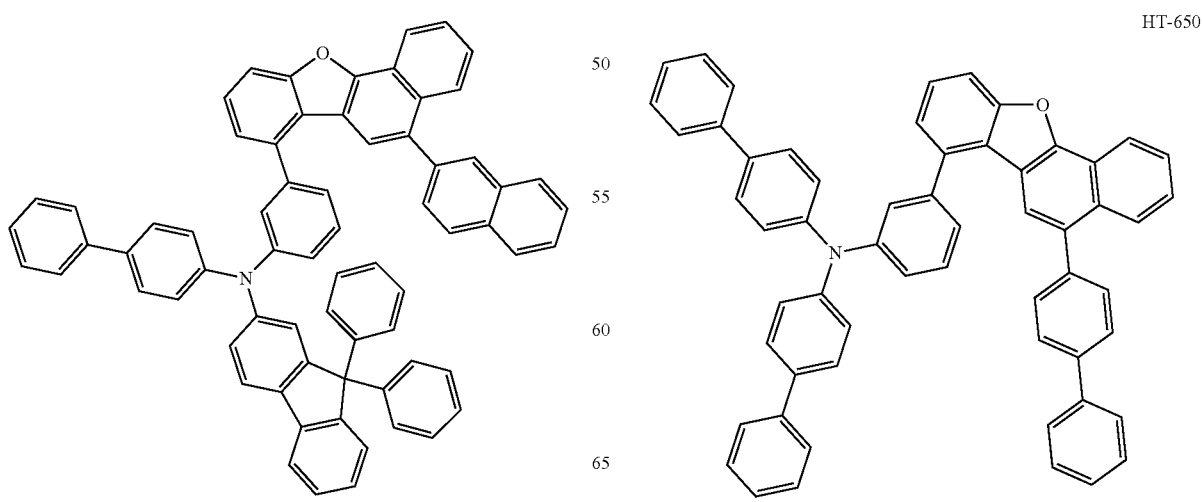

513
-continued
514
-continued
HT-651
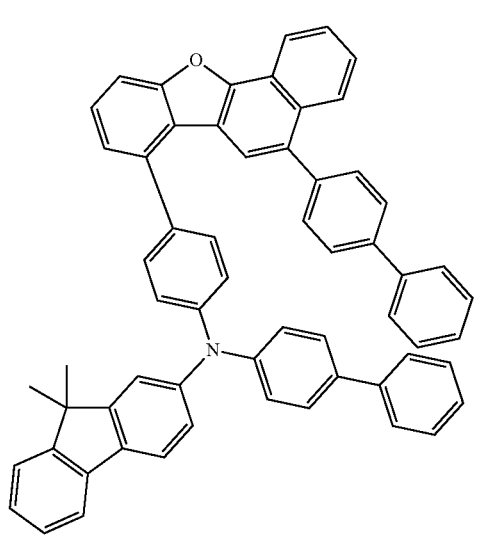
HT-654
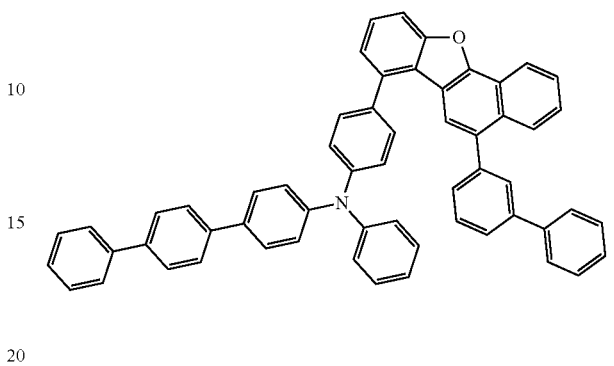
HT-652
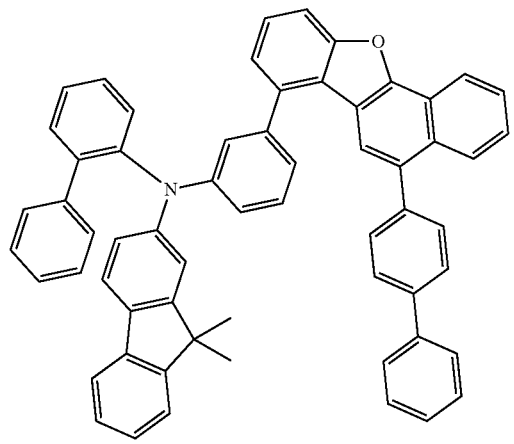
HT-655
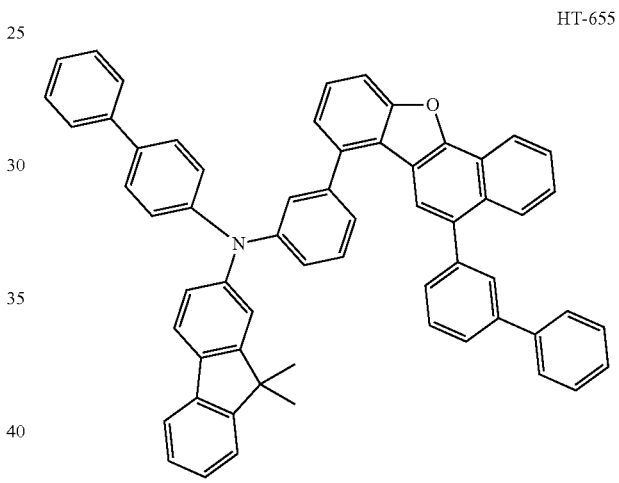
HT-653
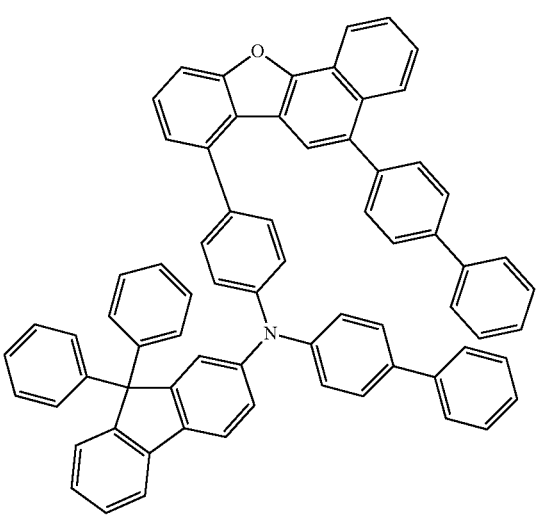
HT-656
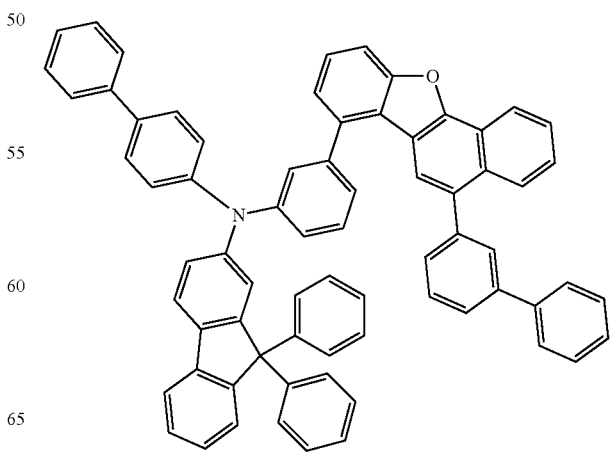

HT-657
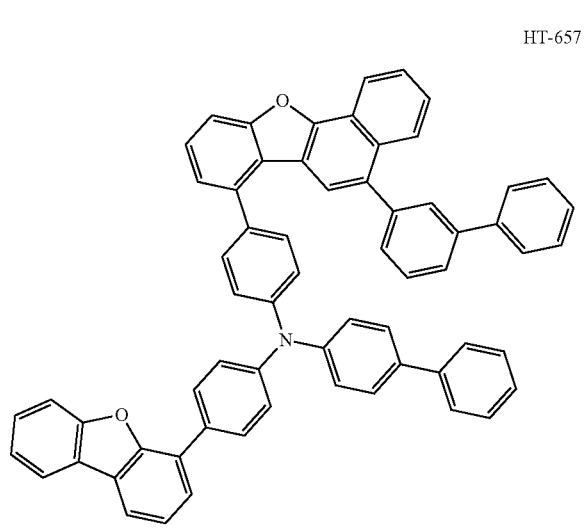
HT-660
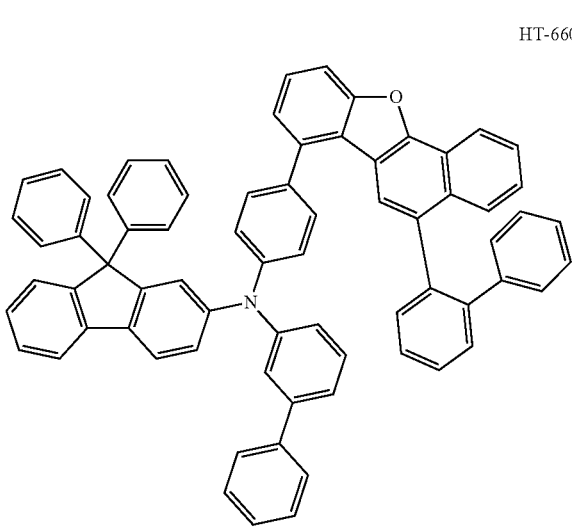
HT-658
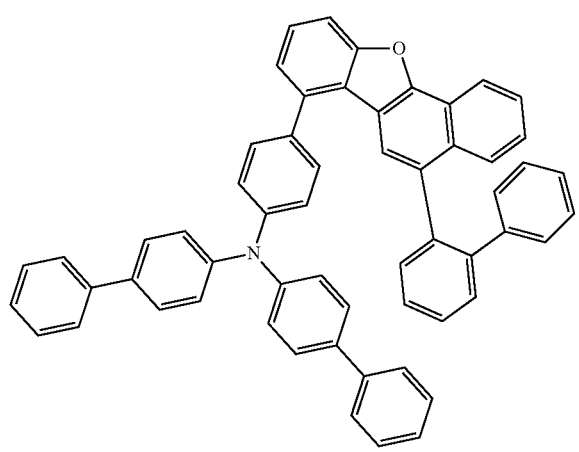
HT-661
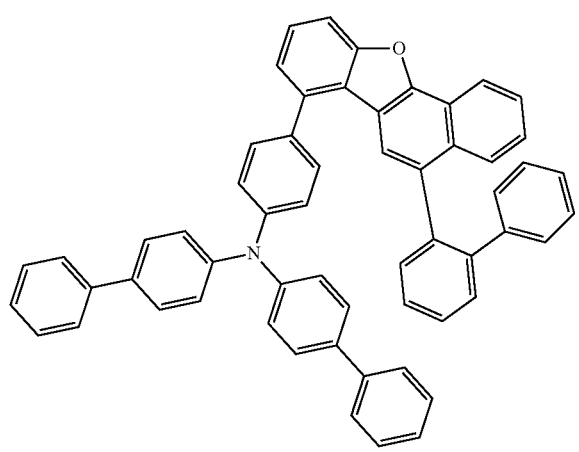
HT-659
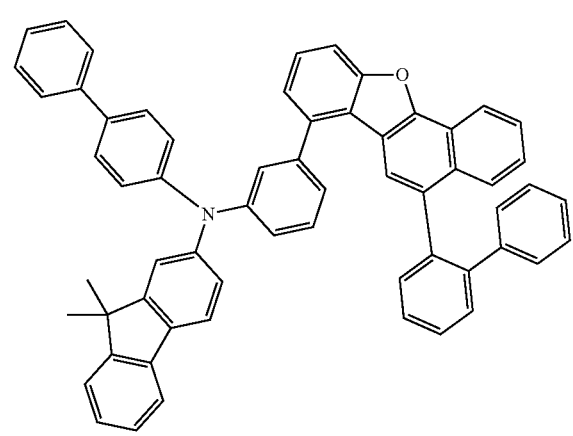
HT-662
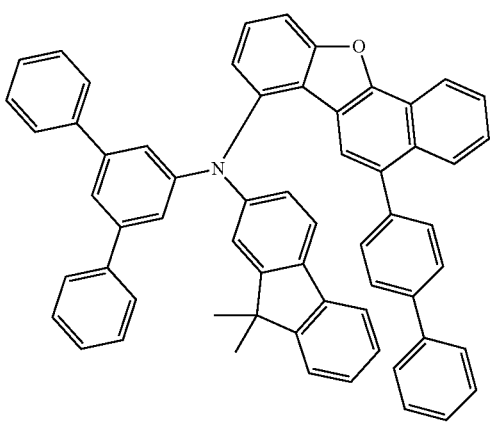

517
-continued
HT-663
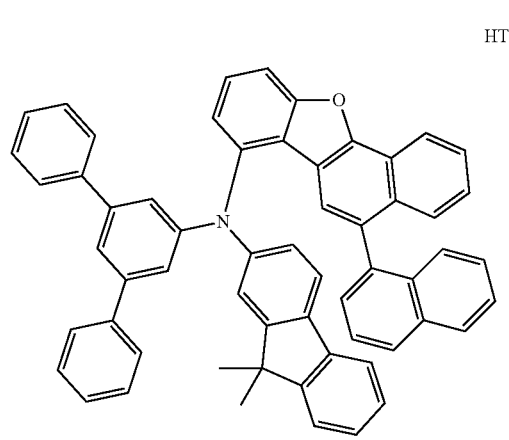
HT-664
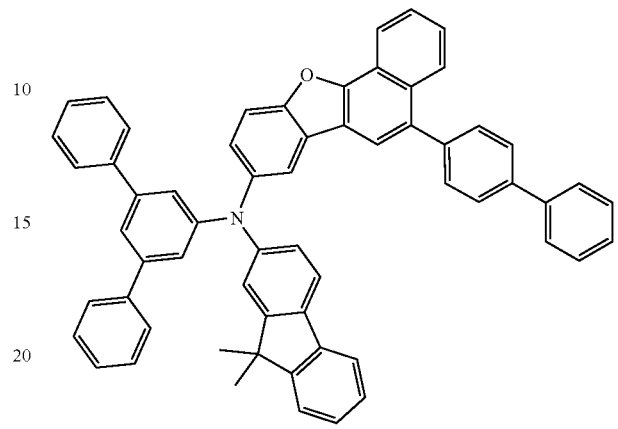
HT-665
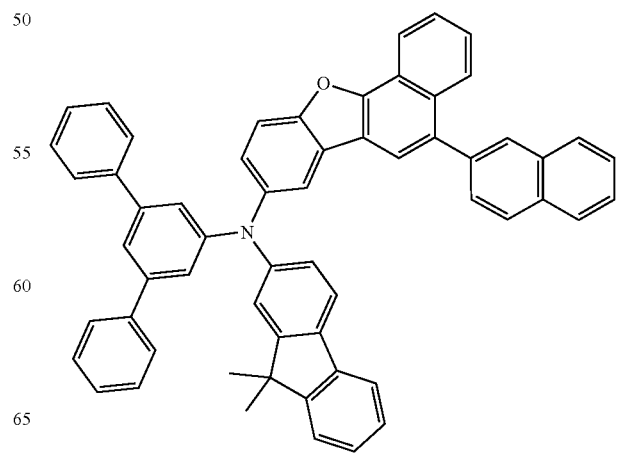
518
-continued
HT-666
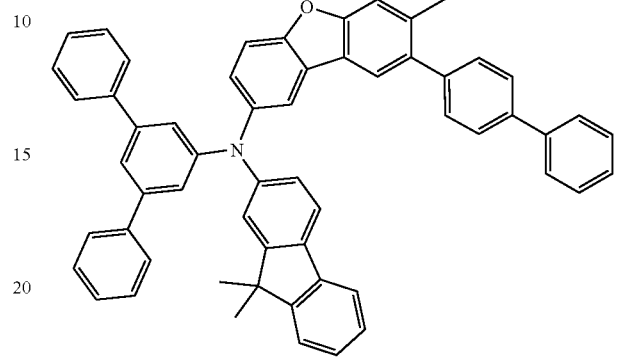
HT-667
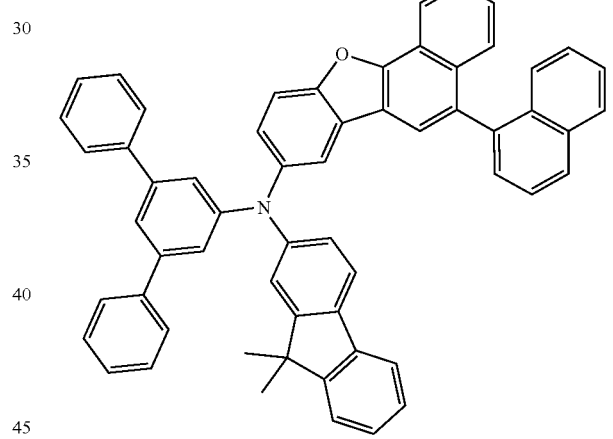
HT-668
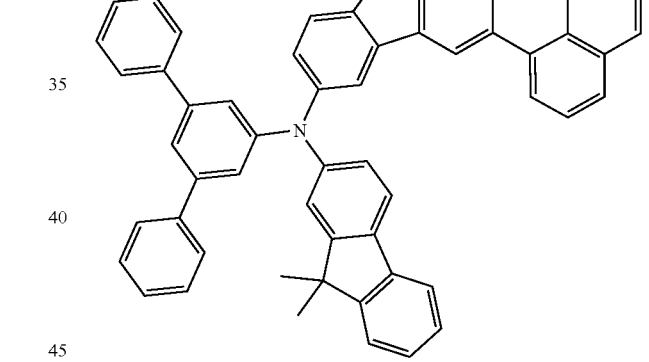

519
-continued
HT-669
HT-670
HT-671
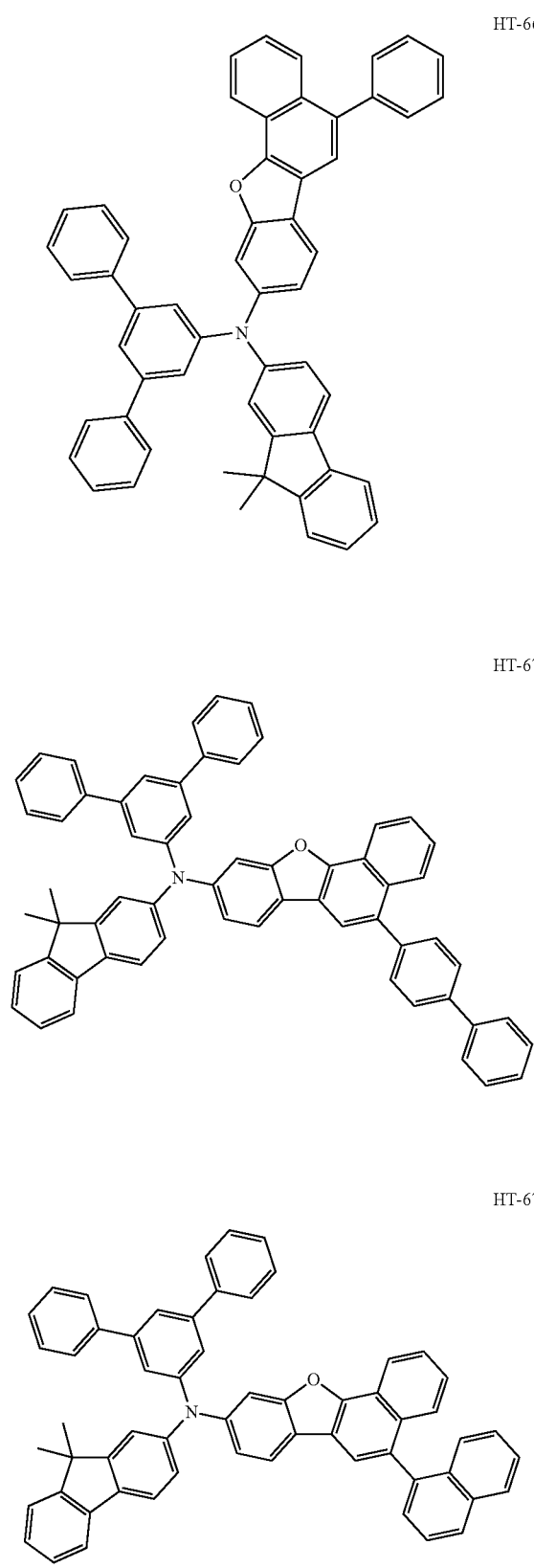
520
-continued
HT-672
HT-673
HT-674
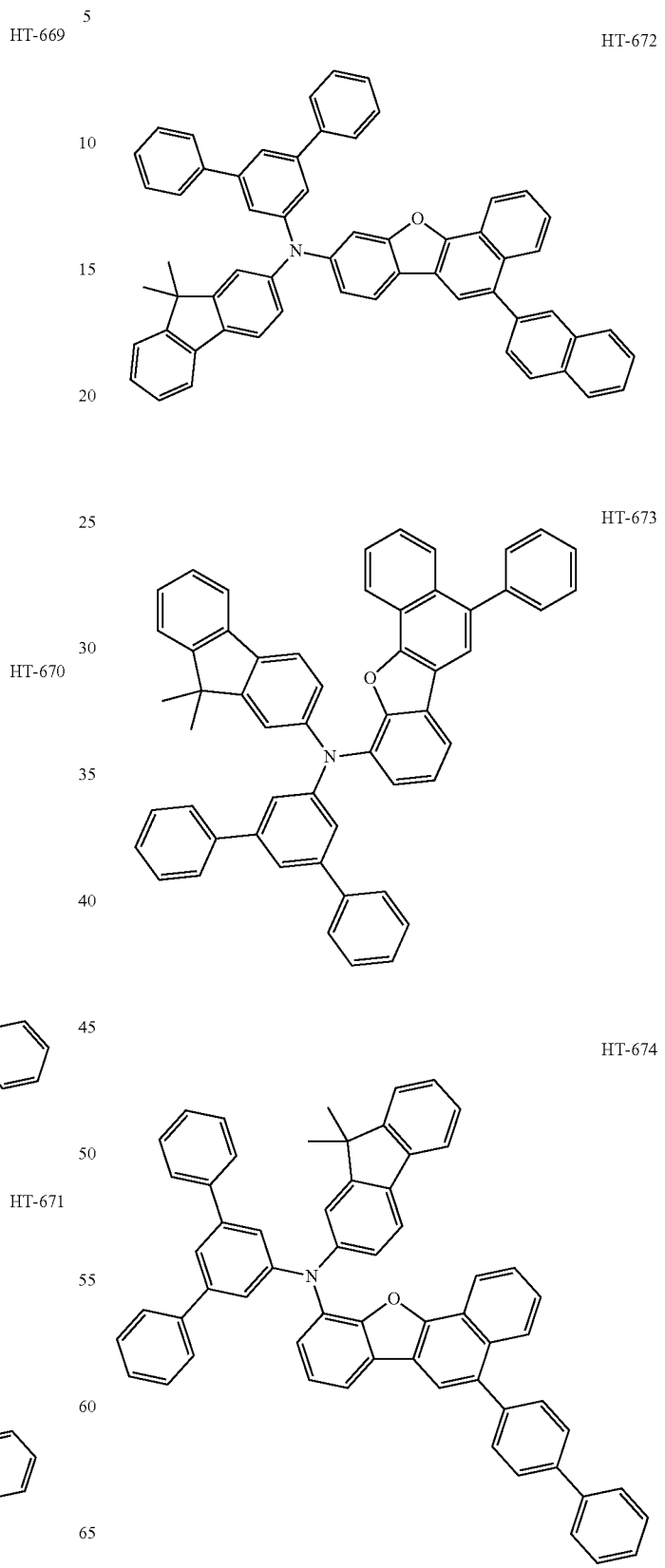

-continued
HT-675
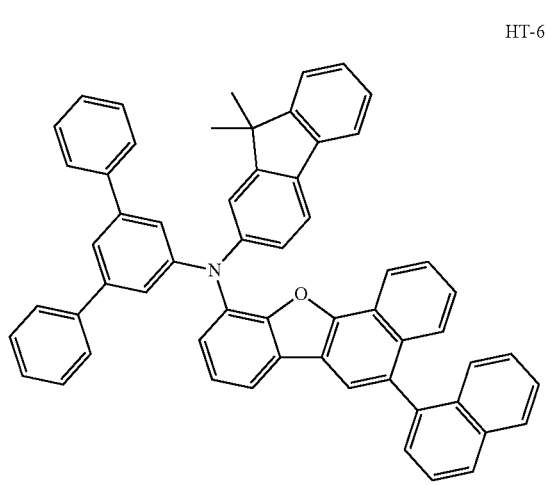
HT-676
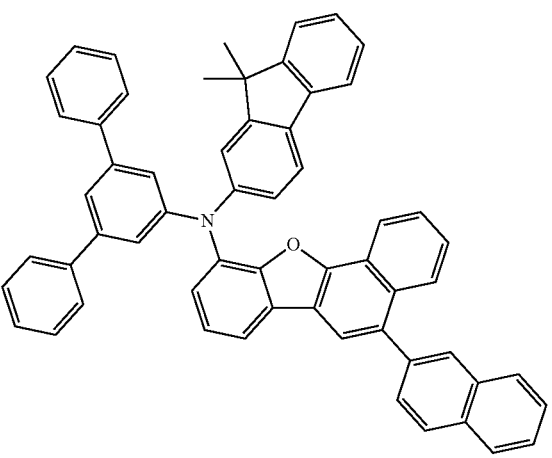
HT-677
-continued
HT-678
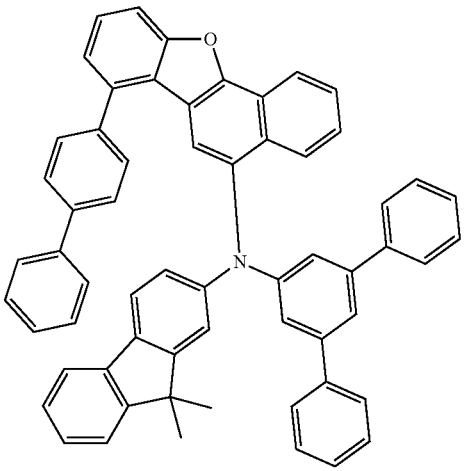
HT-679
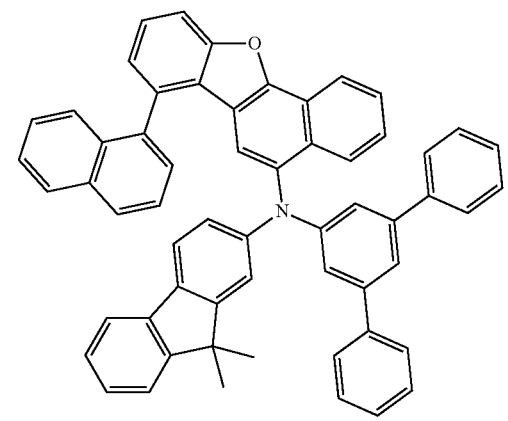
HT-680
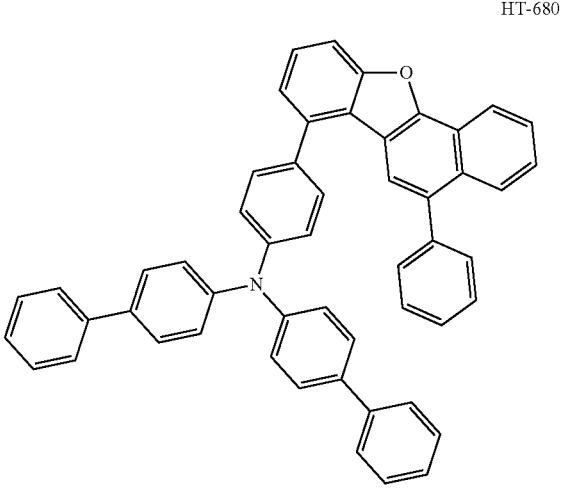

HT-681
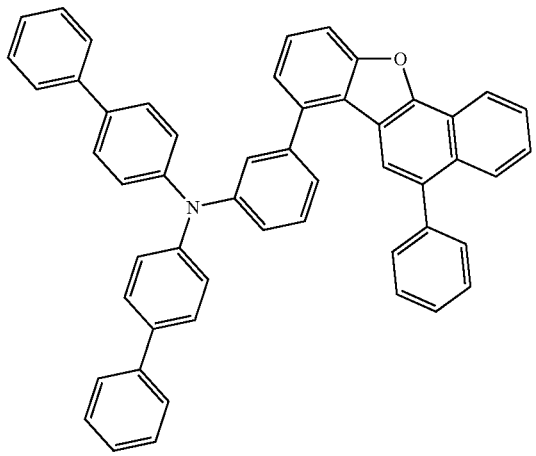
HT-682
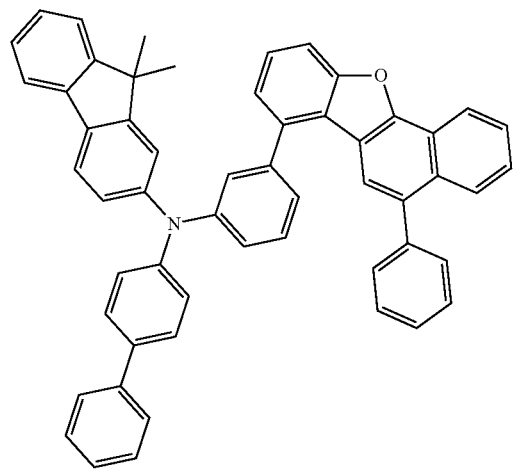
HT-683
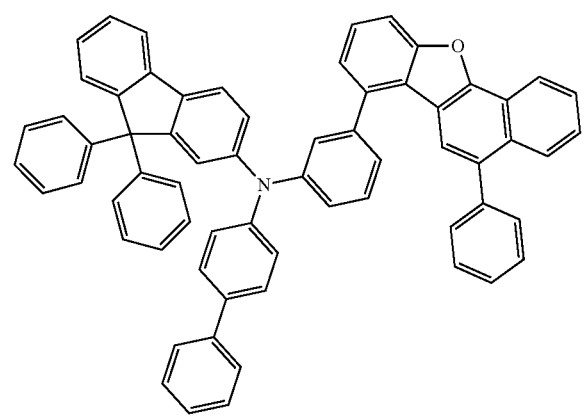
HT-684
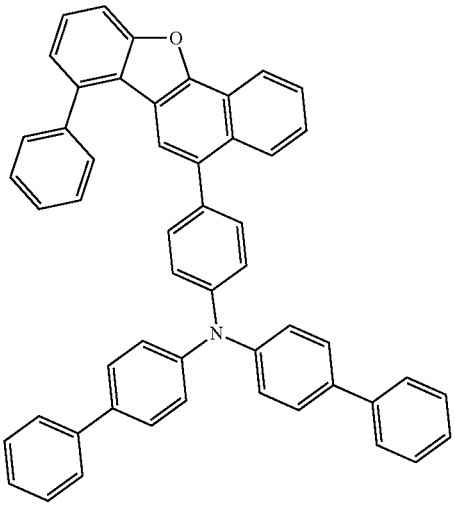
HT-685
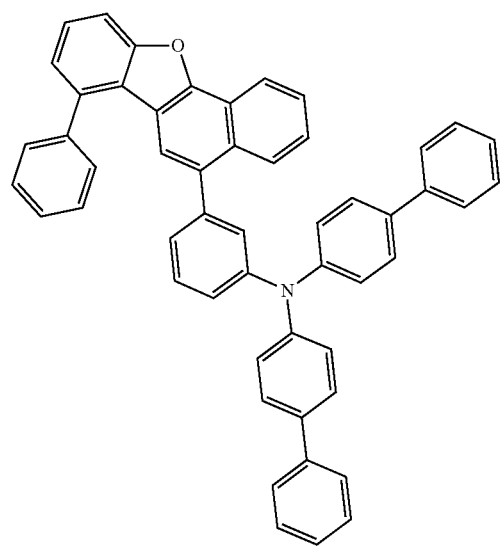
HT-686
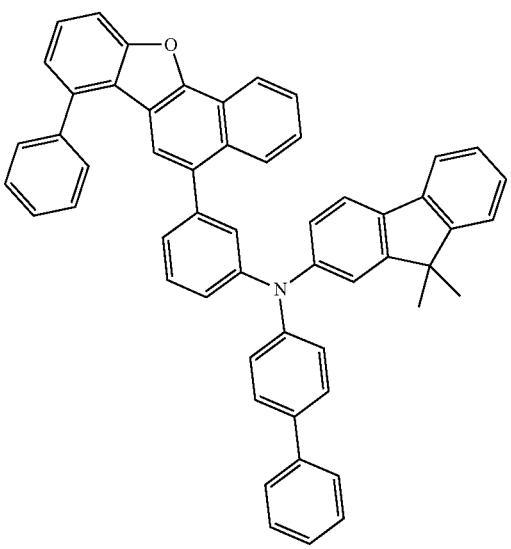

HT-687
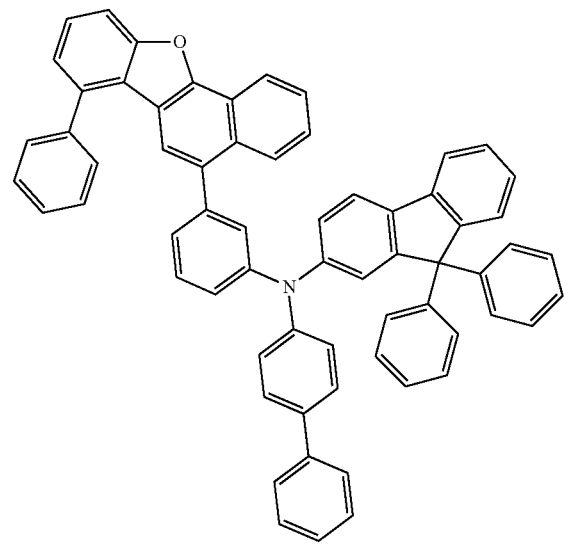
HT-688
HT-689
HT-690
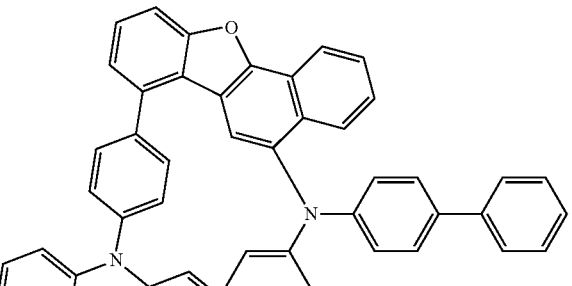
HT-691
HT-692
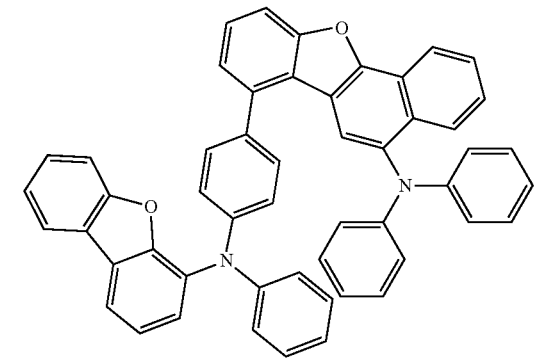
HT-693
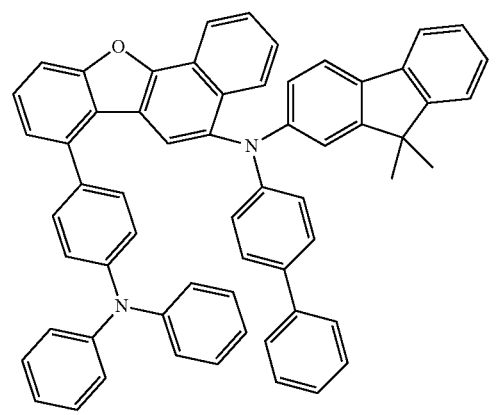

HT-694
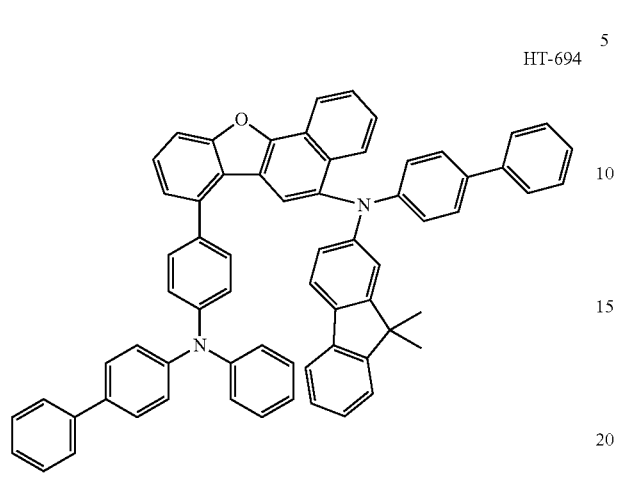
HT-695
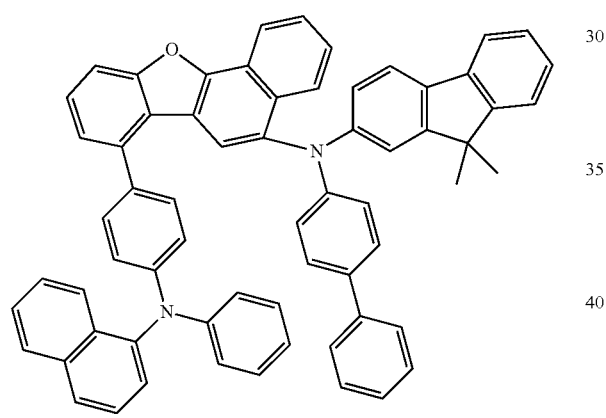
HT-696
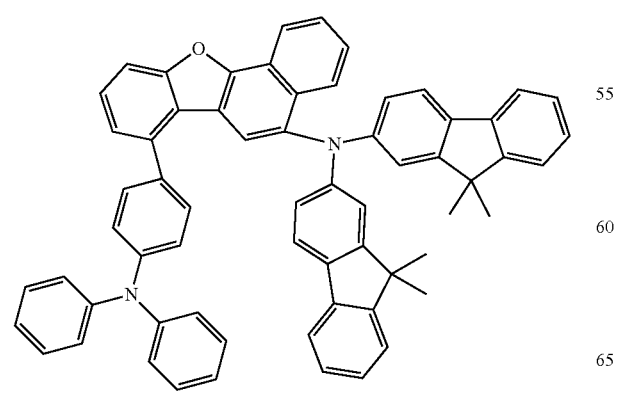
HT-697
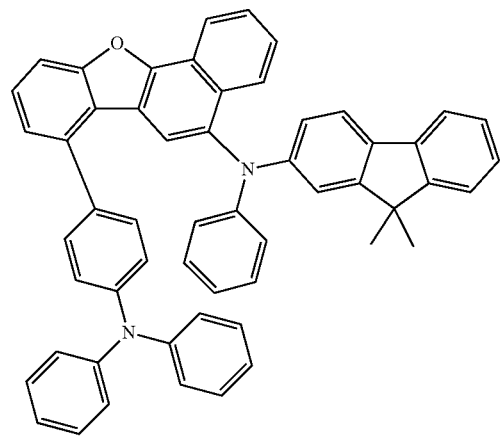
HT-698
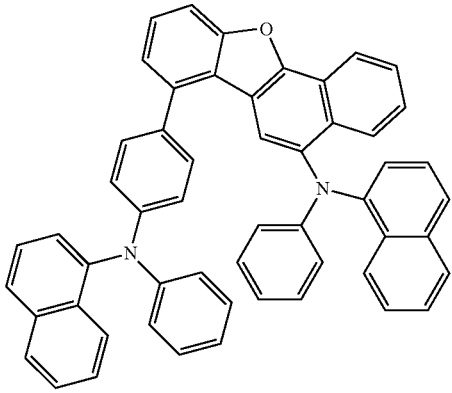
HT-699
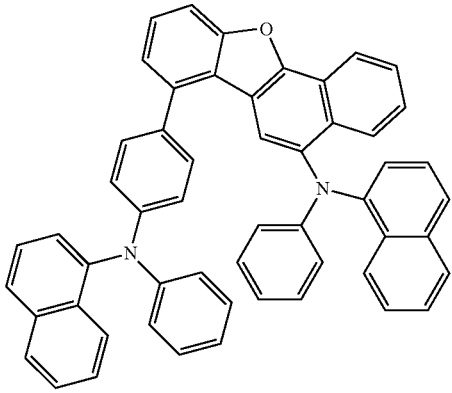
HT-700
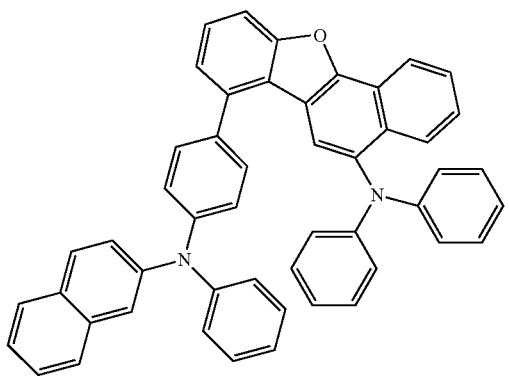

HT-701
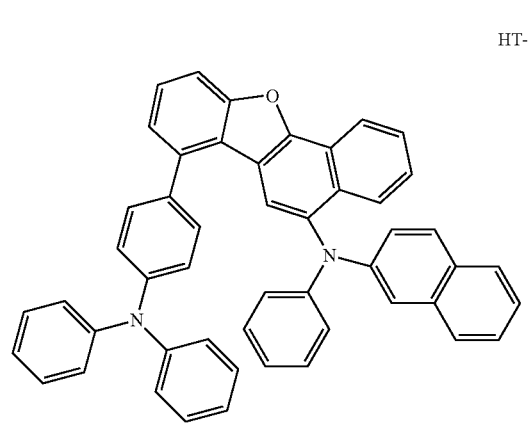
HT-704
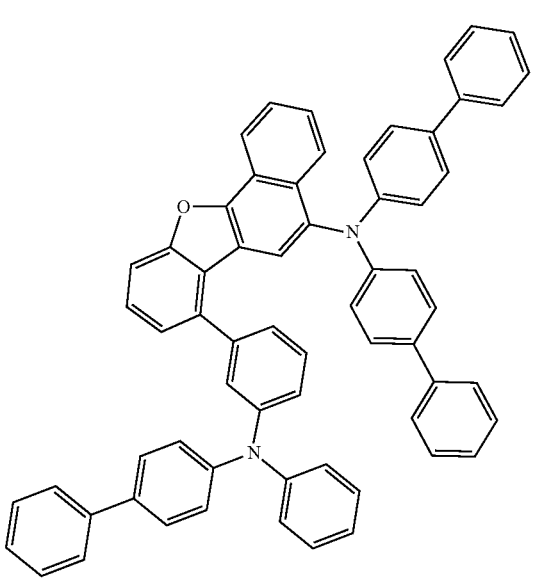
HT-702
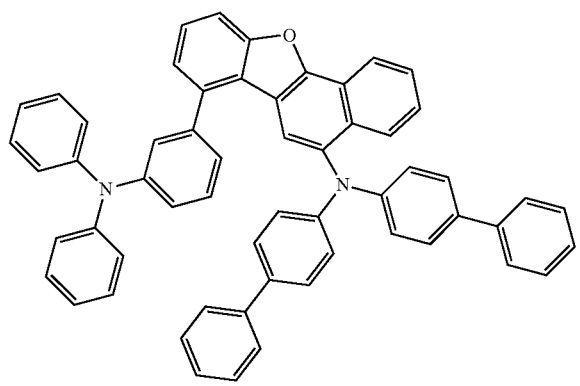
HT-705
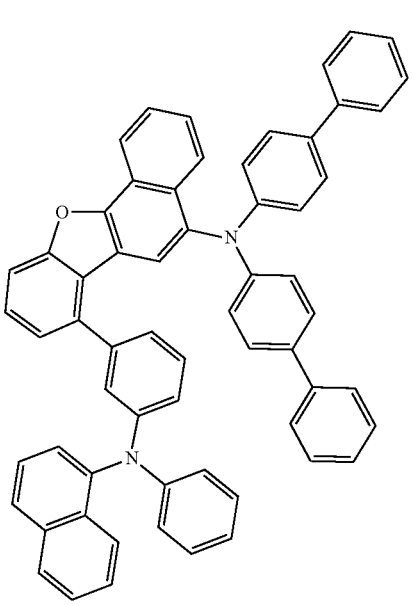
HT-703
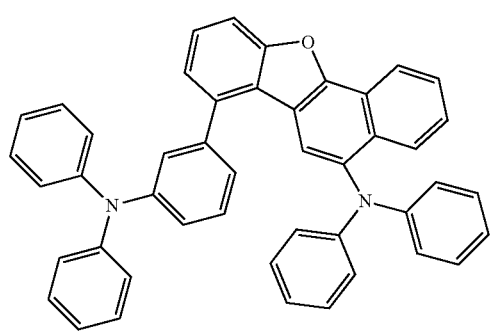
HT-706
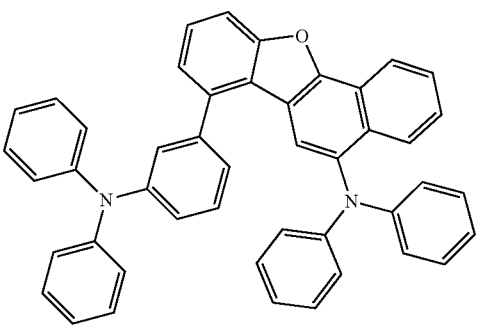

-continued
HT-707
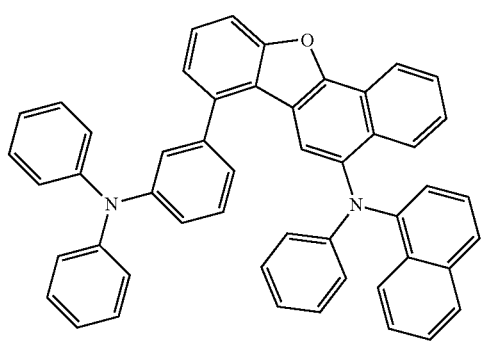
HT-708
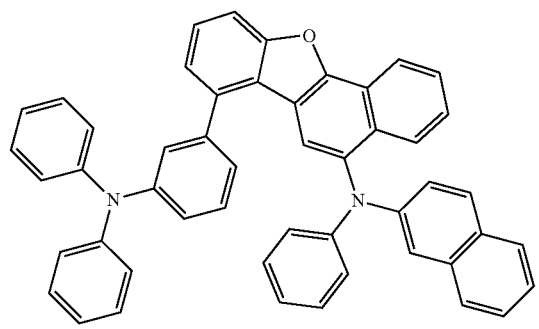
HT-709
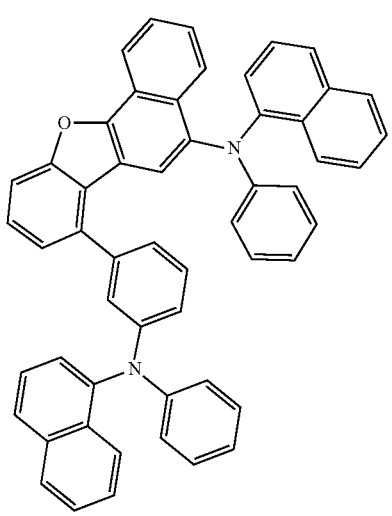
-continued
HT-710
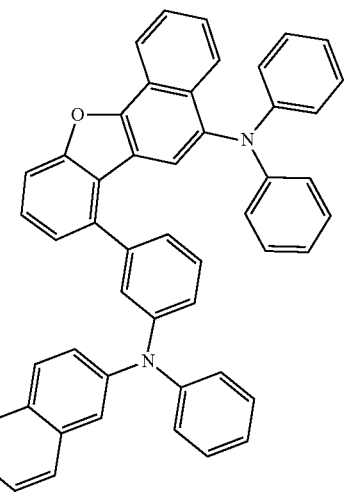
HT-711
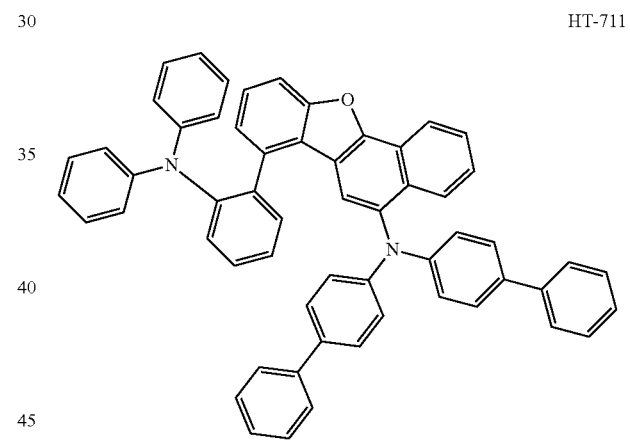
HT-712
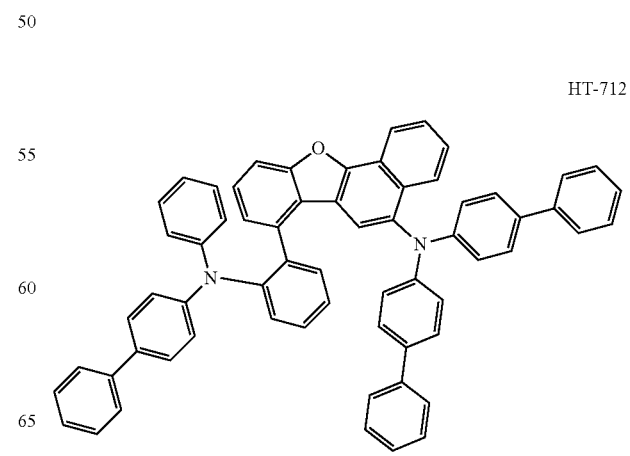

HT-713
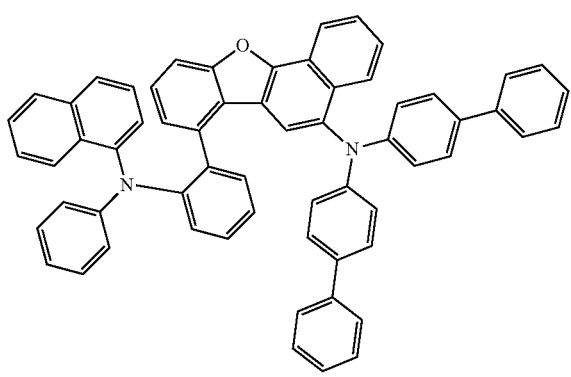

HT-714
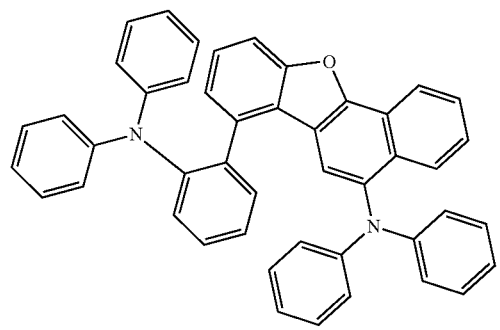

HT-715
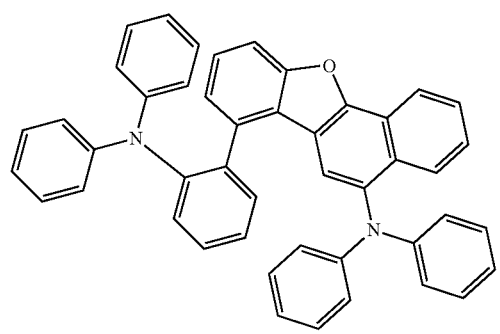

HT-716
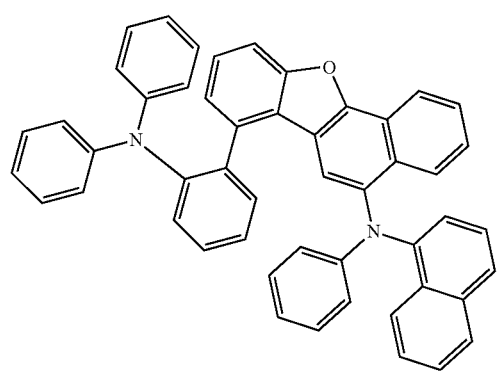

HT-717
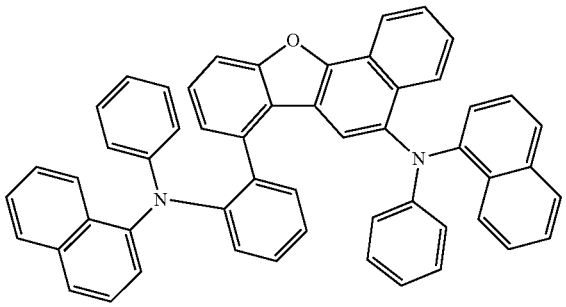

HT-718
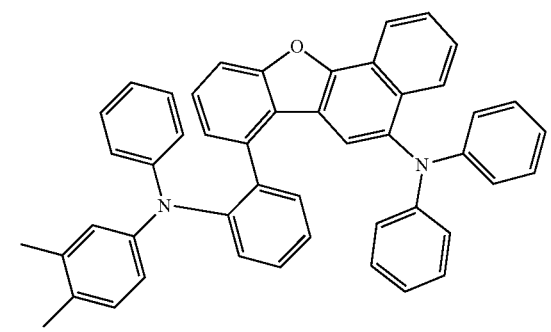

HT-719
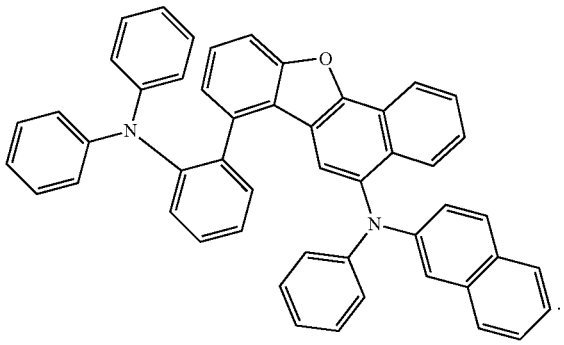

3. An organic light emitting device comprising:
an anode;
a cathode; and
one or more organic material layers provided between the anode and the cathode, wherein one or more layers of the organic material layers comprise the hetero-cyclic compound of claim 1.

4. The organic light emitting device of claim 3, wherein the organic material layer comprises one or more hole transfer layers, and the hole transfer layer comprises the hetero-cyclic compound.

5. The organic light emitting device of claim 3, wherein the organic material layer comprises one or more electron blocking layers, and the electron blocking layer comprises the hetero-cyclic compound.

6. The organic light emitting device of claim 3, wherein the organic material layer comprises one or more light emitting layers, and the light emitting layer comprises the hetero-cyclic compound.

7. The organic light emitting device of claim 3, wherein the organic material layer comprises one or more prime layers, and the prime layer comprises the hetero-cyclic compound.

8. The organic light emitting device of claim 3 comprising:
- an anode;
- a first stack provided on the anode and comprising a first light emitting layer;
- a charge generation layer provided on the first stack;
- a second stack provided on the charge generation layer and comprising a second light emitting layer; and
- a cathode provided on the second stack.

* * * * *